US012595482B2

(12) United States Patent
Anderson et al.

(10) Patent No.: US 12,595,482 B2
(45) **Date of Patent: *Apr. 7, 2026**

(54) LINKAGE MODIFIED OLIGOMERIC COMPOUNDS AND USES THEREOF

(71) Applicant: Ionis Pharmaceuticals, Inc., Carlsbad, CA (US)

(72) Inventors: Brooke A. Anderson, San Diego, CA (US); Xue-Hai Liang, Del Mar, CA (US); William John Drury, III, Oceanside, CA (US); Michael Oestergaard, Carlsbad, CA (US); Michael T. Migawa, Carlsbad, CA (US); Punit P. Seth, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 18/159,465

(22) Filed: Jan. 25, 2023

(65) Prior Publication Data

US 2024/0002851 A1 Jan. 4, 2024

Related U.S. Application Data

(63) Continuation of application No. 17/671,924, filed on Feb. 15, 2022, now Pat. No. 11,629,348, which is a continuation of application No. PCT/US2020/046561, filed on Aug. 14, 2020.

(60) Provisional application No. 63/050,042, filed on Jul. 9, 2020, provisional application No. 62/989,442, filed on Mar. 13, 2020, provisional application No. 62/953,121, filed on Dec. 23, 2019, provisional application No. 62/887,525, filed on Aug. 15, 2019.

(51) Int. Cl.
*C12N 15/113* (2010.01)

(52) U.S. Cl.
CPC ........ *C12N 15/113* (2013.01); *C12N 2310/11* (2013.01); *C12N 2310/314* (2013.01); *C12N 2310/315* (2013.01); *C12N 2310/321* (2013.01); *C12N 2310/341* (2013.01); *C12N 2310/351* (2013.01)

(58) Field of Classification Search
CPC .............. C12N 15/113; C12N 2310/11; C12N 2310/315; C12N 2310/321; C12N 2310/351; C12N 2310/14; C12N 2320/51
USPC ...... 424/9.1; 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lableu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |

(Continued)

FOREIGN PATENT DOCUMENTS

| | | |
|---|---|---|
| EP | 0679657 | 11/1995 |
| WO | WO 1989/009221 | 10/1989 |

(Continued)

OTHER PUBLICATIONS

U.S. Appl. No. 18/264,705, filed 2023.*

(Continued)

*Primary Examiner* — Jane J Zara
(74) *Attorney, Agent, or Firm* — McNeill PLLC

(57) ABSTRACT

The present disclosure provides oligomeric compounds (including oligomeric compounds that are antisense agents or portions thereof) comprising a modified oligonucleotide having at least one modified internucleoside linking group.

21 Claims, 2 Drawing Sheets

Specification includes a Sequence Listing.

(56) References Cited

U.S. PATENT DOCUMENTS 5,319,080 A 6/1994 Leumann
5,321,131 A 6/1994 Agrawal et al.
5,359,044 A 10/1994 Cook et al.
5,366,878 A 11/1994 Pederson et al.
5,367,066 A 11/1994 Urdea et al.
5,378,825 A 1/1995 Cook et al.
5,386,023 A 1/1995 Sanghvi et al.
5,393,878 A 2/1995 Leumann
5,399,676 A 3/1995 Froehler
5,403,711 A 4/1995 Walder et al.
5,405,938 A 4/1995 Sumerton et al.
5,405,939 A 4/1995 Suhadolnik et al.
5,432,272 A 7/1995 Benner
5,434,257 A 7/1995 Matteucci
5,446,137 A 8/1995 Maag et al.
5,453,496 A 9/1995 Caruthers et al.
5,455,233 A 10/1995 Spielvogel et al.
5,457,187 A 10/1995 Gmelner et al.
5,459,255 A 10/1995 Cook et al.
5,466,677 A 11/1995 Baxter et al.
5,466,786 A 11/1995 Buhr et al.
5,470,967 A 11/1995 Huie et al.
5,476,925 A 12/1995 Letsinger et al.
5,484,908 A 1/1996 Froehler et al.
5,489,677 A 2/1996 Sanghvi et al.
5,491,133 A 2/1996 Walder et al.
5,502,177 A 3/1996 Matteucci et al.
5,508,270 A 4/1996 Baxter et al.
5,514,785 A 5/1996 Van Ness et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,555 A 10/1996 Froehler et al.
5,567,811 A 10/1996 Mistura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,591,722 A 1/1997 Montgomery et al.
5,594,121 A 1/1997 Froehler et al.
5,596,086 A 1/1997 Matteucci
5,596,091 A 1/1997 Switzer
5,597,909 A 1/1997 Urdea et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,627,053 A 5/1997 Usman et al.
5,633,360 A 5/1997 Bishofberger et al.
5,639,873 A 6/1997 Barascut et al.
5,645,985 A 7/1997 Froehler et al.
5,646,265 A 7/1997 McGee
5,646,269 A 7/1997 Matteucci
5,652,355 A 7/1997 Metelev et al.
5,652,356 A 7/1997 Agrawal
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,700,920 A 12/1997 Altmann et al.
5,700,922 A 12/1997 Cook
5,721,218 A 2/1998 Froehler
5,750,692 A 5/1998 Cook et al.
5,763,588 A 6/1998 Matteucci et al.
5,792,608 A 8/1998 Swaminathan et al.
5,792,847 A 8/1998 Buhr et al.
5,830,653 A 11/1998 Froehler et al.
6,005,096 A 12/1999 Matteucci et al.
6,268,490 B1 7/2001 Imanishi et al.
6,365,577 B1 4/2002 Iversen
6,426,220 B1 7/2002 Bennett et al.
6,600,032 B1 7/2003 Manoharan et al.
6,770,748 B2 8/2004 Imanishi et al.
6,794,499 B2 9/2004 Wengel et al.
7,053,207 B2 5/2006 Wengel
7,067,641 B2 6/2006 Dellinger
7,399,845 B2 7/2008 Seth et al.
7,427,672 B2 9/2008 Imanishi et al.
8,987,435 B2 3/2015 Swayze et al.
11,629,348 B2 * 4/2023 Anderson ............ A61K 31/352
536/24.5
2003/0082807 A1 5/2003 Wengel
2003/0207841 A1 11/2003 Kaneko et al.
2003/0224377 A1 12/2003 Wengel et al.
2004/0143114 A1 7/2004 Imanishi et al.
2004/0171570 A1 9/2004 Allerson et al.
2004/0192918 A1 9/2004 Imanishi et al.
2005/0130923 A1 6/2005 Bhat et al.
2011/0313019 A1 12/2011 Swayze et al.
2013/0323836 A1 12/2013 Manoharan et al.
2016/0122761 A1 5/2016 Prakash et al.
2017/0130224 A1 5/2017 Oestergaard et al.
2022/0186222 A1 6/2022 Anderson et al.
2024/0287520 A1 8/2024 Rodriguez
2024/0360448 A1 10/2024 Gaus et al.

FOREIGN PATENT DOCUMENTS

WO WO 1994/002499 2/1994
WO WO 1994/017093 8/1994
WO WO 1999/014226 3/1999
WO WO 2002/036743 5/2002
WO WO 2003/002587 1/2003
WO WO 2005/121371 12/2005
WO WO 2005/121372 12/2005
WO WO 2007/059816 5/2007
WO WO 2007/134181 11/2007
WO WO 2007/146511 12/2007
WO WO 2008/101157 8/2008
WO WO 2008/109080 9/2008
WO WO 2008/150729 12/2008
WO WO 2008/154401 12/2008
WO WO 2009/006478 1/2009
WO WO 2009/067647 5/2009
WO 2010060599 6/2010
WO WO 2011/139699 11/2011
WO WO 2011/139702 11/2011
WO WO 2013/075035 5/2013
WO 2014090837 6/2014
WO 2014179620 A1 11/2014
WO WO 2016/028187 2/2016
WO WO 2016/028649 2/2016
WO WO 2018/098328 5/2018
WO WO 2018/156056 8/2018
WO 2008128686 10/2018
WO WO 2019/073018 4/2019
WO WO 2019/157531 8/2019
WO 2019193144 10/2019
WO WO 2019/200185 10/2019
WO WO 2019/217459 11/2019
WO WO 2020/072991 4/2020
WO WO 2020/160163 8/2020
WO WO 2021/030763 2/2021
WO WO 2021/030778 2/2021
WO 2021092371 5/2021
WO 2022026589 2/2022
WO 2022174053 8/2022
WO 2023023550 2/2023

(56) References Cited

FOREIGN PATENT DOCUMENTS

| | | |
|---|---|---|
| WO | 2024173759 | 8/2024 |
| WO | 2024173762 | 8/2024 |
| WO | 2024173783 | 8/2024 |

OTHER PUBLICATIONS

Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al. "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides & Nucleotides (1997) 16: 917-926.

Altmann et al. "Second Generation of Antisense Oligonucleotides: Structure-activity relationships and the design of improved signal-transduction inhibitors" RNA Interactions (1996) 24: 630-637.

Altmann et al. "Second Generation of Antisense Oligonucleotides: From Nuclease Resistance to Biological Efficacy in Animals" Chimia (1996) 168-176.

Altschul et al., "Basic Local Alignment Search Tool" J. Mol. Biol. (1990) 215:403-410.

Anderson et al., "Towards next generation antisense oligonucleotides: mesylphosphoramidate modification improves therapeutic index and duration of effect of gapmer antisense oligonucleotides" Nucl Acids Res (2021) 1-16.

Anderson et al., "Towards Next Generation Antisense Oligonucleotides—Mesylphosphoramidate Modification Improves Therapeutic Index and Duration of Effect of Gapmer Antisense Oligonucleotides" Abstract for 17th Annual OTS—Oligonucleotide Therapeutics Society Meeting (Sep. 26-29, 2021).

Anderson et al., "Towards Next Generation Antisense Oligonucleotides—Mesylphosphoramidate Modification Improves Therapeutic Index and Duration of Effect of Gapmer Antisense Oligonucleotides" Poster for 17th Annual OTS—Oligonucleotide Therapeutics Society Meeting (Sep. 26-29, 2021).

Baker et al. "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J Biol Chem (1997) 272(18):11994-12000.

Bala et al., "Synthesis of α-l-Threofuranosyl Nucleoside 3'-Monophosphates, 3'-Phosphoro(2-Methyl)imidazolides, and 3'-Triphosphates" J Org Chem (2017) 82: 5910-5916.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

Beaucage et al., "Advances in the Synthesis of Oligonucleotides by the Phosphoramidite Approach" Tetrahedron (1992) 48(12):2223-2311.

Beaucage et al., "The Functionalization of Oligonucleotides Via Phosphoramidite Derivatives" Tetrahedron (1993) 49(10):1925-1963.

Beaucage et al., "The Synthesis of Specific Ribonucleotides and Unrelated Phosphorylated Biomolecules by the Phosphoramidite Method" Tetrahedron (1993) 49(46):10441-10488.

Belikova et al., "Synthesis of Ribonucleosides and Diribonucleoside Phosphates Containing 2-Chloro-Ethylamine and Nitrogen Mustard Residues" Tet. Lett. (1967) 37:3557-3562.

Biscans et al., "The chemical structure and phosphorothioate content of hydrophobically modified siRNAs impact extra hepatic distribution and efficacy" Nucl Ac Res (2020) 1-16.

Boissonnet et al., "α,β-D-CAN featuring canonical and noncanonical α/β torsional angles behaviours within oligonucleotides" New J. Chem. (2011) 35: 1528-1533.

Borsting et al. "Dinucleotides containing two allyl groups by combinations of allyl phosphotriesters, 5-allyl-, 2'-O-allyl- and 2'-arabino-O-allyl uridine derivatives as substrates for ring-closing metathesis" Tetrahedron (2004) 60: 10955-10966.

Braasch et al., "Locked nucleic acid (LNA): fine-tuning the recognition of DNA and RNA" Chem. Biol. (2001) 8:1-7.

Brazma et al., "Gene expression data analysis" FEBS Letters (2000) 480:17-24.

Burakova et al., "New Oligodeoxynucleotide Derivatives Containing N-(Sulfonyl)-Phosphoramide Groups" Russian J of Bioorg Chem (2019) 45: 662-668.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

Chappell et al., "Mechanisms of palmitic acid-conjugated antisense oligonucleotide distribution in mice" Nucleic Acids Res (2020) 48(8): 4382-4395.

Chelobanov et al., "New Oligodeoxynucleotide Derivatives Containing N-(Methanesulfonyl)-Phosphoramidate (Mesyl Phosphoramidate) Internucleotide Group" Russain J Bioorg Chem (2017) 43: 664-668.

Chiang et al., "Antisense Oligonucleotides Inhibit Intercellular Adhesion Molecule 1 Expression by Two Distinct Mechanisms" J. Biol. Chem. (1991) 266:18162-18171.

Conte et al. "Conformational properties and thermodynamics of the RNA duplex r(CGCAAAUUUGCG)2: comparison with the DNA analogue d(CGCAAATTTGCG)2" Nucleic Acids Research (1997) 25: 2627-2634.

Crooke et al., "Pharmacokinetic Properties of Several Novel Oligonucleotide Analogs in mice" J. Pharmacol. Exp. Ther. (1996) 277(2):923-937.

Dupouy et al., "Watson-Crick Base-Pairing Properties of Nucleic Acid Analogues with Stereocontrolled α and β Torsion Angles (α,β-D-CNAs)" Angew. Chem. Int. Ed. Engl. (2014) 45: 3623-3627.

Dupouy et al., "Synthesis and Structure of Dinucleotides with S-Type Sugar Puckering and Noncanonical ϵ and ζ Torsion Angle Combination" Eur. J. Org. Chem.., 2008, 1285-1294.

Dupouy et al., "Synthesis and Structure of Dinucleotides Featuring Canonical and Non-canonical A-Type Duplex α, β and δ Torsion Angle Combinations (LNA/α,β-D-CAN)" Eur. J. Org. Chem. (2007) 5256-5264.

Egli et al., "Probing the Influence of Stereoelectronic Effects on the Biophysical Properties of Oligonucleotides: Comprehensive Analysis of the RNA Affinity, Nuclease Resistance, and Crystal Structure of Ten 2'-O-Ribonucleic Acid Modifications" Biochemistry (2005) 44(25):9045-9057.

Elayadi et al., "Application of PNA and LNA oligomers to chemotherapy" Curr. Opinion Invens. Drugs (2001) 2:558-561.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Englisch et al., "Chemically Modified Oligonucleotides as Probes and Inhibitors" Agnew Chem. Int. Ed. Engl. (1991) 30:613-629.

Fire et al., "Potent and Specific Genetic Interference by Double-Stranded RNA in Caenorhabditis Elegans" Nature (1998) 391:806-811.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

(56) References Cited

OTHER PUBLICATIONS

Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gait, "Oligoribonucleotides" Antisense Research and Applications (1993), CRC Press, Boca Raton, pp. 289-301.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Going et al., "Molecular Pathology and Future Developments" Eur. J. Cancer (1999) 35:1895-1904.
International Search Report for PCT/US20/046561 dated Dec. 31, 2020.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Letsinger et al., "Cholesteryl-conjugated oligonucleotides: Synthesis, properties, and activity as inhibitors of replication of human immunodeficiency virus in cell culture" PNAS (1989) 86:6553-6556.
Lesnik et al. "Relative Thermodynamic Stability of DNA, RNA, and DNA:RNA Hybrid Duplexes: Relationship with Base Composition and Structure" Biochemistry (1995) 34: 10807-10815.
Leumann et al., "DNA Analogues: From Supramolecular Principles to Biological Properties" Bioorganic & Medicinal Chemistry (2002) 10:841-854.
Madden et al., "Serial analysis of gene expression: from gene discovery to target identification" DDT (2000) 5:415-425.
Manoharan et al., "Chemical Modifications to Improve Uptake and Bioavailability of Antisense Oligonucleotides" Ann. N. Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5): 969-973.
Manoharan et al., "Lipidic Nucleic Acids" Tetrahedron Lett. (1995) 36(21):3651-3654.
Manoharan et al. "Oligonucleotide Conjugates as Potential Antisense Drugs with Improved Uptake, Biodistribution, Targeted Delivery, and Mechanism of Action" Antisense & Nucleic Acid Drug Development (2002) 12:103-128.
Martin et al. "A New Access to 2'O-Alkylated Ribonucleosides and Properties of 2'-O-Alkylated Oligoribonucleotides" Helvetica Chimica Acta (1995) 78: 486-504.
Martinez et al., "α,β-D-constrained nucleic acids are strong terminators of thermostable DNA polymerases in polymerase chain reaction" PLoS One (2011) 6: e25510.
Miroshnichenko et al., "Mesyl phosphoramidate antisense oligonucleotides as an alternative to phosphorothioates with improved biochemical and biological properties" PNAS (2019) 116: 1229-1234.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caenorhabditis elegans" Proc Natl. Acad. Sci. (1998) 95:15502-7.
Nishikura et al., "A Short Primer on RNAi: RNA-Directed RNA Polymerase Acts as a Key Catalyst" Cell (2001) 107:415-418.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Ostergaard et al., "Differential effects on allele selective silencing of mutant huntingtin by two stereoisomers of α,β-constrained nucleic acid" ACS Chem. Biol. (2014) 9: 1975-1979.
Patutina et al., "Mesyl phosphoramidate backbone modified antisense oligonucleotides targeting niR-21 with enhanced in vivo therapeutic potency" PNAS (2020) 117: 32370-32379.
Prashar et al., "READS: A Method for Display of 3'-End Fragment of Restriction Enzyme-Digested cDNAs for Analysis of Differential Gene Expression" Methods Enzymol. (1999) 303:258-272.
Pubchem, Substance Record for SID 136357381, Modify Date: Oct. 9, 2015 [retrieved on Oct. 19, 2020] from https://pubchem.ncbi.nlm.nih.gov/substance/136357381 : entire document.
Pubchem, Substance Record for SID 57553290, Available Date: Apr. 13, 2009 [retrieved on Oct. 19, 2020] from https://pubchem.ncbi.nlm.nih.gov/substance/57553290 : entire document.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Scaringe, "RNA Oligonucleotide Synthesis via 5'-Silyl-2'-Orthoester Chemistry" Methods (2001) 23:206-217.
Searle et al. "On the stability of nucleic acid structures in solution: enthalpy—entropy compensations, internal rotations and reversability" Nucleic Acids Research (1993) 21: 2051-2056.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Singh et al. "Synthesis of Novel Bicyclo[2.2.1] Ribonucleosides: 2'-Amino- and 2'-Thio-LNA Monomeric Nucleosides" J Org Chem (1998) 63: 6078-6079.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Sutcliffe et al., "TOGA: An automated parsing technology for analyzing expression of nearly all genes" PNAS (2000) 97:1976-1981.

(56) References Cited

OTHER PUBLICATIONS

Svinarchuk et al., "Inhibition of HIV proliferation in MT-4 cells by antisense oligonucleotide conjugated to lipophilic groups" Biochimie (1993) 75:49-54.
Tabara et al., "RNAi in C. elegans: Soaking in the Genome Sequence" Science (1998) 282:430-431.
Tijsterman et al., "RNA hellcase MUT-14-dependent gene silencing triggered in C. elegans by short antisense RNAs" Science (2002) 295:694-7.
Timmons et al., "Ingestion of bacterially expressed dsRNAs can produce specific and potent genetic interference in Caenorhabditis Elegans" Gene (2001) 263:103-112.
Timmons et al., "Specific Interference by Ingested dsRNA" Nature (1998) 395:854.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Wahlestedt et al., "Potent and nontoxic antisense oligonucleotide containing locked nucleic acids" Proc. Natl. Acad. Sci. USA (2000) 97: 5633-5638.
Wouters et al., "5-Substituted Pyrimidine 1,5-Anhydrohexitols: Conformational Analysis and Interaction with Viral Thymidine Kinase" Bioorg. Med. Chem. Lett. (1999) 9:1563-1566.
Zamecnik et al., "Inhibition of Rous sarcoma virus replication and cell transformation by a specific oligodeoxynucleotide" PNAS (1978) 75:280-284.
Zhang et al., "PowerBLAST: A New Network BLAST Application for Interactive or Automated Sequence Analysis and Annotation" Genome Res. (1997) 7:649-656.
Zhou et al., "Double sugar and phosphate backbone-constrained nucleotides: synthesis, structure, stability and their incorporation into oligodeoxynucleotides" J. Org. Chem. (2009) 74(1):3248-3265.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Su et al., "Neutral and Negatively Charged Phosphate Modifications Altering Thermal Stability, Kinetics of Formation and Monovalent Ion Dependence of DNA G-Quadruplexes," Chem Asian J, (2019) 14:1212-1220.
Derzhalova et al., "Novel Lipid-Oligonucleotide Conjugates Containing Long-Chain Sulfonyl Phosphoramidate Groups: Synthesis and Biological Properties," Applied Sciences (2021) 11: 1174.
Extended European Search Report and European Search Opinion for European Application No. 20853270.5, dated Sep. 25, 2023, (75 pages).
Extended European Search Report issued in European Application No. 22753422.9, dated Feb. 13, 2025, (11 pages).
Glazier et al., "Chemical Synthesis and Biological Application of Modified Oligonucleotides" Bioconjug Cehm (2020) 31: 1213-1233.
International Search Report and Written Opinion for International Application No. PCT/US22/075073 dated Nov. 7, 2022, (10 pages).
International Search Report and Written Opinion for PCT/US22/016143 dated Jul. 1, 2022, (15 pages).
Ostanin et al., "Phosphate-modif ied CpG oligonucleotides induce in vitro maturation of human myeloid dendritic cells" Vaviloskii Zhurnal Genet Selektsii (2020) 24: 653-660.
Prakash, TP, "Exploring Chemical Space for Improving Properties of RNA Therapeutics" Presentation for OPT Congress in Boston MA (Mar. 15-16, 2022).
Prokhorova et al. "New oligodeoxyribonucleotide derivatives bearing internucleotideN-tosyl phosphoramidate groups: Synthesis and complementary binding to DNA and RNA", Russian Journal of BioOrganic Chemistry (2017) 43 (1): 38-42.
Seth, P., "Redefining the chemical space for nucleic acid therapeutics" Presentation at TIDES Boston MA, (Sep. 20-23, 2021).
Su et al., "DNA with zwitterionic and negatively charged phosphate modifications: Formation of DNA triplexes, duplexes and cell uptake studies," Beilstein J Org Chem, 2021, 17:749-761. doi: 10.3762/bjoc.17.65. eCollection 2021.
Zhang et al., "The Combination of Mesyl-Phosphoramidate Inter-Nucleotide Linkages and 2'-O-Methyl in Selected Positions in the Antisense Oligonucleotide Enhances the Performance of RNaseH1 Active PS-ASOs" Nucleic Acid Ther (2022) 32(5): 401-411.

* cited by examiner

2′-β-D-deoxyribosyl
"DNA"
d

2′-α-D-deoxyribosyl
[aDd]

2′-β-D-deoxyxylosyl
[dx]

2′-α-D-deoxyxylosyl
[aDdx]

2′-β-L-deoxyribosyl
[bLd]

2′-α-L-deoxyribosyl
[aLd]

2′-β-L-deoxyxylosyl
[bLdx]

2′-α-L-deoxyxylosyl
[aLdx]

2′-O-methyl-
β-D-xylosyl
[m2bDx]

2′-O-methyl-
β-D-arabinosyl
[m2bDa]

2′-O-methyl-
α-D-arabinosyl
[m2aDa]

2′-O-methyl-
α-L-arabinosyl
[m2aLa]

2′-fluoro-
β-D-arabinosyl
[f2bDa]

2′-fluoro-
β-D-xylosyl
[f2bDx]

2′-fluoro-
α-D-ribosyl
[f2aDr]

2′-fluoro-
α-D-arabinosyl
[f2aDa]

2′-fluoro-
α-D-xylosyl
[f2aDx]

2′-fluoro-
α-L-ribosyl
[f2aLr]

2′-fluoro-
β-L-xylosyl
[f2bLx]

2′-fluoro-
α-L-arabinosyl
[f2aLa]

2′-fluoro-
α-L-xylosyl
[f2aLx]

2′-fluoro-
β-L-ribosyl
[f2bLr]

2′-fluoro-
β-L-arabinosyl
[f2bLa]

LINKAGE MODIFIED OLIGOMERIC COMPOUNDS AND USES THEREOF

SEQUENCE LISTING

The present application is being filed along with a Sequence Listing in electronic format. The Sequence Listing is provided as a file entitled CHEM0101SEQ.xml created Dec. 16, 2022 which is 527 kb in size. The information in the electronic format of the sequence listing is incorporated herein by reference in its entirety.

FIELD

The present disclosure provides oligomeric compounds (including oligomeric compounds that are antisense agents or portions thereof) comprising a modified oligonucleotide having at least one modified internucleoside linking group.

BACKGROUND

The principle behind antisense technology is that an antisense compound hybridizes to a target nucleic acid and modulates the amount, activity, and/or function of the target nucleic acid. For example, in certain instances, antisense compounds result in altered transcription or translation of a target. Such modulation of expression can be achieved by, for example, target RNA degradation or occupancy-based inhibition. An example of modulation of RNA target function by degradation is RNase H-based degradation of the target RNA upon hybridization with a DNA-like antisense compound.

Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Another example of modulation of gene expression is the use of antisense compounds in a CRISPR system. Regardless of the specific mechanism, sequence-specificity makes antisense compounds attractive as tools for target validation and gene functionalization, as well as therapeutics to selectively modulate the expression of genes involved in the pathogenesis of disease.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, tolerability, pharmacokinetics, or affinity for a target nucleic acid.

SUMMARY

The present disclosure provides oligomeric compounds (including oligomeric compounds that are antisense agents or portions thereof) comprising modified oligonucleotides consisting of linked nucleosides linked through internucleoside linking groups, wherein at least one of the internucleoside linking groups has Formula VIII:

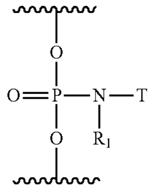

VIII wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

The present disclosure provides oligomeric compounds (including oligomeric compounds that are antisense agents or portions thereof) comprising modified oligonucleotides consisting of linked nucleosides linked through internucleoside linking groups, wherein at least one of the internucleoside linking groups has Formula VIII:

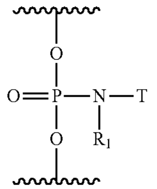

VIII wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, a $C_1$-$C_6$ alkyl, and a substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl;

provided that if $R_1$ is H, then T is not:

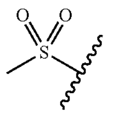
or
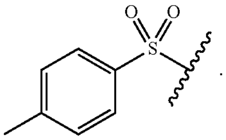
.

The present disclosure provides oligomeric compounds (including oligomeric compounds that are antisense agents or portions thereof) comprising modified oligonucleotides consisting of linked nucleosides linked through internucleoside linking groups, wherein at least one of the internucleoside linking groups has Formula XVJI:

XVII

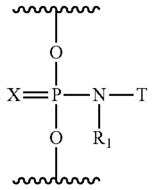

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, C(=O)$R_3$, and P(=O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

In certain embodiments, oligomeric compounds (including oligomeric compounds that are antisense agents or portions thereof) having at least one internucleoside linking group of Formula VIII or Formula XVII have an increased maximum tolerated dose when administered to an animal compared to an otherwise identical oligomeric compound, except that the otherwise identical oligomeric compound lacks the internucleoside linking group of Formula VIII or Formula XVII.

In certain embodiments, the modified oligonucleotides having at least one internucleoside linking group of Formula VIII or Formula XVII have an increased therapeutic index compared to an otherwise identical oligomeric compound, except that the otherwise identical oligomeric compound lacks the at least one internucleoside linking group of Formula VIII or Formula XVII.

DETAILED DESCRIPTION

Figure 1:
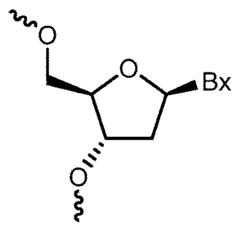
FIG. 1 depicts isomers of 2'-deoxyfuranosyl sugar moieties having formulas I-VII.
Figure 1:
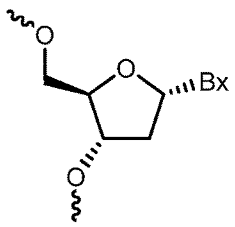
Figure 1:
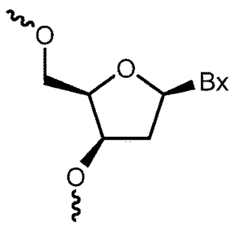
Figure 1:
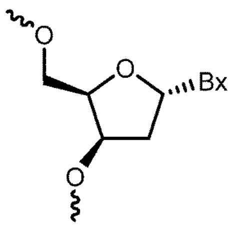
Figure 1:
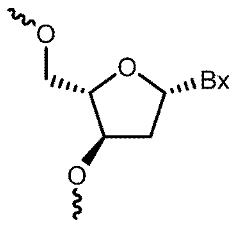
Figure 1:
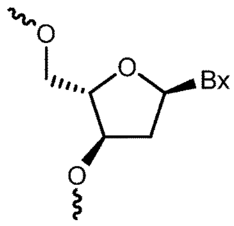
Figure 1:
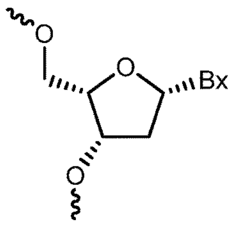
Figure 1:
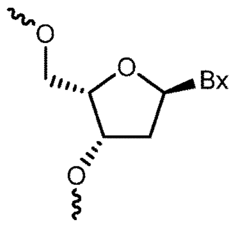

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH(H) sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, a modified oligonucleotide having the nucleobase sequence "ATCGATCG" encompasses any modified oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and modified oligonucleotides having other modified nucleobases, such as "AT$^m$CGAUCG," wherein $^m$C indicates a cytosine base comprising a methyl group at the 5-position.

As used herein, "2'-substituted" in reference to a furanosyl sugar moiety or nucleoside comprising a furanosyl sugar moiety means the furanosyl sugar moiety or nucleoside comprising the furanosyl sugar moiety comprises a substituent other than H or OH at the 2'-position and is a non-bicyclic furanosyl sugar moiety. 2'-substituted furanosyl sugar moieties do not comprise additional substituents at other positions of the furanosyl sugar moiety other than a nucleobase and/or internucleoside linkage(s) when in the context of an oligonucleotide.

As used herein, "4'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 4'-position and is a non-bicyclic furanosyl sugar moiety. 4'-substituted furanosyl sugar moieties do not comprise additional substituents at other positions of the furanosyl sugar moiety other than a nucleobase and/or internucleoside linkage(s) when in the context of an oligonucleotide.

As used herein, "5'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 5'-position and is a non-bicyclic furanosyl sugar moiety. 5'-substituted furanosyl sugar moieties do not comprise additional substituents at other positions of the furanosyl sugar moiety other than a nucleobase and/or internucleoside linkage(s) when in the context of an oligonucleotide.

As used herein, "administration" or "administering" refers to routes of introducing a compound or composition provided herein to a subject to perform its intended function. Examples of routes of administration that can be used include, but are not limited to, administration by inhalation, subcutaneous injection, intrathecal injection, and oral administration.

As used herein, "antisense activity" means any detectable and/or measurable change attributable to the hybridization of an antisense oligonucleotide to its target nucleic acid. In certain embodiments, antisense activity is a decrease in the amount or expression of a target nucleic acid or protein encoded by such target nucleic acid compared to target nucleic acid levels or target protein levels in the absence of the antisense oligonucleotide.

As used herein, "antisense agent" means an antisense oligonucleotide or an oligonucleotide duplex comprising an antisense oligonucleotide.

As used herein, "antisense compound" means an antisense oligonucleotide or an oligonucleotide duplex comprising an antisense oligonucleotide.

As used herein, "antisense oligonucleotide" means an oligonucleotide that is complementary to a target nucleic acid and is capable of achieving at least one antisense activity. Antisense oligonucleotides include but are not limited to RNAi antisense modified oligonucleotides and RNase H antisense modified oligonucleotides. In certain embodiments, an antisense oligonucleotide is paired with a sense oligonucleotide to form an oligonucleotide duplex. In certain embodiments, an antisense oligonucleotide is unpaired and is a single-stranded antisense oligonucleotide. In certain embodiments, an antisense oligonucleotide comprises a conjugate group.

As used herein, "artificial mRNA compound" is a modified oligonucleotide, or portion thereof, having a nucleobase sequence comprising one or more codons.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety, and the bicyclic sugar moiety is a modified bicyclic furanosyl sugar moiety. In certain embodiments, the bicyclic sugar moiety does not comprise a furanosyl moiety.

As used herein, "cEt" or "constrained ethyl" or "cEt sugar moiety" means a bicyclic sugar moiety, wherein the first ring of the bicyclic sugar moiety is a ribosyl sugar moiety, the second ring of the bicyclic sugar is formed via a bridge connecting the 4'-carbon and the 2'-carbon, the bridge has the formula 4'-$CH(CH_3)$—O-2', and the methyl group of the bridge is in the S configuration. A cEt bicyclic sugar moiety is in the β-D configuration.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases are nucleobase pairs that are capable of forming hydrogen bonds with one another. Complementary nucleobase pairs include adenine (A) and thymine (T), adenine (A) and uracil (U), cytosine (C) and guanine (G), 5-methyl cytosine ($^{m}$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms consisting of a conjugate moiety and a conjugate linker.

As used herein, "conjugate moiety" means a group of atoms that modifies one or more properties of a molecule compared to the identical molecule lacking the conjugate moiety, including but not limited to pharmacodynamics, pharmacokinetics, stability, binding, absorption, tissue distribution, cellular distribution, cellular uptake, charge and clearance.

As used herein, "conjugate linker" means a group of atoms comprising at least one bond.

As used herein, "CRISPR compound" means a modified oligonucleotide that comprises a DNA recognition portion and a tracrRNA recognition portion. As used herein, "DNA recognition portion" is nucleobase sequence that is complementary to a DNA target. As used herein, "tracrRNA recognition portion" is a nucleobase sequence that is bound to or is capable of binding to tracrRNA. The tracrRNA recognition portion of crRNA may bind to tracrRNA via hybridization or covalent attachment.

As used herein, "cytotoxic" or "cytotoxicity" in the context of an effect of an oligomeric compound or a parent oligomeric compound on cultured cells means an at least 2-fold increase in caspase activation following administration of 10 μM or less of the oligomeric compound or parent oligomeric compound to the cultured cells relative to cells cultured under the same conditions but that are not administered the oligomeric compound or parent oligomeric compound. In certain embodiments, cytotoxicity is measured using a standard in vitro cytotoxicity assay.

As used herein, "deoxy region" means a region of 5-12 contiguous nucleotides, wherein at least 70% of the nucleosides are stereo-standard DNA nucleosides. In certain embodiments, each nucleoside is selected from a stereo-standard DNA nucleoside (a nucleoside comprising a β-D-2'-deoxyribosyl sugar moiety), a stereo-non-standard nucleoside of Formula I-VII, a bicyclic nucleoside, and a substituted stereo-standard nucleoside. In certain embodiments, a deoxy region supports RNase H activity. In certain embodiments, a deoxy region is the gap of a gapmer.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "expression" includes all the functions by which a gene's coded information is converted into structures present and operating in a cell. Such structures include, but are not limited to, the products of transcription and translation. As used herein, "modulation of expression" means any change in amount or activity of a product of transcription or translation of a gene. Such a change may be an increase or a reduction of any amount relative to the expression level prior to the modulation.

As used herein, "gapmer" means an oligonucleotide having a central region comprising a plurality of nucleosides that support RNase H cleavage positioned between a 5'-region and a 3'-region. Herein, the nucleosides of the 5'-region and 3'-region each comprise a 2'-substituted furanosyl sugar moiety or a bicyclic sugar moiety, and the 3'- and 5'-most nucleosides of the central region each comprise a sugar moiety independently selected from a 2'-deoxyfuranosyl sugar moiety or a sugar surrogate. The positions of the central region refer to the order of the nucleosides of the central region and are counted starting from the 5'-end of the central region. Thus, the 5'-most nucleoside of the central region is at position 1 of the central region. The "central region" may be referred to as a "gap", and the "5'-region" and "3'-region" may be referred to as "wings". Gaps of gapmers are deoxy regions.

As used herein, "hepatotoxic" in the context of a mouse means a plasma ALT level that is above 300 units per liter. Hepatotoxicity of an oligomeric compound or parent oligomeric compound that is administered to a mouse is determined by measuring the plasma ALT level of the mouse 24 hours to 2 weeks following at least one dose of 1-150 mg/kg of the compound.

As used herein, "hepatotoxic" in the context of a human means a plasma ALT level that is above 150 units per liter. Hepatotoxicity of an oligomeric compound or parent oligomeric compound that is administered to a human is determined by measuring the plasma ALT level of the human 24 hours to 2 weeks following at least one dose of 10-300 mg of the compound.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibiting the expression or activity" refers to a reduction or blockade of the expression or activity relative to the expression or activity in an untreated or control sample and does not necessarily indicate a total elimination of expression or activity.

As used herein, "internucleoside linkage" or "internucleoside linking group" means a group or bond that forms a covalent linkage between adjacent nucleosides in an oligonucleotide. As used herein "modified internucleoside linkage" means any internucleoside linkage other than a naturally occurring, phosphodiester internucleoside linkage. "Phosphorothioate linkage" means a modified internucleoside linkage in which one of the non-bridging oxygen atoms of a phosphodiester is replaced with a sulfur atom. Modified internucleoside linkages may or may not contain a phosphorus atom. A "neutral internucleoside linkage" is a modified internucleoside linkage that does not have a negatively charged phosphate in a buffered aqueous solution at pH=7.0. A modified internucleoside linkage may optionally comprise a conjugate group.

As used herein, "linked nucleosides" are nucleosides that are connected in a continuous sequence (i.e. no additional nucleosides are present between those that are linked).

As used herein, "maximum tolerated dose" means the highest dose of a compound that does not cause unacceptable side effects. In certain embodiments, the maximum tolerated dose is the highest dose of a modified oligonucleotide that does not cause an ALT elevation of three times the upper limit of normal as measured by a standard assay.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "modulating" refers to changing or adjusting a feature in a cell, tissue, organ or organism.

As used herein, "MOE" means O-methoxyethyl. "2'-MOE" or "2'-O-methoxyethyl" means a 2'-$OCH_2CH_2OCH_3$ group at the 2'-position of a furanosyl ring. In certain embodiments, the 2'-$OCH_2CH_2OCH_3$ group is in place of the 2'-OH group of a ribosyl ring or in place of a 2'-H in a 2'-deoxyribosyl ring. A "2'-MOE sugar moiety" is a sugar moiety with a 2'-$OCH_2CH_2OCH_3$ group in place of the 2'-OH group of a furanosyl sugar moiety. Unless otherwise indicated, a 2'-MOE sugar moiety is in the β-D ribosyl configuration.

As used herein, a "2'-OMe sugar moiety" is a sugar moiety with a 2'-$CH_3$ group in place of the 2'-OH group of a furanosyl sugar moiety. Unless otherwise indicated, a 2'-OMe sugar moiety is in the β-D ribosyl configuration and is a "stereo-standard 2'OMe sugar moiety".

As used herein, a "2'-F sugar moiety" is a sugar moiety with a 2'-F group in place of the 2'-OH group of a furanosyl sugar moiety. Unless otherwise indicated, a 2'-F sugar moiety is in the β-D ribosyl configuration and is a "stereo-standard 2'-F sugar moiety".

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a modified nucleobase is a group of atoms capable of pairing with at least one unmodified nucleobase. A universal base is a nucleobase that can pair with any one of the five unmodified nucleobases. 5-methylcytosine ($^{m}$C) is one example of a modified nucleobase.

As used herein, "nucleobase sequence" means the order of contiguous nucleobases in a nucleic acid or oligonucleotide independent of any sugar moiety or internucleoside linkage modification.

As used herein, "nucleoside" means a moiety comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. A modified nucleoside may comprise a conjugate group.

As used herein, "oligomeric compound" means a compound consisting of (1) an oligonucleotide (a single-stranded oligomeric compound) or two oligonucleotides hybridized to one another (a double-stranded oligomeric compound); and (2) optionally one or more additional features, such as a conjugate group or terminal group which may be attached to the oligonucleotide of a single-stranded oligomeric compound or to one or both oligonucleotides of a double-stranded oligomeric compound.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 12-3000 linked nucleosides, and optionally a conjugate group or terminal group. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "parent antisense agent" means an antisense agent other than an RNAi agent that is identical to an antisense agent having at least one internucleoside linkage of Formula XVII, except that the parent antisense agent has a phosphorothioate internucleoside linkage in place of each internucleoside linkage of Formula XVII in the antisense agent having at least one internucleoside linkage of Formula XVII.

As used herein, "parent RNAi agent" means an RNAi agent that is identical to an RNAi agent having at least one internucleoside linkage of Formula XVII, except that the parent RNAi agent has a phosphodiester internucleoside linkage in place of each internucleoside linkage of Formula XVII in the RNAi agent having at least one internucleoside linkage of Formula XVII.

As used herein, "pharmaceutically acceptable carrier or diluent" means any substance suitable for use in administering to an animal. Certain such carriers enable pharmaceutical compositions to be formulated as, for example, liquids, powders, or suspensions that can be aerosolized or otherwise dispersed for inhalation by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds (including oligomeric compounds that are antisense agents or portions thereof), i.e., salts that retain the desired biological activity of the compound and do not impart undesired toxicological effects thereto.

As used herein "pharmaceutical composition" means a mixture of substances suitable for administering to a subject. For example, a pharmaceutical composition may comprise an antisense compound and an aqueous solution.

As used herein, "RNAi agent" means an antisense agent that acts, at least in part, through RISC or Ago2 to modulate a target nucleic acid and/or protein encoded by a target nucleic acid. RNAi agents include, but are not limited to double-stranded siRNA, single-stranded RNA (ssRNA), and microRNA, including microRNA mimics. RNAi agents may comprise conjugate groups and/or terminal groups. In certain embodiments, an RNAi agent modulates the amount, activity, and/or splicing of a target nucleic acid. The term RNAi agent excludes antisense agents that act through RNase H.

As used herein, "RNAi oligonucleotide" means an RNAi antisense modified oligonucleotide or a RNAi sense modified oligonucleotide.

As used herein, "RNAi antisense modified oligonucleotide" means an oligonucleotide comprising a region that is complementary to a target sequence, and which includes at least one chemical modification suitable for RNAi.

As used herein, "RNAi antisense oligomeric compound" means a single-stranded oligomeric compound comprising a region that is complementary to a target sequence, and which includes at least one chemical modification suitable for RNAi.

As used herein, "RNAi sense modified oligonucleotide" means an oligonucleotide comprising a region that is complementary to a region of an RNAi antisense modified oligonucleotide, and which is capable of forming a duplex with such RNAi antisense modified oligonucleotide.

As used herein, "RNAi sense oligomeric compound" means a single-stranded oligomeric compound comprising a region that is complementary to a region of an RNAi antisense modified oligonucleotide and/or an RNAi antisense oligomeric compound, and which is capable of forming a duplex with such RNAi antisense modified oligonucleotide and/or RNAi antisense oligomeric compound.

A duplex formed by an RNAi antisense modified oligonucleotide and/or an RNAi antisense oligomeric compound with a RNAi sense modified oligonucleotide and/or an RNAi sense oligomeric compound is referred to as a double-stranded RNAi compound (dsRNAi) or a short interfering RNA (siRNA).

As used herein, "RNase H agent" means an antisense agent that acts, at least in part, through RNase H to modulate a target nucleic acid and/or protein encoded by a target nucleic acid. In certain embodiments, RNase H agents are single-stranded. In certain embodiments, RNase H agents are double-stranded. RNase H compounds may comprise conjugate groups and/or terminal groups. In certain embodiments, an RNase H agent modulates the amount or activity of a target nucleic acid. The term RNase H agent excludes antisense agents that act principally through RISC/Ago2.

As used herein, "RNase H antisense modified oligonucleotide" means an oligonucleotide comprising a region that is complementary to a target sequence, and which includes at least one chemical modification suitable for RNase H-mediated nucleic acid reduction.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case the compound would no longer be single-stranded.

As used herein, “stabilized phosphate group” refers to a 5'-chemical moiety that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phophate group includes but is not limited to resistance to removal by phosphatases. Stabilized phosphate groups include, but are not limited to, 5'-vinyl phosphonates and 5'-cyclopropyl phosphonate.

As used herein, “stereo-standard nucleoside” means a nucleoside comprising a non-bicyclic furanosyl sugar moiety having the configuration of naturally occurring DNA and RNA as shown below. A “stereo-standard DNA nucleoside” is a nucleoside comprising a β-D-2'-deoxyribosyl sugar moiety. A “stereo-standard RNA nucleoside” is a nucleoside comprising a β-D-ribosyl sugar moiety. A “substituted stereo-standard nucleoside” is a stereo-standard nucleoside other than a stereo-standard DNA or stereo-standard RNA nucleoside. In certain embodiments, $R_1$ is a 2'-substituent and $R_2$-$R_5$ are each H. In certain embodiments, the 2'-substituent is selected from OMe, F, $OCH_2CH_2OCH_3$, O-alkyl, SMe, or NMA. In certain embodiments, $R_1R_4$ are H and $R_5$ is a 5'-substituent selected from methyl, allyl, or ethyl. In certain embodiments, the heterocyclic base moiety Bx is selected from uracil, thymine, cytosine, 5-methyl cytosine, adenine or guanine. In certain embodiments, the heterocyclic base moiety Bx is other than uracil, thymine, cytosine, 5-methyl cytosine, adenine or guanine.

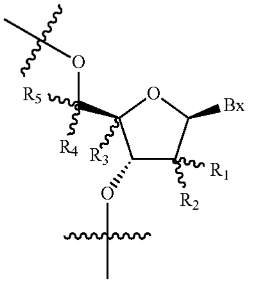

Stereo-standard nucleoside

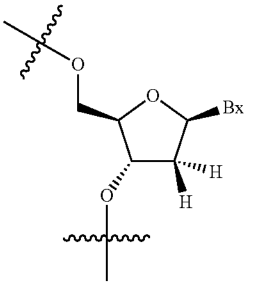

Stereo-standard DNA nucleoside

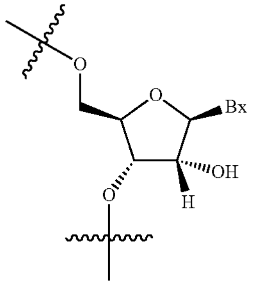

Stereo-standard RNA nucleoside

As used herein, “stereo-non-standard nucleoside” means a nucleoside comprising a non-bicyclic furanosyl sugar moiety having a configuration other than that of a stereo-standard sugar moiety. In certain embodiments, a “stereo-non-standard nucleoside” is represented by formulas I-VII below. In certain embodiments, $J_1$-$J_{14}$ are independently selected from H, OH, F, $OCH_3$, $OCH_2CH_2OCH_3$, O—$C_1$-$C_6$ alkoxy, and $SCH_3$. A “stereo-non-standard RNA nucleoside” has one of formulas I-VII below, wherein each of $J_1$, $J_3$, $J_5$, $J_7$, $J_9$, $J_{11}$, and $J_{13}$ is H, and each of $J_2$, $J_4$, $J_6$, $J_8$, $J_{10}$, $J_{12}$, and $J_{14}$ is OH. A “stereo-non-standard DNA nucleoside” has one of formulas I-VII below, wherein each J is H. A “2'-substituted stereo-non-standard nucleoside” has one of formulas I-VII below, wherein either $J_1$, $J_3$, $J_5$, $J_7$, $J_9$, $J_{11}$, and $J_{13}$ is other than H and/or or $J_2$, $J_4$, $J_6$, $J_8$, $J_{10}$, $J_{12}$, and $J_{14}$ is other than H or OH. In certain embodiments, the heterocyclic base moiety Bx is selected from uracil, thymine, cytosine, 5-methyl cytosine, adenine or guanine. In certain embodiments, the heterocyclic base moiety Bx is other than uracil, thymine, cytosine, 5-methyl cytosine, adenine or guanine.

I

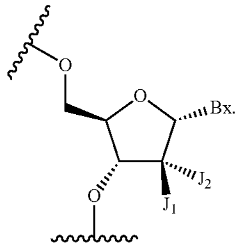

II

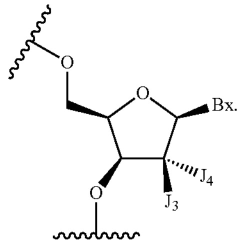

III

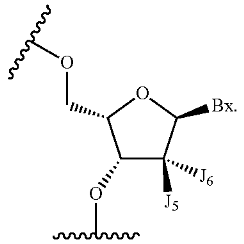

IV

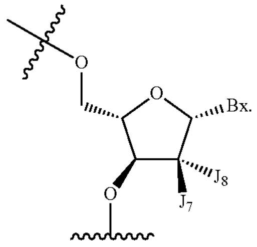

V

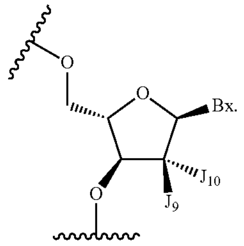

-continued

VI

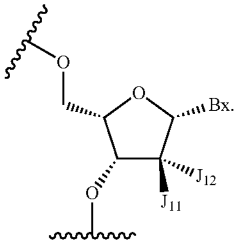

VII

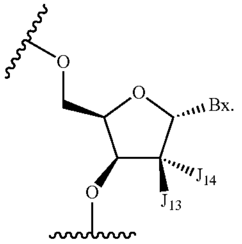

As used herein, "stereo-standard sugar moiety" means the sugar moiety of a stereo-standard nucleoside.

As used herein, "stereo-non-standard sugar moiety" means the sugar moiety of a stereo-non-standard nucleoside.

As used herein, "substituted stereo-non-standard nucleoside" means a stereo-non-standard nucleoside comprising a substituent other than the substituent corresponding to natural RNA or DNA. Substituted stereo-non-standard nucleosides include but are not limited to nucleosides of Formula I-VII wherein the J groups are other than: (1) both H or (2) one H and the other OH.

As used herein, "subject" means a human or non-human animal selected for treatment or therapy.

As used herein, "sugar moiety" means an unmodified sugar moiety or a modified sugar moiety. As used herein, "unmodified sugar moiety" means a β-D-ribosyl moiety, as found in naturally occurring RNA, or a β-D-2'-deoxyribosyl sugar moiety as found in naturally occurring DNA. As used herein, "modified sugar moiety" or "modified sugar" means a sugar surrogate or a furanosyl sugar moiety other than a β-D-ribosyl or a β-D-2'-deoxyribosyl. Modified furanosyl sugar moieties may be modified or substituted at a certain position(s) of the sugar moiety, or unsubstituted, and they may or may not be stereo-non-standard sugar moieties. Modified furanosyl sugar moieties include bicyclic sugars and non-bicyclic sugars. As used herein, "sugar surrogate" means a modified sugar moiety that does not comprise a furanosyl or tetrahydrofuranyl ring (is not a "furanosyl sugar moiety") and that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid," "target RNA," "target RNA transcript" and "nucleic acid target" means a nucleic acid that an oligomeric compound, such as an antisense compound, is designed to affect. In certain embodiments, an oligomeric compound comprises an oligonucleotide having a nucleobase sequence that is complementary to more than one RNA, only one of which is the target RNA of the oligomeric compound. In certain embodiments, the target RNA is an RNA present in the species to which an oligomeric compound is administered.

As used herein, "therapeutic index" means a comparison of the amount of a compound that causes a therapeutic effect to the amount that causes toxicity. Compounds having a high therapeutic index have strong efficacy and low toxicity. In certain embodiments, increasing the therapeutic index of a compound increases the amount of the compound that can be safely administered.

As used herein, "treat" refers to administering a compound or pharmaceutical composition to an animal in order to effect an alteration or improvement of a disease, disorder, or condition in the animal.

As used herein, "translation suppression element," means any sequence and/or secondary structure in the 5'-UTR of a target transcript that reduces, inhibits, and/or suppresses translation of the target transcript. In certain embodiments, a translation suppression element comprises a uORF. In certain embodiments, a translation suppression element does not comprise a uORF. In certain embodiments, a translation suppression element comprises one or more stem-loops. In certain embodiments, a translation suppression element comprises greater than 60%, greater than 70%, or greater than 80% GC content. In certain embodiments, the translation suppression element is a uORF. In certain embodiments, the translation suppression element is a stem-loop.

CERTAIN EMBODIMENTS

The present disclosure provides the following non-limiting embodiments:

Embodiment 1. An oligomeric compound comprising a modified oligonucleotide consisting of linked nucleosides linked through internucleoside linking groups, wherein at least one of the internucleoside linking groups has Formula VIII:

VIII

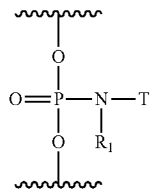

wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, an amine, a substituted amine, $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

Embodiment 2. An oligomeric compound comprising a modified oligonucleotide consisting of linked nucleosides linked through internucleoside linking groups, wherein at least one of the internucleoside linking groups has Formula VIII:

VIII

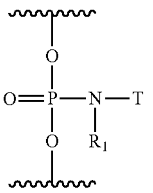

wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, a $C_1$-$C_6$ alkyl, and a substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl;

provided that if $R_1$ is H, then T is not:

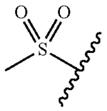

or

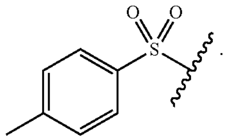

.

Embodiment 3. The oligomeric compound of embodiment 1 or 2, wherein $R_1$ is H.

Embodiment 4. The oligomeric compound of embodiment 1 or 2, wherein $R_1$ is a $C_1$-$C_6$ alkyl.

Embodiment 5. The oligomeric compound of embodiment 4, wherein $R_1$ is methyl.

Embodiment 6. The oligomeric compound of embodiment 1 or 2, wherein $R_1$ is a substituted $C_1$-$C_6$ alkyl;

Embodiment 7. The oligomeric compound of any of embodiments 1-6, wherein T is $SO_2R_2$.

Embodiment 8. The oligomeric compound of embodiment 7, wherein $R_2$ is an aryl.

Embodiment 9. The oligomeric compound of embodiment 7, wherein $R_2$ is a substituted aryl.

Embodiment 10. The oligomeric compound of embodiment 7, wherein $R_2$ is a heterocycle.

Embodiment 11. The oligomeric compound of embodiment 7, wherein $R_2$ is a substituted heterocycle.

Embodiment 12. The oligomeric compound of embodiment 7, wherein $R_2$ is an aromatic heterocycle.

Embodiment 13. The oligomeric compound of embodiment 7, wherein $R_2$ is a substituted aromatic heterocycle.

Embodiment 14. The oligomeric compound of embodiment 7, wherein $R_2$ is a diazole.

Embodiment 15. The oligomeric compound of embodiment 7, wherein $R_2$ is a substituted diazole.

Embodiment 16. The oligomeric compound of embodiment 7, wherein $R_2$ is an amine.

Embodiment 17. The oligomeric compound of embodiment 7, wherein $R_2$ is a substituted amine.

Embodiment 18. The oligomeric compound of embodiment 7, wherein $R_2$ is a $C_1$-$C_6$ alkoxy.

Embodiment 19. The oligomeric compound of embodiment 7, wherein $R_2$ is $C_1$-$C_6$ alkyl.

Embodiment 20. The oligomeric compound of embodiment 7, wherein $R_2$ is substituted $C_1$-$C_6$ alkyl.

Embodiment 21. The oligomeric compound of embodiment 7, wherein T is:

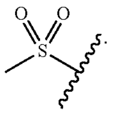 [SMILES: *S(C)(=O)=O]

Embodiment 22. The oligomeric compound of embodiment 7, wherein T is:

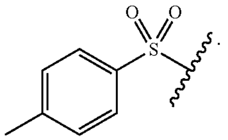 [SMILES: *S(=O)(=O)c1ccc(C)cc1]

Embodiment 23. The oligomeric compound of embodiment 7, wherein T is:

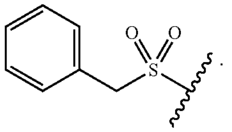

Embodiment 24. The oligomeric compound of embodiment 7, wherein T is:

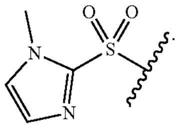 [SMILES: *S(=O)(=O)c1nccn1C]

Embodiment 25. The oligomeric compound of embodiment 7, wherein T is:

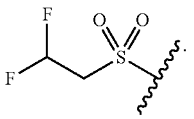 [SMILES: *S(=O)(=O)CC(F)F]

Embodiment 26. The oligomeric compound of embodiment 7, wherein T is:

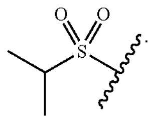 [SMILES: *S(=O)(=O)C(C)C]

Embodiment 27. The oligomeric compound of embodiment 7, wherein T is:

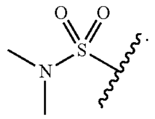 [SMILES: *S(=O)(=O)N(C)C]

Embodiment 28. The oligomeric compound of embodiment 7, wherein T is:

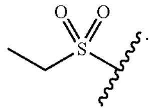 [SMILES: *S(=O)(=O)CC]

Embodiment 29. The oligomeric compound of embodiment 7, wherein T is:

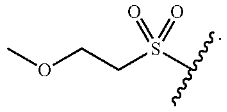 [SMILES: *S(=O)(=O)CCOC]

Embodiment 30. The oligomeric compound of any of embodiments 1-6, wherein T is $C(=O)R_3$.

Embodiment 31. The oligomeric compound of embodiment 30, wherein $R_3$ is an aryl.

Embodiment 32. The oligomeric compound of embodiment 30, wherein $R_3$ is a substituted aryl.

Embodiment 33. The oligomeric compound of embodiment 30, wherein $R_3$ is $CH_3$.

Embodiment 34. The oligomeric compound of embodiment 30, wherein $R_3$ is $N(CH_3)_2$.

Embodiment 35. The oligomeric compound of embodiment 30, wherein $R_3$ is $OCH_3$.

Embodiment 36. The oligomeric compound of embodiment 30, wherein T is:

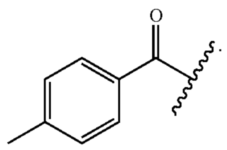 [SMILES: *C(=O)c1ccc(C)cc1]

Embodiment 37. The oligomeric compound of embodiment 30, wherein T is:

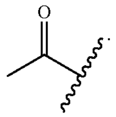

Embodiment 38. The oligomeric compound of embodiment 30, wherein T is:

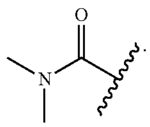 [SMILES: *C(=O)N(C)C]

Embodiment 39. The oligomeric compound of embodiment 30, wherein T is:

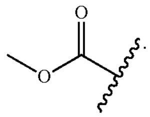 [SMILES: *C(=O)OC]

Embodiment 40. The oligomeric compound of any of embodiments 1-6, wherein T is $P(=O)R_4R_5$ Embodiment 41. The oligomeric compound of embodiment 40, wherein $R_4$ is $OCH_3$.

Embodiment 42. The oligomeric compound of embodiment 40, wherein $R_4$ is OH

Embodiment 43. The oligomeric compound of embodiment 40, wherein $R_4$ is $C_1$-$C_6$ alkyl.

Embodiment 44. The oligomeric compound of embodiment 40, wherein $R_4$ is substituted $C_1$-$C_6$ alkyl.

Embodiment 45. The oligomeric compound of any of embodiments 40-42, wherein $R_5$ is $OCH_3$.

Embodiment 46. The oligomeric compound of any of embodiments 40-42, wherein $R_5$ is OH.

Embodiment 47. The oligomeric compound of any of embodiments 40-42, wherein $R_5$ is $C_1$-$C_6$ alkyl.

Embodiment 48. The oligomeric compound of any of embodiments 40-42, wherein $R_5$ is substituted $C_1$-$C_6$ alkyl.

Embodiment 49. The oligomeric compound of embodiment 40, wherein T is:

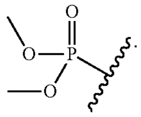

Embodiment 50. The oligomeric compound of embodiment 40, wherein T is:

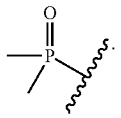

Embodiment 51. The oligomeric compound of any of embodiments 1-50, wherein at least one internucleoside linking group of the modified oligonucleotide is not a linking group of Formula VIII.

Embodiment 52. The oligomeric compound of any of embodiments 1-50, wherein exactly one internucleoside linking group of the modified oligonucleotide is an internucleoside linking group of any of embodiments 1-50.

Embodiment 53. The oligomeric compound of any of embodiments 1-50, wherein exactly two internucleoside linking groups of the modified oligonucleotide are internucleoside linking groups of any of embodiments 1-50.

Embodiment 54. The oligomeric compound of any of embodiments 1-50, wherein exactly three internucleoside linking groups of the modified oligonucleotide are internucleoside linking groups of any of embodiments 1-50.

Embodiment 55. The oligomeric compound of any of embodiments 1-50, wherein exactly four internucleoside linking groups of the modified oligonucleotide are internucleoside linking groups of any of embodiments 1-50.

Embodiment 56. The oligomeric compound of any of embodiments 1-50, wherein exactly five internucleoside linking groups of the modified oligonucleotide are internucleoside linking groups of any of embodiments 1-50.

Embodiment 57. The oligomeric compound of any of embodiments 1-50, wherein at least six internucleoside linking groups of the modified oligonucleotide are internucleoside linking groups of any of embodiments 1-50.

Embodiment 58. The oligomeric compound of any of embodiment 1-51 or 53-57 having at least two linking groups of any of embodiments 1-50, wherein at least two of the linking groups of any of embodiments 1-50 are the same as one another.

Embodiment 59. The oligomeric compound of any of embodiments 1-58, wherein each internucleoside linking group of the modified oligonucleotide that is not an internucleoside linking group of any of embodiments 1-50 is either a phosphodiester internucleoside linking group or a phosphorothioate internucleoside linking group.

Embodiment 60. The oligomeric compound of any of embodiments 1-58, wherein each internucleoside linking group of the modified oligonucleotide is an internucleoside linking group of any of embodiments 1-50.

Embodiment 61. The oligomeric compound of any of embodiments 1-60, wherein at least one nucleoside of the modified oligonucleotide is a modified nucleoside.

Embodiment 62. The oligomeric compound of embodiment 61, wherein at least one nucleoside of the modified oligonucleotide is a modified nucleoside selected from a bicyclic nucleoside and a non-bicyclic substituted nucleoside.

Embodiment 63. The oligomeric compound of any of embodiments 1-62, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 64. The oligomeric compound of any of embodiments 1-62, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 65. The oligomeric compound of any of embodiments 1-62, wherein at least one nucleoside of the modified oligonucleotide is selected from: a 2'-OMe nucleoside, a 2'-F nucleoside, and an RNA nucleoside.

Embodiment 66. The oligomeric compound of any of embodiments 1-62, wherein at least one nucleoside of the modified oligonucleotide is a 2'-OMe nucleoside, and at least one nucleoside of the modified oligonucleotide is an RNA nucleoside.

Embodiment 67. The oligomeric compound of any of embodiments 61-66, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 68. The oligomeric compound of embodiment 67, wherein A and B are selected from 2'-F substituted nucleosides, 2'-OMe substituted nucleosides, and stereo-standard RNA nucleosides.

Embodiment 69. The oligomeric compound of any of embodiments 1-68, wherein the 5'-end of the modified oligonucleotide comprises a stabilized phosphate group.

Embodiment 70. The oligomeric compound of any of embodiments 1-69, wherein the modified oligonucleotide consists of 12-30 linked nucleosides.

Embodiment 71. The oligomeric compound of any of embodiments 1-69, wherein the modified oligonucleotide consists of 16-24 linked nucleosides.

Embodiment 72. The oligomeric compound of any of embodiments 1-69, wherein the modified oligonucleotide consists of 18-22 linked nucleosides.

Embodiment 73. The oligomeric compound of any of embodiments 1-69, wherein the modified oligonucleotide consists of 16 linked nucleosides.

Embodiment 74. The oligomeric compound of any of embodiments 1-69, wherein the modified oligonucleotide consists of 17 linked nucleosides.

Embodiment 75. The oligomeric compound of any of embodiments 1-69, wherein the modified oligonucleotide consists of 18 linked nucleosides.

Embodiment 76. The oligomeric compound of any of embodiments 1-69, wherein the modified oligonucleotide consists of 19 linked nucleosides.

Embodiment 77. The oligomeric compound of any of embodiments 1-69, wherein the modified oligonucleotide consists of 20 linked nucleosides.

Embodiment 78. The oligomeric compound of any of embodiments 1-69, wherein the modified oligonucleotide consists of 21 linked nucleosides.

Embodiment 79. The oligomeric compound of any of embodiments 1-69, wherein the modified oligonucleotide consists of 22 linked nucleosides.

Embodiment 80. The oligomeric compound of any of embodiments 1-69, wherein the modified oligonucleotide consists of 23 linked nucleosides.

Embodiment 81. The oligomeric compound of any of embodiments 1-80, wherein the oligomeric compound is an RNAi compound.

Embodiment 82. The oligomeric compound of embodiment 81, wherein the RNAi compound is a single-stranded RNAi compound comprising an RNAi antisense modified oligonucleotide, wherein the RNAi antisense modified compound is a modified oligonucleotide of any of embodiments 1-78.

Embodiment 83. The oligomeric compound of embodiment 81, wherein the RNAi compound is a double-stranded RNAi compound comprising an RNAi antisense modified oligonucleotide and an RNAi sense modified oligonucleotide, wherein the RNAi antisense modified oligonucleotide and/or the RNAi sense modified oligonucleotide is a modified oligonucleotide of any of embodiments 1-78.

Embodiment 84. The oligomeric compound of embodiment 82 or 83, wherein at least one internucleoside linking group of the RNAi antisense modified oligonucleotide is an internucleoside linking group of any of embodiments 1-50.

Embodiment 85. The oligomeric compound of embodiment 82 or 83, wherein at least two internucleoside linking groups of the RNAi antisense modified oligonucleotide are independently selected internucleoside linking groups of any of embodiments 1-50.

Embodiment 86. The oligomeric compound of any of embodiments 82-85, wherein at least one of the five 3'-most internucleoside linking groups of the RNAi antisense modified oligonucleotide is an internucleoside linking group of any of embodiments 1-50.

Embodiment 87. The oligomeric compound of any of embodiments 82-86, wherein at least two of the five 3'-most internucleoside linking groups of RNAi antisense modified oligonucleotide is an internucleoside linking group of any of embodiments 1-50.

Embodiment 88. The oligomeric compound of any of embodiments 82-87, wherein at least one internucleoside linking group within the seed region of the RNAi antisense modified oligonucleotide is an internucleoside linking group of any of embodiments 1-50.

Embodiment 89. The oligomeric compound of embodiment 83-88, wherein at least one internucleoside linking group of the RNAi sense modified oligonucleotide is an internucleoside linking group of any of embodiments 1-50.

Embodiment 90. The oligomeric compound of embodiment 89, wherein at least one of the first 5 internucleoside linking groups from the 5'-end of the RNAi sense modified oligonucleotide is an internucleoside linking group of any of embodiments 1-50.

Embodiment 91. The oligomeric compound of any of embodiments 89-90, wherein at least one of the five 3'-most 1 internucleoside linking groups of the RNAi sense modified oligonucleotide is an internucleoside linking group of any of embodiments 1-50.

Embodiment 92. The oligomeric compound of any of embodiments 89-91, wherein at least one of the first 5 internucleoside linking groups from the 5'-end of the RNAi sense modified oligonucleotide and at least one of the five 3'-most linking groups of the RNAi sense modified oligonucleotide is an internucleoside linking group of any of embodiments 1-50.

Embodiment 93. The oligomeric compound of any of embodiments 1-92, wherein at least one nucleoside of the modified oligonucleotide is a stereo-non-standard nucleoside.

Embodiment 94. The oligomeric compound of embodiment 93, wherein the internucleoside linking group linking at least one stereo-non-standard nucleoside to an adjacent nucleoside is an internucleoside linking group of any of embodiments 1-50.

Embodiment 95. The oligomeric compound of embodiment 93 or 94, wherein at least two nucleosides of the modified oligonucleotide are stereo-non-standard nucleosides.

Embodiment 96. The oligomeric compound of embodiment 95, wherein at least two stereo-non-standard nucleosides of the modified oligonucleotide are adjacent to one another.

Embodiment 97. The oligomeric compound of embodiment 96, wherein at least two stereo-non-standard nucleosides of the modified oligonucleotide are linked to one another with an internucleoside linking group of any of embodiments 1-50.

Embodiment 98. The oligomeric compound of any of embodiments 95-97, wherein at least one stereo-non-standard nucleoside of the modified oligonucleotide is a stereo-non-standard DNA nucleoside.

Embodiment 99. The oligomeric compound of any of embodiments 95-97, wherein at least one stereo-non-standard nucleoside of the modified oligonucleotide is a substituted stereo-non-standard nucleoside or a stereo-non-standard RNA nucleoside.

Embodiment 100. The oligomeric compound of embodiment 99, wherein the 2'-substituent of the at least one substituted stereo-non-standard nucleoside of the modified oligonucleotide is selected from: 2'-MOE, 2'-OMe, 2'-F, or 2'-OH.

Embodiment 101. The oligomeric compound of any of embodiments 1-100, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 102. The oligomeric compound of embodiment 101, wherein at least 4 contiguous nucleosides of the deoxy region are stereo-standard DNA nucleosides.

Embodiment 103. The oligomeric compound of embodiment 101, wherein at least 5 contiguous nucleosides of the deoxy region are stereo-standard DNA nucleosides.

Embodiment 104. The oligomeric compound of embodiment 101, wherein at least 6 contiguous nucleosides of the deoxy region are stereo-standard DNA nucleosides.

Embodiment 105. The oligomeric compound of embodiment 101, wherein at least 7 contiguous nucleosides of the deoxy region are stereo-standard DNA nucleosides.

Embodiment 106. The oligomeric compound of embodiment 101, wherein at least 8 contiguous nucleosides of the deoxy region are stereo-standard DNA nucleosides.

Embodiment 107. The oligomeric compound of any of embodiments 101-106, wherein the deoxy region consists of 8-10 linked nucleosides.

Embodiment 108. The oligomeric compound of any of embodiments 101-106, wherein the deoxy region consists of 9 linked nucleosides.

Embodiment 109. The oligomeric compound of any of embodiments 101-106, wherein the deoxy region consists of 10 linked nucleosides.

Embodiment 110. The oligomeric compound of any of embodiments 101-106, wherein the deoxy region consists of 11 linked nucleosides.

Embodiment 111. The oligomeric compound of any of embodiments 101-110 wherein at least 6 nucleosides of the deoxy region are stereo-standard DNA nucleosides.

Embodiment 112. The oligomeric compound of any of embodiments 101-110 wherein at least 7 nucleosides of the deoxy region are stereo-standard DNA nucleosides.

Embodiment 113. The oligomeric compound of any of embodiments 101-110 wherein at least 8 nucleosides of the deoxy region are stereo-standard DNA nucleosides.

Embodiment 114. The oligomeric compound of any of embodiments 101-110 wherein at least 9 nucleosides of the deoxy region are stereo-standard DNA nucleosides.

Embodiment 115. The oligomeric compound of any of embodiments 101-114 wherein two nucleosides of the deoxy region are modified nucleosides.

Embodiment 116. The oligomeric compound of any of embodiments 101-114 wherein one nucleoside of the deoxy region is a modified nucleoside.

Embodiment 117. The oligomeric compound of any of embodiments 101-116 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 118. The oligomeric compound of any of embodiments 101-117 wherein at least one modified nucleoside of the deoxy region is stereo-non-standard nucleoside.

Embodiment 119. The oligomeric compound of embodiment 118 wherein the at least one is stereo-non-standard isomeric nucleoside of the deoxy region is a stereo-non-standard DNA nucleoside.

Embodiment 120. The oligomeric compound of embodiment 119 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 121. The oligomeric compound of embodiment 120 wherein the stereo-non-standard DNA nucleoside is selected from a stereo-non-standard DNA nucleoside having: Formula V and Formula II.

Embodiment 122. The oligomeric compound of any of embodiments 118-121 wherein at least one stereo-non-standard nucleoside of the deoxy region is a substituted stereo-non-standard nucleoside.

Embodiment 123. The oligomeric compound of embodiment 122 wherein at least one substituted stereo-non-standard nucleoside has a 2'-substituent selected from: 2'-MOE, 2'-OMe, 2'-F, or 2'-OH.

Embodiment 124. The oligomeric compound of any of embodiments 101-123, wherein the $2^{nd}$ nucleoside from the 5'-end of the deoxy region is a modified nucleoside.

Embodiment 125. The oligomeric compound of any of embodiments 101-124, wherein the $3^{rd}$ nucleoside from the 5'-end of the deoxy region is a modified nucleoside.

Embodiment 126. The oligomeric compound of any of embodiments 101-125, wherein the $4^{th}$ nucleoside from the 5'-end of the deoxy region is a modified nucleoside.

Embodiment 127. The oligomeric compound of any of embodiments 101-126, wherein each nucleoside of the deoxy region is a stereo-standard DNA nucleoside.

Embodiment 128. The oligomeric compound of any of embodiments 101-127 wherein at least one internucleoside linking group within the deoxy region is an internucleoside linking group of any of embodiments 1-50.

Embodiment 129. The oligomeric compound of any of embodiments 101-128, wherein the internucleoside linking group linking the $1^{st}$ and $2^{nd}$ a nucleosides of the deoxy region as counted from the 5'-end of the deoxy region is an internucleoside linking group of any of embodiments 1-50.

Embodiment 130. The oligomeric compound of any of embodiments 101-129, wherein the internucleoside linking group linking the $2^{nd}$ and $3^{rd}$ nucleosides of the deoxy region as counted from the 5'-end of the deoxy region is an internucleoside linking group of any of embodiments 1-50.

Embodiment 131. The oligomeric compound of any of embodiments 101-130, wherein the internucleoside linking group linking the $3^{rd}$ and $4^{th}$ nucleosides of the deoxy region as counted from the 5'-end of the deoxy region is an internucleoside linking group of any of embodiments 1-50.

Embodiment 132. The oligomeric compound of any of embodiments 101-131, wherein the internucleoside linking group linking the $4^{th}$ and $5^{th}$ nucleosides of the deoxy region as counted from the 5'-end of the deoxy region is an internucleoside linking group of any of embodiments 1-50.

Embodiment 133. The oligomeric compound of any of embodiments 101-132 wherein one internucleoside linking group in the deoxy region is a linking group of any of embodiments 1-50 and the other internucleoside linking groups of the deoxy region are each phosphodiester or phosphorothioate internucleoside linking groups.

Embodiment 134. The oligomeric compound of any of embodiments 101-133 wherein two internucleoside linking groups in the deoxy region are linking groups of any of embodiments 1-50 and the other internucleoside linking groups of the deoxy region are each phosphodiester or phosphorothioate internucleoside linking groups.

Embodiment 135. The oligomeric compound of any of embodiments 101-134 wherein three internucleoside linking groups in the deoxy region are linking groups of any of embodiments 1-50 and the other internucleoside linking groups of the deoxy region are each phosphodiester or phosphorothioate internucleoside linking groups.

Embodiment 136. The oligomeric compound of any of embodiments 101-135 wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region is a modified nucleoside; and the 5'-most nucleoside of the 3'-region is a modified nucleoside.

Embodiment 137. The oligomeric compound of embodiment 136, wherein at least one 5'-region nucleoside is a stereo-standard DNA nucleoside.

Embodiment 138. The oligomeric compound of embodiment 136, wherein each 5'-region nucleoside is a modified nucleoside.

Embodiment 139. The oligomeric compound of any of embodiments 136, wherein at least one 5'-region nucleoside is a 2'-substituted nucleoside.

Embodiment 140. The oligomeric compound of any of embodiments 136, or 138-139 wherein each 5'-region nucleoside is a 2'-substituted nucleoside.

Embodiment 141. The oligomeric compound of any of embodiments 139-140, wherein the 2'-substitutent is selected from among 2'-F, 2'-$OCH_3$, and 2'-MOE.

Embodiment 142. The oligomeric compound of any of embodiments 136-139 or 141, wherein at least one 5'-region nucleoside is a bicyclic nucleoside.

Embodiment 143. The oligomeric compound of embodiment 142, wherein each 5'-region nucleoside is a bicyclic nucleoside.

Embodiment 144. The oligomeric compound of any of embodiments 142-143, wherein the bicyclic 5'-region nucleoside is selected from among a β-D-LNA nucleoside, an α-L-LNA nucleoside, an ENA nucleoside, and a cEt nucleoside.

Embodiment 145. The oligomeric compound of any of embodiments embodiment 136-144, wherein at least one 3'-region nucleoside is a stereo-standard DNA nucleoside.

Embodiment 146. The oligomeric compound of any of embodiments 136-144 wherein each 3'-region nucleoside is a modified nucleoside.

Embodiment 147. The oligomeric compound of any of embodiments 136-146, wherein at least one 3'-region nucleoside is a 2'-substituted nucleoside.

Embodiment 148. The oligomeric compound of any of embodiments 136-144 or 146-147, wherein each 3'-region nucleoside is a 2'-substituted nucleoside.

Embodiment 149. The oligomeric compound of embodiment 147 or 148, wherein the 2'-substituent is selected from among 2'-F, 2'-$OCH_3$, and 2'-MOE.

Embodiment 150. The oligomeric compound of any of embodiments 136-147 or 149, wherein at least one 3'-region nucleoside is a bicyclic nucleoside.

Embodiment 151. The oligomeric compound of embodiment 150, wherein each 3'-region nucleoside is a bicyclic nucleoside.

Embodiment 152. The oligomeric compound of any of embodiments 150-151 wherein the bicyclic 3'-region nucleoside is selected from among a β-D-LNA nucleoside, an α-L-LNA nucleoside, an ENA nucleoside, and a cEt nucleoside.

Embodiment 153. The oligomeric compound of any of embodiments 101-152 wherein the modified oligonucleotide is a gapmer.

Embodiment 154. The oligomeric compound of any of embodiments 1-80 wherein each nucleoside of the modified oligonucleotide is a modified nucleoside and each modified nucleoside of the modified oligonucleotide comprises the same modification.

Embodiment 155. The oligomeric compound of any of embodiments 1-153, wherein the nucleobase sequence of the modified oligonucleotide is complementary to a target nucleic acid.

Embodiment 156. The oligomeric compound of embodiment 155, wherein the nucleobase sequence of the modified oligonucleotide is at least 80% complementary to the target nucleic acid.

Embodiment 157. The oligomeric compound of embodiment 155, wherein the nucleobase sequence of the modified oligonucleotide is at least 85% complementary to the target nucleic acid.

Embodiment 158. The oligomeric compound of embodiment 155, wherein the nucleobase sequence of the modified oligonucleotide is at least 90% complementary to the target nucleic acid.

Embodiment 159. The oligomeric compound of embodiment 155, wherein the nucleobase sequence of the modified oligonucleotide is at least 95% complementary to the target nucleic acid.

Embodiment 160. The oligomeric compound of embodiment 155, wherein the nucleobase sequence of the modified oligonucleotide is 100% complementary to the target nucleic acid.

Embodiment 161. The oligomeric compound of any of embodiments 155-160, wherein the target nucleic acid is a target RNA.

Embodiment 162. The oligomeric compound of embodiment 161, wherein the target RNA is selected from: an mRNA, a pre-mRNA, a microRNA, and a non-coding RNA.

Embodiment 163. The oligomeric compound of embodiment 161, wherein the target RNA is not a microRNA.

Embodiment 164. The oligomeric compound of any of embodiments 1-162, wherein the modified oligonucleotide is not complementary to miR-21.

Embodiment 165. The oligomeric compound of any of embodiments 1-163, comprising a conjugate group.

Embodiment 166. The oligomeric compound of embodiment 164, wherein the conjugate group comprises at least one GalNAc.

Embodiment 167. The oligomeric compound of embodiment 164 or 165, wherein the conjugate group comprises 1-5 linker-nucleosides.

Embodiment 168. The oligomeric compound of any of embodiments 1-80, wherein the oligomeric compound is a CRISPR compound.

Embodiment 169. The oligomeric compound of embodiment 168, wherein the CRISPR compound consists of 20-50 linked nucleosides.

Embodiment 170. The oligomeric compound of embodiment 168, wherein the CRISPR compound consists of 29-32 linked nucleosides.

Embodiment 171. A pharmaceutical composition comprising the CRISPR compound of embodiments 169-170 and a pharmaceutically acceptable carrier or diluent.

Embodiment 172. A method comprising contacting a cell with the CRISPR compound or composition of any of embodiments 169-170.

Embodiment 173. The method of embodiment 172, comprising contacting the cell with a plasmid that encodes Cas9 or Cpf1.

Embodiment 174. The method of embodiment 172-173, wherein the plasmid encodes a tracrRNA.

Embodiment 175. The method of embodiment 174, comprising contacting the cell with an mRNA that encodes Cas9 or Cpf1.

Embodiment 176. The method of any of embodiments 172-175, comprising contacting the cell with a plasmid that encodes a tracrRNA.

Embodiment 177. The method of any of embodiments 172-176 wherein a target gene is edited.

Embodiment 178. The oligomeric compound of any of embodiments 1-80, wherein the oligomeric compound is an artificial mRNA compound.

Embodiment 179. The artificial mRNA compound of embodiment 178, wherein the artificial mRNA oligonucleotide consists of 17-3000 linked nucleosides.

Embodiment 180. The artificial mRNA compound of embodiment 178 or 179, wherein the artificial mRNA oligonucleotide encodes a protein.

Embodiment 181. A pharmaceutical composition comprising the artificial mRNA compound of any of embodiments 178-180 and a pharmaceutically acceptable carrier or diluent.

Embodiment 182. A method comprising contacting a cell with the artificial mRNA compound or composition of any of embodiments 178-181.

Embodiment 183. A pharmaceutical composition comprising the oligomeric compound of any of embodiments 1-182 and a pharmaceutically acceptable carrier or diluent.

Embodiment 184. A method comprising contacting a cell with the oligomeric compound or pharmaceutical composition of any of embodiments 1-167 or 183.

Embodiment 185. A method of modulating the amount or activity of a target nucleic acid in a cell, comprising contacting the cell with the oligomeric compound or pharmaceutical composition of any of embodiments 1-167 or 183, and thereby modulating the amount or activity of the target nucleic acid.

Embodiment 186. A method of modulating the amount or activity of a target nucleic acid in a cell, comprising contacting the cell with the oligomeric compound or pharmaceutical composition of any of embodiments 1-167 or 183.

Embodiment 187. The method of embodiment 186, wherein the amount or activity of a target nucleic acid is reduced.

Embodiment 188. Use of the oligomeric compound or composition of any of embodiments 1-171, 178-181 or 183 for treatment of a disease or condition.

Embodiment 189. Use of the oligomeric compound or composition of any of embodiments 1-171, 178-181 or 183 for a preparation of a medicament for treatment of a disease or condition.

Embodiment 190. An oligomeric compound comprising a modified oligonucleotide consisting of 12-23 linked nucleosides, wherein the modified oligonucleotide comprises a 5'-region, a central region, and a 3'-region wherein:

the 5'-region consists of 1-5 linked nucleosides; wherein at least one 5'-region nucleoside is modified;

the 3'-region consists of 1-5 linked nucleosides; wherein at least one 3'-region nucleoside is modified; and the central region consists of 7-11 linked nucleosides, and has the formula:

$$(N_{d1})_{L1}(N_{d2})_{L2}(N_{d3})_{L3}(N_{d4})_{L4}[(N^{d5})_{L5}]_q;$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $N_{d2}$, $N_{d3}$, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, and $L_4$ are internucleoside linkages having formula VIII:

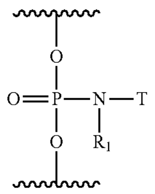

VIII wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, an amine, a substituted amine, $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

Embodiment 191. The oligomeric compound of embodiment 190, wherein one of $N_{d1}$, $N_{d2}$, $N_{d3}$, or $N_{d4}$ is a 2'-substituted nucleoside.

Embodiment 192. The oligomeric compound of embodiment 191, wherein the 2'-substituted nucleoside is a 2'-OMe nucleoside.

Embodiment 193. The oligomeric compound of embodiment 191, wherein the 2'-OMe nucleoside is a stereo-standard 2'-OMe nucleoside.

Embodiment 194. The oligomeric compound of any of embodiments 191-193, wherein the 2'-substituted nucleoside is $N_{d2}$.

Embodiment 195. The oligomeric compound of embodiment 190, wherein each of $N_{d1}$, $N_{d2}$, $N_{d3}$, $N_{d4}$ and each $N_d$ is a DNA nucleoside.

Embodiment 196. The oligomeric compound of embodiment 195, wherein each DNA nucleoside is a stereo-standard DNA nucleoside.

Embodiment 197. The oligomeric compound of any of embodiments 190-196, wherein $L_1$ and $L_2$ are internucleoside linkages having formula VIII.

Embodiment 198. The oligomeric compound of any of embodiments 190-196, wherein $L_2$ and $L_3$ are internucleoside linkages having formula VIII.

Embodiment 199. The oligomeric compound of any of embodiments 190-196, wherein $L_3$ and $L_4$ are internucleoside linkages having formula VIII.

Embodiment 200. The oligomeric compound of any of embodiments 190-196, wherein $L_1$, $L_2$, and $L_3$ are internucleoside linkages having formula VIII.

Embodiment 201. The oligomeric compound of any of embodiments 190-196, wherein $L_2$, $L_3$, and $L_4$, are internucleoside linkages having formula VIII.

Embodiment 202. The oligomeric compound of any of embodiments 190-196, wherein $L_1$, $L_2$, $L_3$, and $L_4$ are internucleoside linkages having formula VIII.

Embodiment 203. The oligomeric compound of any of embodiments 190-202, wherein $R_1$ is H.

Embodiment 204. The oligomeric compound of any of embodiments 190-202, wherein $R_1$ is a $C_1$-$C_6$ alkyl.

Embodiment 205. The oligomeric compound of embodiment 204, wherein $R_1$ is methyl.

Embodiment 206. The oligomeric compound of any of embodiments 190-202, wherein $R_1$ is a substituted $C_1$-$C_6$ alkyl;

Embodiment 207. The oligomeric compound of any of embodiments 190-206, wherein T is $SO_2R_2$.

Embodiment 208. The oligomeric compound of embodiment 207, wherein $R_2$ is an aryl.

Embodiment 209. The oligomeric compound of embodiment 207, wherein $R_2$ is a substituted aryl.

Embodiment 210. The oligomeric compound of embodiment 207, wherein $R_2$ is a heterocycle.

Embodiment 211. The oligomeric compound of embodiment 207, wherein $R_2$ is a substituted heterocycle.

Embodiment 212. The oligomeric compound of embodiment 207, wherein $R_2$ is an aromatic heterocycle.

Embodiment 213. The oligomeric compound of embodiment 207, wherein $R_2$ is a substituted aromatic heterocycle.

Embodiment 214. The oligomeric compound of embodiment 207, wherein $R_2$ is a diazole.

Embodiment 215. The oligomeric compound of embodiment 207, wherein $R_2$ is a substituted diazole.

Embodiment 216. The oligomeric compound of embodiment 207, wherein $R_2$ is an amine.

Embodiment 217. The oligomeric compound of embodiment 207, wherein $R_2$ is a substituted amine.

Embodiment 218. The oligomeric compound of embodiment 207, wherein $R_2$ is a $C_1$-$C_6$ alkoxy.

Embodiment 219. The oligomeric compound of embodiment 207, wherein $R_2$ is $C_1$-$C_6$ alkyl.

Embodiment 220. The oligomeric compound of embodiment 207, wherein $R_2$ is substituted $C_1$-$C_6$ alkyl.

Embodiment 221. The oligomeric compound of embodiment 207, wherein T is:

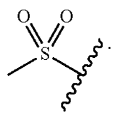

Embodiment 222. The oligomeric compound of embodiment 207, wherein T is:

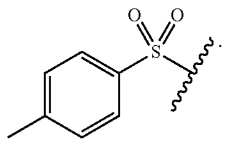 [SMILES: *S(=O)(=O)c1ccc(C)cc1]

Embodiment 223. The oligomeric compound of embodiment 207, wherein T is:

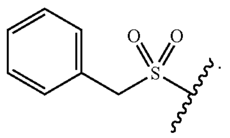 [SMILES: *S(=O)(=O)Cc1ccccc1]

Embodiment 224. The oligomeric compound of embodiment 207, wherein T is:

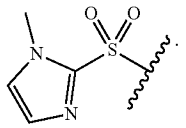 [SMILES: *S(=O)(=O)c1nccn1C]

Embodiment 225. The oligomeric compound of embodiment 207, wherein T is:

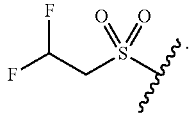

Embodiment 226. The oligomeric compound of embodiment 207, wherein T is:

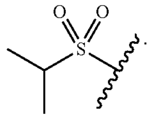 [SMILES: *S(=O)(=O)C(C)C]

Embodiment 227. The oligomeric compound of embodiment 207, wherein T is:

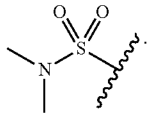 [SMILES: *S(=O)(=O)N(C)C]

Embodiment 228. The oligomeric compound of embodiment 207, wherein T is:

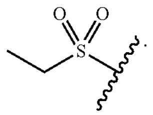 [SMILES: *S(=O)(=O)CC]

Embodiment 229. The oligomeric compound of embodiment 207, wherein T is:

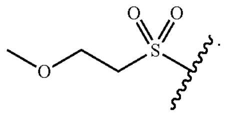 [SMILES: *S(=O)(=O)CCOC]

Embodiment 230. The oligomeric compound of any of embodiments 190-206, wherein T is C(=O)$R_3$.

Embodiment 231. The oligomeric compound of embodiment 230, wherein $R_3$ is an aryl.

Embodiment 232. The oligomeric compound of embodiment 230, wherein $R_3$ is a substituted aryl.

Embodiment 233. The oligomeric compound of embodiment 230, wherein $R_3$ is $CH_3$.

Embodiment 234. The oligomeric compound of embodiment 230, wherein $R_3$ is $N(CH_3)_2$.

Embodiment 235. The oligomeric compound of embodiment 230, wherein $R_3$ is $OCH_3$.

Embodiment 236. The oligomeric compound of embodiment 230, wherein T is:

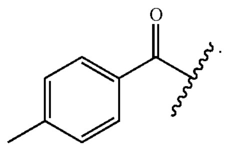 [SMILES: *C(=O)c1ccc(C)cc1]

Embodiment 237. The oligomeric compound of embodiment 230, wherein T is:

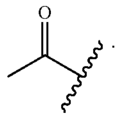 [SMILES: *C(C)=O]

Embodiment 238. The oligomeric compound of embodiment 230, wherein T is:

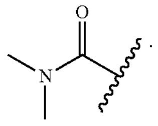 [SMILES: *C(=O)N(C)C]

Embodiment 239. The oligomeric compound of embodiment 230, wherein T is:

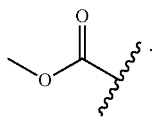 [SMILES: *C(=O)OC]

Embodiment 240. The oligomeric compound of any of embodiments 190-206, wherein T is P(=O)$R_4R_5$.

Embodiment 241. The oligomeric compound of embodiment 240, wherein $R_4$ is $OCH_3$.

Embodiment 242. The oligomeric compound of embodiment 240, wherein $R_4$ is OH

Embodiment 243. The oligomeric compound of embodiment 240, wherein $R_4$ is $C_1$-$C_6$ alkyl.

Embodiment 244. The oligomeric compound of embodiment 240, wherein $R_4$ is substituted $C_1$-$C_6$ alkyl.

Embodiment 245. The oligomeric compound of any of embodiments 240-242, wherein $R_5$ is $OCH_3$.

Embodiment 246. The oligomeric compound of any of embodiments 240-242, wherein $R_5$ is OH.

Embodiment 247. The oligomeric compound of any of embodiments 240-242, wherein $R_5$ is $C_1$-$C_6$ alkyl.

Embodiment 248. The oligomeric compound of any of embodiments 240-242, wherein $R_5$ is substituted $C_1$-$C_6$ alkyl.

Embodiment 249. The oligomeric compound of embodiment 240, wherein T is:

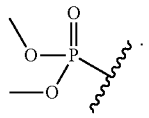 [SMILES: *P(=O)(OC)OC]

Embodiment 250. The oligomeric compound of embodiment 240, wherein T is:

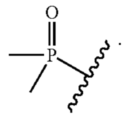 [SMILES: *P(C)(C)=O]

Embodiment 251. The oligomeric compound of any of embodiments 190-250, wherein at least one internucleoside linking group of the modified oligonucleotide is not a linking group of Formula VIII.

Embodiment 252. The oligomeric compound of any of embodiments 190-250, wherein exactly two internucleoside linking groups of the modified oligonucleotide are internucleoside linking groups of any of Formula VIII.

Embodiment 253. The oligomeric compound of any of embodiments 190-250, wherein exactly three internucleoside linking groups of the modified oligonucleotide are internucleoside linking groups of any of Formula VIII.

Embodiment 254. The oligomeric compound of any of embodiments 190-250, wherein exactly four internucleoside linking groups of the modified oligonucleotide are internucleoside linking groups of any of Formula VIII.

Embodiment 255. The oligomeric compound of any of embodiment 190-250 having at least two linking groups of Formula VIII, wherein at least two of the linking groups of Formula VIII are the same as one another.

Embodiment 256. The oligomeric compound of any of embodiments 190-255, wherein each internucleoside linking group of the modified oligonucleotide that is not an internucleoside linking group of Formula VIII is either a phosphodiester internucleoside linking group or a phosphorothioate internucleoside linking group.

Embodiment 257. The oligomeric compound of any of embodiments 190-256, wherein the 5'-region consists of 2-5 linked nucleosides.

Embodiment 258. The oligomeric compound of embodiment 257, wherein the 5'-region consists of 3 linked nucleosides.

Embodiment 259. The oligomeric compound of embodiment 257, wherein the 5'-region consists of 5 linked nucleosides.

Embodiment 260. The oligomeric compound of any of embodiments 190-259 wherein each nucleoside of the 5'-region is a modified nucleoside.

Embodiment 261. The oligomeric compound of any of embodiments 190-259, wherein each nucleoside of the 5'-region is a modified nucleoside comprising a modified sugar.

Embodiment 262. The oligomeric compound of any of embodiments 190-261, wherein each nucleoside of the 5'-region comprises a 2'-substituted furanosyl sugar moiety.

Embodiment 263. The oligomeric compound of any of embodiments 190-261, wherein at least one nucleoside of the 5'-region comprises a bicyclic furanosyl sugar moiety.

Embodiment 264. The oligomeric compound of any of embodiments 190-261, wherein each nucleoside of the 5'-region comprises a bicyclic furanosyl sugar moiety.

Embodiment 265. The oligomeric compound of embodiment 263, wherein each bicyclic sugar moiety of the 5'-region is selected from among cEt, LNA, and ENA.

Embodiment 266. The oligomeric compound of embodiment 263, wherein each bicyclic sugar moiety of the 5'-region is a cEt sugar moiety.

Embodiment 267. The oligomeric compound of embodiment 262, wherein each 2'-substituted furanosyl sugar moiety of the 5'-region is a ribosyl sugar moiety and has a 2'-substituent selected from among 2'-MOE, 2'-OMe, and 2'-NMA.

Embodiment 268. The oligomeric compound of any of embodiments 190-267, wherein each nucleobase of the 5'-region is independently selected from among thymine, uracil, guanine, cytosine, 5-methylcytosine, and adenine.

Embodiment 269. The oligomeric compound of any of embodiments 190-268, wherein the 3'-region consists of 2-5 linked nucleosides.

Embodiment 270. The oligomeric compound of embodiment 269, wherein the 3'-region consists of 3 linked nucleosides.

Embodiment 271. The oligomeric compound of embodiment 269, wherein the 3'-region consists of 5 linked nucleosides.

Embodiment 272. The oligomeric compound of any of embodiments 190-271 wherein each nucleoside of the 3'-region is a modified nucleoside.

Embodiment 273. The oligomeric compound of any of embodiments 190-272, wherein each nucleoside of the 3'-region is a modified nucleoside comprising a modified sugar.

Embodiment 274. The oligomeric compound of any of embodiments 190-273, wherein each nucleoside of the 3'-region comprises a 2'-substituted furanosyl sugar moiety.

Embodiment 275. The oligomeric compound of any of embodiments 190-273, wherein at least one nucleoside of the 3'-region comprises a bicyclic furanosyl sugar moiety.

Embodiment 276. The oligomeric compound of any of embodiments 190-273, wherein each nucleoside of the 3'-region comprises a bicyclic furanosyl sugar moiety.

Embodiment 277. The oligomeric compound of embodiment 276, wherein each bicyclic sugar moiety of the 3'-region is selected from among cEt, LNA, and ENA.

Embodiment 278. The oligomeric compound of embodiment 276, wherein each bicyclic sugar moiety of the 3'-region is a cEt sugar moiety.

Embodiment 279. The oligomeric compound of embodiment 274, wherein each wherein each 2'-substituted furanosyl sugar moiety of the 5'-region is a ribosyl sugar moiety and has a 2'-substituent selected from among 2'-MOE, 2'-OMe, and 2'-NMA.

Embodiment 280. The oligomeric compound of any of embodiments 190-279, wherein each nucleobase of the 5'-region is independently selected from among thymine, uracil, guanine, cytosine, 5-methylcytosine, and adenine.

Embodiment 281. The oligomeric compound of any of embodiments 1-80, wherein each nucleoside of the modified oligonucleotide is a modified nucleoside comprising a modified sugar moiety.

Embodiment 282. The oligomeric compound of embodiment 281, wherein each modified sugar moiety is independently selected from a bicyclic sugar moiety and a 2'-substituted furanosyl sugar moiety.

Embodiment 283. The oligomeric compound of embodiment 282, wherein the three 3'-most nucleosides comprise a bicyclic sugar moiety, and the remaining nucleosides comprise a 2'-substituted furanosyl sugar moiety.

Embodiment 284. The oligomeric compound of embodiment 282, wherein the four 3'-most nucleosides comprise a bicyclic sugar moiety, and the remaining nucleosides comprise a 2'-substituted furanosyl sugar moiety.

Embodiment 285. The oligomeric compound of embodiment 282, wherein the five 3'-most nucleosides comprise a bicyclic sugar moiety, and the remaining nucleosides comprise a 2'-substituted furanosyl sugar moiety.

Embodiment 286. The oligomeric compound of embodiment 282, wherein the six 3'-most nucleosides comprise a bicyclic sugar moiety, and the remaining nucleosides comprise a 2'-substituted furanosyl sugar moiety.

Embodiment 287. The oligomeric compound of any of embodiments 282-286, wherein each bicyclic sugar moiety is selected from among cEt, LNA, and ENA.

Embodiment 288. The oligomeric compound of embodiment 287, wherein the bicyclic sugar moiety is cEt Embodiment 289. The oligomeric compound of any of embodiments 282-289, wherein the 2'-substituted furanosyl sugar moiety is selected from 2'-OMe, 2'-MOE, and 2'-F.

Embodiment 290. The oligomeric compound of any of embodiments 281-289, wherein at least one of the first 10 internucleoside linking groups from the 5'-end of the modified oligonucleotide is an internucleoside linking group of any of embodiments 1-50.

Embodiment 291. The oligomeric compound of embodiment 289, wherein at least 2 of the first 10 internucleoside linking groups from the 5'-end of the modified oligonucleotide are internucleoside linking groups of any of embodiments 1-50.

Embodiment 292. The oligomeric compound of embodiment 289, wherein at least 3 of the first 10 internucleoside linking groups from the 5'-end of the modified oligonucleotide are internucleoside linking groups of any of embodiments 1-50.

Embodiment 293. The oligomeric compound of embodiment 289, wherein at least 4 of the first 10 internucleoside linking groups from the 5'-end of the modified oligonucleotide are internucleoside linking groups of any of embodiments 1-50.

Embodiment 294. The oligomeric compound of embodiment 289, wherein at least 5 of the first 10 internucleoside linking groups from the 5'-end of the modified oligonucleotide are internucleoside linking groups of any of embodiments 1-50.

Embodiment 295. The oligomeric compound of embodiment 289, wherein at least 6 of the first 10 internucleoside linking groups from the 5'-end of the modified oligonucleotide are internucleoside linking groups of any of embodiments 1-50.

Embodiment 296. The oligomeric compound of embodiment 289, wherein the first 2 internucleoside linking groups from the 5'-end of the modified oligonucleotide are internucleoside linking groups of any of embodiments 1-50.

Embodiment 297. The oligomeric compound of embodiment 289, wherein the first 3 internucleoside linking groups from the 5'-end of the modified oligonucleotide are internucleoside linking groups of any of embodiments 1-50.

Embodiment 298. The oligomeric compound of embodiment 289, wherein the first 4 internucleoside linking groups from the 5'-end of the modified oligonucleotide are internucleoside linking groups of any of embodiments 1-50.

Embodiment 299. The oligomeric compound of embodiment 289, wherein the first 5 internucleoside linking groups from the 5'-end of the modified oligonucleotide are internucleoside linking groups of any of embodiments 1-50.

Embodiment 300. The oligomeric compound of embodiment 289, wherein the first 6 internucleoside linking groups from the 5'-end of the modified oligonucleotide are internucleoside linking groups of any of embodiments 1-50.

Embodiment 301. A method of increasing translation of a target protein in a cell, comprising contacting the cell with an oligomeric compound of any of embodiments 281-300.

Embodiment 302. The method of embodiment 301, wherein the target protein is encoded by a target nucleic acid comprising at least one translation suppression element and wherein the modified oligonucleotide is complementary to a target site within a translation suppression element region of the target nucleic acid.

Embodiment 303. The method of embodiment 302, wherein the translation suppression element region comprises at least one stem-loop structure.

Embodiment 304. A pharmaceutical composition comprising the oligomeric compound of any of embodiments 190-300 and a pharmaceutically acceptable carrier or diluent.

Embodiment 305. A method comprising contacting a cell with the oligomeric compound or pharmaceutical composition of any of embodiments 190-300.

Embodiment 306. A method of modulating the amount or activity of a target nucleic acid in a cell, comprising contacting the cell with the oligomeric compound or pharmaceutical composition of any of embodiments 190-300, and thereby modulating the amount or activity of the target nucleic acid.

Embodiment 307. The method of embodiment 306, wherein the amount or activity of a target nucleic acid is reduced.

Embodiment 308. The method of embodiment 306, wherein the amount or activity of a target nucleic acid is increased.

Embodiment 309. Use of the oligomeric compound or composition of any of embodiments 190-300 for treatment of a disease or condition.

Embodiment 310. Use of the oligomeric compound or composition of any of embodiments 190-300 for a preparation of a medicament for treatment of a disease or condition.

Embodiment 311. An antisense agent comprising a modified oligonucleotide consisting of linked nucleosides linked through internucleoside linking groups, wherein at least one of the internucleoside linking groups has Formula XVII:

XVII

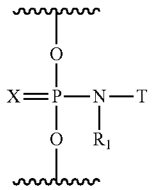

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

Embodiment 312. An antisense agent comprising a modified oligonucleotide consisting of linked nucleosides linked through internucleoside linking groups, wherein at least one of the internucleoside linking groups has Formula XVII:

XVII

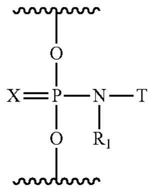

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl; Provided that if X is 0 and that if $R_1$ is H, then T is not:

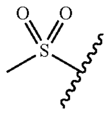
or
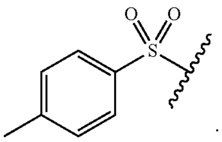
.

Embodiment 313. The modified oligonucleotide of embodiment 311 or 312, wherein for at least one internucleoside linking group of Formula XVII, X is O.

Embodiment 314. The modified oligonucleotide of embodiment 311 or 312, wherein for at least one internucleoside linking group of Formula XVII, X is S.

Embodiment 315. The modified oligonucleotide of embodiment 311 or 312, wherein for at least one internucleoside linking group of Formula XVII, $R_1$ is H.

Embodiment 316. The modified oligonucleotide of embodiment 311 or 312, wherein for at least one internucleoside linking group of Formula XVII, $R_1$ is a $C_1$-$C_6$ alkyl, $C_1$-$C_6$ alkenyl, or $C_1$-$C_6$ alkynyl.

Embodiment 317. The modified oligonucleotide of embodiment 6, wherein $R_1$ is methyl.

Embodiment 318. The modified oligonucleotide of embodiment 311 or 312, wherein for at least one internucleoside linking group of Formula XVII, $R_1$ is a substituted $C_1$-$C_6$ alkyl.

Embodiment 319. The modified oligonucleotide of any of embodiments 311-318, wherein for at least one internucleoside linking group of Formula XVII, T comprises a conjugate group.

Embodiment 320. The modified oligonucleotide of embodiment 319, wherein the conjugate group comprises a carbohydrate or carbohydrate cluster.

Embodiment 321. The modified oligonucleotide of embodiment 319 or 320, wherein the conjugate group comprises at least one GalNAc.

Embodiment 322. The modified oligonucleotide of embodiment 319, wherein the conjugate group comprises a $C_{10}$-$C_{20}$ alkyl chain.

Embodiment 323. The modified oligonucleotide of embodiment 322, wherein the conjugate group comprises $C_{16}$ alkyl.

Embodiment 324. The modified oligonucleotide of any of embodiments 311-318, wherein for at least one internucleoside linking group of formula XVII, T does not comprise a conjugate group.

Embodiment 325. The modified oligonucleotide of any of embodiments 311-324, wherein for at least one internucleoside linking group of Formula XVII, T is $SO_2R_2$.

Embodiment 326. The modified oligonucleotide of embodiment 325, wherein $R_2$ is an aryl.

Embodiment 327. The modified oligonucleotide of embodiment 325, wherein $R_2$ is a substituted aryl.

Embodiment 328. The modified oligonucleotide of embodiment 325, wherein $R_2$ is a heterocycle.

Embodiment 329. The modified oligonucleotide of embodiment 325, wherein $R_2$ is a substituted heterocycle.

Embodiment 330. The modified oligonucleotide of embodiment 325, wherein $R_2$ is an aromatic heterocycle.

Embodiment 331. The modified oligonucleotide of embodiment 325, wherein $R_2$ is a substituted aromatic heterocycle.

Embodiment 332. The modified oligonucleotide of embodiment 325, wherein $R_2$ is a diazole.

Embodiment 333. The modified oligonucleotide of embodiment 325, wherein $R_2$ is a substituted diazole.

Embodiment 334. The modified oligonucleotide of embodiment 325, wherein $R_2$ is an amine.

Embodiment 335. The modified oligonucleotide of embodiment 325, wherein $R_2$ is a substituted amine.

Embodiment 336. The modified oligonucleotide of embodiment 325, wherein $R_2$ is a $C_1$-$C_6$ alkoxy, or $C_1$-$C_6$ alkenyl, $C_1$-$C_6$ alkynyl.

Embodiment 337. The modified oligonucleotide of embodiment 325, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 338. The modified oligonucleotide of embodiment 325, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 339. The modified oligonucleotide of embodiment 325, wherein $R_2$ comprises a carbohydrate or carbohydrate cluster.

Embodiment 340. The modified oligonucleotide of embodiment 325, wherein $R_2$ comprises at least one GalNAc.

Embodiment 341. The modified oligonucleotide of embodiment 325, wherein T is:

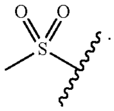 [SMILES: *S(C)(=O)=O]
.

Embodiment 342. The modified oligonucleotide of embodiment 325, wherein T is:

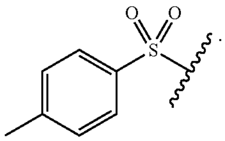 [SMILES: *S(=O)(=O)c1ccc(C)cc1]
.

Embodiment 343. The modified oligonucleotide of embodiment 325, wherein T is:

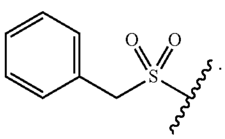 [SMILES: *S(=O)(=O)Cc1ccccc1]
.

Embodiment 344. The modified oligonucleotide of embodiment 325, wherein T is:

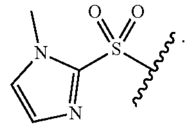

Embodiment 345. The modified oligonucleotide of embodiment 325, wherein T is:

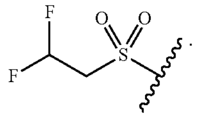

Embodiment 346. The modified oligonucleotide of embodiment 325, wherein T is:

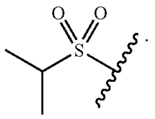 [SMILES: *S(=O)(=O)C(C)C]

Embodiment 347. The modified oligonucleotide of embodiment 325, wherein T is:

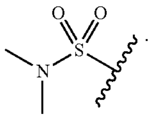 [SMILES: *S(=O)(=O)N(C)C]

Embodiment 348. The modified oligonucleotide of embodiment 325, wherein T is:

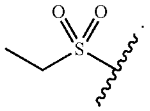 [SMILES: *S(=O)(=O)CC]

Embodiment 349. The modified oligonucleotide of embodiment 325, wherein T is:

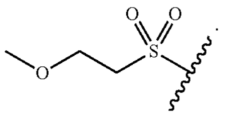 [SMILES: *S(=O)(=O)CCOC]

Embodiment 350. The modified oligonucleotide of embodiment 325, wherein T is:

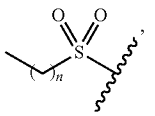

wherein n is from 2 to 20.

Embodiment 351. The modified oligonucleotide of embodiment 350, wherein n is 15.

Embodiment 352. The modified oligonucleotide of any of embodiments 311-324, wherein for at least one internucleoside linking group of Formula XVII, T is C(=O)$R_3$.

Embodiment 353. The modified oligonucleotide of embodiment 352, wherein $R_3$ is an aryl.

Embodiment 354. The modified oligonucleotide of embodiment 352, wherein $R_3$ is a substituted aryl.

Embodiment 355. The modified oligonucleotide of embodiment 352, wherein $R_3$ is $CH_3$.

Embodiment 356. The modified oligonucleotide of embodiment 352, wherein $R_3$ is $N(CH_3)_2$.

Embodiment 357. The modified oligonucleotide of embodiment 352, wherein $R_3$ is $OCH_3$.

Embodiment 358. The modified oligonucleotide of embodiment 352, wherein $R_3$ is a $C_1$-$C_6$ alkoxy.

Embodiment 359. The modified oligonucleotide of embodiment 352, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 360. The modified oligonucleotide of embodiment 352, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 361. The modified oligonucleotide of embodiment 352, wherein $R_3$ comprises a carbohydrate or carbohydrate cluster.

Embodiment 362. The modified oligonucleotide of embodiment 352, wherein $R_{23}$ comprises at least one GalNAc.

Embodiment 363. The modified oligonucleotide of embodiment 352, wherein T is:

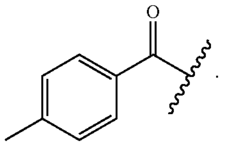 [SMILES: *C(=O)c1ccc(C)cc1]

Embodiment 364. The modified oligonucleotide of embodiment 352, wherein T is:

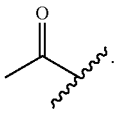

Embodiment 365. The modified oligonucleotide of embodiment 352, wherein T is:

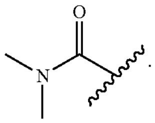 [SMILES: *C(=O)N(C)C]

Embodiment 366. The modified oligonucleotide of embodiment 352, wherein T is:

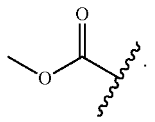 [SMILES: *C(=O)OC]

Embodiment 367. The modified oligonucleotide of embodiment 352, wherein T is:

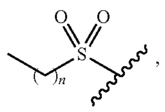

wherein n is from 2 to 20.

Embodiment 368. The modified oligonucleotide of embodiment 367, wherein n is 15.

Embodiment 369. The modified oligonucleotide of any of embodiments 1-14, wherein for at least one internucleoside linking group of Formula XVII, T is P(═O)$R_4R_5$.

Embodiment 370. The modified oligonucleotide of embodiment 369, wherein $R_4$ is $OCH_3$.

Embodiment 371. The modified oligonucleotide of embodiment 369, wherein $R_4$ is OH.

Embodiment 372. The modified oligonucleotide of embodiment 369, wherein $R_4$ is $C_1$-$C_6$ alkyl.

Embodiment 373. The modified oligonucleotide of embodiment 369, wherein $R_4$ is substituted $C_1$-$C_6$ alkyl.

Embodiment 374. The modified oligonucleotide of embodiment 369, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 375. The modified oligonucleotide of embodiment 369, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 376. The modified oligonucleotide of embodiment 369, wherein $R_4$ comprises a carbohydrate or carbohydrate cluster.

Embodiment 377. The modified oligonucleotide of embodiment 369, wherein $R_4$ comprises at least one GalNAc.

Embodiment 378. The modified oligonucleotide of any of embodiments 369-67, wherein $R_5$ is $OCH_3$.

Embodiment 379. The modified oligonucleotide of any of embodiments 369-67, wherein $R_5$ is OH Embodiment 380. The modified oligonucleotide of any of embodiments 369-67, wherein $R_5$ is $C_1$-$C_6$ alkyl.

Embodiment 381. The modified oligonucleotide of any of embodiments 369-67, wherein $R_5$ is substituted $C_1$-$C_6$ alkyl.

Embodiment 382. The modified oligonucleotide of embodiment 369, wherein T is:

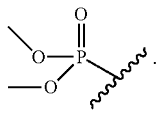

Embodiment 383. The modified oligonucleotide of embodiment 369, wherein T is:

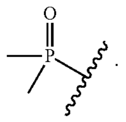

Embodiment 384. The modified oligonucleotide of embodiment 369, wherein T is:

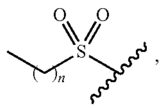

wherein n is from 2 to 20.

Embodiment 385. The modified oligonucleotide of embodiment 384, wherein n is 15.

Embodiment 386. The modified oligonucleotide of any of embodiments 311-385, wherein at least one internucleoside linking group of the modified oligonucleotide is not a linking group of Formula XVII.

Embodiment 387. The modified oligonucleotide of any of embodiments 311-385, wherein exactly one internucleoside linking group of the modified oligonucleotide is an internucleoside linking group of Formula XVII.

Embodiment 388. The modified oligonucleotide of any of embodiments 311-385, wherein exactly two internucleoside linking groups of the modified oligonucleotide are internucleoside linking groups of Formula XVII.

Embodiment 389. The modified oligonucleotide of any of embodiments 311-385, wherein exactly three internucleoside linking groups of the modified oligonucleotide are internucleoside linking groups of Formula XVII.

Embodiment 390. The modified oligonucleotide of any of embodiments 311-385, wherein exactly four internucleoside linking groups of the modified oligonucleotide are internucleoside linking groups of Formula XVII.

Embodiment 391. The modified oligonucleotide of any of embodiments 311-385, wherein exactly five internucleoside linking groups of the modified oligonucleotide are internucleoside linking groups of Formula XVII.

Embodiment 392. The modified oligonucleotide of any of embodiments 311-385, wherein at least six internucleoside linking groups of the modified oligonucleotide are internucleoside linking groups of Formula XVII.

Embodiment 393. The modified oligonucleotide of any of embodiment 311-386 or 388-392 having at least two linking groups of Formula XVII, wherein at least two of the linking groups of Formula XVII are the same as one another.

Embodiment 394. The modified oligonucleotide of any of embodiments 311-393, wherein each internucleoside linking group of the modified oligonucleotide that is not an internucleoside linking group of Formula XVII is either a phosphodiester internucleoside linking group or a phosphorothioate internucleoside linking group.

Embodiment 395. The modified oligonucleotide of any of embodiments 311-386 or 393-394, wherein each internucleoside linking group of the modified oligonucleotide is an internucleoside linking group of Formula XVII.

Embodiment 396. An antisense agent comprising a modified oligonucleotide, wherein at least one region of the modified oligonucleotide has Structure A:

Structure A

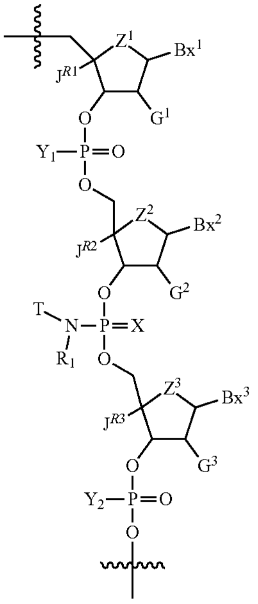

wherein:

each Bx is a heterocyclic base moiety;

X is selected from O or S;

each of $Y_1$ and $Y_2$ is independently selected from OH or SH;

each of $Z^1$, $Z^2$, and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]J-R_8$;

wherein each JR to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 397. An antisense agent comprising a modified olignucleotide, wherein at least one region of the modified oligonucleotide has Structure B:

Structure B

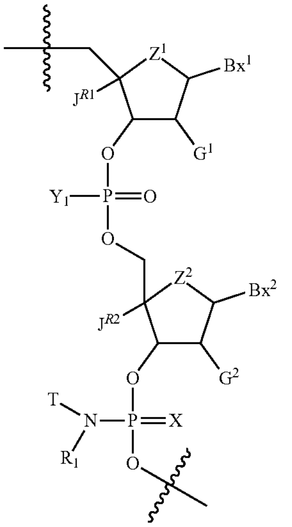

wherein:

each Bx is a heterocyclic base moiety;

X is selected from O or S;

each of $Y_1$ and $Y_2$ is independently selected from OH or SH;

each of $Z^1$ and $Z_2$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—[C($R_6$)($R_7$)]—[(C═O)$_m$—$X^G$]$_j$—$R_8$;

either $J^{R2}$ and $G^2$ form a $J^{R2}$ and $G^2$ bridge, or $J^{R2}$ is H and $G^2$ is selected from H, OH, halogen or O—[C($R_6$)($R_7$)]n-[(C═O)$_m$—$X^G$]$_j$—$R_8$;

wherein each $J^R$ to G bridge has a formula independently selected from —CH($CH_3$)—O— or —($CH_2$)$_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or N($E_1$);

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, N($J_1$)($J_2$), =$NJ_1$, $SJ_1$, $N_3$, CN, OC(═$X_2$)$J_1$, OC(═$X_2$)N($J_1$)($J_2$) and C(═$Q_2$)N($J_1$)($J_2$);

$Q_2$ is O, S or $NJ_3$;

each $J_1$, $J_2$ and $J_3$ is, independently, H or $C_1$-$C_6$ alkyl.

Embodiment 398. An antisense agent comprising a modified olignucleotide, wherein at least one region of the modified oligonucleotide has Structure C:

Structure C

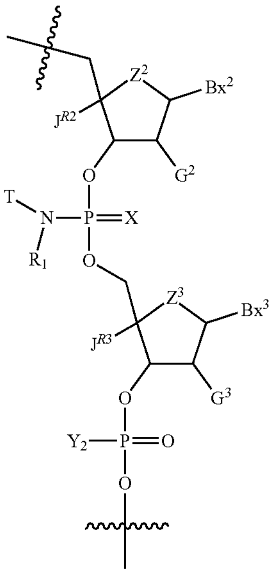

wherein:

each Bx is a heterocyclic base moiety;

X is selected from O or S;

each of $Y_1$ and $Y_2$ is independently selected from OH or SH;

each of $Z^2$ and $Z^3$ are independently selected from —($CH_2$)$_p$—$X^Z$—($CH_2$)$_q$—, wherein p is 0 or 1, q is 0 or 1, and $X^Z$ is O, S, or N($E_1$);

$R_1$ is selected from H, $C_1$-$C_6$ alkyl, and substituted $C_1$-$C_6$ alkyl; and T is selected from $SO_2R_2$, C(═O)$R_3$, and P(═O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J^{R2}$ and $G^2$ bridge, or $J^{R2}$ is H and $G^2$ is selected from H, OH, halogen or O—[C($R_6$)($R_7$)]$_n$—[(C═O)$_m$—$X^G$]$_j$—$R_8$;

either $J^{R3}$ and $G^3$ form a $J^{R3}$ and $G^3$ bridge, or $J^{R3}$ is H and $G^3$ is selected from H, OH, halogen or O—[C($R_6$)($R_7$)]$_n$[(C═O)$_m$—$X^G$]$_j$—$R_8$;

wherein each $J^R$ to G bridge has a formula independently selected from —CH($CH_3$)—O— or —($CH_2$)$_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or N($E_1$);

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, N($J_1$)($J_2$), =$NJ_1$, $SJ_1$, $N_3$, CN, OC(═$X_2$)$J_1$, OC(═$X_2$)N($J_1$)($J_2$) and C(═$Q_2$)N($J_1$)($J_2$); $Q_2$ is O, S or $NJ_3$;

each $J_1$, $J_2$ and $J_3$ is, independently, H or $C_1$-$C_6$ alkyl.

Embodiment 399. An antisense agent comprising a modified olignucleotide, wherein at least one region of the modified oligonucleotide has Structure D:

Structure D

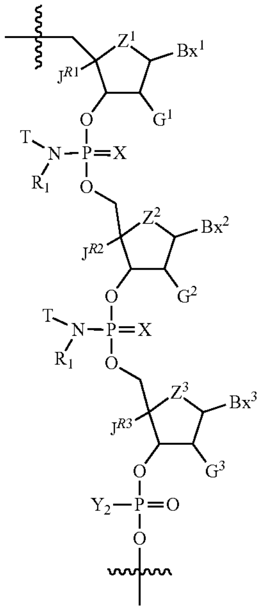

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O—[C(R_6)(R_7)]—[(C=O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C=O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C=O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 400. An antisense agent comprising a modified olignucleotide, wherein at least one region of the modified oligonucleotide has Structure E:

Structure E

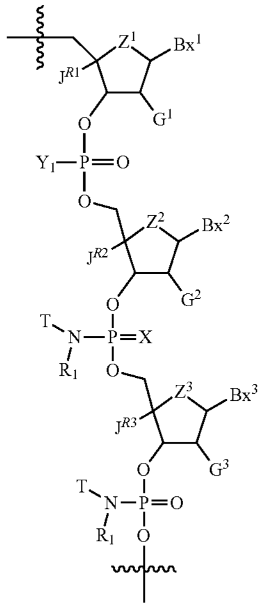

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—[C($R_6$)($R_7$)]—[(C═O)$_m$—$X^G$]$_j$—$R_8$;

either $J^{R2}$ and $G^2$ form a $J^{R2}$ and $G^2$ bridge, or $J^{R2}$ is H and $G^2$ is selected from H, OH, halogen or O—[C($R_6$)($R_7$)]$_n$—[(C═O)$_m$—$X^G$]$_j$—$R_8$;

either $J^{R3}$ and $G^3$ form a $J^{R3}$ and $G^3$ bridge, or $J^{R3}$ is H and $G^3$ is selected from H, OH, halogen or O—[C($R_6$)($R_7$)]$_n$—[(C═O)$_m$—$X^G$]J-$R_8$;

wherein each $J^R$ to G bridge has a formula independently selected from —CH($CH_3$)—O— or —($CH_2$)$_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or N($E_1$);

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, N($J_1$)($J_2$), =$NJ_1$, $SJ_1$, $N_3$, CN, OC(═$X_2$)$J_1$, OC(═$X_2$)N($J_1$)($J_2$) and C(=$Q_2$)N($J_1$)($J_2$); $Q_2$ is O, S or $NJ_3$;

each $J_1$, $J_2$ and $J_3$ is, independently, H or $C_1$-$C_6$ alkyl.

Embodiment 401. The modified oligonucleotide of any of embodiments 396-400, wherein each Z is O.

Embodiment 402. The modified oligonucleotide of any of embodiments 396-401, wherein at least one G is selected from H, OH, halogen, $C_1$-$C_6$ alkoxy, —O($CH_2$)$_2$$OCH_3$, or —$OCH_2$(C═O)$NHCH_3$.

Embodiment 403. The modified oligonucleotide of any of embodiments 396-401, wherein each G is selected from H, OH, halogen, $C_1$-$C_6$ alkoxy, —O($CH_2$)$_2$$OCH_3$, or —$OCH_2$(C═O)$NHCH_3$.

Embodiment 404. The modified oligonucleotide of any of embodiments 396-402, wherein at least one $J^R$ forms a bridge with at least one G, wherein said $J^R$ to G bridge has a formula selected from 4CH($CH_3$)—O— or —($CH_2$)$_k$—O', wherein k is from 1 to 3.

Embodiment 405. The modified oligonucleotide of any of embodiments 396-402, wherein each $J^R$ and G form a bridge, wherein said $J^R$ to G bridge has a formula selected from —CH($CH_3$)—O— or —($CH_2$)$_k$—O—, wherein k is from 1 to 3.

Embodiment 406. The modified oligonucleotide of any of embodiments 404 or 405, wherein at least one Z is O and the corresponding $J^R$ to G bridge has a formula ($CH_2$)$_k$—O—, wherein k is 1.

Embodiment 407. The modified oligonucleotide of any of embodiments 396-406 wherein each nucleoside of structure A, B, C, D, or E is a stereo standard nucleoside.

Embodiment 408. The modified oligonucleotide of any of embodiments 396-406, wherein at least one nucleoside of structure A, B, C, D, or E is a stereo-non-standard nucleoside.

Embodiment 409. The modified oligonucleotide of any of embodiments 404-406 or 408, wherein at least one nucleoside having a $J^R$ to G bridge is in the α-L-ribosyl configuration.

Embodiment 410. The modified oligonucleotide of any of embodiments 396-409, wherein the modified oligonucleotide comprises at least 2, at least 3, at least 4, at least 5, at least 6, at least 7, at least 8, at least 9, or at least 10 regions having structures A, B, C, D, or E.

Embodiment 411. The modified oligonucleotide of any of embodiments 396-410, wherein at least one region having structure A, B, C, D, or E is at the 5' end of the modified oligonucleotide.

Embodiment 412. The modified oligonucleotide of any of embodiments 396-410, wherein at least one region having structure A, B, C, D, or E is at the 3' end of the modified oligonucleotide.

Embodiment 413. The modified oligonucleotide of any of embodiments 396-410, wherein at least one region having structure A, B, C, D, or E is internal to the modified oligonucleotide.

Embodiment 414. An antisense agent, comprising a modified oligonucleotide consisting of 10-30 linked nucleosides, wherein a region of the modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

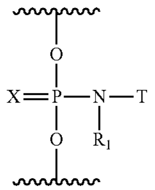

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, C(═O)$R_3$, and P(═O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, N($CH_3$)$_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 415. The modified oligonucleotide of embodiment 414, wherein the modified oligonucleotide comprises at least 2, at least 3, at least 4, at least 5, at least 6, at least 7, at least 8, at least 9, or at least 10 regions having the formula $(N_{g1})_{L1}(N_{g2})_{L2}(N_{g3})_{L3}$.

Embodiment 416. The modified oligonucleotide of embodiment 414, wherein at least one region having the formula $(N_{g1})_{L1}(N_{g2})_{L2}(N_{g3})_{L3}$ is at the 5' end of the oligonucleotide Embodiment 417. The modified oligonucleotide of embodiment 414, wherein at least one region having the formula $(N_{g1})_{L1}(N_{g2})_{L2}(N_{g3})_{L3}$ is internal to the oligonucleotide.

Embodiment 418. The modified oligonucleotide of embodiment 414, wherein at least one region having the formula $(N_{g1})_{L1}(N_{g2})_{L2}(N_{g3})_{L3}$ is at the 3' end of the oligonucleotide.

Embodiment 419. The modified oligonucleotide of any of embodiments 311-418, wherein at least one nucleoside of the modified oligonucleotide is a modified nucleoside.

Embodiment 420. The modified oligonucleotide of embodiment 419, wherein at least one nucleoside of the modified oligonucleotide is a modified nucleoside selected from a bicyclic nucleoside and a non-bicyclic substituted nucleoside.

Embodiment 421. The modified oligonucleotide of any of embodiments 311-420, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 422. The modified oligonucleotide of any of embodiments 311-421, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 423. The modified oligonucleotide of any of embodiments 311-422, wherein at least one nucleoside of the modified oligonucleotide is a stereo-non-standard nucleoside.

Embodiment 424. The modified oligonucleotide of embodiment 423, wherein the internucleoside linking group linking at least one stereo-non-standard nucleoside to an adjacent nucleoside is an internucleoside linking group of Formula XVII.

Embodiment 425. The modified oligonucleotide of embodiment 423 or 424, wherein at least two nucleosides of the modified oligonucleotide are stereo-non-standard nucleosides.

Embodiment 426. The modified oligonucleotide of embodiment 425, wherein at least two stereo-non-standard nucleosides of the modified oligonucleotide are adjacent to one another.

Embodiment 427. The modified oligonucleotide of embodiment 426, wherein at least two stereo-non-standard nucleosides of the modified oligonucleotide are linked to one another with an internucleoside linking group of Formula XVII.

Embodiment 428. The modified oligonucleotide of any of embodiments 423-427, wherein at least one stereo-non-standard nucleoside of the modified oligonucleotide is a stereo-non-standard DNA nucleoside.

Embodiment 429. The modified oligonucleotide of embodiment 428 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 430. The modified oligonucleotide of embodiment 429 wherein the stereo-non-standard DNA nucleoside is selected from a stereo-non-standard DNA nucleoside having: Formula V and Formula II.

Embodiment 431. The modified oligonucleotide of any of embodiments 423-427, wherein at least one stereo-non-standard nucleoside of the modified oligonucleotide is a substituted stereo-non-standard nucleoside or a stereo-non-standard RNA nucleoside.

Embodiment 432. The modified oligonucleotide of embodiment 431, wherein the 2'-substituent of the at least one substituted stereo-non-standard nucleoside of the modified oligonucleotide is selected from: 2'-MOE, 2'-OMe, 2'-F, or 2'-OH.

Embodiment 433. The modified oligonucleotide of any of embodiments 311-432, wherein the modified oligonucleotide consists of 12-30 linked nucleosides.

Embodiment 434. The modified oligonucleotide of any of embodiments 311-433, wherein the modified oligonucleotide consists of 16-24 linked nucleosides.

Embodiment 435. The modified oligonucleotide of any of embodiments 311-434, wherein the modified oligonucleotide consists of 18-22 linked nucleosides.

Embodiment 436. The modified oligonucleotide of any of embodiments 311-434, wherein the modified oligonucleotide consists of 16 linked nucleosides.

Embodiment 437. The modified oligonucleotide of any of embodiments 311-434, wherein the modified oligonucleotide consists of 17 linked nucleosides.

Embodiment 438. The modified oligonucleotide of any of embodiments 311-435, wherein the modified oligonucleotide consists of 18 linked nucleosides.

Embodiment 439. The modified oligonucleotide of any of embodiments 311-435, wherein the modified oligonucleotide consists of 19 linked nucleosides.

Embodiment 440. The modified oligonucleotide of any of embodiments 311-435, wherein the modified oligonucleotide consists of 20 linked nucleosides.

Embodiment 441. The modified oligonucleotide of any of embodiments 311-435, wherein the modified oligonucleotide consists of 21 linked nucleosides.

Embodiment 442. The modified oligonucleotide of any of embodiments 311-435, wherein the modified oligonucleotide consists of 22 linked nucleosides.

Embodiment 443. The modified oligonucleotide of any of embodiments 311-434, wherein the modified oligonucleotide consists of 23 linked nucleosides.

Embodiment 444. The modified oligonucleotide of any of embodiments 311-443, wherein at least one nucleoside of the modified oligonucleotide is selected from: a 2'-OMe nucleoside, a 2'-F nucleoside, and an RNA nucleoside.

Embodiment 445. The modified oligonucleotide of any of embodiments 311-444, wherein at least one nucleoside of the modified oligonucleotide is a 2'-OMe nucleoside, and at least one nucleoside of the modified oligonucleotide is an RNA nucleoside.

Embodiment 446. The modified oligonucleotide of any of embodiments 444-445, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 447. The modified oligonucleotide of embodiment 446, wherein A and B are selected from 2'-F substituted nucleosides, 2'-OMe substituted nucleosides, and stereo-standard RNA nucleosides.

Embodiment 448. The modified oligonucleotide of any of embodiments 311-447, wherein the 5'-end of the modified oligonucleotide comprises a stabilized phosphate group.

Embodiment 449. The modified oligonucleotide of embodiment 448, wherein the stabilized phosphate group is a 5'-vinyl phosphonate or a 5'-cyclopropyl phosphonate.

Embodiment 450. An RNAi agent, comprising a modified oligonucleotide of any of embodiments 311-449.

Embodiment 451. The RNAi agent of embodiment 450, wherein the RNAi agent is a single-stranded RNAi agent comprising an RNAi antisense modified oligonucleotide, wherein the RNAi antisense modified oligonucleotide is a modified oligonucleotide of any of embodiments 311-449.

Embodiment 452. The RNAi agent of embodiment 450, wherein the RNAi agent is an oligomeric duplex comprising an RNAi antisense modified oligonucleotide and an RNAi sense modified oligonucleotide, wherein the RNAi antisense modified oligonucleotide and/or the RNAi sense modified oligonucleotide is a modified oligonucleotide of any of embodiments 311-449.

Embodiment 453. The RNAi agent of embodiment 451 or 452, wherein at least one internucleoside linking group of the RNAi antisense modified oligonucleotide is an internucleoside linking group of Formula XVII.

Embodiment 454. The RNAi agent of embodiment 451 or 452, wherein at least two internucleoside linking groups of the RNAi antisense modified oligonucleotide are independently selected internucleoside linking groups of any of embodiments 311-385.

Embodiment 455. The RNAi agent of any of embodiments 450-454, wherein at least one of the five 3'-most internucleoside linking groups of the RNAi antisense modified oligonucleotide is an internucleoside linking group of Formula XVII.

Embodiment 456. The RNAi agent of any of embodiments 450-454, wherein at least two of the five 3'-most internucleoside linking groups of RNAi antisense modified oligonucleotide is an internucleoside linking group of Formula XVII.

Embodiment 457. The RNAi agent of any of embodiments 450-454, wherein at least one internucleoside linking group within the seed region of the RNAi antisense modified oligonucleotide is an internucleoside linking group of Formula XVII.

Embodiment 458. The RNAi agent of any of embodiments 450-457, wherein at least one region of the RNAi antisense modified oligonucleotide has structure A, B, C, D, or E.

Embodiment 459. The RNAi agent of embodiment 458, wherein at least one region having structure A, B, C, D, or E is within the seed region of the RNAi antisense modified oligonucleotide.

Embodiment 460. The RNAi agent of embodiment 458, wherein at least one region having structure A, B, C, D, or E is at the 3' end of the RNAi antisense modified oligonucleotide.

Embodiment 461. The RNAi agent of any of embodiments 450-457, wherein at least one region of the RNAi antisense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

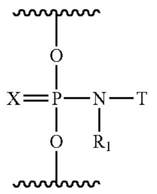

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 462. The RNAi agent of embodiment 461, wherein at least one region having the formula $(N_{g1})_{L1}(N_{g2})_{L2}(N_{g3})_{L3}$ is at the 3' end of the RNAi antisense modified oligonucleotide.

Embodiment 463. The RNAi agent of embodiment 461, wherein at least one region having the formula $(N_{g1})_{L1}(N_{g2})_{L2}(N_{g3})_{L3}$ is within the seed region of the RNAi antisense modified oligonucleotide.

Embodiment 464. The RNAi agent of embodiment 450 or 452-463 wherein at least one internucleoside linking group of the RNAi sense modified oligonucleotide is an internucleoside linking group of Formula XVII.

Embodiment 465. The RNAi agent of embodiment 464, wherein at least one of the first 5 internucleoside linking groups from the 5'-end of the RNAi sense modified oligonucleotide is an internucleoside linking group of Formula XVII.

Embodiment 466. The RNAi agent of any of embodiments 464-465, wherein at least one of the five 3'-most internucleoside linking groups of the RNAi sense modified oligonucleotide is an internucleoside linking group of Formula XVII.

Embodiment 467. The RNAi agent of any of embodiments 464-466, wherein at least one of the first 5 internucleoside linking groups from the 5'-end of the RNAi sense modified oligonucleotide and at least one of the five 3'-most linking groups of the RNAi sense modified oligonucleotide is an internucleoside linking group of Formula XVII.

Embodiment 468. The RNAi agent of any of embodiments 464-467, wherein at least one region of the RNAi sense modified oligonucleotide has structure A, B, C, D, or E.

Embodiment 469. The RNAi agent of embodiment 468, wherein at least one region having structure A, B, C, D, or E is at the 3' end of the RNAi sense modified oligonucleotide.

Embodiment 470. The RNAi agent of embodiment 468, wherein at least one region having structure A, B, C, D, or E is at the 5' end of the RNAi sense modified oligonucleotide.

Embodiment 471. The RNAi agent of any of embodiments 464-467, wherein at least one region of the RNAi sense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

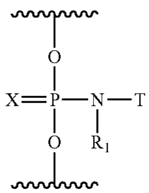

wherein $L_3$ is absent or is phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 472. The RNAi agent of embodiment 471, wherein at least one region having the formula $(N_{g1})_{L1}(N_{g2})_{L2}(N_{g3})_{L3}$ is at the 3' end of the RNAi sense modified oligonucleotide.

Embodiment 473. The RNAi agent of embodiment 471, wherein at least one region having the formula $(N_{g1})_{L1}(N_{g2})_{L2}(N_{g3})_{L3}$ is at the 5' end of the RNAi sense modified oligonucleotide.

Embodiment 474. The modified oligonucleotide of any of embodiments 311-443, wherein each nucleoside of the modified oligonucleotide is a modified nucleoside comprising a modified sugar moiety.

Embodiment 475. The modified oligonucleotide of embodiment 474, wherein each modified sugar moiety is independently selected from a bicyclic sugar moiety and a 2'-substituted furanosyl sugar moiety.

Embodiment 476. The modified oligonucleotide of embodiment 474 or 475, wherein each modified sugar moiety comprises the same modification.

Embodiment 477. The modified oligonucleotide of any of embodiments 474-476, wherein each modified sugar moiety is selected from a 2'-OMe sugar moiety, a 2'-MOE sugar moiety, and a 2'-NMA sugar moiety.

Embodiment 478. The modified oligonucleotide of embodiment 476 or 477, wherein the three 3'-most nucleosides comprise a bicyclic sugar moiety, and the remaining nucleosides comprise a 2'-substituted furanosyl sugar moiety.

Embodiment 479. The modified oligonucleotide of embodiment 476 or 477, wherein the four 3'-most nucleosides comprise a bicyclic sugar moiety, and the remaining nucleosides comprise a 2'-substituted furanosyl sugar moiety.

Embodiment 480. The modified oligonucleotide of embodiment 476 or 477, wherein the five 3'-most nucleosides comprise a bicyclic sugar moiety, and the remaining nucleosides comprise a 2'-substituted furanosyl sugar moiety.

Embodiment 481. The modified oligonucleotide of embodiment 476 or 477, wherein the six 3'-most nucleosides comprise a bicyclic sugar moiety, and the remaining nucleosides comprise a 2'-substituted furanosyl sugar moiety.

Embodiment 482. The modified oligonucleotide of any of embodiments 476 or 478-481, wherein each bicyclic sugar moiety is selected from among cEt, LNA, and ENA.

Embodiment 483. The modified oligonucleotide of embodiment 482, wherein the bicyclic sugar moiety is cEt.

Embodiment 484. The modified oligonucleotide of any of embodiments 476 or 478-481, wherein the 2'-substituted furanosyl sugar moiety is selected from 2'-OMe, 2'-MOE, and 2'-F.

Embodiment 485. The modified oligonucleotide of any of embodiments 474-484, wherein at least one of the ten 5'-most linking groups of the modified oligonucleotide is an internucleoside linking group of Formula XVII.

Embodiment 486. The modified oligonucleotide of embodiment 485, wherein at least 2 of the ten 5'-most linking groups of the modified oligonucleotide are internucleoside linking groups of Formula XVII.

Embodiment 487. The modified oligonucleotide of embodiment 485, wherein at least 3 of the ten 5'-most linking groups of the modified oligonucleotide are internucleoside linking groups of Formula XVII.

Embodiment 488. The modified oligonucleotide of embodiment 485, wherein at least 4 of the ten 5'-most linking groups of the modified oligonucleotide are internucleoside linking groups of Formula XVII.

Embodiment 489. The modified oligonucleotide of embodiment 485, wherein at least 5 of the ten 5'-most linking groups of the modified oligonucleotide are internucleoside linking groups of Formula XVII.

Embodiment 490. The modified oligonucleotide of embodiment 485, wherein at least 6 of the ten 5'-most linking groups of the modified oligonucleotide are internucleoside linking groups of Formula XVII.

Embodiment 491. The modified oligonucleotide of embodiment 485, wherein the two 5'-most internucleoside linking groups are internucleoside linking groups of Formula XVII.

Embodiment 492. The modified oligonucleotide of any of embodiments 478-491, wherein at least one of the ten 3'-most internucleoside linking groups of the modified oligonucleotide is an internucleoside linking group of Formula XVII.

Embodiment 493. The modified oligonucleotide of embodiment 492, wherein at least 2 of the ten 3'-most internucleoside linking groups of the modified oligonucleotide are internucleoside linking groups of Formula XVII.

Embodiment 494. The modified oligonucleotide of embodiment 492, wherein at least 3 of the ten 3'-most internucleoside linking groups are internucleoside linking groups of Formula XVII.

Embodiment 495. The modified oligonucleotide of embodiment 492, wherein at least 4 of the ten 3'-most internucleoside linking groups are internucleoside linking groups of Formula XVII.

Embodiment 496. The modified oligonucleotide of embodiment 492, wherein at least 5 of the ten 3'-most internucleoside linking groups are internucleoside linking groups of Formula XVII.

Embodiment 497. The modified oligonucleotide of embodiment 492, wherein at least 6 of the ten 3'-most internucleoside linking groups are internucleoside linking groups of Formula XVII.

Embodiment 498. The modified oligonucleotide of embodiment 492, wherein the two 3'-most internucleoside linking groups of the modified oligonucleotide are internucleoside linking groups of Formula XVII.

Embodiment 499. The modified oligonucleotide of any of embodiments 474-484, wherein the modified oligonucleotide comprises at least one block of at least 3 consecutive internucleoside linking groups of Formula XVII.

Embodiment 500. The modified oligonucleotide of any of embodiments 474-484, wherein the modified oligonucleotide comprises at least one block of at least 4 consecutive internucleoside linking groups of Formula XVII.

Embodiment 501. The modified oligonucleotide of any of embodiments 474-484, wherein the modified oligonucleotide comprises at least one block of at least 5 consecutive internucleoside linking groups of Formula XVII.

Embodiment 502. The modified oligonucleotide of any of embodiments 474-484, wherein the modified oligonucleotide comprises at least one block of at least 6 consecutive internucleoside linking groups of Formula XVII.

Embodiment 503. The modified oligonucleotide of any of embodiments 499-502, wherein at least one block of consecutive internucleoside linking groups of Formula XVII is at the 5' end of the modified oligonucleotide.

Embodiment 504. The modified oligonucleotide of any of embodiments 499-502, wherein at least one block of consecutive internucleoside linking groups of Formula XVII is at the 3' end of the modified oligonucleotide.

Embodiment 505. The modified oligonucleotide of any of embodiments 311-443, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 506. The modified oligonucleotide of embodiment 505, wherein at least 4 contiguous nucleosides of the deoxy region are stereo-standard DNA nucleosides.

Embodiment 507. The modified oligonucleotide of embodiment 505, wherein at least 5 contiguous nucleosides of the deoxy region are stereo-standard DNA nucleosides.

Embodiment 508. The modified oligonucleotide of embodiment 505, wherein at least 6 contiguous nucleosides of the deoxy region are stereo-standard DNA nucleosides.

Embodiment 509. The modified oligonucleotide of embodiment 505, wherein at least 7 contiguous nucleosides of the deoxy region are stereo-standard DNA nucleosides.

Embodiment 510. The modified oligonucleotide of embodiment 505, wherein at least 8 contiguous nucleosides of the deoxy region are stereo-standard DNA nucleosides.

Embodiment 511. The modified oligonucleotide of any of embodiments 505-510, wherein the deoxy region consists of 8-10 linked nucleosides.

Embodiment 512. The modified oligonucleotide of any of embodiments 505-510, wherein the deoxy region consists of 9 linked nucleosides.

Embodiment 513. The modified oligonucleotide of any of embodiments 505-510, wherein the deoxy region consists of 10 linked nucleosides.

Embodiment 514. The modified oligonucleotide of any of embodiments 505-510, wherein the deoxy region consists of 11 linked nucleosides.

Embodiment 515. The modified oligonucleotide of any of embodiments 505-510, wherein at least 6 nucleosides of the deoxy region are stereo-standard DNA nucleosides.

Embodiment 516. The modified oligonucleotide of any of embodiments 505-510, wherein at least 7 nucleosides of the deoxy region are stereo-standard DNA nucleosides.

Embodiment 517. The modified oligonucleotide of any of embodiments 505-510, wherein at least 8 nucleosides of the deoxy region are stereo-standard DNA nucleosides.

Embodiment 518. The modified oligonucleotide of any of embodiments 505-510, wherein at least 9 nucleosides of the deoxy region are stereo-standard DNA nucleosides.

Embodiment 519. The modified oligonucleotide of any of embodiments 505-518 wherein two nucleosides of the deoxy region are modified nucleosides.

Embodiment 520. The modified oligonucleotide of any of embodiments 505-518 wherein one nucleoside of the deoxy region is a modified nucleoside.

Embodiment 521. The modified oligonucleotide of any of embodiments 505-520 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 522. The modified oligonucleotide of any of embodiments 505-520 wherein at least one modified nucleoside of the deoxy region is stereo-non-standard nucleoside.

Embodiment 523. The modified oligonucleotide of embodiment 522 wherein the at least one is stereo-non-standard nucleoside of the deoxy region is a stereo-non-standard DNA nucleoside.

Embodiment 524. The modified oligonucleotide of embodiment 523 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 525. The modified oligonucleotide of embodiment 524 wherein the stereo-non-standard DNA nucleoside is selected from a stereo-non-standard DNA nucleoside having: Formula V and Formula II.

Embodiment 526. The modified oligonucleotide of embodiment 525 wherein at least one stereo-non-standard nucleoside of the deoxy region is a substituted stereo-non-standard nucleoside.

Embodiment 527. The modified oligonucleotide of embodiment 526 wherein at least one substituted stereo-non-standard nucleoside has a 2'-substituent selected from: 2'-MOE, 2'-OMe, 2'-F, or 2'-OH.

Embodiment 528. The modified oligonucleotide of any of embodiments 505-527, wherein the $2^{nd}$ nucleoside from the 5'-end of the deoxy region is a modified nucleoside.

Embodiment 529. The modified oligonucleotide of any of embodiments 505-527, wherein the $3^{rd}$ nucleoside from the 5'-end of the deoxy region is a modified nucleoside.

Embodiment 530. The modified oligonucleotide of any of embodiments 505-527, wherein the $4^{th}$ nucleoside from the 5'-end of the deoxy region is a modified nucleoside.

Embodiment 531. The modified oligonucleotide of any of embodiments 528-530, wherein the modified nucleoside in the deoxy region is a 2'-OMe nucleoside.

Embodiment 532. The modified oligonucleotide of any of embodiments 505-518, wherein each nucleoside of the deoxy region is a stereo-standard DNA nucleoside.

Embodiment 533. The modified oligonucleotide of any of embodiments 505-532 wherein at least one internucleoside linking group within the deoxy region is an internucleoside linking group of Formula XVII.

Embodiment 534. The modified oligonucleotide of any of embodiments 505-532, wherein the internucleoside linking group linking the $1^{st}$ and $2^{nd}$ nucleosides of the deoxy region as counted from the 5'-end of the deoxy region is an internucleoside linking group of Formula XVII.

Embodiment 535. The modified oligonucleotide of any of embodiments 505-534, wherein the internucleoside linking group linking the $2^{nd}$ and $3^{rd}$ nucleosides of the deoxy region as counted from the 5'-end of the deoxy region is an internucleoside linking group of Formula XVII.

Embodiment 536. The modified oligonucleotide of any of embodiments 505-535, wherein the internucleoside linking group linking the $3^{rd}$ and $4^{th}$ nucleosides of the deoxy region as counted from the 5'-end of the deoxy region is an internucleoside linking group of Formula XVII.

Embodiment 537. The modified oligonucleotide of any of embodiments 505-536, wherein the internucleoside linking group linking the $4^{th}$ and $5^{th}$ nucleosides of the deoxy region as counted from the 5'-end of the deoxy region is an internucleoside linking group of Formula XVII.

Embodiment 538. The modified oligonucleotide of any of embodiments 505-537, wherein one internucleoside linking group in the deoxy region is a linking group of Formula XVII and the other internucleoside linking groups of the deoxy region are each phosphodiester or phosphorothioate internucleoside linking groups.

Embodiment 539. The modified oligonucleotide of any of embodiments 505-537, wherein two internucleoside linking groups in the deoxy region are linking groups of Formula XVII and the other internucleoside linking groups of the deoxy region are each phosphodiester or phosphorothioate internucleoside linking groups.

Embodiment 540. The modified oligonucleotide of any of embodiments 505-537, wherein three internucleoside linking groups in the deoxy region are linking groups linking groups of Formula XVII and the other internucleoside linking groups of the deoxy region are each phosphodiester or phosphorothioate internucleoside linking groups.

Embodiment 541. The modified oligonucleotide of any of embodiments 505-540, wherein the deoxy region comprises at least one region having structure A, B, C, D, or E.

Embodiment 542. The modified oligonucleotide of embodiment 541, wherein the region having structure A, B, C, D, or E is at the 3' end of the deoxy region.

Embodiment 543. The modified oligonucleotide of embodiment 541, wherein the region having structure A, B, C, D, or E is at the 5' end of the deoxy region.

Embodiment 544. The modified oligonucleotide of any of embodiments 505-540, wherein the deoxy region comprises at least one region having the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

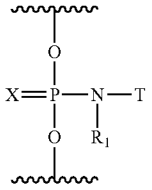

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 545. The modified oligonucleotide of any of embodiments 544, wherein the region having the formula $(N_{g1})_{L1}(N_{g2})_{L2}(N_{g3})_{L3}$ is at the 3' end of the deoxy region.

Embodiment 546. The modified oligonucleotide of any of embodiments 544, wherein the region having the formula $(N_{g1})_{L1}(N_{g2})_{L2}(N_{g3})_{L3}$ is at the 5' end of the deoxy region.

Embodiment 547. The modified oligonucleotide of any of embodiments 505-546 wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region is a modified nucleoside; and the 5'-most nucleoside of the 3'-region is a modified nucleoside.

Embodiment 548. The modified oligonucleotide of embodiment 547, wherein the deoxy region consists of 7-11 linked nucleosides, and has the formula:

$(N_{d1})_{L1}(N_{d2})_{L2}(N_{d3})_{L3}(N_{d4})_{L4}[(N_d)_{L5}]_q$;

wherein $N_{d1}$, $Na_2$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $Na_2$, $N_{d3}$, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, $L_4$ are internucleoside linkages of Formula XVII.

Embodiment 549. The modified oligonucleotide of embodiment 548, wherein one of $N_{d1}$, $Na_2$, $N_{d3}$, or $N_{d4}$ is a 2'-substituted nucleoside.

Embodiment 550. The modified oligonucleotide of embodiment 549, wherein the 2'-substituted nucleoside is a 2'-OMe nucleoside.

Embodiment 551. The modified oligonucleotide of embodiment 550, wherein the 2'-OMe nucleoside is a stereo-standard 2'-OMe nucleoside.

Embodiment 552. The modified oligonucleotide of any of embodiments 548-551, wherein the 2'-substituted nucleoside is $N_{d2}$.

Embodiment 553. The modified oligonucleotide of embodiment 548, wherein each of $N_{d1}$, $N_{d2}$, $N_{d3}$, $N_{d4}$ and each $N_d$ is a DNA nucleoside.

Embodiment 554. The modified oligonucleotide of embodiment 553, wherein each DNA nucleoside is a stereo-standard DNA nucleoside.

Embodiment 555. The modified oligonucleotide of any of embodiments 548-554, wherein $L_1$ and $L_2$ are internucleoside linkages of Formula XVII.

Embodiment 556. The modified oligonucleotide of any of embodiments 548-554, wherein $L_2$ and $L_3$ are internucleoside linkages of Formula XVII.

Embodiment 557. The modified oligonucleotide of any of embodiments 548-554, wherein $L_3$ and $L_4$ are internucleoside linkages of Formula XVII.

Embodiment 558. The modified oligonucleotide of any of embodiments 548-554, wherein $L_1$, $L_2$, and $L_3$ are internucleoside linkages of Formula XVII.

Embodiment 559. The modified oligonucleotide of any of embodiments 548-554, wherein $L_2$, $L_3$, and $L_4$, are internucleoside linkages of Formula XVII.

Embodiment 560. The modified oligonucleotide of any of embodiments 548-554, wherein $L_1$, $L_2$, $L_3$, and $L_4$ are internucleoside linkages of Formula XVII.

Embodiment 561. The modified oligonucleotide of any of embodiments 547-560, wherein the 5'-region consists of 2-5 linked nucleosides.

Embodiment 562. The modified oligonucleotide of embodiment 561, wherein the 5'-region consists of 3 linked nucleosides.

Embodiment 563. The modified oligonucleotide of embodiment 561, wherein the 5'-region consists of 5 linked nucleosides.

Embodiment 564. The modified oligonucleotide of any of embodiments 547-563 wherein each nucleoside of the 5'-region is a modified nucleoside.

Embodiment 565. The modified oligonucleotide of any of embodiments 547-564, wherein each nucleoside of the 5'-region is a modified nucleoside comprising a modified sugar.

Embodiment 566. The modified oligonucleotide of any of embodiments 547-565, wherein at least one nucleoside of the 5'-region comprises a 2'-substituted furanosyl sugar moiety.

Embodiment 567. The modified oligonucleotide of any of embodiments 547-566, wherein each nucleoside of the 5'-region comprises a 2'-substituted furanosyl sugar moiety.

Embodiment 568. The modified oligonucleotide of any or embodiments 547-567, wherein each 2'-substituted furanosyl sugar moiety of the 5'-region has a 2'-substituent selected from among 2'-MOE, 2'-OMe, and 2'-NMA.

Embodiment 569. The modified oligonucleotide of any of embodiments 547-566 or 568, wherein at least one nucleoside of the 5'-region comprises a bicyclic furanosyl sugar moiety.

Embodiment 570. The modified oligonucleotide of any of embodiments 547-566 or 568-569, wherein each nucleoside of the 5'-region comprises a bicyclic furanosyl sugar moiety.

Embodiment 571. The modified oligonucleotide of embodiment 569 or 570, wherein each bicyclic sugar moiety of the 5'-region is selected from among cEt, LNA, and ENA.

Embodiment 572. The modified oligonucleotide of embodiment 571, wherein each bicyclic sugar moiety of the 5'-region is a cEt sugar moiety.

Embodiment 573. The modified oligonucleotide of any of embodiments 547-563, 566 or 569, wherein at least one nucleoside of the 5' region is a stereo-standard DNA nucleoside.

Embodiment 574. The modified oligonucleotide of any of embodiments 547-572, wherein at least one nucleoside of the 5' region is a stereo-non-standard nucleoside.

Embodiment 575. The modified oligonucleotide of any of embodiments 547-574, wherein each nucleobase of the 5'-region is independently selected from among thymine, uracil, guanine, cytosine, 5-methylcytosine, and adenine.

Embodiment 576. The modified oligonucleotide of any of embodiments 547-575, wherein the 3'-region consists of 2-5 linked nucleosides.

Embodiment 577. The modified oligonucleotide of embodiment 576, wherein the 3'-region consists of 3 linked nucleosides.

Embodiment 578. The modified oligonucleotide of embodiment 576, wherein the 3'-region consists of 5 linked nucleosides.

Embodiment 579. The modified oligonucleotide of any of embodiments 547-578, wherein each nucleoside of the 3'-region is a modified nucleoside.

Embodiment 580. The modified oligonucleotide of any of embodiments 547-578, wherein each nucleoside of the 3'-region is a modified nucleoside comprising a modified sugar.

Embodiment 581. The modified oligonucleotide of any of embodiments 547-580, wherein at least one nucleoside of the 3'-region comprises a 2'-substituted furanosyl sugar moiety.

Embodiment 582. The modified oligonucleotide of any of embodiments 547-581, wherein each nucleoside of the 3'-region comprises a 2'-substituted furanosyl sugar moiety.

Embodiment 583. The modified oligonucleotide of any or embodiments 547-582, wherein each 2'-substituted furanosyl sugar moiety of the 3'-region has a 2'-substituent selected from among 2'-MOE, 2'-OMe, and 2'-NMA.

Embodiment 584. The modified oligonucleotide of any of embodiments 547-581 or 583, wherein at least one nucleoside of the 3'-region comprises a bicyclic furanosyl sugar moiety.

Embodiment 585. The modified oligonucleotide of any of embodiments 547-580 or 584, wherein each nucleoside of the 3'-region comprises a bicyclic furanosyl sugar moiety.

Embodiment 586. The modified oligonucleotide of embodiment 584 or 585, wherein each bicyclic sugar moiety of the 3'-region is selected from among cEt, LNA, and ENA.

Embodiment 587. The modified oligonucleotide of embodiment 586, wherein each bicyclic sugar moiety of the 3'-region is a cEt sugar moiety.

Embodiment 588. The modified oligonucleotide of any of embodiments 547-578, 581 or 584, wherein at least one nucleoside of the 3' region is a stereo-standard DNA nucleoside.

Embodiment 589. The modified oligonucleotide of any of embodiments 547-588, wherein at least one nucleoside of the 3' region is a stereo-non-standard nucleoside.

Embodiment 590. The modified oligonucleotide of any of embodiments 547-589, wherein each nucleobase of the 3'-region is independently selected from among thymine, uracil, guanine, cytosine, 5-methylcytosine, and adenine.

Embodiment 591. The modified oligonucleotide of any of embodiments 547-590 wherein the modified oligonucleotide is a gapmer.

Embodiment 592. The modified oligonucleotide of any of embodiments 311-432, wherein the modified oligonucleotide is a CRISPR compound.

Embodiment 593. The modified oligonucleotide of embodiment 592, wherein the CRISPR compound consists of 20-50 linked nucleosides.

Embodiment 594. The modified oligonucleotide of embodiment 592, wherein the CRISPR compound consists of 29-32 linked nucleosides.

Embodiment 595. The modified oligonucleotide of any of embodiments 311-432, wherein the modified oligonucleotide is an artificial mRNA compound.

Embodiment 596. The artificial mRNA compound of embodiment 595, wherein the artificial mRNA oligonucleotide consists of 17-3000 linked nucleosides.

Embodiment 597. The artificial mRNA compound of embodiment 595 or 596, wherein the artificial mRNA oligonucleotide encodes a protein.

Embodiment 598. The modified oligonucleotide of any of embodiments 396-597, wherein each X is O.

Embodiment 599. The modified oligonucleotide of any of embodiments 396-597, wherein each X is S.

Embodiment 600. The modified oligonucleotide of any of embodiments 396-599, wherein at least one $R_1$ is H.

Embodiment 601. The modified oligonucleotide of any of embodiments 396-599, wherein at least one $R_1$ is a $C_1$-$C_6$ alkyl.

Embodiment 602. The modified oligonucleotide of embodiment 601, wherein the at least one $R_1$ is methyl.

Embodiment 603. The modified oligonucleotide of any of embodiments 396-602, at least one $R_1$ is a substituted $C_1$-$C_6$ alkyl.

Embodiment 604. The modified oligonucleotide of any of embodiments 396-603, wherein at least one T comprises a conjugate group.

Embodiment 605. The modified oligonucleotide of embodiment 604, wherein the conjugate group comprises a carbohydrate or carbohydrate cluster.

Embodiment 606. The modified oligonucleotide of embodiment 604 or 605, wherein the conjugate group comprises at least one GalNAc.

Embodiment 607. The modified oligonucleotide of embodiment 604, wherein the conjugate group comprises a $C_{10}$-$C_{20}$ alkyl chain.

Embodiment 608. The modified oligonucleotide of embodiment 607, wherein the conjugate group comprises $C_{16}$ alkyl.

Embodiment 609. The modified oligonucleotide of any of embodiments 396-603, wherein at least one T does not comprise a conjugate group.

Embodiment 610. The modified oligonucleotide of any of embodiments 396-603, wherein each T does not comprise a conjugate group.

Embodiment 611. The modified oligonucleotide of any of embodiments 396-603, wherein at least one T is $SO_2R_2$.

Embodiment 612. The modified oligonucleotide of embodiment 611, wherein $R_2$ is an aryl.

Embodiment 613. The modified oligonucleotide of embodiment 611, wherein $R_2$ is a substituted aryl.

Embodiment 614. The modified oligonucleotide of embodiment 611, wherein $R_2$ is a heterocycle.

Embodiment 615. The modified oligonucleotide of embodiment 611, wherein $R_2$ is a substituted heterocycle.

Embodiment 616. The modified oligonucleotide of embodiment 611, wherein $R_2$ is an aromatic heterocycle.

Embodiment 617. The modified oligonucleotide of embodiment 611, wherein $R_2$ is a substituted aromatic heterocycle.

Embodiment 618. The modified oligonucleotide of embodiment 611, wherein $R_2$ is a diazole.

Embodiment 619. The modified oligonucleotide of embodiment 611, wherein $R_2$ is a substituted diazole.

Embodiment 620. The modified oligonucleotide of embodiment 611, wherein $R_2$ is an amine.

Embodiment 621. The modified oligonucleotide of embodiment 611, wherein $R_2$ is a substituted amine.

Embodiment 622. The modified oligonucleotide of embodiment 611, wherein $R_2$ is a $C_1$-$C_6$ alkoxy, $C_1$-$C_6$ alkenyl, or $C_1$-$C_6$ alkynyl.

Embodiment 623. The modified oligonucleotide of embodiment 611, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 624. The modified oligonucleotide of embodiment 611, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 625. The modified oligonucleotide of embodiment 611, wherein $R_2$ comprises a carbohydrate or carbohydrate cluster.

Embodiment 626. The modified oligonucleotide of embodiment 611, wherein $R_2$ comprises at least one GalNAc.

Embodiment 627. The modified oligonucleotide of embodiment 611, wherein T is:

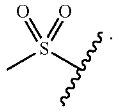

Embodiment 628. The modified oligonucleotide of embodiment 611, wherein T is:

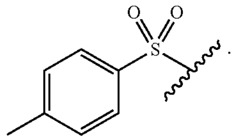 [SMILES: *S(=O)(=O)c1ccc(C)cc1]

Embodiment 629. The modified oligonucleotide of embodiment 611, wherein T is:

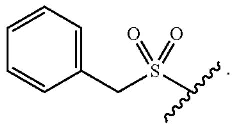 [SMILES: *S(=O)(=O)Cc1ccccc1]

Embodiment 630. The modified oligonucleotide of embodiment 611, wherein T is:

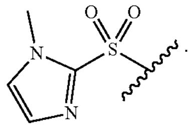 [SMILES: *S(=O)(=O)c1nccn1C]

Embodiment 631. The modified oligonucleotide of embodiment 611, wherein T is:

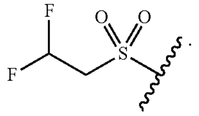 [SMILES: *S(=O)(=O)CC(F)F]

Embodiment 632. The modified oligonucleotide of embodiment 611, wherein T is:

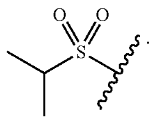 [SMILES: *S(=O)(=O)C(C)C]

Embodiment 633. The modified oligonucleotide of embodiment 611, wherein T is:

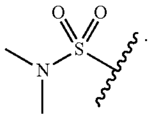

Embodiment 634. The modified oligonucleotide of embodiment 611, wherein T is:

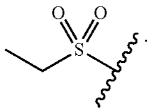 [SMILES: *S(=O)(=O)CC]

Embodiment 635. The modified oligonucleotide of embodiment 611, wherein T is:

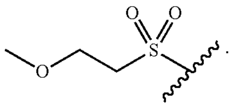 [SMILES: *S(=O)(=O)CCOC]

Embodiment 636. The modified oligonucleotide of embodiment 611, wherein T is:

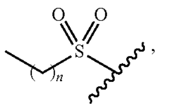

wherein n is from 2 to 20.

Embodiment 637. The modified oligonucleotide of embodiment 636, wherein n is 15.

Embodiment 638. The modified oligonucleotide of any of embodiments 396-603, wherein at least one T is $C(=O)R_3$.

Embodiment 639. The modified oligonucleotide of embodiment 638, wherein $R_3$ is an aryl.

Embodiment 640. The modified oligonucleotide of embodiment 638, wherein $R_3$ is a substituted aryl.

Embodiment 641. The modified oligonucleotide of embodiment 638, wherein $R_3$ is $CH_3$.

Embodiment 642. The modified oligonucleotide of embodiment 638, wherein $R_3$ is $N(CH_3)_2$.

Embodiment 643. The modified oligonucleotide of embodiment 638, wherein $R_3$ is $OCH_3$.

Embodiment 644. The modified oligonucleotide of embodiment 638, wherein $R_3$ is a $C_1$-$C_6$ alkoxy.

Embodiment 645. The modified oligonucleotide of embodiment 638, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 646. The modified oligonucleotide of embodiment 638, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 647. The modified oligonucleotide of embodiment 638, wherein $R_3$ comprises a carbohydrate or carbohydrate cluster.

Embodiment 648. The modified oligonucleotide of embodiment 638, wherein $R_{23}$ comprises at least one GalNAc.

Embodiment 649. The modified oligonucleotide of embodiment 638, wherein T is:

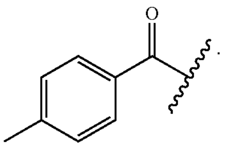 [SMILES: *C(=O)c1ccc(C)cc1]

Embodiment 650. The modified oligonucleotide of embodiment 638, wherein T is:

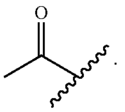 [SMILES: *C(C)=O]

Embodiment 651. The modified oligonucleotide of embodiment 638, wherein T is:

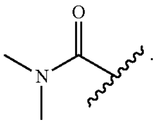 [SMILES: *C(=O)N(C)C]

Embodiment 652. The modified oligonucleotide of embodiment 638, wherein T is:

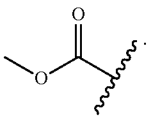

Embodiment 653. The modified oligonucleotide of embodiment 638, wherein T is:

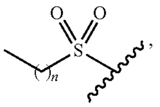

wherein n is from 2 to 20.

Embodiment 654. The modified oligonucleotide of embodiment 653, wherein n is 15.

Embodiment 655. The modified oligonucleotide of any of embodiments 396-603, wherein at least one T is $P(=O)R_4R_5$.

Embodiment 656. The modified oligonucleotide of embodiment 655, wherein $R_4$ is $OCH_3$.

Embodiment 657. The modified oligonucleotide of embodiment 655, wherein $R_4$ is OH.

Embodiment 658. The modified oligonucleotide of embodiment 655, wherein $R_4$ is $C_1$-$C_6$ alkyl.

Embodiment 659. The modified oligonucleotide of embodiment 655, wherein $R_4$ is substituted $C_1$-$C_6$ alkyl.

Embodiment 660. The modified oligonucleotide of embodiment 655, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 661. The modified oligonucleotide of embodiment 655, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 662. The modified oligonucleotide of embodiment 655, wherein $R_4$ comprises a carbohydrate or carbohydrate cluster.

Embodiment 663. The modified oligonucleotide of embodiment 655, wherein $R_4$ comprises at least one GalNAc.

Embodiment 664. The modified oligonucleotide of any of embodiments 655-663, wherein $R_5$ is $OCH_3$.

Embodiment 665. The modified oligonucleotide of any of embodiments 655-663, wherein $R_5$ is OH.

Embodiment 666. The modified oligonucleotide of any of embodiments 655-663, wherein $R_5$ is $C_1$-$C_6$ alkyl.

Embodiment 667. The modified oligonucleotide of any of embodiments 655-663, wherein $R_5$ is substituted $C_1$-$C_6$ alkyl.

Embodiment 668. The modified oligonucleotide of embodiment 655, wherein T is:

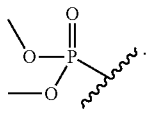 [SMILES: *P(=O)(OC)OC]

Embodiment 669. The modified oligonucleotide of embodiment 655, wherein T is:

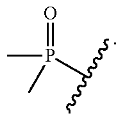

Embodiment 670. The modified oligonucleotide of embodiment 655, wherein T is:

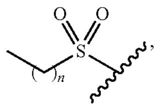

wherein n is from 2 to 20.

Embodiment 671. The modified oligonucleotide of embodiment 670, wherein n is 15.

Embodiment 672. A chirally enriched population of modified oligonucleotides of any of embodiments 311-671, wherein the population is enriched for modified oligonucleotides comprising at least one particular internucleoside linking group having a particular stereochemical configuration.

Embodiment 673. The chirally enriched population of modified oligonucleotides of embodiment 672, wherein the particular internucleoside linking group having a particular stereochemical configuration is an internucleoside linking group of Formula XVIII as indicated in Formula XVIIIa and XVIIIb below:

XVIIIa

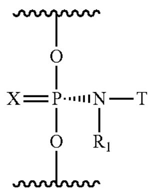

XVIIIb

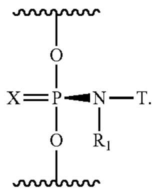

Embodiment 674. The chirally enriched population of modified oligonucleotides of embodiment 672, wherein the particular internucleoside linking group having a particular stereochemical configuration is a phosphorothioate internucleoside linking group.

Embodiment 675. The chirally enriched population of any of embodiments 672-674, wherein the population is enriched for modified oligonucleotides comprising at least one particular internucleoside linkage having the (Sp) configuration.

Embodiment 676. The chirally enriched population of any of embodiments 672-675, wherein the population is enriched for modified oligonucleotides comprising at least one particular internucleoside linkage having the (Rp) configuration.

Embodiment 677. The chirally enriched population of embodiment 672, wherein the population is enriched for modified oligonucleotides having a particular, independently selected stereochemical configuration at each chiral internucleoside linkage.

Embodiment 678. The chirally enriched population of any of embodiments 672-677, wherein the population is enriched for modified oligonucleotides having the (Sp) configuration at each chiral internucleoside linkage.

Embodiment 679. The chirally enriched population of any of embodiments 672-677, wherein the population is enriched for modified oligonucleotides having the (Rp) configuration at each chiral internucleoside linkage.

Embodiment 680. The chirally enriched population of any of embodiments 672-677, wherein the population is enriched for modified oligonucleotides having the (Rp) configuration at one particular chiral internucleoside linkage and the (Sp) configuration at each of the remaining chiral internucleoside linkages.

Embodiment 681. The chirally enriched population of embodiment 673, wherein each phosphorothioate internucleoside linkage is stereorandom.

Embodiment 682. The modified oligonucleotide of any of embodiments 311-681, wherein the nucleobase sequence of the modified oligonucleotide is complementary to a target nucleic acid.

Embodiment 683. The modified oligonucleotide of embodiment 682, wherein the nucleobase sequence of the modified oligonucleotide is at least 80% complementary to the target nucleic acid.

Embodiment 684. The modified oligonucleotide of embodiment 682, wherein the nucleobase sequence of the modified oligonucleotide is at least 85% complementary to the target nucleic acid.

Embodiment 685. The modified oligonucleotide of embodiment 682, wherein the nucleobase sequence of the modified oligonucleotide is at least 90% complementary to the target nucleic acid.

Embodiment 686. The modified oligonucleotide of embodiment 682, wherein the nucleobase sequence of the modified oligonucleotide is at least 95% complementary to the target nucleic acid.

Embodiment 687. The modified oligonucleotide of embodiment 682, wherein the nucleobase sequence of the modified oligonucleotide is 100% complementary to the target nucleic acid.

Embodiment 688. The modified oligonucleotide of any of embodiments 682-687, wherein the target nucleic acid is a target RNA.

Embodiment 689. The modified oligonucleotide of embodiment 688, wherein the target RNA is selected from: an mRNA, a pre-mRNA, a microRNA, and a non-coding RNA.

Embodiment 690. The modified oligonucleotide of embodiment 688, wherein the target RNA is not a microRNA.

Embodiment 691. The modified oligonucleotide of any of embodiments 311-690, wherein the modified oligonucleotide is not complementary to miR-21.

Embodiment 692. The modified oligonucleotide of any of embodiments 311-691, comprising a conjugate group.

Embodiment 693. The modified oligonucleotide of embodiment 692, wherein the conjugate group comprises at least one GalNAc.

Embodiment 694. The modified oligonucleotide of embodiment 692 or 693, wherein the conjugate group comprises 1-5 linker-nucleosides.

Embodiment 695. A pharmaceutical composition comprising the modified oligonucleotide of any of embodiments 311-694 and a pharmaceutically acceptable carrier or diluent.

Embodiment 696. A method comprising contacting a cell with the modified oligonucleotide or pharmaceutical composition of any of embodiments 311-695.

Embodiment 697. A method of modulating the amount or activity of a target nucleic acid in a cell, comprising contacting the cell with the modified oligonucleotide or pharmaceutical composition of any of embodiments 311-695 and thereby modulating the amount or activity of the target nucleic acid.

Embodiment 698. A method of modulating the amount or activity of a target nucleic acid in a cell, comprising contacting the cell with the modified oligonucleotide or pharmaceutical composition of any of embodiments 311-695.

Embodiment 699. The method of embodiments 696-698, wherein the amount or activity of a target nucleic acid is reduced.

Embodiment 700. The method of embodiments 696-698, wherein the amount or activity of a target nucleic acid is increased.

Embodiment 701. The method of embodiment 700, wherein the target protein is encoded by a target nucleic acid comprising at least one translation suppression element and wherein the modified oligonucleotide is complementary to a target site within a translation suppression element region of the target nucleic acid.

Embodiment 702. The method of embodiment 701, wherein the translation suppression element region comprises at least one stem-loop structure.

Embodiment 703. Use of the modified oligonucleotide or composition of any of embodiments 311-695 for treatment of a disease or condition.

Embodiment 704. Use of the modified oligonucleotide or composition of any of embodiments 311-695 for a preparation of a medicament for treatment of a disease or condition.

Embodiment 705. An antisense agent comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVII:

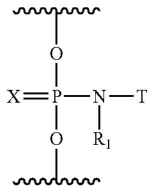

XVII wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

Embodiment 706. An antisense agent comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVII:

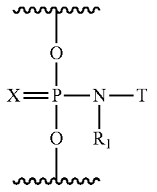

XVII wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, C(═O)$R_3$, and P(═O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl, Provided that if X is 0 and that if $R_1$ is H, then T is not:

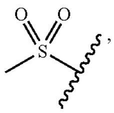,
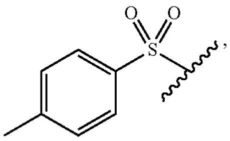,
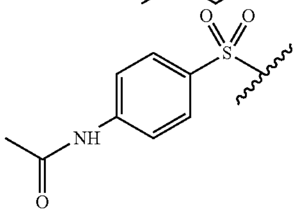,
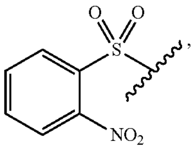,
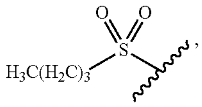, or
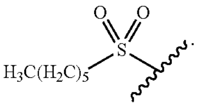.

Embodiment 707. The antisense agent of embodiment 705 or embodiment 706, wherein at least one internucleoside linking group is a phosphodiester or a phosphorothioate internucleoside linking group.

Embodiment 708. The antisense agent of any of embodiments 705-707, wherein at least one nucleoside comprises a 2'-β-D-deoxyribosyl sugar moiety.

Embodiment 709. The modified oligonucleotide of any of embodiments 705-708, wherein for at least one internucleoside linking group of Formula XVII, X is O.

Embodiment 710. The modified oligonucleotide of any of embodiments 705-709, wherein for at least one internucleoside linking group of Formula XVII, X is S.

Embodiment 711. The modified oligonucleotide of embodiment 705 or 706, wherein for at least one internucleoside linking group of Formula XVII, $R_1$ is H.

Embodiment 712. The modified oligonucleotide of embodiment 705 or 706, wherein for at least one internucleoside linking group of Formula XVII, $R_1$ is a $C_1$-$C_6$ alkyl.

Embodiment 713. The modified oligonucleotide of embodiment 710, wherein $R_1$ is methyl.

Embodiment 714. The modified oligonucleotide of embodiment 705 or 706, wherein for at least one internucleoside linking group of Formula XVII, $R_1$ is a substituted $C_1$-$C_6$ alkyl.

Embodiment 715. The modified oligonucleotide of any of embodiments 705-714, wherein for at least one internucleoside linking group of Formula XVII, T comprises a conjugate group.

Embodiment 716. The modified oligonucleotide of embodiment 715, wherein the conjugate group comprises a cell-targeting moiety.

Embodiment 717. The modified oligonucleotide of embodiment 715, wherein the conjugate group comprises a carbohydrate or carbohydrate cluster.

Embodiment 718. The modified oligonucleotide of any of embodiments 715-717, wherein the conjugate group comprises at least one GalNAc.

Embodiment 719. The modified oligonucleotide of embodiment 715, wherein the conjugate group comprises a $C_{10}$-$C_{20}$ alkyl chain.

Embodiment 720. The modified oligonucleotide of embodiment 719, wherein the conjugate group comprises $C_{16}$ alkyl.

Embodiment 721. The modified oligonucleotide of any of embodiments 705-714, wherein for at least one internucleoside linking group of Formula XVII, T does not comprise a conjugate group.

Embodiment 722. The modified oligonucleotide of any of embodiments 705-714, wherein for at least one internucleoside linking group of Formula XVII, T does not comprise a cell-targeting moiety.

Embodiment 723. The modified oligonucleotide of any of embodiments 705-722, wherein for at least one internucleoside linking group of Formula XVII, T is $SO_2R_2$.

Embodiment 724. The modified oligonucleotide of embodiment 723, wherein $R_2$ is an aryl.

Embodiment 725. The modified oligonucleotide of embodiment 723, wherein $R_2$ is a substituted aryl.

Embodiment 726. The modified oligonucleotide of embodiment 723, wherein $R_2$ is a heterocycle.

Embodiment 727. The modified oligonucleotide of embodiment 723, wherein $R_2$ is a substituted heterocycle.

Embodiment 728. The modified oligonucleotide of embodiment 723, wherein $R_2$ is an aromatic heterocycle.

Embodiment 729. The modified oligonucleotide of embodiment 723, wherein $R_2$ is a substituted aromatic heterocycle.

Embodiment 730. The modified oligonucleotide of embodiment 723, wherein $R_2$ is a diazole.

Embodiment 731. The modified oligonucleotide of embodiment 723, wherein $R_2$ is a substituted diazole.

Embodiment 732. The modified oligonucleotide of embodiment 723, wherein $R_2$ is an amine.

Embodiment 733. The modified oligonucleotide of embodiment 723, wherein $R_2$ is a substituted amine.

Embodiment 734. The modified oligonucleotide of embodiment 723, wherein $R_2$ is a $C_1$-$C_6$ alkoxy, $C_1$-$C_6$ alkenyl, or $C_1$-$C_6$-alkynl.

Embodiment 735. The modified oligonucleotide of embodiment 723, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 736. The modified oligonucleotide of embodiment 723, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 737. The modified oligonucleotide of embodiment 723, wherein $R_2$ comprises a carbohydrate or carbohydrate cluster.

Embodiment 738. The modified oligonucleotide of embodiment 723, wherein $R_2$ comprises at least one GalNAc.

Embodiment 739. The modified oligonucleotide of embodiment 723, wherein T is:

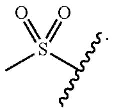

Embodiment 740. The modified oligonucleotide of embodiment 723, wherein T is:

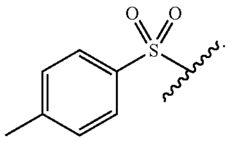 [SMILES: *S(=O)(=O)c1ccc(C)cc1]

Embodiment 741. The modified oligonucleotide of embodiment 723, wherein T is:

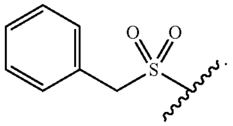 [SMILES: *S(=O)(=O)Cc1ccccc1]

Embodiment 742. The modified oligonucleotide of embodiment 723, wherein T is:

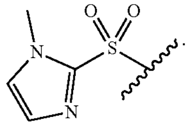 [SMILES: *S(=O)(=O)c1nccn1C]

Embodiment 743. The modified oligonucleotide of embodiment 723, wherein T is:

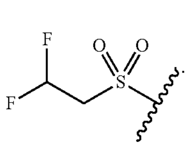 [SMILES: *S(=O)(=O)CC(F)F]

Embodiment 744. The modified oligonucleotide of embodiment 723, wherein T is:

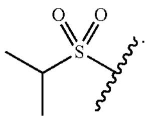 [SMILES: *S(=O)(=O)C(C)C]

Embodiment 745. The modified oligonucleotide of embodiment 723, wherein T is:

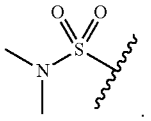

Embodiment 746. The modified oligonucleotide of embodiment 723, wherein T is:

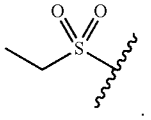

Embodiment 747. The modified oligonucleotide of embodiment 723, wherein T is:

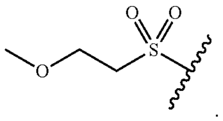 [SMILES: *S(=O)(=O)CCOC]

Embodiment 748. The modified oligonucleotide of embodiment 723, wherein T is:

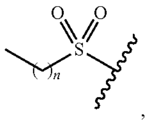

wherein n is from 2 to 20.

Embodiment 749. The modified oligonucleotide of embodiment 748, wherein n is 15.

Embodiment 750. The modified oligonucleotide of any of embodiments 705-722, wherein for at least one internucleoside linking group of Formula XVII, T is C(═O)$R_3$.

Embodiment 751. The modified oligonucleotide of embodiment 750, wherein $R_3$ is an aryl.

Embodiment 752. The modified oligonucleotide of embodiment 750, wherein $R_3$ is a substituted aryl.

Embodiment 753. The modified oligonucleotide of embodiment 750, wherein $R_3$ is $CH_3$.

Embodiment 754. The modified oligonucleotide of embodiment 750, wherein $R_3$ is $N(CH_3)_2$.

Embodiment 755. The modified oligonucleotide of embodiment 750, wherein $R_3$ is $OCH_3$.

Embodiment 756. The modified oligonucleotide of embodiment 750, wherein $R_3$ is a $C_1$-$C_6$ alkoxy.

Embodiment 757. The modified oligonucleotide of embodiment 750, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 758. The modified oligonucleotide of embodiment 750, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 759. The modified oligonucleotide of embodiment 750, wherein $R_3$ comprises a carbohydrate or carbohydrate cluster.

Embodiment 760. The modified oligonucleotide of embodiment 750, wherein $R_{23}$ comprises at least one GalNAc.

Embodiment 761. The modified oligonucleotide of embodiment 750, wherein T is:

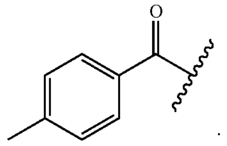 [SMILES: *C(=O)c1ccc(C)cc1]

Embodiment 762. The modified oligonucleotide of embodiment 750, wherein T is:

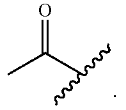 [SMILES: *C(C)=O]

Embodiment 763. The modified oligonucleotide of embodiment 750, wherein T is:

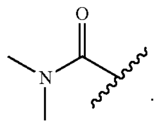 [SMILES: *C(=O)N(C)C]

Embodiment 764. The modified oligonucleotide of embodiment 750, wherein T is:

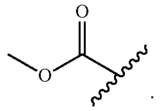 [SMILES: *C(=O)OC]

Embodiment 765. The modified oligonucleotide of embodiment 750, wherein T is:

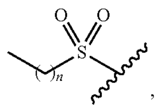

wherein n is from 2 to 20.

Embodiment 766. The modified oligonucleotide of embodiment 765, wherein n is 15.

Embodiment 767. The modified oligonucleotide of any of embodiments 705-722, wherein for at least one internucleoside linking group of Formula XVII, T is P(=O)$R_4R_5$.

Embodiment 768. The modified oligonucleotide of embodiment 767, wherein $R_4$ is $OCH_3$.

Embodiment 769. The modified oligonucleotide of embodiment 767, wherein $R_4$ is OH.

Embodiment 770. The modified oligonucleotide of embodiment 767, wherein $R_4$ is $C_1$-$C_6$ alkyl.

Embodiment 771. The modified oligonucleotide of embodiment 767, wherein $R_4$ is substituted $C_1$-$C_6$ alkyl.

Embodiment 772. The modified oligonucleotide of embodiment 767, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 773. The modified oligonucleotide of embodiment 767, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 774. The modified oligonucleotide of embodiment 767, wherein $R_4$ comprises a carbohydrate or carbohydrate cluster.

Embodiment 775. The modified oligonucleotide of embodiment 767, wherein $R_4$ comprises at least one GalNAc.

Embodiment 776. The modified oligonucleotide of any of embodiments 767-775, wherein $R_5$ is $OCH_3$.

Embodiment 777. The modified oligonucleotide of any of embodiments 767-775, wherein $R_5$ is OH.

Embodiment 778. The modified oligonucleotide of any of embodiments 767-775, wherein $R_5$ is $C_1$-$C_6$ alkyl.

Embodiment 779. The modified oligonucleotide of any of embodiments 767-775, wherein $R_5$ is substituted $C_1$-$C_6$ alkyl.

Embodiment 780. The modified oligonucleotide of embodiment 767, wherein T is:

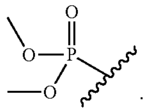

Embodiment 781. The modified oligonucleotide of embodiment 767, wherein T is:

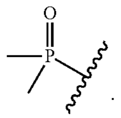 [SMILES: *P(C)(C)=O]

Embodiment 782. The modified oligonucleotide of embodiment 767, wherein T is:

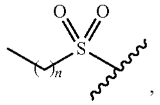

wherein n is from 2 to 20.

Embodiment 783. The modified oligonucleotide of embodiment 782, wherein n is 15.

Embodiment 784. The modified oligonucleotide of any of embodiments 705-783, wherein at least one internucleoside linking group of the modified oligonucleotide is not a linking group of Formula XVII.

Embodiment 785. The modified oligonucleotide of any of embodiments 705-784, wherein exactly one internucleoside linking group of the modified oligonucleotide is an internucleoside linking group of Formula XVII.

Embodiment 786. The modified oligonucleotide of any of embodiments 705-784, wherein exactly two internucleoside linking groups of the modified oligonucleotide are internucleoside linking groups of Formula XVII.

Embodiment 787. The modified oligonucleotide of any of embodiments 705-784, wherein exactly three internucleoside linking groups of the modified oligonucleotide are internucleoside linking groups of Formula XVII.

Embodiment 788. The modified oligonucleotide of any of embodiments 705-784, wherein exactly four internucleoside linking groups of the modified oligonucleotide are internucleoside linking groups of Formula XVII.

Embodiment 789. The modified oligonucleotide of any of embodiments 705-784, wherein exactly five internucleoside linking groups of the modified oligonucleotide are internucleoside linking groups of Formula XVII.

Embodiment 790. The modified oligonucleotide of any of embodiments 705-784, wherein at least six internucleoside linking groups of the modified oligonucleotide are internucleoside linking groups of Formula XVII.

Embodiment 791. The modified oligonucleotide of any of embodiment 705-783 or 785-787 having at least two linking groups of Formula XVII, wherein at least two of the linking groups of Formula XVII are the same as one another.

Embodiment 792. The modified oligonucleotide of any of embodiments 705-791, wherein each internucleoside linking group of the modified oligonucleotide that is not an internucleoside linking group of Formula XVII is either a phosphodiester internucleoside linking group or a phosphorothioate internucleoside linking group.

Embodiment 793. The modified oligonucleotide of any of embodiments 705-784 or 790, wherein each internucleoside linking group of the modified oligonucleotide is an internucleoside linking group of Formula XVII.

Embodiment 794. An antisense agent comprising a modified oligonucleotide, wherein at least one region of the modified oligonucleotide has Structure A:

Structure A

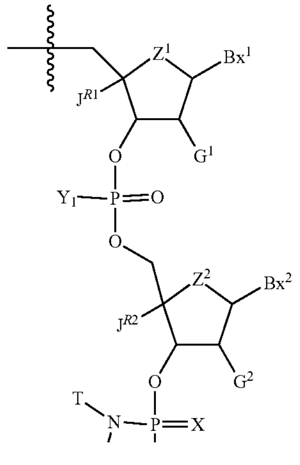

-continued

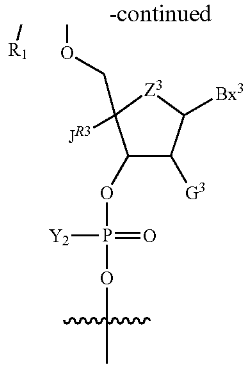

wherein:

each Bx is a heterocyclic base moiety;

X is selected from O or S;

each of $Y_1$ and $Y_2$ is independently selected from OH or SH;

each of $Z^1$, $Z^2$, and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$; and each $J_1$, $J_2$ and $J_3$ is, independently, H or $C_1$-$C_6$ alkyl.

Embodiment 795. An antisense agent comprising a modified oligonucleotide, wherein at least one region of the modified olignucleotide has Structure B:

Structure B

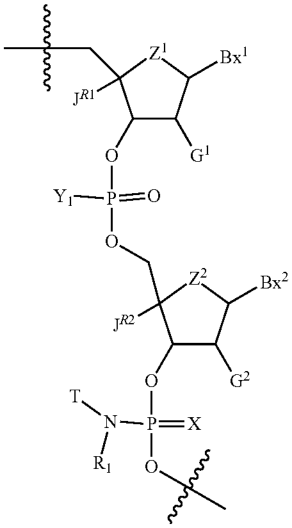

wherein:

each Bx is a heterocyclic base moiety;

X is selected from O or S;

each of $Y_1$ and $Y_2$ is independently selected from OH or SH;

each of $Z^1$ and $Z^2$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O—[C(R_6)(R_7)]_n[(C=O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C=O)_m—X^G]J-R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 796. An antisense agent comprising a modified oligonucleotide, wherein at least one region of the modified oligonucleotide has Structure C:

Structure C

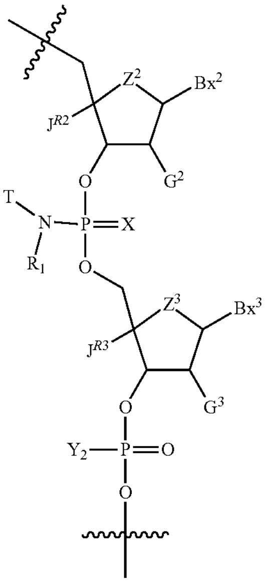

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J^{R2}$ and $G^2$ bridge, or $J^{R2}$ is H and $G^2$ is selected from H, OH, halogen or O—[C$(R_6)(R_7)]_n[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—[C$(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 797. An antisense agent comprising a modified oligonucleotide, wherein at least one region of the modified oligonucleotide has Structure D:

Structure D

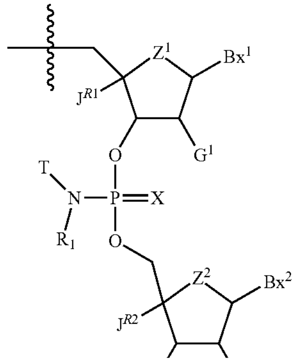

-continued

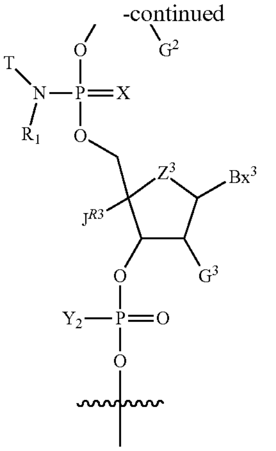

wherein:

each Bx is a heterocyclic base moiety;

X is selected from O or S;

each of $Y_1$ and $Y_2$ is independently selected from OH or SH;

each of $Z^2$ and $Z^3$ are independently selected from —$(CH_2)_p$—$X^Z$—$(CH_2)_q$—, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n[(C{=}O)_m$—$X^G]_j$—$R_8$;

either $J^{R2}$ and $G^2$ form a $J^{R2}$ and $G^2$ bridge, or $J^{R2}$ is H and $G^2$ is selected from H, OH, halogen or O—[C$(R_6)(R_7)]_n[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—[C$(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 798. An antisense agent comprising a modified oligonucleotide, wherein at least one region of the modified oligonucleotide has Structure E:

Structure E

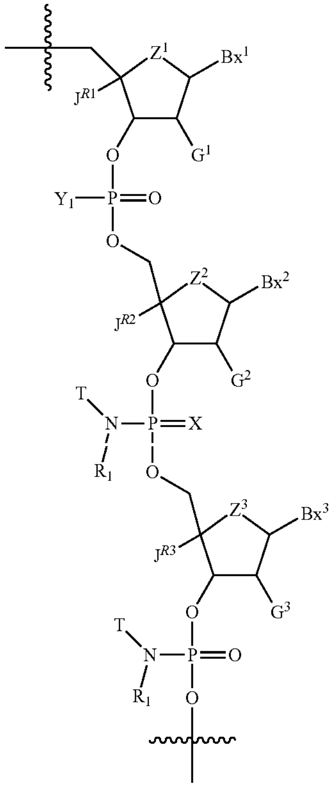

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]J$-$R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 799. The modified oligonucleotide of any of embodiments 794-798, wherein each Z is O.

Embodiment 800. The modified oligonucleotide of any of embodiments 794-799, wherein at least one G is selected from H, OH, halogen, $C_1$-$C_6$ alkoxy, $-O(CH_2)_2OCH_3$, or $-OCH_2(C=O)NHCH_3$.

Embodiment 801. The modified oligonucleotide of any of embodiments 794-799, wherein each G is selected from H, OH, halogen, $C_1$-$C_6$ alkoxy, $-O(CH_2)_2OCH_3$, or $-OCH_2(C=O)NHCH_3$.

Embodiment 802. The modified oligonucleotide of any of embodiments 794-801, wherein at least one $J^R$ forms a bridge with at least one G, wherein said $J^R$ to G bridge has a formula selected from $-CH(CH_3)-O-$ or $-(CH_2)_k-O'$, wherein k is from 1 to 3.

Embodiment 803. The modified oligonucleotide of any of embodiments 794-802, wherein each $J^R$ and G form a bridge, wherein said $J^R$ to G bridge has a formula selected from $-CH(CH_3)-O-$ or $-(CH_2)_k-O-$, wherein k is from 1 to 3.

Embodiment 804. The modified oligonucleotide of any of embodiments 802 or 803, wherein at least one Z is 0 and the corresponding $J^R$ to G bridge has a formula $(CH_2)_k-O-$, wherein k is 1.

Embodiment 805. The modified oligonucleotide of any of embodiments 794-804 wherein each nucleoside of structure A, B, C, D, or E is a stereo standard nucleoside.

Embodiment 806. The modified oligonucleotide of any of embodiments 794-804, wherein at least one nucleoside of structure A, B, C, D, or E is a stereo-non-standard nucleoside.

Embodiment 807. The modified oligonucleotide of any of embodiments 802-804 or 806, wherein at least one nucleoside having a $J^R$ to G bridge is in the α-L-ribosyl configuration.

Embodiment 808. The modified oligonucleotide of any of embodiments 794-807, wherein the modified oligonucleotide comprises at least 2, at least 3, at least 4, at least 5, at least 6, at least 7, at least 8, at least 9, or at least 10 regions having structures A, B, C, D, or E.

Embodiment 809. The modified oligonucleotide of any of embodiments 794-807, wherein at least one region having structure A, B, C, D, or E is at the 5' end of the modified oligonucleotide.

Embodiment 810. The modified oligonucleotide of any of embodiments 794-807, wherein at least one region having structure A, B, C, D, or E is at the 3' end of the modified oligonucleotide.

Embodiment 811. The modified oligonucleotide of any of embodiments 794-807, wherein at least one region having structure A, B, C, D, or E is internal to the modified oligonucleotide.

Embodiment 812. An antisense agent comprising a modified oligonucleotide consisting of 10-30 linked nucleosides, wherein a region of the modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

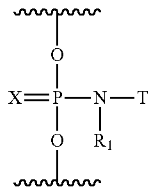

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ is an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 813. The modified oligonucleotide of embodiment 812, wherein the modified oligonucleotide comprises at least 2, at least 3, at least 4, at least 5, at least 6, at least 7, at least 8, at least 9, or at least 10 regions having the formula $(N_{g1})_{L1}(N_{g2})_{L2}(N_{g3})_{L3}$.

Embodiment 814. The modified oligonucleotide of embodiment 812 or 813, wherein at least one region having the formula $(N_{g1})_{L1}(N_{g2})_{L2}(N_{g3})_{L3}$ is at the 5' end of the oligonucleotide Embodiment 815. The modified oligonucleotide of embodiment 812 or 813, wherein at least one region having the formula $(N_{g1})_{L1}(N_{g2})_{L2}(N_{g3})_{L3}$ is internal to the oligonucleotide.

Embodiment 816. The modified oligonucleotide of embodiment 812 or 813, wherein at least one region having the formula $(N_{g1})_{L1}(N_{g2})_{L2}(N_{g3})_{L3}$ is at the 3' end of the oligonucleotide.

Embodiment 817. The modified oligonucleotide of any of embodiments 705-816, wherein at least one nucleoside of the modified oligonucleotide is a modified nucleoside selected from a bicyclic nucleoside and a non-bicyclic substituted nucleoside.

Embodiment 818. The modified oligonucleotide of any of embodiments 705-817, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 819. The modified oligonucleotide of any of embodiments 705-818, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 820. The modified oligonucleotide of any of embodiments 705-819, wherein at least one nucleoside of the modified oligonucleotide is a stereo-non-standard nucleoside.

Embodiment 821. The modified oligonucleotide of embodiment 820, wherein the internucleoside linking group linking at least one stereo-non-standard nucleoside to an adjacent nucleoside is an internucleoside linking group of Formula XVII.

Embodiment 822. The modified oligonucleotide of embodiment 820 or 821, wherein at least two nucleosides of the modified oligonucleotide are stereo-non-standard nucleosides.

Embodiment 823. The modified oligonucleotide of embodiment 822, wherein at least two stereo-non-standard nucleosides of the modified oligonucleotide are adjacent to one another.

Embodiment 824. The modified oligonucleotide of embodiment 823, wherein at least two stereo-non-standard nucleosides of the modified oligonucleotide are linked to one another with an internucleoside linking group of Formula XVII.

Embodiment 825. The modified oligonucleotide of any of embodiments 820-824, wherein at least one stereo-nonstandard nucleoside of the modified oligonucleotide is a stereo-non-standard DNA nucleoside.

Embodiment 826. The modified oligonucleotide of embodiment 825 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 827. The modified oligonucleotide of embodiment 826 wherein the stereo-non-standard DNA nucleoside is selected from a stereo-non-standard DNA nucleoside having: Formula V and Formula II.

Embodiment 828. The modified oligonucleotide of any of embodiments 820-827, wherein at least one stereo-non-standard nucleoside of the modified oligonucleotide is a substituted stereo-non-standard nucleoside or a stereo-non-standard RNA nucleoside.

Embodiment 829. The modified oligonucleotide of embodiment 828, wherein the 2'-substituent of the at least one substituted stereo-non-standard nucleoside of the modified oligonucleotide is selected from: 2'-MOE, 2'-OMe, 2'-F, or 2'-OH.

Embodiment 830. The modified oligonucleotide of any of embodiments 705-819, wherein each nucleoside is a stereo-standard nucleoside.

Embodiment 831. The modified oligonucleotide of any of embodiments 705-829, wherein the modified oligonucleotide consists of 12-30 linked nucleosides.

Embodiment 832. The modified oligonucleotide of any of embodiments 705-829, wherein the modified oligonucleotide consists of 16-24 linked nucleosides.

Embodiment 833. The modified oligonucleotide of any of embodiments 705-829, wherein the modified oligonucleotide consists of 18-22 linked nucleosides.

Embodiment 834. The modified oligonucleotide of any of embodiments 705-832, wherein the modified oligonucleotide consists of 16 linked nucleosides.

Embodiment 835. The modified oligonucleotide of any of embodiments 705-832, wherein the modified oligonucleotide consists of 17 linked nucleosides.

Embodiment 836. The modified oligonucleotide of any of embodiments 705-833, wherein the modified oligonucleotide consists of 18 linked nucleosides.

Embodiment 837. The modified oligonucleotide of any of embodiments 705-833, wherein the modified oligonucleotide consists of 19 linked nucleosides.

Embodiment 838. The modified oligonucleotide of any of embodiments 705-833, wherein the modified oligonucleotide consists of 20 linked nucleosides.

Embodiment 839. The modified oligonucleotide of any of embodiments 705-833, wherein the modified oligonucleotide consists of 21 linked nucleosides.

Embodiment 840. The modified oligonucleotide of any of embodiments 705-833, wherein the modified oligonucleotide consists of 22 linked nucleosides.

Embodiment 841. The modified oligonucleotide of any of embodiments 705-832, wherein the modified oligonucleotide consists of 23 linked nucleosides.

Embodiment 842. The modified oligonucleotide of any of embodiments 705-841, wherein at least one nucleoside of the modified oligonucleotide is selected from: a 2'-OMe nucleoside, a 2'-F nucleoside, and an RNA nucleoside.

Embodiment 843. The modified oligonucleotide of any of embodiments 705-842, wherein at least one nucleoside of the modified oligonucleotide is a 2'-OMe nucleoside, and at least one nucleoside of the modified oligonucleotide is a 2'-F nucleoside.

Embodiment 844. The modified oligonucleotide of embodiment 843, wherein each nucleoside of the modified oligonucleotide is selected from a 2'-OMe nucleoside or a 2'-F nucleoside.

Embodiment 845. The modified oligonucleotide of any of embodiments 705-743, wherein at least one nucleoside of the modified oligonucleotide is a 2'-OMe nucleoside, at least one nucleoside of the modified oligonucleotide is a 2'-F nucleoside, and at least one nucleoside of the modified oligonucleotide comprises a sugar surrogate.

Embodiment 846. The modified oligonucleotide of embodiment 845, wherein each nucleoside of the modified oligonucleotide is selected from a 2'-OMe nucleoside, a 2'-F nucleoside, and a nucleoside comprising a sugar surrogate.

Embodiment 847. The modified oligonucleotide of any of embodiments 845-846, wherein the nucleoside comprising a sugar surrogate is selected from:

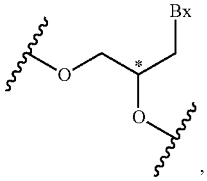
,
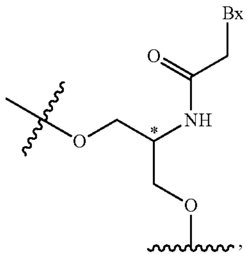
,
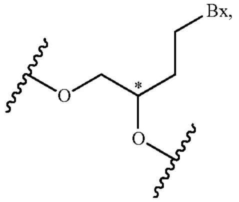

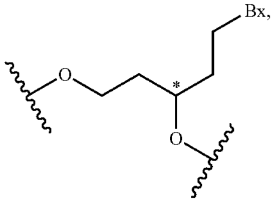

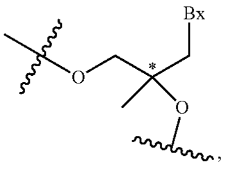
, or
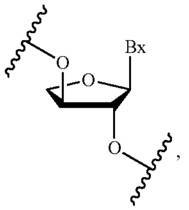
, wherein Bx is a heterocyclic base moiety.

Embodiment 848. The modified oligonucleotide of embodiment 847, wherein the nucleoside comprising a sugar surrogate is GNA.

Embodiment 849. The modified oligonucleotide of any of embodiments 842-848, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 850. The modified oligonucleotide of embodiment 849, wherein A and B are selected from 2'-F substituted nucleosides, 2'-OMe substituted nucleosides, and stereo-standard RNA nucleosides.

Embodiment 851. The modified oligonucleotide of any of embodiments 705-850, wherein the 5'-end of the modified oligonucleotide comprises a terminal group.

Embodiment 852. The modified oligonucleotide of embodiment 851, wherein the terminal group is a stabilized phosphate group.

Embodiment 853. The modified oligonucleotide of embodiment 852, wherein the stabilized phosphate group is a 5'-vinyl phosphonate or a 5'-cyclopropyl phosphonate.

Embodiment 854. The modified oligonucleotide of embodiment 851, wherein the terminal group is selected from

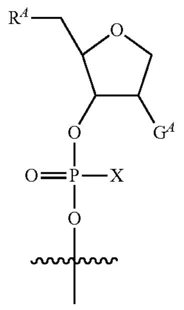

or

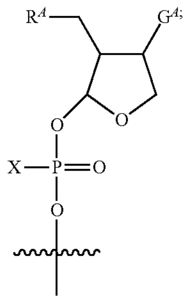

;

wherein $R^A$ is OH, OP(=O)OH, OP(=O)SH, or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

Embodiment 855. The modified oligonucleotide of embodiment 854, wherein GA is selected from H or OH and X is SH.

Embodiment 856. The antisense agent of any of embodiments 705-855, wherein the antisense agent is an RNAi agent.

Embodiment 857. The RNAi agent of embodiment 856, wherein the RNAi agent is a single-stranded RNAi agent comprising an RNAi antisense modified oligonucleotide, wherein the RNAi antisense modified oligonucleotide is a modified oligonucleotide of any of embodiments 705-855.

Embodiment 858. The RNAi agent of embodiment 856, wherein the RNAi agent is an oligonucleotide duplex comprising an RNAi antisense modified oligonucleotide and an RNAi sense modified oligonucleotide, wherein the RNAi antisense modified oligonucleotide and/or the RNAi sense modified oligonucleotide is a modified oligonucleotide of any of embodiments 705-855.

Embodiment 859. The RNAi agent of embodiment 857 or 858, wherein at least one internucleoside linking group of the RNAi antisense modified oligonucleotide is an internucleoside linking group of Formula XVII.

Embodiment 860. The RNAi agent of embodiment 857 or 858, wherein at least two internucleoside linking groups of the RNAi antisense modified oligonucleotide are independently selected internucleoside linking groups of Formula XVII.

Embodiment 861. The RNAi agent of any of embodiments 857-860, wherein at least one of the five 3'-most internucleoside linking groups of the RNAi antisense modified oligonucleotide is an internucleoside linking group of Formula XVII.

Embodiment 862. The RNAi agent of any of embodiments 857-861, wherein at least two of the five 3'-most internucleoside linking groups of RNAi antisense modified oligonucleotide is an internucleoside linking group of Formula XVII.

Embodiment 863. The RNAi agent of any of embodiments 857-862, wherein 1-3 of the three 3'-most internucleoside linking groups are internucleoside linking groups of Formula XVII, and each of these three internucleoside linking groups that is not an internucleoside linking group of Formula XVII is a phosphodiester or phosphorothioate internucleoside linking group.

Embodiment 864. The RNAi agent of embodiment 863, wherein the two 3'-most internucleoside linking groups are internucleoside linking groups of Formula XVII.

Embodiment 865. The RNAi agent of any of embodiments 857-864, wherein exactly one of the 5'-most and penultimate 5'-most internucleoside linking groups is an internucleoside linking group of Formula XVII.

Embodiment 866. The RNAi agent of any of embodiments 857-865, wherein exactly one of the 5'-most and penultimate 5'-most internucleoside linking groups of the RNAi antisense oligonucleotide is an internucleoside linking groups of Formula XVII, the other of the 5'-most and penultimate 5'-most internucleoside linking groups of the RNAi antisense oligonucleotide is selected from a phosphodiester and a phosphorothioate internucleoside linkage, the two 3'-most internucleoside linking groups of the RNAi antisense oligonucleotide are internucleoside linking groups of Formula XVII, and the remaining internucleoside linking groups of the RNAi antisense oligonucleotide are phosphodiester internucleoside linkages.

Embodiment 867. The RNAi agent of any of embodiments 857-866, wherein the antisense modified oligonucleotide comprises a 3'-overhang.

Embodiment 868. The RNAi agent of embodiment 867, wherein the 3'-overhang consists of two nucleosides.

Embodiment 869. The RNAi agent of any of embodiments 857-865 or 867-868, wherein at least one internucleoside linking group within the seed region of the RNAi antisense modified oligonucleotide is an internucleoside linking group of Formula XVII.

Embodiment 870. The RNAi agent of any of embodiments 857-869, wherein for each internucleoside linking group of Formula XVII, $R_1$ is H and T is $SO_2Me$.

Embodiment 871. The RNAi agent of any of embodiments 857-870, wherein the RNAi antisense modified oligonucleotide consists of 23 linked nucleosides, and the internucleoside linkage motif is selected from:
ooooooooooooooooooooaa,
aaoooooooooooooooooooo, aaooooooooooooooooaa, asooooooooooooooooss, saoooooooooooooooooo, oooooooooooooooooaaa, ooooooooooooooaaaoss, ooooooooooooaaaoooss, ooooooooooaaaoooooss, oooooooaaaooooooooss, ooooaaaoooooooooooss, saoooaooooooaoaoooss, ssoooaooooooaoaoooss, or ssooooooooooooooooaa, wherein each "a" represents an internucleoside linkage of Formula XVII, each "s" represents a phosphorothioate internucleoside linkage, and each "o" represents a phosphodiester internucleoside linkage.

Embodiment 872. The RNAi agent of embodiment 871, wherein the internucleoside linkage motif of the RNAi antisense modified oligonucleotide is selected from ooooooooooooooooooaa, asooooooooooooooooss, or saoooooooooooooooooo.

Embodiment 873. The RNAi agent of embodiment 871 or 872, wherein the sugar motif of the RNAi antisense modified oligonucleotide from 5' to 3' is yfyfyfyfyfyfyfyfyfyfy or yfyyyfyyyyyyyfyfyyyyyyy, wherein "y" represents a 2'-OMe sugar moiety and "f" represents a 2'-F sugar moiety.

Embodiment 874. The RNAi agent of any of embodiments 857-870, wherein the RNAi antisense modified oligonucleotide consists of 21 linked nucleosides, and the internucleoside linkage motif is selected from: aaososososossssss, ssaaososososossssss, ssosaaosososossssss, ssososaaososossssss, ssosososaaosossssss, ssososososaaossssss, ssososososaasssss, ssosososososaassss, ssosososososssaass, ssosososososssaa wherein each "a" represents an internucleoside linkage of Formula XVII, each "s" represents a phosphorothioate internucleoside linkage, and each "o" represents a phosphodiester internucleoside linkage.

Embodiment 875. The RNAi agent of embodiment 874, wherein the internucleoside linkage motif of the RNAi antisense modified oligonucleotide is selected from aaososososossssss, ssaaososososossssss, ssosaaosososossssss, ssososaaososossssss, ssosososososssaass, or ssosososososossssssaa, wherein each "a" represents an internucleoside linkage of Formula XVII, each "s" represents a phosphorothioate internucleoside linkage, and each "o" represents a phosphodiester internucleoside linkage.

Embodiment 876. The RNAi agent of embodiment 874 or 875, wherein the sugar motif of the RNAi antisense modified oligonucleotide from 5' to 3' is yfyfyfyfyfyfyfyfyfyfy, wherein "y" represents a 2'-OMe sugar moiety and "f" represents a 2'-F sugar moiety.

Embodiment 877. The RNAi agent of any of embodiments 873-876 wherein each "a" is a mesyl phosphoramidate linkage.

Embodiment 878. The RNAi agent of any of embodiments 857-878, wherein at least one region of the RNAi antisense modified oligonucleotide has structure A, B, C, D, or E.

Embodiment 879. The RNAi agent of embodiment 878, wherein at least one region having structure A, B, C, D, or E is within the seed region of the RNAi antisense modified oligonucleotide.

Embodiment 880. The RNAi agent of embodiment 878, wherein at least one region having structure A, B, C, D, or E is at the 3' end of the RNAi antisense modified oligonucleotide.

Embodiment 881. The RNAi agent of any of embodiments 857-880, wherein at least one region of the RNAi antisense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

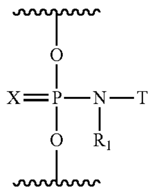

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, substituted $C_1$-$C_6$ alkyl, and a conjugate;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 882. The RNAi agent of embodiment 881, wherein the region having the formula $(N_{g1})_{L1}(N_{g2})_{L2}(N_{g3})_{L3}$ includes one or two 3'-overhang nucleosides.

Embodiment 883. The RNAi agent of embodiment 881, wherein at least one region having the formula $(N_{g1})_{L1}(N_{g2})_{L2}(N_{g3})_{L3}$ is at the 3' end of the RNAi antisense modified oligonucleotide.

Embodiment 884. The RNAi agent of embodiment 883, wherein L1 and L2 are each internucleoside linkages of Formula XVII wherein $R_1$ is H and T is $SO_2Me$, and L3 is a phosphodiester internucleoside linkage.

Embodiment 885. The RNAi agent of embodiment 881, wherein at least one region having the formula $(N_{g1})_{L1}(N_{g2})_{L2}(N_{g3})_{L3}$ is at the 5' end of the RNAi antisense modified oligonucleotide.

Embodiment 886. The RNAi agent of embodiment 885, wherein one of L1 or L2 is an internucleoside linkages of Formula XVII wherein $R_1$ is H and T is $SO_2Me$, the other of L1 or L2 is a phosphorothioate internucleoside linkage, and L3 is a phosphodiester internucleoside linkage.

Embodiment 887. The RNAi agent of embodiment 881, wherein at least one region having the formula $(N_{g1})_{L1}(N_{g2})_{L2}(N_{g3})_{L3}$ is within the seed region of the RNAi antisense modified oligonucleotide.

Embodiment 888. The RNAi agent of any of embodiments 857-887, wherein the region of the RNAi antisense oligonucleotide that is complementary to a target is at least 15 nucleobases.

Embodiment 889. The RNAi agent of any of embodiments 857-888, wherein the region of the RNAi antisense oligonucleotide that is complementary to a target is at least 17 nucleobases.

Embodiment 890. The RNAi agent of any of embodiments 857-889, wherein the region of the RNAi antisense oligonucleotide that is complementary to a target is at least 19 nucleobases.

Embodiment 891. The RNAi agent of any of embodiments 857-890, wherein the region of the RNAi antisense oligonucleotide that is complementary to a target is at least 21 nucleobases.

Embodiment 892. The RNAi agent of any of embodiments 857-890, wherein the region of the RNAi antisense oligonucleotide that is complementary to a target is exactly 19 nucleobases.

Embodiment 893. The RNAi agent of any of embodiments 857-891, wherein the region of the RNAi antisense oligonucleotide that is complementary to a target is exactly 21 nucleobases.

Embodiment 894. The RNAi agent of any of embodiments 857-893, wherein at least one nucleoside of the RNAi antisense modified oligonucleotide is selected from: a 2'-OMe nucleoside, a 2'-F nucleoside, and an RNA nucleoside.

Embodiment 895. The RNAi agent of any of embodiments 857-894, wherein at least one nucleoside of the modified oligonucleotide is a 2'-OMe nucleoside, and at least one nucleoside of the modified oligonucleotide is an RNA nucleoside.

Embodiment 896. The RNAi agent of any of embodiments 857-894, wherein at least one nucleoside of the RNAi antisense modified oligonucleotide is a 2'-OMe nucleoside, and at least one nucleoside of the RNAi antisense modified oligonucleotide is a 2'-F nucleoside.

Embodiment 897. The RNAi agent of embodiment 896, wherein each nucleoside of the RNAi antisense modified oligonucleotide is selected from a 2'-OMe nucleoside or a 2'-F nucleoside.

Embodiment 898. The RNAi agent of any of embodiments 887-894, wherein at least one nucleoside of the RNAi antisense modified oligonucleotide is a 2'-OMe nucleoside, at least one nucleoside of the RNAi antisense modified oligonucleotide is a 2'-F nucleoside, and at least one nucleoside of the modified oligonucleotide comprises a sugar surrogate.

Embodiment 899. The RNAi agent of embodiment 898, wherein each nucleoside of the RNAi antisense modified oligonucleotide is selected from a 2'-OMe nucleoside, a 2'-F nucleoside, and a nucleoside comprising a sugar surrogate.

Embodiment 900. The RNAi agent of any of embodiments 898-899, wherein the nucleoside comprising a sugar surrogate is selected from:

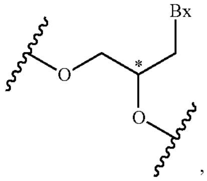
,
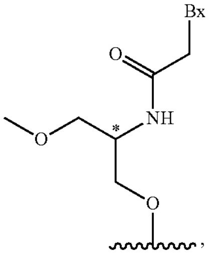
,
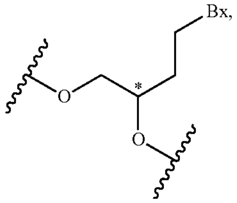

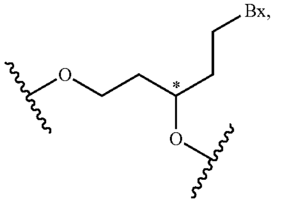

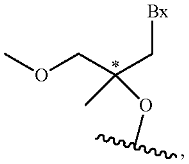
, or
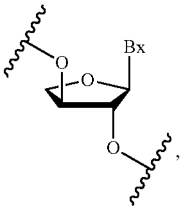
, wherein Bx is a heterocyclic base moiety.

Embodiment 901. The RNAi agent of embodiment 900, wherein the nucleoside comprising a sugar surrogate is GNA.

Embodiment 902. The RNAi agent of embodiment 900 or 901, wherein at least one nucleoside comprising a sugar surrogate is one of the nine 5'-most nucleosides of the RNAi antisense modified oligonucleotide.

Embodiment 903. The RNAi agent of any of embodiments 857-902, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 904. The RNAi agent of embodiment 903, wherein A and B are selected from 2'-F substituted nucleosides, 2'-OMe substituted nucleosides, and stereo-standard RNA nucleosides.

Embodiment 905. The RNAi agent of any of embodiments 857-904, wherein the 5'-end of the RNAi antisense modified oligonucleotide comprises a terminal group.

Embodiment 906. The RNAi agent of embodiment 905, wherein the terminal group is a stabilized phosphate group.

Embodiment 907. The RNAi agent of embodiment 906, wherein the stabilized phosphate group is a 5'-vinyl phosphonate or a 5'-cyclopropyl phosphonate.

Embodiment 908. The RNAi agent of embodiment 905, wherein the terminal group is selected from

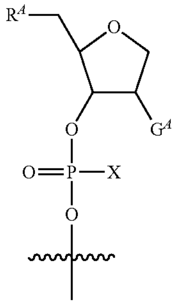

or

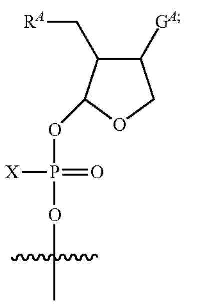

Wherein $R^A$ is OH, OP(=O)OH, OP(=O)SH or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

Embodiment 909. The RNAi agent of embodiment 908, wherein $G^A$ is selected from H or OH and X is SH.

Embodiment 910. The RNAi agent of any of embodiments 858-909, wherein at least one internucleoside linking group of the RNAi sense modified oligonucleotide is an internucleoside linking group of Formula XVII.

Embodiment 911. The RNAi agent of embodiment 910, wherein at least one of the five 5'-most internucleoside linking groups of the RNAi sense modified oligonucleotide is an internucleoside linking group of Formula XVII.

Embodiment 912. The RNAi agent of embodiment 910, wherein at least two of the five 5'-most internucleoside linking groups of the RNAi sense modified oligonucleotide are internucleoside linking groups of Formula XVII.

Embodiment 913. The RNAi agent of embodiment 910, wherein the two 5'-most internucleoside linking groups of the RNAi sense modified oligonucleotide are internucleoside linking groups of Formula XVII.

Embodiment 914. The RNAi agent of any of embodiments 910-913, wherein at least one of the five 3'-most internucleoside linking groups of the RNAi sense modified oligonucleotide is an internucleoside linking group of Formula XVII.

Embodiment 915. The RNAi agent of any of embodiments 910-913, wherein at least two of the five 3'-most internucleoside linking groups of RNAi sense modified oligonucleotide is an internucleoside linking group of Formula XVII.

Embodiment 916. The RNAi agent of any of embodiments 910-913, wherein the two 3'-most internucleoside linking groups are internucleoside linking groups of Formula XVII.

Embodiment 917. The RNAi agent of embodiment 910, wherein the two 3'-most and the two 5'-most internucleoside linking groups of the RNAi sense oligonucleotide are internucleoside linking groups of Formula XVII, and the remaining internucleoside linking groups of the RNAi sense oligonucleotide are phosphodiester internucleoside linkages.

Embodiment 918. The RNAi agent of any of embodiments 910-917, wherein for each internucleoside linking group of Formula XVII, $R_1$ is H and T is $SO_2Me$.

Embodiment 919. The RNAi agent of any of embodiments 910-918, wherein the RNAi sense modified oligonucleotide consists of 21 linked nucleosides, and the internucleoside linkage motif is selected from: ooooooooooooooooooaa, aaooooooooooooooooaa, ooooooooooooooooooaa, or ssooooaoaaaooooooooo, wherein each "a" represents an internucleoside linkage of Formula XVII, each "s" represents a phosphorothioate internucleoside linkage, and each "o" represents a phosphodiester internucleoside linkage.

Embodiment 920. The RNAi agent of embodiment 919, wherein the internucleoside linkage motif of the RNAi sense modified oligonucleotide is selected from ooooooooooooooooooaa, aaooooooooooooooooaa, or ooooooooooooooooooaa, wherein each "a" represents an internucleoside linkage of Formula XVII, each "s" represents a phosphorothioate internucleoside linkage, and each "o" represents a phosphodiester internucleoside linkage.

Embodiment 921. The RNAi agent of embodiment 919 or 920, wherein the sugar motif of the RNAi sense modified oligonucleotide is selected from: yyyyyyfyfffyyyyyyyyyy or fyfyfyfyfyfyfyfyfyfyf, wherein "y" represents a 2'-OMe sugar moiety and "f" represents a 2'-F sugar moiety.

Embodiment 922. The RNAi agent of embodiment 921, wherein the RNAi sense modified oligonucleotide has an internucleoside linkage motif of aaooooooooooooooooaa wherein each "a" represents an internucleoside linkage of Formula XVII, each "s" represents a phosphorothioate internucleoside linkage, and each "o" represents a phosphodiester internucleoside linkage, and a sugar motif of yyyyyyfyfffyyyyyyyyyy, wherein "y" represents a 2'-OMe sugar moiety and "f" represents a 2'-F sugar moiety.

Embodiment 923. The RNAi agent of any of embodiments 919-922 wherein each "a" is a mesyl phosphoramidate linkage.

Embodiment 924. The RNAi agent of any of embodiments 910-923, wherein at least one region of the RNAi sense modified oligonucleotide has structure A, B, C, D, or E.

Embodiment 925. The RNAi agent of embodiment 924, wherein at least one region having structure A, B, C, D, or E is at the 3' end of the RNAi sense modified oligonucleotide.

Embodiment 926. The RNAi agent of embodiment 924, wherein at least one region having structure A, B, C, D, or E is at the 5' end of the RNAi sense modified oligonucleotide.

Embodiment 927. The RNAi agent of any of embodiments 910-926, wherein at least one region of the RNAi sense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

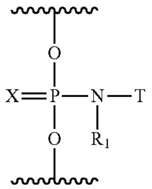

XVII wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 928. The RNAi agent of embodiment 927, wherein at least one region having the formula $(N_{g1})_{L1}(N_{g2})_{L2}(N_{g3})_{L3}$ is at the 3' end of the RNAi sense modified oligonucleotide.

Embodiment 929. The RNAi agent of embodiment 928, wherein L1 and L2 are internucleoside linking groups of Formula XVII, wherein $R_1$ is H and T is $SO_2Me$, and L3 is a phosphodiester internucleoside linkage.

Embodiment 930. The RNAi agent of embodiment 927, wherein at least one region having the formula $(N_{g1})_{L1}(N_{g2})_{L2}(N_{g3})_{L3}$ is at the 5' end of the RNAi sense modified oligonucleotide.

Embodiment 931. The RNAi agent of embodiment 930, wherein L1 is a phosphodiester internucleoside linking group and L2 and L3 are each internucleoside linking groups of Formula XVII, wherein $R_1$ is H and T is $SO_2Me$.

Embodiment 932. The RNAi agent of any of embodiments 858-931, wherein the RNAi sense modified oligonucleotide comprises a 3' terminal group and/or a 5' terminal group.

Embodiment 933. The RNAi agent of any of embodiments 858-932, wherein the RNAi sense strand comprises a conjugate group.

Embodiment 934. The RNAi agent of embodiment 933, wherein the conjugate group comprises a cell-targeting moiety.

Embodiment 935. The RNAi agent of embodiment 933, wherein the conjugate group comprises a carbohydrate or carbohydrate cluster.

Embodiment 936. The RNAi agent of embodiment 933, wherein the conjugate group comprises at least one GalNAc.

Embodiment 937. The RNAi agent of embodiment 933, wherein the conjugate group comprises a $C_{10}$-$C_{20}$ alkyl chain.

Embodiment 938. The RNAi agent of embodiment 933, wherein the conjugate group comprises $C_{16}$ alkyl.

Embodiment 939. The RNAi agent of any of embodiments 858-938, wherein the double-stranded region of the oligonucleotide duplex is at least 15 nucleosides.

Embodiment 940. The RNAi agent of any of embodiments 858-938, wherein the double-stranded region of the oligonucleotide duplex is at least 17 nucleosides.

Embodiment 941. The RNAi agent of any of embodiments 858-938, wherein the double-stranded region of the oligonucleotide duplex is at least 19 nucleosides.

Embodiment 942. The RNAi agent of any of embodiments 858-938, wherein the double-stranded region of the oligonucleotide duplex is exactly 19 nucleosides.

Embodiment 943. The modified oligonucleotide of any of embodiments 705-841, wherein each nucleoside of the modified oligonucleotide is a modified nucleoside comprising a modified sugar moiety.

Embodiment 944. The modified oligonucleotide of embodiment 943, wherein each modified sugar moiety is independently selected from a bicyclic sugar moiety and a 2'-substituted furanosyl sugar moiety.

Embodiment 945. The modified oligonucleotide of embodiment 943 or 944, wherein each modified sugar moiety comprises the same modification.

Embodiment 946. The modified oligonucleotide of any of embodiments 943-945, wherein each modified sugar moiety is selected from a 2'-OMe sugar moiety, a 2'-MOE sugar moiety, and a 2'-NMA sugar moiety.

Embodiment 947. The modified oligonucleotide of embodiment 943 or 944, wherein the three 3'-most nucleosides comprise a bicyclic sugar moiety, and the remaining nucleosides comprise a 2'-substituted furanosyl sugar moiety.

Embodiment 948. The modified oligonucleotide of embodiment 943 or 944, wherein the four 3'-most nucleosides comprise a bicyclic sugar moiety, and the remaining nucleosides comprise a 2'-substituted furanosyl sugar moiety.

Embodiment 949. The modified oligonucleotide of embodiment 943 or 944, wherein the five 3'-most nucleosides comprise a bicyclic sugar moiety, and the remaining nucleosides comprise a 2'-substituted furanosyl sugar moiety.

Embodiment 950. The modified oligonucleotide of embodiment 943 or 944, wherein the six 3'-most nucleosides comprise a bicyclic sugar moiety, and the remaining nucleosides comprise a 2'-substituted furanosyl sugar moiety.

Embodiment 951. The modified oligonucleotide of any of embodiments 947-950, wherein each bicyclic sugar moiety is selected from among cEt, LNA, and ENA.

Embodiment 952. The modified oligonucleotide of embodiment 951, wherein the bicyclic sugar moiety is cEt.

Embodiment 953. The modified oligonucleotide of any of embodiments 947-952, wherein the 2'-substituted furanosyl sugar moiety is selected from 2'-OMe, 2'-MOE, and 2'-F.

Embodiment 954. The modified oligonucleotide of any of embodiments 943-953, wherein at least one of the ten 5'-most linking groups of the modified oligonucleotide is an internucleoside linking group of Formula XVII.

Embodiment 955. The modified oligonucleotide of embodiment 954, wherein at least 2 of the ten 5'-most linking groups of the modified oligonucleotide are internucleoside linking groups of Formula XVII.

Embodiment 956. The modified oligonucleotide of embodiment 954, wherein at least 3 of the ten 5'-most linking groups of the modified oligonucleotide are internucleoside linking groups of Formula XVII.

Embodiment 957. The modified oligonucleotide of embodiment 954, wherein at least 4 of the ten 5'-most linking groups of the modified oligonucleotide are internucleoside linking groups of Formula XVII.

Embodiment 958. The modified oligonucleotide of embodiment 954, wherein at least 5 of the ten 5'-most linking groups of the modified oligonucleotide are internucleoside linking groups of Formula XVII.

Embodiment 959. The modified oligonucleotide of embodiment 954, wherein at least 6 of the ten 5'-most linking groups of the modified oligonucleotide are internucleoside linking groups of Formula XVII.

Embodiment 960. The modified oligonucleotide of embodiment 954, wherein the two 5'-most internucleoside linking groups are internucleoside linking groups of Formula XVII.

Embodiment 961. The modified oligonucleotide of any of embodiments 943-960, wherein at least one of the ten 3'-most internucleoside linking groups of the modified oligonucleotide is an internucleoside linking group of Formula XVII.

Embodiment 962. The modified oligonucleotide of embodiment 961, wherein at least 2 of the ten 3'-most internucleoside linking groups of the modified oligonucleotide are internucleoside linking groups of Formula XVII.

Embodiment 963. The modified oligonucleotide of embodiment 961, wherein at least 3 of the ten 3'-most internucleoside linking groups are internucleoside linking groups of Formula XVII.

Embodiment 964. The modified oligonucleotide of embodiment 961, wherein at least 4 of the ten 3'-most internucleoside linking groups are internucleoside linking groups of Formula XVII.

Embodiment 965. The modified oligonucleotide of embodiment 961, wherein at least 5 of the ten 3'-most internucleoside linking groups are internucleoside linking 961 of Formula XVII.

Embodiment 966. The modified oligonucleotide of embodiment 961, wherein at least 6 of the ten 3'-most internucleoside linking groups are internucleoside linking groups of Formula XVII.

Embodiment 967. The modified oligonucleotide of embodiment 961, wherein the two 3'-most internucleoside linking groups of the modified oligonucleotide are internucleoside linking groups of Formula XVII.

Embodiment 968. The modified oligonucleotide of any of embodiments 943-953, wherein the modified oligonucleotide comprises at least one block of at least 3 consecutive internucleoside linking groups of Formula XVII.

Embodiment 969. The modified oligonucleotide of any of embodiments 943-953, wherein the modified oligonucleotide comprises at least one block of at least 4 consecutive internucleoside linking groups of Formula XVII.

Embodiment 970. The modified oligonucleotide of any of embodiments 943-953, wherein the modified oligonucleotide comprises at least one block of at least 5 consecutive internucleoside linking groups of Formula XVII.

Embodiment 971. The modified oligonucleotide of any of embodiments 943-953, wherein the modified oligonucleotide comprises at least one block of at least 6 consecutive internucleoside linking groups of Formula XVII.

Embodiment 972. The modified oligonucleotide of any of embodiments 968-971, wherein at least one block of consecutive internucleoside linking groups of Formula XVII is at the 5' end of the modified oligonucleotide.

Embodiment 973. The modified oligonucleotide of any of embodiments 968-971, wherein at least one block of consecutive internucleoside linking groups of Formula XVII is at the 3' end of the modified oligonucleotide.

Embodiment 974. The modified oligonucleotide of any of embodiments 943-973, wherein for each internucleoside linking group of Formula XVII, $R_1$ is H and T is $SO_2Me$.

Embodiment 975. The modified oligonucleotide of any of embodiments 943-953, wherein the internucleoside linkage motif is selected from: aaaaaaasssssssss, sssssaaaaaassss, or ssssssssaaaaaa, wherein each "a" represents an internucleoside linkage of Formula XVII, each "s" represents a phosphorothioate internucleoside linkage, and each "o" represents a phosphodiester internucleoside linkage.

Embodiment 976. The modified oligonucleotide of embodiment 975, wherein each "a" represents a mesyl phosphoramidate internucleoside linkage.

Embodiment 977. The modified oligonucleotide of any of embodiments 705-841, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 978. The modified oligonucleotide of embodiment 977, wherein at least 5 contiguous nucleosides of the deoxy region are stereo-standard DNA nucleosides.

Embodiment 979. The modified oligonucleotide of embodiment 977, wherein at least 6 contiguous nucleosides of the deoxy region are stereo-standard DNA nucleosides.

Embodiment 980. The modified oligonucleotide of embodiment 977, wherein at least 7 contiguous nucleosides of the deoxy region are stereo-standard DNA nucleosides.

Embodiment 981. The modified oligonucleotide of embodiment 977, wherein at least 8 contiguous nucleosides of the deoxy region are stereo-standard DNA nucleosides.

Embodiment 982. The modified oligonucleotide of any of embodiments 977-981, wherein the deoxy region consists of 8-10 linked nucleosides.

Embodiment 983. The modified oligonucleotide of any of embodiments 977-981, wherein the deoxy region consists of 9 linked nucleosides.

Embodiment 984. The modified oligonucleotide of any of embodiments 977-981, wherein the deoxy region consists of 10 linked nucleosides.

Embodiment 985. The modified oligonucleotide of any of embodiments 977-981, wherein the deoxy region consists of 11 linked nucleosides.

Embodiment 986. The modified oligonucleotide of any of embodiments 977-981, wherein at least 6 nucleosides of the deoxy region are stereo-standard DNA nucleosides.

Embodiment 987. The modified oligonucleotide of any of embodiments 977-981, wherein at least 7 nucleosides of the deoxy region are stereo-standard DNA nucleosides.

Embodiment 988. The modified oligonucleotide of any of embodiments 977-981, wherein at least 8 nucleosides of the deoxy region are stereo-standard DNA nucleosides.

Embodiment 989. The modified oligonucleotide of any of embodiments 977-981, wherein at least 9 nucleosides of the deoxy region are stereo-standard DNA nucleosides.

Embodiment 990. The modified oligonucleotide of any of embodiments 977-989 wherein exactly two nucleosides of the deoxy region are modified nucleosides.

Embodiment 991. The modified oligonucleotide of any of embodiments 977-989 wherein exactly one nucleoside of the deoxy region is a modified nucleoside.

Embodiment 992. The modified oligonucleotide of any of embodiments 977-991 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 993. The modified oligonucleotide of any of embodiments 977-991, wherein at least one modified nucleoside of the deoxy region is stereo-non-standard nucleoside.

Embodiment 994. The modified oligonucleotide of embodiment 993, wherein the at least one is stereo-non-standard nucleoside of the deoxy region is a stereo-non-standard DNA nucleoside.

Embodiment 995. The modified oligonucleotide of embodiment 994, wherein the stereo-non-standard DNA nucleoside is selected from a stereo-non-standard DNA nucleoside having: Formula I, Formula II, Formula III, Formula IV, Formula V, Formula VI, and Formula VII.

Embodiment 996. The modified oligonucleotide of embodiment 995, wherein the stereo-non-standard DNA nucleoside is selected from a stereo-non-standard DNA nucleoside having: Formula V and Formula II.

Embodiment 997. The modified oligonucleotide of embodiment 996, wherein at least one stereo-non-standard nucleoside of the deoxy region is a substituted stereo-non-standard nucleoside.

Embodiment 998. The modified oligonucleotide of embodiment 997, wherein at least one substituted stereo-non-standard nucleoside has a 2'-substituent selected from: 2'-MOE, 2'-OMe, 2'-F, or 2'-OH.

Embodiment 999. The modified oligonucleotide of any of embodiments 977-998, wherein the $2^{nd}$ nucleoside from the 5'-end of the deoxy region is a modified nucleoside.

Embodiment 1000. The modified oligonucleotide of any of embodiments 977-998, wherein the $3^{rd}$ nucleoside from the 5'-end of the deoxy region is a modified nucleoside.

Embodiment 1001. The modified oligonucleotide of any of embodiments 977-998 wherein the $4^{th}$ nucleoside from the 5'-end of the deoxy region is a modified nucleoside.

Embodiment 1002. The modified oligonucleotide of any of embodiments 999-1001, wherein the modified nucleoside in the deoxy region is a 2'-OMe nucleoside.

Embodiment 1003. The modified oligonucleotide of any of embodiments 977-989, wherein each nucleoside of the deoxy region is a stereo-standard DNA nucleoside.

Embodiment 1004. The modified oligonucleotide of any of embodiments 977-1003 wherein at least one internucleoside linking group within the deoxy region is an internucleoside linking group of Formula XVII.

Embodiment 1005. The modified oligonucleotide of any of embodiments 977-1004, wherein the internucleoside linking group linking the $1^{st}$ and $2^{nd}$ nucleosides of the deoxy region as counted from the 5'-end of the deoxy region is an internucleoside linking group of Formula XVII.

Embodiment 1006. The modified oligonucleotide of any of embodiments 977-1005, wherein the internucleoside linking group linking the $2^{nd}$ and $3^{rd}$ nucleosides of the deoxy region as counted from the 5'-end of the deoxy region is an internucleoside linking group of Formula XVII.

Embodiment 1007. The modified oligonucleotide of any of embodiments 977-1006, wherein the internucleoside linking group linking the $3^{rd}$ and $4^{th}$ nucleosides of the deoxy region as counted from the 5'-end of the deoxy region is an internucleoside linking group of Formula XVII.

Embodiment 1008. The modified oligonucleotide of any of embodiments 977-1007, wherein the internucleoside linking group linking the $4^{th}$ and $5^{th}$ nucleosides of the deoxy region as counted from the 5'-end of the deoxy region is an internucleoside linking group of Formula XVII.

Embodiment 1009. The modified oligonucleotide of any of embodiments 977-1008, wherein one internucleoside linking group in the deoxy region is a linking group of Formula XVII and the other internucleoside linking groups of the deoxy region are independently selected from phosphodiester and phosphorothioate internucleoside linking groups.

Embodiment 1010. The modified oligonucleotide of any of embodiments 977-1008, wherein two internucleoside linking groups in the deoxy region are linking groups of Formula XVII and the other internucleoside linking groups of the deoxy region are independently selected from phosphodiester and phosphorothioate internucleoside linking groups.

Embodiment 1011. The modified oligonucleotide of any of embodiments 977-1008, wherein three internucleoside linking groups in the deoxy region are linking groups linking groups of Formula XVII and the other internucleoside linking groups of the deoxy region are independently selected from phosphodiester and phosphorothioate internucleoside linking groups.

Embodiment 1012. The modified oligonucleotide of any of embodiments 977-1008, wherein four internucleoside linking groups in the deoxy region are linking groups linking groups of Formula XVII and the other internucleoside linking groups of the deoxy region are each phosphodiester or phosphorothioate internucleoside linking groups.

Embodiment 1013. The modified oligonucleotide of any of embodiments 1009-1012, wherein the internucleoside linking groups of Formula XVII are linking the $1^{st}$ and $2^{nd}$ $2^{nd}$ and 3V, $3^{rd}$ and $4^{th}$, and/or the $4^{th}$ and $5^{th}$ nucleosides of the deoxy region, as counted from the 5'-end of the deoxy region.

Embodiment 1014. The modified oligonucleotide of any of embodiments 877-1013, wherein the deoxy region comprises at least one region having structure A, B, C, D, or E.

Embodiment 1015. The modified oligonucleotide of embodiment 1014, wherein the region having structure A, B, C, D, or E is at the 3' end of the deoxy region.

Embodiment 1016. The modified oligonucleotide of embodiment 1014, wherein the region having structure A, B, C, D, or E is at the 5' end of the deoxy region.

Embodiment 1017. The modified oligonucleotide of any of embodiments 877-1016, wherein the deoxy region comprises at least one region having the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

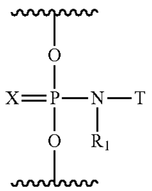

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1018. The modified oligonucleotide of embodiment 1017, wherein the region having the formula $(N_{g1})_{L1}(N_{g2})_{L2}(N_{g3})_{L3}$ is at the 3' end of the deoxy region.

Embodiment 1019. The modified oligonucleotide of embodiment 1017, wherein the region having the formula $(N_{g1})_{L1}(N_{g2})_{L2}(N_{g3})_{L3}$ is at the 5' end of the deoxy region.

Embodiment 1020. The modified oligonucleotide of any of embodiments 1004-1019, wherein for each internucleoside linkage of Formula XVII, $R_1$ is H and T is $SO_2Me$.

Embodiment 1021. The modified oligonucleotide of any of embodiments 877-1020 wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region comprises a modified sugar moiety; and the 5'-most nucleoside of the 3'-region comprises a modified sugar moiety.

Embodiment 1022. The modified oligonucleotide of embodiment 1021, wherein the deoxy region consists of 7-11 linked nucleosides, and has the formula:

$$(N_{d1})_{L1}(N_{d2})_{L2}(N_{d3})_{L3}(N_{d4})_{L4}[(N_d)_{L5}]_q;$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $N_{d2}$, $N_{d3}$, or $N_{d4}$ is a 2'-substituted nucleoside; each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, $L_4$ are internucleoside linkages of Formula XVII.

Embodiment 1023. The modified oligonucleotide of embodiment 1022, wherein one of $N_{d1}$, $Na_2$, $Na_3$, or $N_{d4}$ is a 2'-substituted nucleoside.

Embodiment 1024. The modified oligonucleotide of embodiment 1023, wherein the 2'-substituted nucleoside is a 2'-OMe nucleoside.

Embodiment 1025. The modified oligonucleotide of embodiment 1024, wherein the 2'-OMe nucleoside is a stereo-standard 2'-OMe nucleoside.

Embodiment 1026. The modified oligonucleotide of any of embodiments 1022-1025, wherein the 2'-substituted nucleoside is $N_d2$.

Embodiment 1027. The modified oligonucleotide of embodiment 1022, wherein each of $N_{d1}$, $Na_2$, $Na_3$, $N_{d4}$ and each $N_d$ is a DNA nucleoside.

Embodiment 1028. The modified oligonucleotide of embodiment 1027, wherein each DNA nucleoside is a stereo-standard DNA nucleoside.

Embodiment 1029. The modified oligonucleotide of any of embodiments 1022-1028, wherein $L_1$ and $L_2$ are internucleoside linkages of Formula XVII.

Embodiment 1030. The modified oligonucleotide of any of embodiments 1022-1028, wherein $L_2$ and $L_3$ are internucleoside linkages of Formula XVII.

Embodiment 1031. The modified oligonucleotide of any of embodiments 1022-1028, wherein $L_3$ and $L_4$ are internucleoside linkages of Formula XVII.

Embodiment 1032. The modified oligonucleotide of any of embodiments 1022-1028, wherein $L_1$, $L_2$, and $L_3$ are internucleoside linkages of Formula XVII.

Embodiment 1033. The modified oligonucleotide of any of embodiments 1022-1028, wherein $L_2$, $L_3$, and $L_4$ are internucleoside linkages of Formula XVII.

Embodiment 1034. The modified oligonucleotide of any of embodiments 1022-1028, wherein $L_1$, $L_2$, $L_3$, and $L_4$ are internucleoside linkages of Formula XVII.

Embodiment 1035. The modified oligonucleotide of embodiments 1029-1034, wherein each internucleoside linkage that is not an internucleoside linkage of Formula XVII is a phosphorothioate internucleoside linkage.

Embodiment 1036. The modified oligonucleotide of any of embodiments 1029-1035, wherein for each internucleoside linkage of Formula XVII, $R_1$ is H and T is $SO_2Me$ Embodiment 1037. The modified oligonucleotide of any of embodiments 1021-1036, wherein the 5'-region consists of 2-5 linked nucleosides.

Embodiment 1038. The modified oligonucleotide of embodiment 1037, wherein the 5'-region consists of 3 linked nucleosides.

Embodiment 1039. The modified oligonucleotide of embodiment 1037, wherein the 5'-region consists of 5 linked nucleosides.

Embodiment 1040. The modified oligonucleotide of any of embodiments 1021-1039 wherein each nucleoside of the 5'-region is a modified nucleoside.

Embodiment 1041. The modified oligonucleotide of any of embodiments 1021-1040, wherein each nucleoside of the 5'-region is a modified nucleoside comprising a modified sugar.

Embodiment 1042. The modified oligonucleotide of any of embodiments 1021-1041, wherein at least one nucleoside of the 5'-region comprises a 2'-substituted furanosyl sugar moiety.

Embodiment 1043. The modified oligonucleotide of any of embodiments 1021-1041, wherein each nucleoside of the 5'-region comprises a 2'-substituted furanosyl sugar moiety.

Embodiment 1044. The modified oligonucleotide of any of embodiments 1021-1043, wherein each 2'-substituted furanosyl sugar moiety of the 5'-region has a 2'-substituent selected from among 2'-MOE, 2'-OMe, and 2'-NMA.

Embodiment 1045. The modified oligonucleotide of any of embodiments 1021-1042 or 1044, wherein at least one nucleoside of the 5'-region comprises a bicyclic furanosyl sugar moiety.

Embodiment 1046. The modified oligonucleotide of any of embodiments 1021-1042 or 1044-1045, wherein each nucleoside of the 5'-region comprises a bicyclic furanosyl sugar moiety.

Embodiment 1047. The modified oligonucleotide of embodiment 341 or 342, wherein each bicyclic sugar moiety of the 5'-region is selected from among cEt, LNA, and ENA.

Embodiment 1048. The modified oligonucleotide of embodiment 1047, wherein each bicyclic sugar moiety of the 5'-region is a cEt sugar moiety.

Embodiment 1049. The modified oligonucleotide of any of embodiments 1021-1039, 1042 or 1045, wherein at least one nucleoside of the 5' region is a stereo-standard DNA nucleoside.

Embodiment 1050. The modified oligonucleotide of any of embodiments 1021-1048, wherein at least one nucleoside of the 5' region is a stereo-non-standard nucleoside.

Embodiment 1051. The modified oligonucleotide of any of embodiments 1021-1050, wherein each nucleobase of the 5'-region is independently selected from among thymine, uracil, guanine, cytosine, 5-methylcytosine, and adenine.

Embodiment 1052. The modified oligonucleotide of any of embodiments 1021-1051, wherein the 3'-region consists of 2-5 linked nucleosides.

Embodiment 1053. The modified oligonucleotide of embodiment 1052, wherein the 3'-region consists of 3 linked nucleosides.

Embodiment 1054. The modified oligonucleotide of embodiment 1052, wherein the 3'-region consists of 5 linked nucleosides.

Embodiment 1055. The modified oligonucleotide of any of embodiments 1021-1054, wherein each nucleoside of the 3'-region is a modified nucleoside.

Embodiment 1056. The modified oligonucleotide of any of embodiments 1021-1055, wherein each nucleoside of the 3'-region is a modified nucleoside comprising a modified sugar.

Embodiment 1057. The modified oligonucleotide of any of embodiments 1021-1056, wherein at least one nucleoside of the 3'-region comprises a 2'-substituted furanosyl sugar moiety.

Embodiment 1058. The modified oligonucleotide of any of embodiments 1021-1057, wherein each nucleoside of the 3'-region comprises a 2'-substituted furanosyl sugar moiety.

Embodiment 1059. The modified oligonucleotide of any of embodiments 1021-1058, wherein each 2'-substituted furanosyl sugar moiety of the 3'-region has a 2'-substituent selected from among 2'-MOE, 2'-OMe, and 2'-NMA.

Embodiment 1060. The modified oligonucleotide of any of embodiments 1021-1057 or 1059, wherein at least one nucleoside of the 3'-region comprises a bicyclic furanosyl sugar moiety.

Embodiment 1061. The modified oligonucleotide of any of embodiments 1021-1057 or 1059-1060, wherein each nucleoside of the 3'-region comprises a bicyclic furanosyl sugar moiety.

Embodiment 1062. The modified oligonucleotide of embodiment 1060 or 1061, wherein each bicyclic sugar moiety of the 3'-region is selected from among cEt, LNA, and ENA.

Embodiment 1063. The modified oligonucleotide of embodiment 1062, wherein each bicyclic sugar moiety of the 3'-region is a cEt sugar moiety.

Embodiment 1064. The modified oligonucleotide of any of embodiments 1021-1054, 1057 or 1060, wherein at least one nucleoside of the 3' region is a stereo-standard DNA nucleoside.

Embodiment 1065. The modified oligonucleotide of any of embodiments 1021-1064, wherein at least one nucleoside of the 3' region is a stereo-non-standard nucleoside.

Embodiment 1066. The modified oligonucleotide of any of embodiments 1021-1065, wherein each nucleobase of the 3'-region is independently selected from among thymine, uracil, guanine, cytosine, 5-methylcytosine, and adenine.

Embodiment 1067. The modified oligonucleotide of any of embodiments 1021-1066 wherein the modified oligonucleotide is a gapmer.

Embodiment 1068. The modified oligonucleotide of any of embodiments 1021-1066, wherein the modified oligonucleotide has a sugar motif selected from kkkddddddddddkkk and kkkdyddddddddkkk, wherein each "k" represents a cEt sugar moiety, "y" represents a 2'-OMe sugar moiety, and each "d" represents a β-D-2'-deoxyribosyl sugar moiety.

Embodiment 1069. The modified oligonucleotide of any of embodiments 1021-1066, wherein the modified oligonucleotide has an internucleoside linkage motif selected from: sssssssssssssa, sssssssssssssas, sssssssssssass, sssssssssssasss, ssssssssssassss, sssssssssasssss, ssssssssasssss, sssssssasssssss, ssssssasssssssss, ssssssassssssss, sssasssssssssss, sssassssssssss, ssassssssssssss, sasssssssssssss, assssssssssssss, ssssssssssssaa, sssssssssssaas, ssssssssssaass, sssssssssaasss, ssssssssaassss, ssssssssaasssss, ssssssaassssss, sssssaasssssss, sssssaassssssss, ssssaassssssss, sssaasssssssss, ssaasssssssssss, saassssssssssss, aassssssssssss, aaaaaaaaaaaaaa, ssaaaaaaaaaass, ssaaaaaaaaasss, sssaaaaaaaasss, aasssssssssaaa, sssaaassssssss, ssssaaasssssss, sssaaaassssssss, ssaaassssssssss, ssaaaassssssss, ssaaaaassssssss, ssaaaaaasssssss, ssaaaaaaasssss, ssaaaaaaaasssss, ssaaaaaaaaassss, ssssssssssaaass, sssssssssaaaass, ssssssssaaaaass, sssssssaaaaaass, ssssssaaaaaaass, sssssaaaaaaaass, ssssaaaaaaaaass, sssaaaaaaaaaass, ssasasasasasass, sssasasasasasss, ooosssssssssoo, soosssssssssos, aoosssssssssooa, aoasssssssssaoa, aoaaaasssssaoa, aoossssssssssoa, ooasssssssssaoo, aoosaasssssssoa, aossaassssssssoa, aooaaaassssaoa, aoosssssssaaaaoa, sssssaaassssss, ssssssaaasssss, sssssssaaasssss, ssssssssaaassss, sssssssssaaasss, ssssaaassssssss, sssssaaaassssss, ssssssaaaasssss, sssssssaaaasss, sssssssaaaasss, sssaassssssaass, sssaassssssaasss, sssaassssaassss, sssaasssaassss, sssaassaasssss, sssaasaassssss, ssaassssssssaass, ssssaasssssaass, sssssaassssaass, ssssssaasssaass, sssssssaassaass, sssssssaasaass, ssssaasssaassss, sssssaasaasssss, sssssssssssssss, aaassssssssssss, aaasssssssssaa, aaaaaasssssssss, aooosaassssssssooaa, aoooossssssssssooaa, soooaasssssssssooss, soooosaasssssssooss, sooossaasssssssooss, soooossssssaassooss, sssaaaaassssss, sssssaaaaaassss, or sssssssssaaaaaa wherein each "a" represents an internucleoside linkage of Formula XVII, each "s" represents a phosphorothioate internucleoside linkage, and each "o" represents a phosphodiester internucleoside linkage.

Embodiment 1070. The modified oligonucleotide of embodiment 1069, wherein the modified oligonucleotide has an internucleoside linkage motif selected from: sssaaaassssssss, sssaaasssssssss, ssssaaasssssssss, ssssaassssaass, sssaassssssssss, ssssaassssssssss, sssssaassssssss, or sssssssssaassss, wherein each "a" represents an internucleoside linkage of Formula XVII, each "s" represents a phosphorothioate internucleoside linkage, and each "o" represents a phosphodiester internucleoside linkage.

Embodiment 1071. The modified oligonucleotide of embodiment 1069-1070, wherein each "a" represents a mesyl phosphoramidate internucleoside linkage.

Embodiment 1072. The modified oligonucleotide of any of embodiments 705-841, wherein the modified oligonucleotide is a CRISPR compound.

Embodiment 1073. The modified oligonucleotide of embodiment 1072, wherein the CRISPR compound consists of 20-50 or 29-32 linked nucleosides.

Embodiment 1074. The modified oligonucleotide of any of embodiments 794-1073, wherein each X is O.

Embodiment 1075. The modified oligonucleotide of any of embodiments 794-1073, wherein each X is S.

Embodiment 1076. The modified oligonucleotide of any of embodiments 794-1075, wherein at least one $R_1$ is H.

Embodiment 1077. The modified oligonucleotide of any of embodiments 794-1075, wherein at least one $R_1$ is a $C_1$-$C_6$ alkyl.

Embodiment 1078. The modified oligonucleotide of embodiment 1077, wherein the at least one $R_1$ is methyl.

Embodiment 1079. The modified oligonucleotide of any of embodiments 794-1075, at least one $R_1$ is a substituted $C_1$-$C_6$ alkyl.

Embodiment 1080. The modified oligonucleotide of any of embodiments 794-1079, wherein at least one T comprises a conjugate group.

Embodiment 1081. The modified oligonucleotide of embodiment 1080, wherein the conjugate group comprises a cell-targeting moiety.

Embodiment 1082. The modified oligonucleotide of embodiment 1080, wherein the conjugate group comprises a carbohydrate or carbohydrate cluster.

Embodiment 1083. The modified oligonucleotide of any of embodiments 1080-1082, wherein the conjugate group comprises at least one GalNAc.

Embodiment 1084. The modified oligonucleotide of embodiment 1080, wherein the conjugate group comprises a $C_{10}$-$C_{20}$ alkyl chain.

Embodiment 1085. The modified oligonucleotide of embodiment 1084, wherein the conjugate group comprises $C_{16}$ alkyl.

Embodiment 1086. The modified oligonucleotide of any of embodiments 794-1085, wherein at least one T does not comprise a conjugate group.

Embodiment 1087. The modified oligonucleotide of any of embodiments 794-1079, wherein each T does not comprise a conjugate group.

Embodiment 1088. The modified oligonucleotide of any of embodiments 794-1087, wherein at least one T is $SO_2R_2$.

Embodiment 1089. The modified oligonucleotide of embodiment 1088, wherein $R_2$ is an aryl.

Embodiment 1090. The modified oligonucleotide of embodiment 1088, wherein $R_2$ is a substituted aryl.

Embodiment 1091. The modified oligonucleotide of embodiment 1088, wherein $R_2$ is a heterocycle.

Embodiment 1092. The modified oligonucleotide of embodiment 1088, wherein $R_2$ is a substituted heterocycle.

Embodiment 1093. The modified oligonucleotide of embodiment 1088, wherein $R_2$ is an aromatic heterocycle.

Embodiment 1094. The modified oligonucleotide of embodiment 1088, wherein $R_2$ is a substituted aromatic heterocycle.

Embodiment 1095. The modified oligonucleotide of embodiment 1088, wherein $R_2$ is a diazole.

Embodiment 1096. The modified oligonucleotide of embodiment 1088, wherein $R_2$ is a substituted diazole.

Embodiment 1097. The modified oligonucleotide of embodiment 1088, wherein $R_2$ is an amine.

Embodiment 1098. The modified oligonucleotide of embodiment 1088, wherein $R_2$ is a substituted amine.

Embodiment 1099. The modified oligonucleotide of embodiment 1088, wherein $R_2$ is a $C_1$-$C_6$ alkoxy, $C_1$-$C_6$ alkenyl, or $C_1$-$C_6$ alkynyl.

Embodiment 1100. The modified oligonucleotide of embodiment 1088, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 1101. The modified oligonucleotide of embodiment 1088, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 1102. The modified oligonucleotide of embodiment 1088, wherein $R_2$ comprises a carbohydrate or carbohydrate cluster.

Embodiment 1103. The modified oligonucleotide of embodiment 1088, wherein $R_2$ comprises at least one GalNAc.

Embodiment 1104. The modified oligonucleotide of embodiment 1088, wherein T is:

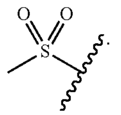 [SMILES: *S(C)(=O)=O]

Embodiment 1105. The modified oligonucleotide of embodiment 1088, wherein T is:

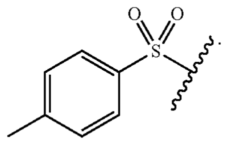 [SMILES: *S(=O)(=O)c1ccc(C)cc1]

Embodiment 1106. The modified oligonucleotide of embodiment 1088, wherein T is:

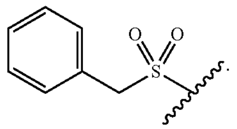 [SMILES: *S(=O)(=O)Cc1ccccc1]

Embodiment 1107. The modified oligonucleotide of embodiment 1088, wherein T is:

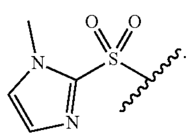 [SMILES: *S(=O)(=O)c1nccn1C]

Embodiment 1108. The modified oligonucleotide of embodiment 1088, wherein T is:

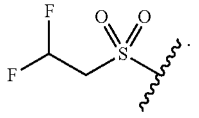

Embodiment 1109. The modified oligonucleotide of embodiment 1088, wherein T is:

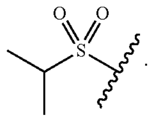

Embodiment 1110. The modified oligonucleotide of embodiment 1088, wherein T is:

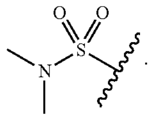 [SMILES: *S(=O)(=O)N(C)C]

Embodiment 1111. The modified oligonucleotide of embodiment 1088, wherein T is:

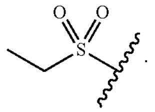 [SMILES: *S(=O)(=O)CC]

Embodiment 1112. The modified oligonucleotide of embodiment 1088, wherein T is:

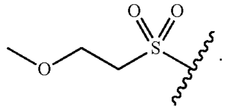

Embodiment 1113. The modified oligonucleotide of embodiment 1088, wherein T is:

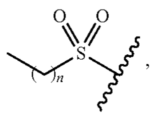

wherein n is from 2 to 20.

Embodiment 1114. The modified oligonucleotide of embodiment 1113, wherein n is 15.

Embodiment 1115. The modified oligonucleotide of any of embodiments 794-1114, wherein at least one T is $C(=O)R_3$.

Embodiment 1116. The modified oligonucleotide of embodiment 1115, wherein $R_3$ is an aryl.

Embodiment 1117. The modified oligonucleotide of embodiment 1115, wherein $R_3$ is a substituted aryl.

Embodiment 1118. The modified oligonucleotide of embodiment 1115, wherein $R_3$ is $CH_3$.

Embodiment 1119. The modified oligonucleotide of embodiment 1115, wherein $R_3$ is $N(CH_3)_2$.

Embodiment 1120. The modified oligonucleotide of embodiment 1115, wherein $R_3$ is $OCH_3$.

Embodiment 1121. The modified oligonucleotide of embodiment 1115, wherein $R_3$ is a $C_1$-$C_6$ alkoxy.

Embodiment 1122. The modified oligonucleotide of embodiment 1115, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 1123. The modified oligonucleotide of embodiment 1115, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 1124. The modified oligonucleotide of embodiment 1115, wherein $R_3$ comprises a carbohydrate or carbohydrate cluster.

Embodiment 1125. The modified oligonucleotide of embodiment 1115, wherein $R_{23}$ comprises at least one GalNAc.

Embodiment 1126. The modified oligonucleotide of embodiment 1115, wherein T is:

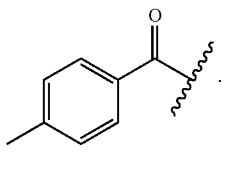 [SMILES: *C(=O)c1ccc(C)cc1]

Embodiment 1127. The modified oligonucleotide of embodiment 1115, wherein T is:

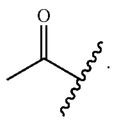 [SMILES: *C(C)=O]

Embodiment 1128. The modified oligonucleotide of embodiment 1115, wherein T is:

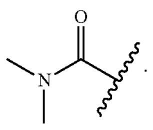 [SMILES: *C(=O)N(C)C]

Embodiment 1129. The modified oligonuclotides of embodiment 1115, wherein Tis:

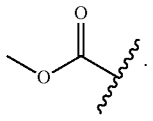 [SMILES: *C(=O)OC]

Embodiment 1130. The modified oligonucleotide of embodiment 1115, wherein T is:

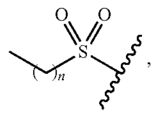

wherein n is from 2 to 20.

Embodiment 1131. The modified oligonucleotide of embodiment 1130, wherein n is 15.

Embodiment 1132. The modified oligonucleotide of any of embodiments 794-1131, wherein at least one T is $P(=O)R_4R_5$.

Embodiment 1133. The modified oligonucleotide of embodiment 1132, wherein $R_4$ is $OCH_3$.

Embodiment 1134. The modified oligonucleotide of embodiment 1132, wherein $R_4$ is OH.

Embodiment 1135. The modified oligonucleotide of embodiment 1132, wherein $R_4$ is $C_1$-$C_6$ alkyl.

Embodiment 1136. The modified oligonucleotide of embodiment 1132, wherein $R_4$ is substituted $C_1$-$C_6$ alkyl.

Embodiment 1137. The modified oligonucleotide of embodiment 1132, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 1138. The modified oligonucleotide of embodiment 1132, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 1139. The modified oligonucleotide of embodiment 1132, wherein $R_4$ comprises a carbohydrate or carbohydrate cluster.

Embodiment 1140. The modified oligonucleotide of embodiment 1132, wherein $R_4$ comprises at least one GalNAc.

Embodiment 1141. The modified oligonucleotide of any of embodiments 1132-1140, wherein $R_5$ is $OCH_3$.

Embodiment 1142. The modified oligonucleotide of any of embodiments 1132-1140, wherein $R_5$ is OH.

Embodiment 1143. The modified oligonucleotide of any of embodiments 1132-1140, wherein $R_5$ is $C_1$-$C_6$ alkyl.

Embodiment 1144. The modified oligonucleotide of any of embodiments 1132-1140, wherein $R_5$ is substituted $C_1$-$C_6$ alkyl.

Embodiment 1145. The modified oligonucleotide of embodiment 1132, wherein T is:

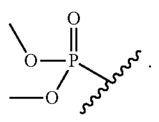 [SMILES: *P(=O)(OC)OC]

Embodiment 1146. The modified oligonucleotide of embodiment 1132, wherein T is:

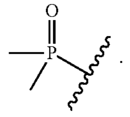 [SMILES: *P(C)(C)=O]

Embodiment 1147. The modified oligonucleotide of embodiment 1132, wherein T is:

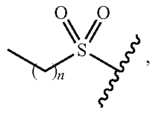

wherein n is from 2 to 20.

Embodiment 1148. The modified oligonucleotide of embodiment 1147, wherein n is 15.

Embodiment 1149. An antisense agent comprising a modified oligonucleotide consisting of 12-50 linked nucleosides linked through internucleoside linking groups, wherein at least one internucleoside linking group is a phosphodiester or a phosphorothioate internucleoside linking group, and wherein at least one of the internucleoside linking groups has Formula XX:

XX

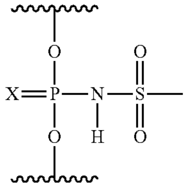

wherein independently for each internucleoside linking group of the modified oligonucleotide having Formula XX, X is selected from O or S.

Embodiment 1150. An antisense agent comprising a modified oligonucleotide, wherein the 5'-terminus of the modified oligonucleotide has Structure F:

Structure F

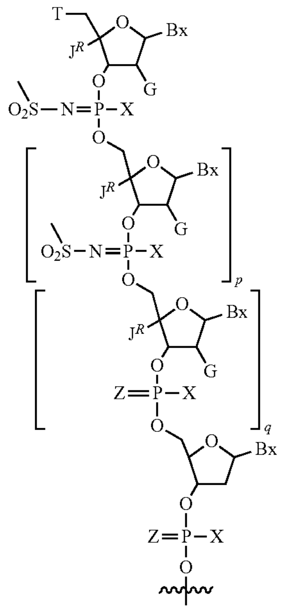

wherein:

p is from 0 to 6;

q is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1151. An antisense agent comprising a modified oligonucleotide, wherein the 3'-terminus of the modified oligonucleotide has Structure G:

Structure G

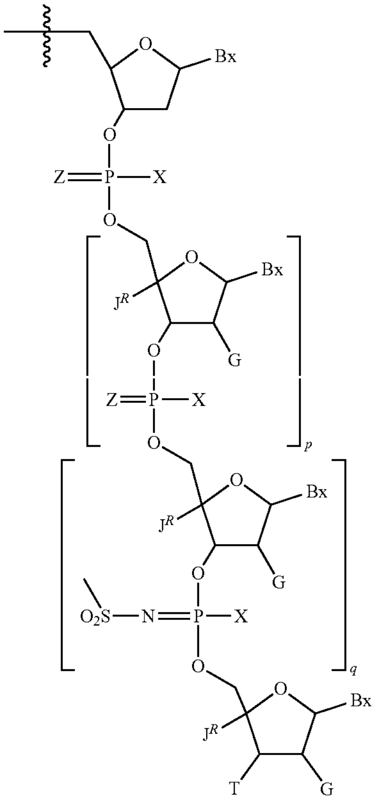

wherein:

p is from 0 to 6;

q is from 1 to 6;

T is OH or a conjugate group;

each Bx is an independently selected heterocyclic base moiety;

each X is independently selected from OH or SH;

each Z is independently selected from O, S, or $NSO_2Me$;

for each $J^R$ and G of the same furanosyl sugar moiety, either $J^R$ and G form a $J^R$ to G bridge, or $J^R$ is H and G is selected from OH, halogen or O—$[C(R_6)(R_7)]_n$ $[(C{=}O)_m—X^G]_j—R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1152. The antisense agent of embodiment 1150 or 1151, wherein the sum of p+q is selected from 2, 3, 4, or 5.

Embodiment 1153. An antisense agent comprising a modified oligonucleotide, wherein the 5'-terminus of the modified oligonucleotide has Structure H:

Structure H

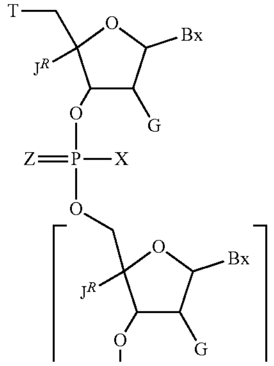

-continued

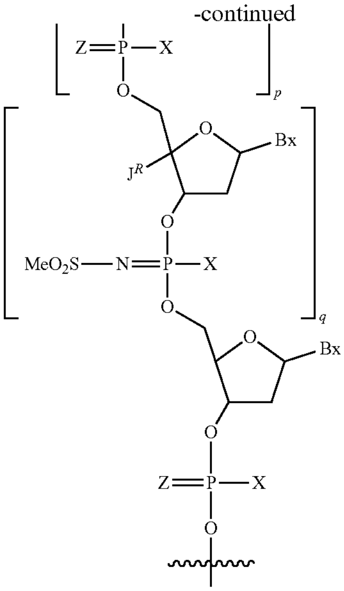

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

for each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m—X^G]_j—R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1154. An antisense agent comprising a modified oligonucleotide, wherein the 5'-terminus of the modified oligonucleotide has Structure I:

Structure I

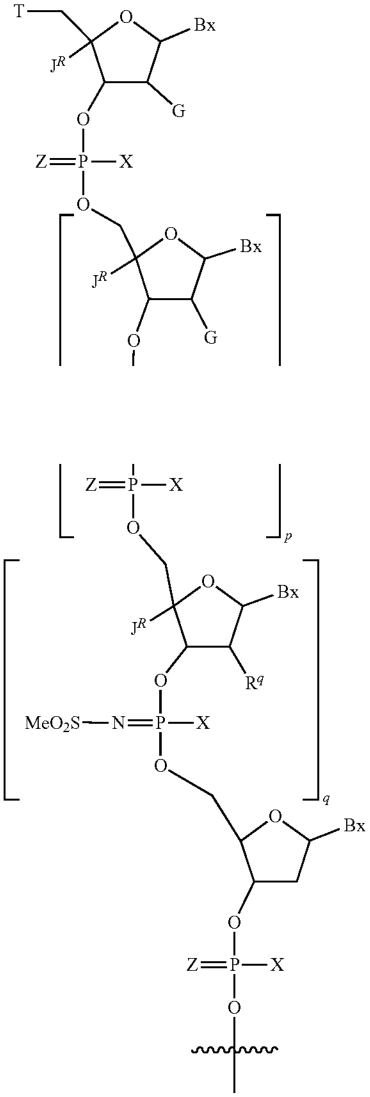

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

each $R^q$ is H or exactly one $R^q$ is OMe and the other $R^q$ are H;

for each $J^R$ and G of the same furanosyl sugar moiety, either $J^R$ and G form a $J^R$ to G bridge, or $J^R$ is H and G is selected from OH, halogen or $O—[C(R_6)(R_7)]_n[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1155. The antisense agent of embodiment 1154, wherein exactly one $R^q$ is —OMe.

Embodiment 1156. The antisense agent of any of embodiments 1153-1155, wherein the sum of p+q is 2, 3, or 4.

Embodiment 1157. An antisense agent comprising a modified oligonucleotide, wherein the 3'-terminus of the modified oligonucleotide has Structure J:

Structure J

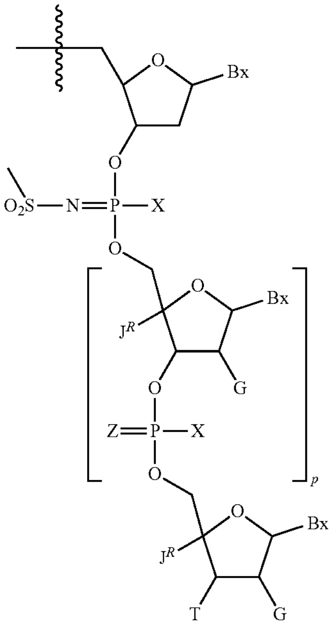

wherein:

p is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1158. The antisense agent of embodiment 1157, wherein p is 2, 3, or 4.

Embodiment 1159. The antisense agent of any of embodiments 1150-1158, wherein each $J^R$ is H and each G is $OCH_2CH_2OCH_3$.

Embodiment 1160. The antisense agent of any of embodiments 1150-1158, wherein each $J^R$ is H and each G is $OCH_3$.

Embodiment 1161. The antisense agent of any of embodiments 1150-1158, wherein each $J^R$ and G form a $J^R$ to G bridge.

Embodiment 1162. The antisense agent of embodiment 1161, wherein the $J^R$ to G bridge has the formula —$CH(CH_3)$—O—.

Embodiment 1163. The antisense agent of embodiment 1149, wherein the antisense agent is an RNAi agent.

Embodiment 1164. The RNAi agent of embodiment 1163, wherein the RNAi agent is a single-stranded RNAi agent comprising an RNAi antisense modified oligonucleotide, wherein the RNAi antisense modified oligonucleotide is a modified oligonucleotide of embodiment 1149.

Embodiment 1165. The RNAi agent of embodiment 1163, wherein the RNAi agent is an oligonucleotide duplex comprising an RNAi antisense modified oligonucleotide and an RNAi sense modified oligonucleotide, wherein the RNAi antisense modified oligonucleotide and/or the RNAi sense modified oligonucleotide is a modified oligonucleotide of embodiment 1149.

Embodiment 1166. The RNAi agent of any of embodiments 1164-1165, wherein the 5'-terminus of the RNAi antisense oligonucleotide has structure K:

Structure K

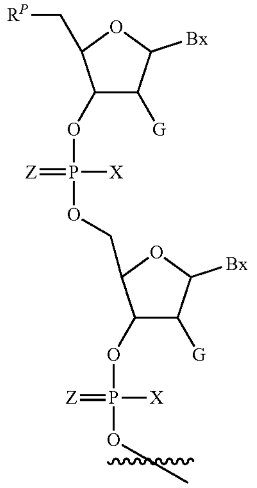

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1167. The RNAi agent of embodiment 1166, wherein the stabilized phosphate group is 5'-vinyl phosphonate or 5'-cyclopropyl phosphonate.

Embodiment 1168. The RNAi agent of embodiment 1166 or 1167, wherein each G within structure K is independently selected from F or OMe.

-

Embodiment 1169. The RNAi agent of any of embodiments 1164-1168, wherein the 3'-terminus of the RNAi antisense oligonucleotide has structure L:

Structure L

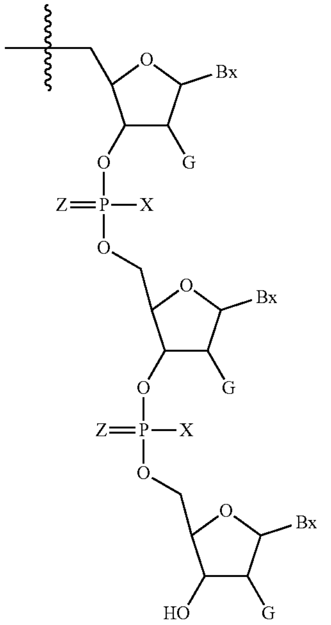

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C═O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(═X_2)J_1$, $OC(═X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1170. The RNAi agent of embodiment 1169, wherein each G within Structure L of the RNAi antisense oligonucleotide is independently selected from F or OMe.

Embodiment 1171. The RNAi agent of any of embodiments 1164-1170, wherein at least one region of the RNAi antisense oligonucleotide has structure M:

Structure M

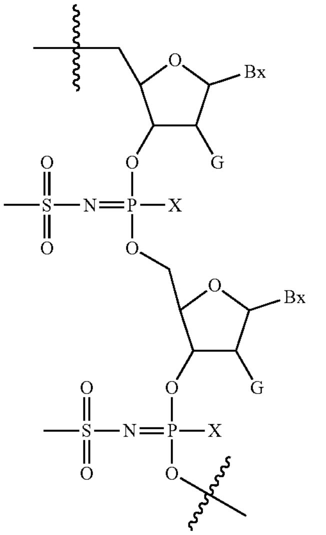

wherein:

each Bx is an independently selected heterocyclic base moiety;

each X is independently selected from OH or SH;

each G is independently selected from OH, halogen or $O—[C(R_6)(R_7)]_n—[(C═O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(═X_2)J_1$, $OC(═X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1172. The RNAi agent of embodiment 1171, wherein each G of Structure M within the RNAi antisense oligonucleotide is selected from F or OMe.

Embodiment 1173. The RNAi agent of embodiment 1172, wherein one G is F and the other G is OMe.

Embodiment 1174. The RNAi agent of any of embodiments 1164-1165 or 1169-1173, wherein the 5'-terminus of the RNAi antisense oligonucleotide has structure N:

Structure N

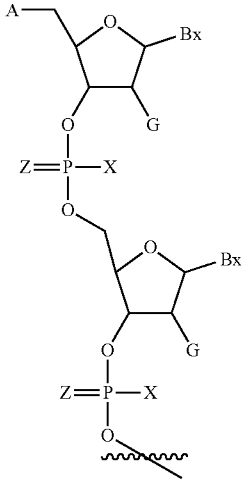

A is selected from

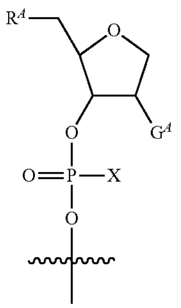

or

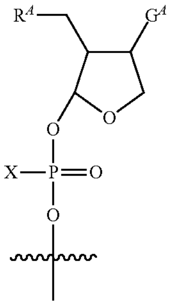

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1175. The RNAi agent of embodiment 1174, wherein each G within structure N of the RNAi antisense oligonucleotide is selected from F or OMe.

Embodiment 1176. The RNAi agent of any of embodiments 1164-1168 or 1171-1175, wherein the 3'-terminus of the RNAi antisense oligonucleotide has structure O:

Structure O

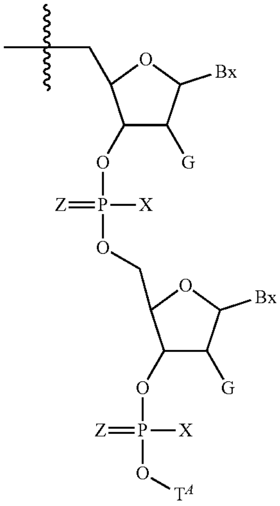

wherein:

$T^A$ is selected from

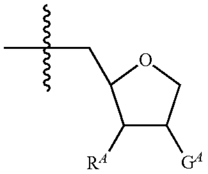

or

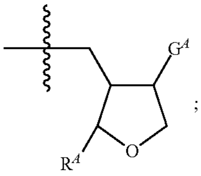

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1177. The RNAi agent of embodiment 1176, wherein each G within structure O of the RNAi antisense oligonucleotide is selected from F or OMe.

Embodiment 1178. The RNAi agent of embodiment 1165, wherein the 5'-terminus of the RNAi sense oligonucleotide has structure K:

Structure K

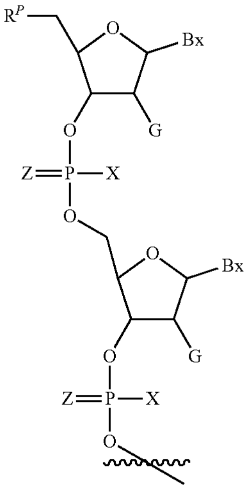

wherein:

R is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1179. The RNAi agent of embodiment 1178, wherein the stabilized phosphate group is 5'-vinyl phosphonate or 5'-cyclopropyl phosphonate.

Embodiment 1180. The RNAi agent of embodiment 1178 or 1179, wherein each G within structure K is independently selected from F or OMe.

Embodiment 1181. The RNAi agent of any of embodiments 1165 or 1178-1180, wherein the 3'-terminus of the RNAi sense oligonucleotide has structure L:

Structure L

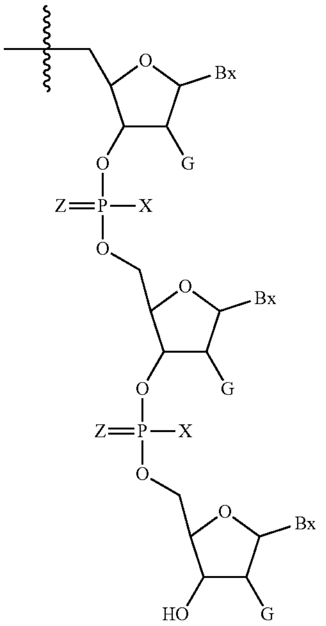

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1182. The RNAi agent of embodiment 1181, wherein each G within Structure L of the RNAi sense oligonucleotide is independently selected from F or OMe.

Embodiment 1183. The RNAi agent of any of embodiments 1165 or 1178-1182 wherein at least one region of the RNAi sense oligonucleotide has structure M:

Structure M

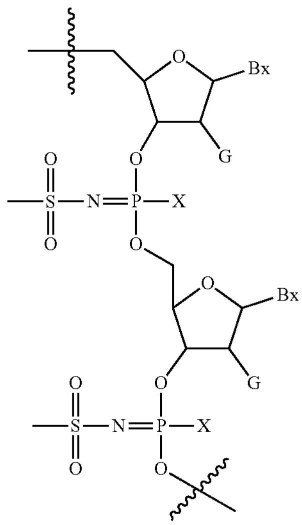

wherein:

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1184. The RNAi agent of embodiment 1183, wherein each G of Structure M within the RNAi sense oligonucleotide is selected from F or OMe.

Embodiment 1185. The RNAi agent of embodiment 1184, wherein one G is F and the other G is OMe.

Embodiment 1186. The RNAi agent of any of embodiments 1165 or 1181-1185, wherein the 5'-terminus of the RNAi sense oligonucleotide has structure N:

Structure N

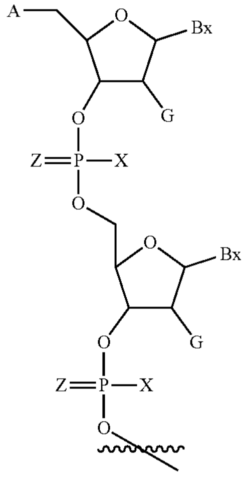

wherein:

A is selected from or

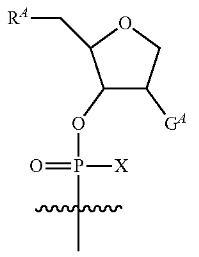

or

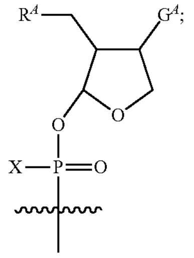

$R^A$ is OH, $OP(=O)OH$, $OP(=O)SH$, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1187. The RNAi agent of embodiment 1186, wherein each G within structure N of the RNAi sense oligonucleotide is selected from F or OMe.

Embodiment 1188. The RNAi agent of any of embodiments 1165, 1178-1180 or 1183-1187, wherein the 3'-terminus of the RNAi sense oligonucleotide has structure O:

Structure O

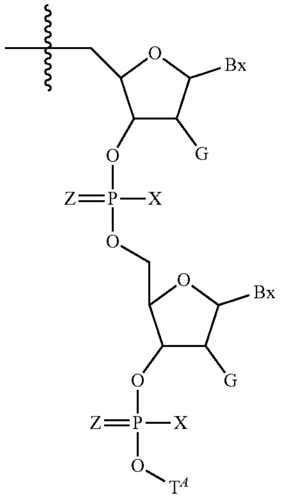

wherein:

$T^A$ is selected from

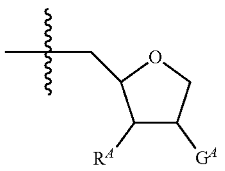

or

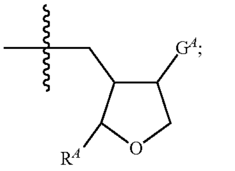

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1189. The RNAi agent of embodiment 1188, wherein each G within structure O of the RNAi sense oligonucleotide is selected from F or OMe.

Embodiment 1190. The antisense agent of any of embodiments 705-909 or 943-1177, comprising a modified oligonucleotide, wherein the nucleobase sequence of the modified oligonucleotide is complementary to a target nucleic acid.

Embodiment 1191. The modified oligonucleotide of embodiment 1190, wherein the nucleobase sequence of the modified oligonucleotide is at least 80% complementary to the target nucleic acid.

Embodiment 1192. The modified oligonucleotide of embodiment 1190, wherein the nucleobase sequence of the modified oligonucleotide is at least 85% complementary to the target nucleic acid.

Embodiment 1193. The modified oligonucleotide of embodiment 1190, wherein the nucleobase sequence of the modified oligonucleotide is at least 90% complementary to the target nucleic acid.

Embodiment 1194. The modified oligonucleotide of embodiment 1190, wherein the nucleobase sequence of the modified oligonucleotide is at least 95% complementary to the target nucleic acid.

Embodiment 1195. The modified oligonucleotide of embodiment 1190, wherein the nucleobase sequence of the modified oligonucleotide is 100% complementary to the target nucleic acid.

Embodiment 1196. The modified oligonucleotide of any of embodiments 1190-1195, wherein the target nucleic acid is a target RNA.

Embodiment 1197. The modified oligonucleotide of embodiment 1196, wherein the target RNA is selected from: an mRNA, a pre-mRNA, a microRNA, and a non-coding RNA.

Embodiment 1198. The modified oligonucleotide of embodiment 1197, wherein the target RNA is not a microRNA.

Embodiment 1199. The antisense agent comprising a modified oligonucleotide of any of embodiments 1-1198, wherein the modified oligonucleotide is not complementary to miR-21.

Embodiment 1200. The antisense agent of any of embodiments 705-1199, comprising a conjugate group.

Embodiment 1201. The antisense agent of embodiment 1200, wherein the conjugate group comprises at least one GalNAc.

Embodiment 1202. The antisense agent of embodiment 1200 or 1201, wherein the conjugate group comprises 1-5 linker-nucleosides.

Embodiment 1203. A pharmaceutical composition comprising the antisense agent of any of embodiments 705-1202 and a pharmaceutically acceptable carrier or diluent.

Embodiment 1204. A method comprising contacting a cell with the antisense agent or pharmaceutical composition of any of embodiments 705-1203.

Embodiment 1205. A method of modulating the amount or activity of a target nucleic acid in a cell, comprising contacting the cell with the antisense agent or pharmaceutical composition of any of embodiments 705-1204 and thereby modulating the amount or activity of the target nucleic acid.

Embodiment 1206. A method of modulating the amount or activity of a target nucleic acid in a cell, comprising contacting the cell with the antisense agent or pharmaceutical composition of any of embodiments 705-1204.

Embodiment 1207. The method of embodiments 1204-1206, wherein the amount or activity of a target nucleic acid is reduced.

Embodiment 1208. The method of embodiments 1204-1206, wherein the amount or activity of a target nucleic acid is increased.

Embodiment 1209. The method of embodiment 1204, wherein the target protein is encoded by a target nucleic acid comprising at least one translation suppression element and wherein the modified oligonucleotide is complementary to a target site within a translation suppression element region of the target nucleic acid.

Embodiment 1210. The method of embodiment 1209, wherein the translation suppression element region comprises at least one stem-loop structure.

Embodiment 1211. Use of the antisense agent or composition of any of embodiments 705-1203 for treatment of a disease or condition.

Embodiment 1212. Use of the antisense agent or composition of any of embodiments 705-1203 for a preparation of a medicament for treatment of a disease or condition.

Embodiment 1213. The antisense agent of any of embodiments 705-856, 943-1162, or 1190-1202, wherein the antisense agent is not an RNAi agent and the parent antisense agent is cytotoxic in vitro.

Embodiment 1214. The antisense agent of embodiment 1213, wherein the parent antisense agent is cytotoxic in a standard in vitro cytotoxicity assay.

Embodiment 1215. The antisense agent of embodiment 1213, wherein the antisense agent of any of embodiments 705-856, 943-1162, or 1190-1202 is not cytotoxic in vitro.

Embodiment 1216. The antisense agent of any of embodiments 1213-1215, wherein the antisense agent of any of embodiments 705-856, 943-1162, or 1190-1202 is not cytotoxic in a standard in vitro cytoxicity assay.

Embodiment 1217. The antisense agent of any of embodiments 705-856, 943-1162, or 1190-1202, wherein the antisense agent is not an siRNA agent and the parent antisense agent is hepatotoxic to the mouse.

Embodiment 1218. The antisense agent of embodiment 1217, wherein the mouse is a BALB/c mouse, wherein 50 mg/kg of the parent antisense agent is administered to the mouse, and wherein the plasma ALT level in the mouse is measured 72 hours following the administration of the parent antisense agent.

Embodiment 1219. The antisense agent of any of embodiments 1217-1218, wherein administration of 50 mg/kg of the antisense agent of any of embodiments 705-856, 943-1162, or 1190-1202 to a mouse is not hepatotoxic to the mouse.

Embodiment 1220. The antisense agent of any of embodiments 705-856, 943-1162, or 1190-1202, wherein the therapeutic index in a mouse of the antisense agent of any of embodiments 705-856, 943-1162, or 1190-1202 is increased relative to the therapeutic index of the parent antisense agent.

Embodiment 1221. The antisense agent of embodiment 1220, wherein the therapeutic index in a mouse of the antisense agent of embodiment 516 is at least two-fold greater than the therapeutic index of the parent antisense agent.

Embodiment 1222. The antisense agent of any of embodiments 1213-1221, wherein the parent antisense agent is identical to the antisense agent of any of embodiments 705-856, 943-1162, or 1190-1202, except that each internucleoside linkage of Formula XVII is replaced with a phosphorothioate internucleoside linkage in the parent antisense agent.

Embodiment 1223. The antisense agent of any of embodiments 1213-1222, wherein the antisense agent is an RNAse H agent.

Embodiment 1224. The antisense agent of any of embodiments 1213-1222, wherein the antisense agent is a gapmer.

Embodiment 1225. The antisense agent of any of embodiments 1213-1222, wherein the antisense agent modulates splicing.

Embodiment 1226. The antisense agent of any of embodiments 1213-1222, wherein the antisense agent increases protein expression.

Embodiment 1227. The antisense agent of any of embodiments 705-942, 1074-1148 or 1163-1202, wherein the antisense agent is an RNAi agent, and the parent RNAi agent is cytoxic in vitro.

Embodiment 1228. The antisense agent of embodiment 1227, wherein the RNAi agent of any of embodiments 705-942, 1074-1148 or 1163-1202, is not cytotoxic in vitro.

Embodiment 1229. The antisense agent of any of embodiments 1227-1228 wherein the RNAi agent of any of embodiments 705-942, 1074-1148 or 1163-1202 is not cytotoxic in a standard in vitro cytoxicity assay.

Embodiment 1230. The antisense agent of any of embodiments 705-942, 1074-1148 or 1163-1202, wherein the antisense agent is an RNAi agent and is hepatotoxic to the mouse.

Embodiment 1231. The RNAi agent of embodiment 1230, wherein the mouse is a BALB/c mouse, wherein 50 mg/kg of the parent RNAi agent is administered to the mouse, and wherein the plasma ALT level in the mouse is measured 72 hours following the administration of the parent RNAi agent.

Embodiment 1232. The RNAi agent of any of embodiments 1230-1231, wherein administration of 50 mg/kg of the RNAi agent of any of embodiments 705-942, 1074-1148 or 1163-1202 to a mouse is not hepatotoxic to the mouse.

Embodiment 1233. The RNAi agent of any of embodiments 705-942, 1074-1148 or 1163-1202, wherein the therapeutic index in a mouse of the RNAi agent of any of embodiments 705-942, 1074-1148 or 1163-1202 is increased relative to the therapeutic index of the parent RNAi agent.

Embodiment 1234. The RNAi agent of embodiment 1233, wherein the therapeutic index in a mouse of the RNAi agent of embodiment 1233 is at least two-fold greater than the therapeutic index of the parent RNAi agent.

Embodiment 1235. The RNAi agent of any of embodiments 1127-1234, wherein the parent RNAi agent is identical to the RNAi agent of any of embodiments 705-942, 1074-1148 or 1163-1202, except that each internucleoside linkage of Formula XVII is replaced with a phosphodiester internucleoside linkage in the parent RNAi agent.

Embodiment 1236. A method of designing an antisense agent comprising starting with a parent antisense agent or a parent RNAi agent and changing the design of that compound in order to arrive at an antisense agent of any one of embodiments 705-1202.

Embodiment 1237. A method of designing an antisense agent comprising identifying an antisense agent or parent RNAi agent and changing the design of that parent antisense agent or parent RNAi agent to arrive at a second antisense agent, wherein the second antisense agent is an antisense agent of any one of embodiments 705-1202.

Embodiment 1238. A method of improving hepatotoxicity of an antisense agent comprising the steps of (i) identifying a parent antisense agent or parent RNAi agent that has plasma ALT levels above 300 units per liter in a mouse, and (ii) providing an antisense agent according to any one of embodiments 705-1202.

Embodiment 1239. The method of embodiment 1236, wherein the method designs antisense agent with improved therapeutic index relative to the parent antisense agent or parent RNAi agent.

Embodiment 1240. The method of embodiment 1236, wherein the method designs an antisense agent with lower hepatotoxicity relative to the parent antisense agent or parent RNAi agent.

Embodiment 1241. The method of embodiment 1237, wherein the second antisense agent has an improved therapeutic index relative to the parent antisense agent or parent RNAi agent.

Embodiment 1242. The method of embodiment 1237, wherein the second antisense agent has reduced hepatotoxicity in a mouse relative to the parent antisense agent or parent RNAi agent.

Embodiment 1243. The method of embodiment 1238, wherein the antisense agent according to any one of embodiments 705-1202 has improved therapeutic index relative to the parent antisense agent or parent RNAi agent.

Embodiment 1244. The method of embodiment 1238, wherein the antisense agent according to any one of embodiments 705-1202 has reduced hepatotoxicity relative to the parent antisense agent or parent RNAi agent.

Embodiment 1245. A method comprising administering an antisense agent of any of embodiments 705-1202 to a mouse and separately administering the parent antisense agent or parent RNAi agent of the antisense agent of any of embodiments 705-1202 to a second mouse, wherein the therapeutic index of the antisense agent of any of embodiments 705-1202 is improved relative to the therapeutic index of the parent antisense agent or parent RNAi agent.

Embodiment 1246. An oligomeric compound comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVII:

XVII

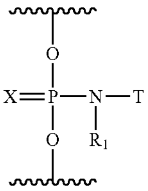

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

Embodiment 1247. An oligomeric compound comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVII:

XVII

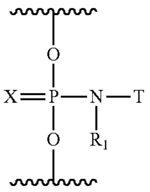

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl, Provided that if X is O and that if $R_1$ is H, then T is not:

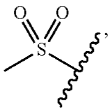,

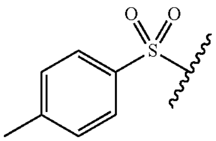,

-continued

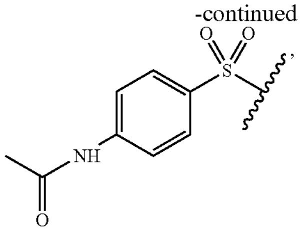

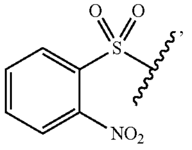

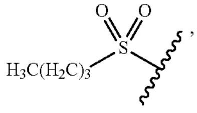

or

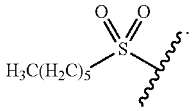

Embodiment 1248. The oligomeric compound of embodiment 1246 or embodiment 1247, wherein at least one internucleoside linking group is a phosphodiester or a phosphorothioate internucleoside linking group.

Embodiment 1249. The oligomeric compound of any of embodiments 1246-1248, wherein at least one nucleoside comprises a 2'-β-D-deoxyribosyl sugar moiety.

Embodiment 1250. The oligomeric compound of any of embodiments 1246-1249, wherein for at least one internucleoside linking group of Formula XVII, X is O.

Embodiment 1251. The oligomeric compound of any of embodiments 1246-1250, wherein for at least one internucleoside linking group of Formula XVII, X is S.

Embodiment 1252. The oligomeric compound of embodiment 1246 or 1247, wherein for at least one internucleoside linking group of Formula XVII, $R_1$ is H.

Embodiment 1253. The oligomeric compound of embodiment 1246 or 1247, wherein for at least one internucleoside linking group of Formula XVII, $R_1$ is a $C_1$-$C_6$ alkyl.

Embodiment 1254. The oligomeric compound of embodiment 1253, wherein $R_1$ is methyl.

Embodiment 1255. The oligomeric compound of embodiment 1246 or 1247, wherein for at least one internucleoside linking group of Formula XVII, $R_1$ is a substituted $C_1$-$C_6$ alkyl.

Embodiment 1256. The oligomeric compound of any of embodiments 1246-1255, wherein for at least one internucleoside linking group of Formula XVII, T comprises a conjugate group.

Embodiment 1257. The oligomeric compound of embodiment 1256, wherein the conjugate group comprises a cell-targeting moiety.

Embodiment 1258. The oligomeric compound of embodiment 1256, wherein the conjugate group comprises a carbohydrate or carbohydrate cluster.

Embodiment 1259. The oligomeric compound of any of embodiments 1256-1258, wherein the conjugate group comprises at least one GalNAc.

Embodiment 1260. The oligomeric compound of embodiment 1256, wherein the conjugate group comprises a $C_{10}$-$C_{20}$ alkyl chain.

Embodiment 1261. The oligomeric compound of embodiment 1257, wherein the conjugate group comprises $C_{16}$ alkyl.

Embodiment 1262. The oligomeric compound of any of embodiments 1246-1255, wherein for at least one internucleoside linking group of Formula XVII, T does not comprise a conjugate group.

Embodiment 1263. The oligomeric compound of any of embodiments 1246-1255, wherein for at least one internucleoside linking group of Formula XVII, T does not comprise a cell-targeting moiety.

Embodiment 1264. The oligomeric compound of any of embodiments 1246-1263, wherein for at least one internucleoside linking group of Formula XVII, T is $SO_2R_2$.

Embodiment 1265. The oligomeric compound of embodiment 1264, wherein $R_2$ is an aryl.

Embodiment 1266. The oligomeric compound of embodiment 1264, wherein $R_2$ is a substituted aryl.

Embodiment 1267. The oligomeric compound of embodiment 1264, wherein $R_2$ is a heterocycle.

Embodiment 1268. The oligomeric compound of embodiment 1264, wherein $R_2$ is a substituted heterocycle.

Embodiment 1269. The oligomeric compound of embodiment 1264, wherein $R_2$ is an aromatic heterocycle.

Embodiment 1270. The oligomeric compound of embodiment 1264, wherein $R_2$ is a substituted aromatic heterocycle.

Embodiment 1271. The oligomeric compound of embodiment 1264, wherein $R_2$ is a diazole.

Embodiment 1272. The oligomeric compound of embodiment 1264, wherein $R_2$ is a substituted diazole.

Embodiment 1273. The oligomeric compound of embodiment 1264, wherein $R_2$ is an amine.

Embodiment 1274. The oligomeric compound of embodiment 1264, wherein $R_2$ is a substituted amine.

Embodiment 1275. The oligomeric compound of embodiment 1264, wherein $R_2$ is a $C_1$-$C_6$ alkoxy, $C_1$-$C_6$ alkenyl, or $C_1$-$C_6$-alkynl.

Embodiment 1276. The oligomeric compound of embodiment 1264, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 1277. The oligomeric compound of embodiment 1264, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 1278. The oligomeric compound of embodiment 1264, wherein $R_2$ comprises a carbohydrate or carbohydrate cluster.

Embodiment 1279. The oligomeric compound of embodiment 1264, wherein $R_2$ comprises at least one GalNAc.

Embodiment 1280. The oligomeric compound of embodiment 1264, wherein T is:

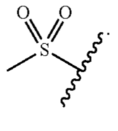

Embodiment 1281. The oligomeric compound of embodiment 1264, wherein T is:

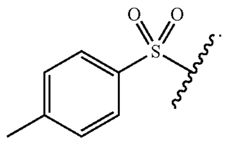 [SMILES: *S(=O)(=O)c1ccc(C)cc1]

Embodiment 1282. The oligomeric compound of embodiment 1264, wherein T is:

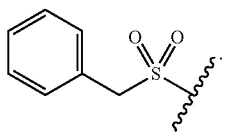 [SMILES: *S(=O)(=O)Cc1ccccc1]

Embodiment 1283. The oligomeric compound of embodiment 1264, wherein T is:

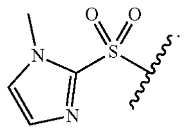 [SMILES: *S(=O)(=O)c1nccn1C]

Embodiment 1284. The oligomeric compound of embodiment 1264, wherein T is:

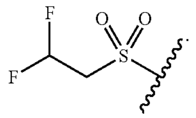

Embodiment 1285. The oligomeric compound of embodiment 1264, wherein T is:

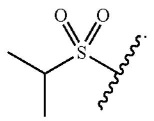

Embodiment 1286. The oligomeric compound of embodiment 1264, wherein T is:

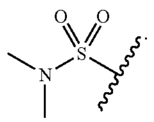 [SMILES: *S(=O)(=O)N(C)C]

Embodiment 1287. The oligomeric compound of embodiment 1264, wherein T is:

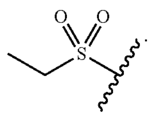

Embodiment 1288. The oligomeric compound of embodiment 1264, wherein T is:

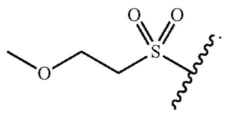 [SMILES: *S(=O)(=O)CCOC]

Embodiment 1289. The oligomeric compound of embodiment 1264, wherein T is:

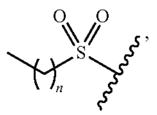

wherein n is from 2 to 20.

Embodiment 1290. The oligomeric compound of embodiment 1289, wherein n is 15.

Embodiment 1291. The oligomeric compound of any of embodiments 1246-1290, wherein for at least one internucleoside linking group of Formula XVII, T is C(═O)$R_3$.

Embodiment 1292. The oligomeric compound of embodiment 1291, wherein $R_3$ is an aryl.

Embodiment 1293. The oligomeric compound of embodiment 1291, wherein $R_3$ is a substituted aryl.

Embodiment 1294. The oligomeric compound of embodiment 1291, wherein $R_3$ is $CH_3$.

Embodiment 1295. The oligomeric compound of embodiment 1291, wherein $R_3$ is $N(CH_3)_2$.

Embodiment 1296. The oligomeric compound of embodiment 1291, wherein $R_3$ is $OCH_3$.

Embodiment 1297. The oligomeric compound of embodiment 1291, wherein $R_3$ is a $C_1$-$C_6$ alkoxy.

Embodiment 1298. The oligomeric compound of embodiment 1291, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 1299. The oligomeric compound of embodiment 1291, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 1300. The oligomeric compound of embodiment 1291, wherein $R_3$ comprises a carbohydrate or carbohydrate cluster.

Embodiment 1301. The oligomeric compound of embodiment 1291, wherein $R_{23}$ comprises at least one GalNAc.

Embodiment 1302. The oligomeric compound of embodiment 1291, wherein T is:

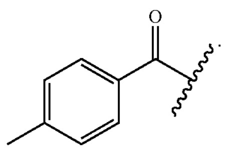 [SMILES: *C(=O)c1ccc(C)cc1]

Embodiment 1303. The oligomeric compound of embodiment 1291, wherein T is:

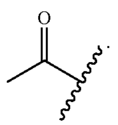 [SMILES: *C(C)=O]

Embodiment 1304. The oligomeric compound of embodiment 1291, wherein T is:

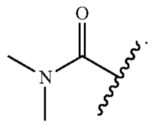 [SMILES: *C(=O)N(C)C]

Embodiment 1305. The oligomeric compound of embodiment 1291, wherein T is:

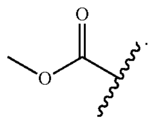

Embodiment 1306. The oligomeric compound of embodiment 1291, wherein T is:

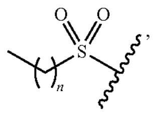

wherein n is from 2 to 20.

Embodiment 1307. The oligomeric compound of embodiments 1306, wherein n is 15.

Embodiment 1308. The oligomeric compound of any of embodiments 1246-1263, wherein for at least one internucleoside linking group of Formula XVII, T is P(=O)$R_4R_5$.

Embodiment 1309. The oligomeric compound of embodiment 1308, wherein $R_4$ is $OCH_3$.

Embodiment 1310. The oligomeric compound of embodiment 1308, wherein $R_4$ is OH Embodiment 1311. The oligomeric compound of embodiment 1308, wherein $R_4$ is $C_1$-$C_6$ alkyl.

Embodiment 1312. The oligomeric compound of embodiment 1308, wherein $R_4$ is substituted $C_1$-$C_6$ alkyl.

Embodiment 1313. The oligomeric compound of embodiment 1308, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 1314. The oligomeric compound of embodiment 1308, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 1315. The oligomeric compound of embodiment 1308, wherein $R_4$ comprises a carbohydrate or carbohydrate cluster.

Embodiment 1316. The oligomeric compound of embodiment 1308, wherein $R_4$ comprises at least one GalNAc.

Embodiment 1317. The oligomeric compound of any of embodiments 1308-1316, wherein $R_5$ is $OCH_3$.

Embodiment 1318. The oligomeric compound of any of embodiments 1308-1316, wherein $R_5$ is OH.

Embodiment 1319. The oligomeric compound of any of embodiments 1308-1316, wherein $R_5$ is $C_1$-$C_6$ alkyl.

Embodiment 1320. The oligomeric compound of any of embodiments 1308-1316, wherein $R_5$ is substituted $C_1$-$C_6$ alkyl.

Embodiment 1321. The oligomeric compound of embodiment 1308, wherein T is:

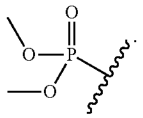 [SMILES: *P(=O)(OC)OC]

Embodiment 1322. The oligomeric compound of embodiment 1308, wherein T is:

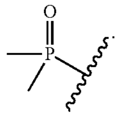 [SMILES: *P(C)(C)=O]

Embodiment 1323. The oligomeric compound of embodiment 1308, wherein T is:

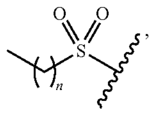

wherein n is from 2 to 20.

Embodiment 1324. The oligomeric compound of embodiment 1323, wherein n is 15.

Embodiment 1325. The oligomeric compound of any of embodiments 1246-1324, wherein at least one internucleoside linking group of the modified oligonucleotide is not a linking group of Formula XVII.

Embodiment 1326. The oligomeric compound of any of embodiments 1246-1325, wherein exactly one internucleoside linking group of the modified oligonucleotide is an internucleoside linking group of Formula XVII.

Embodiment 1327. The oligomeric compound of any of embodiments 1246-1325, wherein exactly two internucleoside linking groups of the modified oligonucleotide are internucleoside linking groups of Formula XVII.

Embodiment 1328. The oligomeric compound of any of embodiments 1246-1325, wherein exactly three internucleoside linking groups of the modified oligonucleotide are internucleoside linking groups of Formula XVII.

Embodiment 1329. The oligomeric compound of any of embodiments 1246-1325, wherein exactly four internucleoside linking groups of the modified oligonucleotide are internucleoside linking groups of Formula XVII.

Embodiment 1330. The oligomeric compound of any of embodiments 1246-1325, wherein exactly five internucleoside linking groups of the modified oligonucleotide are internucleoside linking groups of Formula XVII.

Embodiment 1331. The oligomeric compound of any of embodiments 1246-1325, wherein at least six internucleoside linking groups of the modified oligonucleotide are internucleoside linking groups of Formula XVII.

Embodiment 1332. The oligomeric compound of any of embodiment 1246-1324 or 1326-1331 having at least two linking groups of Formula XVII, wherein at least two of the linking groups of Formula XVII are the same as one another.

Embodiment 1333. The oligomeric compound of any of embodiments 1246-1332, wherein each internucleoside linking group of the modified oligonucleotide that is not an internucleoside linking group of Formula XVII is either a phosphodiester internucleoside linking group or a phosphorothioate internucleoside linking group.

Embodiment 1334. The oligomeric compound of any of embodiments 1246-1325 or 1331, wherein each internucleoside linking group of the modified oligonucleotide is an internucleoside linking group of Formula XVII.

Embodiment 1335. An oligomeric compound comprising a modified oligonucleotide, wherein at least one region of the modified oligonucleotide has Structure A:

Structure A

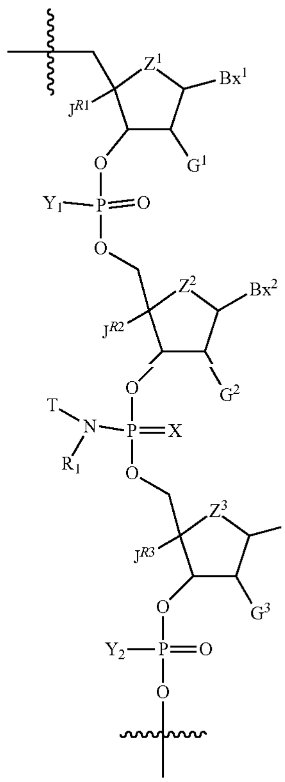

each Bx is a heterocyclic base moiety;

X is selected from O or S;

each of $Y_1$ and $Y_2$ is independently selected from OH or SH;

each of $Z^1$, $Z^2$, and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R2}$ to $G^1$ bridge, or $J^R{}_1$ is H and $G^1$ is selected from H, OH, halogen or $O—[C(R_6)(R_7)]—[(C{=}O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C{=}O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1336. An oligomeric compound comprising a modified olignucleotide, wherein at least one region of the modified oligonucleotide has Structure B:

Structure B

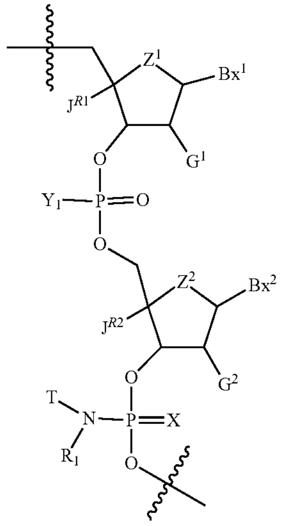

wherein:

each Bx is a heterocyclic base moiety;

X is selected from O or S;

each of $Y_1$ and $Y_2$ is independently selected from OH or SH;

each of $Z^1$ and $Z_2$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(═O)R_3$, and $P(═O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R{}_1$ and $G^1$ form a $J^R{}_1$ to $G^1$ bridge, or $J^R{}_1$ is H and $G^1$ is selected from H, OH, halogen or $O—[C(R_6)(R_7)]—[(C═O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C═O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(═X_2)J_1$, $OC(═X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1337. An oligomeric compound comprising a modified olignucleotide, wherein at least one region of the modified oligonucleotide has Structure C:

Structure C

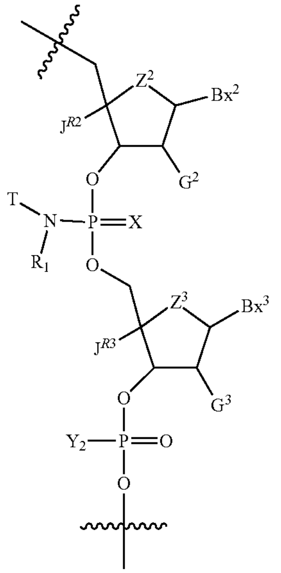

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(═O)R_3$, and $P(═O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C═O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C═O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1338. An oligomeric compound comprising a modified olignucleotide, wherein at least one region of the modified oligonucleotide has Structure D:

Structure D

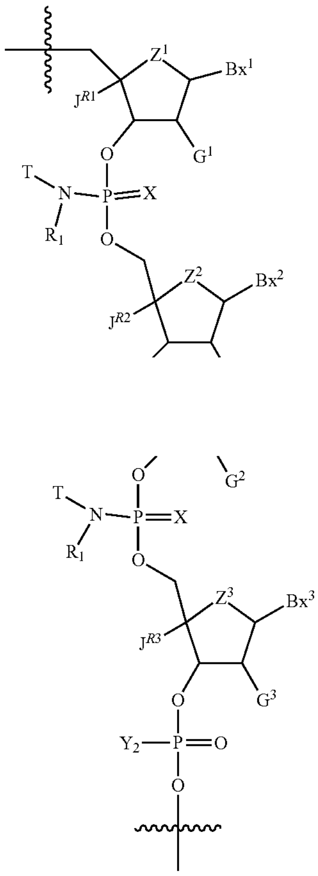

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R{}_1$ and $G^1$ form a $J^R{}_1$ to $G^1$ bridge, or $J^R{}_1$ is H and $G^1$ is selected from H, OH, halogen or $O-[C(R_6)(R_7)]-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1339. An oligomeric compound comprising a modified olignucleotide, wherein at least one region of the modified oligonucleotide has Structure E:

Structure E

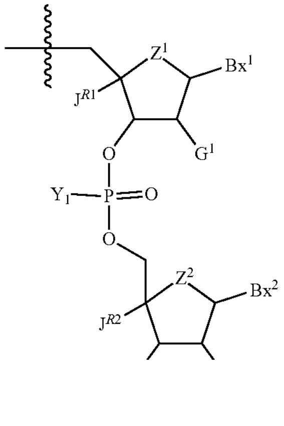

-continued

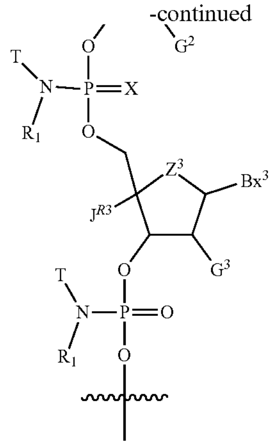

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(═O)R_3$, and $P(═O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R{}_1$ and $G^1$ form a $J^R{}_1$ to $G^1$ bridge, or $J^R{}_1$ is H and $G^1$ is selected from H, OH, halogen or $O—[C(R_6)(R_7)]—[(C═O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C═O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C═O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(═X_2)J_1$, $OC(═X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1340. An oligomeric compound comprising a modified oligonucleotide, wherein the 5'-terminus of the modified oligonucleotide has structure P:

Structure P

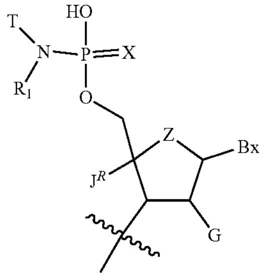

wherein:

each Bx is a heterocyclic base moiety;

X is selected from O or S;

Z is $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(═O)R_3$, and $P(═O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R$ and G form a $J^R$ to G bridge, or $J^R$ is H and G is selected from H, OH, halogen or $O—[C(R_6)(R_7)]—[(C═O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1341. The oligomeric compound of any of embodiments 1335-1340, wherein each Z is O.

Embodiment 1342. The oligomeric compound of any of embodiments 1335-1341, wherein at least one G is selected from H, OH, halogen, $C_1$-$C_6$ alkoxy, $-O(CH_2)_2OCH_3$, or $-OCH_2(C{=}O)NHCH_3$.

Embodiment 1343. The oligomeric compound of any of embodiments 1335-1342, wherein each G is selected from H, OH, halogen, $C_1$-$C_6$ alkoxy, $-O(CH_2)_2OCH_3$, or $-OCH_2(C{=}O)NHCH_3$.

Embodiment 1344. The oligomeric compound of any of embodiments 1335-1343, wherein at least one $J^R$ forms a bridge with at least one G, wherein said $J^R$ to G bridge has a formula selected from $-CH(CH_3)-O-$ or $-(CH_2)_k-O'$, wherein k is from 1 to 3.

Embodiment 1345. The oligomeric compound of any of embodiments 1335-1342 or 1344, wherein each $J^R$ and G form a bridge, wherein said $J^R$ to G bridge has a formula selected from $-CH(CH_3)-O-$ or $-(CH_2)_k-O-$, wherein k is from 1 to 3.

Embodiment 1346. The oligomeric compound of any of embodiments 1344 or 1345, wherein at least one Z is O and the corresponding $J^R$ to G bridge has a formula $(CH_2)_k-O-$, wherein k is 1.

Embodiment 1347. The oligomeric compound of any of embodiments 1335-1346 wherein each nucleoside of structure A, B, C, D, E, or P is a stereo standard nucleoside.

Embodiment 1348. The oligomeric compound of any of embodiments 1335-1346, wherein at least one nucleoside of structure A, B, C, D, E or P is a stereo-non-standard nucleoside.

Embodiment 1349. The oligomeric compound of any of embodiments 1344-1346 or 1348, wherein at least one nucleoside having a $J^R$ to G bridge is in the α-L-ribosyl configuration.

Embodiment 1350. The oligomeric compound of any of embodiments 1335-1349, wherein the modified oligonucleotide comprises at least 2, at least 3, at least 4, at least 5, at least 6, at least 7, at least 8, at least 9, or at least 10 regions having structures A, B, C, D, or E.

Embodiment 1351. The oligomeric compound of any of embodiments 1335-1350, wherein at least one region having structure A, B, C, D, or E is at the 5' end of the modified oligonucleotide.

Embodiment 1352. The oligomeric compound of any of embodiments 1335-1350, wherein at least one region having structure A, B, C, D, or E is at the 3' end of the modified oligonucleotide.

Embodiment 1353. The oligomeric compound of any of embodiments 1335-1350, wherein at least one region having structure A, B, C, D, or E is internal to the modified oligonucleotide.

Embodiment 1354. An oligomeric compound comprising a modified oligonucleotide consisting of 10-30 linked nucleosides, wherein a region of the modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

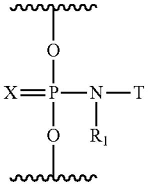

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ is an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1355. The oligomeric compound of embodiment 1354, wherein the modified oligonucleotide comprises at least 2, at least 3, at least 4, at least 5, at least 6, at least 7, at least 8, at least 9, or at least 10 regions having the formula $(N_{g1})_{L1}(N_{g2})_{L2}(N_{g3})_{L3}$.

Embodiment 1356. The oligomeric compound of embodiment 1354 or 1355, wherein at least one region having the formula $(N_{g1})_{L1}(N_{g2})_{L2}(N_{g3})_{L3}$ is at the 5' end of the oligonucleotide Embodiment 1357. The oligomeric compound of embodiment 1354 or 1355, wherein at least one region having the formula $(N_{g1})_{L1}(N_{g2})_{L2}(N_{g3})_{L3}$ is internal to the oligonucleotide.

Embodiment 1358. The oligomeric compound of embodiment 1354 or 1355, wherein at least one region having the formula $(N_{g1})_{L1}(N_{g2})_{L2}(N_{g3})_{L3}$ is at the 3' end of the oligonucleotide.

Embodiment 1359. The oligomeric compound of any of embodiments 1246-1358, wherein at least one nucleoside of the modified oligonucleotide is a modified nucleoside selected from a bicyclic nucleoside and a non-bicyclic substituted nucleoside.

Embodiment 1360. The oligomeric compound of any of embodiments 1246-1359, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 1361. The oligomeric compound of any of embodiments 1246-1360, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 1362. The oligomeric compound of any of embodiments 1246-1361, wherein at least one nucleoside of the modified oligonucleotide is a stereo-non-standard nucleoside.

Embodiment 1363. The oligomeric compound of embodiment 1362, wherein the internucleoside linking group linking at least one stereo-non-standard nucleoside to an adjacent nucleoside is an internucleoside linking group of Formula XVII.

Embodiment 1364. The oligomeric compound of embodiment 1362 or 1363, wherein at least two nucleosides of the modified oligonucleotide are stereo-non-standard nucleosides.

Embodiment 1365. The oligomeric compound of embodiment 1364, wherein at least two stereo-non-standard nucleosides of the modified oligonucleotide are adjacent to one another.

Embodiment 1366. The oligomeric compound of embodiment 1365, wherein at least two stereo-non-standard nucleosides of the modified oligonucleotide are linked to one another with an internucleoside linking group of Formula XVII.

Embodiment 1367. The oligomeric compound of any of embodiments 1362-1367, wherein at least one stereo-non-standard nucleoside of the modified oligonucleotide is a stereo-non-standard DNA nucleoside.

Embodiment 1368. The oligomeric compound of embodiment 1367, wherein the stereo-non-standard DNA nucleoside is selected from a stereo-non-standard DNA nucleoside having: Formula I, Formula II, Formula III, Formula IV, Formula V, Formula VI, and Formula VII.

Embodiment 1369. The oligomeric compound of embodiment 1368 wherein the stereo-non-standard DNA nucleoside is selected from a stereo-non-standard DNA nucleoside having: Formula V and Formula II.

Embodiment 1370. The oligomeric compound of any of embodiments 1362-1369, wherein at least one stereo-non-standard nucleoside of the oligomeric compound is a substituted stereo-non-standard nucleoside.

Embodiment 1371. The oligomeric compound of embodiment 1370, wherein the 2'-substituent of the at least one substituted stereo-non-standard nucleoside of the modified oligonucleotide is selected from: 2'-MOE, 2'-OMe, 2'-F, or 2'-OH.

Embodiment 1372. The oligomeric compound of any of embodiments 1246-1371, wherein each nucleoside of the modified oligonucleotide is a stereo-standard nucleoside.

Embodiment 1373. The oligomeric compound of any of embodiments 1246-1371, wherein the modified oligonucleotide consists of 12-30 linked nucleosides.

Embodiment 1374. The oligomeric compound of any of embodiments 1246-1371, wherein the modified oligonucleotide consists of 16-24 linked nucleosides.

Embodiment 1375. The oligomeric compound of any of embodiments 1246-1371, wherein the modified oligonucleotide consists of 18-22 linked nucleosides.

Embodiment 1376. The oligomeric compound of any of embodiments 1246-1374, wherein the modified oligonucleotide consists of 16 linked nucleosides.

Embodiment 1377. The oligomeric compound of any of embodiments 1246-1374, wherein the modified oligonucleotide consists of 17 linked nucleosides.

Embodiment 1378. The oligomeric compound of any of embodiments 1246-1375, wherein the modified oligonucleotide consists of 18 linked nucleosides.

Embodiment 1379. The oligomeric compound of any of embodiments 1246-1375, wherein the modified oligonucleotide consists of 19 linked nucleosides.

Embodiment 1380. The oligomeric compound of any of embodiments 1246-1375, wherein the modified oligonucleotide consists of 20 linked nucleosides.

Embodiment 1381. The oligomeric compound of any of embodiments 1246-1375, wherein the modified oligonucleotide consists of 21 linked nucleosides.

Embodiment 1382. The oligomeric compound of any of embodiments 1246-1375, wherein the modified oligonucleotide consists of 22 linked nucleosides.

Embodiment 1383. The oligomeric compound of any of embodiments 1246-1374, wherein the modified oligonucleotide consists of 23 linked nucleosides.

Embodiment 1384. The oligomeric compound of any of embodiments 1246-1383, wherein at least one nucleoside of the modified oligonucleotide is selected from: a 2'-OMe nucleoside, a 2'-F nucleoside, and an RNA nucleoside.

Embodiment 1385. The oligomeric compound of any of embodiments 1246-139, wherein at least one nucleoside of the modified oligonucleotide is a 2'-OMe nucleoside, and at least one nucleoside of the modified oligonucleotide is a 2'-F nucleoside.

Embodiment 1386. The oligomeric compound of embodiment 1385, wherein each nucleoside of the modified oligonucleotide is selected from a 2'-OMe nucleoside or a 2'-F nucleoside.

Embodiment 1387. The oligomeric compound of any of embodiments 1246-1385, wherein at least one nucleoside of the modified oligonucleotide is a 2'-OMe nucleoside, at least one nucleoside of the modified oligonucleotide is a 2'-F nucleoside, and at least one nucleoside of the modified oligonucleotide comprises a sugar surrogate.

Embodiment 1388. The oligomeric compound of embodiment 1387, wherein each nucleoside of the modified oligonucleotide is selected from a 2'-OMe nucleoside, a 2'-F nucleoside, and a nucleoside comprising a sugar surrogate.

Embodiment 1389. The oligomeric compound of any of embodiments 1387-1388, wherein the nucleoside comprising a sugar surrogate is selected from:

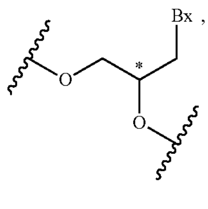
,
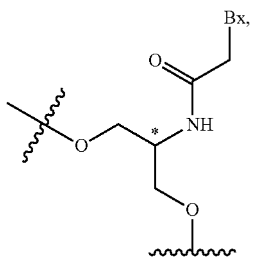
,

-continued

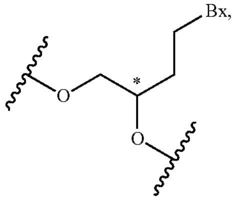

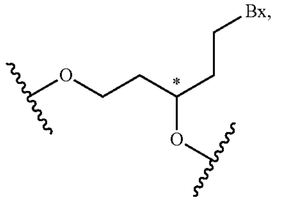

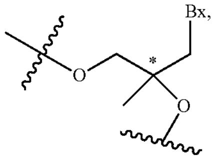

or

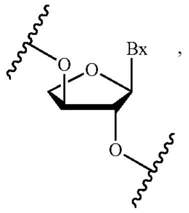

wherein Bx is a heterocyclic base moiety.

Embodiment 1390. The oligomeric compound of embodiment 1389, wherein the nucleoside comprising a sugar surrogate is GNA.

Embodiment 1391. The oligomeric compound of any of embodiments 1384-1390, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 1392. The oligomeric compound of embodiment 1391, wherein A and B are selected from 2'-F substituted nucleosides, 2'-OMe substituted nucleosides, and stereo-standard RNA nucleosides.

Embodiment 1393. The oligomeric compound of any of embodiments 1246-1392, wherein the 5'-end of the modified oligonucleotide comprises a terminal group.

Embodiment 1394. The oligomeric compound of embodiment 1393, wherein the terminal group is a stabilized phosphate group.

Embodiment 1395. The oligomeric compound of embodiment 1394, wherein the stabilized phosphate group is a 5'-vinyl phosphonate or a 5'-cyclopropyl phosphonate.

Embodiment 1396. The compound of embodiment 1393, wherein the terminal group has Formula XXII:

XXII

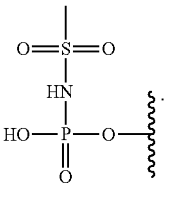

Embodiment 1397. The oligomeric compound of embodiment 1393, wherein the terminal group is selected from

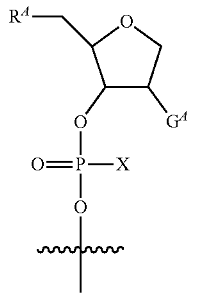

or

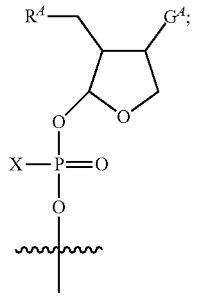

wherein $R^A$ is OH, OP(=O)OH, OP(=O)SH, a mesyl phosphoramidate, or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

Embodiment 1398. The oligomeric compound of embodiment 1397, wherein $G^A$ is selected from H or OH and X is SH.

Embodiment 1399. An antisense agent consisting or comprising an oligomeric compound of any of embodiments 1246-1398.

Embodiment 1400. The antisense agent of embodiment 1399, wherein the antisense agent is an RNAi agent.

Embodiment 1401. The RNAi agent of embodiment 1400, wherein the RNAi agent is a single-stranded RNAi agent comprising an RNAi antisense oligomeric compound, wherein the RNAi antisense oligomeric compound is an oligomeric compound of any of embodiments 1246-1398.

Embodiment 1402. The RNAi agent of embodiment 1401, wherein the RNAi agent is an oligonucleotide duplex comprising an RNAi antisense oligomeric compound and an RNAi sense oligomeric compound, wherein the RNAi antisense oligomeric compound and/or the RNAi sense oligomeric compound is an oligomeric compound of any of embodiments 1-153.

Embodiment 1403. The RNAi agent of embodiment 1401 or 1402, wherein at least one internucleoside linking group of the RNAi antisense oligomeric compound is an internucleoside linking group of Formula XVII.

Embodiment 1404. The RNAi agent of embodiment 1401 or 1402, wherein at least two internucleoside linking groups of the RNAi antisense oligomeric compound are independently selected internucleoside linking groups of Formula XVII.

Embodiment 1405. The RNAi agent of any of embodiments 1401-1404, wherein at least one of the five 3'-most internucleoside linking groups of the RNAi antisense oligomeric compound is an internucleoside linking group of Formula XVII.

Embodiment 1406. The RNAi agent of any of embodiments 1401-1404, wherein at least two of the five 3'-most internucleoside linking groups of RNAi antisense oligomeric compound is an internucleoside linking group of Formula XVII.

Embodiment 1407. The RNAi agent of any of embodiments 1401-1406, wherein 1-3 of the three 3'-most internucleoside linking groups are internucleoside linking groups of Formula XVII, and each of these three internucleoside linking groups that is not an internucleoside linking group of Formula XVII is a phosphodiester or phosphorothioate internucleoside linking group.

Embodiment 1408. The RNAi agent of embodiment 1407, wherein the two 3'-most internucleoside linking groups are internucleoside linking groups of Formula XVII.

Embodiment 1409. The RNAi agent of any of embodiments 1401-1408, wherein exactly one of the 5'-most and penultimate 5'-most internucleoside linking groups is an internucleoside linking group of Formula XVII.

Embodiment 1410. The RNAi agent of any of embodiments 1401-1409, wherein exactly one of the 5'-most and penultimate 5'-most internucleoside linking groups of the RNAi antisense oligonucleotide is an internucleoside linking groups of Formula XVII, the other of the 5'-most and penultimate 5'-most internucleoside linking groups of the RNAi antisense oligonucleotide is selected from a phosphodiester and a phosphorothioate internucleoside linkage, the two 3'-most internucleoside linking groups of the RNAi antisense oligonucleotide are internucleoside linking groups of Formula XVII, and the remaining internucleoside linking groups of the RNAi antisense oligonucleotide are phosphodiester internucleoside linkages.

Embodiment 1411. The RNAi agent of any of embodiments 1401-1410, wherein the antisense oligomeric compound comprises a 3'-overhang.

Embodiment 1412. The RNAi agent of embodiment 1411, wherein the 3'-overhang consists of two nucleosides.

Embodiment 1413. The RNAi agent of any of embodiments 1401-1409 or 1411-1412, wherein at least one internucleoside linking group within the seed region of the RNAi antisense oligomeric compound is an internucleoside linking group of Formula XVII.

Embodiment 1414. The RNAi agent of any of embodiments 1401-1413, wherein for each internucleoside linking group of Formula XVII, $R_1$ is H and T is $SO_2Me$.

Embodiment 1415. The RNAi agent of any of embodiments 1401-1414, wherein the RNAi antisense oligomeric compound comprises an RNAi antisense modified oligonucleotide, wherein the RNAi antisense modified oligonucleotide consists of 23 linked nucleosides, and the internucleoside linkage motif is selected from: ooooooooooooooooooooaa, aaoooooooooooooooooooo, aaooooooooooooooooooaa, asooooooooooooooooooss, saoooooooooooooooooooo, oooooooooooooooooooaaa, ooooooooooooooooaaaoss, oooooooooooooaaaooooss, ooooooooooaaaoooooooss, oooooooaaaoooooooooooss, ooooaaaoooooooooooooss, saoooaoooooooaoaooooss, ssoooaoooooooaoaooooss, or ssooooooooooooooooooaa, wherein each "a" represents an internucleoside linkage of Formula XVII, each "s" represents a phosphorothioate internucleoside linkage, and each "o" represents a phosphodiester internucleoside linkage.

Embodiment 1416. The RNAi agent of embodiment 1415, wherein the internucleoside linkage motif of the RNAi antisense modified oligonucleotide is selected from ooooooooooooooooooooaa, asooooooooooooooooooss, or saoooooooooooooooooooo.

Embodiment 1417. The RNAi agent of embodiment 1415 or 1416, wherein the sugar motif of the RNAi antisense oligomeric compound from 5' to 3' is yfyfyfyfyfyfyfyfyfyfyfy or yfyyyfyyyyyyyfyfyyyyyyy, wherein "y" represents a 2'-OMe sugar moiety and "f" represents a 2'-F sugar moiety.

Embodiment 1418. The RNAi agent of any of embodiments 1401-1414, wherein the RNAi antisense oligomeric compound comprises an RNAi antisense modified oligonucleotide, wherein the RNAi antisense modified oligonucleotide consists of 21 linked nucleosides, and the internucleoside linkage motif is selected from: aaosososososossssssss, ssaaososososossssssss, ssosaaosososossssssss, ssososaaososossssssss, ssosososaaosossssssss, ssososososaaossssssss, ssososososossaassssss, ssosososososossaassss, ssosososososossssaass, ssosososososossssssaa wherein each "a" represents an internucleoside linkage of Formula XVII, each "s" represents a phosphorothioate internucleoside linkage, and each "o" represents a phosphodiester internucleoside linkage.

Embodiment 1419. The RNAi agent of embodiment 1418, wherein the internucleoside linkage motif of the RNAi antisense modified oligonucleotide is selected from aaosososososossssssss, ssaaososososossssssss, or ssosososososossssssaa, wherein each "a" represents an internucleoside linkage of Formula XVII, each "s" represents a phosphorothioate internucleoside linkage, and each "o" represents a phosphodiester internucleoside linkage.

Embodiment 1420. The RNAi agent of embodiment 1418 or 1419, wherein the sugar motif of the RNAi antisense oligomeric compound from 5' to 3' is yfyfyfyfyfyfyfyfyfyfy, wherein "y" represents a 2'-OMe sugar moiety and "f" represents a 2'-F sugar moiety.

Embodiment 1421. The RNAi agent of any of embodiments 1415-1420 wherein each "a" is a mesyl phosphoramidate linkage.

Embodiment 1422. The RNAi agent of any of embodiments 1401-1421, wherein at least one region of the RNAi antisense oligomeric compound has structure A, B, C, D, E, or P.

Embodiment 1423. The RNAi agent of embodiment 1422, wherein at least one region having structure A, B, C, D, or E is within the seed region of the RNAi antisense oligomeric compound.

Embodiment 1424. The RNAi agent of embodiment 1422, wherein at least one region having structure A, B, C, D, or E is at the 3' end of the RNAi antisense oligomeric compound.

Embodiment 1425. The RNAi agent of embodiment 1422, wherein at least one region having structure A, B, C, D, E, or P is at the 5' end of the RNAi antisense oligomeric compound.

Embodiment 1426. The RNAi agent of any of embodiments 1401-1425, wherein at least one region of the RNAi antisense oligomeric compound has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

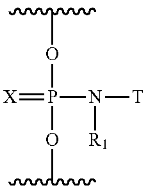

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the RNAi antisense oligomeric compound having Formula XVII: X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, substituted $C_1$-$C_6$ alkyl, and a conjugate;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1427. The RNAi agent of embodiment 1426, wherein the region having the formula $(N_{g1})_{L1}(N_{g2})_{L2}(N_{g3})_{L3}$ includes one or two 3'-overhang nucleosides.

Embodiment 1428. The RNAi agent of embodiment 1426, wherein at least one region having the formula $(N_{g1})_{L1}(N_{g2})_{L2}(N_{g3})_{L3}$ is at the 3' end of the RNAi antisense oligomeric compound.

Embodiment 1429. The RNAi agent of embodiment 1428, wherein L1 and L2 are each internucleoside linkages of Formula XVII wherein $R_1$ is H and T is $SO_2Me$, and L3 is a phosphodiester internucleoside linkage.

Embodiment 1430. The RNAi agent of embodiment 1428, wherein at least one region having the formula $(N_{g1})_{L1}(N_{g2})_{L2}(N_{g3})_{L3}$ is at the 5' end of the RNAi antisense oligomeric compound.

Embodiment 1431. The RNAi agent of embodiment 1429, wherein one of L1 or L2 is an internucleoside linkages of Formula XVII wherein $R_1$ is H and T is $SO_2Me$, the other of L1 or L2 is a phosphorothioate internucleoside linkage, and L3 is a phosphodiester internucleoside linkage.

Embodiment 1432. The RNAi agent of embodiment 1426, wherein at least one region having the formula $(N_{g1})_{L1}(N_{g2})_{L2}(N_{g3})_{L3}$ is within the seed region of the RNAi antisense oligomeric compound.

Embodiment 1433. The RNAi agent of any of embodiments 1401-1432, wherein the region of the RNAi antisense oligonucleotide that is complementary to a target is at least 15 nucleobases.

Embodiment 1434. The RNAi agent of any of embodiments 1401-1433, wherein the region of the RNAi antisense oligonucleotide that is complementary to a target is at least 17 nucleobases.

Embodiment 1435. The RNAi agent of any of embodiments 1401-1434, wherein the region of the RNAi antisense oligonucleotide that is complementary to a target is at least 19 nucleobases.

Embodiment 1436. The RNAi agent of any of embodiments 1401-1435, wherein the region of the RNAi antisense oligonucleotide that is complementary to a target is at least 21 nucleobases.

Embodiment 1437. The RNAi agent of any of embodiments 1401-1435, wherein the region of the RNAi antisense oligonucleotide that is complementary to a target is exactly 19 nucleobases.

Embodiment 1438. The RNAi agent of any of embodiments 1401-1436, wherein the region of the RNAi antisense oligonucleotide that is complementary to a target is exactly 21 nucleobases.

Embodiment 1439. The RNAi agent of any of embodiments 1401-1438, wherein at least one nucleoside of the RNAi antisense oligomeric compound is selected from: a 2'-OMe nucleoside, a 2'-F nucleoside, and an RNA nucleoside.

Embodiment 1440. The RNAi agent of any of embodiments 1401-1439, wherein at least one nucleoside of the RNAi antisense oligomeric compound is a 2'-OMe nucleoside, and at least one nucleoside of the RNAi antisense oligomeric compound is an RNA nucleoside.

Embodiment 1441. The RNAi agent of any of embodiments 1401-1440, wherein at least one nucleoside of the RNAi antisense oligomeric compound is a 2'-OMe nucleoside, and at least one nucleoside of the RNAi antisense oligomeric compound is a 2'-F nucleoside.

Embodiment 1442. The RNAi agent of embodiment 1441, wherein each nucleoside of the RNAi antisense oligomeric compound is selected from a 2'-OMe nucleoside or a 2'-F nucleoside.

Embodiment 1443. The RNAi agent of any of embodiments 1401-1439, wherein at least one nucleoside of the RNAi antisense oligomeric compound is a 2'-OMe nucleoside, at least one nucleoside of the RNAi antisense oligomeric compound is a 2'-F nucleoside, and at least one nucleoside of the oligomeric compound comprises a sugar surrogate.

Embodiment 1444. The RNAi agent of embodiment 1443, wherein each nucleoside of the RNAi antisense oligomeric compound is selected from a 2'-OMe nucleoside, a 2'-F nucleoside, and a nucleoside comprising a sugar surrogate.

Embodiment 1445. The RNAi agent of any of embodiments 1443-1444, wherein the nucleoside comprising a sugar surrogate is selected from:

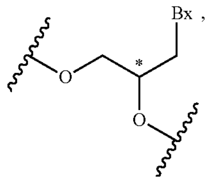

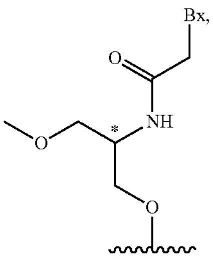

-continued

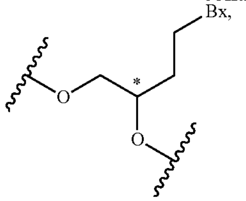

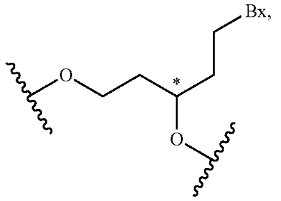

,

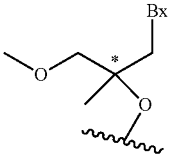

or

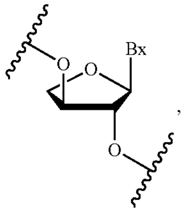

, wherein Bx is a heterocyclic base moiety.

Embodiment 1446. The RNAi agent of embodiment 1445, wherein the nucleoside comprising a sugar surrogate is GNA.

Embodiment 1447. The RNAi agent of embodiment 1445 or 1446, wherein at least one nucleoside comprising a sugar surrogate is one of the nine 5'-most nucleosides of the RNAi antisense oligomeric compound.

Embodiment 1448. The RNAi agent of any of embodiments 1401-1447, wherein the oligomeric compound has a region of alternating nucleoside types having the motif ABABA, wherein each A is a stereo-standard nucleoside of a first type and each B is a stereo-standard nucleoside of a second type, wherein the first type and the second type are different from one another.

Embodiment 1449. The RNAi agent of embodiment 1448, wherein A and B are selected from 2'-F substituted nucleosides, 2'-OMe substituted nucleosides, and stereo-standard RNA nucleosides.

Embodiment 1450. The RNAi agent of any of embodiments 1401-1449, wherein the 5'-end of the RNAi antisense oligomeric compound comprises a terminal group.

Embodiment 1451. The RNAi agent of embodiment 1450, wherein the terminal group is a stabilized phosphate group.

Embodiment 1452. The RNAi agent of embodiment 1451, wherein the stabilized phosphate group is a 5'-vinyl phosphonate or a 5'-cyclopropyl phosphonate.

Embodiment 1453. The RNAi agent of embodiment 1542, wherein the terminal group has Formula XXII:

XXII

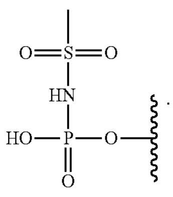

Embodiment 1454. The RNAi agent of embodiment 1450, wherein the terminal group is selected from:

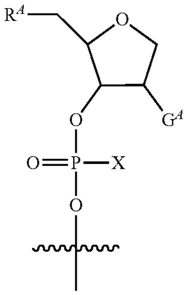

or

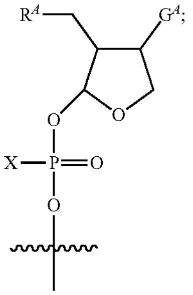

wherein $R^A$ is OH, OP(=O)OH, OP(=O)SH, a mesyl phosphoramidate, or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

Embodiment 1455. The RNAi agent of embodiment 1454, wherein $G^A$ is selected from H or OH and X is SH.

Embodiment 1456. The RNAi agent of embodiment 1402-1455, wherein at least one internucleoside linking group of the RNAi sense oligomeric compound is an internucleoside linking group of Formula XVII.

Embodiment 1457. The RNAi agent of embodiment 1456, wherein at least one of the five 5'-most internucleoside linking groups of the RNAi sense oligomeric compound is an internucleoside linking group of Formula XVII.

Embodiment 1458. The RNAi agent of embodiment 1456, wherein at least two of the five 5'-most internucleoside linking groups of the RNAi sense oligomeric compound are internucleoside linking groups of Formula XVII.

Embodiment 1459. The RNAi agent of embodiment 1456, wherein the two 5'-most internucleoside linking groups of the RNAi sense oligomeric compound are internucleoside linking groups of Formula XVII.

Embodiment 1460. The RNAi agent of any of embodiments 1456-1459, wherein at least one of the five 3'-most internucleoside linking groups of the RNAi sense oligomeric compound is an internucleoside linking group of Formula XVII.

Embodiment 1461. The RNAi agent of any of embodiments 1456-1459, wherein at least two of the five 3'-most internucleoside linking groups of RNAi sense oligomeric compound is an internucleoside linking group of Formula XVII.

Embodiment 1462. The RNAi agent of any of embodiments 1456-1459, wherein the two 3'-most internucleoside linking groups are internucleoside linking groups of Formula XVII.

Embodiment 1463. The RNAi agent of embodiment 1456, wherein the two 3'-most and the two 5'-most internucleoside linking groups of the RNAi sense oligonucleotide are internucleoside linking groups of Formula XVII, and the remaining internucleoside linking groups of the RNAi sense oligonucleotide are phosphodiester internucleoside linkages.

Embodiment 1464. The RNAi agent of any of embodiments 1456-1463, wherein for each internucleoside linking group of Formula XVII, $R_1$ is H and T is $SO_2Me$.

Embodiment 1465. The RNAi agent of any of embodiments 1456-1464, wherein the RNAi sense oligomeric compound consists of 21 linked nucleosides, and the internucleoside linkage motif is selected from: ooooooooooooooooooaa, aaooooooooooooooooaa, ooooooooooooooooooaa, or ssooooaoaaaooooooooo, wherein each "a" represents an internucleoside linkage of Formula XVII, each "s" represents a phosphorothioate internucleoside linkage, and each "o" represents a phosphodiester internucleoside linkage.

Embodiment 1466. The RNAi agent of embodiment 1465, wherein the internucleoside linkage motif of the RNAi sense oligomeric compound is selected from ooooooooooooooooooaa, aaooooooooooooooooaa, or ooooooooooooooooooaa, wherein each "a" represents an internucleoside linkage of Formula XVII, each "s" represents a phosphorothioate internucleoside linkage, and each "o" represents a phosphodiester internucleoside linkage.

Embodiment 1467. The RNAi agent of embodiment 1465 or 1466, wherein the sugar motif of the RNAi sense oligomeric compound is selected from: yyyyyyfyfffyyyyyyyyyy or fyfyfyfyfyfyfyfyfyfyf, wherein "y" represents a 2'-OMe sugar moiety and "f" represents a 2'-F sugar moiety.

Embodiment 1468. The RNAi agent of any of embodiments 1465-1467 wherein each "a" is a mesyl phosphoramidate linkage.

Embodiment 1469. The RNAi agent of any of embodiments 1456-1468, wherein at least one region of the RNAi sense oligomeric compound has structure A, B, C, D, E or P.

Embodiment 1470. The RNAi agent of embodiment 1469, wherein at least one region having structure A, B, C, D, or E is at the 3' end of the RNAi sense oligomeric compound.

Embodiment 1471. The RNAi agent of embodiment 1469, wherein at least one region having structure A, B, C, D, or E is at the 5' end of the RNAi sense oligomeric compound.

Embodiment 1472. The RNAi agent of any of embodiments 1456-1471, wherein at least one region of the RNAi sense oligomeric compound has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothionate internucleoside linking group, or an internucleoside linking group of Formula XVII:

XVII

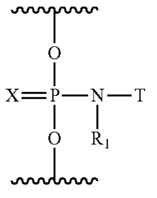

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the RNAi sense oligomeric compound having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1473. The RNAi agent of embodiment 1472, wherein at least one region having the formula $(N_{g1})_{L1}(N_{g2})_{L2}(N_{g3})_{L3}$ is at the 3' end of the RNAi sense oligomeric compound.

Embodiment 1474. The RNAi agent of embodiment 1473, wherein L1 and L2 are internucleoside linking groups of Formula XVII, wherein $R_1$ is H and T is $SO_2Me$, and L3 is a phosphodiester internucleoside linkage.

Embodiment 1475. The RNAi agent of embodiment 1472, wherein at least one region having the formula $(N_{g1})_{L1}(N_{g2})_{L2}(N_{g3})_{L3}$ is at the 5' end of the RNAi sense oligomeric compound.

Embodiment 1476. The RNAi agent of embodiment 1475, wherein L1 is a phosphodiester internucleoside linking group and L2 and L3 are each internucleoside linking groups of Formula XVII, wherein $R_1$ is H and T is $SO_2Me$.

Embodiment 1477. The RNAi agent of any of embodiments 1402-1476, wherein the RNAi sense oligomeric compound comprises a 3' terminal group and/or a 5' terminal group.

Embodiment 1478. The RNAi agent of any of embodiments 1402-1476, wherein the RNAi sense oligomeric compound comprises a conjugate group.

Embodiment 1479. The RNAi agent of embodiment 1478, wherein the conjugate group comprises a cell-targeting moiety.

Embodiment 1480. The RNAi agent of embodiment 1478, wherein the conjugate group comprises a carbohydrate or carbohydrate cluster.

Embodiment 1481. The RNAi agent of embodiment 1478, wherein the conjugate group comprises at least one GalNAc.

Embodiment 1482. The RNAi agent of embodiment 1478, wherein the conjugate group comprises a $C_{10}$-$C_{20}$ alkyl chain.

Embodiment 1483. The RNAi agent of embodiment 1478, wherein the conjugate group comprises $C_{16}$ alkyl.

Embodiment 1484. The RNAi agent of any of embodiments 1402-1483, wherein the double-stranded region of the oligonucleotide duplex is at least 15 nucleosides.

Embodiment 1485. The RNAi agent of any of embodiments 1402-1483, wherein the double-stranded region of the oligonucleotide duplex is at least 17 nucleosides.

Embodiment 1486. The RNAi agent of any of embodiments 1402-1483, wherein the double-stranded region of the oligonucleotide duplex is at least 19 nucleosides.

Embodiment 1487. The RNAi agent of any of embodiments 1402-1483, wherein the double-stranded region of the oligonucleotide duplex is exactly 19 nucleosides.

Embodiment 1488. The oligomeric compound of any of embodiments 1246-1383, wherein each nucleoside of the modified oligonucleotide is a modified nucleoside comprising a modified sugar moiety.

Embodiment 1489. The oligomeric compound of embodiment 1488, wherein each modified sugar moiety of the modified oligonucleotide is independently selected from a bicyclic sugar moiety and a 2'-substituted furanosyl sugar moiety.

Embodiment 1490. The oligomeric compound of embodiment 1488 or 1489, wherein each modified sugar moiety of the modified oligonucleotide comprises the same modification.

Embodiment 1491. The oligomeric compound of any of embodiments 1488-1490, wherein each modified sugar moiety of the modified oligonucleotide is selected from a 2'-OMe sugar moiety, a 2'-MOE sugar moiety, and a 2'-NMA sugar moiety.

Embodiment 1492. The oligomeric compound of embodiment 1488 or 1489, wherein the three 3'-most nucleosides of the modified oligonucleotide comprise a bicyclic sugar moiety, and the remaining nucleosides of the modified oligonucleotide comprise a 2'-substituted furanosyl sugar moiety.

Embodiment 1493. The oligomeric compound of embodiment 1488 or 1489, wherein the four 3'-most nucleosides of the modified oligonucleotide comprise a bicyclic sugar moiety, and the remaining nucleosides of the modified oligonucleotide comprise a 2'-substituted furanosyl sugar moiety.

Embodiment 1494. The oligomeric compound of embodiment 1488 or 1489, wherein the five 3'-most nucleosides of the modified oligonucleotide comprise a bicyclic sugar moiety, and the remaining nucleosides of the modified oligonucleotide comprise a 2'-substituted furanosyl sugar moiety.

Embodiment 1495. The oligomeric compound of embodiment 1488 or 1489, wherein the six 3'-most nucleosides of the modified oligonucleotide comprise a bicyclic sugar moiety, and the remaining nucleosides of the modified oligonucleotide comprise a 2'-substituted furanosyl sugar moiety.

Embodiment 1496. The oligomeric compound of any of embodiments 1488 or 1489, wherein each bicyclic sugar moiety of the modified oligonucleotide is selected from among cEt, LNA, and ENA.

Embodiment 1497. The oligomeric compound of embodiment 1496, wherein the bicyclic sugar moiety is cEt.

Embodiment 1498. The oligomeric compound of any of embodiments 1492-1497, wherein the 2'-substituted furanosyl sugar moiety is selected from 2'-OMe, 2'-MOE, and 2'-F.

Embodiment 1499. The oligomeric compound of any of embodiments 1488-1498, wherein at least one of the ten 5'-most linking groups of the modified oligonucleotide is an internucleoside linking group of Formula XVII.

Embodiment 1500. The oligomeric compound of embodiment 1499, wherein at least 2 of the ten 5'-most linking groups of the modified oligonucleotide are internucleoside linking groups of Formula XVII.

Embodiment 1501. The oligomeric compound of embodiment 1499, wherein at least 3 of the ten 5'-most linking groups of the modified oligonucleotide are internucleoside linking groups of Formula XVII.

Embodiment 1502. The oligomeric compound of embodiment 1499, wherein at least 4 of the ten 5'-most linking groups of the modified oligonucleotide are internucleoside linking groups of Formula XVII.

Embodiment 1503. The oligomeric compound of embodiment 1499, wherein at least 5 of the ten 5'-most linking groups of the modified oligonucleotide are internucleoside linking groups of Formula XVII.

Embodiment 1504. The oligomeric compound of embodiment 1499, wherein at least 6 of the ten 5'-most linking groups of the modified oligonucleotide are internucleoside linking groups of Formula XVII.

Embodiment 1505. The oligomeric compound of embodiment 1499, wherein the two 5'-most internucleoside linking groups are internucleoside linking groups of Formula XVII.

Embodiment 1506. The oligomeric compound of any of embodiments 1489-1505, wherein at least one of the ten 3'-most internucleoside linking groups of the modified oligonucleotide is an internucleoside linking group of Formula XVII.

Embodiment 1507. The oligomeric compound of embodiment 1506, wherein at least 2 of the ten 3'-most internucleoside linking groups of the modified oligonucleotide are internucleoside linking groups of Formula XVII.

Embodiment 1508. The oligomeric compound of embodiment 1506, wherein at least 3 of the ten 3'-most internucleoside linking groups are internucleoside linking groups of Formula XVII.

Embodiment 1509. The oligomeric compound of embodiment 1506, wherein at least 4 of the ten 3'-most internucleoside linking groups are internucleoside linking groups of Formula XVII.

Embodiment 1510. The oligomeric compound of embodiment 1506, wherein at least 5 of the ten 3'-most internucleoside linking groups are internucleoside linking groups of Formula XVII.

Embodiment 1511. The oligomeric compound of embodiment 1506, wherein at least 6 of the ten 3'-most internucleoside linking groups are internucleoside linking groups of Formula XVII.

Embodiment 1512. The oligomeric compound of embodiment 1506, wherein the two 3'-most internucleoside linking groups of the oligomeric compound are internucleoside linking groups of Formula XVII.

Embodiment 1513. The oligomeric compound of any of embodiments 1484-1494, wherein the modified oligonucleotide comprises at least one block of at least 3 consecutive internucleoside linking groups of Formula XVII.

Embodiment 1514. The oligomeric compound of any of embodiments 1484-1494, wherein the modified oligonucleotide comprises at least one block of at least 4 consecutive internucleoside linking groups of Formula XVII.

Embodiment 1515. The oligomeric compound of any of embodiments 1484-1494, wherein the modified oligonucleotide comprises at least one block of at least 5 consecutive internucleoside linking groups of Formula XVII.

Embodiment 1516. The oligomeric compound of any of embodiments 1484-1494, wherein the modified oligonucleotide comprises at least one block of at least 6 consecutive internucleoside linking groups of Formula XVII.

Embodiment 1517. The oligomeric compound of any of embodiments 1513-1516, wherein at least one block of consecutive internucleoside linking groups of Formula XVII is at the 5' end of the modified oligonucleotide.

Embodiment 1518. The oligomeric compound of any of embodiments 1513-1516, wherein at least one block of consecutive internucleoside linking groups of Formula XVII is at the 3' end of the modified oligonucleotide.

Embodiment 1519. The oligomeric compound of any of embodiments 1484-1518, wherein for each internucleoside linking group of Formula XVII of the modified oligonucleotide, $R_1$ is H and T is $SO_2Me$.

Embodiment 1520. The oligomeric compound of any of embodiments 1484-1494, wherein the internucleoside linkage motif of the modified oligonucleotide is selected from: aaaaaassssssssss, sssssaaaaaassss, or ssssssssaaaaaa, wherein each "a" represents an internucleoside linkage of Formula XVII, each "s" represents a phosphorothioate internucleoside linkage, and each "o" represents a phosphodiester internucleoside linkage.

Embodiment 1521. The oligomeric compound of embodiment 1520, wherein each "a" represents a mesyl phosphoramidate internucleoside linkage.

Embodiment 1522. The oligomeric compound of any of embodiments 1246-1383, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 1523. The oligomeric compound of embodiment 1522, wherein at least 5 contiguous nucleosides of the deoxy region are stereo-standard DNA nucleosides.

Embodiment 1524. The oligomeric compound of embodiment 1522, wherein at least 6 contiguous nucleosides of the deoxy region are stereo-standard DNA nucleosides.

Embodiment 1525. The oligomeric compound of embodiment 1522, wherein at least 7 contiguous nucleosides of the deoxy region are stereo-standard DNA nucleosides.

Embodiment 1526. The oligomeric compound of embodiment 1522, wherein at least 8 contiguous nucleosides of the deoxy region are stereo-standard DNA nucleosides.

Embodiment 1527. The oligomeric compound of any of embodiments 1522-1526, wherein the deoxy region consists of 8-10 linked nucleosides.

Embodiment 1528. The oligomeric compound of any of embodiments 1522-1526, wherein the deoxy region consists of 9 linked nucleosides.

Embodiment 1529. The oligomeric compound of any of embodiments 1522-1526, wherein the deoxy region consists of 10 linked nucleosides.

Embodiment 1530. The oligomeric compound of any of embodiments 1522-1526, wherein the deoxy region consists of 11 linked nucleosides.

Embodiment 1531. The oligomeric compound of any of embodiments 1522-1526, wherein at least 6 nucleosides of the deoxy region are stereo-standard DNA nucleosides.

Embodiment 1532. The oligomeric compound of any of embodiments 1522-1526, wherein at least 7 nucleosides of the deoxy region are stereo-standard DNA nucleosides.

Embodiment 1533. The oligomeric compound of any of embodiments 1522-1526, wherein at least 8 nucleosides of the deoxy region are stereo-standard DNA nucleosides.

Embodiment 1534. The oligomeric compound of any of embodiments 1522-1526, wherein at least 9 nucleosides of the deoxy region are stereo-standard DNA nucleosides.

Embodiment 1535. The oligomeric compound of any of embodiments 1522-1534 wherein exactly two nucleosides of the deoxy region are modified nucleosides.

Embodiment 1536. The oligomeric compound of any of embodiments 1522-1535 wherein exactly one nucleoside of the deoxy region is a modified nucleoside.

Embodiment 1537. The oligomeric compound of any of embodiments 1522-1536 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 1538. The oligomeric compound of any of embodiments 1522-1537, wherein at least one modified nucleoside of the deoxy region is stereo-non-standard nucleoside.

Embodiment 1539. The oligomeric compound of embodiment 1538, wherein the at least one is stereo-non-standard nucleoside of the deoxy region is a stereo-non-standard DNA nucleoside.

Embodiment 1540. The oligomeric compound of embodiment 1539, wherein the stereo-non-standard DNA nucleoside is selected from a stereo-non-standard DNA nucleoside having: Formula I, Formula II, Formula III, Formula IV, Formula V, Formula VI, and Formula VII.

Embodiment 1541. The oligomeric compound of embodiment 1540, wherein the stereo-non-standard DNA nucleoside is selected from a stereo-non-standard DNA nucleoside having: Formula V and Formula II.

Embodiment 1542. The oligomeric compound of embodiment 1541, wherein at least one stereo-non-standard nucleoside of the deoxy region is a substituted stereo-non-standard nucleoside.

Embodiment 1543. The oligomeric compound of embodiment 1542, wherein at least one substituted stereo-non-standard nucleoside has a 2'-substituent selected from: 2'-MOE, 2'-OMe, 2'-F, or 2'-OH.

Embodiment 1544. The oligomeric compound of any of embodiments 1522-1543, wherein the $2^{nd}$ nucleoside from the 5'-end of the deoxy region is a modified nucleoside.

Embodiment 1545. The oligomeric compound of any of embodiments 1522-1543, wherein the $3^{rd}$ nucleoside from the 5'-end of the deoxy region is a modified nucleoside.

Embodiment 1546. The oligomeric compound of any of embodiments 1522-1543, wherein the $4^{th}$ nucleoside from the 5'-end of the deoxy region is a modified nucleoside.

Embodiment 1547. The oligomeric compound of any of embodiments 299-1546, wherein the modified nucleoside in the deoxy region is a 2'-OMe nucleoside.

Embodiment 1548. The oligomeric compound of any of embodiments 1522-1537, wherein each nucleoside of the deoxy region is a stereo-standard DNA nucleoside.

Embodiment 1549. The oligomeric compound of any of embodiments 1522-1548, wherein at least one internucleoside linking group within the deoxy region is an internucleoside linking group of Formula XVII.

Embodiment 1550. The oligomeric compound of any of embodiments 1522-1549, wherein the internucleoside linking group linking the $1^{st}$ and $2^{nd}$ nucleosides of the deoxy region as counted from the 5'-end of the deoxy region is an internucleoside linking group of Formula XVII.

Embodiment 1551. The oligomeric compound of any of embodiments 1522-1550, wherein the internucleoside linking group linking the $2^{nd}$ and $3^{rd}$ nucleosides of the deoxy region as counted from the 5'-end of the deoxy region is an internucleoside linking group of Formula XVII.

Embodiment 1552. The oligomeric compound of any of embodiments 1522-1551, wherein the internucleoside linking group linking the $3^{rd}$ and $4^{th}$ nucleosides of the deoxy region as counted from the 5'-end of the deoxy region is an internucleoside linking group of Formula XVII.

Embodiment 1553. The oligomeric compound of any of embodiments 1522-1552, wherein the internucleoside linking group linking the $4^{th}$ and $5^{th}$ nucleosides of the deoxy region as counted from the 5'-end of the deoxy region is an internucleoside linking group of Formula XVII.

Embodiment 1554. The oligomeric compound of any of embodiments 1522-1553, wherein one internucleoside linking group in the deoxy region is a linking group of Formula XVII and the other internucleoside linking groups of the deoxy region are independently selected from phosphodiester and phosphorothioate internucleoside linking groups.

Embodiment 1555. The oligomeric compound of any of embodiments 1522-1555, wherein two internucleoside linking groups in the deoxy region are linking groups of Formula XVII and the other internucleoside linking groups of the deoxy region are independently selected from phosphodiester and phosphorothioate internucleoside linking groups.

Embodiment 1556. The oligomeric compound of any of embodiments 1522-1555, wherein three internucleoside linking groups in the deoxy region are linking groups linking groups of Formula XVII and the other internucleoside linking groups of the deoxy region are independently selected from phosphodiester and phosphorothioate internucleoside linking groups.

Embodiment 1557. The oligomeric compound of any of embodiments 1522-1555, wherein four internucleoside linking groups in the deoxy region are linking groups linking groups of Formula XVII and the other internucleoside linking groups of the deoxy region are each phosphodiester or phosphorothioate internucleoside linking groups.

Embodiment 1558. The oligomeric compound of any of embodiments 1554-1557, wherein the internucleoside linking groups of Formula XVII are linking the $1^{st}$ and $2^{nd}$, $2^{nd}$ and $3^{rd}$, $3^{rd}$ and $4^{th}$, and/or the $4^{th}$ and $5^{th}$ nucleosides of the deoxy region, as counted from the 5'-end of the deoxy region.

Embodiment 1559. The oligomeric compound of any of embodiments 1522-1558, wherein the deoxy region comprises at least one region having structure A, B, C, D, E, or P.

Embodiment 1560. The oligomeric compound of embodiment 1559, wherein the region having structure A, B, C, D, or E is at the 3' end of the deoxy region.

Embodiment 1561. The oligomeric compound of embodiment 1560, wherein the region having structure A, B, C, D, E, or P is at the 5' end of the deoxy region.

Embodiment 1562. The oligomeric compound of any of embodiments 1522-1561, wherein the deoxy region comprises at least one region having the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

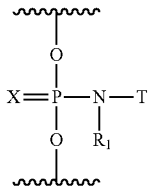

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1563. The oligomeric compound of embodiment 1562, wherein the region having the formula $(N_{g1})_{L1}(N_{g2})_{L2}(N_{g3})_{L3}$ is at the 3' end of the deoxy region.

Embodiment 1564. The oligomeric compound of embodiment 1562, wherein the region having the formula $(N_{g1})_{L1}(N_{g2})_{L2}(N_{g3})_{L3}$ is at the 5' end of the deoxy region.

Embodiment 1565. The oligomeric compound of any of embodiments 1549-1564, wherein for each internucleoside linkage of Formula XVII, $R_1$ is H and T is $SO_2Me$.

Embodiment 1566. The oligomeric compound of any of embodiments 1522-1565, wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region comprises a modified sugar moiety; and the 5'-most nucleoside of the 3'-region comprises a modified sugar moiety.

Embodiment 1567. The oligomeric compound of embodiment 1566, wherein the deoxy region consists of 7-11 linked nucleosides, and has the formula:

$$(N_{d1})_{L1}(N_{d2})_{L2}(N_{d3})_{L3}(N_{d4})_{L4}[(N_d)_{L5}]_q;$$

wherein $N_{d1}$, $N_{d2}$, $Na_3$, $N_{d4}$ are independently selected from among a stereo-standard DNA nucleoside, a stereo-non-standard DNA nucleoside, or a 2'-substituted nucleoside; with the proviso that no more than one of $N_{d1}$, $N_{d2}$, $N_{d3}$, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of L1, $L_2$, $L_3$, $L_4$ are internucleoside linkages of Formula XVII.

Embodiment 1568. The oligomeric compound of embodiment 1567, wherein one of $N_{d1}$, $N_{d2}$, $Na_3$, or $N_{d4}$ is a 2'-substituted nucleoside.

Embodiment 1569. The oligomeric compound of embodiment 1568, wherein the 2'-substituted nucleoside is a 2'-OMe nucleoside.

Embodiment 1570. The oligomeric compound of embodiment 1569, wherein the 2'-OMe nucleoside is a stereo-standard 2'-OMe nucleoside.

Embodiment 1571. The oligomeric compound of any of embodiments 1566-1569, wherein the 2'-substituted nucleoside is $N_{d2}$.

Embodiment 1572. The oligomeric compound of embodiment 1567, wherein each of $N_{d1}$, $N_{d2}$, $N_{d3}$, $N_{d4}$ and each $N_d$ is a DNA nucleoside.

Embodiment 1573. The oligomeric compound of embodiment 1572, wherein each DNA nucleoside is a stereo-standard DNA nucleoside.

Embodiment 1574. The oligomeric compound of any of embodiments 1567-1573, wherein $L_1$ and $L_2$ are internucleoside linkages of Formula XVII.

Embodiment 1575. The oligomeric compound of any of embodiments 1567-1573, wherein $L_2$ and $L_3$ are internucleoside linkages of Formula XVII.

Embodiment 1576. The oligomeric compound of any of embodiments 1567-1573, wherein $L_3$ and $L_4$ are internucleoside linkages of Formula XVII.

Embodiment 1577. The oligomeric compound of any of embodiments 1567-1573, wherein $L_1$, $L_2$, and $L_3$ are internucleoside linkages of Formula XVII.

Embodiment 1578. The oligomeric compound of any of embodiments 1567-1573, wherein $L_2$, $L_3$, and $L_4$ are internucleoside linkages of Formula XVII.

Embodiment 1579. The oligomeric compound of any of embodiments 1567-1573, wherein $L_1$, $L_2$, $L_3$, and $L_4$ are internucleoside linkages of Formula XVII.

Embodiment 1580. The oligomeric compound of any of embodiments 1567-1573, wherein each $L_5$ is a phosphorothioate internucleoside linkage.

Embodiment 1581. The oligomeric compound of embodiments 1567-1580, wherein each internucleoside linkage that is not an internucleoside linkage of Formula XVII is a phosphorothioate internucleoside linkage.

Embodiment 1582. The oligomeric compound of any of embodiments 1567-1581, wherein for each internucleoside linkage of Formula XVII, $R_1$ is H and T is $SO_2Me$ Embodiment 1583. The oligomeric compound of any of embodiments 1567-1582, wherein the 5'-region consists of 2-5 linked nucleosides.

Embodiment 1584. The oligomeric compound of embodiment 1583, wherein the 5'-region consists of 3 linked nucleosides.

Embodiment 1585. The oligomeric compound of embodiment 1583, wherein the 5'-region consists of 5 linked nucleosides.

Embodiment 1586. The oligomeric compound of any of embodiments 1566-1585 wherein each nucleoside of the 5'-region is a modified nucleoside.

Embodiment 1587. The oligomeric compound of any of embodiments 1566-1586, wherein each nucleoside of the 5'-region is a modified nucleoside comprising a modified sugar.

Embodiment 1588. The oligomeric compound of any of embodiments 1566-1587, wherein at least one nucleoside of the 5'-region comprises a 2'-substituted furanosyl sugar moiety.

Embodiment 1589. The oligomeric compound of any of embodiments 1566-1588, wherein each nucleoside of the 5'-region comprises a 2'-substituted furanosyl sugar moiety.

Embodiment 1590. The oligomeric compound of any of embodiments 1566-1589, wherein each 2'-substituted furanosyl sugar moiety of the 5'-region has a 2'-substituent selected from among 2'-MOE, 2'-OMe, and 2'-NMA.

Embodiment 1591. The oligomeric compound of any of embodiments 1566-1588 or 1590, wherein at least one nucleoside of the 5'-region comprises a bicyclic furanosyl sugar moiety.

Embodiment 1592. The oligomeric compound of any of embodiments 1566-1588 or 1590-1591, wherein each nucleoside of the 5'-region comprises a bicyclic furanosyl sugar moiety.

Embodiment 1593. The oligomeric compound of embodiment 1591 or 1592, wherein each bicyclic sugar moiety of the 5'-region is selected from among cEt, LNA, and ENA.

Embodiment 1594. The oligomeric compound of embodiment 1593, wherein each bicyclic sugar moiety of the 5'-region is a cEt sugar moiety.

Embodiment 1595. The oligomeric compound of any of embodiments 1566-1594, wherein at least one nucleoside of the 5' region is a stereo-standard DNA nucleoside.

Embodiment 1596. The oligomeric compound of any of embodiments 1566-1595, wherein at least one nucleoside of the 5' region is a stereo-non-standard nucleoside.

Embodiment 1597. The oligomeric compound of any of embodiments 1566-1596, wherein each nucleobase of the 5'-region is independently selected from among thymine, uracil, guanine, cytosine, 5-methylcytosine, and adenine.

Embodiment 1598. The oligomeric compound of any of embodiments 1566-1597, wherein the 3'-region consists of 2-5 linked nucleosides.

Embodiment 1599. The oligomeric compound of embodiment 1598, wherein the 3'-region consists of 3 linked nucleosides.

Embodiment 1600. The oligomeric compound of embodiment 1598, wherein the 3'-region consists of 5 linked nucleosides.

Embodiment 1601. The oligomeric compound of any of embodiments 1566-1600, wherein each nucleoside of the 3'-region is a modified nucleoside.

Embodiment 1602. The oligomeric compound of any of embodiments 1566-1601, wherein each nucleoside of the 3'-region is a modified nucleoside comprising a modified sugar.

Embodiment 1603. The oligomeric compound of any of embodiments 1566-1602, wherein at least one nucleoside of the 3'-region comprises a 2'-substituted furanosyl sugar moiety.

Embodiment 1604. The oligomeric compound of any of embodiments 1566-1603, wherein each nucleoside of the 3'-region comprises a 2'-substituted furanosyl sugar moiety.

Embodiment 1605. The oligomeric compound of any of embodiments 1566-1604, wherein each 2'-substituted furanosyl sugar moiety of the 3'-region has a 2'-substituent selected from among 2'-MOE, 2'-OMe, and 2'-NMA.

Embodiment 1606. The oligomeric compound of any of embodiments 1566-1603 or 1605, wherein at least one nucleoside of the 3'-region comprises a bicyclic furanosyl sugar moiety.

Embodiment 1607. The oligomeric compound of any of embodiments 1566-1603 or 1606, wherein each nucleoside of the 3'-region comprises a bicyclic furanosyl sugar moiety.

Embodiment 1608. The oligomeric compound of embodiment 1606 or 1607, wherein each bicyclic sugar moiety of the 3'-region is selected from among cEt, LNA, and ENA.

Embodiment 1609. The oligomeric compound of embodiment 1608, wherein each bicyclic sugar moiety of the 3'-region is a cEt sugar moiety.

Embodiment 1610. The oligomeric compound of any of embodiments 1566-1609, wherein at least one nucleoside of the 3' region is a stereo-standard DNA nucleoside.

Embodiment 1611. The oligomeric compound of any of embodiments 1566-1610, wherein at least one nucleoside of the 3' region is a stereo-non-standard nucleoside.

Embodiment 1612. The oligomeric compound of any of embodiments 1566-1611, wherein each nucleobase of the 3'-region is independently selected from among thymine, uracil, guanine, cytosine, 5-methylcytosine, and adenine.

Embodiment 1613. The oligomeric compound of any of embodiments 1566-1612 wherein the oligomeric compound is a gapmer.

Embodiment 1614. The oligomeric compound of any of embodiments 1566-1613, wherein the modified oligonucleotide has a sugar motif selected from kkkddddddddddkkk and kkkdydddddddddkkk, wherein each "k" represents a cEt sugar moiety, "y" represents a 2'-OMe sugar moiety, and each "d" represents a β-D-2'-deoxyribosyl sugar moiety.

Embodiment 1615. The oligomeric compound of any of embodiments 1566-1614, wherein the modified oligonucleotide has an internucleoside linkage motif selected from: sssssssssssssa, sssssssssssssas, ssssssssssssass, sssssssssssasss, ssssssssssassss, sssssssssasssss, ssssssssassssss, sssssssasssssss, ssssssassssssss, sssssasssssssss, ssssassssssssss, sssasssssssssss, ssassssssssssss, sasssssssssssss, assssssssssssss, sssssssssssssaa, ssssssssssssaas, sssssssssssaass, ssssssssssaasss, sssssssssaassss, ssssssssaasssss, sssssssaassssss, ssssssaasssssss, sssssaassssssss, ssssaasssssssss, sssaassssssssss, ssaasssssssssss, saassssssssssss, aasssssssssssss, aaaaaaaaaaaaaaa, ssaaaaaaaaaaass, ssaaaaaaaaaasss, sssaaaaaaaaasss, aassssssssssaaa, sssaaassssssssss, sssaaasssssssss, sssaaaasssssssss, ssaaasssssssssss, ssaaaassssssssss, ssaaaaassssssss, ssaaaaaasssssss, ssaaaaaaasssss, ssaaaaaaaassss, ssaaaaaaaaassss, ssssssssssaaass, sssssssssaaaass, ssssssssaaaaass, sssssssaaaaaass, ssssssaaaaaaass, sssssaaaaaaaass, ssssaaaaaaaaass, sssaaaaaaaaaass, ssasasasasasass, sssasasasasasss, ooossssssssssoo, soossssssssssos, aoossssssssooa, aoasssssssssaoa, aoaaaassssssaoa, aoossssssssssoa, ooasssssssssaoo, aoosaassssssssoa, aossaassssssssoa, aooaaaasssssaoa, aoossssssaaaaoa, sssssaaassssssss, ssssssaaasssssss, ssssssssaaasssss, sssssssssaaassss, ssssssssssaaasss, ssssaaaasssssss, sssssaaaasssssss, ssssssaaaasssss, sssssssaaaassss, sssssssaaaasss, sssaasssssaass, sssaassssaasss, sssaassssaassss, sssaasssaassss, sssaassaassssss, sssaasaassssss, ssaassssssaass, ssssaassssaass, sssssaassssaass, sssssaasssaass, ssssssssaassaass, sssssssssaasaass, ssssaasssaassss, sssssaasaassss, sssssssssssssss, aaassssssssssss, aaassssssssssaa, aaaaaassssssss, aoooosaassssssooaa, aoooosssssssssssooaa, soooaasssssssssooss, soooosaassssssooss, sooooossaasssssooss, soooossssssaassooss, sssaaaaassssssss, sssssaaaaaassss, or ssssssssssaaaaaa, wherein each "a" represents an internucleoside linkage of Formula XVII, each "s" represents a phosphorothioate internucleoside linkage, and each "o" represents a phosphodiester internucleoside linkage.

Embodiment 1616. The oligomeric compound of embodiment 1615, wherein the modified oligonucleotide has an internucleoside linkage motif selected from: sssaaaasssssssss, sssaaassssssssss, ssssaaassssssssss, ssssaassssssaass, sssaassssssssssss, ssssaasssssssssss, sssssaasssssssss, or sssssssssaassss, wherein each "a" represents an internucleoside linkage of Formula XVII, each "s" represents a phosphorothioate internucleoside linkage, and each "o" represents a phosphodiester internucleoside linkage.

Embodiment 1617. The oligomeric compound of embodiment 1615 or 1616, wherein each "a" represents a mesyl phosphoramidate internucleoside linkage.

Embodiment 1618. The oligomeric compound of any of embodiments 1246-1383, wherein the modified oligonucleotide is a CRISPR compound.

Embodiment 1619. The oligomeric compound of embodiment 1618, wherein the CRISPR compound consists of 20-50 or 29-32 linked nucleosides.

Embodiment 1620. The oligomeric compound of any of embodiments 1335-1619, wherein each X is O.

Embodiment 1621. The oligomeric compound of any of embodiments 1335-1619, wherein each X is S.

Embodiment 1622. The oligomeric compound of any of embodiments 1335-1621, wherein at least one $R_1$ is H.

Embodiment 1623. The oligomeric compound of any of embodiments 1335-1621, wherein at least one $R_1$ is a $C_1$-$C_6$ alkyl.

Embodiment 1624. The oligomeric compound of embodiment 1623, wherein the at least one $R_1$ is methyl.

Embodiment 1625. The oligomeric compound of any of embodiments 1335-1621, at least one $R_1$ is a substituted $C_1$-$C_6$ alkyl.

Embodiment 1626. The oligomeric compound of any of embodiments 1335-1625, wherein at least one T comprises a conjugate group.

Embodiment 1627. The oligomeric compound of embodiment 1626, wherein the conjugate group comprises a cell-targeting moiety.

Embodiment 1628. The oligomeric compound of embodiment 1626, wherein the conjugate group comprises a carbohydrate or carbohydrate cluster.

Embodiment 1629. The oligomeric compound of any of embodiments 1626-1627, wherein the conjugate group comprises at least one GalNAc.

Embodiment 1630. The oligomeric compound of embodiment 1626, wherein the conjugate group comprises a $C_{10}$-$C_{20}$ alkyl chain.

Embodiment 1631. The oligomeric compound of embodiment 1630, wherein the conjugate group comprises $C_{16}$ alkyl.

Embodiment 1632. The oligomeric compound of any of embodiments 1335-1631, wherein at least one T does not comprise a conjugate group.

Embodiment 1633. The oligomeric compound of any of embodiments 1335-1625, wherein each T does not comprise a conjugate group.

Embodiment 1634. The oligomeric compound of any of embodiments 1335-1633, wherein at least one T is $SO_2R_2$.

Embodiment 1635. The oligomeric compound of embodiment 1634, wherein $R_2$ is an aryl.

Embodiment 1636. The oligomeric compound of embodiment 1634, wherein $R_2$ is a substituted aryl.

Embodiment 1637. The oligomeric compound of embodiment 1634, wherein $R_2$ is a heterocycle.

Embodiment 1638. The oligomeric compound of embodiment 1634, wherein $R_2$ is a substituted heterocycle.

Embodiment 1639. The oligomeric compound of embodiment 1634, wherein $R_2$ is an aromatic heterocycle.

Embodiment 1640. The oligomeric compound of embodiment 1634, wherein $R_2$ is a substituted aromatic heterocycle.

Embodiment 1641. The oligomeric compound of embodiment 1634, wherein $R_2$ is a diazole.

Embodiment 1642. The oligomeric compound of embodiment 1634, wherein $R_2$ is a substituted diazole.

Embodiment 1643. The oligomeric compound of embodiment 1634, wherein $R_2$ is an amine.

Embodiment 1644. The oligomeric compound of embodiment 1634, wherein $R_2$ is a substituted amine.

Embodiment 1645. The oligomeric compound of embodiment 1634, wherein $R_2$ is a $C_1$-$C_6$ alkoxy, $C_1$-$C_6$ alkenyl, or $C_1$-$C_6$ alkynyl.

Embodiment 1646. The oligomeric compound of embodiment 1634, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 1647. The oligomeric compound of embodiment 1634, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 1648. The oligomeric compound of embodiment 1634, wherein $R_2$ comprises a carbohydrate or carbohydrate cluster.

Embodiment 1649. The oligomeric compound of embodiment 1634, wherein $R_2$ comprises at least one GalNAc.

Embodiment 1650. The oligomeric compound of embodiment 1634, wherein T is:

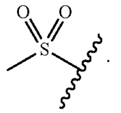

Embodiment 1651. The oligomeric compound of embodiment 1634, wherein T is:

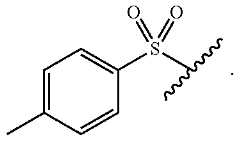 [SMILES: *S(=O)(=O)c1ccc(C)cc1]

Embodiment 1652. The oligomeric compound of embodiment 1634, wherein T is:

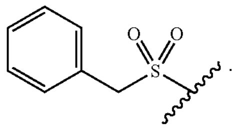 [SMILES: *S(=O)(=O)Cc1ccccc1]

Embodiment 1653. The oligomeric compound of embodiment 1634, wherein T is:

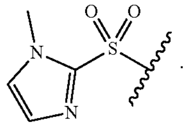 [SMILES: *S(=O)(=O)c1nccn1C]

Embodiment 1654. The oligomeric compound of embodiment 1634, wherein T is:

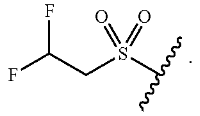

Embodiment 1655. The oligomeric compound of embodiment 1634, wherein T is:

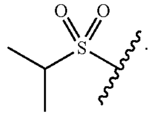 [SMILES: *S(=O)(=O)C(C)C]

Embodiment 1656. The oligomeric compound of embodiment 1634, wherein T is:

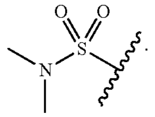 [SMILES: *S(=O)(=O)N(C)C]

Embodiment 1657. The oligomeric compound of embodiment 1634, wherein T is:

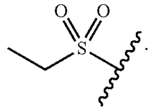 [SMILES: *S(=O)(=O)CC]

Embodiment 1658. The oligomeric compound of embodiment 1634, wherein T is:

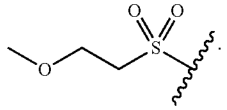 [SMILES: *S(=O)(=O)CCOC]

Embodiment 1659. The oligomeric compound of embodiment 1634, wherein T is:

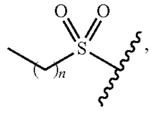

wherein n is from 2 to 20.

Embodiment 1660. The oligomeric compound of embodiment 1659, wherein n is 15.

Embodiment 1661. The oligomeric compound of any of embodiments 1335-1660, wherein at least one T is C(=O)$R_3$.

Embodiment 1662. The oligomeric compound of embodiment 1661, wherein $R_3$ is an aryl.

Embodiment 1663. The oligomeric compound of embodiment 1661, wherein $R_3$ is a substituted aryl.

Embodiment 1664. The oligomeric compound of embodiment 1661, wherein $R_3$ is $CH_3$.

Embodiment 1665. The oligomeric compound of embodiment 1661, wherein $R_3$ is $N(CH_3)_2$.

Embodiment 1666. The oligomeric compound of embodiment 1661, wherein $R_3$ is $OCH_3$.

Embodiment 1667. The oligomeric compound of embodiment 1661, wherein $R_3$ is a $C_1$-$C_6$ alkoxy.

Embodiment 1668. The oligomeric compound of embodiment 1661, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 1669. The oligomeric compound of embodiment 1661, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 1670. The oligomeric compound of embodiment 1661, wherein $R_3$ comprises a carbohydrate or carbohydrate cluster.

Embodiment 1671. The oligomeric compound of embodiment 1661, wherein $R_{23}$ comprises at least one GalNAc.

Embodiment 1672. The oligomeric compound of embodiment 1661, wherein T is:

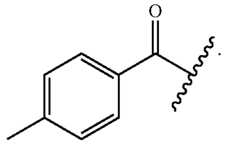 [SMILES: *C(=O)c1ccc(C)cc1]

Embodiment 1673. The oligomeric compound of embodiment 1661, wherein T is:

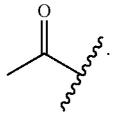

Embodiment 1674. The oligomeric compound of embodiment 1661, wherein T is:

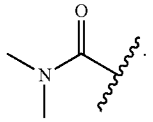 [SMILES: *C(=O)N(C)C]

Embodiment 1675. The oligomeric compound of embodiment 1661, wherein T is:

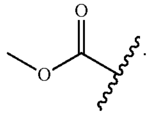 [SMILES: *C(=O)OC]

Embodiment 1676. The oligomeric compound of embodiment 1661, wherein T is:

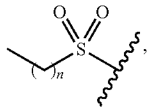

wherein n is from 2 to 20.

Embodiment 1677. The oligomeric compound of embodiment 1676, wherein n is 15.

Embodiment 1678. The oligomeric compound of any of embodiments 1335-1677, wherein at least one T is $P(=O)R_4R_5$.

Embodiment 1679. The oligomeric compound of embodiment 1678, wherein $R_4$ is $OCH_3$.

Embodiment 1680. The oligomeric compound of embodiment 1678, wherein $R_4$ is OH Embodiment 1681. The oligomeric compound of embodiment 1678, wherein $R_4$ is $C_1$-$C_6$ alkyl.

Embodiment 1682. The oligomeric compound of embodiment 1678, wherein $R_4$ is substituted $C_1$-$C_6$ alkyl.

Embodiment 1683. The oligomeric compound of embodiment 1678, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 1684. The oligomeric compound of embodiment 1678, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 1685. The oligomeric compound of embodiment 1678, wherein $R_4$ comprises a carbohydrate or carbohydrate cluster.

Embodiment 1686. The oligomeric compound of embodiment 1678, wherein $R_4$ comprises at least one GalNAc.

Embodiment 1687. The oligomeric compound of any of embodiments 1678-1686, wherein $R_5$ is $OCH_3$.

Embodiment 1688. The oligomeric compound of any of embodiments 1678-1686, wherein $R_5$ is OH.

Embodiment 1689. The oligomeric compound of any of embodiments 1678-1686, wherein $R_5$ is $C_1$-$C_6$ alkyl.

Embodiment 1690. The oligomeric compound of any of embodiments 1678-1686, wherein $R_5$ is substituted $C_1$-$C_6$ alkyl.

Embodiment 1691. The oligomeric compound of embodiment 1678, wherein T is:

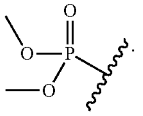 [SMILES: *P(=O)(OC)OC]

Embodiment 1692. The oligomeric compound of embodiment 1678, wherein T is:

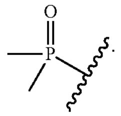

Embodiment 1693. The oligomeric compound of embodiment 1678, wherein T is:

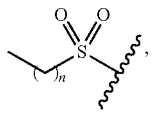

wherein n is from 2 to 20.

Embodiment 1694. The oligomeric compound of embodiment 1693, wherein n is 15.

Embodiment 1695. An antisense agent comprising a modified oligonucleotide consisting of 12-50 linked nucleosides linked through internucleoside linking groups, wherein at least one internucleoside linking group is a phosphodiester or a phosphorothioate internucleoside linking group, and wherein at least one of the internucleoside linking groups has Formula XX:

XX

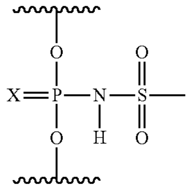

wherein independently for each internucleoside linking group of the modified oligonucleotide having Formula XX, X is selected from O or S.

Embodiment 1696. An antisense agent comprising a modified oligonucleotide, wherein the 5'-terminus of the modified oligonucleotide has Structure F:

Structure F

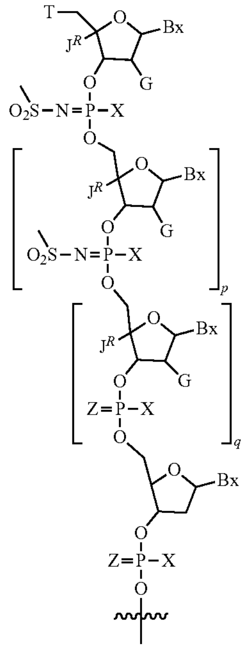

wherein:

p is from 0 to 6;

q is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —CH($CH_3$)—O— or —($CH_2$)$_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or N($E_1$);

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, N($J_1$)($J_2$), =$NJ_1$, $SJ_1$, $N_3$, CN, OC(=$X_2$)$J_1$, OC(=$X_2$)N($J_1$)($J_2$) and C(=$Q_2$)N($J_1$)($J_2$);

$Q_2$ is O, S or $NJ_3$;

each $J_1$, $J_2$ and $J_3$ is, independently, H or $C_1$-$C_6$ alkyl.

Embodiment 1697. An antisense agent comprising a modified oligonucleotide, wherein the 3'-terminus of the modified olionucleotide has Structure G:

Structure G

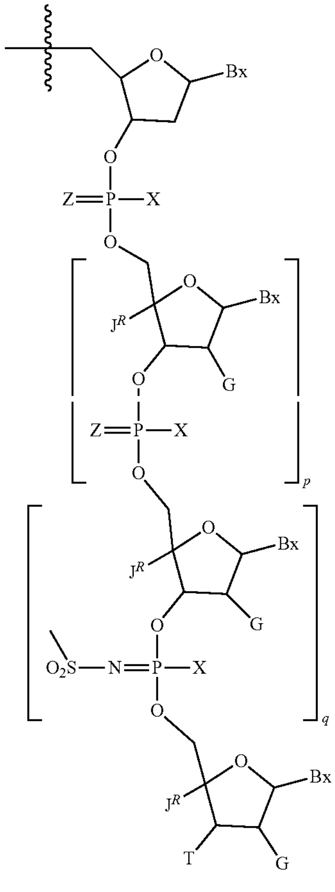

wherein:

p is from 0 to 6;

q is from 1 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—[C($R_6$)($R_7$)]$_n$[(C=O)$_m$—$X^G$]$_j$—$R_8$;

wherein each $J^R$ to G bridge has a formula independently selected from —CH($CH_3$)—O— or —($CH_2$)$_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or N($E_1$);

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, N($J_1$)($J_2$), =$NJ_1$, $SJ_1$, $N_3$, CN, OC(=$X_2$)$J_1$, OC(=$X_2$)N($J_1$)($J_2$) and C(=$Q_2$)N($J_1$)($J_2$);

$Q_2$ is O, S or $NJ_3$;

each $J_1$, $J_2$ and $J_3$ is, independently, H or $C_1$-$C_6$ alkyl.

Embodiment 1698. The antisense agent of embodiment 1696 or 1697, wherein the sum of p+q is selected from 2, 3, 4, or 5.

Embodiment 1699. An antisense agent comprising a modified oligonucleotide, wherein the 5'-terminus of the modified oligonucleotide has Structure H:

Structure H

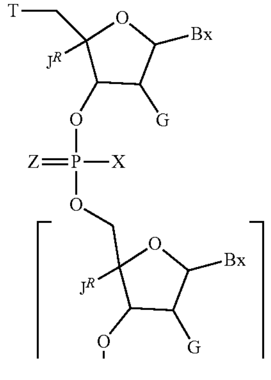

-continued

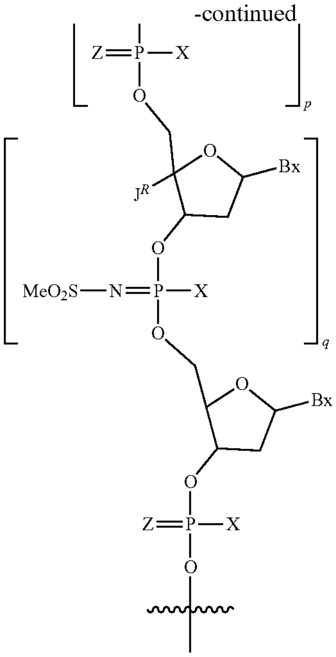

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1700. An antisense agent comprising a modified oligonucleotide, wherein the 5'-terminus of the modified oligonucleotide has Structure I:

Structure I

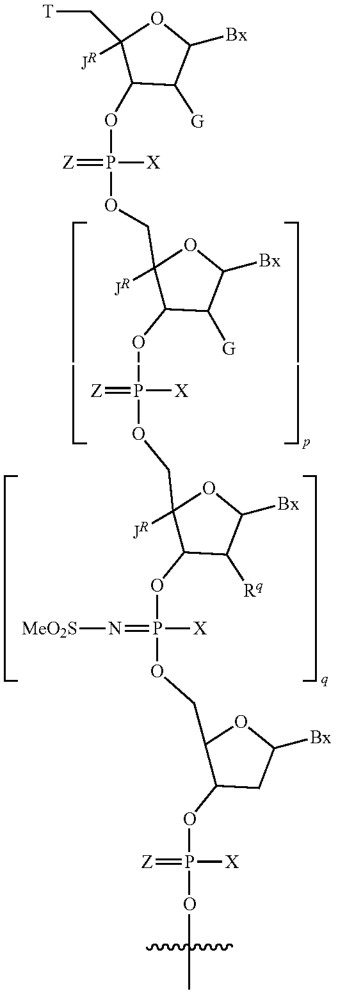

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

each $R^q$ is H or exactly one $R^q$ is OMe and the other $R^q$ are H;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1701. The antisense agent of embodiment 1700, wherein exactly one $R^q$ is —OMe.

Embodiment 1702. The antisense agent of any of embodiments 1699-1701, wherein the sum of p+q is 2, 3, or 4.

Embodiment 1703. An antisense agent comprising a modified oligonucleotide, wherein the 3'-terminus of the modified oligonucleotide has Structure J:

Structure J

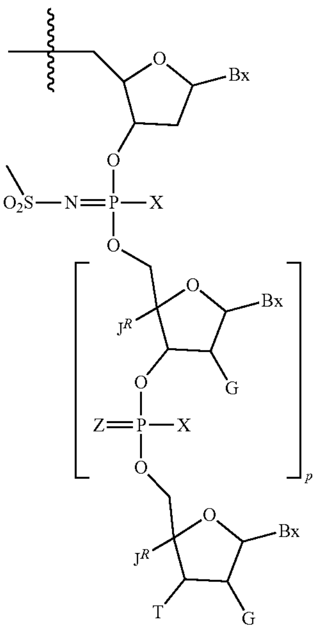

wherein:

p is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$, is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1704. The antisense agent of embodiment 1703, wherein p is 2, 3, or 4.

Embodiment 1705. The antisense agent of any of embodiments 1696-1704, wherein each $J^R$ is H and each G is $OCH_2CH_2OCH_3$.

Embodiment 1706. The antisense agent of any of embodiments 1696-1704, wherein each $J^R$ is H and each G is $OCH_3$.

Embodiment 1707. The antisense agent of any of embodiments 1696-1704, wherein each $J^R$ and Gform a JRto G bridge.

Embodiment 1708. The antisense agent of embodiment 1707, wherein the $J^R$ to G bridge has the formula $-CH(CH_3)-O-$.

Embodiment 1709. The antisense agent of embodiment 1695, wherein the antisense agent is an RNAi agent.

Embodiment 1710. The RNAi agent of embodiment 1709, wherein the RNAi agent is a single-stranded RNAi agent comprising an RNAi antisense modified oligonucleotide.

Embodiment 1711. The RNAi agent of embodiment 1709, wherein the RNAi agent is an oligonucleotide duplex comprising an RNAi antisense modified oligonucleotide and an RNAi sense modified oligonucleotide.

Embodiment 1712. The RNAi agent of any of embodiments 1710-1711, wherein the 5'-terminus of the RNAi antisense oligonucleotide has structure K:

Structure K

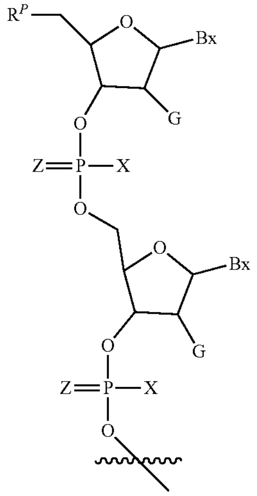

wherein:

$R^P$ is a phosphate, stabilized phosphate group, or a mesyl phosphoramidate;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1713. The RNAi agent of embodiment 1712, wherein the stabilized phosphate group is 5'-vinyl phosphonate or 5'-cyclopropyl phosphonate.

Embodiment 1714. The RNAi agent of embodiment 1712, wherein the stabilized phosphate group is a mesyl phosphoramidate.

Embodiment 1715. The RNAi agent of any of embodiments 1712-1714, wherein each G within structure K is independently selected from F or OMe.

Embodiment 1716. The RNAi agent of any of embodiments 1712-1715, wherein the 3'-terminus of the RNAi antisense oligonucleotide has structure L:

Structure L

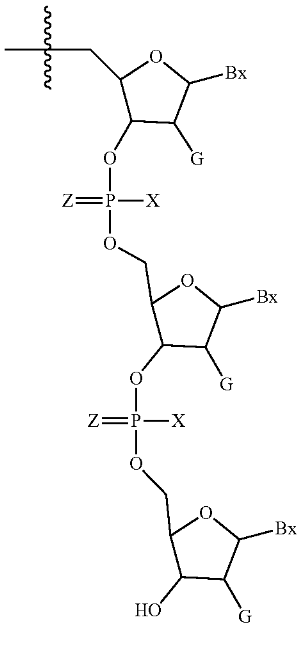

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1717. The RNAi agent of embodiment 1716, wherein each G within Structure L of the RNAi antisense oligonucleotide is independently selected from F or OMe.

Embodiment 1718. The RNAi agent of any of embodiments 1710-1717, wherein at least one region of the RNAi antisense oligonucleotide has structure M:

Structure M

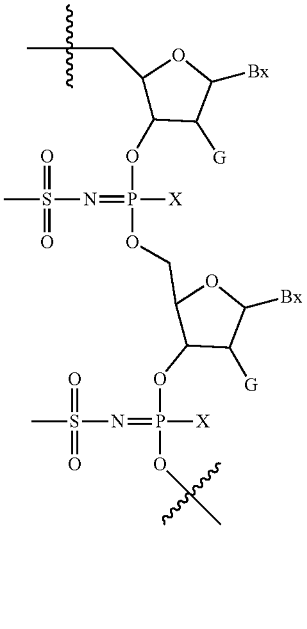

wherein:

each Bx is an independently selected heterocyclic base moiety;

each X is independently selected from OH or SH;

each G is independently selected from OH, halogen or $O—[C(R_6)(R_7)]_n—[(C═O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(═X_2)J_1$, $OC(═X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1719. The RNAi agent of embodiment 1718, wherein each G of Structure M within the RNAi antisense oligonucleotide is selected from F or OMe.

Embodiment 1720. The RNAi agent of embodiment 1719, wherein one G is F and the other G is OMe.

Embodiment 1721. The RNAi agent of any of embodiments 1710-1711 or 1716-1720, wherein the 5'-terminus of the RNAi antisense oligonucleotide has structure N:

Structure N

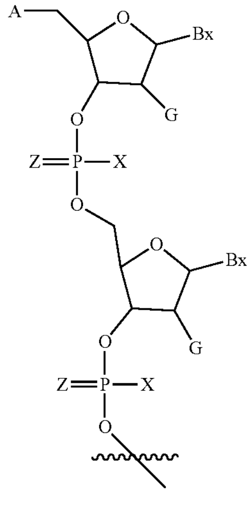

wherein:

A is selected from

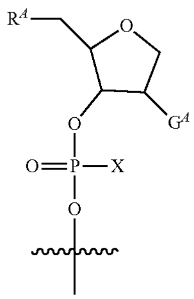

or

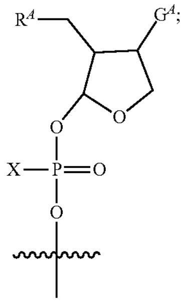

$R^A$ is OH, OP(═O)OH, OP(═O)SH, a stabilized phosphate group, or a mesyl phosphoramidate;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C═O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(═X_2)J_1$, $OC(═X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1722. The RNAi agent of embodiment 1722, wherein each G within structure N of the RNAi antisense oligonucleotide is selected from F or OMe.

Embodiment 1723. The RNAi agent of any of embodiments 1710-1714 or 1718-1722, wherein the 3'-terminus of the RNAi antisense oligonucleotide has structure O:

Structure O

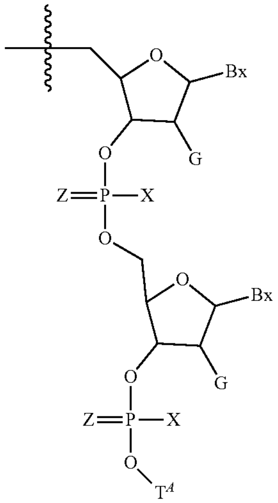

wherein

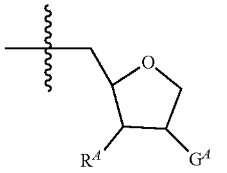

or

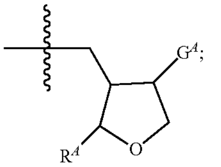

$T^A$ is selected from $R^A$ $G^A$ or $R^A$ O.

$R^A$ is OH, OP(═O)OH, OP(═O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$, is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1724. The RNAi agent of embodiment 1723, wherein each G within structure 0 of the RNAi antisense oligonucleotide is selected from F or OMe.

Embodiment 1725. The RNAi agent of embodiment 1711, wherein the 5'-terminus of the RNAi sense oligonucleotide has structure K:

Structure K

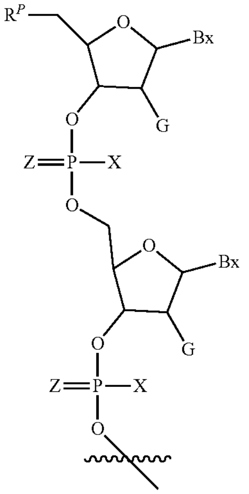

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1726. The RNAi agent of embodiment 1725, wherein the stabilized phosphate group is 5'-vinyl phosphonate, 5'-cyclopropyl phosphonate, or 5'-mesyl phosphoramidate.

Embodiment 1727. The RNAi agent of embodiment 1725 or 1726, wherein each G within structure K is independently selected from F or OMe.

Embodiment 1728. The RNAi agent of any of embodiments 1711 or 1725-1727, wherein the 3'-terminus of the RNAi sense oligonucleotide has structure L:

Structure L

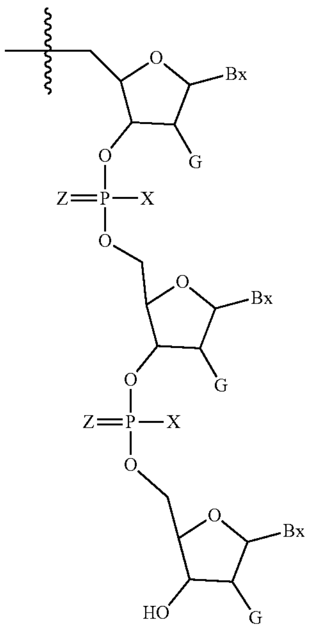

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is or 1;

each substituted group comprises one or more optionally protected substituent groups independently selected from halogen, $OJ_1$, $N(J_1)(J_2)$, $=NJ_1$, $SJ_1$, $N_3$, CN, $OC(X_2)J$, $OC(X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1729. The RNAi agent of embodiment 1728, wherein each G within Structure L of the RNAi sense oligonucleotide is independently selected from F or OMe.

Embodiment 1730. The RNAi agent of any of embodiments 1711 or 1725-1729 wherein at least one region of the RNAi sense oligonucleotide has structure M:

Structure M

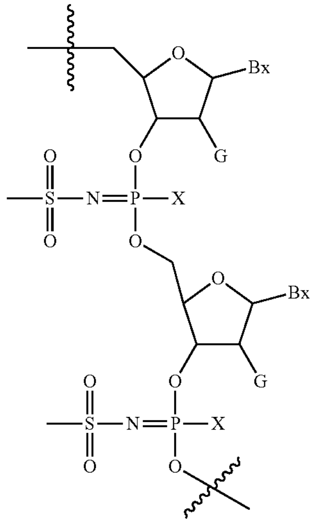

wherein:

each Bx is an independently selected heterocyclic base moiety;

each X is independently selected from OH or SH;

each G is independently selected from OH, halogen or O—$[C(R_6)(R_7)]$~$n[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1731. The RNAi agent of embodiment 1730, wherein each G of Structure M within the RNAi sense oligonucleotide is selected from F or OMe.

Embodiment 1732. The RNAi agent of embodiment 1731, wherein one G is F and the other G is OMe.

Embodiment 1733. The RNAi agent of any of embodiments 1711 or 1728-1732, wherein the 5'-terminus of the RNAi sense oligonucleotide has structure N:

Structure N

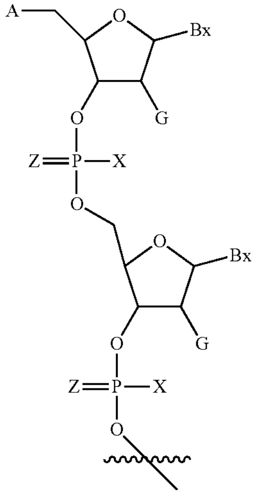

wherein:

A is selected from H or

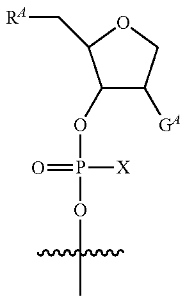

or

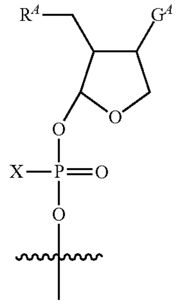

;

$R^A$ is OH, OP(=O)OH, OP(=O)SH, a stabilized phosphate group or a mesyl phosphoramidate;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1734. The RNAi agent of embodiment 1733, wherein each G within structure N of the RNAi sense oligonucleotide is selected from F or OMe.

Embodiment 1735. The RNAi agent of any of embodiments 1711, 1725-1727, or 1730-1734, wherein the 3'-terminus of the RNAi sense oligonucleotide has structure 0:

Structure O

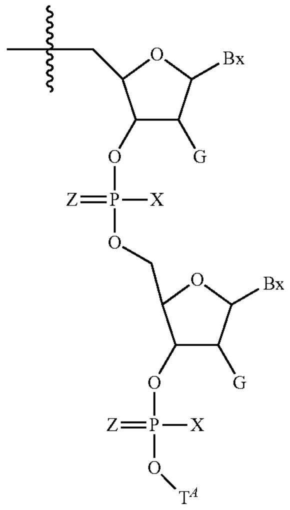

wherein:

$T^A$ is selected from

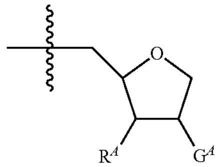

or

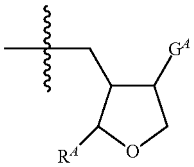

;

$R^A$ is OH, OP(=O)OH, OP(=O)SH, or a stabilized phosphate group, $G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1736. The RNAi agent of embodiment 1735, wherein each G within structure O of the RNAi sense oligonucleotide is selected from F or OMe.

Embodiment 1737. The oligomeric compound or antisense agent of any of embodiments 1246-1456 or 1484-1724, comprising at least one modified oligonucleotide, wherein the nucleobase sequence of at least one modified oligonucleotide is complementary to a target nucleic acid.

Embodiment 1738. The modified oligonucleotide of embodiment 1737, wherein the nucleobase sequence of the modified oligonucleotide is at least 80% complementary to the target nucleic acid.

Embodiment 1739. The modified oligonucleotide of embodiment 1737, wherein the nucleobase sequence of the modified oligonucleotide is at least 85% complementary to the target nucleic acid.

Embodiment 1740. The modified oligonucleotide of embodiment 1737, wherein the nucleobase sequence of the modified oligonucleotide is at least 90% complementary to the target nucleic acid.

Embodiment 1741. The modified oligonucleotide of embodiment 1737, wherein the nucleobase sequence of the modified oligonucleotide is at least 95% complementary to the target nucleic acid.

Embodiment 1742. The modified oligonucleotide of embodiment 1737, wherein the nucleobase sequence of the modified oligonucleotide is 100% complementary to the target nucleic acid.

Embodiment 1743. The modified oligonucleotide of any of embodiments 1737-1742, wherein the target nucleic acid is a target RNA.

Embodiment 1744. The modified oligonucleotide of embodiment 1743, wherein the target RNA is selected from: an mRNA, a pre-mRNA, a microRNA, and a non-coding RNA.

Embodiment 1745. The modified oligonucleotide of embodiment 1744, wherein the target RNA is not a microRNA.

Embodiment 1746. The antisense agent comprising a modified oligonucleotide of any of embodiments 1-500, wherein the modified oligonucleotide is not complementary to miR-21.

Embodiment 1747. The antisense agent of any of embodiments 1246-1746, comprising a conjugate group.

Embodiment 1748. The antisense agent of embodiment 1747, wherein the conjugate group comprises at least one GalNAc.

Embodiment 1749. The antisense agent of embodiment 1747 or 1748, wherein the conjugate group comprises 1-5 linker-nucleosides.

Embodiment 1750. A pharmaceutical composition comprising the oligomeric compound of any of embodiments 1246-1694 or the antisense agent of any of embodiments 1695-1730 and a pharmaceutically acceptable carrier or diluent.

Embodiment 1751. A method comprising contacting a cell with the oligomeric compound, antisense agent, or pharmaceutical composition of any of embodiments 1246-1750.

Embodiment 1752. A method of modulating the amount or activity of a target nucleic acid in a cell, comprising contacting the cell with the oligomeric compound, antisense agent, or pharmaceutical composition of any of embodiments 1246-1750 and thereby modulating the amount or activity of the target nucleic acid.

Embodiment 1753. A method of modulating the amount or activity of a target nucleic acid in a cell, comprising contacting the cell with the oligomeric compound, antisense agent or pharmaceutical composition of any of embodiments 1246-1750.

Embodiment 1754. The method of embodiments 1751-1753, wherein the amount or activity of a target nucleic acid is reduced.

Embodiment 1755. The method of embodiments 1751-1753, wherein the amount or activity of a target nucleic acid is increased.

Embodiment 1756. The method of embodiment 1753, wherein the target nucleic acid comprises at least one translation suppression element and wherein the modified oligonucleotide is complementary to a target site within a translation suppression element region of the target nucleic acid.

Embodiment 1757. The method of embodiment 1756, wherein the translation suppression element region comprises at least one stem-loop structure.

Embodiment 1758. Use of the antisense agent or composition of any of embodiments 1246-1750 for treatment of a disease or condition.

Embodiment 1759. Use of the antisense agent or composition of any of embodiments 1246-1750 for a preparation of a medicament for treatment of a disease or condition.

Embodiment 1760. The oligomeric compound or antisense agent of any of embodiments 1246-1749, wherein the oligomeric compound or antisense agent is not an RNAi agent and the parent oligomeric compound or antisense agent is cytotoxic in vitro.

Embodiment 1761. The oligomeric compound or antisense agent of embodiment 1760, wherein the parent oligomeric compound or antisense agent is cytotoxic in a standard in vitro cytotoxicity assay.

Embodiment 1762. The oligomeric compound or antisense agent of embodiment 1760, wherein the oligomeric compound or antisense agent of any of embodiments 1246-1749 is not cytotoxic in vitro.

Embodiment 1763. The oligomeric compound or antisense agent of any of embodiments 1760-1762, wherein the oligomeric compound or antisense agent of any of embodiments 1246-1749 is not cytotoxic in a standard in vitro cytotoxicity assay.

Embodiment 1764. The oligomeric compound or antisense agent of any of embodiments 1246-1749, wherein the antisense agent is not an siRNA agent and the parent antisense agent is hepatotoxic to the mouse.

Embodiment 1765. The oligomeric compound or antisense agent of embodiment 1764, wherein the mouse is a BALB/c mouse, wherein 50 mg/kg of the parent antisense agent is administered to the mouse, and wherein the plasma ALT level in the mouse is measured 72 hours following the administration of the parent antisense agent.

Embodiment 1766. The oligomeric compound or antisense agent of any of embodiments 1764-1765, wherein administration of 50 mg/kg of the oligomeric compound or antisense agent of any of embodiments 1246-1749 to a mouse is not hepatotoxic to the mouse.

Embodiment 1767. The oligomeric compound or antisense agent of any of embodiments 1246-1749, wherein the therapeutic index in a mouse of the antisense agent of any of embodiments 1246-1749 is increased relative to the therapeutic index of the parent antisense agent.

Embodiment 1768. The oligomeric compound or antisense agent of embodiment 1767, wherein the therapeutic index in a mouse of the antisense agent of embodiment 516 is at least two-fold greater than the therapeutic index of the parent antisense agent.

Embodiment 1769. The oligomeric compound or antisense agent of any of embodiments 1760-1768, wherein the parent oligomeric compound or antisense agent is identical to the antisense agent of any of embodiments 1246-1749, except that each internucleoside linkage of Formula XVII is replaced with a phosphorothioate internucleoside linkage in the parent antisense agent.

Embodiment 1770. The oligomeric compound or of any of embodiments 1760-1769, wherein the oligomeric compound or antisense agent is an RNAse H agent.

Embodiment 1771. The oligomeric compound or antisense agent of any of embodiments 1760-1769, wherein the oligomeric compound or antisense agent is a gapmer.

Embodiment 1772. The oligomeric compound or antisense agent of any of embodiments 1760-1769, wherein the oligomeric compound or antisense agent modulates splicing.

Embodiment 1773. The oligomeric compound or antisense agent of any of embodiments 1760-1769, wherein the oligomeric compound or antisense agent increases protein expression.

Embodiment 1774. The oligomeric compound or antisense agent of any of embodiments 1246-1749, wherein the oligomeric compound or antisense agent is an RNAi agent, and the parent RNAi agent is cytotoxic in vitro.

Embodiment 1775. The oligomeric compound or antisense agent of embodiment 1774, wherein the RNAi agent of any of embodiments 1246-1749 is not cytotoxic in vitro.

Embodiment 1776. The oligomeric compound or antisense agent of any of embodiments 1774-1775, wherein the oligomeric compound or antisense agent is an RNAi agent and the RNAi agent is not cytotoxic in a standard in vitro cytotoxicity assay.

Embodiment 1777. The oligomeric compound or antisense agent of any of embodiments 1246-1749, wherein the oligomeric compound or antisense agent is an RNAi agent and is hepatotoxic to the mouse.

Embodiment 1778. The RNAi agent of embodiment 1777, wherein the mouse is a BALB/c mouse, wherein 50 mg/kg of the parent RNAi agent is administered to the mouse, and wherein the plasma ALT level in the mouse is measured 72 hours following the administration of the parent RNAi agent.

Embodiment 1779. The RNAi agent of any of embodiments 1777-1778, wherein administration of 50 mg/kg of the RNAi agent to a mouse is not hepatotoxic to the mouse.

Embodiment 1780. The oligomeric compound or antisense agent of any of embodiments 1246-1749, which is an RNAi agent, wherein the therapeutic index in a mouse of the RNAi agent is increased relative to the therapeutic index of the parent RNAi agent.

Embodiment 1781. The RNAi agent of embodiment 1780, wherein the therapeutic index in a mouse of the RNAi agent of embodiment 535 is at least two-fold greater than the therapeutic index of the parent RNAi agent.

Embodiment 1782. The RNAi agent of any of embodiments 1771-1781, wherein the parent RNAi agent is identical to the oligomeric compound or antisense agent any of embodiments 1246-1749, except that each internucleoside linkage of Formula XVII is replaced with a phosphodiester internucleoside linkage in the parent RNAi agent.

Embodiment 1783. A method of designing an oligomeric compound or antisense agent comprising starting with a parent oligomeric compound or antisense agent or parent RNAi agent and changing the design of that compound in order to arrive at an oligomeric compound or antisense agent of any one of embodiments 1246-1749.

Embodiment 1784. A method of designing an oligomeric compound or an antisense agent comprising identifying an oligomeric compound or antisense agent or parent RNAi agent and changing the design of that parent oligomeric compound or antisense agent or parent RNAi agent to arrive at a second antisense agent, wherein the second oligomeric compound antisense agent is an oligomeric compound or antisense agent of any one of embodiments 1246-1749.

Embodiment 1785. A method of improving hepatotoxicity of an oligomeric compound or antisense agent comprising the steps of (i) identifying a parent oligomeric compound, parent antisense agent or parent RNAi agent that has plasma ALT levels above 300 units per liter in a mouse, and (ii) providing an oligomeric compound or antisense agent according to any one of embodiments 1246-1749.

Embodiment 1786. The method of embodiment 1785, wherein the method designs an oligomeric compound or antisense agent with improved therapeutic index relative to the parent oligomeric compound, parent antisense agent, or parent RNAi agent.

Embodiment 1787. The method of embodiment 1785, wherein the method designs an oligomeric compound or antisense agent with lower hepatotoxicity relative to the parent oligomeric compound, parent antisense agent or parent RNAi agent.

Embodiment 1788. The method of embodiment 1785, wherein the second oligomeric compound or antisense agent has an improved therapeutic index relative to the parent oligomeric compound, parent antisense agent or parent RNAi agent.

Embodiment 1789. The method of embodiment 1785, wherein the second oligomeric compound or antisense agent has reduced hepatotoxicity in a mouse relative to the parent oligomeric compound, parent antisense agent or parent RNAi agent.

Embodiment 1790. The method of embodiment 1785, wherein the oligomeric compound or antisense agent according to any one of embodiments 1246-1749 has improved therapeutic index relative to the parent oligomeric compound, parent antisense agent or parent RNAi agent.

Embodiment 1791. The method of embodiment 1785, wherein the oligomeric compound or antisense agent according to any one of embodiments 1246-1749 has reduced hepatotoxicity relative to the parent oligomeric compound, antisense agent or parent RNAi agent.

Embodiment 1792. A method comprising administering an oligomeric compound or antisense agent of any of embodiments 1246-1749 to a mouse and separately administering the parent oligomeric comopund, parent antisense agent or parent RNAi agent of the antisense agent of any of embodiments 1246-1749 to a second mouse, wherein the therapeutic index of the antisense agent of any of embodiments 1246-1749 is improved relative to the therapeutic index of the parent antisense agent or parent RNAi agent.

Certain Compounds

In certain embodiments, compounds described herein are oligomeric compounds (including oligomeric compounds that are antisense agents or portions thereof) comprising or consisting of oligonucleotides consisting of linked nucleosides and having at least one modified internucleoside linking group having Formula VIII or Formula XVII. Oligonucleotides may be unmodified oligonucleotides or may be modified oligonucleotides. Modified oligonucleotides comprise at least one modification relative to an unmodified oligonucleotide (i.e., comprise at least one modified nucleoside (comprising a modified sugar moiety, a stereo-non-standard nucleoside, and/or a modified nucleobase) and/or at least one modified internucleoside linkage). In certain embodiments, the modified internucleoside linkage is a modified internucleoside linking group having Formula VIII or Formula XVII. In certain embodiments, compounds described herein are oligomeric compounds (including oligomeric compounds that are antisense agents or portions thereof) having at least one modified internucleoside linking group having Formula XVII.

I. Modifications

A. Modified Nucleosides

Modified nucleosides comprise a stereo-non-standard nucleoside, or a modified sugar moiety, or a modified nucleobase, or any combination thereof.

1. Certain Modified Sugar Moieties

In certain embodiments, modified sugar moieties are stereo-non-standard sugar moieties. In certain embodiments, sugar moieties are substituted furanosyl stereo-standard sugar moieties. In certain embodiments, modified sugar moieties are bicyclic or tricyclic furanosyl sugar moieties. In certain embodiments, modified sugar moieties are sugar surrogates. Such sugar surrogates may comprise one or more substitutions corresponding to those of other types of modified sugar moieties.

a. Stereo-Non-Standard Sugar Moieties

In certain embodiments, modified sugar moieties are stereo-non-standard sugar moieties shown in Formula I, Formula II, Formula III, Formula IV, Formula V, Formula VI, and Formula VII:

I

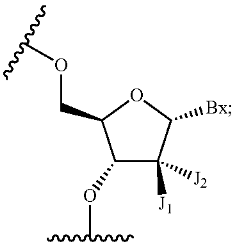

-continued

II

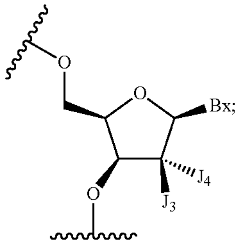

III

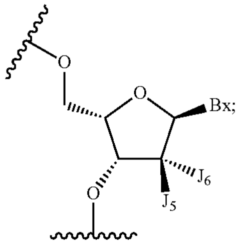

IV

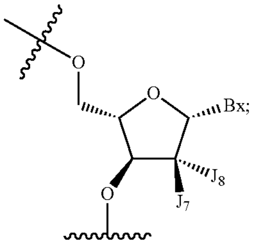

V

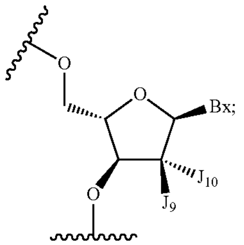

VI

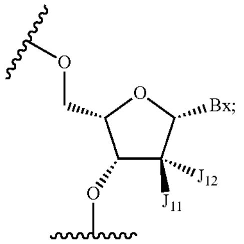

VII

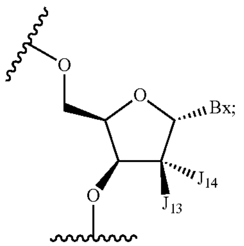

wherein one of $J_1$ and $J_2$ is H and the other of $J_1$ and $J_2$ is selected from H, OH, F, $OCH_3$, $OCH_2CH_2OCH_3$, O—$C_1$-$C_6$ alkoxy, and $SCH_3$;

one of $J_3$ and $J_4$ is H and the other of $J_3$ and $J_4$ is selected from H, OH, F, $OCH_3$, $OCH_2CH_2OCH_3$, O—$C_1$-$C_6$ alkoxy, and SC-3; and wherein one of $J_5$ and $J_6$ is H and the other of $J_5$ and $J_6$ is selected from H, OH, F, $OCH_3$, $OCH_2CH_2OCH_3$, O—$C_1$-$C_6$ alkoxy, and $SCH_3$; and wherein one of $J_7$ and $J_8$ is H and the other of $J_7$ and $J_8$ is selected from H, OH, F, $OCH_3$, $OCH_2CH_2OCH_3$, O—$C_1$-$C_6$ alkoxy, and $SCH_3$; and wherein one of $J_9$ and $J_{10}$ is H and the other of $J_9$ and $J_{10}$ is selected from H, OH, F, $OCH_3$, $OCH_2CH_2OCH_3$, O—$C_1$-$C_6$ alkoxy, and $SCH_3$; and wherein one of $J_1$ and $J_{12}$ is H and the other of $J_{11}$ and $J_{12}$ is selected from H, OH, F, $OCH_3$, $OCH_2CH_2OCH_3$, O—$C_1$-$C_6$ alkoxy, and $SCH_3$; and wherein one of $J_{13}$ and $J_{14}$ is H and the other of $J_{13}$ and $J_{14}$ is selected from H, OH, F, $OCH_3$, $OCH_2CH_2OCH_3$, O—$C_1$-$C_6$ alkoxy, and $SCH_3$; and Bx is a is a heterocyclic base moiety.

Certain stereo-non-standard sugar moieties have been previously described in, e.g., Seth et al., WO2020/072991 and Seth et al., WO2019/157531, both of which are incorporated by reference herein in their entirety.

b. Substituted Stereo-Standard Sugar Moieties

In certain embodiments, modified sugar moieties are substituted stereo-standard furanosyl sugar moieties comprising one or more acyclic substituent, including but not limited to substituents at the 2', 3', 4', and/or 5' positions. In certain embodiments, the furanosyl sugar moiety is a ribosyl sugar moiety. In certain embodiments one or more acyclic substituent of substituted stereo-standard sugar moieties is branched. Examples of 2'-substituent groups suitable for substituted stereo-standard sugar moieties include but are not limited to: 2'-F, 2'-$OCH_3$ ("2'-OMe" or "2'-O-methyl"), and 2'-$O(CH_2)_2OCH_3$ ("2'-MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 3'-substituent groups include 3'-methyl (see Frier, et al., The ups and downs of nucleic acid duplex stability: structure-stability studies on chemically-modified DNA:RNA duplexes. Nucleic Acids Res., 25, 4429-4443, 1997.) Examples of 4'-substituent groups suitable for substituted stereo-standard sugar moieties include but are not limited to alkoxy (e.g., methoxy), alkyl, and those described in Manoharan et al., WO 2015/106128. Examples of 5'-substituent groups suitable for substituted stereo-standard sugar moieties include but are not limited to: 5'-methyl (R or S), 5'-allyl, 5'-ethyl, 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836. 2',4'-difluoro modified sugar moieties have been described in Martinez-Montero, et al., Rigid 2',4'-difluororibonucleosides: synthesis, conformational analysis, and incorporation into nascent RNA by HCV polymerase. *J. Org. Chem.,* 2014, 79:5627-5635. Modified sugar moieties comprising a 2'-modification (OMe or F) and a 4'-modification (OMe or F) have also been described in Malek-Adamian, et al., *J. Org. Chem,* 2018, 83: 9839-9849.

In certain embodiments, a 2'-substituted stereo-standard nucleoside comprises a sugar moiety comprising a non-bridging 2'-substituent group selected from: F, $NH_2$, $N_3$, $OCF_3$, $OCH_3$, $SCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)—N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted stereo-standard nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)—N(H)CH_3$ ("NMA").

In certain embodiments, a 2'-substituted stereo-standard nucleoside comprises a sugar moiety comprising a 2'-substituent group selected from: F, $OCH_3$, and $OCH_2CH_2OCH_3$.

In certain embodiments, the 4' 0 of 2'-deoxyribose can be substituted with a S to generate 4'-thio DNA (see Takahashi, et al., *Nucleic Acids Research* 2009, 37: 1353-1362). This modification can be combined with other modifications detailed herein. In certain such embodiments, the sugar moiety is further modified at the 2' position. In certain embodiments the sugar moiety comprises a 2'-fluoro. A thymidine with this sugar moiety has been described in Watts, et al., *J Org. Chem.* 2006, 71(3): 921-925 (4'-S-fluoro5-methylarauridine or FAMU).

c. Bicyclic Nucleosides

Certain nucleosides comprise modified sugar moieties that comprise a bridging sugar substituent that forms a second ring resulting in a bicyclic sugar moiety. In certain such embodiments, the bicyclic sugar moiety comprises a 4' to 2' bridge between the 4' and the 2' furanose ring atoms. In certain such embodiments, the furanose ring is a ribose ring. Examples of sugar moieties comprising such 4' to 2' bridging sugar substituents include but are not limited to bicyclic sugars comprising: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., *J. Org. Chem.,* 2009, 74, 118-134), 4'-$CH_2$—$C(=CH_2)$-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672), 4'-C(=O)—$N(CH_3)_2$-2', 4'-C(=O)—$N(R)_2$-2', 4'-C(=S)—$N(R)_2$-2' and analogs thereof (see, e.g., Obika et al., WO2011052436A1, Yusuke, WO2017018360A1).

Additional bicyclic sugar moieties are known in the art, see, for example: Freier et al., *Nucleic Acids Research,* 1997, 25(22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2017, 129, 8362-8379; Elayadi et al.; Christiansen, et al., *J. Am. Chem. Soc.* 1998, 120, 5458-5463; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

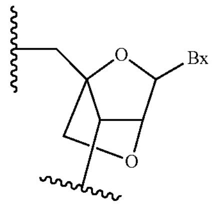

LNA (β-D-configuration) bridge = 4'-$CH_2$—O-2'

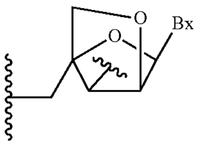

α-L-LNA (α-L-configuration) bridge = 4'-$CH_2$—O-2'

α-L-methyleneoxy (4'-$CH_2$—O-2') or α-L-LNA bicyclic nucleosides have been incorporated into antisense oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

The term "substituted" following a position of the furanosyl ring, such as "2'-substituted" or "2'-4'-substituted", indicates that is the only position(s) having a substituent other than those found in unmodified sugar moieties in oligonucleotides.

d. Sugar Surrogates

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), altritol nucleic acid ("ANA"), mannitol nucleic acid ("MNA") (see, e.g., Leumann, CJ. *Bioorg. & Med. Chem.* 2002, 10, 841-854), fluoro HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran).

In certain embodiments, sugar surrogates comprise rings having no heteroatoms. For example, nucleosides comprising bicyclo [3.1.0]-hexane have been described (see, e.g., Marquez, et al., *J. Med. Chem.* 1996, 39:3739-3749).

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate comprising the following structure:

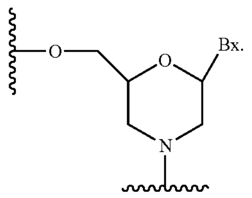

In certain embodiments, morpholinos may be modified, for example by adding or altering various substituent groups from the above morpholino structure. Such sugar surrogates are referred to herein as "modified morpholinos." In certain embodiments, morpholino residues replace a full nucleotide, including the internucleoside linkage, and have the structures shown below, wherein Bx is a heterocyclic base moiety.

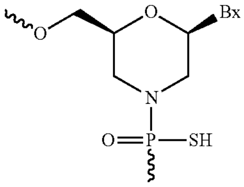

morpholino PS

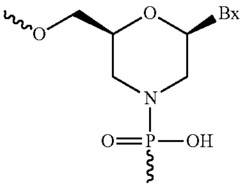

morpholino PO

In curtain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), glycol nucleic acid ("GNA", see Schlegel, et al., *J. Am. Chem. Soc.* 2017, 139:8537-8546) and nucleosides and oligonucleotides described in Manoharan et al., WO2011/133876. In certain embodiments, acyclic sugar surrogates are selected from:

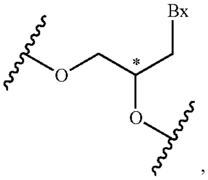

,

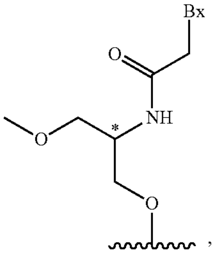

,

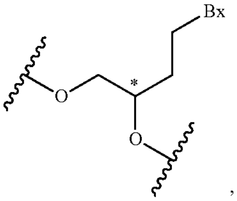

,

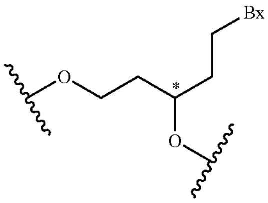

, or

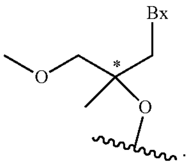

.

Many other bicyclic and tricyclic sugar and sugar surrogate ring systems are known in the art that can be used in modified nucleosides. Certain such ring systems are described in Hanessian, et al., *J Org. Chem.,* 2013, 78: 9051-9063 and include bcDNA and tcDNA. Modifications to bcDNA and tcDNA, such as 6'-fluoro, have also been described (Dogovic and Leumann, *J. Org. Chem.,* 2014, 79: 1271-1279).

e. Conjugated Nucleosides and Terminal Groups

In certain embodiments, modified sugar moieties comprise a conjugate group and/or a terminal group. Modified sugar moieties are linked to conjugate groups through a conjugate linker. In certain embodiments, modified furanosyl sugar moieties comprise conjugate groups attached at the 2', 3', or 5' positions. In certain embodiments, the 3'-most sugar moiety of the nucleoside is modified with a conjugate group or a terminal group. In certain embodiments, the 5'-most sugar moiety of the nucleoside is modified with a conjugate group or a terminal group. In certain embodiments, a sugar moiety near the 3' end of the nucleoside is modified with a conjugate group. In certain embodiments, a sugar moiety near the 5' end of the nucleoside is modified with a conjugate group.

Examples of terminal groups include but are not limited to conjugate groups, capping groups, phosphate moieties, protecting groups, modified or unmodified nucleosides, and two or more nucleosides that are independently modified or unmodified.

In certain embodiments, terminal groups at the 5'-terminus comprise a stabilized phosphate group. In certain such embodiments, the phosphorus atom of the stabilized phosphate group is attached to the 5'-terminal nucleoside through a phosphorus-carbon bond. In certain embodiments, the carbon of that phosphorus-carbon bond is in turn bound to the 5'-position of the nucleoside.

In certain embodiments, the oligonucleotide comprises a 5'-stabilized phosphate group having the following formula:

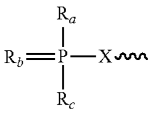

wherein:

$R_a$ and $R_e$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C; and wherein X is attached to the 5'-terminal nucleoside. In certain embodiments, X is bound to an atom at the 5'-position of the 5'-terminal nucleoside. In certain such embodiments, the 5'-atom is a carbon and the bond between X and the 5'-carbon of the 5'-terminal nucleoside is a carbon-carbon single bond. In certain embodiments, it is a carbon-carbon double bond. In certain embodiments, it is a carbon-carbon triple bond. In certain embodiments, the 5'-carbon is substituted. In certain embodiments, X is substituted. In certain embodiments, X is unsubstituted.

In certain embodiments, the oligonucleotide comprises a 5'-stabilized phosphate group having the following formula:

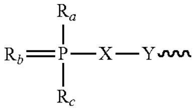

wherein:

$R_a$ and $R_e$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C;

Y is selected from C, S, and N. In certain embodiments, Y is substituted or unsubstituted C. The bond between X and Y may be a single-, double-, or triple-bond.

Certain 5'-stabilized phosphate groups have been previously described; see, e.g., Prakash et al., WO2011/139699 and Prakash et al., WO2011/139702, hereby incorporated by reference herein in their entirety.

In certain embodiments, the stabilized phosphate group is 5'-vinyl phosphonate or 5'-cyclopropyl phosphonate.

In certain embodiments, a terminal group at the 5'-terminus is a 5'-mesyl phosphoramidate, having formula XXI:

XXI

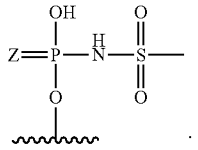

wherein Z is O or S.

In certain embodiments, a terminal group at the 5'-terminus is a 5'-mesyl phosphoramidate, having formula XXII:

XXII

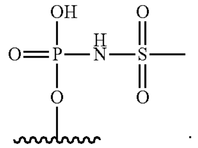

2. Modified Nucleobases

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($—C≡C—CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie, International Edition,* 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443. In certain embodiments, modified nucleosides comprise double-headed nucleosides having two nucleobases. Such compounds are described in detail in Sorinas et al., *J. Org. Chem,* 2014 79: 8020-8030.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

In certain embodiments, compounds comprise or consist of a modified oligonucleotide complementary to a target nucleic acid comprising one or more modified nucleobases. In certain embodiments, the modified nucleobase is 5-methylcytosine. In certain embodiments, each cytosine is a 5-methylcytosine.

B. Modified Internucleoside Linkages a. Internucleoside Linkages of Formula VIII and XVII In certain embodiments, antisense agents, oligomeric compounds, and modified oligonucleotides described herein having one or more modified internucleoside linkages having Formula VIII or Formula XVII are selected over compounds lacking such internucleoside linkages having Formula VIII or Formula XVII because of one or more desirable properties. In certain embodiments, antisense agents, oligomeric compounds, and modified oligonucleotides described herein having one or more modified internucleoside linkages having Formula VIII or Formula XVII have enhanced cellular uptake. In certain embodiments, antisense agents, oligomeric compounds, and modified oligonucleotides described herein having one or more modified internucleoside linkages having Formula VIII or Formula XVII have enhanced affinity for target nucleic acids. In certain embodiments, antisense agents, oligomeric compounds, and modified oligonucleotides described herein having one or more modified internucleoside linkages having Formula VIII or Formula XVII have increased stability in the presence of nucleases. In certain embodiments, antisense agents, oligomeric compounds, and modified oligonucleotides described herein having one or more modified internucleoside linkages having Formula VIII or Formula XVII have enhanced cellular uptake, enhanced affinity for target nucleic acids, and increased stability in the presence of nucleases. In certain embodiments, antisense agents, oligomeric compounds, and modified oligonucleotides described herein having one or more modified internucleoside linkages having Formula VIII or Formula XVII have enhanced bioavailability. In certain embodiments, antisense agents, oligomeric compounds, and modified oligonucleotides described herein having one or more modified internucleoside linkages having Formula VIII or Formula XVII have enhanced RNase H activity. In certain embodiments, antisense agents, oligomeric compounds, and modified oligonucleotides described herein having one or more modified internucleoside linkages having Formula VIII or Formula XVII have enhanced RNAi activity. In certain embodiments, antisense agents, oligomeric compounds, and modified oligonucleotides described herein having one or more modified internucleoside linkages having Formula VIII or Formula XVII have enhanced CRISPR activity. In certain embodiments, antisense agents, oligomeric compounds, and modified oligonucleotides described herein having one or more modified internucleoside linkages having Formula VIII or Formula XVII have reduced interactions with certain proteins. In certain embodiments, antisense agents, oligomeric compounds, and modified oligonucleotides described herein having one or more modified internucleoside linkages having Formula VIII or Formula XVII have increased interactions with certain proteins.

In certain embodiments, oligomeric compounds (including oligomeric compounds that are antisense agents or portions thereof) comprise or consist of a modified oligonucleotide complementary to a target nucleic acid comprising one or more modified internucleoside linkages having Formula VIII:

VIII

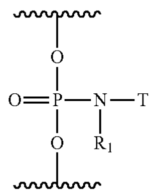

wherein independently for each internucleoside linking group of the oligomeric compound having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

In certain embodiments, oligomeric compounds (including oligomeric compounds that are antisense agents or portions thereof) comprise or consist of a modified oligonucleotide complementary to a target nucleic acid comprising one or more modified internucleoside linkages having Formula VIII:

VIII

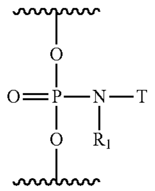

wherein independently for each internucleoside linking group of the oligomeric compound having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, a $C_1$-$C_6$ alkyl, and a substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl;

provided that if $R_1$ is H, then T is not:

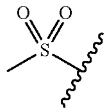

or

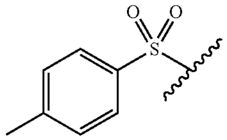

.

In certain embodiments, oligomeric compounds (including oligomeric compounds that are antisense agents or portions thereof) comprise or consist of a modified oligonucleotide complementary to a target nucleic acid comprising one or more modified internucleoside linkages having Formula XVII:

XVII

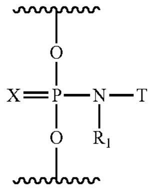

wherein independently for each internucleoside linking group of the oligomeric compound having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

In certain embodiments, compounds comprise or consist of a modified oligonucleotide complementary to a target nucleic acid comprising one or more modified internucleoside linkages having Formula IX:

IX

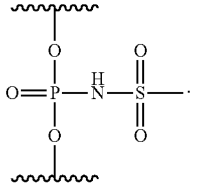

In certain embodiments, compounds comprise or consist of a modified oligonucleotide complementary to a target nucleic acid comprising one or more modified internucleoside linkages having Formula XX:

XX

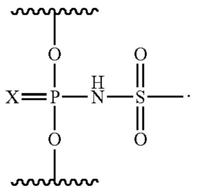

wherein independently for each internucleoside linking group of the oligomeric compound having Formula XX, X is selected from O or S.

b. Other Internucleoside Linkages

In certain embodiments, antisense agents, oligomeric compounds, and modified oligonucleotides comprise or consist of a modified oligonucleotide complementary to a target nucleic acid comprising one or more modified internucleoside linkages. In certain embodiments, the modified internucleoside linkages are phosphorothioate linkages. In certain embodiments, each internucleoside linkage of an antisense compound is a phosphorothioate internucleoside linkage.

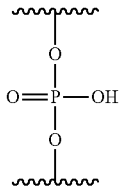

Phosphodiester internucleoside linking group

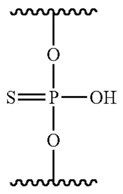

Phosphorothioate internucleoside linking group

In certain embodiments, nucleosides of modified oligonucleotides may be linked together using any internucleoside linkage. The two main classes of internucleoside linkages are defined by the presence or absence of a phosphorus atom. Representative phosphorus-containing internucleoside linkages include unmodified phosphodiester internucleoside linkages, modified phosphotriesters such as THP phosphotriester and isopropyl phosphotriester, phosphonates such as methylphosphonate, isopropyl phosphonate, isobutyl phosphonate, and phosphonoacetate, phosphoramidates, phosphorothioate, and phosphorodithioate ("HS—P═S"). Representative non-phosphorus containing internucleoside linkages include but are not limited to methylenemethylimino ($—CH_2—N(CH_3)—O—CH_2—$), thiodiester, thionocarbamate (—O—C(═O)(NH)—S—); siloxane ($—O—SiH_2—O—$); formacetal, thioacetamido (TANA), alt-thioformacetal, glycine amide, and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Neutral internucleoside linkages include, without limitation, phosphotriesters, phosphonates, MMI ($3'-CH_2—N(CH_3)—O-5'$), amide-3 ($3'-CH_2—C(═O)—N(H)-5'$), amide-4 ($3'-CH_2—N(H)—C(═O)-5'$), formacetal ($3'-O—CH_2—O-5'$), methoxypropyl, and thioformacetal ($3'-S—CH_2—O-5'$). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

c. Chiral Internucleoside Linkages

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. All phosphorothioate linkages described herein are stereorandom unless otherwise specified. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

($R_p$)

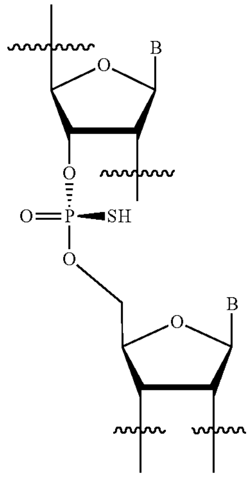

($S_p$)

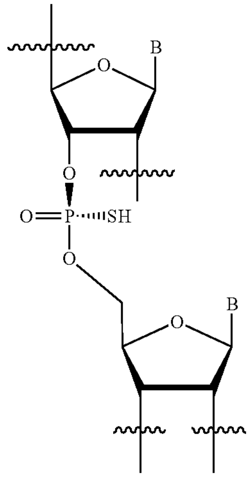

Unless otherwise indicated, chiral internucleoside linkages of modified oligonucleotides described herein can be stereorandom or in a particular stereochemical configuration.

In certain embodiments, an internucleoside linkage of Formula XVII may comprise a chiral center. An internucleoside linkage of Formula XVIII (XVII where X is S) comprises a chiral center. In certain embodiments, modified oligonucleotides comprise chiral linkages of Formula XVIII, illustrated below as XVIIIa and XVIIIb.

XVII

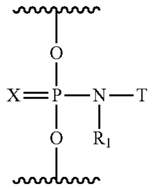

XVIII

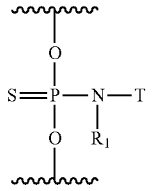

XVIIIa

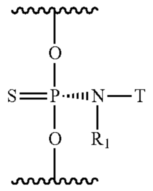

XVIIIb

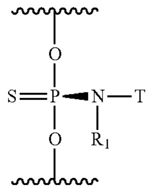

d. Alternatives to 5' to 3' Internucleoside Linkages

In certain embodiments, nucleic acids can be linked 2' to 5' rather than the standard 3' to 5' linkage. Such a linkage is illustrated below.

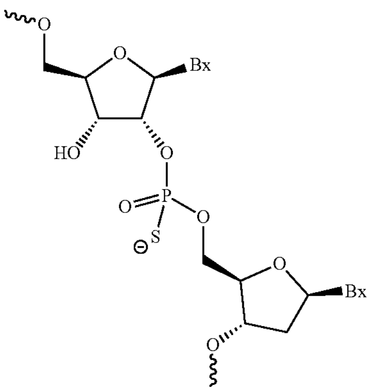

In certain embodiments, nucleosides can be linked by vicinal 2', 3'-phosphodiester bonds. In certain such embodiments, the nucleosides are threofuranosyl nucleosides (TNA; see Bala, et al., *J Org. Chem.* 2017, 82:5910-5916). A TNA linkage is shown below.

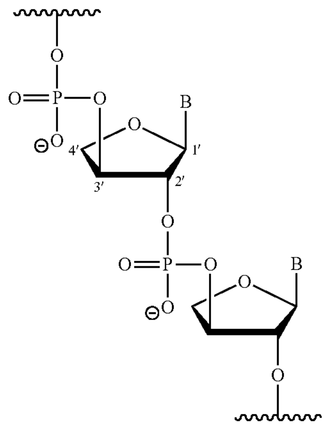

threose nucleic acid (TNA)

Additional modified linkages include α,β-D-CNA type linkages and related conformationally-constrained linkages, shown below. Synthesis of such molecules has been described previously (see Dupouy, et al, *Angew. Chem. Int. Ed. Engl.*, 2014, 45: 3623-3627; Borsting, et al. *Tetrahedron*, 2004, 60:10955-10966; Ostergaard, et al., *Angew. Chem. Biol.* 2014, 9: 1975-1979; Dupouy, et al., *Eur. J Org. Chem.*, 2008, 1285-1294; Martinez. et al., *PLoS One*, 2011, 6:e25510; Dupouy, et al., *Eur. J Org. Chem.*, 2007, 5256-5264; Boissoinet, et al., *New J. Chem.*, 2011, 35: 1528-1533.)

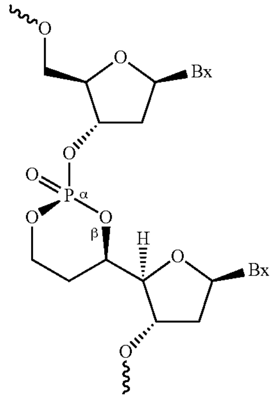

α,β-D-CNA ($R_{C5'}$, $R_P$)

-continued

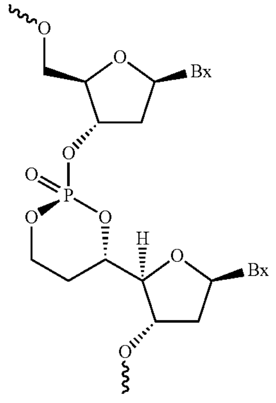

α,β-D-CNA ($R_{C5'}$, $R_P$)

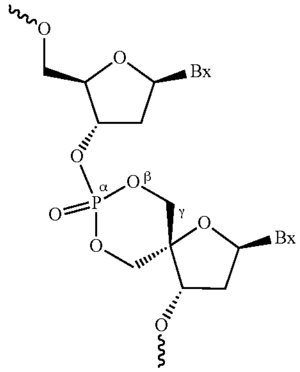

α,β-γ-D-CNA

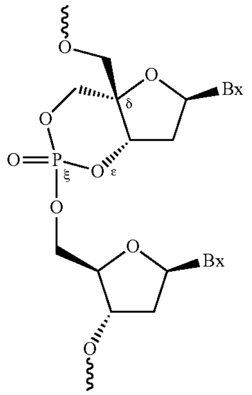

δ,ε,ξ-D-CNA

-continued

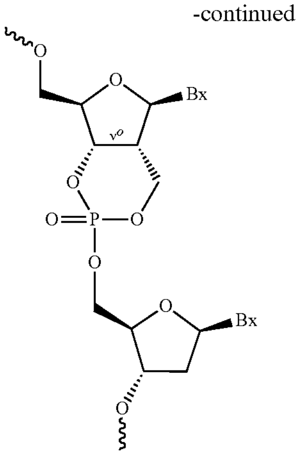

$\nu^{o}$,ε,ξ-D-CNA e. Linkages Having Conjugate Groups

In certain embodiments, an internucleoside linking group may comprise a conjugate group. In certain embodiments, an internucleoside linking group of Formula XVII comprises a conjugate group. In certain embodiments, the conjugate group of a modified oligonucleotide may be attached to the remainder of the modified oligonucleotide through a modified internucleoside having Formula XVII:

XVII

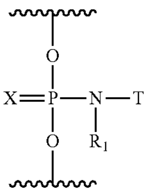

wherein T comprises a conjugate group. In certain embodiments, T is selected from $SO_2R_2$, $C(=O)R_3$, and $P(=O)R_4R_5$, wherein $R_2$, $R_3$, or $R_4$ is a conjugate group. In certain embodiments, the conjugate group comprises a cell-targeting moiety. In certain embodiments, the conjugate group comprises a carbohydrate or carbohydrate cluster. In certain embodiments, the conjugate group comprises GalNAc. In certain embodiments, the conjugate group comprises a lipid. In certain embodiments, the conjugate group comprises $C_{10}$-$C_{20}$ alkyl. In certain embodiments, the conjugate group comprises $C_{16}$ alkyl.

In certain embodiments, the internucleoside linking group comprising a conjugate group has Formula XIX:

XIX

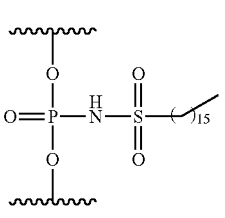

II. Certain Motifs

In certain embodiments, antisense agents, oligomeric compounds, and modified oligonucleotides described herein comprise or consist of oligonucleotides. Modified oligonucleotides can be described by their motif, e.g. a pattern of unmodified and/or modified sugar moieties, nucleobases, and/or internucleoside linkages. In certain embodiments, modified oligonucleotides comprise one or more stereo-non-standard nucleosides. In certain embodiments, modified oligonucleotides comprise one or more stereo-standard nucleosides. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

A. Certain Sugar Motifs

In certain embodiments, antisense agents, oligomeric compounds, and modified oligonucleotides described herein comprise or consist of oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include without limitation any of the sugar modifications discussed herein.

In certain embodiments, a modified oligonucleotide comprises or consists of a gapmer. The sugar motif of a gapmer defines the regions of the gapmer: 5'-region, central region (gap), and 3'-region. The central region is linked directly to the 5'-region and to the 3'-region with no nucleosides intervening. The central region is a deoxy region. The nucleoside at the first position (position 1) from the 5'-end of the central region and the nucleoside at the last position of the central region are adjacent to the 5'-region and 3'-region, respectively, and each comprise a sugar moiety independently selected from a 2'-deoxyfuranosyl sugar moiety or a sugar surrogate. In certain embodiments, the nucleoside at position 1 of the central region and the nucleoside at the last position of the central region are DNA nucleosides, selected from stereo-standard DNA nucleosides or stereo-non-standard DNA nucleosides having any of formulas I-VII, wherein each J is H. In certain embodiments, the nucleoside at the first and last positions of the central region adjacent to the 5' and 3' regions are stereo-standard DNA nucleosides. Unlike the nucleosides at the first and last positions of the central region, the nucleosides at the other positions within the central region may comprise a 2'-substituted furanosyl sugar moiety or a substituted stereo-non-standard sugar moiety or a bicyclic sugar moiety. In certain embodiments, each nucleoside within the central region supports RNase H cleavage. In certain embodiments, a plurality of nucleosides within the central region support RNase H cleavage.

Herein, the lengths (number of nucleosides) of the three regions of a gapmer may be provided using the notation [# of nucleosides in the 5'-region]-[# of nucleosides in the central region]-[# of nucleosides in the 3'-region]. Thus, a 3-10-3 gapmer consists of 3 linked nucleosides in each of the 3' and 5' regions and 10 linked nucleosides in the central region. Where such nomenclature is followed by a specific modification, that modification is the modification of each sugar moiety of each 5' and 3'-region and the central region nucleosides comprise stereo-standard DNA sugar moieties. Thus, a 5-10-5 MOE gapmer consists of 5 linked nucleosides each comprising 2'-MOE-stereo-standard sugar moieties in the 5'-region, 10 linked nucleosides each comprising a stereo-standard DNA sugar moiety in the central region, and 5 linked nucleosides each comprising 2'-MOE-stereo-standard sugar moieties in the 3'-region. A 5-10-5 MOE gapmer having a substituted stereo-non-standard nucleoside at position 2 of the gap has a gap of 10 nucleosides wherein the $2^{nd}$ nucleoside of the gap is a substituted stereo-non-standard nucleoside rather than the stereo-standard DNA nucleoside. Such oligonucleotide may also be described as a 5-1-1-8-5 MOE/substituted stereo-non-standard/MOE gapmer. A 3-10-3 cEt gapmer consists of 3 linked nucleosides each comprising a cEt in the 5'-region, 10 linked nucleosides each comprising a stereo-standard DNA sugar moiety in the central region, and 3 linked nucleosides each comprising a cEt in the 3'-region. A 3-10-3 cEt gapmer having a substituted stereo-non-standard nucleoside at position 2 of the gap has a gap of 10 nucleoside wherein the $2^{nd}$ nucleoside of the gap is a substituted stereo-non-standard nucleoside rather than the stereo-standard DNA nucleoside. Such oligonucleotide may also be described as a 3-1-1-8-3 cEt/substituted stereo-non-standard/cEt gapmer.

The sugar motif of a 3-10-3 cEt gapmer may also be denoted by the notation kkk-d(10)-kkk, wherein each "k" represents a cEt and each "d" represents a 2'-β-D-deoxyribosyl sugar moiety. This sugar motif is independent of the nucleobase sequence, the internucleoside linkage motif, and any nucleobase modifications. A 5-10-5 MOE gapmer may be denoted by the notation eeeee-d(10)-eeeee or e(5)-d(10)-e(5), wherein each "e" represents a 2'-MOE-β-D-ribofuranosyl sugar moiety, and each "d" represents a 2'-β-D-deoxyribosyl sugar moiety.

In certain embodiments, each nucleoside of a modified oligonucleotide, or portion thereof, comprises a 2'-substituted sugar moiety, a bicyclic sugar moiety, a sugar surrogate, or a 2'-deoxyribosyl sugar moiety. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, PNA, THP, and F-HNA.

In certain embodiments, modified oligonucleotides comprise at least 12, at least 13, at least 14, at least 15, at least 16, at least 17, at least 18, at least 19, or at least 20 nucleosides comprising a modified sugar moiety. In certain embodiments, the modified sugar moiety is selected independently from a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA.

In certain embodiments, each nucleoside of a modified oligonucleotide comprises a modified sugar moiety ("fully modified oligonucleotide"). In certain embodiments, each nucleoside of a fully modified oligonucleotide comprises a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA. In certain embodiments, each nucleoside of a fully modified oligonucleotide comprises the same modified sugar moiety ("uniformly modified sugar motif"). In certain embodiments, the uniformly modified sugar motif is 7 to 20 nucleosides in length. In certain embodiments, each nucleoside of the uniformly modified sugar motif comprises a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA. In certain embodiments, modified oligonucleotides having at least one fully modified sugar motif may also comprise at least 1, at least 2, at least 3, or at least 4 2'-deoxyribonucleosides.

B. Certain Nucleobase Motifs

In certain embodiments antisense agents, oligomeric compounds, and modified oligonucleotides described herein comprise or consist of oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, one nucleoside comprising a modified nucleobase is in the central region of a modified oligonucleotide. In certain such embodiments, the sugar moiety of said nucleoside is a 2'-β-D-deoxyribosyl moiety. In certain such embodiments, the modified nucleobase is selected from: 5-methyl cytosine, 2-thiopyrimidine, 2-thiothymine, 6-methyladenine, inosine, pseudouracil, or 5-propynepyrimidine.

C. Certain Internucleoside Linkage Motifs

In certain embodiments, antisense agents, oligomeric compounds, and modified oligonucleotides described herein comprise or consist of oligonucleotides. In certain embodiments, oligonucleotides comprise modified and/or unmodified internucleoside linkages arranged along the oligonucleotide or region thereof in a defined pattern or motif. In certain embodiments, the modified internucleoside linkages are internucleoside linking groups having Formula VIII. In certain embodiments, some or all of the internucleoside linkages in the 5'-region and 3'-region are modified internucleoside linkages having Formula VIII or Formula XVII. In certain embodiments, the terminal internucleoside linkages are modified internucleoside linkages having Formula VIII or Formula XVII. In certain embodiments, the internucleoside linkage motif comprises at least one phosphodiester internucleoside linkage in at least one of the 5'-region and the 3'-region, and at least one modified internucleoside linkage having Formula VIII or Formula XVII. In certain embodiments, the internucleoside linkage motif comprises at least one phosphorothioate internucleoside linkage in at least one of the 5'-region and the 3'-region, and at least one modified internucleoside linkage having Formula VIII or Formula XVII.

In certain embodiments, modified oligonucleotides comprise at least one region having Structure A:

Structure A

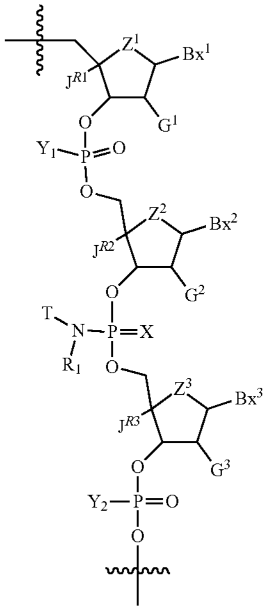

wherein:

each Bx is a heterocyclic base moiety;

X is selected from O or S;

each of $Y_1$ and $Y_2$ is independently selected from OH or SH;

each of $Z^1$, $Z^2$, and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R{}_1$ and $G^1$ form a $J^R{}_1$ to $G^1$ bridge, or $J^R{}_1$ is H and $G^1$ is selected from H, OH, halogen or $O—[C(R_6)(R_7)]—[(C{=}O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C{=}O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure B:

Structure B

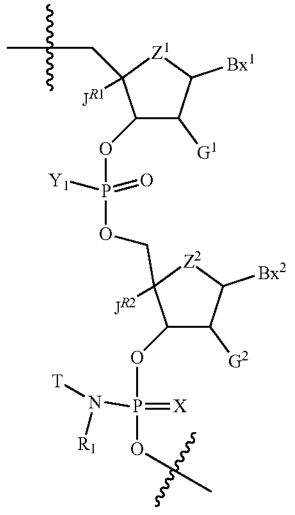

wherein:

each Bx is a heterocyclic base moiety;

X is selected from O or S;

each of $Y_1$ and $Y_2$ is independently selected from OH or SH;

each of $Z^1$ and $Z_2$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R{}_1$ and $G^1$ form a $J^R{}_1$ to $G^1$ bridge, or $J^R{}_1$ is H and $G^1$ is selected from H, OH, halogen or O—[C($R_6$)($R_7$)]—[(C=O)$_m$—$X^G$]$_j$—$R_8$;

either $J^{R2}$ and $G^2$ form a $J^{R2}$ and $G^2$ bridge, or $J^{R2}$ is H and $G^2$ is selected from H, OH, halogen or O—[C($R_6$)($R_7$)]$_n$—[(C=O)$_m$—$X^G$]$_j$—$R_8$;

wherein each $J^R$ to G bridge has a formula independently selected from —CH($CH_3$)—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or N($E_1$);

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure C:

Structure C

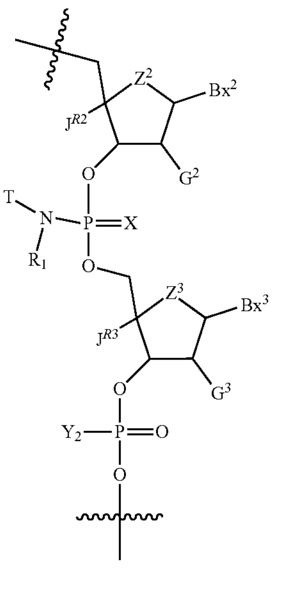

wherein:

each Bx is a heterocyclic base moiety;

X is selected from O or S;

each of $Y_1$ and $Y_2$ is independently selected from OH or SH;

each of $Z^2$ and $Z^3$ are independently selected from —$(CH_2)_p$—$X^Z$—$(CH_2)_q$—, wherein p is 0 or 1, q is 0 or 1, and $X^Z$ is O, S, or N($E_1$);

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J^{R2}$ and $G^2$ bridge, or $J^{R2}$ is H and $G^2$ is selected from H, OH, halogen or O—[C($R_6$)($R_7$)]$_n$—[(C=O)$_m$—$X^G$]$_j$—$R_8$;

either $J^{R3}$ and $G^3$ form a $J^{R3}$ and $G^3$ bridge, or $J^{R3}$ is H and $G^3$ is selected from H, OH, halogen or O—[C($R_6$)($R_7$)]$_n$—[(C=O)$_m$—$X^G$]$_j$—$R_8$;

wherein each $J^R$ to G bridge has a formula independently selected from —CH($CH_3$)—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or N($E_1$);

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure D:

Structure D

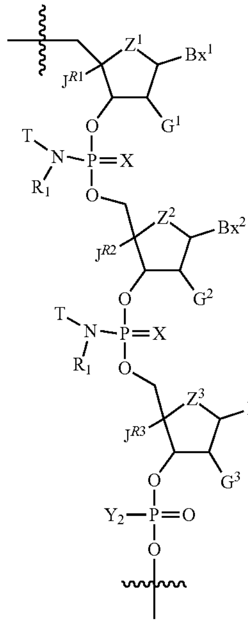

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R{}_1$ and $G^1$ form a $J^R{}_1$ to $G^1$ bridge, or $J^R{}_1$ is H and $G^1$ is selected from H, OH, halogen or $O—[C(R_6)(R_7)]—[(C=O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C=O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C=O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure E:

Structure E

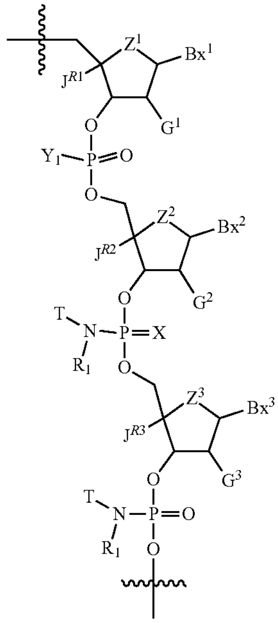

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^R_1$ is H and $G^1$ is selected from H, OH, halogen or O—$[C(R_6)(R_7)]$—$[(C{=}O)_m$—$X^G]_j$—$R_8$;

either $J^{R2}$ and $G^2$ form a $J^{R2}$ and $G^2$ bridge, or $J^{R2}$ is H and $G^2$ is selected from H, OH, halogen or O—$[C(R_6)(R_7)]_n$—$[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]_n[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C({=}Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure F:

Structure F

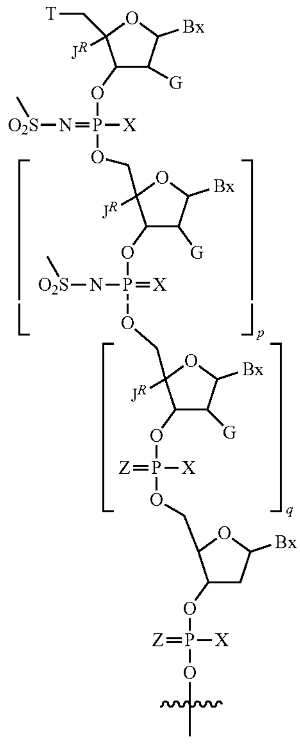

wherein:

p is from 0 to 6;

q is from 0 to 6;

T is OH, a stabilized phosphate group, or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C({=}Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 3'-terminus having structure G:

Structure G

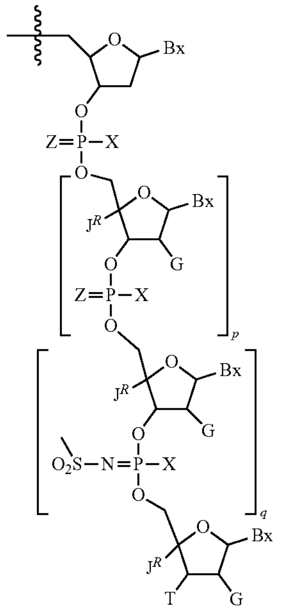

wherein:

p is from 0 to 6;

q is from 1 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure H:

Structure H

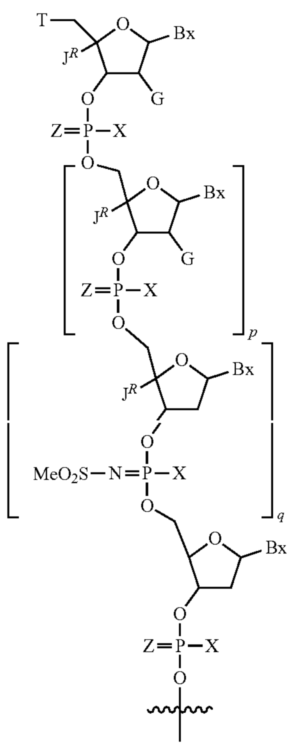

wherein:

p is from 0 to 5;

q is from 1 to 4;

T is OH, a stabilized phosphate group, or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure I:

Structure I

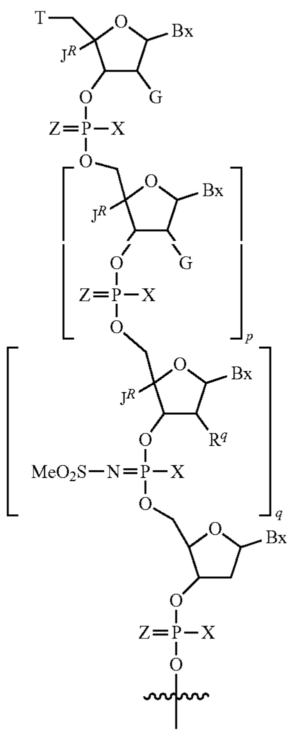

p is from 0 to 5;

q is from 1 to 4;

T is OH, a stabilized phosphate group, or a conjugate group;

each Bx is an independently selected heterocyclic base moiety;

each X is independently selected from OH or SH;

each Z is independently selected from O, S, or $NSO_2Me$;

each $R^q$ is H or exactly one $R^q$ is OMe and the other $R^q$ are H;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$ $[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 3'-terminus having structure J:

Structure J

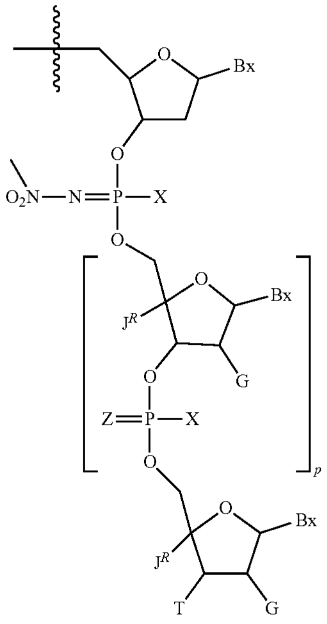

wherein:

p is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$, is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure K:

Structure K

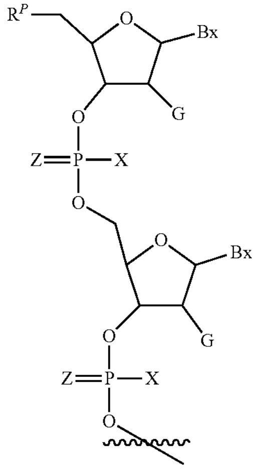

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$, is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 3'-terminus having structure L:

Structure L

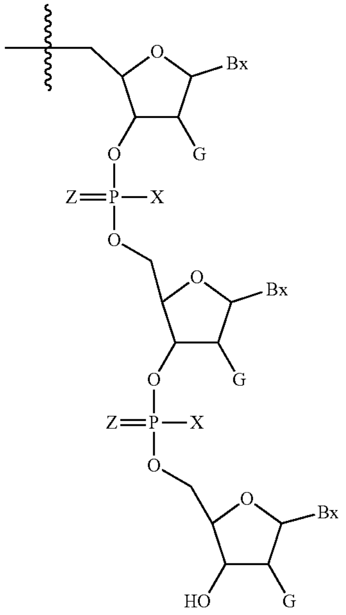

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having structure M:

Structure M

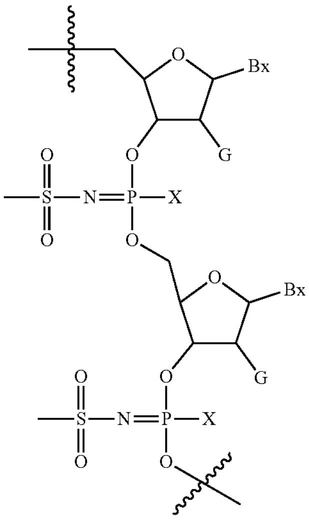

wherein:

each Bx is an independently selected heterocyclic base moiety;

each X is independently selected from OH or SH;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure N:

Structure N

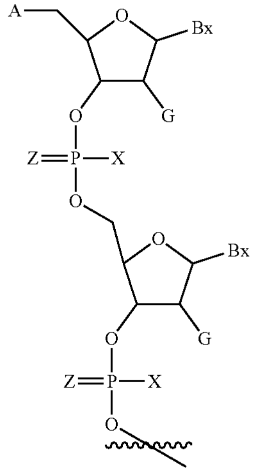

wherein:

A is selected from

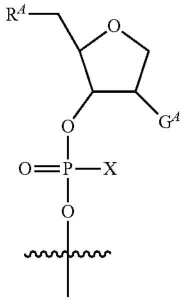

or

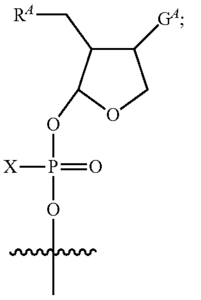

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides have a 3'-terminus having structure 0:

Structure O

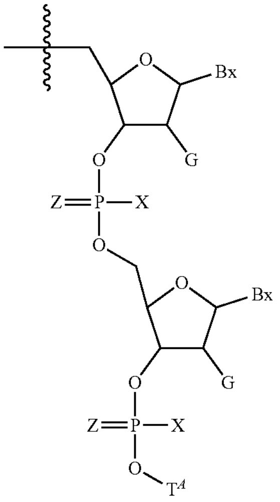

wherein:

$T^A$ is selected from

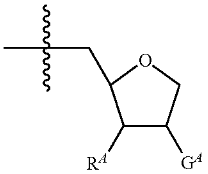

or

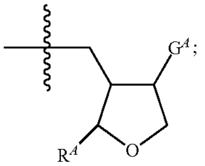

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having the formula: $(N_{g1})_L1(N_{g2})_{L2}(N_{g3})_{L3}$, wherein each $N_g$ is a nucleoside comprising furanosyl sugar moiety or a sugar surrogate and each L is an internucleoside linking group; wherein each of $L_1$, $L_2$, and $L_3$ is a phosphodiester internucleoside linking group, a phosphorothioate internucleoside linking group, or an internucleoside linking group of Formula XVII:

XVII

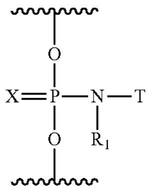

wherein each of $L_1$, and $L_2$ is a phosphodiester internucleoside linking group, a phosphorothioate internucleoside linking group, or an internucleoside linking group of Formula XVII:

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of L1, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

In certain embodiments, the internucleoside linkages within the central region of a modified oligonucleotide are all modified with internucleoside linking groups having Formula VIII or Formula XVII. In certain embodiments, one internucleoside linkage within the central region of a modified oligonucleotide is an internucleoside linking group having Formula VIII or Formula XVII. In certain embodiments, two internucleoside linkages within the central region of a modified oligonucleotide are internucleoside linking groups having Formula VIII or Formula XVII. In certain embodiments, three internucleoside linkages within the central region of a modified oligonucleotide are internucleoside linking groups having Formula VIII or Formula XVII. In certain embodiments, four internucleoside linkages within the central region of a modified oligonucleotide are internucleoside linking groups having Formula VIII or Formula XVII. In certain embodiments, five internucleoside linkages within the central region of a modified oligonucleotide are internucleoside linking groups having Formula VIII or Formula XVII. In certain embodiments, six internucleoside linkages within the central region of a modified oligonucleotide are internucleoside linking groups having Formula VIII or Formula XVII. In certain embodiments, seven internucleoside linkages within the central region of a modified oligonucleotide are internucleoside linking groups having Formula VIII or Formula XVII. In certain embodiments, eight internucleoside linkages within the central region of a modified oligonucleotide are internucleoside linking groups having Formula VIII or Formula XVII. In certain embodiments, nine internucleoside linkages within the central region of a modified oligonucleotide are internucleoside linking groups having Formula VIII or Formula XVII. In certain embodiments, ten internucleoside linkages within the central region of a modified oligonucleotide are internucleoside linking groups having Formula VIII or Formula XVII. In certain embodiments, each internucleoside linkage within the central region of a modified oligonucleotide is an internucleoside linking groups having Formula VIII or Formula XVII.

In certain embodiments, the internucleoside linking group linking the $2^{nd}$ and $3^{rd}$ nucleosides of the central region as counted from the 5'-end of the central region is an internucleoside linking group of Formula VIII or Formula XVII. In certain embodiments, the internucleoside linking group linking the $3^{rd}$ and $4^{th}$ nucleosides of the central region as counted from the 5'-end of the central region is an internucleoside linking group of Formula VIII or Formula XVII.

In certain embodiments, the internucleoside linking group linking the $4^{th}$ and $5^{th}$ nucleosides of the central region as counted from the 5'-end of the central region is an internucleoside linking group of Formula VIII or Formula XVII.

In certain embodiments, the central region consists of 7-11 linked nucleosides, and has the formula:

$$(N_{d1})_{L1}(N_{d2})_{L2}(N_{d3})_{L3}(N_{d4})_{L4}[(N_d)_{L5}]_q;$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $Na_2$, N3, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of L1, $L_2$, $L_3$, $L_4$, and each $L_5$ is an internucleoside linkage;

wherein at least two of $L_1$, $L_2$, $L_3$, $L_4$ is an internucleoside linkage of Formula VIII or Formula XVII.

In certain embodiments, the oligonucleotide comprises at least one block of at least 3 consecutive internucleoside linking groups of Formula VIII or Formula XVII. In certain embodiments, the oligonucleotide comprises at least one block of at least 4 consecutive internucleoside linking groups of Formula VIII or Formula XVII. In certain embodiments, the oligonucleotide comprises at least one block of at least 5 consecutive internucleoside linking groups of Formula VIII or Formula XVII. In certain embodiments, the oligonucleotide comprises at least one block of at least 5 consecutive internucleoside linking groups of Formula VIII or Formula XVII. In certain embodiments, the oligonucleotide comprises at least one block of at least 6 consecutive internucleoside linking groups of Formula VIII or Formula XVII. In certain embodiments, the oligonucleotide comprises at least one block of at least 7 consecutive internucleoside linking groups of Formula VIII or Formula XVII. In certain embodiments, the oligonucleotide comprises at least one block of at least 8 consecutive internucleoside linking groups of Formula VIII or Formula XVII. In certain embodiments, the oligonucleotide comprises at least one block of at least 10 consecutive internucleoside linking groups of Formula VIII or Formula XVII. In certain embodiments, the oligonucleotide comprises at least one block of at least 12 consecutive internucleoside linking groups of Formula VIII or Formula XVII. In certain such embodiments, at least one such block is located at the 3' end of the oligonucleotide. In certain such embodiments, at least one such block is located within 3 nucleosides of the 3' end of the oligonucleotide. In certain such embodiments, at least one such block is located at the 5' end of the oligonucleotide. In certain such embodiments, at least one such block is located within 3 nucleosides of the 5' end of the oligonucleotide.

In certain such embodiments, some or all of the internucleoside linkages in the 5'-region and 3'-region are unmodified phosphate linkages. In certain embodiments, the terminal internucleoside linkages are modified. In certain embodiments, the internucleoside linkage motif comprises at least one phosphodiester internucleoside linkage in at least one of the 5'-region and the 3'-region, wherein the at least one phosphodiester linkage is not a terminal internucleoside linkage, and the remaining internucleoside linkages are internucleoside linking groups of Formula VIII or Formula XVII or phosphorothioate internucleoside linkages.

In certain embodiments, oligonucleotides comprise a region having an alternating internucleoside linkage motif. In certain embodiments, oligonucleotides comprise a region of uniformly modified internucleoside linkages. In certain such embodiments, the internucleoside linkages are internucleoside linking groups of Formula VIII or Formula XVII. In certain embodiments, each internucleoside linkage of the oligonucleotide is selected from phosphodiester, a phosphorothioate, and internucleoside linking group of Formula VIII or Formula XVII. In certain embodiments, each internucleoside linkage of the oligonucleotide is selected from phosphodiester or and an internucleoside linking groups of Formula VIII or Formula XVII. In certain embodiments, each internucleoside linkage of the oligonucleotide is selected from phosphorothioate and an internucleoside linking group of Formula VIII or Formula XVII.

In certain embodiments, each phosphorothioate internucleoside linkage is independently selected from a stereorandom phosphorothioate, a (Sp) phosphorothioate, and a (Rp) phosphorothioate. In certain embodiments, the internucleoside linkages within the central region of a modified oligonucleotide are all modified. In certain such embodiments, all of the phosphorothioate linkages are stereorandom. In certain embodiments, all of the phosphorothioate linkages in the 5'-region and 3'-region are (Sp) phosphorothioates, and the central region comprises at least one Sp, Sp, Rp motif. In certain embodiments, populations of modified oligonucleotides are enriched for modified oligonucleotides comprising such internucleoside linkage motifs.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, modified oligonucleotides comprise a linkage motif comprising all phosphorothioate linkages except for one or two methylphosphonate linkages. In certain embodiments, one methylphosphonate linkage is in the central region of an oligonucleotide.

In certain embodiments, it is desirable to arrange the number of modified internucleoside linking groups having Formula VIII or Formula XVII, phosphorothioate internucleoside linkages, and phosphodiester internucleoside linkages to maintain nuclease resistance. In certain embodiments, it is desirable to arrange the number and position of modified internucleoside linking groups having Formula VIII or Formula XVII, phosphorothioate internucleoside linkages, and the number and position of phosphodiester internucleoside linkages to maintain nuclease resistance. In certain embodiments, the number of phosphorothioate internucleoside linkages may be decreased and the number of modified internucleoside linking groups having Formula VIII or Formula XVII and/or phosphodiester internucleoside linkages may be increased. In certain embodiments, the number of phosphorothioate internucleoside linkages may be decreased and the number of modified internucleoside linking groups having Formula VIII or Formula XVII and/or phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

In certain embodiments, the number of phosphodiester internucleoside linkages may be decreased by replacing phosphodiester internucleoside linkages with modified internucleoside linking groups having Formula VIII or Formula XVII. In certain embodiments, decreasing the number of phosphodiester internucleoside linkages and increasing the number of modified internucleoside linking groups having Formula VIII or Formula XVII increases the therapeutic index of a modified oligonucleotide or oligomeric compound. In certain embodiments, the number of phosphorothioate internucleoside linkages may be decreased by replacing phosphorothioate internucleoside linkages with modified internucleoside linking groups having Formula VIII or Formula XVII. In certain embodiments, decreasing the number of phosphorothioate internucleoside linkages and increasing the number of modified internucleoside linking groups having Formula VIII or Formula XVII increases the therapeutic index of a modified oligonucleotide or oligomeric compound.

In certain embodiments, a double-stranded antisense compound is a double-stranded RNAi compound comprising an RNAi antisense modified oligonucleotide and an RNAi sense modified oligonucleotide, wherein one or both of the RNAi antisense modified oligonucleotide and/or RNAi sense oligomeric compound have one or more modified internucleoside linking groups having Formula VIII or Formula XVII. In certain embodiments, the RNAi antisense modified oligonucleotide comprises at least two, at least three, at least four, at least five, or at least six modified internucleoside linking groups having Formula VIII or Formula XVII. In certain embodiments, the RNAi sense modified oligonucleotide comprises at least two, at least three, at least four, at least five, or at least six modified internucleoside linking groups having Formula VIII or Formula XVII.

In certain embodiments, the RNAi antisense modified oligonucleotide comprises exactly one modified internucleoside linking group having Formula VIII or Formula XVII. In certain embodiments, the RNAi antisense modified oligonucleotide comprises exactly two modified internucleoside linking groups having Formula VIII or Formula XVII. In certain embodiments, the RNAi antisense modified oligonucleotide comprises exactly three modified internucleoside linking groups having Formula VIII or Formula XVII. In certain embodiments, the RNAi antisense modified oligonucleotide comprises exactly four modified internucleoside linking groups having Formula VIII or Formula XVII. In certain embodiments, the RNAi antisense modified oligonucleotide comprises exactly five modified internucleoside linking groups having Formula VIII or Formula XVII. In certain embodiments, the RNAi antisense modified oligonucleotide comprises exactly six modified internucleoside linking groups having Formula VIII or Formula XVII. In certain embodiments, the RNAi antisense modified oligonucleotide comprises at least 6, at least 7, at least 8, or at least 9 modified internucleoside linking groups having Formula VIII or Formula XVII. In certain embodiments, each internucleoside linking group of the RNAi antisense modified oligonucleotide is a modified internucleoside linking groups having Formula VIII or Formula XVII.

In certain embodiments, the RNAi sense modified oligonucleotide comprises exactly one modified internucleoside linking group having Formula VIII or Formula XVII. In certain embodiments, the RNAi sense modified oligonucleotide comprises exactly two modified internucleoside linking groups having Formula VIII or Formula XVII. In certain embodiments, the RNAi sense modified oligonucleotide comprises exactly three modified internucleoside linking groups having Formula VIII or Formula XVII. In certain embodiments, the RNAi sense modified oligonucleotide comprises exactly four modified internucleoside linking groups having Formula VIII or Formula XVII. In certain embodiments, the RNAi sense modified oligonucleotide comprises exactly five modified internucleoside linking groups having Formula VIII or Formula XVII. In certain embodiments, the RNAi sense modified oligonucleotide comprises exactly six modified internucleoside linking groups having Formula VIII or Formula XVII. In certain embodiments, the RNAi sense modified oligonucleotide comprises at least 6, at least 7, at least 8, or at least 9 modified internucleoside linking groups having Formula VIII or Formula XVII. In certain embodiments, each internucleoside linking group of the RNAi sense modified oligonucleotide is a modified internucleoside linking groups having Formula VIII or Formula XVII.

In certain embodiments, at least one of the five 3'-most internucleoside linking groups of the RNAi antisense modified oligonucleotide is a modified internucleoside linking group having Formula VIII or Formula XVII. In certain embodiments, at least two of the five 3'-most internucleoside linking groups of the RNAi antisense modified oligonucleotide are modified internucleoside linking groups having Formula VIII or Formula XVII. In certain embodiments, at least one nucleoside of the seed region of the RNAi antisense modified oligonucleotide is a modified internucleoside linking group having Formula VIII or Formula XVII. In certain embodiments, at least one nucleoside within nucleosides 2 to 8 of the RNAi antisense modified oligonucleotide, counting from the 5' end, is a modified internucleoside linking group having Formula VIII or Formula XVII.

In certain embodiments, the 5'-terminus of the RNAi antisense oligonucleotide has structure K:

Structure K

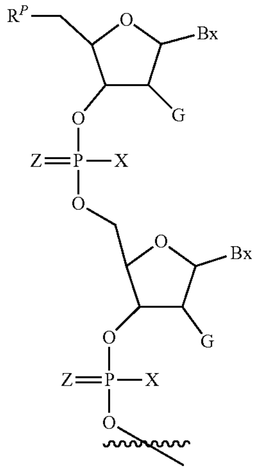

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 3'-terminus of the RNAi antisense oligonucleotide has structure L:

Structure L

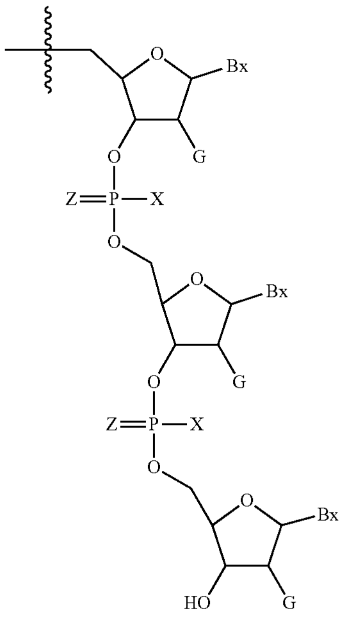

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, at least one region of the RNAi antisense oligonucleotide has structure M:

Structure M

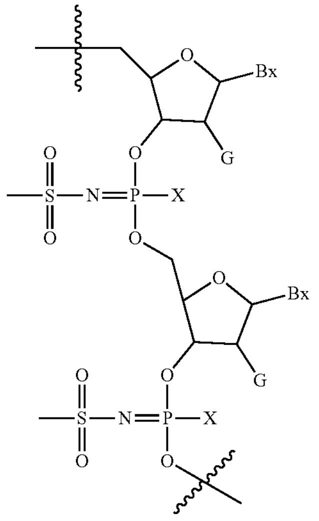

wherein:

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 5'-terminus of the RNAi antisense oligonucleotide has structure N:

Structure N

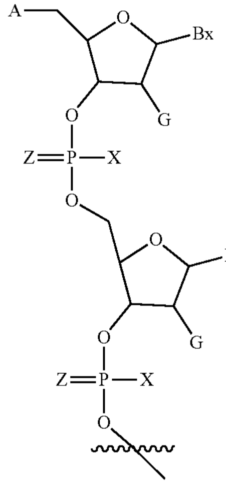

wherein:

A is selected from or;

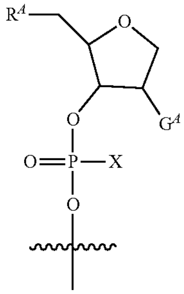

or

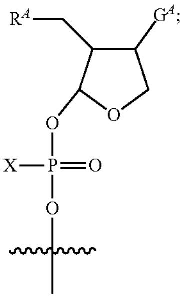

$R^A$ is OH, OP(═O)OH, OP(═O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 3'-terminus of the RNAi antisense oligonucleotide has structure O:

Structure O

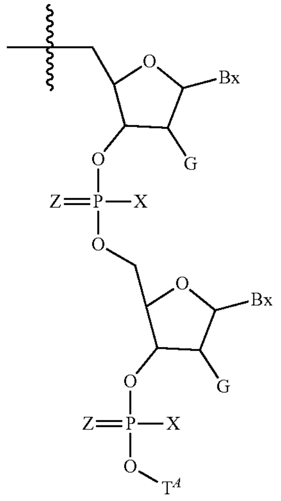

wherein:

$T^A$ is selected from

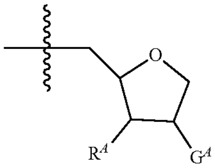

or

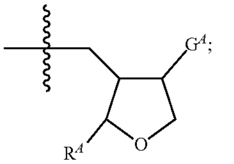

$R^A$ is OH, OP(═O)OH, OP(═O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, at least one of the first 5 internucleoside linkages from the 5' end of the RNAi sense modified oligonucleotide is a modified internucleoside linking group having Formula VIII or Formula XVII. In certain embodiments, at least one of the five 3'-most internucleoside linking groups of the RNAi sense modified oligonucleotide is a modified internucleoside linking group having Formula VIII or Formula XVII. In certain embodiments, at least one of the first 5 internucleoside linkages from the 5' end of the RNAi sense modified oligonucleotide and at least one of the five 3'-most internucleoside linking groups of the RNAi sense modified oligonucleotide is a modified internucleoside linking group having Formula VIII or Formula XVII. In certain embodiments, at least one nucleoside within nucleosides 2 to 8 of the RNAi sense modified oligonucleotide, counting from the 5' end, is a modified internucleoside linking group having Formula VIII or Formula XVII.

In certain embodiments, the 5'-terminus of the RNAi sense oligonucleotide has structure K:

Structure K

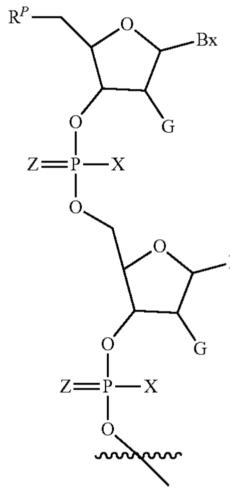

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 3'-terminus of the RNAi sense oligonucleotide has structure L:

Structure L

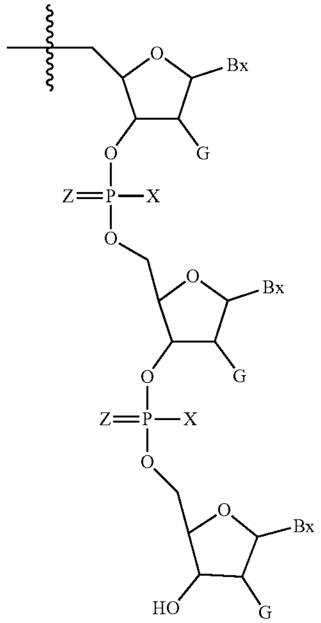

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, at least one region of the RNAi sense oligonucleotide has structure M:

Structure M

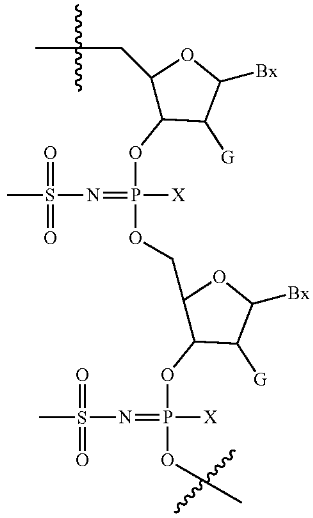

wherein:

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 5'-terminus of the RNAi sense oligonucleotide has structure N:

Structure N

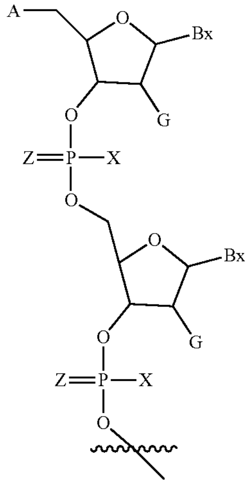

wherein:

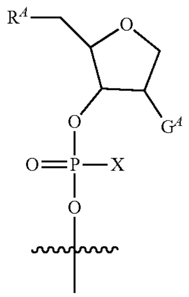

or

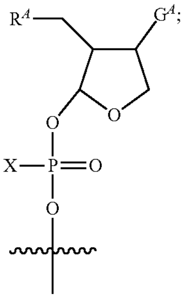

A is selected from $R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments the 3'-terminus of the RNAi sense oligonucleotide has structure 0:

Structure O

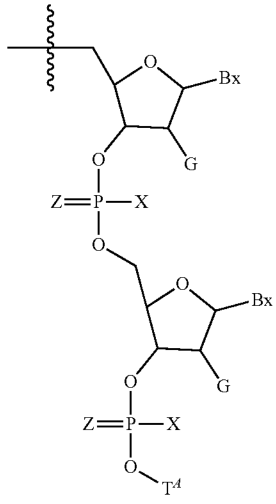

wherein:

$T^A$ is selected from

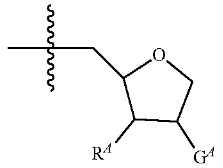

or

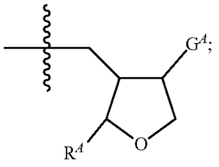

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 5' terminus of the antisense oligonucleotide has structure P:

Structure P

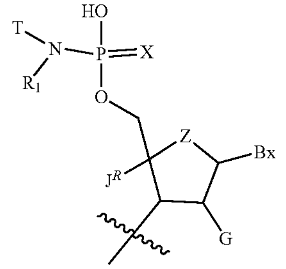

wherein:

each Bx is a heterocyclic base moiety;

X is selected from O or S;

Z is $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R$ and G form a $J^R$ to G bridge, or $J^R$ is H and G is selected from H, OH, halogen or $O—[C(R_6)(R_7)]—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, an oligomeric compound (including an oligomeric compound that is an antisense agent or a portion thereof) is a single-stranded RNAi compound or RNAi agent comprising an RNAi antisense modified oligonucleotide. In certain embodiments, the single-stranded RNAi compound or RNAi agent comprising an RNAi antisense modified oligonucleotide comprises at least two, at least three, at least four, at least five, or at least six modified internucleoside linking groups having Formula VIII or Formula XVII. In certain embodiments, the single-stranded RNAi compound or RNAi agent comprising an RNAi antisense modified oligonucleotide comprises exactly one modified internucleoside linking group having Formula VIII or Formula XVII. In certain embodiments, the single-stranded RNAi compound or RNAi agent comprising an RNAi antisense modified oligonucleotide comprises exactly two modified internucleoside linking groups having Formula VIII or Formula XVII. In certain embodiments, the single-stranded RNAi compound or RNAi agent comprising an RNAi antisense modified oligonucleotide comprises exactly three modified internucleoside linking groups having Formula VIII or Formula XVII. In certain embodiments, the single-stranded RNAi compound or RNAi agent comprising an RNAi antisense modified oligonucleotide comprises exactly four modified internucleoside linking groups having Formula VIII or Formula XVII. In certain embodiments, the single-stranded RNAi compound or RNAi agent comprising an RNAi antisense modified oligonucleotide comprises exactly five modified internucleoside linking groups having Formula VIII or Formula XVII. In certain embodiments, the single-stranded RNAi compound or RNAi agent comprising an RNAi antisense modified oligonucleotide comprises exactly six modified internucleoside linking groups having Formula VIII or Formula XVII. In certain embodiments, the single-stranded RNAi compound or RNAi agent comprising an RNAi antisense modified oligonucleotide comprises at least 6, at least 7, at least 8, or at least 9 modified internucleoside linking groups having Formula VIII or Formula XVII. In certain embodiments, each internucleoside linking group of the single-stranded RNAi compound or RNAi agent comprising an RNAi antisense modified oligonucleotide is a modified internucleoside linking groups having Formula VIII or Formula XVII.

In certain embodiments, at least one of the first 5 internucleoside linkages from the 5' end of the single-stranded RNAi compound or RNAi agent comprising an RNAi antisense modified oligonucleotide is a modified internucleoside linking group having Formula VIII or Formula XVII. In certain embodiments, at least one of the five 3'-most internucleoside linking groups from the 3' end of the single-stranded RNAi compound or RNAi agent comprising an RNAi antisense modified oligonucleotide is a modified internucleoside linking group having Formula VIII or Formula XVII. In certain embodiments, at least one nucleoside of the seed region of the single-stranded RNAi compound or RNAi agent comprising an RNAi antisense modified oligonucleotide is a modified internucleoside linking group having Formula VIII or Formula XVII. In certain embodiments, at least one nucleoside within nucleosides 2 to 8 of the single-stranded RNAi compound or RNAi agent comprising an RNAi antisense modified oligonucleotide, counting from the 5' end, is a modified internucleoside linking group having Formula VIII or Formula XVII.

In certain embodiments, the 5'-terminus of the single-stranded RNAi compound or RNAi agent comprising an RNAi antisense modified oligonucleotide has a 5'-terminal group having formula XXI or XXII.

In certain embodiments, an oligomeric compound is a CRISPR compound. In certain embodiments, CRISPR compounds comprise a modified oligonucleotide that comprises a DNA recognition region and a tracrRNA recognition region. In certain embodiments, the DNA recognition region includes a seed region. In certain embodiments, CRISPR compounds have at least one modified internucleoside linking group having Formula VIII or Formula XVJI. In certain embodiments, CRISPR compounds have at least two modified internucleoside linking groups having Formula VIII or Formula XVII. In certain embodiments, CRISPR compounds have at least three modified internucleoside linking groups having Formula VIII or Formula XVII. In certain embodiments, CRISPR compounds have at least four modified internucleoside linking groups having Formula VIII or Formula XVII. In certain embodiments, CRISPR compounds have at least five modified internucleoside linking groups having Formula VIII or Formula XVII. In certain embodiments, CRISPR compounds have at least six modified internucleoside linking groups having Formula VIII or Formula XVII. In certain embodiments, CRISPR compounds have at least 10 modified internucleoside linking groups having Formula VIII or Formula XVII. In certain embodiments, CRISPR compounds have at least 15 modified internucleoside linking groups having Formula VIII or Formula XVII. In certain embodiments, CRISPR compounds have at least 20 modified internucleoside linking groups having Formula VIII or Formula XVII. In certain embodiments, CRISPR compounds have at least 25 modified internucleoside linking groups having Formula VIII or Formula XVII. In certain embodiments, each internucleoside linking group of the CRISPR compound is a modified internucleoside linking group having Formula VIII or Formula XVII.

In certain embodiments, CRISPR compounds have exactly one modified internucleoside linking group having Formula VIII or Formula XVII. In certain embodiments, CRISPR compounds have exactly two modified internucleoside linking groups having Formula VIII or Formula XVII. In certain embodiments, CRISPR compounds have exactly three modified internucleoside linking groups having Formula VIII or Formula XVII. In certain embodiments, CRISPR compounds have exactly four modified internucleoside linking groups having Formula VIII or Formula XVII. In certain embodiments, CRISPR compounds have exactly five modified internucleoside linking groups having Formula VIII or Formula XVII. In certain embodiments, CRISPR compounds have exactly six modified internucleoside linking groups having Formula VIII or Formula XVII.

In certain embodiments, the DNA recognition portion of a CRISPR compound has at least one modified internucleoside linking group having Formula VIII or Formula XVII. In certain embodiments, the DNA recognition portion of a CRISPR compound has at least two modified internucleoside linking groups having Formula VIII or Formula XVII. In certain embodiments, the DNA recognition portion of a CRISPR compound has at least three modified internucleoside linking groups having Formula VIII or Formula XVII. In certain embodiments, the DNA recognition portion of a CRISPR compound has at least four modified internucleoside linking groups having Formula VIII or Formula XVII. In certain embodiments, the DNA recognition portion of a CRISPR compound has at least five modified internucleoside linking groups having Formula VIII or Formula XVII. In certain embodiments, the DNA recognition portion of a CRISPR compound has at least six modified internucleoside linking groups having Formula VIII or Formula XVII. In certain embodiments, the DNA recognition portion of a CRISPR compound has at least 10 modified internucleoside linking groups having Formula VIII or Formula XVII. In certain embodiments, each internucleoside linking group of the DNA recognition portion of a CRISPR compound is a modified internucleoside linking group having Formula VIII or Formula XVII.

In certain embodiments, the DNA recognition portion of a CRISPR compound has exactly one modified internucleoside linking group having Formula VIII or Formula XVII. In certain embodiments, the DNA recognition portion of a CRISPR compound has exactly two modified internucleoside linking groups having Formula VIII or Formula XVII. In certain embodiments, the DNA recognition portion of a CRISPR compound has exactly three modified internucleoside linking groups having Formula VIII or Formula XVII. In certain embodiments, the DNA recognition portion of a CRISPR compound has exactly four modified internucleoside linking groups having Formula VIII or Formula XVII. In certain embodiments, the DNA recognition portion of a CRISPR compound has exactly five modified internucleoside linking groups having Formula VIII or Formula XVII. In certain embodiments, the DNA recognition portion of a CRISPR compound has exactly six modified internucleoside linking groups having Formula VIII or Formula XVII. In certain embodiments, at least one internucleoside linking group of the of the seed region of the CRISPR oligonucleotide is a modified internucleoside linking group having Formula VIII or Formula XVII.

In certain embodiments, the tracrRNA recognition portion of a CRISPR compound has at least one modified internucleoside linking group having Formula VIII or Formula XVII. In certain embodiments, the tracrRNA recognition portion of a CRISPR compound has at least two modified internucleoside linking groups having Formula VIII or Formula XVII. In certain embodiments, the tracrRNA recognition portion of a CRISPR compound has at least three modified internucleoside linking groups having Formula VIII or Formula XVII. In certain embodiments, the tracrRNA recognition portion of a CRISPR compound has at least four modified internucleoside linking groups having Formula VIII or Formula XVII. In certain embodiments, the tracrRNA recognition portion of a CRISPR compound has at least five modified internucleoside linking groups having Formula VIII or Formula XVII. In certain embodiments, the tracrRNA recognition portion of a CRISPR compound has at least six modified internucleoside linking groups having Formula VIII or Formula XVII. In certain embodiments, the tracrRNA recognition portion of a CRISPR compound has at least 10 modified internucleoside linking groups having Formula VIII or Formula XVII. In certain embodiments, each internucleoside linking group of the tracrRNA recognition portion of a CRISPR compound is a modified internucleoside linking group having Formula VIII or Formula XVII.

In certain embodiments, the tracrRNA recognition portion of a CRISPR compound has exactly one modified internucleoside linking group having Formula VIII or Formula XVII. In certain embodiments, the tracrRNA recognition portion of a CRISPR compound has exactly two modified internucleoside linking groups having Formula VIII or Formula XVII. In certain embodiments, the tracrRNA recognition portion of a CRISPR compound has exactly three modified internucleoside linking groups having Formula VIII or Formula XVII. In certain embodiments, the tracrRNA recognition portion of a CRISPR compound has exactly four modified internucleoside linking groups having Formula VIII or Formula XVII. In certain embodiments, the tracrRNA recognition portion of a CRISPR compound has exactly five modified internucleoside linking groups having Formula VIII or Formula XVII. In certain embodiments, the tracrRNA recognition portion of a CRISPR compound has exactly six modified internucleoside linking groups having Formula VIII or Formula XVII.

In certain embodiments, an oligomeric compound is an artificial mRNA oligonucleotide. In certain embodiments, an oligomeric compound is an artificial mRNA oligonucleotide having a 5'UTR and a 3'UTR. In certain embodiments, the artificial mRNA oligonucleotide comprises more than 10, more than 20, more than 30, more than 40, more than 50, or more than 100 internucleoside linking groups having Formula VIII or Formula XVII.

In certain embodiments, the artificial mRNA oligonucleotide has exactly one modified internucleoside linking group having Formula VIII or Formula XVII. In certain embodiments, the artificial mRNA oligonucleotide has exactly two modified internucleoside linking groups having Formula VIII or Formula XVII. In certain embodiments, the artificial mRNA oligonucleotide has exactly three modified internucleoside linking groups having Formula VIII or Formula XVII. In certain embodiments, the artificial mRNA oligonucleotide has exactly four modified internucleoside linking groups having Formula VIII or Formula XVII. In certain embodiments, the artificial mRNA oligonucleotide has exactly five modified internucleoside linking groups having Formula VIII or Formula XVII. In certain embodiments, the artificial mRNA oligonucleotide has exactly six modified internucleoside linking groups having Formula VIII or Formula XVII.

In certain embodiments, the artificial mRNA oligonucleotide comprises exactly one modified internucleoside linking group having Formula VIII or Formula XVII. In certain embodiments, the artificial mRNA oligonucleotide comprises exactly two modified internucleoside linking groups having Formula VIII or Formula XVII. In certain embodiments, the artificial mRNA oligonucleotide comprises exactly three modified internucleoside linking groups having Formula VIII or Formula XVII. In certain embodiments, the artificial mRNA oligonucleotide comprises exactly four modified internucleoside linking groups having Formula VIII or Formula XVII. In certain embodiments, the artificial mRNA oligonucleotide comprises exactly five modified internucleoside linking groups having Formula VIII or Formula XVII. In certain embodiments, the artificial mRNA oligonucleotide comprises exactly 6, 7, 8, 9, 10, 11, 12, 13, 14, 15, 16, 17, 18, 19, 20, 21, or 22 modified internucleoside linking groups having Formula VIII or Formula XVII.

In certain embodiments, the artificial mRNA oligonucleotide comprises more than 10, more than 20, more than 30, more than 40, more than 50, or more than 100 modified internucleoside linking groups having Formula VIII or Formula XVII. In certain embodiments, at least one of the first 5 internucleoside linking groups from the 5'-end of the artificial mRNA oligonucleotide is a modified internucleoside linking group having Formula VIII or Formula XVII. In certain embodiments, at least one of the five 3'-most internucleoside linking groups of the artificial mRNA oligonucleotide is a modified internucleoside linking group having Formula VIII or Formula XVII. In certain embodiments, at least one internucleoside linking group of the 5'-UTR of the artificial mRNA oligonucleotide is a modified internucleoside linking group having Formula VIII or Formula XVII. In certain embodiments, at least one internucleoside linking group of the 3'-UTR of the artificial mRNA oligonucleotide is a modified internucleoside linking group having Formula VIII or Formula XVII. In certain embodiments, at least one internucleoside linking group of the coding region of the artificial mRNA oligonucleotide is a modified internucleoside linking group having Formula VIII or Formula XVII.

II. Certain Modified Oligonucleotides

In certain embodiments, antisense agents, oligomeric compounds, and modified oligonucleotides described herein comprise or consist of modified oligonucleotides. In certain embodiments, the above modifications (sugar, nucleobase, internucleoside linkage) are incorporated into a modified oligonucleotide. In certain embodiments, modified oligonucleotides are characterized by their modifications, motifs, and overall lengths. In certain embodiments, such parameters are each independent of one another. Thus, unless otherwise indicated, each internucleoside linkage of a modified oligonucleotide may be modified or unmodified and may or may not follow the modification pattern of the sugar moieties. Likewise, such modified oligonucleotides may comprise one or more modified nucleobase independent of the pattern of the sugar modifications. Furthermore, in certain instances, a modified oligonucleotide is described by an overall length or range and by lengths or length ranges of two or more regions (e.g., a region of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions or segments, A, B, and C, wherein region or segment A consists of 2-6 linked nucleosides having a specified sugar moiety, region or segment B consists of 6-10 linked nucleosides having a specified sugar moiety, and region or segment C consists of 2-6 linked nucleosides having a specified sugar moiety. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of 20 for the overall length of the modified oligonucleotide. Unless otherwise indicated, all modifications are independent of nucleobase sequence except that the modified nucleobase 5-methylcytosine is necessarily a "C" in an oligonucleotide sequence. In certain embodiments, when a DNA nucleoside or DNA-like nucleoside that comprises a T in a DNA sequence is replaced with a RNA-like nucleoside, the nucleobase T is replaced with the nucleobase U. Each of these compounds has an identical target RNA.

In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that $X \leq Y$. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments oligonucleotides have a nucleobase sequence that is complementary to a second oligonucleotide or an identified reference nucleic acid, such as a target nucleic acid. In certain embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. Certain Conjugated Compounds

In certain embodiments, antisense agents, oligomeric compounds, and modified oligonucleotides described herein comprise or consist of a modified oligonucleotide that optionally comprises a conjugate group. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate moieties or terminal groups are attached at the 3' and/or 5'-end of oligonucleotides. In certain such embodiments, conjugate moieties (or terminal groups) are attached at the 3'-end of oligonucleotides. In certain embodiments, conjugate moieties are attached near the 3'-end of oligonucleotides. In certain embodiments, conjugate moieties (or terminal groups) are attached at the 5'-end of oligonucleotides. In certain embodiments, conjugate moieties are attached near the 5'-end of oligonucleotides.

Examples of terminal groups include but are not limited to conjugate moieties, conjugate groups, capping groups, phosphate moieties, protecting groups, modified or unmodified nucleosides, and two or more nucleosides that are independently modified or unmodified.

A. Certain Conjugate Groups and Conjugate Moieties

In certain embodiments, modified oligonucleotides comprise one or more conjugate moieties or conjugate groups. In certain embodiments, conjugate groups modify one or more properties of the molecule, including but not limited to pharmacodynamics, pharmacokinetics, stability, binding, absorption, tissue distribution, cellular distribution, cellular uptake, charge and clearance. In certain embodiments, conjugate moieties impart a new property on the molecule, e.g., fluorophores or reporter groups that enable detection of the molecule.

Certain conjugate groups have been described previously, for example: cholesterol moiety (Letsinger et al., Proc. Natl.

Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N. Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

a. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

b. Conjugate Linkers

In certain embodiments, conjugate groups comprise a conjugate linker that attaches a conjugate moiety to the remainder of the modified oligonucleotide. In certain embodiments, a conjugate linker is a single chemical bond (i.e. conjugate moiety is attached to the remainder of the modified oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to oligomeric compounds, such as the oligonucleotides provided herein. In general, a bifunctional linking moiety comprises at least two functional groups. One of the functional groups is selected to bind to a particular site on an oligomeric compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group or conjugate moiety to be cleaved from the remainder of the oligonucleotide. For example, in certain circumstances oligomeric compounds (including oligomeric compounds that are antisense agents or portions thereof) or modified oligonucleotides comprising a particular conjugate moiety are better taken up by a particular cell type, but once the compound has been taken up, it is desirable that the conjugate group be cleaved to release an unconjugated oligonucleotide. Thus, certain conjugate moieties may comprise one or more cleavable moieties, typically within the conjugate linker. In certain embodiments, a cleavable moiety is a cleavable bond. In certain embodiments, a cleavable moiety is a group of atoms comprising at least one cleavable bond.

In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is a nucleoside comprising a 2'-deoxyfuranosyl that is attached to either the 3' or 5'-terminal nucleoside of an oligonucleotide by a phosphodiester internucleoside linkage and covalently attached to the remainder of the conjugate linker or conjugate moiety by a phosphodiester or phosphorothioate linkage. In certain such embodiments, the cleavable moiety is a nucleoside comprising a 2'-β-D-deoxyribosyl sugar moiety. In certain such embodiments, the cleavable moiety is 2'-deoxyadenosine.

c. Certain Cell-Targeting Conjugate Moieties

In certain embodiments, a conjugate group comprises a cell-targeting conjugate moiety. In certain embodiments, a conjugate group has the general formula:

[Ligand—Tether]$_n$—[Branching group]$_m$—[Conjugate Linker]$_j$—[Cleavable Moiety]$_k$—

Cell-targeting moiety wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian lung cell.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry,* 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, oligomeric compounds (including oligomeric compounds that are antisense agents or portions thereof) or modified oligonucleotides described herein comprise a conjugate group found in any of the following references: Lee, *Carbohydr Res,* 1978, 67, 509-514; Connolly et al., *J Biol Chem,* 1982, 257, 939-945; Pavia et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al., *Glycoconj J,* 2004, 21, 227-241; Lee et al., *Bioorg Med Chem Lett,* 2006, 16(19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., *Analyt Biochem,* 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618; Rensen et al., *J Med Chem,* 2004, 47, 5798-5808; Rensen et al., *Arterioscler Thromb Vasc Biol,* 2006, 26, 169-175; van Rossenberg et al., *Gene Ther,* 2004, 11, 457-464; Sato et al., *J Am Chem Soc,* 2004, 126, 14013-14022; Lee et al., *J Org Chem,* 2012, 77, 7564-7571; Biessen et al., *FASEB J,* 2000, 14, 1784-1792; Rajur et al., *Bioconjug Chem,* 1997, 8, 935-940; Duff et al., *Methods Enzymol,* 2000, 313, 297-321; Maier et al., *Bioconjug Chem,* 2003, 14, 18-29; Jayaprakash et al., *Org Lett,* 2010, 12, 5410-5413; Manoharan, *Antisense Nucleic Acid Drug Dev,* 2002, 12, 103-128; Merwin et al., *Bioconjug Chem,* 1994, 5, 612-620; Tomiya et al., *Bioorg Med Chem,* 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

Compositions and Methods for Formulating Pharmaceutical Compositions

Antisense agents, oligomeric compounds, and modified oligonucleotides described herein may be admixed with pharmaceutically acceptable active or inert substances for the preparation of pharmaceutical compositions. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more oligomeric compounds (including oligomeric compounds that are antisense agents or portions thereof) or a salt thereof. In certain such embodiments, the pharmaceutical composition comprises a suitable pharmaceutically acceptable diluent or carrier. In certain embodiments, a pharmaceutical composition comprises a sterile saline solution and one or more oligomeric compound. In certain embodiments, such pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

An oligomeric compound described herein complementary to a target nucleic acid can be utilized in pharmaceutical compositions by combining the oligomeric compound with a suitable pharmaceutically acceptable diluent or carrier and/or additional components such that the pharmaceutical composition is suitable for injection. In certain embodiments, a pharmaceutically acceptable diluent is phosphate buffered saline. Accordingly, in one embodiment, employed in the methods described herein is a pharmaceutical composition comprising an oligomeric compound complementary to a target nucleic acid and a pharmaceutically acceptable diluent. In certain embodiments, the pharmaceutically acceptable diluent is phosphate buffered saline. In certain embodiments, the oligomeric compound comprises or consists of a modified oligonucleotide provided herein.

Pharmaceutical compositions comprising oligomeric compounds (including oligomeric compounds that are antisense agents or portions thereof) provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the oligomeric compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

Certain Mechanisms

In certain embodiments, oligomeric compounds (including oligomeric compounds that are antisense agents or portions thereof) described herein comprise or consist of modified oligonucleotides. In certain such embodiments, the oligomeric compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Nucleosides that are sufficiently "DNA-like" to elicit RNase H activity are referred to as DNA mimics herein. Further, in certain embodiments, one or more non-DNA-like nucleoside in in the RNA:DNA duplex is tolerated.

In certain antisense activities, hybridization of an antisense agent, oligomeric compound, or modified oligonucleotide described herein to a target nucleic acid results in modulation of the splicing of a target pre-mRNA. For example, in certain embodiments, hybridization of a compound described herein will increase exclusion of an exon. For example, in certain embodiments, hybridization of a compound described herein will increase inclusion of an exon.

In certain antisense activities, antisense agents described herein or a portion of the antisense agent is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain antisense activities, antisense agents, oligomeric compounds, or modified oligonucleotides described herein result in a CRISPR system cleaving a target DNA. In certain antisense activities, compounds described herein result in a CRISPR system editing a target DNA.

In certain antisense activities, hybridization of an antisense agent, oligomeric compound, or modified oligonucleotide described herein to a target nucleic acid results in disruption of secondary structural elements, such as stem-loops and hairpins. For example, in certain embodiments, hybridization of a compound described herein to a stem-loop that is part of a translation suppression element leads to an increase in protein expression.

In certain antisense activities, hybridization of an antisense agent, oligomeric compound, or modified oligonucleotide described herein to a target nucleic acid leads to no-go decay mediated mRNA degradation.

In certain antisense activities, hybridization of an antisense agent, oligomeric compound, or modified oligonucleotide described herein to a target nucleic acid leads to activation of nonsense-mediated decay mRNA degradation.

In certain embodiments, antisense agents, oligomeric compounds, or modified oligonucleotides described herein are artificial mRNA compounds, the nucleobase sequence of which encodes for a protein.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Certain RNAi Agents

In certain embodiments, oligomeric compounds described herein having one or more stinternucleoside linkages Formula VIII or Formula XVII are RNAi agents. In certain embodiments, internucleoside linkages having Formula VIII or Formula XVII can replace one or more phosphorothioate or phosphodiester internucleoside linkages in any RNAi motif. Certain RNAi motifs are described in, e.g., Freier, et al., WO2020/160163, incorporated by reference herein in its entirety; as well as, e.g., Rajeev, et al., WO2013/075035; Maier, et al., WO2016/028649; Theile, et al., WO2018/098328; Nair, et al., WO2019/217459; each of which is incorporated by reference herein.

Target Nucleic Acids, Target Regions and Nucleotide Sequences

In certain embodiments, antisense agents, oligomeric compounds, or modified oligonucleotides described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain embodiments, a pre-mRNA and corresponding mRNA are both target nucleic acids of a single compound. In certain such embodiments, the target region is entirely within an intron of a target pre-mRNA. In certain embodiments, the target region spans an intron/exon junction. In certain embodiments, the target region is at least 50% within an intron. In certain embodiments, the target nucleic acid is a microRNA. In certain embodiments, the target region is in the 5' UTR of a gene. In certain embodiments, the target region is within a translation suppression element region of a target nucleic acid.

Certain Compounds

Certain compounds described herein (e.g., antisense agents, oligomeric compounds, and modified oligonucleotides) have one or more asymmetric center and thus give rise to enantiomers, diastereomers, and other stereoisomeric configurations that may be defined, in terms of absolute stereochemistry, as (R) or (S), as a or $ such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{15}N$ in place of $^{14}N$, $^{17}O$ or $^{18}O$ in place of $^{16}O$ and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples are intended to illustrate certain aspects of the invention and are not intended to limit the invention in any way.

Example 1: Synthesis of Modified Oligonucleotides with Mesyl Phosphoramidate Internucleoside Linkages Modified oligonucleotides comprising a single mesyl phosphoramidate internucleoside linkage (Formula IX) were synthesized and tested. As shown in Table 1, each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each internucleoside linkage is either a phosphorothioate internucleoside linkage ("s") or a mesyl phosphoramidate internucleoside linkage ("z"). Each of the compounds in Table 1 has exactly one mesyl phosphoramidate internucleoside linkage of formula IX.

IX

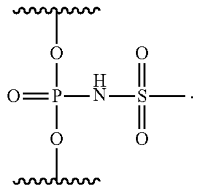

Activity Assay

The modified oligonucleotides were tested for their ability to reduce target RNA in a series of experiments. Cultured mouse 3T3-L1 cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, CXCL12 RNA levels were measured using mouse primer-probe set RTS2605 (forward sequence CCAGAGCCAACGTCAAGCAT, SEQ ID NO: 2; reverse sequence: CAGCCGTGCAACAATCTGAA, SEQ ID NO: 3; probe sequence: TGAAAATCCTCAACACTCCAAACTGTGCC, SEQ ID NO: 4). CXCL12 RNA levels were normalized to total RNA content, as measured by RIBOGREEN®. Activity expressed as half maximal inhibitory concentration (IC50) was calculated using the log (inhibitor) vs response (three parameter) function in GraphPad Prism 7 and is presented in the table below.

TABLE 1

Design and activity of modified oligonucleotides having a single mesyl phosphoramidate internucleoside linkage

| Compound Number | Chemistry Notation (5'-3') | IC50 (nM) | SEQ ID NO. |
|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 84 | 5 |
| 1375403 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{kz}A_{k}$ | 72 | 5 |
| 1375404 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{kz}}T_{ks}A_{k}$ | 61 | 5 |
| 1375405 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{\underline{dz}}T_{ks}T_{ks}A_{k}$ | 97 | 5 |
| 1375406 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{\underline{dz}}A_{ds}T_{ks}T_{ks}A_{k}$ | 101 | 5 |
| 1375407 | $G_{ks}{}^{m}C_{ks}A_{ks}T_{ds}G_{ds}T_{ds}T_{ds}{}^{m}C_{ds}T_{ds}{}^{m}C_{ds}A_{\underline{dz}}{}^{m}C_{ds}A_{ds}T_{ks}T_{ks}A_{k}$ | 121 | 5 |
| 1375408 | $G_{ks}{}^{m}C_{ks}A_{ks}T_{ds}G_{ds}T_{ds}T_{ds}{}^{m}C_{ds}T_{ds}{}^{m}C_{\underline{dz}}A_{ds}{}^{m}C_{ds}A_{ds}T_{ks}T_{ks}A_{k}$ | 103 | 5 |
| 1375409 | $G_{ks}{}^{m}C_{ks}A_{ks}T_{ds}G_{ds}T_{ds}T_{ds}{}^{m}C_{ds}T_{\underline{dz}}{}^{m}C_{ds}A_{ds}{}^{m}C_{ds}A_{ds}T_{ks}T_{ks}A_{k}$ | 83 | 5 |
| 1375410 | $G_{ks}{}^{m}C_{ks}A_{ks}T_{ds}G_{ds}T_{ds}T_{ds}{}^{m}C_{\underline{dz}}T_{ds}{}^{m}C_{ds}A_{ds}{}^{m}C_{ds}A_{ds}T_{ks}T_{ks}A_{k}$ | 98 | 5 |
| 1375411 | $G_{ks}{}^{m}C_{ks}A_{ks}T_{ds}G_{ds}T_{ds}T_{\underline{dz}}{}^{m}C_{ds}T_{ds}{}^{m}C_{ds}A_{ds}{}^{m}C_{ds}A_{ds}T_{ks}T_{ks}A_{k}$ | 90 | 5 |
| 1375412 | $G_{ks}{}^{m}C_{ks}A_{ks}T_{ds}G_{ds}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | 74 | 5 |
| 1375413 | $G_{ks}{}^{m}C_{ks}A_{ks}T_{ds}G_{\underline{dz}}T_{ds}T_{ds}{}^{m}C_{ds}T_{ds}{}^{m}C_{ds}A_{ds}{}^{m}C_{ds}A_{ds}T_{ks}T_{ks}A_{k}$ | 105 | 5 |

TABLE 1-continued

Design and activity of modified oligonucleotides having a single mesyl phosphoramidate internucleoside linkage

| Compound Number | Chemistry Notation (5'-3') | IC50 (nM) | SEQ ID NO. |
|---|---|---|---|
| 1375414 | $G_{ks}{}^{m}C_{ks}A_{ks}T_{\underline{dz}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 89 | 5 |
| 1375415 | $G_{ks}{}^{m}C_{ks}A_{\underline{kz}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 43 | 5 |
| 1375416 | $G_{ks}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 84 | 5 |
| 1375417 | $G_{\underline{kz}}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 76 | 5 |

A subscript "k" represents a cEt nucleoside, a subscript "d" represents a stereo-standard DNA nucleoside, a subscript "s" indicates phosphorothioate internucleoside linkage, a subscript "z" represents an internucleoside linkage of formula IX, which is a mesyl phosphoramidate linkage. A superscript "m" before a C represents a 5-methyl Cytosine The phosphorothioate linkages were incorporated into the modified oligonucleotide using known processes. The phosphoramidate internucleoside linkages were incorporated into the modified oligonucleotides during synthesis using a Staudinger reaction with mesyl azide, a schematic of which is shown below:

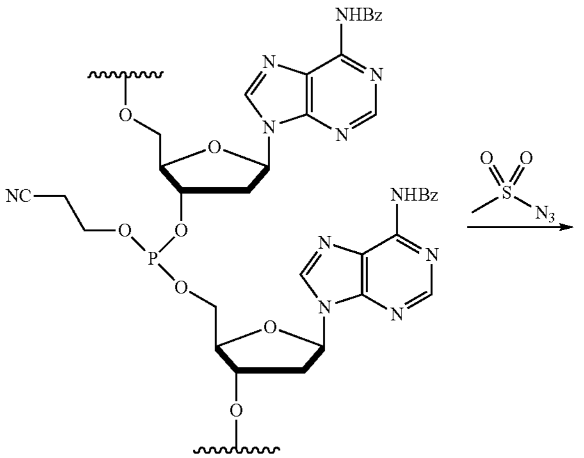

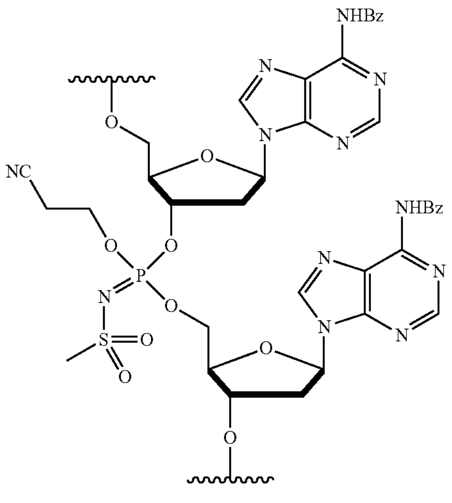

After the final nucleoside was added to the modified oligonucleotide, the modified oligonucleotide was deprotected and the intermediate linkage shown above was converted to the phosphoramidate internucleoside linkage shown below:

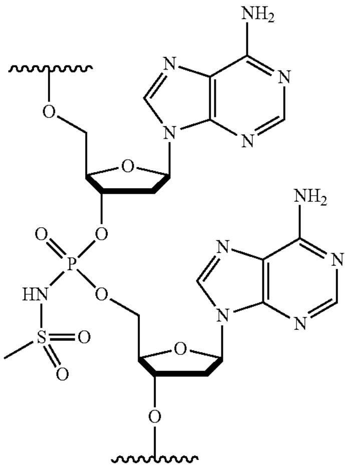

Example 2: Design and Activity of Modified Oligonucleotides with Multiple Mesyl Phosphoramidate Internucleoside Linkages Modified oligonucleotides comprising two consecutive (Table 2) or multiple (Table 3) mesyl phosphoramidate internucleoside linkages (Formula IX) were synthesized and tested. As shown in the tables below, each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each internucleoside linkage is either a phosphorothioate internucleoside linkage ("s") or a mesyl phosphoramidate internucleoside linkage ("z"). Each of the compounds in Table 2 has two mesyl phosphoramidate internucleoside linkages of formula IX, and each compound in Table 3 has multiple mesyl phosphoramidate internucleoside linkages of formula IX.

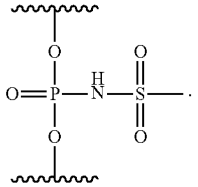

IX

Activity Assay

The modified oligonucleotides were tested for their ability to reduce target RNA in a series of experiments. Cultured mouse 3T3-L1 cells at a density of 20,000 cells per well were transfected using electroporation with modified oligonucleotides diluted to 20 µM, 7 µM, 2 µM, 0.7 µM, 0.3 µM, 0.1 µM, and 0.03 µM. After a treatment period of approximately 16 hours, CXCL12 RNA levels were measured using mouse primer-probe set RTS2605 (forward sequence CCAGAGCCAACGTCAAGCAT, SEQ ID NO: 2; reverse sequence: CAGCCGTGCAACAATCTGAA, SEQ ID NO: 3; probe sequence: TGAAAATCCTCAACACTCCAAACTGTGCC, SEQ ID NO: 4). CXCL12 RNA levels were normalized to total RNA content, as measured by RIBOGREENR. Activity expressed as half maximal inhibitory concentration (IC50) was calculated using the log (inhibitor) vs response (three parameter) function in GraphPad Prism 7 and is presented in the table below.

TABLE 2

Design and activity of modified oligonucleotides having two consecutive mesyl phosphoramidate internucleoside linkages

| Compound Number | Chemistry Notation (5'-3') | IC50 (nM) Study 1 | IC50 (nM) Study 2 | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 84 | 170 | 5 |
| 1375418 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{kz}}T_{\underline{kz}}A_{k}$ | 16 | 117 | 5 |
| 1375419 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{\underline{dz}}T_{\underline{kz}}T_{ks}A_{k}$ | 23 | 105 | 5 |
| 1375420 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{\underline{dz}}A_{\underline{dz}}T_{ks}T_{ks}A_{k}$ | 41 | 138 | 5 |
| 1375421 | $G_{ks}{}^{m}C_{ks}A_{ks}T_{ds}G_{ds}T_{ds}T_{ds}{}^{m}C_{ds}T_{ds}{}^{m}C_{ds}A_{\underline{dz}}{}^{m}C_{\underline{dz}}A_{ds}T_{ks}T_{ks}A_{k}$ | 37 | 83 | 5 |
| 1375422 | $G_{ks}{}^{m}C_{ks}A_{ks}T_{ds}G_{ds}T_{ds}T_{ds}{}^{m}C_{ds}T_{ds}{}^{m}C_{\underline{dz}}A_{\underline{dz}}{}^{m}C_{ds}A_{ds}T_{ks}T_{ks}A_{k}$ | 61 | 83 | 5 |
| 1375423 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{ds}{}^{m}C_{ds}A_{ds}T_{ks}T_{ks}A_{k}$ | 40 | 123 | 5 |
| 1375424 | $G_{ks}{}^{m}C_{ks}A_{ks}T_{ds}G_{ds}T_{ds}T_{ds}{}^{m}C_{\underline{dz}}T_{\underline{dz}}{}^{m}C_{ds}A_{ds}{}^{m}C_{ds}A_{ds}T_{ks}T_{ks}A_{k}$ | 38 | 146 | 5 |
| 1375425 | $G_{ks}{}^{m}C_{ks}A_{ks}T_{ds}G_{ds}T_{ds}T_{\underline{dz}}{}^{m}C_{\underline{dz}}T_{ds}{}^{m}C_{ds}A_{ds}{}^{m}C_{ds}A_{ds}T_{ks}T_{ks}A_{k}$ | 33 | 71 | 5 |
| 1375426 | $G_{ks}{}^{m}C_{ks}A_{ks}T_{ds}G_{ds}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | 32 | 100 | 5 |
| 1375427 | $G_{ks}{}^{m}C_{ks}A_{ks}T_{ds}G_{\underline{dz}}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | 28 | 87 | 5 |
| 1375428 | $G_{ks}{}^{m}C_{ks}A_{ks}T_{\underline{dz}}G_{\underline{dz}}T_{ds}T_{ds}{}^{m}C_{ds}T_{ds}{}^{m}C_{ds}A_{ds}{}^{m}C_{ds}A_{ds}T_{ks}T_{ks}A_{k}$ | 33 | 99 | 5 |
| 1375429 | $G_{ks}{}^{m}C_{ks}A_{\underline{kz}}T_{\underline{dz}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 39 | 83 | 5 |
| 1375430 | $G_{ks}{}^{m}C_{\underline{kz}}A_{\underline{kz}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 21 | 83 | 5 |
| 1375431 | $G_{\underline{kz}}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 27 | 108 | 5 |

A subscript "k" represents a cEt nucleoside, a subscript "d" represents a stereo-standard DNA nucleoside, a subscript "s" indicates phosphorothioate internucleoside linkage, a subscript "z" represents an internucleoside linkage of formula IX, which is a mesyl phosphoramidate linkage. A superscript "m" before a C represents a 5-methyl Cytosine

TABLE 3

Design and activity of modified oligonucleotides containing multiple mesyl phosphoramidate internucleoside linkages

| Compound Number | Chemistry Notation (5'-3') | IC50 (nM) | SEQ ID NO. |
|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 61 | 5 |
| 1375432 | $G_{\underline{kz}}{}^{m}C_{\underline{kz}}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{\underline{kz}}T_{\underline{kz}}A_{k}$ | 232 | 5 |
| 1386094 | $G_{ks}{}^{m}C_{ks}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | 810 | 5 |
| 1378793 | $G_{ks}{}^{m}C_{ks}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{ds}T_{ks}T_{ks}A_{k}$ | 646 | 5 |

TABLE 3-continued

| Design and activity of modified oligonucleotides containing multiple mesyl phosphoramidate internucleoside linkages | | | |
|---|---|---|---|
| Compound Number | Chemistry Notation (5'-3') | IC50 (nM) | SEQ ID NO. |
| 1386355 | $G_{ks}{}^{m}C_{ks}A_{ks}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{ds}T_{ks}T_{ks}A_{k}$ | 1158 | 5 |
| 1378794 | $G_{\underline{kz}}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{\underline{dz}}T_{\underline{kz}}T_{\underline{kz}}A_{k}$ | 83 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. A superscript "m" before a C represents a 5-methyl Cytosine.

Example 3: Caspase Activity of Modified Oligonucleotides in In Vitro Caspase Activation Assays The modified oligonucleotides were tested for their ability to mediate caspase activity in a series of experiments. Cultured mouse HEPA1-6 cells at a density of 20,000 cells per well were transfected using electroporation with modified oligonucleotides diluted to 20 μM. After a treatment period of approximately 16 hours, caspase-3 and caspase-7 activation was measured using the Caspase-Glo® 3/7 Assay System (G8090, Promega). Results are shown in the tables below. Increased levels of caspase activation correlate with apoptotic cell death and cytotoxicity.

In some cases, the caspase activation mediated by the modified oligonucleotide was confirmed in an additional study. In such cases, the table shows % mock values for both studies 1 and 2 in separate columns.

TABLE 4

| In vitro Caspase activation by modified oligonucleotides containing a single mesyl phosphoramidate internucleoside linkage | |
|---|---|
| Compound No. | Caspase Activation (% Mock) |
| 558807 | 2727 |
| 1375403 | 2508 |
| 1375404 | 3089 |
| 1375405 | 2660 |
| 1375406 | 2427 |
| 1375407 | 2938 |
| 1375408 | 2546 |
| 1375409 | 2966 |
| 1375410 | 2744 |
| 1375411 | 2571 |
| 1375412 | 1808 |
| 1375413 | 2639 |
| 1375414 | 3028 |
| 1375415 | 2733 |
| 1375416 | 2714 |
| 1375417 | 2627 |

TABLE 5

| In vitro Caspase activation by modified oligonucleotides containing two consecutive mesyl phosphoramidate internucleoside linkages | | |
|---|---|---|
| Compound No. | Caspase Activation (% Mock) Study 1 | Caspase Activation (% Mock) Study 2 |
| 558807 | 738 | 848 |
| 1375418 | 821 | 955 |

TABLE 5-continued

| In vitro Caspase activation by modified oligonucleotides containing two consecutive mesyl phosphoramidate internucleoside linkages | | |
|---|---|---|
| Compound No. | Caspase Activation (% Mock) Study 1 | Caspase Activation (% Mock) Study 2 |
| 1375419 | 1163 | 1192 |
| 1375420 | 683 | 623 |
| 1375421 | 814 | 749 |
| 1375422 | 662 | 767 |
| 1375423 | 900 | 1165 |
| 1375424 | 1305 | 1212 |
| 1375425 | 606 | 609 |
| 1375426 | 297 | 292 |
| 1375427 | 204 | 193 |
| 1375428 | 398 | 550 |
| 1375429 | 1032 | 728 |
| 1375430 | 1157 | 1271 |
| 1375431 | 869 | 844 |

TABLE 6

| In vitro Caspase activation by modified oligonucleotides containing multiple mesyl phosphoramidate internucleoside linkages | |
|---|---|
| Compound No. | Caspase Activation (% Mock) |
| 558807 | 2290 |
| 1375432 | 161 |
| 1386094 | 142 |
| 1378793 | 165 |
| 1386355 | 141 |
| 1378794 | 2500 |

Example 4: Stability of Modified Oligonucleotides Containing Mesyl Phosphoramidate Internucleoside Linkages The thermal stability (Tm) of duplexes of each of modified oligonucleotides described in the examples above with a complementary RNA 20-mer having the sequence GAUAAUGUGAGAACAUGCCU (SEQ ID NO: 6) was tested. Each modified oligonucleotide was separately hybridized with the complementary RNA strand to form a duplex. Once the duplex was formed, it was slowly heated and the melting temperature was measured using a spectrophotometer and the hyperchromicity method. Results are provided in the table below. This example demonstrates that mesyl phosphoramidate internucleoside linkages can be incorporated into modified oligonucleotides without destabilizing the interaction between the modified oligonucleotide and its complement.

TABLE 7

| Tm of modified oligonucleotides complementary to CXCL12 | |
|---|---|
| Compound No. | Tm (° C.) |
| 558807 | 63.5 |
| 1375403 | 63.8 |
| 1375404 | 63.9 |
| 1375405 | 63.5 |
| 1375406 | 63.7 |
| 1375407 | 63.6 |
| 1375408 | 63.9 |
| 1375409 | 64.2 |
| 1375410 | 63.9 |
| 1375411 | 64.0 |
| 1375412 | 63.7 |
| 1375413 | 63.6 |
| 1375414 | 63.3 |
| 1375415 | 63.7 |
| 1375416 | 63.7 |
| 1375417 | 63.3 |
| 1375418 | 63.3 |
| 1375419 | 63.7 |
| 1375420 | 63.4 |
| 1375421 | 63.6 |
| 1375422 | 63.8 |
| 1375423 | 64.2 |
| 1375424 | 64.2 |
| 1375425 | 64.4 |
| 1375426 | 64.4 |
| 1375427 | 63.9 |
| 1375428 | 63.1 |
| 1375429 | 63.4 |
| 1375430 | 63.8 |
| 1375431 | 64.1 |
| 1375432 | 63.7 |
| 1386094 | 64.6 |
| 1378793 | 63.9 |
| 1386355 | 63.3 |
| 1378794 | 63.7 |

Example 5: Design and Synthesis of Modified Internucleoside Linkages

Additional modified internucleoside linkages described herein may be prepared via a Staudinger reaction similar to the reaction in Example 1, but where a substituted azide is used in place of the mesyl azide in Example 1.

For example, during the synthesis of a modified oligonucleotide, reaction of substituted azide (1) below with a 2-cyanoethyl phosphite internucleoside linkage will form the modified oligonucleotide intermediate shown below:

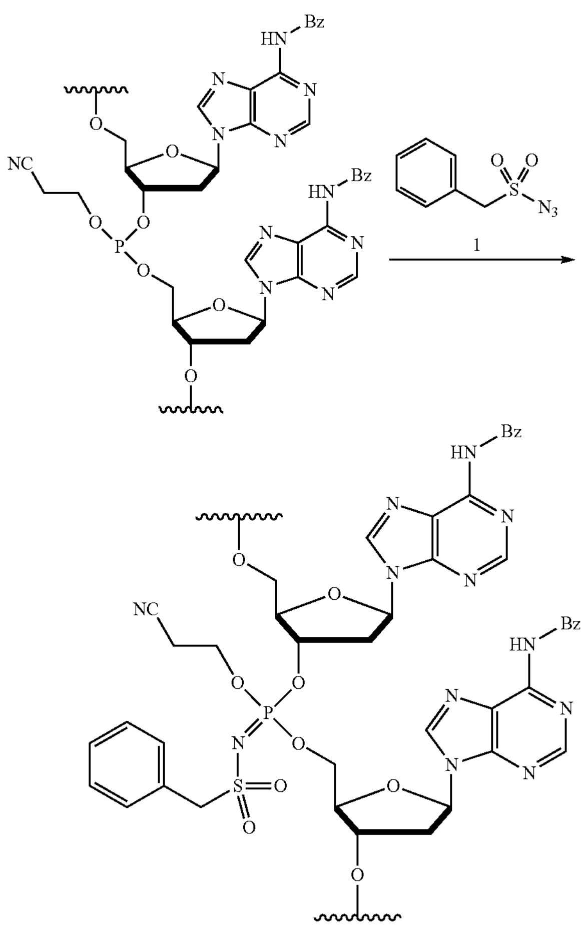

Upon deprotection and purification of the modified oligonucleotide the modified internucleoside linkage intermediate above becomes the modified internucleoside linkage below:

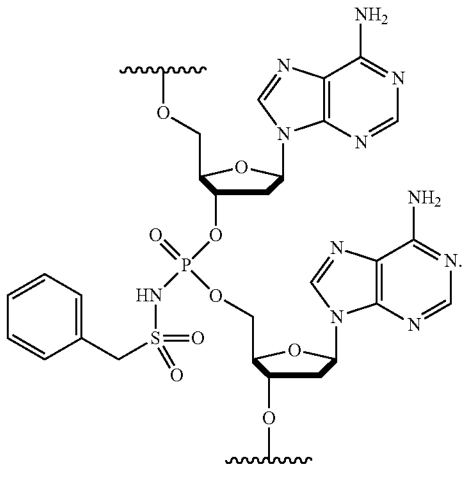

Alternatively, during the synthesis of a modified oligonucleotide, reaction of substituted azide (2) below with a 2-cyanoethyl phosphite internucleoside linkage will form the modified oligonucleotide intermediate shown below:

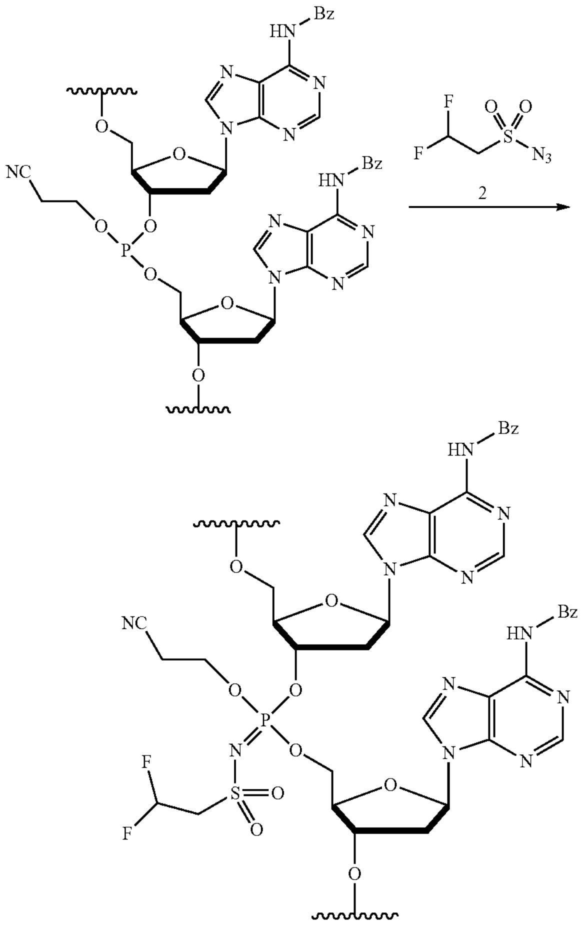

Upon deprotection and purification of the modified oligonucleotide, the modified internucleoside linkage intermediate above becomes the modified internucleoside linkage below:

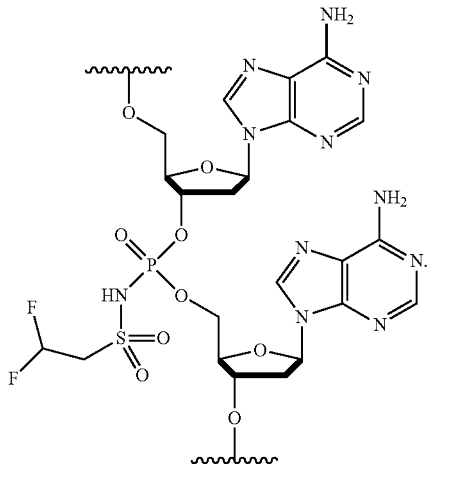

Alternatively, during the synthesis of a modified oligonucleotide, reaction of substituted azide (3) below with a 2-cyanoethyl phosphite internucleoside linkage will form the modified oligonucleotide intermediate shown below:

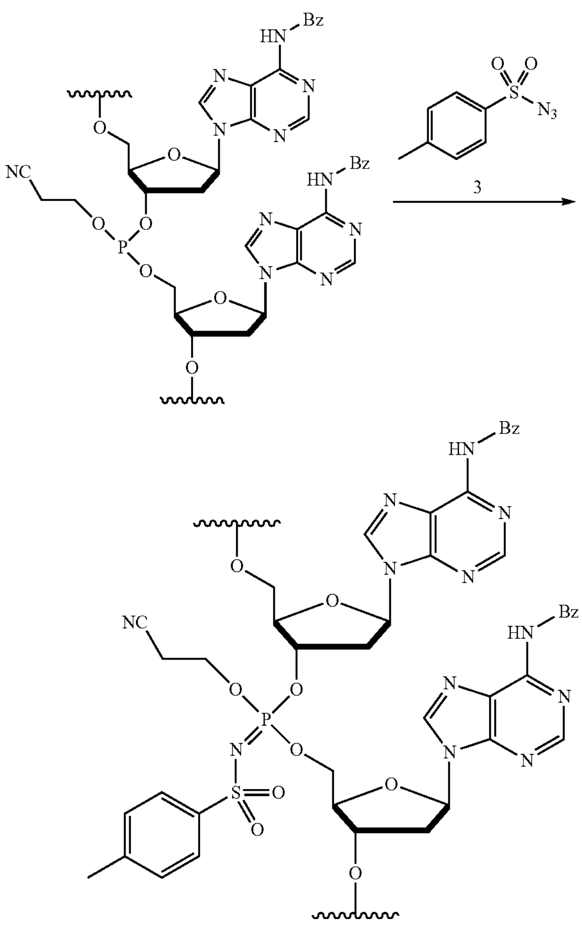

Upon deprotection and purification of the modified oligonucleotide, the modified internucleoside linkage intermediate above becomes the modified internucleoside linkage below:

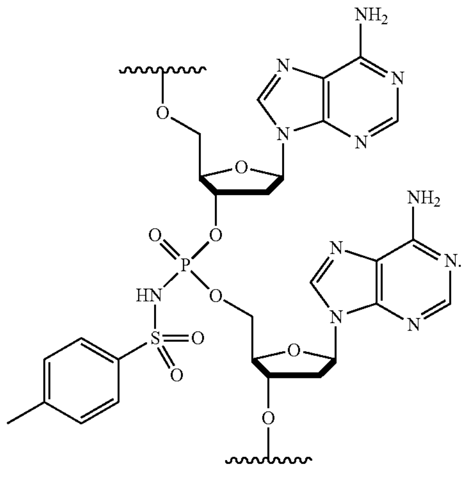

Alternatively, during the synthesis of a modified oligonucleotide, reaction of substituted azide (4) below with a 2-cyanoethyl phosphite internucleoside linkage will form the modified oligonucleotide intermediate shown below:

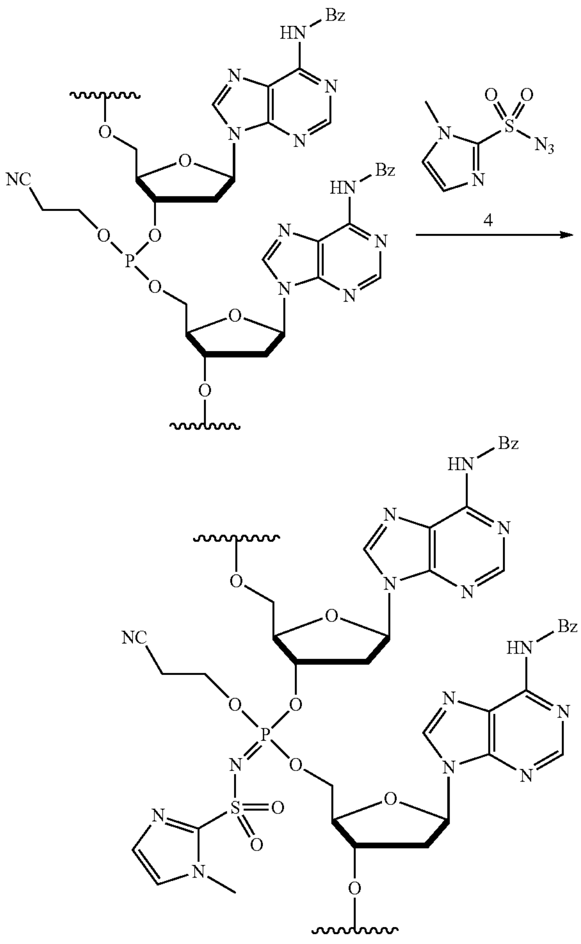

Upon deprotection and purification of the modified oligonucleotide, the modified internucleoside linkage intermediate above becomes the modified internucleoside linkage below:

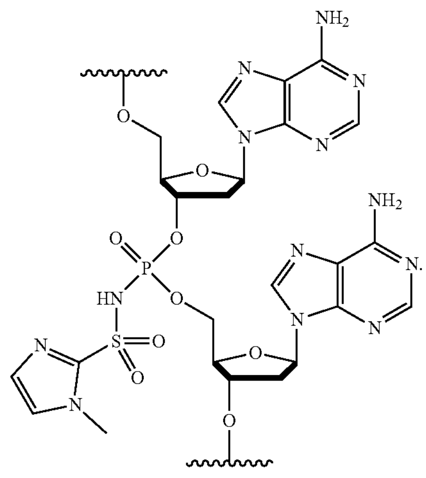

Alternatively, during the synthesis of a modified oligonucleotide, reaction of substituted azide (5) below with a 2-cyanoethyl phosphite internucleoside linkage will form the modified oligonucleotide intermediate shown below:

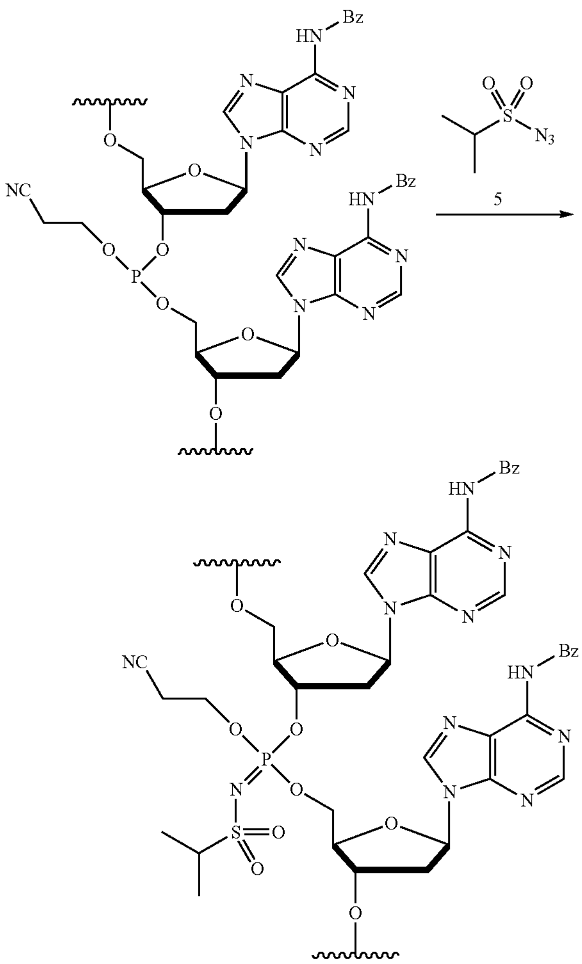

Upon deprotection and purification of the modified oligonucleotide, the modified internucleoside linkage intermediate above becomes the modified internucleoside linkage below:

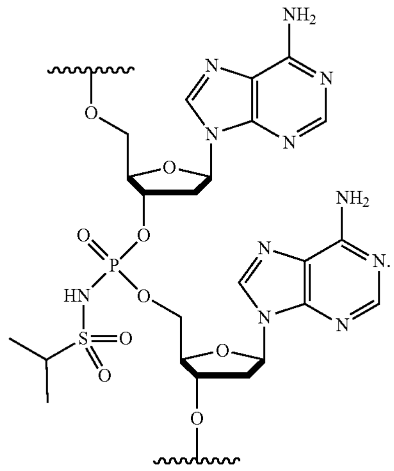

Alternatively, during the synthesis of a modified oligonucleotide, reaction of substituted azide (6) below with a 2-cyanoethyl phosphite internucleoside linkage will form the modified oligonucleotide intermediate shown below:

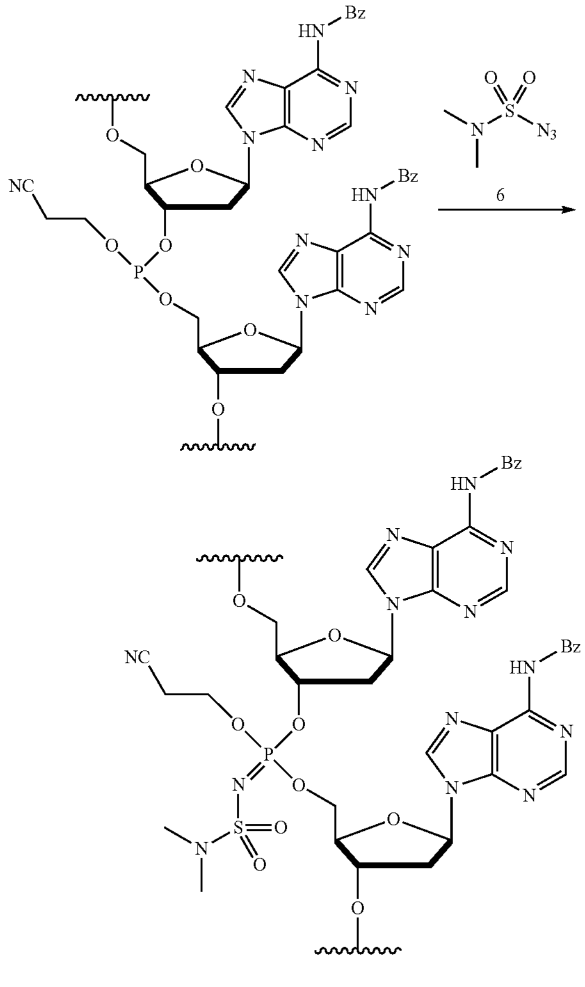

Upon deprotection and purification of the modified oligonucleotide, the modified internucleoside linkage intermediate above becomes the modified internucleoside linkage below:

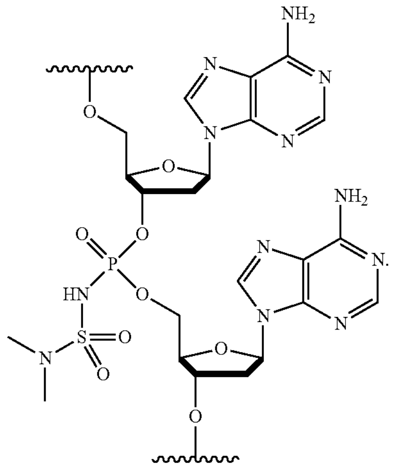

Alternatively, during the synthesis of a modified oligonucleotide, reaction of substituted azide (7) below with a 2-cyanoethyl phosphite internucleoside linkage will form the modified oligonucleotide intermediate shown below:

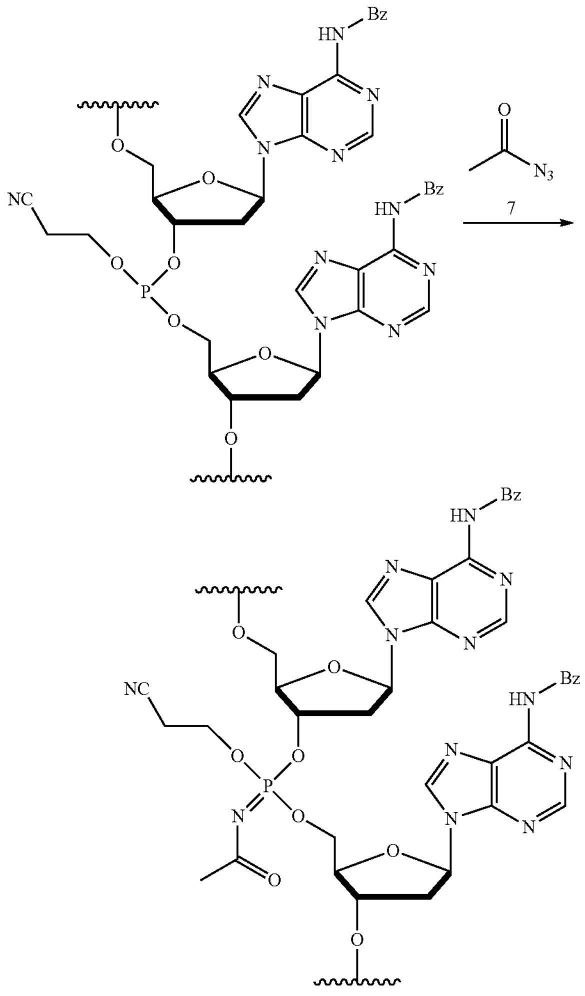

Upon deprotection and purification of the modified oligonucleotide, the modified internucleoside linkage intermediate above becomes the modified internucleoside linkage below:

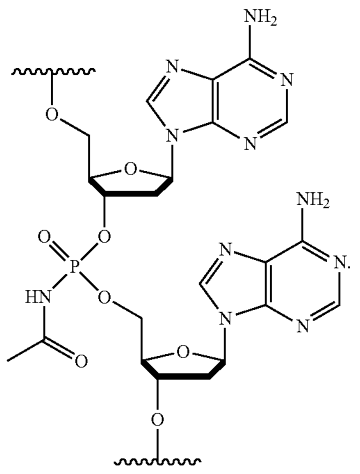

Alternatively, during the synthesis of a modified oligonucleotide, reaction of substituted azide (8) below with a 2-cyanoethyl phosphite internucleoside linkage will form the modified oligonucleotide intermediate shown below:

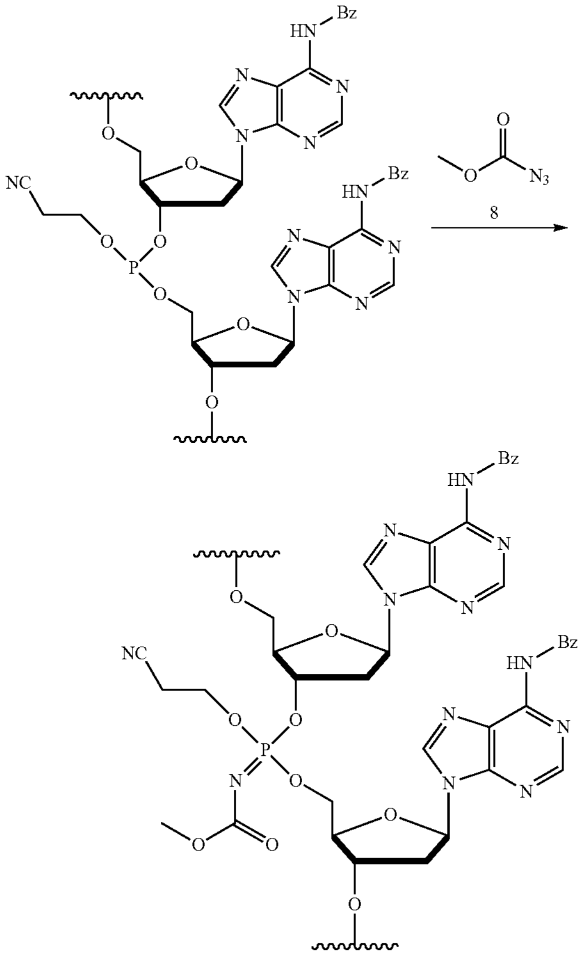

Upon deprotection and purification of the modified oligonucleotide, the modified internucleoside linkage intermediate above becomes the modified internucleoside linkage below:

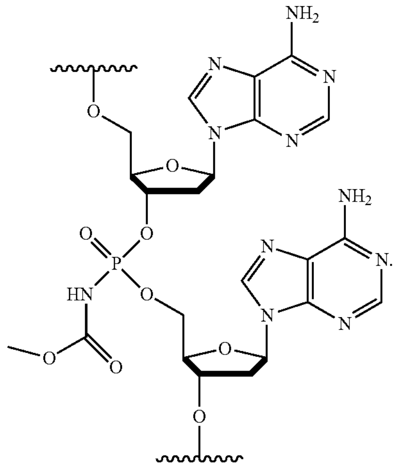

Alternatively, during the synthesis of a modified oligonucleotide, reaction of substituted azide (9) below with a 2-cyanoethyl phosphite internucleoside linkage will form the modified oligonucleotide intermediate shown below:

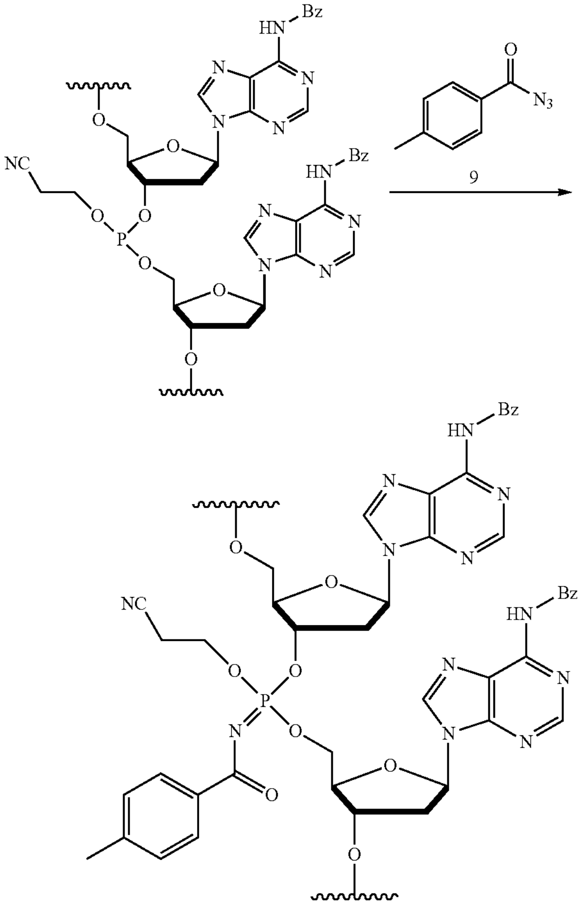

Upon deprotection and purification of the modified oligonucleotide, the modified internucleoside linkage intermediate above becomes the modified internucleoside linkage below:

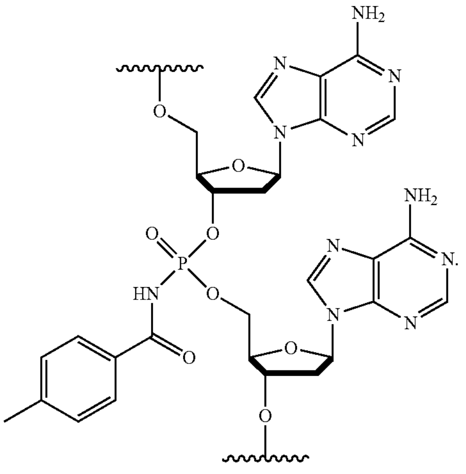

Alternatively, during the synthesis of a modified oligonucleotide, reaction of substituted azide (10) below with a 2-cyanoethyl phosphite internucleoside linkage will form the modified oligonucleotide intermediate shown below:

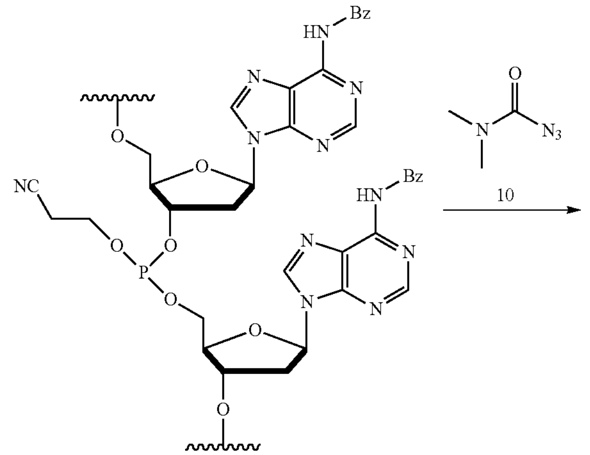

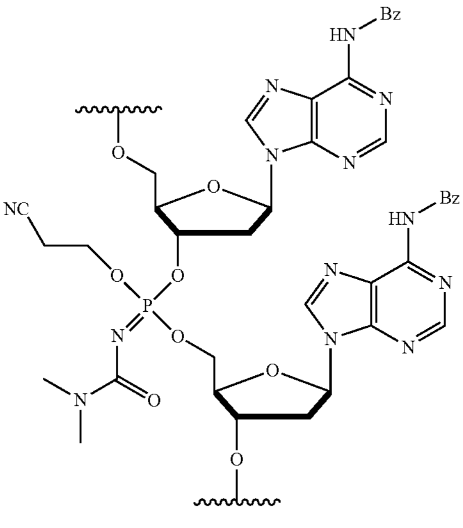

Upon deprotection and purification of the modified oligonucleotide, the modified internucleoside linkage intermediate above becomes the modified internucleoside linkage below:

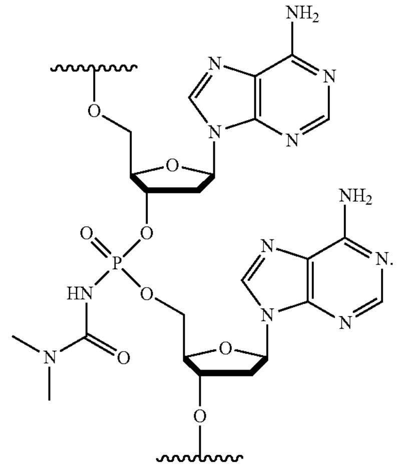

Alternatively, during the synthesis of a modified oligonucleotide, reaction of substituted azide (11) below with a 2-cyanoethyl phosphite internucleoside linkage will form the modified oligonucleotide intermediate shown below:

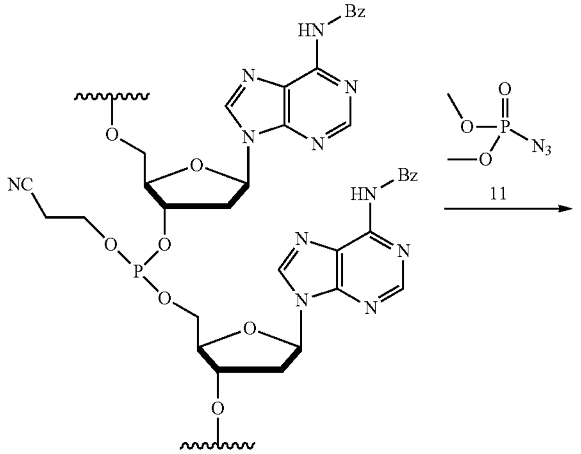

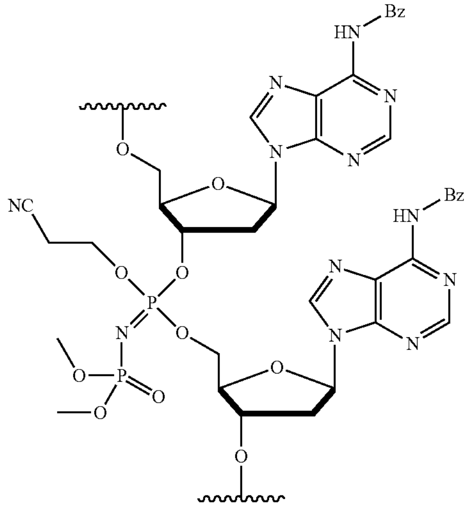

Upon deprotection and purification of the modified oligonucleotide, the modified internucleoside linkage intermediate above becomes the modified internucleoside linkage below:

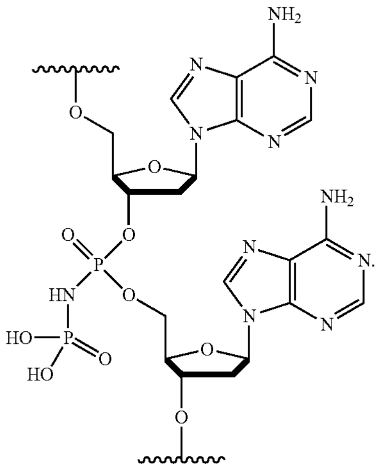

Alternatively, during the synthesis of a modified oligonucleotide, reaction of substituted azide (12) below with a 2-cyanoethyl phosphite internucleoside linkage will form the modified oligonucleotide intermediate shown below:

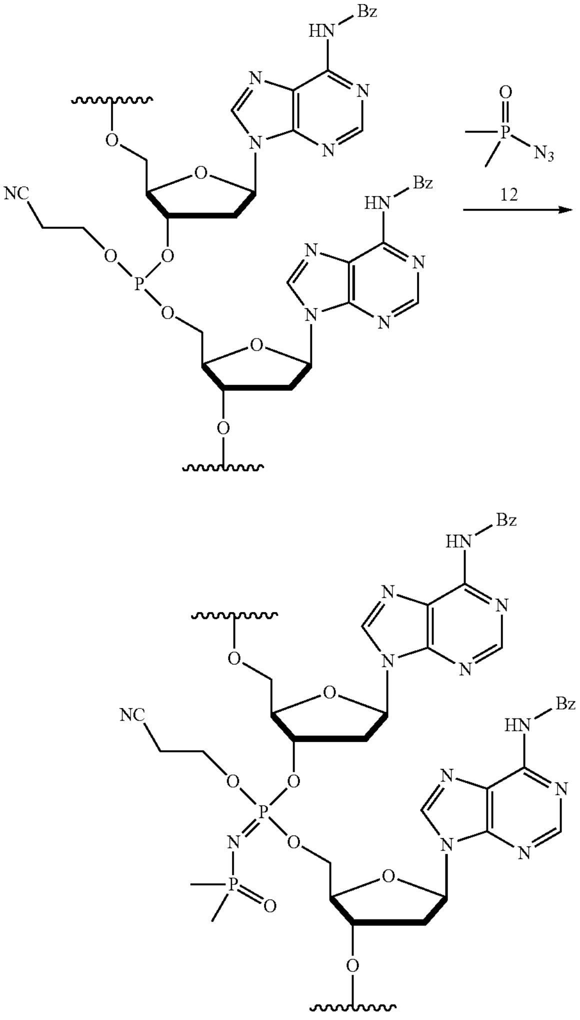

Upon deprotection and purification of the modified oligonucleotide, the modified internucleoside linkage intermediate above becomes the modified internucleoside linkage below:

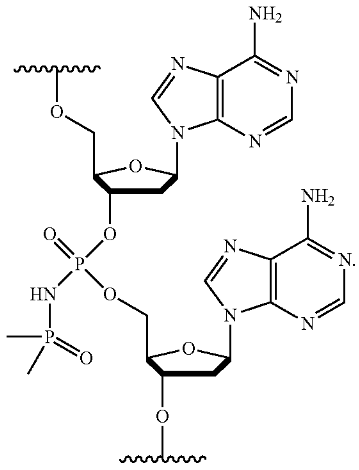

Alternatively, during the synthesis of a modified oligonucleotide, reaction of substituted azide (13) below with a 2-cyanoethyl phosphite internucleoside linkage will form the modified oligonucleotide intermediate shown below:

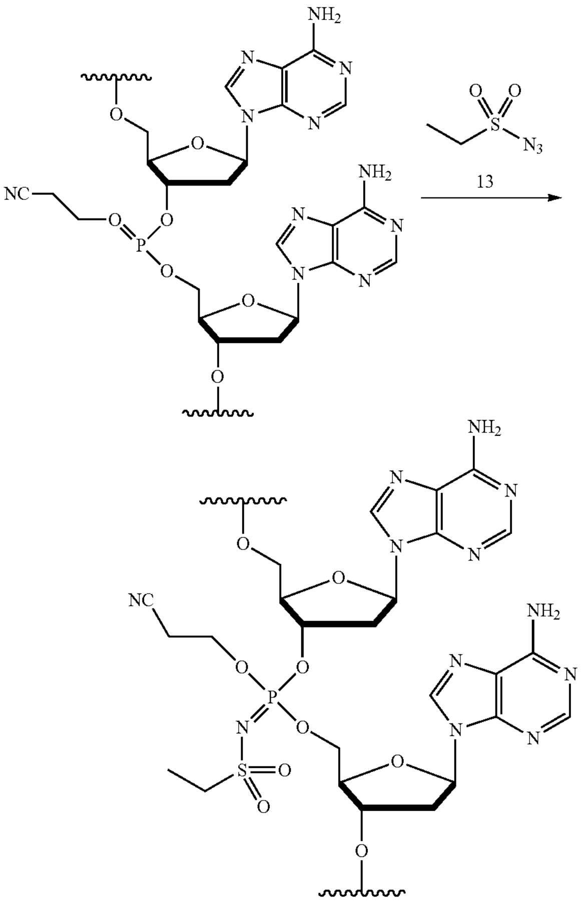

Upon deprotection and purification of the modified oligonucleotide, the modified internucleoside linkage intermediate above becomes the modified internucleoside linkage below:

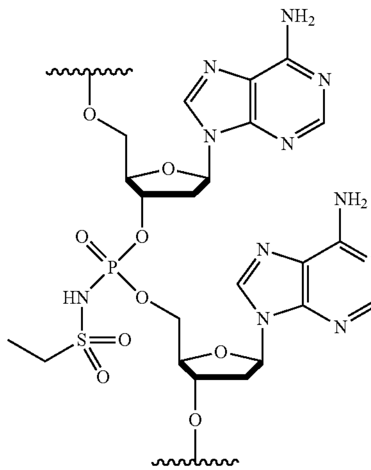

Alternatively, during the synthesis of a modified oligonucleotide, reaction of substituted azide (14) below with a 2-cyanoethyl phosphite internucleoside linkage will form the modified oligonucleotide intermediate shown below:

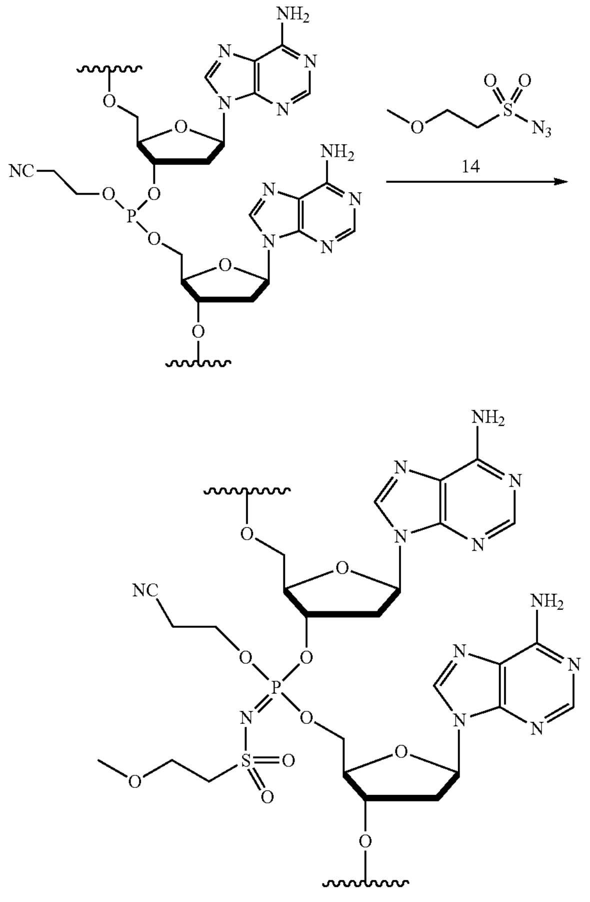

Upon deprotection and purification of the modified oligonucleotide, the modified internucleoside linkage intermediate above becomes the modified internucleoside linkage below:

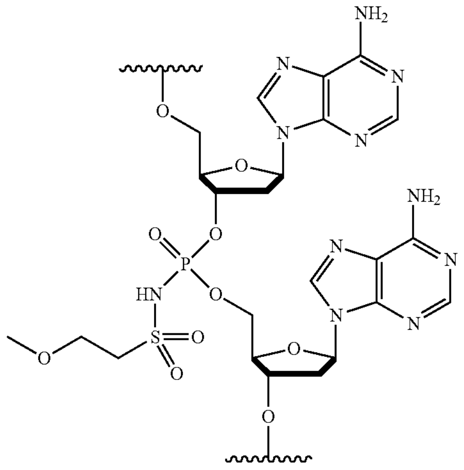

Additional substituted azides are known and readily available or easily synthesized.

Example 6: Activity and Tolerability of Modified Oligonucleotides with Mesyl Phosphoramidate Internucleoside Linkages In Vivo For the in vivo activity and tolerability study in the tables below, 3 BALB/C mice per group were administered modified oligonucleotide by subcutaneous injection and sacrificed after 72 hours. Compound 558807 was dosed at 1.8, 5.5, 16.7, or 50 mg/kg, while other modified oligonucleotides were dosed at 1.8, 5.5, 16.7, 50, or 150 mg/kg.

Tissue were collected and mRNA was isolated and levels of CXCL12 in both liver and kidney samples were measured by RT-qPCR with primer probe set RTS2605 as described above. Levels of P21 were analyzed using primer probe set Mm04207341_m1 (ThermoFisher) in liver and kidney and levels of Tnfrsf10b were analyzed using primer probe set Mm00457866_m1 (ThermoFisher) in liver. Elevated P21 or Tnfrsf10b indicates toxicity. Plasma ALT was measured. Elevations in ALT are associated with liver toxicity.

Expression levels were normalized with Ribogreen® and are presented relative to levels in mice treated with PBS. In addition to compounds containing a mesyl phosphoramidate internucleoside linkage, Compound No. 936053 was tested. This compound has the sequence GCATGTTCTCACATTA (SEQ ID NO: 5) and a sugar motif of kkk-d-m-dddddddd-kkk, wherein each "k" represents a cEt nucleoside, each "d" represents a stereo-standard DNA nucleoside, and "m" represents a 2'-OMe nucleoside. Compound No. 936053 was described in WO2019/157531, and is included as a comparator compound as it has reduced toxicity relative to 558807 as well as reduced potency in vivo. Note that at least some of the observed potency of 558807 is "false"; that is, the RNA reduction observed is not specific to RNAse H mediated reduction of CXCL12 RNA, but rather, is related to global reductions in RNA due to cellular toxicity. Therefore, Compound No. 936503 represents a better comparator compound for determining the relative in vivo potency of compounds comprising mesyl phosphoramidate internucleoside linkages.

TABLE 8

In Vivo Activity and Toxicity of modified oligonucleotides complementary to CXCL12

| Compound ID | position of modifications in the gap (5' to 3') | in vivo CXCL12 ED50 liver (mg/kg) | in vivo CXCL12 ED50 kidney (mg/kg) | ALT @50 mg/kg (IU/L) | ALT @ 150 mg/kg (IU/L) |
|---|---|---|---|---|---|
| 558807 | n/a | 1.0 | 31 | 7666 @ 50 mg/kg | |
| 936053 | nucleoside 2 | 5.5 | 38 | 23 | 29 |
| 1375426 | linkages 3-4, 4-5 | 4.1 | 41 | 55 | 4325 |
| 1375427 | linkages 2-3, 3-4 | 4.5 | 52 | 29 | 1519 |
| 1375428 | linkages 1-2, 2-3 | 4.7 | 38 | 473 | 3945 |

TABLE 9

In Vivo Dose-response of liver P21 mRNA upon treatment with modified oligonucleotides complementary CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 48 | 87 | 1148 | 11488 | n.d. |
| 936053 | 98 | 142 | 137 | 132 | 169 |
| 1375426 | 113 | 114 | 106 | 250 | 6388 |
| 1375427 | 79 | 230 | 179 | 180 | 2171 |
| 1375428 | 142 | 111 | 45 | 788 | 12412 |

TABLE 10

In Vivo Dose-response of kidney P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 108 | 140 | 149 | 649 | n.d. |
| 936053 | 100 | 162 | 151 | 105 | 122 |
| 1375426 | 125 | 151 | 132 | 133 | 156 |
| 1375427 | 156 | 170 | 167 | 122 | 208 |
| 1375428 | 143 | 116 | 104 | 109 | 237 |

TABLE 11

In Vivo Dose-response of liver Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 96 | 122 | 870 | 11757 | n.d. |
| 936053 | 151 | 121 | 132 | 148 | 191 |
| 1375426 | 124 | 150 | 115 | 213 | 4869 |
| 1375427 | 116 | 178 | 127 | 280 | 971 |
| 1375428 | 149 | 104 | 118 | 586 | 12528 |

Example 7: Design, Activity and Tolerability of Modified Oligonucleotides Complementary to SOD1 with Mesyl Phosphoramidate Internucleoside Linkages In Vitro

Modified Oligonucleotides

Modified oligonucleotides comprising two consecutive mesyl phosphoramidate internucleoside linkages (Formula IX) were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each internucleoside linkage is either a phosphorothioate internucleoside linkage ("s") or a mesyl phosphoramidate internucleoside linkage ("z"). Each of the compounds in the tables below has two consecutive internucleoside linkages of formula IX.

IX

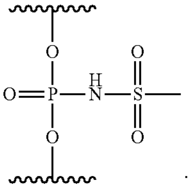

The compounds in the table below have the sequence TGAGGTCCTGCACTGG (SEQ ID NO: 11) and are 100% complementary to mouse SOD1, GENBANK NT_039625.7 truncated from 24924000 to 24933000 (SEQ ID NO: 7), at position 5685 to 5880.

In Vitro Activity Assay

The modified oligonucleotides were tested for their ability to reduce target RNA in a series of experiments. Cultured mouse 3T3-L1 cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, RNA levels were measured using mouse primer-probe set RTS3025 (SOD1; forward sequence: TTTTTTGCGCGGTCCTTTC (SEQ ID NO: 8); reverse sequence: GAGGGACCAGAGAGAGCAAGAC (SEQ ID NO: 9), probe sequence: CGCCTTCCGTCCGTCGGCT (SEQ ID NO: 10)). RNA levels for each target were normalized to total RNA content, as measured by RIBOGREEN®. Activity expressed as half maximal inhibitory concentration (IC50) was calculated using the log (inhibitor) vs response (three parameter) function in GraphPad Prism 7.

In Vitro Toxicity Assay

In vitro toxicity of modified oligonucleotides described above was determined as described in Example 3.

TABLE 12

Design, Activity, and Toxicity of modified oligonucleotides having two consecutive mesyl phosphoramidates linkages complementary to SOD1

| Compound Number | Chemistry Notation (5'-3') | SOD1 $IC_{50}$ (μM) | Caspase Activation (% Mock) | SEQ ID NO. |
|---|---|---|---|---|
| 508031 | $T_{ks}G_{ks}A_{ks}G_{ds}G_{ds}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 0.69 | 902 | 11 |
| 1405473 | $T_{ks}G_{ks}A_{ks}G_{ds}\ G_{\underline{dz}}T_{\underline{dz}}\ {}^{m}C_{ds}{}^{m}C_{ds}T_{ds}G_{ds}{}^{m}C_{ds}A_{ds}{}^{m}C_{ds}T_{ks}G_{ks}G_{k}$ | 0.38 | 273 | 11 |

TABLE 12-continued

| Design, Activity, and Toxicity of modified oligonucleotides having two consecutive mesyl phosphoramidates linkages complementary to SOD1 | | | | |
|---|---|---|---|---|
| Compound Number | Chemistry Notation (5'-3') | SOD1 $IC_{50}$ (μM) | Caspase Activation (% Mock) | SEQ ID NO. |
| 1405474 | $T_{ks}G_{ks}A_{ks}G_{ds}G_{ds}T_{\underline{\mathbf{dz}}}{}^{m}C_{\underline{\mathbf{dz}}}{}^{m}C_{ds}T_{ds}G_{ds}{}^{m}C_{ds}A_{ds}{}^{m}C_{ds}T_{ks}G_{ks}G_{k}$ | 0.33 | 345 | 11 |
| 1405475 | $T_{ks}G_{ks}A_{ks}G_{ds}G_{ds}T_{ds}{}^{m}C_{ds}{}^{m}C_{ds}T_{ds}G_{\underline{\mathbf{dz}}}{}^{m}C_{\underline{\mathbf{dz}}}A_{ds}{}^{m}C_{ds}T_{ks}G_{ks}G_{k}$ | 0.47 | 844 | 11 |

A subscript "k" represents a cEt nucleoside, a subscript "d" represents a stereo-standard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage offormula IX are bold and underlined. A superscript "m" before a C represents a 5-methyl Cytosine.

Example 8: Design, Activity and Tolerability of Modified Oligonucleotides Complementary to HDAC2 with Mesyl Phosphoramidate Internucleoside Linkages In Vitro Modified Oligonucleotides Modified oligonucleotides comprising two consecutive mesyl phosphoramidate internucleoside linkages (Formula IX) were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each internucleoside linkage is either a phosphorothioate internucleoside linkage ("s") or a mesyl phosphoramidate internucleoside linkage ("z"). Each of the compounds in the tables below has two consecutive internucleoside linkages of formula IX.

IX

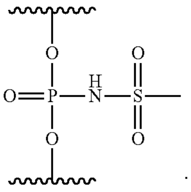

The compounds in the table below are 100% complementary to mouse HDAC2, GENBANK NC_000076.6 truncated from 36972001 to 37005000 (SEQ ID NO: 12), at several positions, as indicated in the table below.

TABLE 13

| Positions of modified oligonucleotides complementary to HDAC2 | | | | |
|---|---|---|---|---|
| Compound Number | Sequence (5' to 3') | Start Site | Stop Site | SEQ ID NO: |
| 546108 | TAGTCTCTGTCAGTTA | 8162 | 8177 | 13 |
| | | 8204 | 8219 | |
| | | 8246 | 8261 | |
| | | 8330 | 8345 | |

TABLE 13-continued

| Positions of modified oligonucleotides complementary to HDAC2 | | | | |
|---|---|---|---|---|
| Compound Number | Sequence (5' to 3') | Start Site | Stop Site | SEQ ID NO: |
| 546110 | TCATGTACCTATAGTC | 8173 | 8188 | 14 |
| | | 8215 | 8230 | |
| | | 8257 | 8272 | |
| | | 8299 | 8314 | |
| | | 8341 | 8356 | |

In Vitro Activity Assay

The modified oligonucleotides were tested for their ability to reduce target RNA in a series of experiments. Cultured mouse 3T3-L1 cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, RNA levels were measured using mouse HDAC2 primer-probe set RTS3500 (forward sequence TGATGGTGTTGAGGAAGCTTTTT (SEQ ID NO: 15, reverse sequence: TCCCTCAAGTCTCCTGTTCCA (SEQ ID NO: 16), probe sequence: ACAACAGATCGCGTGATGACCGTCTC, (SEQ ID NO: 17)). RNA levels for each target were normalized to total RNA content, as measured by RIBOGREEN Activity expressed as half maximal inhibitory concentration ($IC_{50}$) was calculated using the log (inhibitor) vs response (three parameter) function in GraphPad Prism 7.

In Vitro Toxicity Assay

In vitro toxicity of modified oligonucleotides described above was determined as described in Example 3.

TABLE 14

Modified oligonucleotides having two consecutive mesyl phosphoramidate linkages complementary to HDAC2

| Compound Number | Chemistry Notation (5'-3') | HDAC2 $IC_{50}$ (µM) | Caspase Activation (% Mock) | SEQ ID NO. |
|---|---|---|---|---|
| 546108 | $T_{ks}A_{ks}G_{ks}T_{ds}{}^{m}C_{ds}T_{ds}{}^{m}C_{ds}T_{ds}G_{ds}T_{ds}{}^{m}C_{ds}A_{ds}G_{ds}T_{ks}T_{ks}A_{k}$ | 0.57 | 602 | 13 |
| 1405476 | $T_{ks}A_{ks}G_{ks}T_{ds}{}^{m}C_{\underline{\mathbf{dz}}}T_{\underline{\mathbf{dz}}}{}^{m}C_{ds}T_{ds}G_{ds}T_{ds}{}^{m}C_{ds}A_{ds}G_{ds}T_{ks}T_{ks}A_{k}$ | 0.24 | 178 | 13 |
| 1405477 | $T_{ks}A_{ks}G_{ks}T_{ds}{}^{m}C_{ds}T_{\underline{\mathbf{dz}}}{}^{m}C_{\underline{\mathbf{dz}}}T_{ds}G_{ds}T_{ds}{}^{m}C_{ds}A_{ds}G_{ds}T_{ks}T_{ks}A_{k}$ | 0.31 | 225 | 13 |
| 1405478 | $T_{ks}A_{ks}G_{ks}T_{ds}{}^{m}C_{ds}T_{ds}{}^{m}C_{ds}T_{ds}G_{ds}T_{dz}{}^{m}C_{dz}A_{ds}G_{ds}T_{ks}T_{ks}A_{k}$ | 0.28 | 207 | 13 |
| 546110 | $T_{ks}{}^{m}C_{ks}A_{ks}T_{ds}G_{ds}T_{ds}A_{ds}{}^{m}C_{ds}{}^{m}C_{ds}T_{ds}A_{ds}T_{ds}A_{ds}G_{ks}T_{ks}{}^{m}C_{k}$ | 0.20 | 142 | 14 |
| 1405479 | $T_{ks}{}^{m}C_{ks}A_{ks}T_{ds}G_{dz}T_{dz}A_{ds}{}^{m}C_{ds}{}^{m}C_{ds}T_{ds}A_{ds}T_{ds}A_{ds}G_{ks}T_{ks}{}^{m}C_{k}$ | 0.61 | 74 | 14 |
| 1405480 | $T_{ks}{}^{m}C_{ks}A_{ks}T_{ds}G_{ds}T_{\underline{\mathbf{dz}}}A_{\underline{\mathbf{dz}}}{}^{m}C_{ds}{}^{m}C_{ds}T_{ds}A_{ds}T_{ds}A_{ds}G_{ks}T_{ks}{}^{m}C_{k}$ | 0.43 | 79 | 14 |
| 1405481 | $T_{ks}{}^{m}C_{ks}A_{ks}T_{ds}G_{ds}T_{ds}A_{ds}{}^{m}C_{ds}{}^{m}C_{ds}T_{dz}A_{dz}T_{ds}A_{ds}G_{ks}T_{ks}{}^{m}C_{k}$ | 0.63 | 113 | 14 |

A subscript "k" represents a cEt nucleoside, a subscript "d" represents a stereo-standard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 9: Design, Activity and Tolerability of Modified Oligonucleotides Having Multiple Mesyl Phosphoramidate Internucleoside Linkages In Vitro Modified Oligonucleotides Modified oligonucleotides comprising multiple mesyl phosphoramidate internucleoside linkages (Formula IX) were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s") or a mesyl phosphoramidate internucleoside linkage ("z").

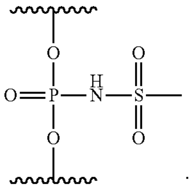

IX

In Vitro Assays

In vitro activity of modified oligonucleotides described above was determined as described in Example 1. In vitro toxicity of modified oligonucleotides described above was determined as described in Example 3.

Each of the compounds in the table below has three or four consecutive internucleoside linkages of formula IX.

TABLE 15

Design, Activity, and Tolerability of modified oligonucleotides having three or four consecutive mesyl phosphoramidates linkages complementary to CXCL12

| Compound Number | Chemistry Notation (5'-3') | CXCL12 $IC_{50}$ (µM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 0.17 | 1329 | 5 |
| 1405434 | $G_{ks}{}^{m}C_{ks}A_{ks}T_{\underline{\mathbf{dz}}}G_{\underline{\mathbf{dz}}}T_{\underline{\mathbf{dz}}}T_{ds}{}^{m}C_{ds}T_{ds}{}^{m}C_{ds}A_{ds}{}^{m}C_{ds}A_{ds}T_{ks}T_{ks}A_{k}$ | 0.16 | 211 | 5 |
| 1405435 | $G_{ks}{}^{m}C_{ks}A_{ks}T_{ds}G_{\underline{\mathbf{dz}}}T_{\underline{\mathbf{dz}}}T_{\underline{\mathbf{dz}}}{}^{m}C_{ds}T_{ds}{}^{m}C_{ds}A_{ds}{}^{m}C_{ds}A_{ds}T_{ks}T_{ks}A_{k}$ | 0.12 | 240 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Each of the compounds in the table below has multiple internucleoside linkages of formula IX.

TABLE 16

Design, Activity, and Tolerability of modified oligonucleotides having multiple mesyl phosphoramidate linkages complementary to CXCL12

| Compound Number | Chemistry Notation (5'-3') | CXCL1 $IC_{50}$ (μM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 0.20 | 2727 | 5 |
| 1437592 | $G_{ks}{}^{m}C_{ks}A_{\underline{\mathbf{kz}}}T_{\underline{\mathbf{dz}}}G_{\underline{\mathbf{dz}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 0.11 | 1708 | 5 |
| 1437593 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{ds}{}^{m}C_{ds}T_{ds}{}^{m}C_{ds}A_{ds}{}^{m}C_{ds}A_{ds}T_{ks}T_{ks}A_{k}$ | 0.15 | 500 | 5 |
| 1437594 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{ds}T_{ds}{}^{m}C_{ds}A_{ds}{}^{m}C_{ds}A_{ds}T_{ks}T_{ks}A_{k}$ | 0.24 | 308 | 5 |
| 1437595 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{ds}{}^{m}C_{ds}A_{ds}{}^{m}C_{ds}A_{ds}T_{ks}T_{ks}A_{k}$ | 0.26 | 309 | 5 |
| 1437596 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{ds}A_{ds}{}^{m}C_{ds}A_{ds}T_{ks}T_{ks}A_{k}$ | 0.50 | 324 | 5 |
| 1437597 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{ds}{}^{m}C_{ds}A_{ds}T_{ks}T_{ks}A_{k}$ | 0.28 | 193 | 5 |
| 1437598 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{ds}A_{ds}T_{ks}T_{ks}A_{k}$ | 0.44 | 181 | 5 |
| 1437599 | $G_{ks}{}^{m}C_{ks}A_{ks}T_{ds}G_{ds}T_{ds}T_{ds}{}^{m}C_{ds}T_{ds}{}^{m}C_{ds}A_{\underline{\mathbf{dz}}}{}^{m}C_{\underline{\mathbf{dz}}}A_{\underline{\mathbf{dz}}}T_{ks}T_{ks}A_{k}$ | 0.16 | 1290 | 5 |
| 1437600 | $G_{ks}{}^{m}C_{ks}A_{ks}T_{ds}G_{ds}T_{ds}T_{ds}{}^{m}C_{ds}T_{ds}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 0.14 | 1807 | 5 |
| 1437601 | $G_{ks}{}^{m}C_{ks}A_{ks}T_{ds}G_{ds}T_{ds}T_{ds}{}^{m}C_{ds}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 0.18 | 1941 | 5 |
| 1437602 | $G_{ks}{}^{m}C_{ks}A_{ks}T_{ds}G_{ds}T_{ds}T_{ds}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 0.13 | 1927 | 5 |
| 1437603 | $G_{ks}{}^{m}C_{ks}A_{ks}T_{ds}G_{ds}T_{ds}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 0.32 | 866 | 5 |
| 1437604 | $G_{ks}{}^{m}C_{ks}A_{ks}T_{ds}G_{ds}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 0.97 | 250 | 5 |
| 1437605 | $G_{ks}{}^{m}C_{ks}A_{ks}T_{ds}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 1.84 | 152 | 5 |
| 1437606 | $G_{ks}{}^{m}C_{ks}A_{ks}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 1.69 | 155 | 5 |
| 1441068 | $G_{ks}{}^{m}C_{ks}A_{\underline{\mathbf{kz}}}T_{ds}G_{\underline{\mathbf{dz}}}T_{ds}T_{\underline{\mathbf{dz}}}{}^{m}C_{ds}T_{\underline{\mathbf{dz}}}{}^{m}C_{ds}A_{\underline{\mathbf{dz}}}{}^{m}C_{ds}A_{\underline{\mathbf{dz}}}T_{ks}T_{ks}A_{k}$ | 0.29 | 759 | 5 |
| 1441069 | $G_{ks}{}^{m}C_{ks}A_{ks}T_{\underline{\mathbf{dz}}}G_{ds}T_{\underline{\mathbf{dz}}}T_{ds}{}^{m}C_{\underline{\mathbf{dz}}}T_{ds}{}^{m}C_{\underline{\mathbf{dz}}}A_{ds}{}^{m}C_{\underline{\mathbf{dz}}}A_{ds}T_{ks}T_{ks}A_{k}$ | 0.39 | 1122 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 10: Design, Synthesis, Activity, and Tolerability of Modified Oligonucleotides Having Various Modified Phosphoramidate Internucleoside Linkages In Vitro Modified oligonucleotides comprising mesyl phosphoramidate internucleoside linkages were synthesized and tested. The modified oligonucleotides are each 3-10-3 cEt gapmers with a sugar motif of (from 5' to 3'): kkkddddddddddkkk (a 3-10-3 cEt motif) wherein "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s") or a modified phosphoramidate internucleoside linkage represented by formulas X-XVI, as indicated in the table below.

X

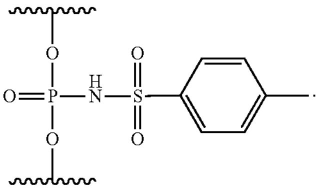

tosyl phosphoramidate

XI

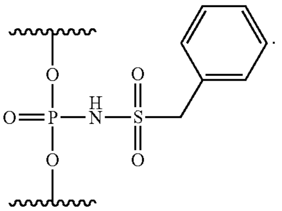

benzylsulfonyl phosphoramidate

-continued

XII

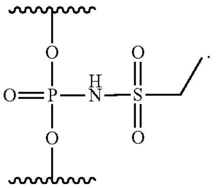

ethylsulfonyl phosphoramidate

XIII

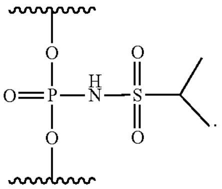

isopropylsulfonyl phoshporamidate

XIV

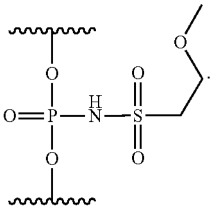

methoxyethylsulfonyl phoshporamidate

XV

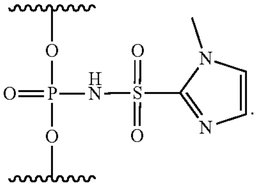

N-methyl imidazole sulfonyl phoshporamidate

XVI

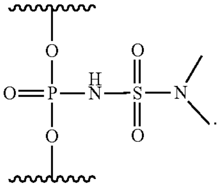

dimethylamino sylfonyl phosphoramidate

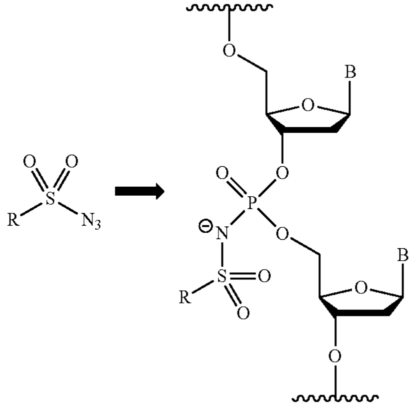

Oligonucleotides were synthesized on a 2 μmol scale using VIMAD UnyLinker support (200 μmol/g) on an ABI 394 DNA/RNA synthesizer. Fully protected nucleoside phosphoramidites were incorporated using standard solid-phase oligonucleotide synthesis, i.e. 3% dichloroacetic acid in dichloromethane for deblocking, 1 M 4,5-dicyanoimidazole 0.1 M N-methylimidazole in acetonitrile as activator for amidite couplings, 20% acetic anhydride in THF and 10% 1-methylimidazole in THF/pyridine for capping and 0.1 M xanthane hydride in pyridine:acetonitrile 3:2 (v:v) for thiolation. Mesyl phosphoramidate couplings were oxidized instead of thiolated using 0.5 M mesyl azide in acetonitrile: toluene 1:1 (v:v) with oxidation times varying (3x500s to 6x900s) depending on the steric hindrance of the substituted azide or the steric hindrance of the phosphoramidite being oxidized (Table 17 and Table 18). Amidites were dissolved to 0.1 M in acetonitrile:toluene 1:1 (v:v) and incorporated using 6 min coupling recycling time for DNA amidites and 10 min for all other amidites. At the end of the solid phase synthesis cyanoethyl protecting groups were removed by a 30 min treatment with 20% diethylamine in toluene. Modified oligonucleotides were deprotected and cleaved using conc. aq. ammonia at room temperature for 48 h or at 55° C. overnight.

TABLE 17

Oxidation times for the various substituted azide analogs using an ABI oligonucleotides synthesizer on 2 μmol scale

| Substituted Azide | R= | Oxidation time |
|---|---|---|
| | methyl | 3 × 500 s |
| | ethyl | 3 × 500 s |
| | methoxy ethyl | 3 × 650 s |
| | isopropyl | 3 × 999 s |
| | tosyl | 3 × 500 s |
| 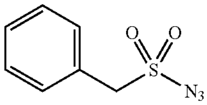 | benzyl | 3 × 500 s |
| 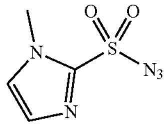 | N-methyl imidazole | 3 × 500 s |

TABLE 17-continued

| Oxidation times for the various substituted azide analogs using an ABI oligonucleotides synthesizer on 2 μmol scale | | |
|---|---|---|
| Substituted Azide | R= | Oxidation time |
| 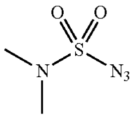 | dimethylamine | 4 × 900 s |

TABLE 18

| Oxidation times for various sugar phosphoramidites to form mesyl phosphoramidate linkages (R = methyl) | |
|---|---|
| Sugar modification | Oxidation time |
| DNA | 3 × 500 s |
| cEt | 6 × 900 s |

TABLE 18-continued

| Oxidation times for various sugar phosphoramidites to form mesyl phosphoramidate linkages (R = methyl) | |
|---|---|
| Sugar modification | Oxidation time |
| OMe | 3 × 650 s |
| MOE | 3 × 650 s |
| 2'-F | 4 × 750 s |
| LNA | 6 × 900 s |

In Vitro Assays

In vitro activity of modified oligonucleotides described above was determined as described in Example 1. In vitro toxicity of modified oligonucleotides described above was determined as described in Example 3. Each experiment is presented in a separate table.

TABLE 19

Design, activity, and tolerability of modified oligonucleotides having modified phosphoramidate linkages of formulas X, XI, or XII complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 150 | 1336 | 5 |
| 1419483 | $G_{ks}{}^{m}C_{ks}A_{ks}T_{\underline{\mathbf{dX}}}G_{\underline{\mathbf{dX}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 263 | 141 | 5 |
| 1419482 | $G_{ks}{}^{m}C_{ks}A_{ks}T_{ds}G_{\underline{\mathbf{dX}}}T_{\underline{\mathbf{dX}}}T_{ds}{}^{m}C_{ds}T_{ds}{}^{m}C_{ds}A_{ds}{}^{m}C_{ds}A_{ds}T_{ks}T_{ks}A_{k}$ | 299 | 88 | 5 |
| 1419481 | $G_{ks}{}^{m}C_{ks}A_{ks}T_{ds}G_{ds}T_{\underline{\mathbf{dX}}}T_{\underline{\mathbf{dX}}}{}^{m}C_{ds}T_{ds}{}^{m}C_{ds}A_{ds}{}^{m}C_{ds}A_{ds}T_{ks}T_{ks}A_{k}$ | 404 | 79 | 5 |
| 1419480 | $G_{ks}{}^{m}C_{ks}A_{ks}T_{ds}G_{ds}T_{ds}T_{ds}{}^{m}C_{ds}T_{ds}{}^{m}C_{\underline{\mathbf{dX}}}A_{\underline{\mathbf{dX}}}{}^{m}C_{ds}A_{ds}T_{ks}T_{ks}A_{k}$ | 171 | 433 | 5 |
| 1427921 | $G_{ks}{}^{m}C_{ks}A_{ks}T_{\underline{\mathbf{dXI}}}G_{\underline{\mathbf{dXI}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 439 | 134 | 5 |
| 1427922 | $G_{ks}{}^{m}C_{ks}A_{ks}T_{ds}G_{\underline{\mathbf{dXI}}}T_{\underline{\mathbf{dXI}}}T_{ds}{}^{m}C_{ds}T_{ds}{}^{m}C_{ds}A_{ds}{}^{m}C_{ds}A_{ds}T_{ks}T_{ks}A_{k}$ | 431 | 109 | 5 |
| 1427923 | $G_{ks}{}^{m}C_{ks}A_{ks}T_{ds}G_{ds}T_{\underline{\mathbf{dXI}}}T_{\underline{\mathbf{dXI}}}C_{ds}T_{ds}{}^{m}C_{ds}A_{ds}{}^{m}C_{ds}A_{ds}T_{ks}T_{ks}A_{k}$ | 465 | 90 | 5 |
| 1427924 | $G_{ks}{}^{m}C_{ks}A_{ks}T_{ds}G_{ds}T_{ds}T_{ds}{}^{m}C_{ds}T_{ds}C_{\underline{\mathbf{dXI}}}A_{\underline{\mathbf{dXI}}}{}^{m}C_{ds}A_{ds}T_{ks}T_{ks}A_{k}$ | 181 | 517 | 5 |
| 1417944 | $G_{ks}{}^{m}C_{ks}A_{ks}T_{\underline{\mathbf{dXII}}}G_{\underline{\mathbf{dXII}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 118 | 982 | 5 |
| 1417943 | $G_{ks}{}^{m}C_{ks}A_{ks}T_{ds}G_{\underline{\mathbf{dXII}}}T_{\underline{\mathbf{dXII}}}T_{ds}{}^{m}C_{ds}T_{ds}{}^{m}C_{ds}A_{ds}{}^{m}C_{ds}A_{ds}T_{ks}T_{ks}A_{k}$ | 136 | 274 | 5 |
| 1417942 | $G_{ks}{}^{m}C_{ks}A_{ks}T_{ds}G_{ds}T_{\underline{\mathbf{dXII}}}T_{\underline{\mathbf{dXII}}}{}^{m}C_{ds}T_{ds}{}^{m}C_{ds}A_{ds}{}^{m}C_{ds}A_{ds}T_{ks}T_{ks}A_{k}$ | 167 | 452 | 5 |
| 1417941 | $G_{ks}{}^{m}C_{ks}A_{ks}T_{ds}G_{ds}T_{ds}T_{ds}{}^{m}C_{ds}T_{ds}{}^{m}C_{\underline{\mathbf{dXII}}}A_{\underline{\mathbf{dXII}}}{}^{m}C_{ds}A_{ds}T_{ks}T_{ks}A_{k}$ | 63 | 2029 | 5 |

A subscript "k" represents a cEt leoside, a subscript "d" represents a stereo-standard DNA nucleoside, a subscript "s" indicates a phosphorothioate internucleoside linkage. A subscript "X" represents an internucleoside linkage of formula X; a subscript "XI" represents an internucleoside linkage of formula XI; a subscript "XII" represents an internucleoside linkage of formula XII. Subscripts of nucleotides having a substituted phosphoramidate internucleoside linkage of generic Formula XVII are bold and underlined. A superscript "m" before a C represents a 5-methyl Cytosine.

TABLE 20

Design, activity, and tolerability of modified oligonucleotides having modified phosphoramidate linkages of formulas XIII, XIV, or XV complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 98 | 986 | 5 |
| 1429189 | $G_{ks}{}^{m}C_{ks}A_{ks}T_{\underline{\mathbf{dXIII}}}G_{\underline{\mathbf{dXIII}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 80 | 638 | 5 |

TABLE 20-continued

Design, activity, and tolerability of modified oligonucleotides having modified phosphoramidate linkages of formulas XIII, XIV, or XV complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 1429190 | $G_{ks}{}^{m}C_{ks}A_{ks}T_{ds}G_{\underline{\mathbf{dXIII}}}T_{\underline{\mathbf{dXIII}}}T_{ds}{}^{m}C_{ds}T_{ds}{}^{m}C_{ds}A_{ds}{}^{m}C_{ds}A_{ds}T_{ks}T_{ks}A_{k}$ | 113 | 168 | 5 |
| 1429191 | $G_{ks}{}^{m}C_{ks}A_{ks}T_{ds}G_{ds}T_{\underline{\mathbf{dXIII}}}T_{\underline{\mathbf{dXIII}}}{}^{m}C_{ds}T_{ds}{}^{m}C_{ds}A_{ds}{}^{m}C_{ds}A_{ds}T_{ks}T_{ks}A_{k}$ | 111 | 184 | 5 |
| 1429192 | $G_{ks}{}^{m}C_{ks}A_{ks}T_{ds}G_{ds}T_{ds}T_{ds}{}^{m}C_{ds}T_{ds}{}^{m}C_{\underline{\mathbf{dXIII}}}A_{\underline{\mathbf{dXIII}}}{}^{m}C_{ds}A_{ds}T_{ks}T_{ks}A_{k}$ | 46 | 1004 | 5 |
| 1417948 | $G_{ks}C_{ks}A_{ks}T_{\underline{\mathbf{dXIV}}}G_{\underline{\mathbf{dXIV}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 98 | 1270 | 5 |
| 1417947 | $G_{ks}{}^{m}C_{ks}A_{ks}T_{ds}G_{\underline{\mathbf{dXIV}}}T_{\underline{\mathbf{dXIV}}}T_{ds}{}^{m}C_{ds}T_{ds}{}^{m}C_{ds}A_{ds}{}^{m}C_{ds}A_{ds}T_{ks}T_{ks}A_{k}$ | 141 | 271 | 5 |
| 1417946 | $G_{ks}{}^{m}C_{ks}A_{ks}T_{ds}G_{ds}T_{\underline{\mathbf{dXIV}}}T_{\underline{\mathbf{dXIV}}}{}^{m}C_{ds}T_{ds}{}^{m}C_{ds}A_{ds}{}^{m}C_{ds}A_{ds}T_{ks}T_{ks}A_{k}$ | 128 | 232 | 5 |
| 1417945 | $G_{ks}{}^{m}C_{ks}A_{ks}T_{ds}G_{ds}T_{ds}T_{ds}{}^{m}C_{ds}T_{ds}{}^{m}C_{\underline{\mathbf{dXIV}}}A_{\underline{\mathbf{dXIV}}}{}^{m}C_{ds}A_{ds}T_{ks}T_{ks}A_{k}$ | 276 | 95 | 5 |
| 1431805 | $G_{ks}{}^{m}C_{ks}A_{ks}T_{\underline{\mathbf{dXV}}}G_{\underline{\mathbf{dXV}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 299 | 235 | 5 |
| 1431806 | $G_{ks}{}^{m}C_{ks}A_{ks}T_{ds}G_{\underline{\mathbf{dXV}}}T_{\underline{\mathbf{dXV}}}T_{ds}{}^{m}C_{ds}T_{ds}{}^{m}C_{ds}A_{ds}{}^{m}C_{ds}A_{ds}T_{ks}T_{ks}A_{k}$ | 152 | 137 | 5 |
| 1431807 | $G_{ks}{}^{m}C_{ks}A_{ks}T_{ds}G_{ds}T_{\underline{\mathbf{dXV}}}T_{\underline{\mathbf{dXV}}}{}^{m}C_{ds}T_{ds}{}^{m}C_{ds}A_{ds}{}^{m}C_{ds}A_{ds}T_{ks}T_{ks}A_{k}$ | 243 | 119 | 5 |
| 1431808 | $G_{ks}{}^{m}C_{ks}A_{ks}T_{ds}G_{ds}T_{ds}T_{ds}{}^{m}C_{ds}T_{ds}{}^{m}C_{\underline{\mathbf{dXV}}}A_{\underline{\mathbf{dXV}}}{}^{m}C_{ds}A_{ds}T_{ks}T_{ks}A_{k}$ | 114 | 556 | 5 |

A subscript "k" represents a cEt nucleoside, a subscript "d" represents a stereo-standard DNA nucleoside, a subscript "s" indicates a phosphorothioate internucleoside linkage. A subscript "XIII" represents an internucleoside linkage of formula XIII; a subscript "XIV" represents an internucleoside linkage of formula XIV; a subscript "XV" represents aninternucleoside linkage of formula XV. Subscripts of nucleotides having a modified mesyl phosphoramidate internucleoside linkage of generic Formula XVII are bold and underlined. A superscript "m" before a C represents a 5-methyl Cytosine.

TABLE 21

Design, Activity, and Tolerability of modified oligonucleotides having modified phosphoramidate linkages of formula XVI complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{hs}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 98* | 1026 | 5 |
| 1431745 | $G_{hs}{}^{m}C_{ks}A_{ks}T_{\underline{\mathbf{dXVI}}}G_{\underline{\mathbf{dXVI}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 82 | 786 | 5 |
| 1431746 | $G_{hs}{}^{m}C_{ks}A_{ks}T_{ds}G_{\underline{\mathbf{dXVI}}}T_{\underline{\mathbf{dXVI}}}T_{ds}{}^{m}C_{ds}T_{ds}{}^{m}C_{ds}A_{ds}{}^{m}C_{ds}A_{ds}T_{ks}T_{ks}A_{k}$ | 139 | 344 | 5 |
| 1431747 | $G_{hs}{}^{m}C_{ks}A_{ks}T_{ds}G_{ds}T_{\underline{\mathbf{dXVI}}}T_{\underline{\mathbf{dXVI}}}C_{ds}T_{ds}{}^{m}C_{ds}A_{ds}{}^{m}C_{ds}A_{ds}T_{ks}T_{ks}A_{k}$ | 137 | 317 | 5 |
| 1431748 | $G_{hs}{}^{m}C_{ks}A_{ks}T_{ds}G_{ds}T_{ds}T_{ds}{}^{m}C_{ds}T_{ds}{}^{m}C_{\underline{\mathbf{dXVI}}}A_{\underline{\mathbf{dXVI}}}{}^{m}C_{ds}A_{ds}T_{ks}T_{ks}A_{k}$ | 82 | 1157 | 5 |

*historical data; not determined in this experiment.

A subscript "k" represents a cEt nucleoside, a subscript "d" represents a stereo-standard DNA nucleoside, a subscript "s" indicates a phosphorothioate internucleoside linkage. A subscript "XVI" represents an internucleoside linkage of formula XVI. Subscripts of nucleotides having a substituted phosphoramidate internucleoside linkage of generic Formula XVII are bold and underlined. A superscript "m" before a C represents a 5-methyl Cytosine.

Example 11: Design and Protein Upregulation Activity of Uniformly 2'-Modified Oligonucleotides Having Mesyl Phosphoramidate Internucleoside Linkages In Vitro

Modified Oligonucleotides

Modified oligonucleotides comprising multiple mesyl phosphoramidate internucleoside linkages (Formula IX) were synthesized and tested. The modified oligonucleotides are uniform 2'-OMe modified oligonucleotides. Each of the modified oligonucleotides has the same nucleobase sequence, TGCAGTGGGGTGATTT (SEQ ID NO: 18), which is 100% complementary to human LDLR mRNA GenBank NM_000527.4. (SEQ ID NO: 19), at position 28 to 43. Each internucleoside linkage is either a phosphorothioate internucleoside linkage ("s") or a mesyl phosphoramidate internucleoside linkage ("z").

IX

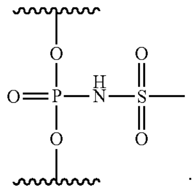

.

Protein Upregulation

Modified oligonucleotides were tested for their ability to upregulate LDLR protein after transfection in HeLa cells. Compound No. 842196 is a uniform 2'-OMe/phosphorothioate oligonucleotide that upregulates expression of LDLR (Liang, et. al., Nucleic Acids Research 2017). Cells were transfected using 25 nM of modified oligonucleotide and Lipofectamine® 2000 (Invitrogen) for 16 hours. Cells were harvested and LDLR protein was quantified using the Quantikine ELISA Human LDLR Kit (Biotechne, Catalog Number: DLDLR0), normalized to the expression level of untreated control cells. The results show that modified oligonucleotides comprising mesyl phosphoramidate linkages at the 5' end are more effective than a full phosphorothioate counterpart for the upregulation of LDLR.

TABLE 22

Design and Activity (protein upregulation) of modified oligonucleotides having mesyl phosphoramidate linkages of formula IX complementary to LDLR

| Compound Number | Chemistry Notation (5'-3') | Relative LDLR Protein Level | SEQ ID NO. |
|---|---|---|---|
| 842196 | $U_{ys}G_{ys}C_{ys}A_{ys}G_{ys}U_{ys}G_{ys}G_{ys}G_{ys}G_{ys}U_{ys}G_{ys}A_{ys}U_{ys}U_{ys}U_{y}$ | 189 | 20 |
| 1405447 | $U_{\underline{\mathbf{yz}}}G_{\underline{\mathbf{yz}}}C_{\underline{\mathbf{yz}}}A_{\underline{\mathbf{yz}}}G_{\underline{\mathbf{yz}}}U_{\underline{\mathbf{yz}}}G_{\underline{\mathbf{yz}}}G_{\underline{\mathbf{yz}}}G_{\underline{\mathbf{yz}}}$ $G_{\underline{\mathbf{yz}}}U_{\underline{\mathbf{yz}}}G_{\underline{\mathbf{yz}}}A_{\underline{\mathbf{yz}}}U_{\underline{\mathbf{yz}}}U_{\underline{\mathbf{yz}}}U_{y}$ | 146 | 20 |
| 1405546 | $U_{\underline{\mathbf{yz}}}G_{\underline{\mathbf{yz}}}C_{\underline{\mathbf{yz}}}A_{\underline{\mathbf{yz}}}G_{\underline{\mathbf{yz}}}U_{\underline{\mathbf{yz}}}G_{ys}G_{ys}G_{ys}G_{ys}U_{ys}G_{ys}A_{ys}U_{ys}U_{ys}U_{y}$ | 235 | 20 |
| 1405547 | $U_{ys}G_{ys}C_{ys}A_{ys}G_{ys}$ $U_{\underline{\mathbf{yz}}}G_{\underline{\mathbf{yz}}}G_{\underline{\mathbf{yz}}}G_{\underline{\mathbf{yz}}}G_{\underline{\mathbf{yz}}}U_{\underline{\mathbf{yz}}}G_{ys}A_{ys}U_{ys}U_{ys}U_{y}$ | 181 | 20 |
| 1405548 | $U_{ys}G_{ys}C_{ys}A_{ys}G_{ys}U_{ys}G_{ys}G_{ys}G_{ys}$ $G_{\underline{\mathbf{yz}}}U_{\underline{\mathbf{yz}}}G_{\underline{\mathbf{yz}}}A_{\underline{\mathbf{yz}}}U_{\underline{\mathbf{yz}}}U_{\underline{\mathbf{yz}}}$ $U_{y}$ | 133 | 20 |

A subscript "y" represents a 2'-OMe modified nucleoside, a subscript "s" indicates a phosphorothioate internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

Example 12: Design and Activity of siRNA to HRPT1 Having Mesyl Phosphoramidate Internucleoside Linkages In Vitro siRNA Double-stranded siRNA comprising modified oligonucleotides having mesyl phosphoramidate internucleoside linkages (Formula IX) in the sense and/or antisense strands were synthesized and tested. Each internucleoside linkage is either a phosphorothioate internucleoside linkage ("s"), a phosphodiester internucleoside linkage ("o"), or a mesyl phosphoramidate internucleoside linkage ("z"), indicated by formula IX below.

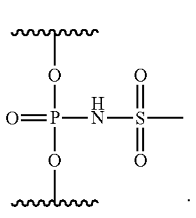

IX

Each antisense strand has the sequence AUAAAAUCUACAGUCAUAGGAAU (SEQ ID NO: 21) and is 100% complementary to GenBank NM_000194.2 (SEQ ID NO: 22) from 444 to 466, and each antisense strand has a 5'-phosphate. Each sense strand has the sequence UCCUAUGACUGUAGAUUUUAU (SEQ ID NO: 23) and is 100% identical to GenBank NM_000194.2 (SEQ ID NO: 22) from 446 to 466. Compound No. 1151789 further comprises a 3'-linked C7 amino modifier (Glen Research), shown below:

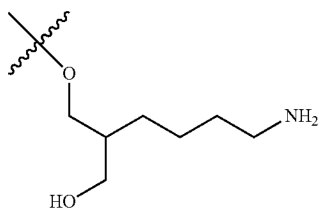 [SMILES: *OCC(CO)CCCCN]

TABLE 23

| Design of antisense strand modified oligonucleotides targeted to human/mouse HRPT1 having mesyl phosphoramidate linkages | | |
|---|---|---|
| Compound ID | Chemical Notation (5' to 3') | SEQ ID NO: |
| 1073762 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}Af_{s}U_{y}$ | 21 |
| 1405420 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{\underline{\mathbf{yz}}}A_{\underline{\mathbf{fz}}}U_{y}$ | 21 |
| 1405427 | p.$A_{\underline{\mathbf{yz}}}U_{\underline{\mathbf{fz}}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{yo}A_{fo}U_{y}$ | 21 |
| 1405428 | p.$A_{\underline{\mathbf{yz}}}U_{\underline{\mathbf{fz}}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{\underline{\mathbf{yz}}}A_{\underline{\mathbf{fz}}}U_{y}$ | 21 |

A "p." represents a 5'-phosphate. A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

TABLE 24

| Design of sense strand modified oligonucleotides targeted to human/mouse HRPT1 having mesyl phosphoramidate linkages | | |
|---|---|---|
| Compound ID | Chemical Notation (5' to 3') | SEQ ID NO: |
| 1151789 | $U_{fo}C_{yo}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{fo}A_{yo}U_{fo}$ [3'-amino C7 Tag] | 23 |
| 1405429 | $U_{fo}C_{yo}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{\underline{\mathbf{fz}}}A_{\underline{\mathbf{yz}}}U_{f}$ | 23 |
| 1405430 | $U_{\underline{\mathbf{fz}}}C_{\underline{\mathbf{yz}}}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{fo}A_{yo}U_{f}$ | 23 |
| 1405431 | $U_{\underline{\mathbf{fz}}}C_{\underline{\mathbf{yz}}}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{\underline{\mathbf{fz}}}A_{\underline{\mathbf{yz}}}U_{f}$ | 23 |

A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

Activity Assay

Activity of various siRNA formed by annealing one antisense strand and one sense strand described above was tested in HeLa cells. HeLa cells were transfected with 6 μL/mL of siRNA using RNAiMAX for 5 hours. RNA was isolated and RNA expression was analyzed via RT-qPCR using primer probe set Hs02800695_m1(ThennoFisher). Incorporation of mesyl phosphoramidate linkages into the 3' end of the antisense strand and into either or both the 3' and 5' ends of the sense strand of siRNA does not lead to a reduction in activity.

TABLE 25

Activity of siRNAs having mesyl phosphoramidate linkages against human HPRT1

| Antisense Strand | Sense Strand | Linkage mod. position in antisense strand | Linkage mod. position in sense strand | IC50 (nM) |
|---|---|---|---|---|
| 1073762 | 1151789 | n/a | n/a | 0.091 |
| 1405420 | 1405429 | 3' | 3' | 0.085 |
| 1405420 | 1405430 | 3' | 5' | 0.065 |
| 1405420 | 1405431 | 3' | 3' and 5' | 0.066 |
| 1405427 | 1405429 | 5' | 3' | 0.457 |
| 1405427 | 1405430 | 5' | 5' | 0.831 |
| 1405427 | 1405431 | 5' | 3' and 5' | 1.391 |
| 1405428 | 1405429 | 3' and 5' | 3' | 1.19 |

TABLE 25-continued

Activity of siRNAs having mesyl phosphoramidate linkages against human HPRT1

| Antisense Strand | Sense Strand | Linkage mod. position in antisense strand | Linkage mod. position in sense strand | IC50 (nM) |
|---|---|---|---|---|
| 1405428 | 1405430 | 3' and 5' | 5' | 0.816 |
| 1405428 | 1405431 | 3' and 5' | 3' and 5' | 0.934 |

Example 13: Design and Activity of siRNA to Human/Mouse PTEN Having Mesyl Phosphoramidate Internucleoside Linkages In Vitro siRNA Single-stranded siRNA and double-stranded siRNA comprising modified oligonucleotides having mesyl phosphoramidate internucleoside linkages (Formula IX) in the antisense strands were synthesized and tested. Each internucleoside linkage is either a phosphorothioate internucleoside linkage ("s"), a phosphodiester internucleoside linkage ("o"), or a mesyl phosphoramidate internucleoside linkage ("z"), indicated by formula IX below.

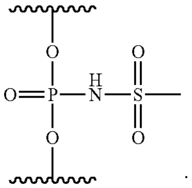

IX

Each antisense strand has the sequence TUAUCUAUAAUGAUCAGGUAA (SEQ ID NO: 24) and has three mismatches to PTEN cDNA, the cDNA of ENSEMBL Accession No. ENST00000371953.8 from ENSEMBL version 99: January 2020, human reference assembly version GRCh38.p13 located on the forward strand of chromosome 10 (CM000682.2) from positions 87,863,625 to 87,971,930 (SEQ ID NO: 26) from 1962 to 1982, and each antisense strand has a 5'-phosphate. For double-stranded siRNA, the sense strand 790973 has the sequence ACCUGAUCAUUAUAGAUAA (SEQ ID NO: 25) and has one mismatch to the cDNA of ENSEMBL Accession No. ENST00000371953.8 from ENSEMBL version 99: January 2020, human reference assembly version GRCh38.p13 located on the forward strand of chromosome 10 (CM000682.2) from positions 87,863,625 to 87,971,930 (SEQ ID NO: 26) from 1964 to 1982. Each internucleoside linkage of the sense strand is either a phosphodiester internucleoside linkage ("o") or a phosphorothioate internucleoside linkage ("s"), and the sense strand has the chemical notation (5' to 3'): $A_{fs}C_{ys}G_{fo}A_{yo}U_{fo}C_{yo}A_{fo}U_{yo}U_{fo}A_{yo}U_{fo}A_{yo}G_{fo}A_{yo}U_{fs}A_{ys}A_{f}$ (SEQ ID ON: 25).

TABLE 26

Design of antisense strand modified oligonucleotides targeted to PTEN having mesyl phosphoramidate linkages

| Compound ID | Chemical Notation (5' to 3') | SEQ ID NO: |
|---|---|---|
| 456963 | $p.T_{es}U_{fs}A_{yo}U_{fs}C_{yo}U_{fs}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1421366 | $p.T_{\underline{ez}}U_{\underline{fz}}A_{yo}U_{fs}C_{yo}U_{fs}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1439694 | $p.T_{es}U_{fs}A_{\underline{yz}}U_{\underline{fz}}C_{yo}U_{fs}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1440988 | $p.T_{es}U_{fs}A_{yo}U_{fs}C_{\underline{yz}}U_{\underline{fz}}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1440992 | $p.T_{es}U_{fs}A_{yo}U_{fs}C_{yo}U_{fs}A_{\underline{yz}}U_{\underline{fz}}A_{yo}A_{fs}U_{yo}G_{fs}A_{yo}U_{fs}C_{ys}A_{fs}G_{ys}G_{fs}U_{ys}A_{es}A_{e}$ | 24 |
| 1440993 | $p.T_{es}U_{fs}A_{yo}U_{fs}C_{yo}U_{fs}A_{yo}U_{fs}A_{\underline{yz}}A_{\underline{fz}}U_{yo}G_{fs}A_{yo}U_{fs}C_{ys}A_{fs}G_{ys}G_{fs}U_{ys}A_{es}A_{e}$ | 24 |
| 1440994 | $p.T_{es}U_{fs}A_{yo}U_{fs}C_{yo}U_{fs}A_{yo}U_{fs}U_{\underline{yz}}G_{\underline{fz}}A_{yo}A_{fs}A_{yo}U_{fs}C_{ys}A_{fs}G_{ys}G_{fs}U_{ys}A_{es}A_{e}$ | 24 |
| 1440995 | $p.T_{es}U_{fs}A_{yo}U_{fs}C_{yo}U_{fs}A_{yo}U_{fs}A_{yo}A_{fs}U_{yo}G_{fs}A_{\underline{yz}}U_{\underline{fz}}C_{ys}A_{fs}G_{ys}G_{fs}U_{ys}A_{es}A_{e}$ | 24 |
| 1441021 | $p.T_{es}U_{fs}A_{yo}U_{fs}C_{yo}U_{fs}A_{yo}U_{fs}A_{yo}A_{fs}U_{yo}G_{fs}A_{yo}U_{fs}C_{\underline{yz}}A_{\underline{fz}}G_{ys}G_{fs}U_{ys}A_{es}A_{e}$ | 24 |
| 1441022 | $p.T_{es}U_{fs}A_{yo}U_{fs}C_{yo}U_{fs}A_{yo}U_{fs}A_{yo}A_{fs}U_{yo}G_{fs}A_{yo}U_{fs}C_{ys}A_{fs}G_{\underline{yz}}G_{\underline{fz}}U_{ys}A_{es}A_{e}$ | 24 |
| 1441023 | $p.T_{es}U_{fs}A_{yo}U_{fs}C_{yo}U_{fs}A_{yo}U_{fs}A_{yo}A_{fs}U_{yo}G_{fs}A_{yo}U_{fs}C_{ys}A_{fs}G_{ys}G_{fs}U_{\underline{yz}}A_{\underline{ez}}A_{e}$ | 24 |

A "p." represents a 5'-phosphate. A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

Activity Assay

Activity of various siRNA formed by annealing one antisense strand and one sense strand described above was tested in HeLa cells. HeLa cells were transfected with 6 µL/mL of siRNA using RNAiMAX for 6 hours. RNA was isolated and RNA expression was analyzed via RT-qPCR using primer probe set Hs02800695_m1(ThennoFisher).

TABLE 27

Activity of double-stranded siRNAs having mesyl phosphoramidate linkages against human PTEN

| Antisense Strand | Sense Strand | Linkage mod. position in antisense strand | IC50 (nM) |
|---|---|---|---|
| 456963 | 790973 | N/A | 0.98 |
| 1421366 | 790973 | Positions 1-2, 2-3 | 2.87 |
| 1439694 | 790973 | Positions 3-4, 4-5 | 2.89 |
| 1440988 | 790973 | Positions 5-6, 6-7 | >10 |
| 1440992 | 790973 | Positions 7-8, 8-9 | 2.17 |
| 1440993 | 790973 | Positions 9-10, 10-11 | 0.84 |
| 1440994 | 790973 | Positions 11-12, 12-13 | >10 |
| 1440995 | 790973 | Positions 13-14, 14-15 | 10.00 |
| 1441021 | 790973 | Positions 15-16, 16-17 | 10.00 |
| 1441022 | 790973 | Positions 17-18, 18-19 | 1.24 |
| 1441023 | 790973 | Positions 19-20, 20-21 | 2.41 |

Example 14: Design of siRNA to SOD-1 Having a C16 Modified-Phosphoramidate Internucleoside Linkage Double-stranded siRNA comprising a modified oligonucleotide having a mesyl phosphoramidate internucleoside linkages of Formula XIX in the sense strand was synthesized and tested in vitro.

For the sense strand, each internucleoside linkage is either a phosphorothioate internucleoside linkage ("s"), a phosphodiester internucleoside linkage ("o"), or a modified phosphoramidate internucleoside linkage ("XIX"), as shown below.

XIX

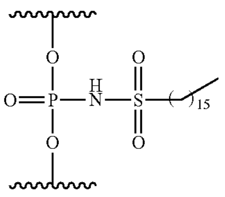

The sense strand has the chemical notation (5' to 3'): $C_{ys}A_{ys}U_{ys}U_{ys}U_{ys}U_{yXIX}A_{fo}A_{yo}U_{fo}C_{fo}A_{yo}C_{yo}U_{yo}C_{yo}U_{yo}C_{yo}U_{yo}A_{ys}A_{ys}A_{y}$, (SEQ ID NO: 30) wherein a subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, and a subscript XIX represents an internucleoside linkage of Formula XIX.

The antisense strand has a 5'-vinyl phosphonate (vP). Each internucleoside linkage of the antisense strand is either a phosphodiester internucleoside linkage ("o") or a phosphorothioate internucleoside linkage ("s"). The antisense strand has the chemical notation (5' to 3'): vP-$U_{yo}U_{fo}U_{yo}A_{yo}G_{yo}A_{fo}G_{yo}U_{fo}G^{fo}A_{yo}G_{yo}G_{yo}A_{yo}U_{fo}U_{yo}A_{fo}A_{yo}A_{yo}A_{yo}U_{yo}G_{ys}A_{ys}A_{y}$ (SEQ ID NO: 31), wherein a subscript "f" represents a 2'-F modified nucleoside, a subscript "y" represents a 2'-OMe modified nucleoside, a subscript "s" indicates a phosphorothioate internucleoside linkage and a subscript "o" represents a phosphodiester internucleoside linkage.

Example 15: Tolerability of Modified Oligonucleotides Having Mesyl Phosphoramidate Internucleoside Linkages In Vivo in Wild-Type Mice Modified Oligonucleotides Modified oligonucleotides comprising multiple mesyl phosphoramidate internucleoside linkages (Formula IX) were synthesized and tested. The modified oligonucleotides are each 5-10-5 MOE gapmers with a sugar motif of: eeeeeddddddddddeeeee where "e" represents a 2'-MOE modified sugar moiety, and "d" represents a β-D-2'-deoxyribosyl sugar moiety. The modified oligonucleotides are 100% complementary to human MAPT, GENBANK accession number NT_010783.15 truncated from 9240000 to 9381000 (SEQ ID NO: 32).

Each internucleoside linkage is a phosphorothioate internucleoside linkage ("s"), a phosphodiester internucleoside linkage ("o") or a mesyl phosphoramidate internucleoside linkage ("z"), as indicated in the table below.

Oligonucleotides described above were tested in wild-type female C57/B16 mice to assess the tolerability of the oligonucleotides. Wild-type female C57/B16 mice each received a single ICV dose of 700 μg of modified oligonucleotide listed in the table below. Each treatment group consisted of 2 mice. A group of 2 mice received PB S as a negative control. At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse. The results are presented in the table below. Oligonucleotides comprising mesyl phosphoramidate internucleoside linkages have similar tolerability in the mouse CNS as the parent oligonucleotide. Oligonucleotides having mesyl terminal phosphoramidate linkages as well as two mesyl phosphoramidate linkages in the deoxy region have improved CNS tolerability.

TABLE 28

CNS Tolerability of modified oligonucleotides containing mesyl phosphoramidate linkages

| Compound ID | Chemical Notation (5' to 3') | SEQ ID NO: | 3 hour FOB |
|---|---|---|---|
| 613039 | $T_{es}G_{eo}{}^{m}C_{eo}A_{eo}T_{eo}G_{ds}G_{ds}T_{ds}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 6 |
| 1405498 | $T_{es}G_{eo}{}^{m}C_{eo}A_{eo}T_{eo}G_{\underline{dz}}G_{\underline{dz}}T_{ds}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 6 |
| 1405499 | $T_{es}G_{eo}{}^{m}C_{eo}A_{eo}T_{eo}G_{ds}G_{\underline{dz}}T_{\underline{dz}}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 6 |
| 1405500 | $T_{es}G_{eo}{}^{m}C_{eo}A_{eo}T_{eo}G_{ds}G_{ds}T_{\underline{dz}}G_{\underline{dz}}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 7 |
| 1405501 | $T_{es}G_{eo}{}^{m}C_{eo}A_{eo}T_{eo}G_{ds}G_{ds}T_{ds}G_{ds}T_{ds}A_{ds}G_{\underline{dz}}{}^{m}C_{\underline{dz}}{}^{m}C_{ds}{}^{m}C_{ds}{}^{m}C_{eo}{}^{m}C_{eo}{}^{m}C_{es}T_{es}G_{e}$ | 27 | 5, 5 |
| 1421514 | $T_{\underline{ez}}G_{eo}{}^{m}C_{eo}A_{eo}T_{eo}G_{ds}G_{ds}T_{ds}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{\underline{ez}}T_{\underline{ez}}G_{e}$ | 27 | 6, 5 |
| 1421517 | $T_{\underline{ez}}G_{eo}{}^{m}C_{eo}A_{eo}T_{eo}G_{ds}G_{\underline{dz}}T_{\underline{dz}}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{\underline{ez}}T_{\underline{ez}}G_{e}$ | 27 | 4, 4 |
| 613369 | $G_{es}T_{eo}T_{eo}T_{eo}T_{eo}{}^{m}C_{ds}A_{ds}A_{ds}A_{ds}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 0, 0 |
| 1405502 | $G_{es}T_{eo}T_{eo}T_{eo}T_{eo}{}^{m}C_{\underline{dz}}A_{\underline{dz}}A_{ds}A_{ds}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 0, 0 |

TABLE 28-continued

CNS Tolerability of modified oligonucleotides containing mesyl phosphoramidate linkages

| Compound ID | Chemical Notation (5' to 3') | SEQ ID NO: | 3 hour FOB |
|---|---|---|---|
| 1405503 | $G_{es}T_{eo}T_{eo}T_{eo}T_{eo}{}^{m}C_{ds}A_{\underline{dz}}A_{\underline{dz}}A_{ds}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 1, 1 |
| 1405504 | $G_{es}T_{eo}T_{eo}T_{eo}T_{eo}{}^{m}C_{ds}A_{ds}A_{\underline{dz}}A_{\underline{dz}}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 1, 1 |
| 1405505 | $G_{es}T_{eo}T_{eo}T_{eo}T_{eo}{}^{m}C_{ds}A_{ds}A_{ds}A_{ds}{}^{m}C_{ds}A_{ds}{}^{m}C_{\underline{dz}}A_{\underline{dz}}{}^{m}C_{ds}{}^{m}C_{ds}T_{eo}T_{eo}{}^{m}C_{es}A_{es}T_{e}$ | 28 | 2, 2 |
| 1421518 | $G_{\underline{ez}}T_{eo}T_{eo}T_{eo}T_{eo}{}^{m}C_{ds}A_{ds}A_{ds}A_{ds}{}^{m}C_{ds}A_{ds}{}^{m}C_{ds}A_{ds}{}^{m}C_{ds}{}^{m}C_{ds}T_{eo}T_{eo}{}^{m}C_{\underline{ez}}A_{\underline{ez}}T_{e}$ | 28 | 0, 0 |
| 1421519 | $G_{\underline{ez}}T_{eo}T_{eo}T_{eo}T_{eo}{}^{m}C_{ds}A_{\underline{dz}}A_{\underline{dz}}A_{ds}{}^{m}C_{ds}A_{ds}{}^{m}C_{ds}A_{ds}{}^{m}C_{ds}{}^{m}C_{ds}T_{eo}T_{eo}{}^{m}C_{\underline{ez}}A_{\underline{ez}}T_{e}$ | 28 | 1, 1 |

A subscript "o" indicates a phosphodiester internucleoside linkage, a subscript "s" indicates a phosphorothioate internucleoside linkage, a subscript "z" represents an internucleoside linkage of formula IX, which is a mesyl phosphoramidate linkage. Subscripts of nucletides having a phosphoramidate internucleoside linkage of generic Formula XVII are bold and underlined. A superscript "m" before a C represents a 5-methyl Cytosine.

Example 16: Design, Activity and Tolerability of Modified Oligonucleotides Having Various Mesyl Phosphoramidate Internucleoside Linkages In Vitro

Modified Oligonucleotides

Modified oligonucleotides comprising multiple mesyl phosphoramidate internucleoside linkages (Formula IX), phosphorothioate internucleoside linkages, and phosphodiester internucleoside linkages, were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s"), a phosphodiester internucleoside linkage ("o"), or a mesyl phosphoramidate internucleoside linkage ("z").

In Vitro Assays

In vitro activity of modified oligonucleotides described above was determined as described in Example 1. In vitro toxicity of modified oligonucleotides described above was determined as described in Example 3. The internucleoside linkages of the modified nucleosides are indicated in subscripts in the table below.

TABLE 29

Design, Activity, and Tolerability of modified oligonucleotides having multiple mesyl phosphoramidates linkages complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 101 | 1223 | 5 |
| 1193271 | $G_{ko}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{ds}T_{ko}T_{ko}A_{k}$ | 87 | 1966 | 5 |
| 1233817 | $G_{ks}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{ds}T_{ko}T_{ks}A_{k}$ | 58 | 1712 | 5 |
| 1467836 | $G_{\underline{kz}}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{ds}T_{ko}T_{\underline{kz}}A_{k}$ | 100 | 1595 | 5 |
| 1467198 | $G_{\underline{kz}}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{do}T_{ko}T_{\underline{kz}}A_{k}$ | 77 | 1733 | 5 |
| 1467199 | $G_{\underline{kz}}{}^{m}C_{ko}A_{\underline{kz}}T_{ds}G_{ds}T_{ds}T_{ds}{}^{m}C_{ds}T_{ds}{}^{m}C_{ds}A_{ds}{}^{m}C_{ds}A_{\underline{dz}}T_{ko}T_{\underline{kz}}A_{k}$ | 63 | 1462 | 5 |
| 1467837 | $G_{ko}{}^{m}C_{ko}A_{\underline{kz}}T_{ds}G_{ds}T_{ds}T_{ds}{}^{m}C_{ds}T_{ds}{}^{m}C_{ds}A_{ds}{}^{m}C_{ds}A_{\underline{dz}}T_{ko}T_{\underline{kz}}A_{k}$ | 72 | 1809 | 5 |
| 1467838 | $G_{\underline{kz}}{}^{m}C_{ko}A_{ko}T_{ds}G_{\underline{dz}}T_{\underline{dz}}T_{ds}{}^{m}C_{ds}T_{ds}{}^{m}C_{ds}A_{ds}{}^{m}C_{ds}A_{ds}T_{ko}T_{\underline{kz}}A_{k}$ | 110 | 693 | 5 |
| 1467839 | $G_{\underline{kz}}{}^{m}C_{ko}A_{ks}T_{ds}G_{\underline{dz}}T_{\underline{dz}}T_{ds}{}^{m}C_{ds}T_{ds}{}^{m}C_{ds}A_{ds}{}^{m}C_{ds}A_{ds}T_{ko}T_{\underline{kz}}A_{k}$ | 208 | 502 | 5 |
| 1467821 | $G_{\underline{kz}}{}^{m}C_{ko}A_{ks}T_{ds}G_{\underline{dz}}T_{\underline{dz}}T_{ds}{}^{m}C_{ds}T_{ds}{}^{m}C_{ds}A_{ds}{}^{m}C_{ds}A_{ds}T_{ko}T_{\underline{kz}}A_{k}$ | 172 | 495 | 5 |
| 1467840 | $G_{\underline{kz}}{}^{m}C_{ko}A_{ko}T_{\underline{dz}}G_{\underline{dz}}T_{\underline{dz}}T_{\underline{dz}}{}^{m}C_{ds}T_{ds}{}^{m}C_{ds}A_{ds}{}^{m}C_{ds}A_{\underline{dz}}T_{ko}T_{\underline{kz}}A_{k}$ | 152 | 654 | 5 |
| 1467841 | $G_{\underline{kz}}{}^{m}C_{ko}A_{ko}T_{ds}G_{ds}T_{ds}T_{ds}{}^{m}C_{ds}T_{ds}{}^{m}C_{\underline{dz}}A_{\underline{dz}}{}^{m}C_{\underline{dz}}A_{\underline{dz}}T_{ko}T_{\underline{kz}}A_{k}$ | 132 | 1216 | 5 |

A subscript "k" represents a cEt nucleoside, a subscript "d" represents a stereostandard DNA nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 17: Activity and Tolerability of Modified Oligonucleotides with Mesyl Phosphoramidate Internucleoside Linkages In Vivo Modified Oligonucleotides GalNAc-conjugated modified oligonucleotides comprising multiple mesyl phosphoramidate internucleoside linkages (Formula IX) and phosphorothioate internucleoside linkages were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s"), a phosphodiester internucleoside linkage ("o"), or a mesyl phosphoramidate internucleoside linkage ("z").

The GalNAc moiety is conjugated to the 5' oxygen of the oligonucleotide via a THA linker, as shown below:

This compound has the sequence GCATGTTCTCACATTA (SEQ ID NO: 5) and a sugar motif of kkk-d-m-dddddddd-kkk, wherein each "k" represents a cEt nucleoside, each "d" represents a stereo-standard DNA nucleoside, and "m" represents a 2'-OMe nucleoside. It has a GalNAc conjugated at the 3'-oxygen of the oligonucleotide via a THA linker as shown above.

Compound No. 936053 was described in WO2019/157531. It was chosen as the parent of the comparator compound because it has reduced toxicity relative to 558807 as well as reduced potency in vivo. Note that at least some of the observed potency of 558807 is "false"; that is, the RNA reduction observed is not specific to RNAse H mediated reduction of CXCL12 RNA, but rather, is related to global reductions in RNA due to cellular toxicity. Therefore, Compound No. 936503 represents a better comparator compound for determining the relative in vivo potency of compounds comprising mesyl phosphoramidate internucleoside linkages.

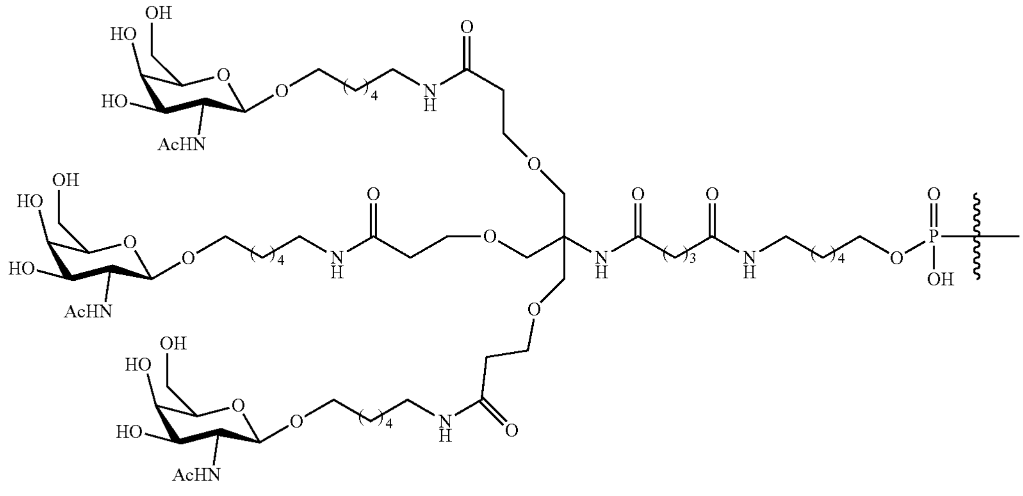

THA-GalNAc

In addition to compounds containing a mesyl phosphoramidate internucleoside linkage, a 3'-GalNAc conjugated version of Compound No. 936053 (1306456) was tested.

TABLE 30

| Compound Number | Chemistry Notation (5'-3') | SEQ ID NO. |
|---|---|---|
| 1306456 | $G_{ks}{}^{m}C_{ks}A_{ks}T_{ds}G_{ys}T_{ds}T_{ds}{}^{m}C_{ds}T_{ds}{}^{m}C_{ds}A_{ds}{}^{m}C_{ds}A_{ds}T_{ks}T_{ks}A_{k}$-THA-GalNAc | 5 |
| 1462752 | THA-GalNAc-$G_{ks}{}^{m}C_{ks}A_{ks}T_{\underline{dz}}G_{\underline{dz}}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | 5 |
| 1462753 | THA-GalNAc-$G_{ks}{}^{m}C_{ks}A_{ks}T_{\underline{dz}}G_{\underline{dz}}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | 5 |
| 1462754 | THA-GalNAc-$G_{ks}{}^{m}C_{ks}A_{ks}T_{\underline{dz}}G_{\underline{dz}}T_{\underline{dz}}T_{\underline{dz}}{}^{m}C_{\underline{dz}}T_{ds}{}^{m}C_{ds}A_{ds}{}^{m}C_{ds}A_{ds}T_{ks}T_{ks}A_{k}$ | 5 |

Study Design

For the in vivo activity and tolerability study in the tables below, 3 BALB/C mice per group were administered modified oligonucleotide by subcutaneous injection and sacrificed after 72 hours. Modified oligonucleotides were dosed at 0.2, 0.6, 1.8, 5.4, or 15 mg/kg.

Tissue were collected and mRNA was isolated and levels of CXCL12 in liver samples were measured by RT-qPCR with primer probe set RTS2605 as described above. Plasma ALT was measured. Elevations in ALT are associated with liver toxicity.

Expression levels were normalized with Ribogreen® and are presented relative to levels in mice treated with PBS.

TABLE 31

In Vivo Activity and Toxicity of modified oligonucleotides complementary to CXCL12

| Compound ID | in vivo CXCL12 ED50 liver (mg/kg) | ALT @5.4 mg/kg (IU/L) | ALT @ 15 mg/kg (IU/L) |
|---|---|---|---|
| 1306456 | 0.39 | 29 | 34 |
| 1462752 | 0.17 | 55 | 336 |
| 1462753 | 0.17 | 32 | 107 |
| 1462754 | 0.30 | 34 | 79 |

Example 18: Design, Activity and Tolerability of Modified Oligonucleotides Having Various Mesyl Phosphoramidate, Phosphorothioate, and Phosphodiester Internucleoside Linkages In Vitro Moped Oligonucleotides Modified oligonucleotides comprising multiple mesyl phosphoramidate internucleoside linkages (Formula IX), phosphorothioate internucleoside linkages, and phosphodiester internucleoside linkages, were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s"), a phosphodiester internucleoside linkage ("o"), or a mesyl phosphoramidate internucleoside linkage ("z").

In Vitro Assays

In vitro activity of modified oligonucleotides described above was determined at 100 nM only, and the results are presented as the % expression relative to untreated control cells. For selected compounds, in vitro activity dose response was tested as described in Example 1. In vitro toxicity of modified oligonucleotides described above was determined as described in Example 3. The internucleoside linkages of the modified nucleosides are indicated in subscripts in the table below

TABLE 32

Design, Activity, and Tolerability of modified oligonucleotides having multiple mesyl phosphoramidates linkages complementary to CXCL12

| Compound Number | Chemistry Notation (5'-3') | CXCL12 at 100 nM (% UTC) | CXCL12 $IC_{50}$ (nM) | Caspase Activation (% Mock) | SEQ ID NO. |
|---|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 34 | 88 | 1287 | 5 |
| 1467797 | $G_{ks}{}^{m}C_{ks}A_{ks}T_{ds}G_{ds}T_{\underline{dz}}T_{\underline{dz}}{}^{m}C_{\underline{dz}}T_{ds}{}^{m}C_{ds}A_{ds}{}^{m}C_{ds}A_{ds}T_{ks}T_{ks}A_{k}$ | 45 | 170 | 393 | 5 |
| 1467798 | $G_{ks}{}^{m}C_{ks}A_{ks}T_{ds}G_{ds}T_{ds}T_{\underline{dz}}{}^{m}C_{\underline{dz}}T_{\underline{dz}}{}^{m}C_{ds}A_{ds}{}^{m}C_{ds}A_{ds}T_{ks}T_{ks}A_{k}$ | 70 | n.d. | 974 | 5 |
| 1467799 | $G_{ks}{}^{m}C_{ks}A_{ks}T_{ds}G_{ds}T_{ds}T_{ds}{}^{m}C_{\underline{dz}}T_{\underline{dz}}{}^{m}C_{\underline{dz}}A_{ds}{}^{m}C_{ds}A_{ds}T_{ks}T_{ks}A_{k}$ | 73 | n.d. | 1023 | 5 |
| 1467800 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{\underline{dz}}{}^{m}C_{ds}A_{ds}T_{ks}T_{ks}A_{k}$ | 59 | n.d. | 939 | 5 |
| 1467801 | $G_{ks}{}^{m}C_{ks}A_{ks}T_{ds}G_{ds}T_{ds}T_{ds}{}^{m}C_{ds}T_{ds}{}^{m}C_{\underline{dz}}A_{\underline{dz}}{}^{m}C_{\underline{dz}}A_{ds}T_{ks}T_{ks}A_{k}$ | 53 | n.d. | 682 | 5 |
| 1467802 | $G_{ks}{}^{m}C_{ks}A_{ks}T_{ds}G_{\underline{dz}}T_{\underline{dz}}T_{\underline{dz}}{}^{m}C_{\underline{dz}}T_{ds}{}^{m}C_{ds}A_{ds}{}^{m}C_{ds}A_{ds}T_{ks}T_{ks}A_{k}$ | 52 | 199 | 269 | 5 |
| 1467803 | $G_{ks}{}^{m}C_{ks}A_{ks}T_{ds}G_{ds}T_{\underline{dz}}T_{\underline{dz}}{}^{m}C_{\underline{dz}}T_{\underline{dz}}{}^{m}C_{ds}A_{ds}{}^{m}C_{ds}A_{ds}T_{ks}T_{ks}A_{k}$ | 75 | n.d. | 792 | 5 |
| 1467804 | $G_{ks}{}^{m}C_{ks}A_{ks}T_{ds}G_{ds}T_{ds}T_{\underline{dz}}{}^{m}C_{\underline{dz}}T_{\underline{dz}}{}^{m}C_{\underline{dz}}A_{ds}{}^{m}C_{ds}A_{ds}T_{ks}T_{ks}A_{k}$ | 60 | n.d. | 983 | 5 |
| 1467805 | $G_{ks}{}^{m}C_{ks}A_{ks}T_{ds}G_{ds}T_{ds}T_{ds}{}^{m}C_{\underline{dz}}T_{\underline{dz}}{}^{m}C_{\underline{dz}}A_{\underline{dz}}{}^{m}C_{ds}A_{ds}T_{ks}T_{ks}A_{k}$ | 50 | n.d. | 1247 | 5 |
| 1467806 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{\underline{dz}}{}^{m}C_{\underline{dz}}A_{ds}T_{ks}T_{ks}A_{k}$ | 50 | n.d. | 1062 | 5 |
| 1467807 | $G_{ks}{}^{m}C_{ks}A_{ks}T_{\underline{dz}}G_{\underline{dz}}T_{ds}T_{ds}{}^{m}C_{ds}T_{ds}{}^{m}C_{ds}A_{ds}{}^{m}C_{\underline{dz}}A_{\underline{dz}}T_{ks}T_{ks}A_{k}$ | 63 | n.d. | 443 | 5 |
| 1467808 | $G_{ks}{}^{m}C_{ks}A_{ks}T_{\underline{dz}}G_{\underline{dz}}T_{ds}T_{ds}{}^{m}C_{ds}T_{ds}{}^{m}C_{ds}A_{\underline{dz}}{}^{m}C_{\underline{dz}}A_{ds}T_{ks}T_{ks}A_{k}$ | 52 | n.d. | 615 | 5 |
| 1467809 | $G_{ks}{}^{m}C_{ks}A_{ks}T_{\underline{dz}}G_{\underline{dz}}T_{ds}T_{ds}{}^{m}C_{ds}T_{ds}{}^{m}C_{\underline{dz}}A_{\underline{dz}}{}^{m}C_{ds}A_{ds}T_{ks}T_{ks}A_{k}$ | 51 | n.d. | 408 | 5 |
| 1467810 | $G_{ks}{}^{m}C_{ks}A_{ks}T_{\underline{dz}}G_{\underline{dz}}T_{ds}T_{ds}{}^{m}C_{ds}T_{\underline{dz}}{}^{m}C_{\underline{dz}}A_{ds}{}^{m}C_{ds}A_{ds}T_{ks}T_{ks}A_{k}$ | 57 | n.d. | 426 | 5 |
| 1467811 | $G_{ks}{}^{m}C_{ks}A_{ks}T_{\underline{dz}}G_{\underline{dz}}T_{ds}T_{ds}{}^{m}C_{\underline{dz}}T_{\underline{dz}}{}^{m}C_{ds}A_{ds}{}^{m}C_{ds}A_{ds}T_{ks}T_{ks}A_{k}$ | 54 | n.d. | 347 | 5 |
| 1467812 | $G_{ks}{}^{m}C_{ks}A_{ks}T_{\underline{dz}}G_{\underline{dz}}T_{ds}T_{\underline{dz}}{}^{m}C_{\underline{dz}}T_{ds}{}^{m}C_{ds}A_{ds}{}^{m}C_{ds}A_{ds}T_{ks}T_{ks}A_{k}$ | 36 | 150 | 327 | 5 |

TABLE 32-continued

Design, Activity, and Tolerability of modified oligonucleotides having multiple mesyl phosphoramidates linkages complementary to CXCL12

| Compound Number | Chemistry Notation (5'-3') | CXCL12 at 100 nM (% UTC) | CXCL12 $IC_{50}$ (nM) | Caspase Activation (% Mock) | SEQ ID NO. |
|---|---|---|---|---|---|
| 1467813 | $G_{ks}{}^{m}C_{ks}A_{\underline{kz}}T_{\underline{dz}}G_{ds}T_{ds}T_{ds}{}^{m}C_{ds}T_{ds}{}^{m}C_{ds}A_{ds}{}^{m}C_{\underline{dz}}A_{\underline{dz}}T_{ks}T_{ks}A_{k}$ | 39 | 83 | 1236 | 5 |
| 1467814 | $G_{ks}{}^{m}C_{ks}A_{ks}T_{ds}G_{\underline{dz}}T_{\underline{dz}}T_{ds}{}^{m}C_{ds}T_{ds}{}^{m}C_{ds}A_{ds}{}^{m}C_{\underline{dz}}A_{\underline{dz}}T_{ks}T_{ks}A_{k}$ | 78 | 220 | 241 | 5 |
| 1467815 | $G_{ks}{}^{m}C_{ks}A_{ks}T_{ds}G_{ds}T_{\underline{dz}}T_{\underline{dz}}{}^{m}C_{ds}T_{ds}{}^{m}C_{ds}A_{ds}{}^{m}C_{\underline{dz}}A_{\underline{dz}}T_{ks}T_{ks}A_{k}$ | 59 | n.d. | 435 | 5 |
| 1467816 | $G_{ks}{}^{m}C_{ks}A_{ks}T_{ds}G_{ds}T_{ds}T_{\underline{dz}}{}^{m}C_{\underline{dz}}T_{ds}{}^{m}C_{ds}A_{ds}{}^{m}C_{\underline{dz}}A_{\underline{dz}}T_{ks}T_{ks}A_{k}$ | 67 | n.d. | 714 | 5 |
| 1467817 | $G_{ks}{}^{m}C_{ks}A_{ks}T_{ds}G_{ds}T_{ds}T_{ds}{}^{m}C_{\underline{dz}}T_{\underline{dz}}{}^{m}C_{ds}A_{ds}{}^{m}C_{\underline{dz}}A_{\underline{dz}}T_{ks}T_{ks}A_{k}$ | 38 | n.d. | 1146 | 5 |
| 1467818 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{ds}{}^{m}C_{\underline{dz}}A_{\underline{dz}}T_{ks}T_{ks}A_{k}$ | 66 | 129 | 812 | 5 |
| 1467819 | $G_{ks}{}^{m}C_{ks}A_{ks}T_{ds}G_{\underline{dz}}T_{\underline{dz}}T_{ds}{}^{m}C_{ds}T_{ds}{}^{m}C_{\underline{dz}}A_{\underline{dz}}{}^{m}C_{ds}A_{ds}T_{ks}T_{ks}A_{k}$ | 84 | n.d. | 181 | 5 |
| 1467820 | $G_{ks}{}^{m}C_{ks}A_{ks}T_{ds}G_{ds}T_{\underline{dz}}T_{\underline{dz}}{}^{m}C_{ds}T_{\underline{dz}}{}^{m}C_{\underline{dz}}A_{ds}{}^{m}C_{ds}A_{ds}T_{ks}T_{ks}A_{k}$ | 78 | 231 | 335 | 5 |

A subscript "k" represents a cEt nucleoside, a subscript "d" represents a stereostandard DNA nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 19: In Vitro Activity and Caspase Activation of Modified Oligonucleotides Comprising

Modified Oligonucleotides

Modified oligonucleotides comprising multiple mesyl phosphoramidate internucleoside linkages (Formula IX), phosphorothioate internucleoside linkages, and phosphodiester internucleoside linkages, were synthesized and tested. The modified oligonucleotides are each 3-10-3 cEt gapmers with a sugar motif of: kkkddddddddddkkk (a 3-10-3 cEt motif) or kkkdyddddddddkkk, where "k" represents a cEt modified sugar moiety, "y" represents a 2'-OMe modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s") or a mesyl phosphoramidate internucleoside linkage ("z").

In Vitro Assays

In vitro activity of modified oligonucleotides described above was tested as described in Example 1. In vitro toxicity of modified oligonucleotides described above was determined as described in Example 3. The internucleoside linkages and sugar modifications of the modified nucleosides are indicated in subscripts in the table below.

TABLE 33

Design, Activity, and Tolerability of modified oligonucleotides having multiple mesyl phosphoramidates linkages complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 54 | 2230 | 5 |
| 936053 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 144 | 102 | 5 |
| 1375418 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{kz}}T_{\underline{kz}}A_{k}$ | 74 | 1983 | 5 |
| 1405468 | $G_{\underline{kz}}{}^{m}C_{\underline{kz}}A_{\underline{kz}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 88 | 1480 | 5 |
| 1405469 | $G_{\underline{kz}}{}^{m}C_{\underline{kz}}A_{\underline{kz}}T_{ds}G_{ds}T_{ds}T_{ds}{}^{m}C_{ds}T_{ds}{}^{m}C_{ds}A_{ds}{}^{m}C_{ds}A_{ds}T_{\underline{kz}}T_{\underline{kz}}A_{k}$ | 58 | 1980 | 5 |
| 1405470 | $G_{\underline{kz}}{}^{m}C_{\underline{kz}}A_{\underline{kz}}T_{ds}G_{ys}T_{ds}T_{ds}{}^{m}C_{ds}T_{ds}{}^{m}C_{ds}A_{ds}{}^{m}C_{ds}A_{ds}T_{ks}T_{ks}A_{k}$ | 86 | 133 | 5 |
| 1405471 | $G_{ks}{}^{m}C_{ks}A_{ks}T_{ds}G_{ys}T_{ds}T_{ds}{}^{m}C_{ds}T_{ds}{}^{m}C_{ds}A_{ds}{}^{m}C_{ds}A_{ds}T_{\underline{kz}}T_{\underline{kz}}A_{k}$ | 78 | 131 | 5 |
| 1405472 | $G_{\underline{kz}}{}^{m}C_{\underline{kz}}A_{\underline{kz}}T_{ds}G_{ys}T_{ds}T_{ds}{}^{m}C_{ds}T_{ds}{}^{m}C_{ds}A_{ds}{}^{m}C_{ds}A_{ds}T_{\underline{kz}}T_{\underline{kz}}A_{k}$ | 73 | 148 | 5 |
| 1405488 | $G_{ks}{}^{m}C_{ks}A_{ks}T_{ds}G_{ys}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | 110 | 128 | 5 |
| 1405489 | $G_{ks}{}^{m}C_{ks}A_{ks}T_{ds}G_{yz}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | 94 | 182 | 5 |

TABLE 33-continued

Design, Activity, and Tolerability of modified oligonucleotides having multiple mesyl phosphoramidates linkages complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 1405490 | $G_{ks}{}^{m}C_{ks}A_{ks}T_{\underline{dz}}G_{yz}T_{ds}T_{ds}{}^{m}C_{ds}T_{ds}{}^{m}C_{ds}A_{ds}{}^{m}C_{ds}A_{ds}T_{ks}T_{ks}A_{k}$ | 78 | 107 | 5 |
| 1405491 | $G_{ks}{}^{m}C_{ks}A_{ks}T_{ds}G_{ys}T_{ds}T_{ds}{}^{m}C_{ds}T_{ds}{}^{m}C_{\underline{dz}}A_{\underline{dz}}{}^{m}C_{ds}A_{ds}T_{ks}T_{ks}A_{k}$ | 130 | 95 | 5 |
| 1405495 | $G_{ks}{}^{m}C_{ks}A_{ks}T_{ds}G_{ys}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | 91 | 74 | 5 |
| 1405496 | $G_{ks}{}^{m}C_{ks}A_{ks}T_{ds}G_{yz}T_{ds}T_{ds}{}^{m}C_{ds}T_{ds}{}^{m}C_{ds}A_{ds}{}^{m}C_{ds}A_{ds}T_{ks}T_{ks}A_{k}$ | 197 | 148 | 5 |
| 1405497 | $G_{ks}{}^{m}C_{ks}A_{ks}T_{ds}G_{ys}T_{ds}T_{ds}{}^{m}C_{ds}T_{ds}{}^{m}C_{ds}A_{\underline{dz}}{}^{m}C_{ds}A_{ds}T_{ks}T_{ks}A_{k}$ | 126 | 95 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage, and a subscript "y" represents a 2'-OMe modified nucleoside. Subscripts of nucleotides having an internucleoside linkage of formula IX are bold and underlined. A superscript "m" before a C represents a 5-methyl Cytosine.

Example 20: Design and Activity of siRNA to HRPT1 Having Mesyl Phosphoramidate Internucleoside Linkages In Vitro siRNA Double-stranded siRNA comprising modified oligonucleotides having mesyl phosphoramidate internucleoside linkages (Formula IX) in the sense and/or antisense strands were synthesized and tested. Each internucleoside linkage is either a phosphorothioate internucleoside linkage ("s"), a phosphodiester internucleoside linkage ("o"), or a mesyl phosphoramidate internucleoside linkage ("z").

Each antisense strand has the sequence AUAAAAUCUACAGUCAUAGGAAU (SEQ ID NO: 21) and is 100% complementary to GenBank NM_000194.2 (SEQ ID NO: 22) from 444 to 466, and each antisense strand has a 5'-phosphate. Each sense strand has the sequence UCCUAUGACUGUAGAUUUUAU (SEQ ID NO: 23) and is 100% identical to GenBank NM_000194.2 (SEQ ID NO: 22) from 446 to 466. Compound No. 1151789, 1337113, 1471455, and 1515982 comprise a 3'-linked C7 amino modifier (Glen Research), shown below:

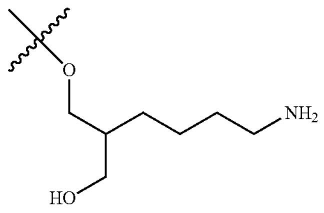 [SMILES: *OCC(CO)CCCCN]

Compound No. 1448688 further comprises a GalNAc conjugated at the 3'-oxygen of the oligonucleotide via a THA linker as shown below:

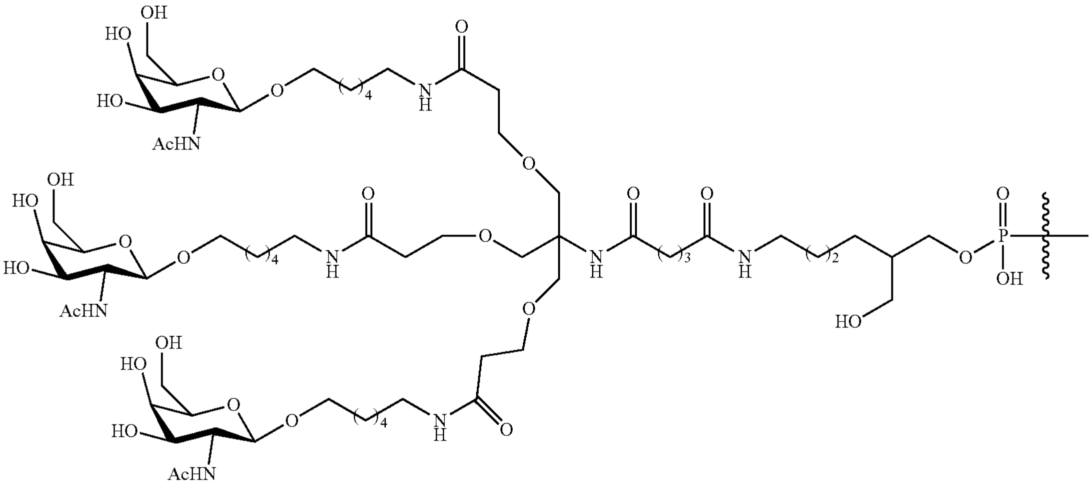

THA-C7-GalNAc

TABLE 34

Design of antisense strand modified oligonucleotides targeted to human/mouse HRPT1 having mesyl phosphoramidate linkages

| Compound ID | Chemical Notation (5' to 3') | SEQ ID NO: |
|---|---|---|
| 1073762 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1337111 | p.$A_{ys}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465680 | p.$A_{\underline{yz}}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465681 | p.$A_{ys}U_{\underline{fz}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465682 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{\underline{fz}}A_{\underline{yz}}A_{\underline{fz}}U_{y}$ | 21 |
| 1465683 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{\underline{yz}}A_{\underline{fz}}G_{\underline{yz}}G_{fo}A_{ys}A_{fs}U_{y}$ | 21 |
| 1465684 | p.$A_{yo}U_{fo}A_{yo}A_{fo}A_{yo}A_{fo}U_{yo}C_{fo}U_{yo}A_{fo}C_{yo}A_{fo}G_{yo}U_{\underline{fz}}C_{\underline{yz}}A_{\underline{fz}}U_{yo}A_{fo}G_{yo}G_{fo}A_{ys}A_{fs}U_{y}$ | 21 |
| 1465685 | p.$A_{yo}U_{fo}A_{yo}A_{fo}A_{yo}A_{fo}U_{yo}C_{fo}U_{yo}A_{fo}C_{\underline{yz}}A_{\underline{fz}}G_{\underline{yz}}U_{fo}C_{yo}A_{fo}U_{yo}A_{fo}G_{yo}G_{fo}A_{ys}A_{fs}U_{y}$ | 21 |
| 1465686 | p.$A_{yo}U_{fo}A_{yo}A_{fo}A_{yo}A_{fo}U_{yo}C_{\underline{fz}}U_{\underline{yz}}A_{\underline{fz}}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465687 | p.$A_{yo}U_{fo}A_{yo}A_{fo}A_{\underline{yz}}A_{\underline{fz}}U_{\underline{yz}}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1449196 | p.$A_{ys}U_{fs}A_{yo}A_{yo}A_{yo}A_{fo}U_{yo}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1466140 | p.$A_{ys}U_{fs}A_{yo}A_{yo}A_{yo}A_{fo}U_{yo}C_{yo}U_{yo}A_{yo}C_{yo}A_{yo}G_{yo}U_{fo}C_{yo}A_{fo}U_{yo}A_{yo}G_{yo}G_{yo}A_{\underline{yz}}A_{\underline{yz}}U_{y}$ | 21 |
| 1515975 | p.$A_{ys}U_{fs}A_{yo}A_{yo}A_{yo}A_{\underline{fz}}U_{yo}C_{yo}U_{yo}A_{yo}C_{yo}A_{yo}G_{yo}U_{\underline{fz}}C_{yo}A_{\underline{fz}}U_{yo}A_{yo}G_{yo}G_{yo}A_{ys}A_{ys}U_{y}$ | 21 |
| 1515976 | p.$A_{ys}U_{\underline{fz}}A_{yo}A_{yo}A_{yo}A_{\underline{fz}}U_{yo}C_{yo}U_{yo}A_{yo}C_{yo}A_{yo}G_{yo}u_{\underline{fz}}C_{yo}A_{\underline{fz}}U_{yo}A_{yo}G_{yo}G_{yo}A_{ys}A_{ys}U_{y}$ | 21 |

A "p." represents a 5'-phosphate. A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined.

TABLE 35

Design of sense strand modified oligonucleotides targeted to human/mouse HRPT1 having mesyl phosphoramidate linkages

| Compound ID | Chemical Notation (5' to 3') | SEQ ID NO: |
|---|---|---|
| 1151789 | $U_{fo}C_{yo}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{fo}A_{yo}U_{fo}$ [3'-amino C7 Tag] | 23 |
| 1448688 | $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{yo}A_{yo}U_{y}$ THA-C7-GalNAc | 23 |
| 1471455 | $U_{\underline{yz}}C_{\underline{yz}}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{\underline{yz}}A_{\underline{yz}}U_{yo}$ [3'-amino C7 Tag] | 23 |
| 1515982 | $U_{ys}C_{ys}C_{yo}U_{yo}A_{yo}U_{yo}G_{\underline{fz}}A_{yo}C_{\underline{fz}}U_{\underline{fz}}G_{\underline{fz}}U_{yo}A_{yo}G_{yo}A_{yo}U_{yo}U_{yo}U_{yo}U_{yo}A_{yo}U_{y}$ [3'-amino C7 tag] | 23 |

A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage.

Activity Assay

Activity of various siRNA formed by annealing one antisense strand and the sense strand 1151789 described above was tested in HeLa cells. HeLa cells were transfected with 6 μL/mL of siRNA using RNAIMAX for 5 hours. RNA was isolated and RNA expression was analyzed via RT-qPCR using primer probe set Hs02800695_m1(ThennoFisher).

TABLE 36

Activity of siRNAs having mesyl phosphoramidate linkages against human HPRT1

| Antisense Strand | Sense Strand | IC50 (nM) |
|---|---|---|
| 1073762 | 1151789 | 0.009 |
| 1337111 | 1151789 | 0.037 |
| 1465680 | 1151789 | 0.083 |
| 1465681 | 1151789 | 0.051 |

TABLE 36-continued

| Activity of siRNAs having mesyl phosphoramidate linkages against human HPRT1 | | |
|---|---|---|
| Antisense Strand | Sense Strand | IC50 (nM) |
| 1465682 | 1151789 | 0.016 |
| 1465683 | 1151789 | 0.023 |
| 1465684 | 1151789 | 0.042 |
| 1465685 | 1151789 | 0.045 |
| 1465686 | 1151789 | 0.082 |
| 1465687 | 1151789 | 0.382 |

TABLE 37

| Activity of siRNAs having mesyl phosphoramidate linkages against HPRT1 | | |
|---|---|---|
| Antisense Strand | Sense Strand | $IC_{50}$ (nM) |
| 1073762 | 1337113 | 0.075 |
| 1449196 | 1471455 | 0.040 |
| 1466140 | 1471455 | 0.049 |
| 1515975 | 1448688 | 0.066 |
| 1515976 | 1448688 | 0.137 |
| 1515975 | 1515982 | 2.531 |
| 1515976 | 1515982 | 3.875 |
| 1449196 | 1515982 | 0.190 |

Example 21: Measurement of Viscosity of Modified Oligonucleotides

The viscosity of modified oligonucleotides comprising mesyl phosphoramidate internucleoside linkages was compared to the viscosity of modified oligonucleotides having only phosphorothioate internucleoside linkages. Each nucleobase in the table below is represented by N, representing A, G, T, or $^{m}$C. Each of oligonucleotides A1, A2, and A3 have the same sequence, and each of oligonucleotides B1, B2, and B3 have the same sequence. Oligonucleotides (32-38 mg) were weighed into a glass vial; approximately 100 µL of water was added, and the modified oligonucleotide was dissolved into solution by heating the vial to 55° C. Part (75 µL) of the pre-heated sample was pipetted to a micro-viscometer (PAC Cambridge Viscosity Viscometer). The temperature of the micro-viscometer was set to 25° C. and the viscosity of the sample was measured. The entire 75 µL of sample was them combined with the remaining portion of the sample was diluted appropriately for UV reading at 260 nM (Cary UV instrument). The data below indicates that the incorporation of mesyl phosphoramidate linkages in the gap can reduce viscosity.

TABLE 38

| Viscosity | | | |
|---|---|---|---|
| Compound ID | Chemistry Notation | Viscosity (cP) | SEQ ID NO: |
| A1 | $N_{ks}N_{ks}N_{ks}N_{ds}N_{ds}N_{ds}N_{ds}N_{ds}N_{ds}N_{ds}N_{ds}N_{ds}N_{ds}N_{ks}N_{ks}N_{k}$ | 90.6 | 29 |
| A2 | $N_{ks}N_{ks}N_{ks}N_{\underline{dz}}N_{\underline{dz}}N_{\underline{dz}}N_{\underline{dz}}N_{ds}N_{ds}N_{ds}N_{ds}N_{ds}N_{ds}N_{ks}N_{ks}N_{k}$ | 46.0 | 29 |
| A3 | $N_{\underline{kz}}N_{\underline{kz}}N_{ks}N_{ds}N_{ds}N_{ds}N_{ds}N_{ds}N_{ds}N_{ds}N_{ds}N_{ds}N_{\underline{dz}}N_{\underline{kz}}N_{\underline{kz}}N_{k}$ | 96.2 | 29 |
| B1 | $N_{ks}N_{ks}N_{ks}N_{ds}N_{ds}N_{ds}N_{ds}N_{ds}N_{ds}N_{ds}N_{ds}N_{ds}N_{ks}N_{ks}N_{ks}N_{e}$ | 44.5 | 29 |
| B2 | $N_{ks}N_{ks}N_{ks}N_{\underline{dz}}N_{\underline{dz}}N_{\underline{dz}}N_{\underline{dz}}N_{ds}N_{ds}N_{ds}N_{ds}N_{ds}N_{ks}N_{ks}N_{ks}N_{e}$ | 17.0 | 29 |
| B3 | $N_{\underline{kz}}N_{\underline{kz}}N_{ks}N_{ds}N_{ds}N_{ds}N_{ds}N_{ds}N_{ds}N_{ds}N_{ds}N_{ds}N_{\underline{kz}}N_{\underline{kz}}N_{\underline{kz}}N_{e}$ | 9.6 | 29 |

A subscript "k" represents a cEt modified nucleoside, a subscript "d" represents a stereostandard DNA nucleoside, a subscript "e" represents a 2'-MOE modified nucleoside, a subscript "s" indicates a phosphorothioate internucleoside and a subscript "z" represents an internucleoside linkage of formula IX

Example 22: Synthesis and In Vivo Activity of siRNA to SOD-1 Having a C16 Modified-Phosphoramidate Internucleoside Linkage Double-stranded siRNA comprising a modified oligonucleotide having a mesyl phosphoramidate internucleoside linkage of Formula XIX in the sense strand was synthesized and tested in vivo.

For the sense strand, each internucleoside linkage is either a phosphorothioate internucleoside linkage ("s"), a phosphodiester internucleoside linkage ("o"), or a modified phosphoramidate internucleoside linkage having a C16 moiety, as shown below ("XIX").

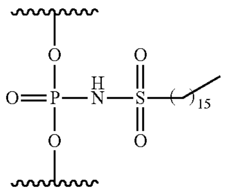

XIX

Synthesis

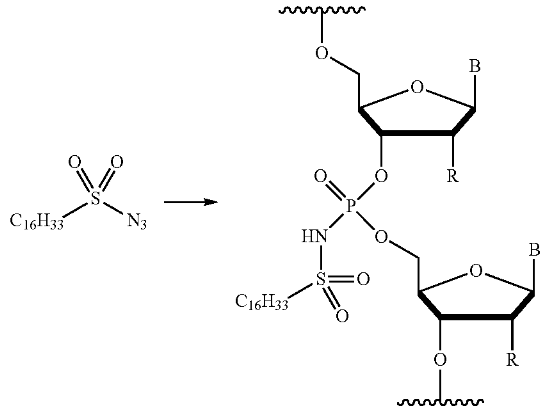

Oligonucleotides were synthesized on a 40 μmol scale using Nittophase UnyLinker support (405 μmol/g) on an AKTA 10 Oligopilot. Fully protected nucleoside phosphoramidites were incorporated using standard solid-phase oligonucleotide synthesis, i.e. 15% dichloroacetic acid in toluene for deblocking, 1 M 4,5-dicyanoimidazole 0.1 M N-methylimidazole in acetonitrile as activator for phosphoramidite couplings, 20% acetic anhydride in THF and 10% 1-methylimidazole in THF/pyridine for capping and 20% tBuOOH in acetonitrile for oxidation or 0.1 M xanthane hydride in pyridine:acetonitrile 3:2 (v:v) for thiolation. Oxidation to form the hexadecyl sulfonyl phosphoramidate linkage (Formula XIX) was performed using 0.5 M $C_{16}H_{33}SO_2N_3$ (hexadecyl sulfonyl azide) in acetonitrile:toluene 1:1 (v/v) with a 90 minute recycle time. Phosphoramidites were dissolved to 0.1 M in acetonitrile:toluene 1:1 (v:v) and incorporated using a 10 min coupling recycling time. At the end of the solid phase synthesis cyanoethyl protecting groups were removed by a 30 min treatment with 20% diethylamine in toluene. Oligonucleotides were deprotected and cleaved using conc. aq. ammonia at room temperature for 48 h. siRNA Design Double-stranded siRNA compounds were formed by annealing one antisense strand and one sense strand described below. Compound No. 1521629 is the antisense strand, wherein the sequence (from 5' to 3') UUAGAGUGAGGAUUAAAAUGAG (SEQ ID NO: 33) is 100% complementary to the genomic sequence of rat SOD-1, SEQ ID NO: 34, the complement of GENBANK Accession No. NW_047354.2, truncated from 29807000 to 29819000, at position 6230 to 6251. The non-complementary overhang is highlighted in bold in the table below.

TABLE 39

Design of antisense strand of modified oligonucleotides

| Compound ID | Chemistry Notation (5' to 3') | SEQ ID NO. |
|---|---|---|
| 1521629 | vP-$\mathbf{T}_{es}U_{fs}U_{yo}A_{yo}G_{yo}A_{fo}G_{yo}U_{fo}G_{fo}A_{yo}G_{yo}G_{yo}A_{yo}U_{fo}U_{yo}A_{fo}A_{yo}A_{yo}A_{yo}U_{yo}G_{ys}A_{ys}G_{y}$ | 33 |

In the table above, a subscript "f" represents a 2'-F modified nucleoside, a subscript "y" represents a 2'-OMe modified nucleoside, a subscript "e" represents a 2'-MOE modified nucleoside, a subscript "s" indicates a phosphorothioate internucleoside linkage, and a subscript "o" represents a phosphodiester internucleoside linkage. Compound No. 1521629 contains a vinyl phosphonate (vP) moiety on the 5'-end.

TABLE 40

Design of sense strand of modified oligonucleotides

| Compound ID | Chemistry Notation (5' to 3') | SEQ ID NO. |
|---|---|---|
| 1523488 | $C_{ys}A_{ys}U_{yo}U_{yo}U_{yo}U_{yo}A_{fo}A_{yo}U_{fo}C_{fo}C_{fo}U_{yo}C_{yo}A_{yo}C_{yo}U_{yo}C_{yo}U_{yo}A_{ys}A_{ys}A_{y}$ | 30 |
| 1524752 | $C_{ys}A_{ys}U_{yo}U_{yo}U_{yo}U_{y[XIX]}A_{fo}A_{yo}U_{fo}C_{fo}C_{fo}U_{yo}C_{yo}A_{yo}C_{yo}U_{yo}C_{yo}U_{yo}A_{ys}A_{ys}A_{y}$ | 30 |

In the table above, a subscript "f" represents a 2'-F modified nucleoside, a subscript "y" represents a 2'-OMe modified nucleoside, a subscript "s" indicates a phosphorothioate internucleoside linkage, and a subscript "o" represents a phosphodiester internucleoside linkage. A subscript "[XIX]" represents an internucleoside linkage of Formula XIX. Subscripts of nucleotides having a substituted phosphoramidate internucleoside linkage of generic Formula XVII are bold and underlined.

In Vivo

For the in vivo activity study in the table below, 2-4 Sprague Dawley rats per group were administered siRNA by intrathecal injection at a total dose of 7.5, 30, 75, 90, 300, or 900 μg. One group of four Sprague Dawley rats was injected with PBS as a control.

RNA Analysis

Two weeks post treatment, rats were sacrificed and RNA was extracted from cortical brain tissue and spinal cord for real-time qPCR analysis of SOD-1 RNA. Primer probe set RTS592 (forward sequence CGGATGAAGAGAGG-CATGTTG, designated herein as SEQ ID NO: 35; reverse sequence TTGGCCACACCGTCCTTT, designated herein as SEQ ID NO: 36; probe sequence AGACCTGGGCAATGTGGCTGCTG, designated herein as SEQ ID NO: 37) was used to determine the amount of SOD-1 RNA. The median effective dose ($ED_{50}$) of each siRNA was calculated in GraphPad Prism using the equation "log(agonist) vs. response—Find ECanything Least squares fit."

As shown in the table below, treatment with siRNA with a C16 modified-phosphoramidate internucleoside linkage resulted in increased potency in both the cortex and the spinal cord compared to an siRNA lacking a C16 modification.

TABLE 41

In vivo activity of siRNA to SOD-1

| Antisense Strand | Sense Strand | Cortex $ED_{50}$ (μg) | Spinal Cord $ED_{50}$ (μg) |
|---|---|---|---|
| 1521629 | 1523488 | 998 | 48 |
| 1521629 | 1524752 | 223 | 15 |

Example 23: Design, Activity, and Tolerability of Modified Oligonucleotides with Mesyl Phosphoramidate Internucleoside Linkages Complementary to Factor XI In Vivo Design of Modified Oligonucleotides GalNAc-conjugated modified oligonucleotides comprising multiple mesyl phosphoramidate internucleoside linkages (Formula IX) and phosphorothioate internucleoside linkages were synthesized and tested. The modified oligonucleotides are 100% complementary to the complement of mouse Factor XI, GENBANK Accession No. NT_039460.6 truncated from 6086000 to 6111000 (SEQ ID NO: 38), at position 22323 to 22338. Each internucleoside linkage is either a phosphorothioate internucleoside linkage ("s") or a mesyl phosphoramidate internucleoside linkage ("z").

The modified oligonucleotides in the table below contain the GalNAc moiety conjugated to the 3-oxygen as shown below:

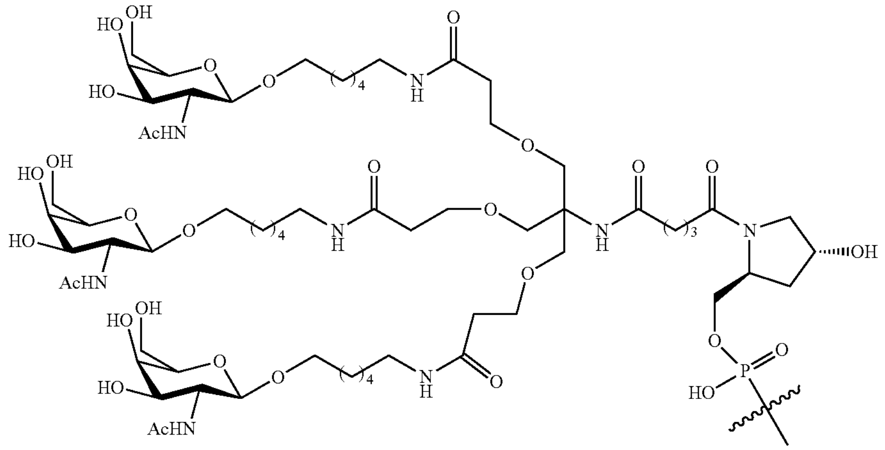

HPPO-GalNAc

TABLE 42

| Design of modified oligonucleotides with mesyl phosphoramidate internucleoside linkages | | |
|---|---|---|
| Compound ID | Chemistry Notation (5' to 3') | SEQ ID NO. |
| 1468445 | $^{m}C_{ks}T_{ks}G_{ks}T_{ds}T_{ds}T_{ds}G_{ds}A_{ds}G_{ds}T_{ds}T_{ds}T_{ds}T_{ds}{}^{m}C_{ks}T_{ks}{}^{m}C_{k}$-HPPO-GalNAc | 39 |
| 1506051 | $^{m}C_{ks}T_{ks}G_{ks}T_{ds}U_{ys}T_{ds}G_{ds}A_{ds}G_{ds}T_{ds}T_{ds}T_{ds}T_{ds}{}^{m}C_{ks}T_{ks}{}^{m}C_{k}$-HPPO-GalNAc | 40 |
| 1505717 | $^{m}C_{ks}T_{ks}G_{ks}T_{\underline{\mathbf{dz}}}T_{\underline{\mathbf{dz}}}T_{\underline{\mathbf{dz}}}G_{\underline{\mathbf{dz}}}A_{ds}G_{ds}T_{ds}T_{ds}T_{ds}T_{ds}{}^{m}C_{ks}T_{ks}{}^{m}C_{k}$-HPPO-GalNAc | 39 |

A subscript "k" represents a cEt nucleoside, a subscript "d" represents a stereo-standard DNA nucleoside, a subscript "s" indicates a phosphorothioate internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methylcytosine. HPPO-GalNAc represents a 3'-GalNAc moiety.

Study Design

For the in vivo activity and tolerability study in the table below, 3 BALB/C mice per group were administered a single dose of modified oligonucleotide by subcutaneous injection and sacrificed after 72 hours. Modified oligonucleotides were administered at 0.31, 0.93, 2.78, 8.33, or 25 mg/kg. One group of four BALB/C mice was injected with PBS.

Liver tissue was collected, mRNA was isolated, and levels of FXI in liver samples were measured by quantitative RTPCR with mouse primer probe set RTS2898 (forward sequence: ACATGACAGGCGCGATCTCT, SEQ ID NO: 41; reverse sequence: TCTAGGTTCACGTACACATCTTTGC, SEQ ID NO: 42; probe sequence: TTCCTTCAAGCAATGCCCTCAGCAAT, SEQ ID NO: 43). Expression levels were normalized to total RNA content as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 36.75 IU/L.

TABLE 43

| In vivo activity and toxicity of modified oligonucleotides complementary to FXI | | |
|---|---|---|
| Compound ID | in vivo FXI $ED_{50}$ liver (mg/kg) | ALT @ 25 mg/kg (IU/L) |
| 1468445 | 1.1 | 42 |
| 1506051 | 31 | 63 |
| 1505717 | 1.4 | 52 |

Example 24: Design, Activity, and Tolerability of Modified Oligonucleotides with Mesyl Phosphoramidate Internucleoside Linkages Complementary to HDAC2 In Vivo Design of Modified Oligonucleotides GalNAc-conjugated modified oligonucleotides having multiple mesyl phosphoramidate internucleoside linkages (Formula IX) and phosphorothioate internucleoside linkages were synthesized and tested. The modified oligonucleotides are 100% complementary to mouse HDAC2 GENBANK Accession No. NT_039492.7 truncated from 29396000 to 29430000 (SEQ ID NO: 44), at position 19150 to 19165. Each internucleoside linkage is either a phosphorothioate internucleoside linkage ("s") or a mesyl phosphoramidate internucleoside linkage ("z").

The modified oligonucleotides in the table below contain the GalNAc moiety conjugated to the 3'-oxygen as shown below:

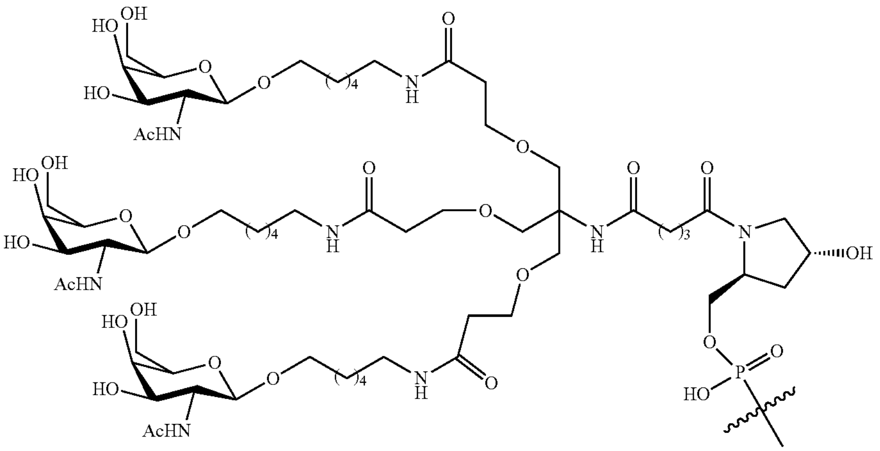

HPPO-GalNAc

TABLE 44

Design of modified oligonucleotides with mesyl phosphoramidate internucleoside linkages

| Compound ID | Chemistry Notation (5' to 3') | SEQ ID NO. |
|---|---|---|
| 1506050 | $A_{ks}{}^{m}C_{ks}{}^{m}C_{ks}{}^{m}C_{ds}U_{ys}{}^{m}C_{ds}A_{ds}A_{ds}G_{ds}T_{ds}{}^{m}C_{ds}T_{ds}{}^{m}C_{ds}{}^{m}C_{ks}T_{ks}G_{k}$ HPPO-GalNAc | 45 |
| 1505715 | $A_{ks}{}^{m}C_{ks}{}^{m}C_{ks}{}^{m}C_{\underline{\mathbf{dz}}}T_{\underline{\mathbf{dz}}}{}^{m}C_{\underline{\mathbf{dz}}}A_{\underline{\mathbf{dz}}}A_{ds}G_{ds}T_{ds}{}^{m}C_{ds}T_{ds}{}^{m}C_{ds}{}^{m}C_{ks}T_{ks}G_{k}$ HPPO-GalNAc | 46 |

A subscript "k" represents a cEt nucleoside, a subscript "d" represents a stereo-standard DNA nucleoside, a subscript "y" represents a 2'-OMe modified nucleoside, a subscript "s" indicates a phosphorothioate internucleoside linkage, and a subscript "z" represents an internucleoside linkage of formula IX, which is a mesyl phosphoramidate linkage.
Subscripts of nucleotides having an internucleoside linkage of formula IX are bold and underlined.
A superscript "m" before a C represents a 5-methylcytosine.

Study Design

For the in vivo activity and tolerability study in the table below, 3 BALB/C mice per group were administered a single dose of modified oligonucleotide by subcutaneous injection and sacrificed after 72 hours. Modified oligonucleotides were dosed at 0.3, 0.9, 2.8, 8.3, or 25 mg/kg. One group of four BALB/C mice was injected with PBS.

Liver tissue was collected, mRNA was isolated, and levels of HDAC2 in liver samples were measured by quantitative RTPCR with mouse primer probe set Mm00515108_m1 (Applied Biosystems). Expression levels were normalized to total RNA as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 53 IU/L.

TABLE 45

In vivo activity and toxicity of modified oligonucleotides complementary to HDAC2

| Compound ID | in vivo HDAC2 $ED_{50}$ liver (mg/kg) | ALT @ 25 mg/kg (IU/L) |
|---|---|---|
| 1506050 | 7.5 | 62 |
| 1505715 | 3.9 | 81 |

Example 25: Design, Activity, and Tolerability of Modified Oligonucleotides with Mesyl Phosphoramidate Internucleoside Linkages Complementary to DNM2 In Vivo Design of Modified Oligonucleotides GalNAc-conjugated modified oligonucleotides having multiple mesyl phosphoramidate internucleoside linkages (Formula IX) and phosphorothioate internucleoside linkages were synthesized and tested. Each of the modified oligonucleotides is 100% complementary to mouse DNM2, GENBANK NC_000075.6 truncated from 21422001 to 21511000 (SEQ ID NO: 47), at position 3046 to 3061. Each internucleoside linkage is either a phosphorothioate internucleoside linkage ("s") or a mesyl phosphoramidate internucleoside linkage ("z").

The modified oligonucleotides in the table below contain the GalNAc moiety conjugated to the 3-oxygen as shown below:

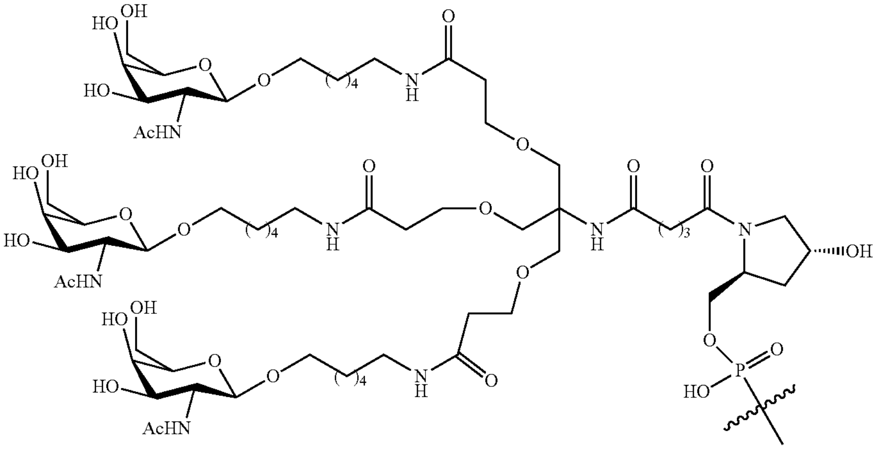

HPPO-GalNAc

TABLE 46

Design of modified oligonucleotides with mesyl phosphoramidate internucleoside linkages

| Compound ID | Chemistry Notation (5' to 3') | SEQ ID NO. |
|---|---|---|
| 1506053 | $A_{ks}G_{ks}A_{ks}{}^{m}C_{ds}U_{ys}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$-HPPO-GalNAc | 48 |
| 1505722 | $A_{ks}G_{ks}A_{ks}{}^{m}C_{\underline{\mathbf{dz}}}T_{\underline{\mathbf{dz}}}{}^{m}C_{\underline{\mathbf{dz}}}T_{\underline{\mathbf{dz}}}{}^{m}C_{ds}G_{ds}G_{ds}T_{ds}T_{ds}{}^{m}C_{ds}{}^{m}C_{ks}G_{ks}A_{k}$-HPPO-GalNAc | 49 |

A subscript "k" represents a cEt nucleoside, a subscript "d" represents a stereo-standard DNA nucleoside, a subscript "s" indicates a phosphorothioate internucleoside linkage, and a subscript "z" represents an internucleoside linkage of formula IX, which is a mesyl phosphoramidate linkage.
Subscripts of nucleotides having an internucleoside linkage of formula IX are bold and underlined.
A superscript "m" before a C represents a 5-methylcytosine.

Study Design

For the in vivo activity and tolerability study in the table below, 3 BALB/C mice per group were administered a single dose of modified oligonucleotide by subcutaneous injection and sacrificed after 72 hours. Modified oligonucleotides were dosed at 0.1, 0.3, 0.9, 2.8, 8.3, or 25 mg/kg. One group of four BALB/C mice was injected with PBS.

Liver tissue was collected, mRNA was isolated, and levels of DNM2 in liver samples were measured by quantitative RTPCR with primer probe set RTS36436 (forward sequence: AGAGGAGACCGAGCGAAT, SEQ ID NO: 50; reverse sequence: CATGGTTTGTGTTGATGTACGAC, SEQ ID NO: 51; probe sequence: CCTACATCAGGGAGCGAGAAGGGA, SEQ ID NO: 52). Expression levels were normalized to total RNA as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 38.75 IU/L.

TABLE 47

In vivo activity and toxicity of modified oligonucleotides complementary to DNM2

| Compound ID | in vivo DNM2 $ED_{50}$ liver (mg/kg) | ALT @ 25 mg/kg (IU/L) |
|---|---|---|
| 1506053 | 0.94 | 35 |
| 1505722 | 0.53 | 110 |

Example 26: Design and Activity of Modified Oligonucleotides Complementary to Mouse FXII In Vitro and a Single Dose Duration of Action Study Design of Modified Oligonucleotides GalNAc-conjugated modified oligonucleotides comprising multiple mesyl phosphoramidate internucleoside linkages (Formula IX) and phosphorothioate internucleoside linkages were synthesized and tested. Each of the modified oligonucleotides has the same nucleobase sequence, AGCACTTTATTGAGTT (SEQ ID NO: 53), which is 100% complementary to mouse FXII, the complement of GENBANK NC_000079.6 truncated from 55415001 to 55430000 (SEQ ID NO: 54), at position 12009 to 12024. Each internucleoside linkage is either a phosphorothioate internucleoside linkage ("s"), a phosphodiester internucleoside linkage ("o"), or a mesyl phosphoramidate internucleoside linkage ("z").

The GalNAc moiety is conjugated to the 5' oxygen of compound 1447171 via a THA linker, as shown below:

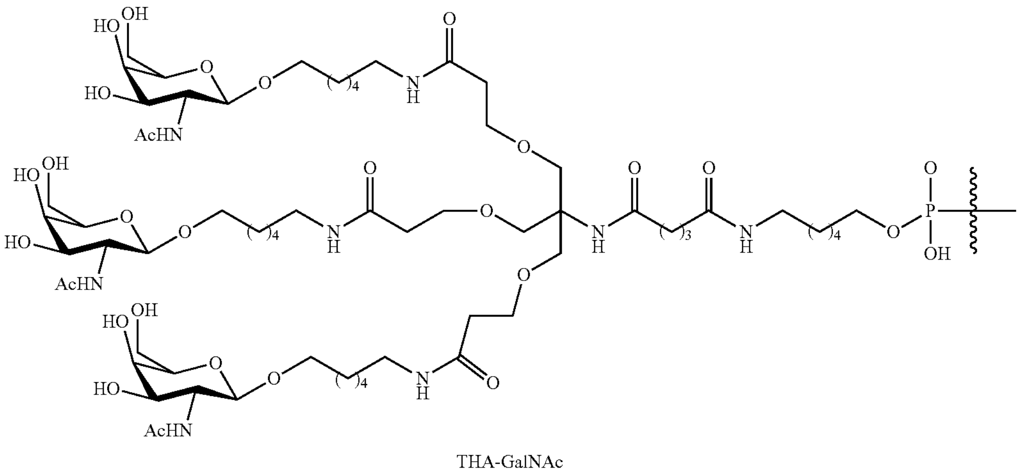

THA-GalNAc

Aside from compound 1447171, the modified oligonucleotides in the table below contain the GalNAc moiety conjugated to the 3-oxygen as shown below:

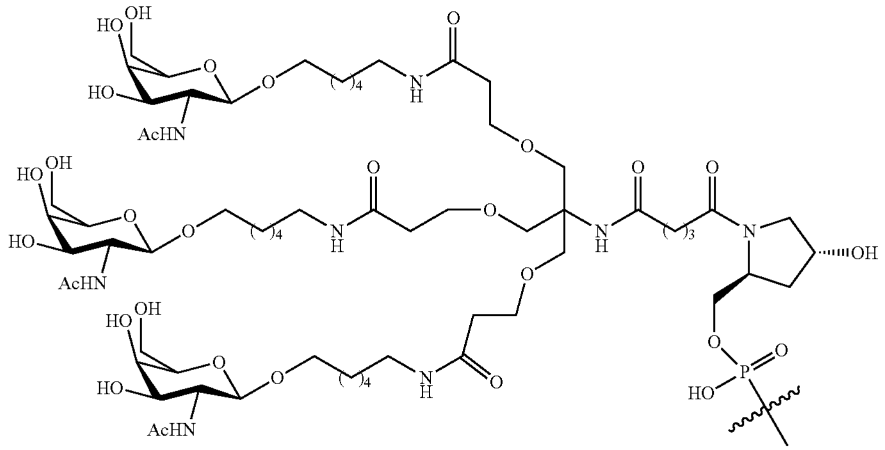

HPPO-GalNAc

Activity Assay

Activity of antisense oligonucleotides was tested in primary mouse hepatocytes. Primary mouse hepatocytes cells were transfected with lipofectamine. Each modified oligonucleotide was transfected at a starting concentration of 200 nM with 5-fold serial dilutions for a total of 8 dilutions. After a treatment period of approximately 24 hours, RNA was isolated and RNA expression was analyzed via quantitative RTPCR using primer probe set RTS2959 (forward sequence CAAAGGAGGGACATGTATCAACAC, SEQ ID NO: 91; reverse sequence: CTGGCAATGTTTCCCAGTGA, SEQ ID NO: 92; probe sequence: CCCAATGGGC-CACACTGTCTCTGC, SEQ ID NO: 93). FXII RNA levels were normalized to total GAPDH. Activity expressed as half maximal inhibitory concentration ($IC_{50}$) was calculated using the log (inhibitor) vs normalized response—Variable slope function in GraphPad Prism 7.

TABLE 48

Design and in vitro activity of modified oligonucleotides complementary to mouse FXII

| Compound ID | Chemistry Notation (5' to 3') | $IC_{50}$ (nM) | SEQ ID NO. |
|---|---|---|---|
| 1447171 | THA-GalNAc-$A_{ks}G_{ks}{}^{m}C_{ks}A_{ds}{}^{m}C_{ds}T_{ds}T_{ds}T_{ds}A_{ds}T_{ds}T_{ds}G_{ds}A_{ds}G_{ks}T_{ks}T_{k}$ | n.d. | 53 |
| 1525915 | $A_{ks}G_{ks}{}^{m}C_{ks}A_{ds}{}^{m}C_{ds}T_{ds}T_{ds}T_{ds}A_{ds}T_{ds}T_{ds}G_{ds}A_{ds}G_{ks}T_{ks}T_{k}$-HPPO-GalNAc | 0.0231 | 53 |
| 1525921 | $A_{ks}G_{ko}{}^{m}C_{ko}A_{ds}{}^{m}C_{ds}T_{ds}T_{ds}T_{ds}A_{ds}T_{ds}T_{ds}G_{ds}A_{ds}G_{ko}T_{ks}T_{k}$-HPPO-GalNAc | 0.0175 | 53 |
| 1525920 | $A_{ko}G_{ko}{}^{m}C_{ko}A_{ds}{}^{m}C_{ds}T_{ds}T_{ds}T_{ds}A_{ds}T_{ds}T_{ds}G_{ds}A_{ds}G_{ko}T_{ko}T_{k}$-HPPO-GalNAc | 0.0118 | 53 |
| 1525922 | $A_{ks}G_{ks}{}^{m}C_{ko}A_{ds}{}^{m}C_{ds}T_{ds}T_{ds}T_{ds}A_{ds}T_{ds}T_{ds}G_{ds}A_{do}G_{ks}T_{ks}T_{k}$-HPPO-GalNAc | 0.0135 | 53 |
| 1525923 | $A_{ks}G_{ks}{}^{m}C_{\underline{\mathbf{kz}}}A_{ds}{}^{m}C_{ds}T_{ds}T_{ds}T_{ds}A_{ds}T_{ds}T_{ds}G_{ds}A_{\underline{\mathbf{dz}}}G_{ks}T_{ks}T_{k}$-HPPO-GalNAc | 0.0155 | 53 |

TABLE 48-continued

Design and in vitro activity of modified oligonucleotides complementary to mouse FXII

| Compound ID | Chemistry Notation (5' to 3') | $IC_{50}$ (nM) | SEQ ID NO. |
|---|---|---|---|
| 1525924 | $A_{ks}G_{ks}{}^{m}C_{ks}A_{\underline{\mathbf{dz}}}{}^{m}C_{\underline{\mathbf{dz}}}T_{\underline{\mathbf{dz}}}T_{\underline{\mathbf{dz}}}T_{ds}A_{ds}T_{ds}T_{ds}G_{ds}A_{ds}G_{ks}T_{ks}T_{k}$-HPPO-GalNAc | 0.0111 | 53 |
| 1525925 | $A_{ks}G_{ko}{}^{m}C_{ko}A_{\underline{\mathbf{dz}}}{}^{m}C_{\underline{\mathbf{dz}}}T_{\underline{\mathbf{dz}}}T_{\underline{\mathbf{dz}}}T_{ds}A_{ds}T_{ds}T_{ds}G_{ds}A_{ds}G_{ko}T_{ks}T_{k}$ HPPO-GalNAc | 0.0118 | 53 |
| 1525919 | $A_{\underline{\mathbf{kz}}}G_{ko}{}^{m}C_{ko}A_{ds}{}^{m}C_{ds}T_{ds}T_{ds}T_{ds}A_{ds}T_{ds}T_{ds}G_{ds}A_{ds}G_{ko}T_{\underline{\mathbf{kz}}}T_{k}$ HPPO-GalNAc | 0.0292 | 53 |

A subscript "k" represents a cEt nucleoside, a subscript "d" represents a stereo-standard DNA nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage.

Subscripts of nucleotides having an internucleoside linkage of formula IX are bold and underlined.

A superscript "m" before a C represents a 5-methylcytosine.

Treatment

C57/B6J mice (Jax) were divided into groups of four male mice each for modified oligonucleotide treatment. Each mouse received a single subcutaneous injection of modified oligonucleotide at a dose of 0.9 mg/kg. One group of four mice received subcutaneous injections of PBS. The PBS-injected group served as the control group to which oligonucleotide-treated groups were compared. Prior to the first dose, a tail bleed was performed to determine plasma FXII protein levels at baseline (BL). Tail bleeds were also performed at 48 h, 96 h, 7 days, 14 days, and 21 days following the dose.

Protein Analysis

Mouse FXII protein levels in plasma were determined using a FXII ELISA kit (Molecular Innovations catalog number: MFXIIKT-TOT). The data is presented as percent change from baseline within each treatment group.

TABLE 49

| Reduction of mouse FXII protein in plasma | | | | | | |
|---|---|---|---|---|---|---|
| | FXII protein (% baseline) in plasma at indicated time after injection | | | | | |
| Compound No. | Day 0 (baseline) | 48 hours | 96 hours | 7 day | 14 day | 21 day |
| PBS | 100 | 168 | 257 | 137 | 138 | 118 |
| 1525915 | 100 | 139 | 93 | 23 | 31 | 67 |
| 1525921 | 100 | 90 | 58 | 23 | 38 | 59 |
| 1525920 | 100 | 119 | 101 | 24 | 29 | 65 |
| 1525922 | 100 | 70 | 45 | 18 | 27 | 41 |
| 1525923 | 100 | 89 | 92 | 35 | 48 | 102 |
| 1525924 | 100 | 88 | 54 | 29 | 43 | 58 |
| 1525925 | 100 | 90 | 52 | 20 | 16 | 35 |
| 1525919 | 100 | 95 | 61 | 21 | 29 | 46 |

Example 27: Design and Activity of siRNA Complementary to Mouse FXII in a Single Dose Duration of Action Study Design of siRNA Double-stranded siRNA compounds were formed by annealing one antisense strand and one sense strand described below. siRNA antisense strands containing mesyl phosphoramidate internucleoside linkages were designed as described in the table below and synthesized as described above. Each antisense strand has the sequence (from 5' to 3') UAAAGCACUUUAUUGAGUUUCUG (SEQ ID NO: 55) or TAAAGCACUUUAUUGAGUUUCUG (SEQ ID NO: 56), wherein the sequence (from 5' to 3') of AAAGCACUUUAUUGAGUUUCUG (SEQ ID NO: 57) is 100% complementary to mouse FXII, the complement of GENBANK NC_000079.6 truncated from 55415001 to 55430000 (SEQ ID NO: 54), at position 12005 to 12026.

TABLE 50

| Design of antisense strand of modified oligonucleotides complementary to mouse FXII | | |
|---|---|---|
| Compound ID | Chemistry Notation (5' to 3') | SEQ ID NO. |
| 1523579 | $U_{ys}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{ys}U_{ys}G_{y}$ | 55 |
| 1525955 | $U_{ys}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 55 |
| 1525956 | $U_{\underline{yz}}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 55 |
| 1525957 | $U_{ys}A_{\underline{fz}}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 55 |
| 1525958 | $U_{\underline{yz}}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 55 |
| 1525959 | $T_{es}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 55 |
| 1527076 | $U_{ys}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 55 |
| 1528437 | $T_{\underline{ez}}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 56 |
| 1528438 | $T_{eo}A_{\underline{fz}}A_{yo}A_{yo}G_{yo}C_{fo}A_{yo}C_{yo}U_{yo}U_{yo}U_{yo}A_{yo}U_{yo}U_{fo}G_{fo}A_{fo}G_{yo}U_{yo}U_{yo}U_{yo}C_{\underline{yz}}U_{\underline{yz}}G_{y}$ | 56 |
| 1526197 | vP-$T_{es}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 56 |
| 1528440 | z.$T_{es}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{yz}}U_{\underline{yz}}G_{y}$ | 56 |

In the table, above, a subscript "e" represents a 2'-MOE modified nucleoside, a subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. Compound No. 1526197 contains a vinyl phosphonate (vP) moiety on the 5'-end. Compound No. 1528440 contains a 5'-mesylphosphoramidate having formula XXII:

XXII

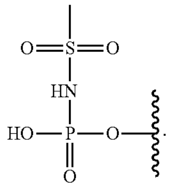

TABLE 51

| Design of sense strand of modified oligonucleotides | | |
|---|---|---|
| Compound ID | Chemistry Notation (5' to 3') | SEQ ID NO. |
| 1523578 | $G_{ys}A_{ys}A_{yo}A_{yo}A_{yo}C_{yo}U_{yo}C_{fo}A_{yo}A_{fo}U_{fo}A_{fo}A_{yo}A_{yo}G_{yo}U_{yo}G_{yo}C_{yo}U_{yo}U_{yo}U_{yo}A_{y}$-HPPO-GalNAc | 58 |
| 1523580 | $A_{ys}A_{ys}C_{yo}U_{yo}C_{yo}A_{yo}A_{fo}U_{yo}A_{fo}A_{fo}A_{fo}G_{yo}U_{yo}G_{yo}C_{yo}U_{yo}U_{yo}U_{yo}G_{yo}A_{yo}A_{y}$-HPPO-GalNAc | 59 |

In the table above, a subscript "f" represents a 2'-F modified nucleoside, a subscript "y" represents a 2'-OMe modified nucleoside, a subscript "s" indicates a phosphorothioate internucleoside linkage, and a subscript "o" represents a phosphodiester internucleoside linkage.

In Vitro Activity

Activity of various siRNA formed by annealing one antisense strand and one sense strand described above was tested in primary mouse hepatocytes. Primary mouse hepatocytes cells were transfected with RNAiMAX formulated siRNA. Each modified oligonucleotide was transfected at a starting concentration of 200 nM with 5-fold serial dilutions for a total of 8 dilutions. After a treatment period of approximately 24 hours, RNA was isolated and RNA expression was analyzed via quantitative RTPCR using primer probe set RTS2959 (described herein above). FXII RNA levels were normalized to total GAPDH. Activity expressed as half maximal inhibitory concentration ($IC_{50}$) was calculated using the log (inhibitor) vs normalized response—Variable slope function in GraphPad Prism 7.

TABLE 52a

Reduction of mouse FXII protein

| siRNA Duplex Compound No. | Antisense Compound No. | Sense Compound No. | $IC_{50}$ (nM) |
|---|---|---|---|
| 1523582 | 1523579 | 1523578 | 0.0015 |
| 1523583 | 1523581 | 1523580 | 0.0076 |
| 1526140 | 1525955 | 1523578 | 0.0060 |
| 1526171 | 1525956 | 1523578 | 0.1304 |
| 1526182 | 1525957 | 1523578 | 0.0086 |
| 1526193 | 1525958 | 1523578 | 0.1171 |
| 1526194 | 1525959 | 1523578 | 0.0376 |
| 1527077 | 1527076 | 1523578 | 0.0053 |
| 1529977 | 1528437 | 1523578 | 0.1266 |
| 1529978 | 1528438 | 1523578 | 0.0292 |
| 1529980 | 1528440 | 1523578 | 0.00003 |
| 1526198 | 1526197 | 1523578 | 0.0014 |

Treatment

C57/B6J mice (Jax) were divided into groups of four male mice each for treatment with siRNAs. Each mouse received a single subcutaneous injection of oligomeric duplex at a dose of 0.5 mg/kg. One group of four mice received subcutaneous injections of PBS. The PBS-injected group served as the control group to which oligonucleotide-treated groups were compared. Prior to the first dose, a tail bleed was performed to determine plasma FXII protein levels at baseline (BL). Tail bleeds were also performed at 48 h, 96 h, 7 days, 14 days, and 21 days following the dose.

Protein Analysis

Mouse FXII protein levels in plasma were determined using a Molecular Innovations FXII ELISA kit (catalog number: MFXIIKT-TOT). The data is presented as percent change in protein, relative to PBS control.

TABLE 52b

Reduction of mouse FXII protein

| siRNA Duplex Compound No. | Antisense Compound No. | Sense Compound No. | FXII protein (% baseline) in plasma at indicated time after injection: Day 0 (baseline) | 48 hours | 96 hours | 7 day | 14 day | 21 day |
|---|---|---|---|---|---|---|---|---|
| PBS | N/A | N/A | 100 | 168 | 257 | 137 | 138 | 118 |
| 1523582 | 1523579 | 1523578 | 100 | 75 | 62 | 30 | 40 | 42 |
| 1523583 | 1523581 | 1523580 | 100 | 108 | 155 | 48 | 25 | 33 |
| 1526140 | 1525955 | 1523578 | 100 | 83 | 69 | 32 | 38 | 47 |
| 1526171 | 1525956 | 1523578 | 100 | 143 | 256 | 193 | 112 | 144 |
| 1526182 | 1525957 | 1523578 | 100 | 71 | 60 | 17 | 26 | 39 |
| 1526193 | 1525958 | 1523578 | 100 | 134 | 228 | 144 | 96 | 127 |
| 1526194 | 1525959 | 1523578 | 100 | 131 | 88 | 65 | 64 | 111 |
| 1527077 | 1527076 | 1523578 | 100 | 78 | 60 | 36 | 36 | 96 |
| 1529977 | 1528437 | 1523578 | 100 | 114 | 99 | 80 | 105 | 107 |
| 1529978 | 1528438 | 1523578 | 100 | 111 | 150 | 167 | 109 | 132 |
| 1526198 | 1526197 | 1523578 | 100 | 64 | 25 | 16 | 19 | 30 |

Example 28: Design, Activity, and Tolerability of Modified Oligonucleotides with Mesyl Phosphoramidate Internucleoside Linkages in Combination with Stereo-Non-Standard Nucleosides Design of Modified Oligonucleotides Modified oligonucleotides comprising multiple mesyl phosphoramidate internucleoside linkages (Formula IX) and phosphorothioate internucleoside linkages were synthesized and tested. Each of the modified oligonucleotides has the same nucleobase sequence, AGACTCTCGGTTCCGA (SEQ ID NO: 49), which is 100% complementary to mouse DNM2, GENBANK Accession No. NC_000075.6 truncated from 21422001 to 21511000 (SEQ ID NO: 47), at position 3046 to 3061. Each internucleoside linkage is either a phosphorothioate internucleoside linkage ("s") or a mesyl phosphoramidate internucleoside linkage ("z").

TABLE 53

Design of modified oligonucleotides with mesyl phosphoramidate internucleoside linkages

| Compound ID | Chemistry Notation (5' to 3') | SEQ ID NO. |
|---|---|---|
| 694804 | $A_{ks}G_{ks}A_{ks}{}^{m}C_{ds}T_{ds}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537106 | $A_{ks}G_{ks}A_{ks}{}^{m}C_{\underline{dz}}T_{\underline{dz}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537108 | $A_{ks}G_{ks}A_{ks}{}^{m}C_{\underline{dz}}U_{\underline{yz}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 48 |
| 1537109 | $A_{ks}G_{ks}A_{ks}{}^{m}C_{\underline{dz}}T_{\underline{[aDd]z}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537110 | $A_{ks}G_{ks}A_{ks}{}^{m}C_{\underline{dz}}T_{\underline{[dx]z}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537111 | $A_{ks}G_{ks}A_{ks}{}^{m}C_{\underline{dz}}T_{\underline{[bLd]z}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537112 | $A_{ks}G_{ks}A_{ks}{}^{m}C_{\underline{dz}}T_{\underline{[aLd]z}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537113 | $A_{ks}G_{ks}A_{ks}{}^{m}C_{\underline{dz}}T_{\underline{[aDdx]z}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537114 | $A_{ks}G_{ks}A_{ks}{}^{m}C_{\underline{dz}}T_{\underline{[bLdx]z}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537115 | $A_{ks}G_{ks}A_{ks}{}^{m}C_{\underline{dz}}T_{\underline{[aLdx]z}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |

In the table above, a subscript "d" represents a stereo-standard DNA nucleoside, a subscript "y" represents a 2'-OMe modified nucleoside, a subscript "k" represents a cEt nucleoside, a subscript "s" indicates a phosphorothioate internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methylcytosine. A subscript "[bLd]" represents a 2'-β-L-deoxyribosyl sugar moiety, a subscript "[aDd]" represents a 2'-α-D-deoxyribosyl sugar moiety, a subscript "[aLd]" represents a 2'-α-L-deoxyribosyl sugar moiety, a subscript "[dx]" represents a 2'-β-D-deoxyxylosyl sugar moiety, a subscript "[bLdx]" represents a 2'-β-L-deoxyxylosyl sugar moiety, a subscript "[aDdx]" represents a 2'-α-D-deoxyxylosyl sugar moiety, a subscript "[aLdx]" represents a 2'-α-L-deoxyxylosyl sugar moiety (See FIG. 1)

In Vitro Activity Assay

The modified oligonucleotides were tested for their ability to reduce target RNA in a series of experiments. Cultured mouse 3T3-L1 cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, RNA levels were measured using DNM2 primer probe set RTS36436 (forward sequence: AGAGGAGACCGAGCGAAT, SEQ ID NO: 50; reverse sequence: CATGGTTTGTGTTGATGTACGAC, SEQ ID NO: 51; probe sequence: CCTACATCAGGGAGCGAGAAGGGA, SEQ ID NO: 52). RNA levels for each target were normalized to total RNA content, as measured by RIBOGREEN®. Activity expressed as half maximal inhibitory concentration ($IC_{50}$) was calculated using the log (inhibitor) vs response (three parameter) function in GraphPad Prism 7.

In Vitro Toxicity Assay

In vitro toxicity of modified oligonucleotides described above was determined as described in Example 3.

TABLE 54

In vitro activity and caspase activation by modified oligonucleotides with mesyl phosphoramidate internucleoside linkages in combination with stereo-non-standard nucleosides

| Compound ID | Caspase Activation (% Mock) | $IC_{50}$ (nM) |
|---|---|---|
| 694804 | 552 | 344 |
| 1537106 | 657 | 295 |
| 1537108 | 178 | 231 |
| 1537109 | 159 | 717 |
| 1537110 | 166 | 421 |
| 1537111 | 144 | 572 |

TABLE 54-continued

In vitro activity and caspase activation by modified oligonucleotides with mesyl phosphoramidate internucleoside linkages in combination with stereo-non-standard nucleosides

| Compound ID | Caspase Activation (% Mock) | $IC_{50}$ (nM) |
|---|---|---|
| 1537112 | 186 | 388 |
| 1537113 | 241 | 860 |
| 1537114 | 278 | 586 |
| 1537115 | 262 | 290 |

Example 29: Design and Activity of siRNA with Mesyl Phosphoramidate Internucleoside Linkages to HPRT1 In Vitro Design of siRNAs Double-stranded siRNAs comprising modified oligonucleotides having mesyl phosphoramidate internucleoside linkages (Formula IX) and having either stereo-standard nucleosides or stereo-non-standard nucleosides were synthesized and tested. Each internucleoside linkage is either a phosphorothioate internucleoside linkage ("s"), a phosphodiester internucleoside linkage ("o"), or a mesyl phosphoramidate internucleoside linkage ("z").

IX

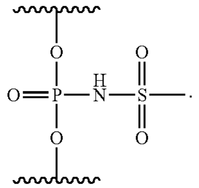

Each antisense strand has either the sequence (from 5' to 3'): TUAAAAUCUACAGUCAUAGGATT (SEQ ID NO: 60) or UUAAAAUCUACAGUCAUAGGATT (SEQ ID NO: 61), wherein the sequence (from 5' to 3') UAAAAUCUACAGUCAUAGGA (SEQ ID NO: 62) is 100% complementary to GenBank Accession No. NM_000194.2 (SEQ ID NO: 22) from 446 to 465, and each antisense strand has a 5'-phosphate.

The sense strand (Compound ID: 1505889) has the chemical notation (5' to 3'): $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{ys}A_{ys}U_{y}$ (SEQ ID NO: 23), wherein a subscript "f" represents a 2'-F modified nucleoside, a subscript "y" represents a 2'-OMe modified nucleoside, a subscript "s" indicates a phosphorothioate internucleoside linkage, and a subscript "o" represents a phosphodiester internucleoside linkage.

TABLE 55

Design of antisense strand modified oligonucleotides targeted to HPRT1 containing mesyl phosphoramidate internucleoside linkages

| Compound ID | Chemistry Notation (5' to 3') | SEQ ID NO. |
|---|---|---|
| 1512935 | P.$T_{ys}U_{fs}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1534483 | p.$U_{ys}U_{fs}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534484 | p.$T_{\underline{\mathbf{yz}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |

TABLE 55-continued

Design of antisense strand modified oligonucleotides targeted to HPRT1 containing mesyl phosphoramidate internucleoside linkages

| Compound ID | Chemistry Notation (5' to 3') | SEQ ID NO. |
|---|---|---|
| 1534485 | p.$U_{\underline{\mathbf{yz}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534486 | P.$U_{\underline{\mathbf{fz}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534487 | p.$U_{\underline{\mathbf{[f2bDa]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534488 | P.$U_{[f2bDx]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534489 | p.$U_{[f2aDr]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534490 | P.$U_{[f2aDa]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534491 | P.$U_{[f2aDx]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534493 | p.$U_{[f2aLr]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534494 | p.$U_{[f2bLx]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534495 | p.$U_{[f2aLa]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534496 | P.$U_{[f2aLx]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534497 | P.$U_{[f2bLr]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534492 | P.$U_{[f2bLa]o}U_{\underline{\mathbf{fz}}}A_{yo}A_{yo}A_{yo}A_{fo}U_{yo}C_{fo}U_{fo}A_{yo}$CycA$_{yo}G_{yo}U_{fo}C_{yo}A_{fo}U_{yo}A_{yo}G_{yo}G_{yo}A_{ys}T_{ds}T_{d}$ | 61 |
| 1537089 | p.$T_{\underline{\mathbf{[m2bDx]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1537090 | p.$T_{\underline{\mathbf{[m2bDa]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1537091 | p.$T_{\underline{\mathbf{[m2aDa]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1537092 | p.$T_{\underline{\mathbf{[m2aLa]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |

Figure 2:
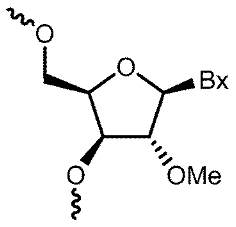
FIG. 2 depicts isomers of 2'-O-methyl furanosyl sugar moieties having formulas I-VII.
Figure 2:
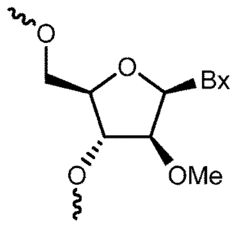
Figure 2:
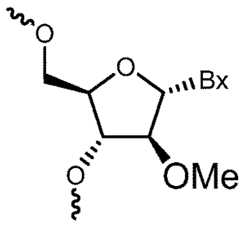
Figure 2:
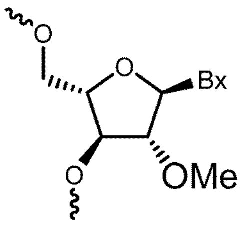
Figure 3:
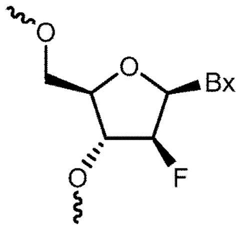
FIG. 3 depicts isomers of 2'-fluoro furanosyl sugar moieties having formulas I-VII.
Figure 3:
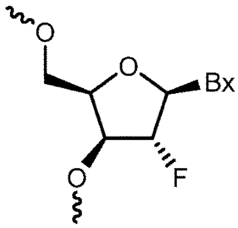
Figure 3:
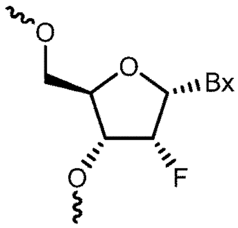
Figure 3:
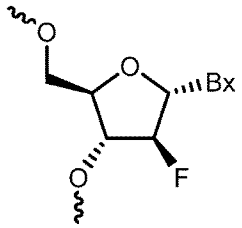
Figure 3:
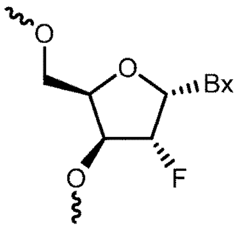
Figure 3:
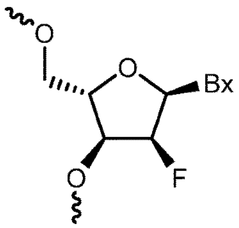
Figure 3:
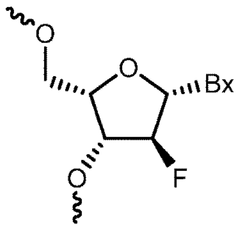
Figure 3:
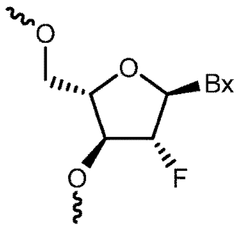
Figure 3:
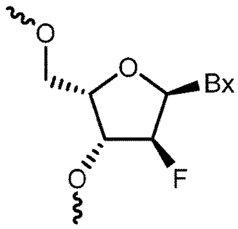
Figure 3:
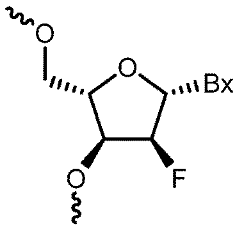
Figure 3:
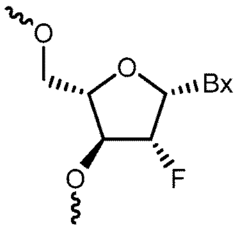

In the table above, a "p." represents a 5'-phosphate, a subscript "d" represents a stereo-standard DNA nucleoside, a subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. A subscript "[f2bDa]" represents a 2'-fluoro-β-D-arabinosyl sugar moiety, a subscript "[f2bDx]" represents a 2'-fluoro-β-D-xylosyl sugar moiety, a subscript "[f2aDr]" represents a 2'-fluoro-α-D-ribosyl sugar moiety, a subscript "[f2aDa]" represents a 2'-fluoro-α-D-arabinosyl sugar moiety, a subscript "[f2aDx]" represents a 2'-fluoro-α-D-xylosyl sugar moiety, a subscript "[f2aLr]" represents a 2'-fluoro-α-L-ribosyl sugar moiety, a subscript "[f2bLx]" represents a 2'-fluoro-β-L-xylosyl sugar moiety, a subscript "[f2aLa]" represents a 2'-fluoro-α-L-arabinosyl sugar moiety, a subscript "[f2aLx]" represents a 2'-fluoro-α-L-xylosyl sugar moiety, a subscript "[f2bLr]" represents a 2'-fluoro-β-L-ribosyl sugar moiety, a subscript "[f2bLa]" represents a 2'-fluoro-β-L-arabinosyl sugar moiety, a subscript "[m2bDx]" represents a 2'-O-methyl-β-D-xylosyl sugar moiety, a subscript "[m2bDa]" represents a 2'-O-methyl-β-D-arabinosyl sugar moiety, a subscript "[m2aDa]" represents a 2'-O-methyl-α-D-arabinosyl sugar moiety, a subscript "[m2aLa]" represents a 2'-O-methyl-α-L-arabinosyl sugar moiety. (See FIG. 2 and FIG. 3)

Activity Assay

Activity of various siRNA formed by annealing one antisense strand and one sense strand described above was tested in HeLa cells. HeLa cells were transfected with RNAiMAX formulated siRNA. Each siRNA compound was transfected at a starting concentration of 10 nM with 5-fold serial dilutions for a total of 8 dilutions. After a treatment period of approximately 6 hours, RNA was isolated and RNA expression was analyzed via quantitative RTPCR using primer probe set RTS35336 (forward sequence TTGTTGTAGGATATGCCCTTGA, SEQ ID NO: 63; reverse sequence: GCGATGTCAATAGGACTCCAG, SEQ ID NO: 64; probe sequence: AGCCTAAGATGAGAGTT-CAAGTTGAGTTTGG, SEQ ID NO: 65). HPRT1 RNA levels were normalized to total RNA content, as measured by RIBOGREEN®. $IC_{50}$ values were calculated and are presented in the table below.

TABLE 56

Activity of siRNAs targeted to HPRT1 containing mesyl phosphoramidate internucleoside linkages and/or stereo-non-standard nucleosides

| Antisense Strand | Sense Strand | $IC_{50}$ (nM) |
|---|---|---|
| 1455005 | 1505889 | 0.01 |
| 1512935 | 1505889 | 0.03 |
| 1534483 | 1505889 | 0.02 |
| 1534484 | 1505889 | 0.06 |
| 1534485 | 1505889 | 0.03 |

TABLE 56-continued

| Activity of siRNAs targeted to HPRT1 containing mesyl phosphoramidate internucleoside linkages and/or stereo-non-standard nucleosides | | |
|---|---|---|
| Antisense Strand | Sense Strand | $IC_{50}$ (nM) |
| 1534486 | 1505889 | 0.04 |
| 1534487 | 1505889 | 0.04 |
| 1534488 | 1505889 | 0.10 |
| 1534489 | 1505889 | 0.04 |
| 1534491 | 1505889 | 0.04 |
| 1534494 | 1505889 | 0.18 |
| 1534496 | 1505889 | 0.04 |
| 1534497 | 1505889 | 0.08 |
| 1534492 | 1505889 | 0.07 |
| 1537090 | 1505889 | 0.05 |
| 1537091 | 1505889 | 0.06 |
| 1537092 | 1505889 | 0.13 |

Example 30: Evaluation of Proinflammatory Effects in BJAB Assay

Modified oligonucleotides targeting human CRP, human neurology Target X, human CXCL12, human oncology target Y, or human oncology target Z were tested for potential immunostimulatory properties in an in vitro human BJAB activation assay.

Immortalized human Burkitt lymphoma B cells, BJAB cells (DSMZ, Cat #ACC 757), were cultured in RPMI1640 medium containing 20% fetal bovine serum at 37° C. and 5% $CO_2$. Cells were maintained at the optimal recommended density of 0.5-0.7×$10^6$ cells per milliliter. Cells were transferred to 50 mL conical Falcon tubes and centrifuged at 330 RCF for 5 minutes. Cells were resuspended at a concentration of 7.5×$10^5$ cells per milliliter in RPMI culture medium. 50 mL per well of RPMI culture medium containing 200 U/mL penicillin and 200 mg/ml streptomycin was added to v-bottom tissue culture treated 96-well microplate. 50 µL of the cell suspension was added to the v-bottom tissue culture treated 96-well microplate. 11 µl of 10× concentrated modified oligonucleotides was then added to the plate and incubated for 24 hours at 37° C. and 5% $CO_2$.

The modified oligonucleotides were designed as described in the table below, wherein "d" represents a 2'-β-D-deoxyribosyl sugar moiety, "k" represents a cEt sugar moiety, and "e" represents a 2'-MOE sugar moiety. Each internucleoside linkage is either a phosphorothioate internucleoside linkage ("s"), a phosphodiester internucleoside linkage ("o"), a mesyl phosphoramidate internucleoside linkage of Formula IX ("z"), a mesyl phosphoramidate internucleoside linkage of Formula XI ("[XI]"), or a mesyl phosphoramidate internucleoside linkage of Formula XIII ("[XIII]"). Subscripts of nucleotides having a modified mesyl phosphoramidate internucleoside linkage of generic Formula XVII are bold and underlined. All cytosine residues are 5-methylcytosines. A nucleobase represented by N in the table below indicates A, G, T, or $^{m}C$. Each oligonucleotide X (X1-X4) has the same sequence; each oligonucleotide Y (Y1-Y3) has the same sequence; and each oligonucleotide Z has the same sequence.

IX

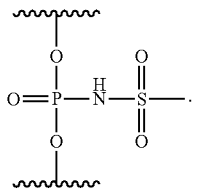

XI

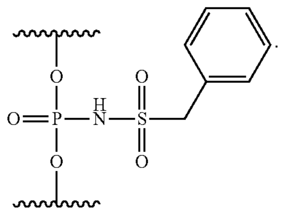

XIII

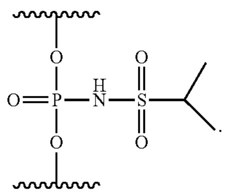

Compound Nos. 353512, 104838, 735746, and 785674 were added to the assay as standards. Compound No. 353512 is an internal standard known to be a high responder for CCL22 release in the assay. Compound No. 104838 is an internal standard known to be a non-responder in the assay (a negative control).

After incubation, total RNA was isolated. The amount of CCL22 mRNA was quantified using quantitative RTPCR. CCL22 PCR results were normalized to total GAPDH. Results are presented in the table below as log fold increase of CCL22, relative to untreated control.

TABLE 57

| Design and BJAB inflammatory response of modified oligonucleotides with mesyl phosphoramidate internucleoside linkages for BJAB assay | | | | |
|---|---|---|---|---|
| Compound ID | Chemistry Notation (5' to 3') | Target | CCL22 log fold increase | SEQ ID NO. |
| 104838 | $G_{es}{}^{m}C_{es}T_{es}G_{es}A_{ds}T_{ds}T_{ds}A_{ds}G_{ds}A_{ds}G_{ds}A_{ds}G_{ds}A_{ds}G_{ds}G_{es}T_{es}{}^{m}C_{es}{}^{m}C_{es}{}^{m}C_{e}$ | Standard-low | 0.32 | 66 |
| 353512 | $T_{es}{}^{m}C_{es}{}^{m}C_{es}{}^{m}C_{ds}A_{ds}T_{ds}T_{ds}T_{ds}{}^{m}C_{ds}A_{ds}G_{ds}G_{ds}A_{ds}G_{ds}A_{ds}{}^{m}C_{ds}{}^{m}C_{ds}T_{es}G_{es}G_{e}$ | Standard-high | 1.48 | 67 |
| X1 | $N_{es}N_{eo}N_{eo}N_{eo}N_{es}N_{ds}N_{ds}N_{ds}N_{ds}N_{ds}N_{ds}N_{ds}N_{ds}N_{ds}N_{ds}N_{eo}N_{eo}N_{es}N_{es}N_{e}$ | Target X | 2.38 | 70 |

TABLE 57-continued

Design and BJAB inflammatory response of modified oligonucleotides with mesyl phosphoramidate internucleoside linkages for BJAB assay

| Compound ID | Chemistry Notation (5' to 3') | Target | CCL22 log fold increase | SEQ ID NO. |
|---|---|---|---|---|
| X2 | $N_{\underline{\mathbf{ez}}}N_{\underline{\mathbf{ez}}}N_{eo}N_{eo}N_{es}N_{ds}N_{ds}N_{ds}N_{ds}N_{ds}$ $N_{ds}N_{ds}N_{ds}N_{ds}N_{ds}N_{eo}N_{eo}N_{\underline{\mathbf{ez}}}N_{\underline{\mathbf{ez}}}N_{e}$ | Target X | 1.63 | 70 |
| X3 | $N_{es}N_{eo}N_{eo}N_{eo}N_{es}N_{\underline{\mathbf{dz}}}N_{\underline{\mathbf{dz}}}N_{\underline{\mathbf{dz}}}N_{ds}N_{ds}$ $N_{ds}N_{ds}N_{ds}N_{ds}N_{ds}N_{eo}N_{eo}N_{es}N_{es}N_{e}$ | Target X | 0.70 | 70 |
| X4 | $N_{es}N_{eo}N_{eo}N_{eo}N_{es}N_{ds}N_{ds}N_{ds}N_{ds}N_{ds}$ $N_{ds}N_{ds}N_{\underline{\mathbf{dz}}}N_{\underline{\mathbf{dz}}}N_{\underline{\mathbf{dz}}}N_{eo}N_{eo}N_{es}N_{es}N_{e}$ | Target X | 0.95 | 70 |
| 353512 | $T_{es}{}^{m}C_{es}{}^{m}C_{es}{}^{m}C_{ds}A_{ds}T_{ds}T_{ds}T_{ds}{}^{m}C_{ds}A_{ds}$ $G_{ds}G_{ds}A_{ds}G_{ds}A_{ds}{}^{m}C_{ds}{}^{m}C_{ds}T_{es}G_{es}G_{e}$ | CRP | 1.40 | 69 |
| 1523450 | $T_{es}{}^{m}C_{es}{}^{m}C_{es}{}^{m}C_{\underline{\mathbf{dz}}}A_{\underline{\mathbf{dz}}}T_{\underline{\mathbf{dz}}}T_{ds}T_{ds}{}^{m}C_{ds}A_{ds}$ $G_{ds}G_{ds}A_{ds}G_{ds}A_{ds}{}^{m}C_{ds}{}^{m}C_{ds}T_{es}G_{es}G_{e}$ | CRP | 0.09 | 69 |
| 1523451 | $T_{es}{}^{m}C_{es}{}^{m}C_{es}{}^{m}C_{ds}A_{ds}T_{ds}T_{ds}T_{ds}{}^{m}C_{ds}A_{ds}$ $G_{ds}G_{ds}A_{ds}G_{ds}A_{\underline{\mathbf{dz}}}{}^{m}C_{\underline{\mathbf{dz}}}{}^{m}C_{\underline{\mathbf{dz}}}T_{es}G_{es}G_{e}$ | CRP | 0.57 | 69 |
| Y1 | $N_{ks}N_{ks}N_{ks}N_{ds}N_{ds}N_{ds}N_{ds}N_{ds}N_{ds}N_{ds}N_{ds}N_{ds}N_{ds}N_{ks}N_{ks}N_{k}$ | Target Y | 1.33 | 29 |
| Y2 | $N_{ks}N_{ks}N_{ks}N_{\underline{\mathbf{dz}}}N_{\underline{\mathbf{dz}}}N_{\underline{\mathbf{dz}}}N_{ds}N_{ds}N_{ds}N_{ds}N_{ds}N_{ds}N_{ds}N_{ks}N_{ks}N_{k}$ | Target Y | 0.77 | 29 |
| Y3 | $N_{ks}N_{ks}N_{ks}N_{ds}N_{ds}N_{ds}N_{ds}N_{ds}N_{ds}N_{ds}N_{\underline{\mathbf{dz}}}N_{\underline{\mathbf{dz}}}N_{\underline{\mathbf{dz}}}N_{ks}N_{ks}N_{k}$ | Target Y | 0.24 | 29 |
| Z1 | $N_{ks}N_{ks}N_{ks}N_{ds}N_{ds}N_{ds}N_{ds}N_{ds}N_{ds}N_{ds}N_{ds}N_{ds}N_{ds}N_{ks}N_{ks}N_{k}$ | Target Z | 1.15 | 29 |
| Z2 | $N_{\underline{\mathbf{kz}}}N_{\underline{\mathbf{kz}}}N_{ks}N_{ds}N_{ds}N_{ds}N_{ds}N_{ds}N_{ds}N_{ds}N_{ds}N_{ds}N_{ds}N_{\underline{\mathbf{kz}}}N_{\underline{\mathbf{kz}}}N_{k}$ | Target Z | 0.03 | 29 |
| Z3 | $N_{ks}N_{ks}N_{ks}N_{\underline{\mathbf{dz}}}N_{\underline{\mathbf{dz}}}N_{\underline{\mathbf{dz}}}N_{ds}N_{ds}N_{ds}N_{ds}N_{ds}N_{ds}N_{ds}N_{ks}N_{ks}N_{k}$ | Target Z | 0.56 | 29 |
| Z4 | $N_{ks}N_{ks}N_{ks}N_{ds}N_{ds}N_{ds}N_{ds}N_{ds}N_{ds}N_{ds}N_{\underline{\mathbf{dz}}}N_{\underline{\mathbf{dz}}}N_{\underline{\mathbf{dz}}}N_{ks}N_{ks}N_{k}$ | Target Z | 0.05 | 29 |
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.33 | 5 |
| 1375403 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{\underline{\mathbf{kz}}}A_{k}$ | CXCL12 | 0.39 | 5 |
| 1375404 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{\mathbf{kz}}}T_{ks}A_{k}$ | CXCL12 | 0.34 | 5 |
| 1375405 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{\underline{\mathbf{dz}}}T_{ks}T_{ks}A_{k}$ | CXCL12 | 0.07 | 5 |
| 1375406 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{\underline{\mathbf{dz}}}A_{ds}T_{ks}T_{ks}A_{k}$ | CXCL12 | 0.23 | 5 |
| 1375407 | $G_{ks}{}^{m}C_{ks}A_{ks}T_{ds}G_{ds}T_{ds}T_{ds}{}^{m}C_{ds}T_{ds}{}^{m}C_{ds}A_{\underline{\mathbf{dz}}}{}^{m}C_{ds}A_{ds}T_{ks}T_{ks}A_{k}$ | CXCL12 | 0.19 | 5 |
| 1375408 | $G_{ks}{}^{m}C_{ks}A_{ks}T_{ds}G_{ds}T_{ds}T_{ds}{}^{m}C_{ds}T_{ds}{}^{m}C_{\underline{\mathbf{dz}}}A_{ds}{}^{m}C_{ds}A_{ds}T_{ks}T_{ks}A_{k}$ | CXCL12 | 0.16 | 5 |
| 1375409 | $G_{ks}{}^{m}C_{ks}A_{ks}T_{ds}G_{ds}T_{ds}T_{ds}{}^{m}C_{ds}T_{\underline{\mathbf{dz}}}{}^{m}C_{ds}A_{ds}{}^{m}C_{ds}A_{ds}T_{ks}T_{ks}A_{k}$ | CXCL12 | 0.24 | 5 |
| 1375410 | $G_{ks}{}^{m}C_{ks}A_{ks}T_{ds}G_{ds}T_{ds}T_{ds}{}^{m}C_{\underline{\mathbf{dz}}}T_{ds}{}^{m}C_{ds}A_{ds}{}^{m}C_{ds}A_{ds}T_{ks}T_{ks}A_{k}$ | CXCL12 | 0.33 | 5 |
| 1375411 | $G_{ks}{}^{m}C_{ks}A_{ks}T_{ds}G_{ds}T_{ds}T_{\underline{\mathbf{dz}}}{}^{m}C_{ds}T_{ds}{}^{m}C_{ds}A_{ds}{}^{m}C_{ds}A_{ds}T_{ks}T_{ks}A_{k}$ | CXCL12 | 0.23 | 5 |
| 1375412 | $G_{ks}{}^{m}C_{ks}A_{ks}T_{ds}G_{ds}T_{\underline{\mathbf{dz}}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.37 | 5 |
| 1375413 | $G_{ks}{}^{m}C_{ks}A_{ks}T_{ds}G_{\underline{\mathbf{dz}}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.32 | 5 |
| 1375414 | $G_{ks}{}^{m}C_{ks}A_{ks}T_{\underline{\mathbf{dz}}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.22 | 5 |
| 1375415 | $G_{ks}{}^{m}C_{ks}A_{\underline{\mathbf{kz}}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.55 | 5 |
| 1375416 | $G_{ks}{}^{m}C_{\underline{\mathbf{kz}}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.29 | 5 |
| 1375417 | $G_{\underline{\mathbf{kz}}}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.21 | 5 |
| 1375418 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{\mathbf{kz}}}T_{\underline{\mathbf{kz}}}A_{k}$ | CXCL12 | 0.25 | 5 |
| 1375419 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{\underline{\mathbf{dz}}}T_{\underline{\mathbf{kz}}}T_{kz}A_{k}$ | CXCL12 | 0.06 | 5 |
| 1375420 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{\underline{\mathbf{dz}}}A_{\underline{\mathbf{dz}}}T_{ks}T_{ks}A_{k}$ | CXCL12 | 0.17 | 5 |
| 1375421 | $G_{ks}{}^{m}C_{ks}A_{ks}T_{ds}G_{ds}T_{ds}T_{ds}{}^{m}C_{ds}T_{ds}{}^{m}C_{ds}A_{\underline{\mathbf{dz}}}{}^{m}C_{\underline{\mathbf{dz}}}A_{ds}T_{ks}T_{ks}A_{k}$ | CXCL12 | 0.05 | 5 |

TABLE 57-continued

Design and BJAB inflammatory response of modified oligonucleotides with mesyl phosphoramidate internucleoside linkages for BJAB assay

| Compound ID | Chemistry Notation (5' to 3') | Target | CCL22 log fold increase | SEQ ID NO. |
|---|---|---|---|---|
| 1375422 | $G_{ks}{}^{m}C_{ks}A_{ks}T_{ds}G_{ds}T_{ds}T_{ds}{}^{m}C_{ds}T_{ds}{}^{m}C_{\underline{dz}}A_{\underline{dz}}{}^{m}C_{ds}A_{ds}T_{ks}T_{ks}A_{k}$ | CXCL12 | 0.13 | 5 |
| 1375423 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{ds}{}^{m}C_{ds}A_{ds}T_{ks}T_{ks}A_{k}$ | CXCL12 | 0.11 | 5 |
| 1375424 | $G_{ks}{}^{m}C_{ks}A_{ks}T_{ds}G_{ds}T_{ds}T_{ds}{}^{m}C_{\underline{dz}}T_{\underline{dz}}{}^{m}C_{ds}A_{ds}{}^{m}C_{ds}A_{ds}T_{ks}T_{ks}A_{k}$ | CXCL12 | 0.18 | 5 |
| 1375425 | $G_{ks}{}^{m}C_{ks}A_{ks}T_{ds}G_{ds}T_{ds}T_{\underline{dz}}{}^{m}C_{\underline{dz}}T_{ds}{}^{m}C_{ds}A_{ds}{}^{m}C_{ds}A_{ds}T_{ks}T_{ks}A_{k}$ | CXCL12 | 0.23 | 5 |
| 1375426 | $G_{ks}{}^{m}C_{ks}A_{ks}T_{ds}G_{ds}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | CXCL12 | 0.65 | 5 |
| 1375427 | $G_{ks}{}^{m}C_{ks}A_{ks}T_{ds}G_{\underline{dz}}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.26 | 5 |
| 1375428 | $G_{ks}{}^{m}C_{ks}A_{ks}T_{\underline{dz}}G_{\underline{dz}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.15 | 5 |
| 1375429 | $G_{ks}{}^{m}C_{ks}A_{\underline{kz}}T_{\underline{dz}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.42 | 5 |
| 1375430 | $G_{ks}{}^{m}C_{\underline{kz}}A_{\underline{kz}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.27 | 5 |
| 1375431 | $G_{\underline{dz}}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.20 | 5 |
| 1375432 | $G_{\underline{kz}}\ {}^{m}C_{\underline{kz}}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{\underline{kz}}T_{\underline{kz}}\ A_{k}$ | CXCL12 | 0.00 | 5 |
| 1378793 | $G_{ks}{}^{m}C_{ks}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{ds}T_{ks}T_{ks}A_{k}$ | CXCL12 | -0.04 | 5 |
| 1378794 | $G_{\underline{kz}}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{\underline{dz}}T_{\underline{kz}}T_{\underline{kz}}\ A_{k}$ | CXCL12 | 0.12 | 5 |
| 1386094 | $G_{ks}{}^{m}C_{ks}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.12 | 5 |
| 1386355 | $G_{ks}{}^{m}C_{ks}A_{ks}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{ds}T_{ks}T_{ks}A_{k}$ | CXCL12 | 0.01 | 5 |
| 1405434 | $G_{ks}{}^{m}C_{ks}A_{ks}T_{\underline{dz}}G_{\underline{dz}}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.08 | 5 |
| 1405435 | $G_{ks}{}^{m}C_{ks}A_{ks}T_{ds}G_{\underline{dz}}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | CXCL12 | 0.21 | 5 |
| 1405436 | $G_{ks}{}^{m}C_{ks}A_{ks}T_{\underline{dz}}G_{\underline{dz}}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | CXCL12 | 0.24 | 5 |
| 1427921 | $G_{ks}{}^{m}C_{ks}A_{ks}T_{\underline{d[XI]}}G_{\underline{d[XI]}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.19 | 5 |
| 1427922 | $G_{ks}{}^{m}C_{ks}A_{ks}T_{ds}G_{\underline{d[XI]}}T_{\underline{d[XI]}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.26 | 5 |
| 1427923 | $G_{ks}{}^{m}C_{ks}A_{ks}T_{ds}G_{ds}T_{\underline{d[XI]}}T_{\underline{d[XI]}}{}^{m}C_{ds}T_{ds}{}^{m}C_{ds}A_{ds}{}^{m}C_{ds}A_{ds}T_{ks}T_{ks}A_{k}$ | CXCL12 | 0.44 | 5 |
| 1427924 | $G_{ks}{}^{m}C_{ks}A_{ks}T_{ds}G_{ds}T_{ds}T_{ds}{}^{m}C_{ds}T_{ds}{}^{m}C_{\underline{d[XI]}}A_{\underline{d[XI]}}{}^{m}C_{ds}A_{ds}T_{ks}T_{ks}A_{k}$ | CXCL12 | 0.13 | 5 |
| 1429189 | $G_{ks}{}^{m}C_{ks}A_{ks}T_{\underline{d[XIII]}}G_{\underline{d[XIII]}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.26 | 5 |
| 1429190 | $G_{ks}{}^{m}C_{ks}A_{ks}T_{ds}G_{\underline{d[XIII]}}T_{\underline{d[XIII]}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.39 | 5 |
| 1429191 | $G_{ks}{}^{m}C_{ks}A_{ks}T_{ds}G_{ds}T_{\underline{d[XIII]}}T_{\underline{d[XIII]}}{}^{m}C_{ds}T_{ds}{}^{m}C_{ds}A_{ds}{}^{m}C_{ds}A_{ds}T_{ks}T_{ks}A_{k}$ | CXCL12 | 0.34 | 5 |
| 1429192 | $G_{ks}{}^{m}C_{ks}A_{ks}T_{ds}G_{ds}T_{ds}T_{ds}{}^{m}C_{ds}T_{ds}{}^{m}C_{\underline{d[XIII]}}A_{\underline{d[XIII]}}{}^{m}C_{ds}A_{ds}T_{ks}T_{ks}A_{k}$ | CXCL12 | 0.16 | 5 |
| 1437601 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | 0.00 | 5 |
| 1437602 | $G_{ks}{}^{m}C_{ks}A_{ks}T_{ds}G_{ds}T_{ds}T_{ds}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.03 | 5 |
| 1437603 | $G_{ks}{}^{m}C_{ks}A_{ks}T_{ds}G_{ds}T_{ds}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.08 | 5 |
| 1437604 | $G_{ks}{}^{m}C_{ks}A_{ks}T_{ds}G_{ds}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.10 | 5 |
| 1437605 | $G_{ks}{}^{m}C_{ks}A_{ks}T_{ds}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.09 | 5 |
| 1437606 | $G_{ks}{}^{m}C_{ks}A_{ks}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.04 | 5 |
| 1441068 | $G_{ks}{}^{m}C_{ks}A_{\underline{kz}}T_{ds}G_{\underline{dz}}T_{ds}T_{\underline{dz}}{}^{m}C_{ds}T_{\underline{dz}}{}^{m}C_{ds}A_{\underline{dz}}{}^{m}C_{ds}A_{\underline{dz}}T_{ks}T_{ks}A_{k}$ | CXCL12 | -0.04 | 5 |
| 1441069 | $G_{ks}{}^{m}C_{ks}A_{ks}T_{\underline{dz}}G_{ds}T_{\underline{dz}}T_{ds}{}^{m}C_{\underline{dz}}T_{ds}{}^{m}C_{\underline{dz}}A_{ds}{}^{m}C_{\underline{dz}}A_{ds}T_{ks}T_{ks}A_{k}$ | CXCL12 | -0.03 | 5 |

In the table above, a subscript "d" represents a 2'-β-D-deoxyribosyl sugar moiety, "k" represents a cEt sugar moiety, and "e" represents a 2'-MOE sugar moiety. Each internucleoside linkage is either a phosphorothioate internucleoside linkage ("s"), a phosphodiester internucleoside linkage ("o"), a mesyl phosphoramidate internucleoside linkage of Formula IX ("z"), a mesyl phosphoramidate internucleoside linkage of Formula XI ("[XI]"), or a mesyl phosphoramidate internucleoside linkage of Formula XIII ("[XIII]"). Subscripts of nucleotides having a modified mesyl phosphoramidate internucleoside linkage of generic Formula XVII are bold and underlined. All cytosine residues are 5-methylcytosines. A nucleobase represented by N in the table above indicates A, G, T, or $^{m}$C.

Example 31: Exonuclease Stability of Modified Oligonucleotides with Mesyl Phosphoramidate Internucleoside Linkages Oligonucleotides comprising mesyl phosphoramidate internucleoside linkages were synthesized using standard techniques or those described herein. Each oligonucleotide in the table below has the sequence TTTTTTTTTTTT (SEQ ID NO:71).

The oligonucleotides described below were incubated at 5 μM concentration in buffer with snake venom phosphodiesterase (SVPD, Sigma P4506, Lot #SLBV4179), a strong 3'-exonuclease, at the standard concentration of 0.5 mU/mL and at a higher concentration of 2 mU/mL. SVPD is commonly used to measure the stability of modified nucleosides (see, e.g., *Antisense Drug Technology*, Crooke S. T., Ed., CRC Press, 2008). Aliquots were removed at various time points and analyzed by MS-HPLC with an internal standard. Relative peak areas were plotted versus time and half-life was determined using GraphPad Prism. A longer half-life means the 3'-terminal nucleosides have increased resistance to the SVPD exonuclease.

The results in the table below show that modified oligonucleotides comprising mesyl phosphoramidate internucleoside linkages are more stable to exonuclease degradation than unmodified DNA, 2'-MOE, and LNA with phosphodiester linkages. Such compounds are also more stable to exonuclease degradation than PS-linked DNA, and adding a second mesyl phosphoramidate internucleoside linkage on the 3' end increases stability even further.

TABLE 58

Exonuclease resistance of modified oligonucleotides with mesyl phosphoramidate internucleoside linkages

| Compound ID | Chemistry Notation (5' to 3') | SVPD (mU/mL) | $T_{1/2}$ (min) | SEQ ID NO. |
|---|---|---|---|---|
| 7157 | $T_{do}T_{do}T_{do}T_{do}T_{do}T_{do}T_{do}T_{do}T_{do}T_{do}T_{do}T_{d}$ | 0.5 | 0.4 | 71 |
| 395421 | $T_{do}T_{do}T_{do}T_{do}T_{do}T_{do}T_{do}T_{do}T_{do}T_{do}T_{eo}T_{e}$ | 0.5 | 7.1, 4.8 | 71 |
| 395422 | $T_{do}T_{do}T_{do}T_{do}T_{do}T_{do}T_{do}T_{do}T_{do}T_{do}T_{lo}T_{l}$ | 0.5 | 27.8 | 71 |
| 1506055 | $T_{do}T_{do}T_{do}T_{do}T_{do}T_{do}T_{do}T_{do}T_{do}T_{do}T_{ds}T_{d}$ | 0.5 | 46.8 | 71 |
| 1506055 | $T_{do}T_{do}T_{do}T_{do}T_{do}T_{do}T_{do}T_{do}T_{do}T_{do}T_{ds}T_{d}$ | 2 | 8.9 | 71 |
| 1468868 | $T_{do}T_{do}T_{do}T_{do}T_{do}T_{do}T_{do}T_{do}T_{do}T_{do}T_{\underline{\mathbf{dz}}}T_{d}$ | 2 | 29.1 | 71 |
| 1468869 | $T_{do}T_{do}T_{do}T_{do}T_{do}T_{do}T_{do}T_{do}T_{do}T_{\underline{\mathbf{dz}}}T_{\underline{\mathbf{dz}}}T_{d}$ | 2 | 69.6 | 71 |
| 1515981 | $T_{do}T_{do}T_{do}T_{do}T_{do}T_{do}T_{do}T_{do}T_{do}T_{do}T_{\underline{\mathbf{lz}}}T_{l}$ | 2 | 26.7 | 71 |

A subscript "d" indicates a nucleoside comprising an unmodified, 2'-β-D-deoxyribosyl sugar moiety.
A subscript "e" indicates a 2'-MOE sugar moiety.
A subscript "l" indicates an LNA.
A subscript "o" indicates a phosphodiester internucleoside linkage.
A subscript "s" indicates a phosphorothioate internucleoside linkage.
A subscript "z" indicates an internucleoside linkage of formula IX, which is a mesyl phosphoramidate linkage.
Subscripts of nucleotides having an internucleoside linkage of formula IX are bold and underlined.

Example 32: Exonuclease Stability of siRNA Antisense Oligonucleotides with Mesyl Phosphoramidate Internucleoside Linkages Oligonucleotides comprising mesyl phosphoramidate internucleoside linkages were synthesized using standard techniques or those described herein. Each oligonucleotide in the table below has the sequence (SEQ ID NO: 21)
AUAAAAUCUACAGUCAUAGGAAU.

SVPD Assay

Selected oligonucleotides described below were tested in a 3'-exonuclease assay. Modified oligonucleotides were incubated at 5 μM concentration in buffer with snake venom phosphodiesterase (SVPD, Sigma P4506, Lot #SLBV4179), a strong 3'-exonuclease, at the standard concentration of 2 mU/mL. SVPD is commonly used to measure the stability of modified nucleosides (see, e.g., Antisense Drug Technology, Crooke S. T., Ed., CRC Press, 2008). Aliquots were removed at various time points and analyzed by MS-HPLC with an internal standard. Relative peak areas were plotted versus time and half-life was determined using GraphPad Prism. A longer half-life means the 3'-terminal nucleosides have increased resistance to the SVPD exonuclease.

BSPDII Assay

Selected oligonucleotides described below were tested in a 5'-exonuclease assay. Modified oligonucleotides were first incubated with 100 units/mL alkaline phosphatase (AP, Sigma P7923, Lot SLCB86083) in Tris-HCl buffer at pH 8.5 for 30 minutes, until the reaction was complete by MS-HPLC. The pH was adjusted to 6.5 and oligonucleotides were incubated with 5 mU/mL or 10 mU/mL bovine spleen phosphodiesterase II (BSPDII) (see Bernardi, A. and G. Bernardi, "Studies on acid hydrolases: IV. Isolation and characterization of spleen exonuclease." *Biochimica et Biophysica Acta-Nucleic Acids and Protein Synthesis* 155(2): 360-370, 1968).

Aliquots were removed at various time points and analyzed by MS-HPLC with an internal standard. Relative peak areas were plotted versus time and half-life was determined using GraphPad Prism. A longer half-life means the 5'-terminal nucleosides have increased resistance to the PD II exonuclease.

*Acids Res* 48(8): 4382-4395) and analyzed by MS-HPLC with an internal standard. Relative peak areas for 0 and 24 h time points were determined and % intact modified oligonucleotide calculated.

Assay for Alkaline Phosphatase Enzyme Stability

Antisense oligonucleotides having modification patterns suitable for RNAi were investigated for phosphatase stability utilizing alkaline phosphatase from bovine intestinal mucosa (AP, Sigma P7923, Lot SLCB86083). Modified oligonucleotides were incubated in Tris-HCl buffer at pH 8.5 containing 100 units/mL alkaline phosphatase (AP, Sigma P7923, Lot mLCB86083). Aliquots were removed at 30 minutes and analyzed by HPLC-MS. The κ'-terminal phosphate groups were removed at this lime point for oligonucleotides 1337111, 1405420 and 1405428 while the 5'-terminal mesyl phosphoramidate group of 1527118 was still intact. 24- and 48-hour time points were taken for this compound and HPLC-MS analysis revealed that the mesyl phosphoramidate group was still present.

TABLE 59

Design of siRNA antisense oligonucleotides with mesyl phosphoramidate internucleoside linkages

| Compound ID | Chemistry Notation (5' to 3') | SEQ ID NO. |
|---|---|---|
| 1527119 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{yo}A_{fo}U_{y}$ | 22 |
| 1073762 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 22 |
| 1337111 | p.$A_{ys}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 22 |
| 1405420 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{\underline{\mathbf{yz}}}A_{\underline{\mathbf{fz}}}U_{y}$ | 22 |
| 1405427 | p.$A_{\underline{\mathbf{yz}}}U_{\underline{\mathbf{fz}}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{yo}A_{fo}U_{y}$ | 22 |
| 1405428 | p.$A_{\underline{\mathbf{yz}}}U_{\underline{\mathbf{fz}}}A_{yo}A_{fo}A_{yo}A_{fo}U_{yo}C_{fo}C_{yo}A_{fo}C_{yo}A_{fo}G_{yo}U_{fo}C_{yo}A_{fo}U_{yo}A_{fo}G_{yo}G_{fo}A_{\underline{\mathbf{yz}}}A_{\underline{\mathbf{fz}}}U_{y}$ | 22 |

A subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage.

Subscripts of nucleotides having an internucleoside linkage of formula IX are bold and underlined.

A superscript "m" before a C represents a 5-methylcytosine.

Assay for Tritosome Stability of siRNA Antisense Oligonucleotides

Antisense oligonucleotides having modification patterns suitable for RNAi were investigated for tritosome stability in rat tritosomes. Modified oligonucleotides were incubated at 5 mM for 0 and 48 hours in 20% rat tritosomes in pH 4.5 acetate buffer. Samples were extracted utilizing standard protocols (Chappell, A. E., et al. (2020). "Mechanisms of palmitic acid-conjugated antisense oligonucleotide distribution in mice." *Nucleic Acids Res* 48(8): 4382-4395) and analyzed by MS-HPLC with an internal standard. Relative peak areas for 0 and 48 h time points were determined and percent of full length modified oligonucleotide was calculated. Oligonucleotides lacking the 5'-terminal phosphate are included as "full length" due to rapid removal of this moiety.

Assay for Plasma Stability of siRNA Antisense Oligonucleotides

Antisense oligonucleotides having modification patterns suitable for RNAi were investigated for plasma stability in fresh mouse serum. Modified oligonucleotides were incubated for 0 and 24 hours in 50% fresh mouse serum. Samples were extracted utilizing standard protocols (Chappell, A. E., et al. (2020). "Mechanisms of palmitic acid-conjugated antisense oligonucleotide distribution in mice." *Nucleic*

TABLE 60

Nuclease stability of siRNA antisense oligonucleotides with mesyl phosphoramidate internucleoside linkages

| | SVPD Assay (3') | BSPII Assay (5') T½ (min) | | Tritosome Stability | Plasma Stability | AP Assay Time to |
|---|---|---|---|---|---|---|
| Compound ID | T½ (min) | T½ (min) | Amount (mU/mL) | % full length | % full length | remove 5'-moiety |
| 1527119 | 0.3 | n.d. | N/A | 0 | 0 | >48 hours |
| 1073762 | 4.2 | n.d. | N/A | 0 | 28 | n.d. |
| 1337111 | 5.5 | 29.7 | 10 | 55 | 28 | <30 min |
| 1405420 | 12.8 | 2.7 | 5 | 0 | 58 | <30 min |
| 1405427 | 0.3 | n.d. | N/A | 0 | 0 | n.d. |
| 1405428 | 9.5 | 42.6 | 10 | 100 | 44 | <30 min |

Example 33: Design, Activity, and Tolerability of Modified Oligonucleotides with Mesyl Phosphoramidate Internucleoside Linkages In Vivo Design of Modified Oligonucleotides Modified oligonucleotides comprising multiple mesyl phosphoramidate internucleoside linkages (Formula IX) and phosphorothioate internucleoside linkages were designed, synthesized and tested. The modified oligonucleotides are each 5-10-5 MOE gapmers with a sugar motif of: eeeeedddddddddddeeeee, where "e" represents a 2'-MOE modified sugar moiety, and "d" represents a 2'-β-D-deoxyribosyl sugar moiety. Each of the modified oligonucleotides has the same nucleobase sequence, GCCAGGCTGGTTATGACTCA (SEQ ID NO: 72), which is 100% complementary to the complement of mouse Malat1, GENBANK Accession No. NC_000085.6 truncated from 5793001 to 5806000 (SEQ ID NO: 73), at position 6668 to 6687. Each internucleoside linkage is either a phosphorothioate internucleoside linkage ("s"), a phosphodiester internucleoside linkage ("o"), or a mesyl phosphoramidate internucleoside linkage ("z").

IX

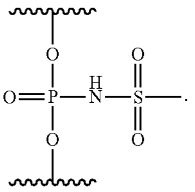

TABLE 61

Design of modified oligonucleotides with mesyl phosphoramidate internucleoside linkages

| Compound ID | Chemistry Notation (5' to 3') | SEQ ID NO. |
|---|---|---|
| 602056 | $G_{es}{}^mC_{es}{}^mC_{es}A_{es}G_{es}G_{ds}{}^mC_{ds}T_{ds}G_{ds}G_{ds}T_{ds}T_{ds}A_{ds}T_{ds}G_{ds}A_{es}{}^mC_{es}T_{es}{}^mC_{es}A_e$ | 72 |
| 626112 | $G_{es}{}^mC_{eo}{}^mC_{eo}A_{eo}G_{eo}G_{ds}{}^mC_{ds}T_{ds}G_{ds}G_{ds}T_{ds}T_{ds}A_{ds}T_{ds}G_{ds}A_{eo}{}^mC_{eo}T_{es}{}^mC_{es}A_e$ | 72 |
| 1454990 | $G_{eo}{}^mC_{eo}{}^mC_{eo}A_{eo}G_{eo}G_{ds}{}^mC_{ds}T_{ds}G_{ds}G_{ds}T_{ds}T_{ds}A_{ds}T_{ds}G_{ds}A_{eo}{}^mC_{eo}T_{eo}{}^mC_{eo}A_e$ | 72 |
| 1469248 | $G_{es}{}^mC_{eo}{}^mC_{eo}A_{eo}G_{eo}G_{ds}{}^mC_{ds}T_{ds}G_{ds}G_{ds}T_{ds}T_{ds}A_{ds}T_{ds}G_{ds}A_{eo}{}^mC_{eo}T_{eo}{}^mC_{es}A_e$ | 72 |
| 1515340 | $G_{es}{}^mC_{es}{}^mC_{es}A_{es}G_{\underline{\mathbf{ez}}}G_{ds}{}^mC_{ds}T_{ds}G_{ds}G_{ds}T_{ds}T_{ds}A_{ds}T_{ds}G_{\underline{\mathbf{dz}}}A_{es}{}^mC_{es}T_{es}{}^mC_{es}A_e$ | 72 |
| 1515341 | $G_{\underline{\mathbf{ez}}}{}^mC_{es}{}^mC_{es}A_{es}G_{es}G_{ds}{}^mC_{ds}T_{ds}G_{ds}G_{ds}T_{ds}T_{ds}A_{ds}T_{ds}G_{ds}A_{es}{}^mC_{es}T_{\underline{\mathbf{ez}}}{}^mC_{\underline{\mathbf{ez}}}A_e$ | 72 |
| 1515342 | $G_{es}{}^mC_{es}{}^mC_{es}A_{es}G_{eo}G_{ds}{}^mC_{ds}T_{ds}G_{ds}G_{ds}T_{ds}T_{ds}A_{ds}T_{ds}G_{do}A_{es}{}^mC_{es}T_{es}{}^mC_{es}A_e$ | 72 |
| 1515344 | $G_{es}{}^mC_{es}{}^mC_{es}A_{es}G_{es}G_{ds}{}^mC_{do}T_{ds}G_{ds}G_{ds}T_{ds}T_{ds}A_{ds}T_{ds}G_{ds}A_{es}{}^mC_{es}T_{es}{}^mC_{es}A_e$ | 72 |
| 1515346 | $G_{es}{}^mC_{es}{}^mC_{es}A_{es}G_{es}G_{\underline{\mathbf{dz}}}{}^mC_{\underline{\mathbf{dz}}}T_{\underline{\mathbf{dz}}}G_{ds}G_{ds}T_{ds}T_{ds}A_{ds}T_{ds}G_{ds}A_{es}{}^mC_{es}T_{es}{}^mC_{es}A_e$ | 72 |
| 1515347 | $G_{es}{}^mC_{es}{}^mC_{es}A_{es}G_{es}G_{\underline{\mathbf{dz}}}{}^mC_{\underline{\mathbf{dz}}}T_{\underline{\mathbf{dz}}}G_{\underline{\mathbf{dz}}}G_{ds}T_{ds}T_{ds}A_{ds}T_{ds}G_{ds}A_{es}{}^mC_{es}T_{es}{}^mC_{es}A_e$ | 72 |
| 1515348 | $G_{es}{}^mC_{es}{}^mC_{es}A_{es}G_{es}G_{\underline{\mathbf{dz}}}{}^mC_{\underline{\mathbf{dz}}}T_{\underline{\mathbf{dz}}}G_{\underline{\mathbf{dz}}}G_{\underline{\mathbf{dz}}}T_{ds}T_{ds}A_{ds}T_{ds}G_{ds}A_{es}{}^mC_{es}T_{es}{}^mC_{es}A_e$ | 72 |
| 1515350 | $G_{\underline{\mathbf{ez}}}{}^mC_{eo}{}^mC_{eo}A_{eo}G_{eo}G_{ds}{}^mC_{ds}T_{ds}G_{ds}G_{ds}T_{ds}T_{ds}A_{ds}T_{ds}G_{ds}A_{eo}{}^mC_{eo}T_{\underline{\mathbf{ez}}}{}^mC_{\underline{\mathbf{ez}}}A_e$ | 72 |
| 1515355 | $G_{es}{}^mC_{eo}{}^mC_{eo}A_{eo}G_{eo}G_{\underline{\mathbf{dz}}}{}^mC_{\underline{\mathbf{dz}}}T_{\underline{\mathbf{dz}}}G_{\underline{\mathbf{dz}}}G_{ds}T_{ds}T_{ds}A_{ds}T_{ds}G_{\underline{\mathbf{dz}}}A_{eo}{}^mC_{eo}T_{es}{}^mC_{es}A_e$ | 72 |
| 1524739 | $G_{\underline{\mathbf{ez}}}{}^mC_{eo}{}^mC_{eo}A_{eo}G_{eo}G_{ds}{}^mC_{ds}T_{ds}G_{ds}G_{ds}T_{ds}T_{ds}A_{ds}T_{ds}G_{ds}A_{eo}{}^mC_{eo}T_{eo}{}^mC_{\underline{\mathbf{ez}}}A_e$ | 72 |
| 1524740 | $G_{\underline{\mathbf{ez}}}{}^mC_{eo}{}^mC_{eo}A_{eo}G_{eo}G_{\underline{\mathbf{dz}}}{}^mC_{ds}T_{ds}G_{ds}G_{ds}T_{ds}T_{ds}A_{ds}T_{ds}G_{ds}A_{eo}{}^mC_{eo}T_{eo}{}^mC_{\underline{\mathbf{ez}}}A_e$ | 72 |
| 1524741 | $G_{\underline{\mathbf{ez}}}{}^mC_{eo}{}^mC_{eo}A_{eo}G_{eo}G_{\underline{\mathbf{dz}}}{}^mC_{\underline{\mathbf{dz}}}T_{ds}G_{ds}G_{ds}T_{ds}T_{ds}A_{ds}T_{ds}G_{ds}A_{eo}{}^mC_{eo}T_{eo}{}^mC_{\underline{\mathbf{ez}}}A_e$ | 72 |
| 1524742 | $G_{\underline{\mathbf{ez}}}{}^mC_{eo}{}^mC_{eo}A_{eo}G_{eo}G_{\underline{\mathbf{dz}}}{}^mC_{\underline{\mathbf{dz}}}T_{\underline{\mathbf{dz}}}G_{ds}G_{ds}T_{ds}T_{ds}A_{ds}T_{ds}G_{ds}A_{eo}{}^mC_{eo}T_{eo}{}^mC_{\underline{\mathbf{ez}}}A_e$ | 72 |
| 1524743 | $G_{\underline{\mathbf{ez}}}{}^mC_{eo}{}^mC_{eo}A_{eo}G_{eo}G_{\underline{\mathbf{dz}}}{}^mC_{\underline{\mathbf{dz}}}T_{\underline{\mathbf{dz}}}G_{\underline{\mathbf{dz}}}G_{ds}T_{ds}T_{ds}A_{ds}T_{ds}G_{ds}A_{eo}{}^mC_{eo}T_{eo}{}^mC_{\underline{\mathbf{ez}}}A_e$ | 72 |
| 1524744 | $G_{\underline{\mathbf{ez}}}{}^mC_{eo}{}^mC_{eo}A_{eo}G_{eo}G_{\underline{\mathbf{dz}}}{}^mC_{\underline{\mathbf{dz}}}T_{\underline{\mathbf{dz}}}G_{\underline{\mathbf{dz}}}G_{\underline{\mathbf{dz}}}T_{ds}T_{ds}A_{ds}T_{ds}G_{ds}A_{eo}{}^mC_{eo}T_{eo}{}^mC_{\underline{\mathbf{ez}}}A_e$ | 72 |
| 1524745 | $G_{\underline{\mathbf{ez}}}{}^mC_{eo}{}^mC_{eo}A_{eo}G_{eo}G_{\underline{\mathbf{dz}}}{}^mC_{\underline{\mathbf{dz}}}T_{\underline{\mathbf{dz}}}G_{\underline{\mathbf{dz}}}G_{\underline{\mathbf{dz}}}T_{\underline{\mathbf{dz}}}T_{ds}A_{ds}T_{ds}G_{ds}A_{eo}{}^mC_{eo}T_{eo}{}^mC_{\underline{\mathbf{ez}}}A_e$ | 72 |

A subscript "e" represents a 2'-MOE modified nucleoside, a subscript "d" represents a stereo-standard DNA nucleoside, a subscript "s" indicates a phosphorothioate internucleoside linkage, a subscript "o" indicates a phosphodiester internucleoside linkage, and a subscript "z" represents an internucleoside linkage of formula 1X, which is a mesyl phosphoramidate linkage.

Subscripts of nucleotides having an internucleoside linkage of formula IX are bold and underlined.

A superscript "m" before a C represents a 5-methylcytosine.

Activity in CNS

Oligonucleotides described above were tested in wild-type female C57/B16 mice to assess the activity of the oligonucleotides. Wild-type female C57/B16 mice each received a single ICV bolus of 30 µg of modified oligonucleotide listed in the table below. Each treatment group consisted of 4 mice. A group of 4 mice received PBS as a negative control. Twelve days post treatment, mice were sacrificed and RNA was extracted from cortical brain tissue and spinal cord for quantitative RTPCR analysis to measure the amount of Malat1 RNA using mouse primer probe set RTS592 (forward sequence CGGATGAAGAGAGG-CATGTTG, designated herein as SEQ ID NO: 74; reverse sequence TTGGCCACACCGTCCTTT, designated herein as SEQ ID NO: 75; probe sequence AGACCTGGGCAATGTGGCTGCTG, designated herein as SEQ ID NO: 76). Results are presented as percent mouse Malat1 RNA relative to PBS control, adjusted to mouse Cyclophilin A RNA.

TABLE 62

In vivo CNS activity of modified oligonucleotides complementary to Malat1

| Compound ID | MALAT1 RNA Cortex (% Control) | MALAT1 RNA Spinal Cord (% Control) |
|---|---|---|
| 602056 | 37 | 16 |
| 626112 | 40 | 26 |
| 1454990 | 93 | 68 |
| 1469248 | 53 | 34 |
| 1515340 | 45 | 11 |
| 1515341 | 48 | 17 |
| 1515342 | 56 | 21 |
| 1515344 | 91 | 64 |
| 1515346 | 49 | 19 |
| 1515347 | 51 | 25 |
| 1515348 | 45 | 22 |

TABLE 62-continued

In vivo CNS activity of modified oligonucleotides complementary to Malat1

| Compound ID | MALAT1 RNA Cortex (% Control) | MALAT1 RNA Spinal Cord (% Control) |
|---|---|---|
| 1515350 | 63 | 38 |
| 1515355 | 78 | 46 |
| 1524739 | 56 | 36 |
| 1524740 | 66 | 29 |
| 1524741 | 69 | 31 |
| 1524742 | 76 | 45 |
| 1524743 | 69 | 48 |
| 1524744 | 72 | 58 |
| 1524745 | 74 | 58 |

Example 34: Activity and Tolerability of siRNA with Mesyl Phosphoramidate Internucleoside Linkages to HPRT1 In Vivo siRNA Double-stranded siRNA comprising modified oligonucleotides having mesyl phosphoramidate internucleoside linkages (Formula IX) in the antisense strand were synthesized and tested. Each internucleoside linkage is either a phosphorothioate internucleoside linkage ("s"), a phosphodiester internucleoside linkage ("o"), or a mesyl phosphoramidate internucleoside linkage ("z").

Each antisense strand has the sequence AUAAAAUC-UACAGUCAUAGGAAU (SEQ ID NO: 21) and is 100% complementary to GenBank NM_000194.2 (SEQ ID NO: 22) from 444 to 466, and each antisense strand has a 5'-phosphate. The sense strand, Compound No. 1448688, has the chemical notation $U_{ys}C_{ys}C_{yo}U_{yo}A_{yo}U_{yo}$Gro$A_{yo}C_{fo}U_{fo}G_{fo}U_{yo}A_{yo}G_{yo}A_{yo}U_{yo}U_{yo}U_{yo}U_{yo}A_{yo}U_{y}$-THA-C7-GalNAc (SEQ ID NO: 23). The THA-C7-GalNAc conjugate is attached to the 3'-oxygen and has the structure below:

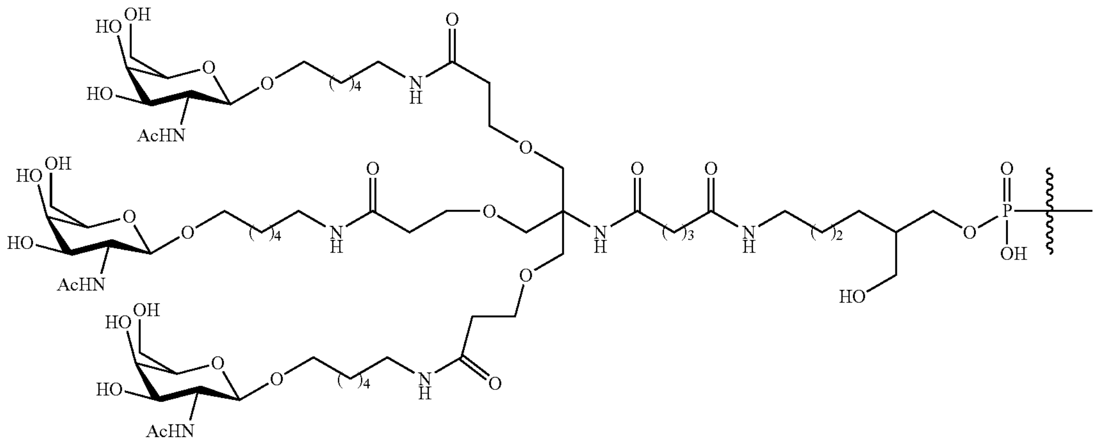

THA-C7-GalNAc

TABLE 63

Design of antisense strand modified oligonucleotides targeted to HPRT1 containing mesyl phosphoramidate internucleoside linkages

| Compound ID | Chemistry Notation (5' to 3') | SEQ ID NO. |
|---|---|---|
| 1337111 | p.$A_{ys}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1405428 | p.$A_{\underline{yz}}U_{\underline{fz}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{\underline{yz}}A_{\underline{fz}}U_{y}$ | 21 |
| 1465680 | p.$A_{\underline{yz}}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465681 | p.$A_{ys}U_{\underline{fz}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |

In the table above, a "p." represents a 5'-phosphate, a subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined.

In Vivo Tolerability and Activity Assay

For the in vivo activity and tolerability study in the table below, 4 C57/B6J male mice per group were administered siRNA by subcutaneous injection and sacrificed after 72 hours. The siRNA compounds were administered at 0.3, 1, or 3 mg/kg. One group of four C57/B6J mice was injected with PBS.

Liver tissue was collected, total RNA was isolated, and levels of HPRT1 in liver samples were measured by quantitative RTPCR with primer probe set RTS43125 (forward sequence: CTCCTCAGACCGCTTTTTGC, SEQ ID NO: 77; reverse sequence: TAACCTGGTTCATCATCGCTAATC, SEQ ID NO: 78; probe sequence: CCGTCATGCCGACCCGCAGT, SEQ ID NO: 79). Expression levels were normalized to total RNA as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 58.8 IU/L.

TABLE 64

In vivo activity and toxicity of siRNA to HPRT1

| Antisense Strand | Sense Strand | in vivo HPRT1 $ED_{50}$ liver (mg/kg) | ALT @ 3 mg/kg (IU/L) |
|---|---|---|---|
| 1337111 | 1448688 | 0.53 | 58.5 |
| 1405428 | 1448688 | >3 | 22.0 |
| 1465680 | 1448688 | 2.6 | 31.3 |
| 1465681 | 1448688 | 0.69 | 66.0 |

Example 35: Design and Activity of Modified Oligonucleotides with Mesyl Phosphoramidate Internucleoside Linkages In Vivo to Mouse NOTCH3

Design of Modified Oligonucleotides

Modified oligonucleotides comprising multiple mesyl phosphoramidate internucleoside linkages (Formula IX) and phosphorothioate internucleoside linkages were designed, synthesized and tested. The modified oligonucleotides are each 3-10-3 cEt gapmers with a sugar motif of: kkkddddddddddkkk (a 3-10-3 cEt motif), wherein "k" represents a cEt modified sugar moiety and "d" represents a β-D-2'-deoxyribosyl sugar moiety. Each of the modified oligonucleotides is 100% complementary to the complement of mouse NOTCH3, GENBANK Accession No. NC_000083.6 truncated from 32118001 to 32170000 (SEQ ID NO: 80). Each internucleoside linkage is either a phosphorothioate internucleoside linkage ("s") or a mesyl phosphoramidate internucleoside linkage ("z").

TABLE 65

Design of modified oligonucleotides with mesyl phosphoramidate internucleoside linkages

| Compound ID | Chemistry Notation (5' to 3') | SEQ ID NO. |
|---|---|---|
| 977131 | $G_{ks}G_{ks}A_{ks}A_{ds}T_{ds}A_{ds}T_{ds}T_{ds}G_{ds}G_{ds}T_{ds}T_{ds}{}^{m}C_{ds}A_{ks}G_{ks}T_{k}$ | 81 |
| 1516016 | $T_{ks}G_{\underline{kz}}T_{\underline{kz}}{}^{m}C_{ds}G_{ds}A_{ds}A_{ds}G_{ds}{}^{m}C_{ds}T_{ds}{}^{m}C_{ds}A_{ds}A_{ds}{}^{m}C_{\underline{kz}}{}^{m}C_{ks}{}^{m}C_{k}$ | 82 |
| 1516017 | $A_{ks}T_{\underline{kz}}{}^{m}C_{\underline{kz}}T_{ds}A_{ds}T_{ds}T_{ds}G_{ds}T_{ds}{}^{m}C_{ds}A_{ds}{}^{m}C_{ds}T_{ds}T_{ds}T_{\underline{kz}}G_{ks}G_{k}$ | 83 |
| 1516018 | $G_{ks}A_{\underline{kz}}A_{\underline{kz}}T_{ds}A_{ds}T_{ds}T_{ds}G_{ds}G_{ds}T_{ds}T_{ds}{}^{m}C_{ds}A_{ds}G_{\underline{kz}}T_{ks}A_{k}$ | 84 |
| 1516019 | $G_{ks}G_{\underline{kz}}A_{\underline{kz}}A_{ds}T_{ds}A_{ds}T_{ds}T_{ds}G_{ds}G_{ds}T_{ds}T_{ds}{}^{m}C_{ds}A_{\underline{kz}}G_{ks}T_{k}$ | 81 |

TABLE 65-continued

| Design of modified oligonucleotides with mesyl phosphoramidate internucleoside linkages | | |
|---|---|---|
| Compound ID | Chemistry Notation (5' to 3') | SEQ ID NO. |
| 1516020 | $T_{ks}G_{\underline{\mathbf{kz}}}T_{\underline{\mathbf{kz}}}A_{ds}T_{ds}G_{ds}T_{ds}{}^{m}C_{ds}G_{ds}{}^{m}C_{ds}A_{ds}{}^{m}C_{ds}A_{ds}G_{\underline{\mathbf{kz}}}G_{ks}{}^{m}C_{k}$ | 85 |
| 1516021 | $A_{ks}{}^{m}C_{\underline{\mathbf{kz}}}A_{\underline{\mathbf{kz}}}A_{ds}T_{ds}T_{ds}{}^{m}C_{ds}T_{ds}A_{ds}T_{ds}G_{ds}G_{ds}T_{ds}{}^{m}C_{\underline{\mathbf{kz}}}T_{ks}{}^{m}C_{k}$ | 86 |

In the table above, a subscript "k" represents a cEt nucleoside, a subscript "d" represents a stereo-standard DNA nucleoside, a subscript "s" indicates a phosphorothioate internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methylcytosine.

Activity Assay in CNS

Modified oligonucleotides described above were tested in wild-type C57BL6/J mice to assess the CNS activity of the oligonucleotides. Wild-type C57BL6/J mice each received a single ICV bolus of 300 μg of modified oligonucleotide listed in the table below. Each treatment group consisted of 4 mice. A group of 4 mice received PBS as a negative control.

Two weeks post treatment, mice were sacrificed. RNA was extracted from cortical brain tissue and spinal cord for quantitative real-time RTPCR analysis to measure the amount of NOTCH3 RNA using mouse primer probe set RTS36973 (forward sequence CATGGTCTTCCCCTATCACC, designated herein as SEQ ID NO: 87; reverse sequence TGTCAATCTCCAGCATCACC, designated herein as SEQ ID NO: 88; probe sequence ATCACCTCAGGACCCAGCTCAC, designated herein as SEQ ID NO: 89). Results are presented as percent mouse NOTCH3 RNA relative to PBS control, adjusted to mouse GAPDH RNA.

TABLE 66

In vivo CNS activity of modified oligonucleotides complementary to mouse NOTCH3

| Compound ID | Mouse NOTCH3 RNA Cortex (% control) | Mouse NOTCH3 RNA Spinal Cord (% control) |
|---|---|---|
| PBS | 100.0 | 100.0 |
| 977131 | 30.5 | 9.5 |
| 1516016 | 14.5 | 8.0 |
| 1516017 | 21.0 | 11.5 |
| 1516018 | 12.0 | 8.0 |
| 1516019 | 10.7 | 6.3 |
| 1516020 | 48.0 | 4.0 |
| 1516021 | 4.0 | 2.7 |

Example 36: Design and Activity of siRNA Having a 5'-Mesyl Phosphoramidate to HPRT1 In Vitro siRNA Design A double-stranded siRNA comprising modified oligonucleotides was synthesized and tested. The antisense strand has the chemical notation $z.A_{ys}Uf_{s}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ (SEQ ID NO: 90). The first 21 nucleosides of the antisense strand is 100% complementary to GenBank NM_000194.2 (SEQ ID NO: 22) from 446 to 466. The antisense strand has a 5'-mesyl phosphoramidate (z.). The sense strand is 1448688, described in Example 20 herein.

TABLE 67

| Activity of siRNAs targeted to HPRT1 containing mesyl phosphoramidate internucleoside linkages and/or stereo-non-standard nucleosides | | | |
|---|---|---|---|
| Compound ID | Antisense Strand | Sense Strand | $IC_{50}$ (nM) |
| 1545957 | 1527118 | 1448688 | 0.02 |

Example 38: Design of siRNA Having 5'-Mesyl Phosphoramidate Moieties

Double-stranded siRNA comprising modified oligonucleotides having 5'-mesyl phosphoramidate terminal groups (Formula XXII.) at the 5'-end of the siRNA antisense oligonucleotide were designed.

XXII

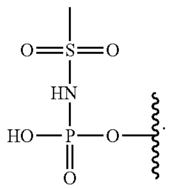

Compound Nos. 1547257, 1547258, 1547259, and 1547296 contain a 2'-O-hexadecyl modified nucleoside ("$16C_2r$"), shown below, wherein Bx is an independently selected heterocyclic base moiety:

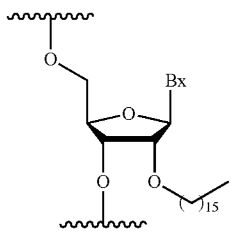

"16C2r"

Compound Nos. 1547286, 1547287, and 1547288 contain the sugar surrogate glycol nucleic acid (GNA) with the chiral center in the S configuration ("Sgna"), shown below, wherein Bx is an independently selected heterocyclic base moiety:

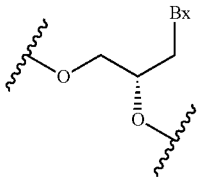

"Sgna"

Compound No. 1448688 has a GalNAc conjugated at the 3'-oxygen of the oligonucleotide via a THA linker as shown below:

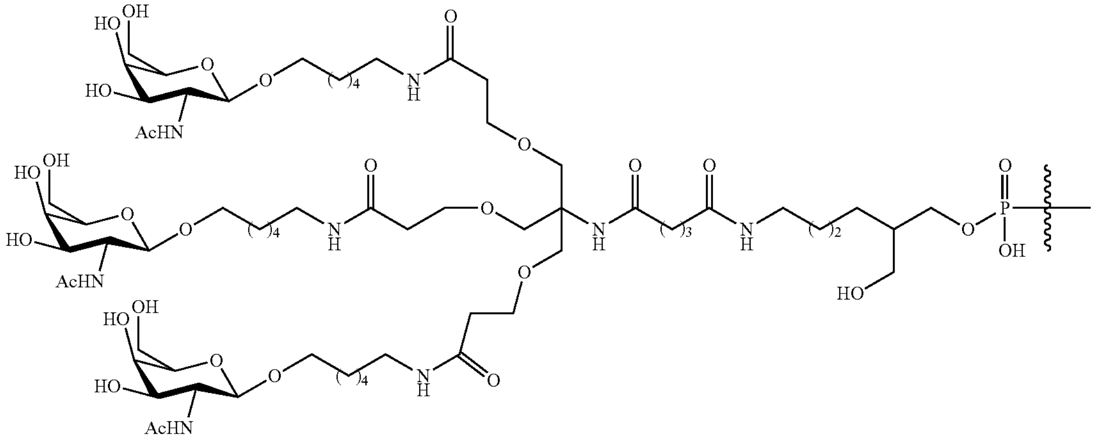

"THA-C7-GalNAc"

TABLE 68

Design of RNAi antisense modified oligonucleotides having 5'-mesyl phosphoramidate modifications

| Compound ID | Chemistry Notation (5' to 3') | SEQ ID NO. |
|---|---|---|
| 1547253 | z.$A_{ys}U_{fs}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1527118 | z.$A_{ys}U_{fs}A_{yo}A_{yo}A_{yo}A_{fo}U_{yo}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547254 | z.$A_{ys}U_{fs}A_{yo}A_{yo}A_{yo}A_{fo}U_{yo}C_{yo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547257 | z.$A_{ys}U_{fs}A_{yo}A_{yo}A_{yo}A_{fo}U_{[16C2r]o}C_{fo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547258 | z.$A_{ys}U_{fs}A_{yo}A_{yo}A_{yo}A_{fo}U_{[16C2r]o}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547259 | z.$A_{ys}U_{fs}A_{yo}A_{yo}A_{yo}A_{fo}U_{[16C2r]o}C_{yo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547286 | z.$A_{ys}U_{fs}A_{yo}A_{yo}A_{yo}A_{[Sgna]o}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547287 | z.$A_{ys}U_{fs}A_{yo}A_{yo}A_{yo}A_{[Sgna]o}U_{yo}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547288 | z.$A_{ys}U_{fs}A_{yo}A_{yo}A_{yo}A_{[Sgna]o}U_{yo}r_{yo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |

In the table above, a "z." represents a 5'-mesyl phosphoramidate, a subscript "y" represents a 2'-OMe modified nucleoside, a subscript "f" represents a 2'-F modified nucleoside, a subscript "s" indicates a phosphorothioate internucleoside linkage, and a subscript "o" indicates a phosphodiester internucleoside linkage. A subscript "16C2r" represents a 2'-O-hexadecyl modified nucleoside, and a subscript "Sgna" represents a (S)-glycol nucleic acid.

TABLE 69

| Design of RNAi sense modified oligonucleotides | | |
|---|---|---|
| Compound ID | Chemistry Notation (5' to 3') | SEQ ID NO. |
| 1448688 | $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{yo}A_{yo}U_{y}$-THA-C7-GalNAc | 23 |
| 1505889 | $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{yo}U_{ys}A_{ys}U_{y}$ | 23 |
| 1547296 | $U_{ys}C_{ys}U_{yo}A_{yo}U_{[6C2r]o}G_{fo}A_{yo}C_{fo}U_{fo}G_{fo}U_{yo}A_{yo}G_{yo}A_{yo}U_{yo}U_{yo}U_{yo}U_{yo}U_{ys}A_{ys}U_{y}$ | 23 |
| 1548003 | $U_{ys}C_{ys}C_{yo}U_{yo}A_{yo}U_{y[XIX]}G_{fo}A_{yo}C_{fo}U_{fo}G_{fo}U_{yo}A_{yo}G_{yo}A_{yo}U_{yo}U_{yo}U_{yo}U_{ys}A_{ys}U_{y}$ | 23 |

In the table above, a subscript "y" represents a 2'-OMe modified nucleoside, a subscript "f" represents a 2'-F modified nucleoside, a subscript "s" indicates a phosphorothioate internucleoside linkage, and a subscript "o" indicates a phosphodiester internucleoside linkage. A subscript "16C2r" represents a 2'-O-hexadecyl modified nucleoside. A subscript "[XIX]" represents an internucleoside linkage of Formula XIX.

TABLE 70

| Design of siRNA compounds | | |
|---|---|---|
| siRNA Duplex Compound No. | Antisense Strand Compound No. | Sense Strand Compound No. |
| 1547255 | 1547253 | 1448688 |
| 1545957 | 1527118 | 1448688 |
| 1547256 | 1547254 | 1448688 |

TABLE 70-continued

| Design of siRNA compounds | | |
|---|---|---|
| siRNA Duplex Compound No. | Antisense Strand Compound No. | Sense Strand Compound No. |
| 1547293 | 1547257 | 1505889 |
| 1547294 | 1547258 | 1505889 |
| 1547295 | 1547259 | 1505889 |
| 1547290 | 1547286 | 1448688 |
| 1547291 | 1547287 | 1448688 |
| 1547292 | 1547288 | 1448688 |
| 1547297 | 1547253 | 1547296 |
| 1547298 | 1527118 | 1547296 |
| 1547299 | 1547254 | 1547296 |
| 1548004 | 1547253 | 1548003 |
| 1548006 | 1527118 | 1548003 |
| 1548007 | 1547254 | 1548003 |

What is claimed:

1. An oligomeric compound comprising a modified oligonucleotide consisting of 12-30 linked nucleosides linked through internucleoside linking groups, wherein:

at least one nucleoside comprises a modified sugar moiety;

the modified oligonucleotide comprises a deoxy region consisting of 6-11 linked nucleosides wherein each nucleoside of the deoxy region is a stereo-standard DNA nucleoside; and at least one of the internucleoside linking groups of the modified oligonucleotide has Formula XVII:

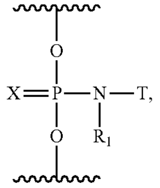

XVII wherein independently for each internucleoside linking group having Formula XVII:

X is selected from O or S;

$R_1$ is selected from H, $C_1$-$C_6$ alkyl, and substituted $C_1$-$C_6$ alkyl; and T is $SO_2R_2$, wherein $R_2$ is selected from a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

2. The oligomeric compound of claim 1, wherein X is O, $R_1$ is H, and T is $SO_2Me$.

3. The oligomeric compound of claim 1, wherein the deoxy region is flanked on the 5'-side by a 5'-region consisting of 1-6 linked 5'-region nucleosides, wherein each of the 5'-region nucleosides comprises a modified sugar moiety.

4. The oligomeric compound of claim 3, wherein each of the 5'-region nucleosides comprises a sugar moiety selected from 2'-MOE and cEt.

5. The oligomeric compound of claim 3, wherein the deoxy region is flanked on the on the 3' side by a 3'-region consisting of 1-6 linked 3'-region nucleosides; wherein each of the 3'-region nucleosides comprises a modified sugar moiety.

6. The oligomeric compound of claim 5, wherein each of the 3'-region nucleosides comprises a sugar moiety selected from 2'-MOE and cEt.

7. The oligomeric compound of claim 1, wherein each internucleoside linkage that is not an internucleoside linkage of Formula XVII is selected from a phosphorothioate internucleoside linkage and a phosphodiester internucleoside linkage.

8. The oligomeric compound of claim 1, wherein the deoxy region comprises at least one region having the formula $(N_{g1})_{L1}(N_{g2})_{L2}(N_{g3})_{L3}$, wherein each Ng is a nucleoside and each L is an internucleoside linking group; wherein each of $L_1$, $L_2$, and $L_3$ is a phosphodiester internucleoside linking group, a phosphorothioate internucleoside linking group, or an internucleoside linking group of Formula XVII:

XVII

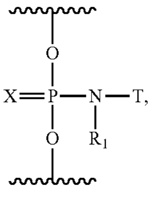

wherein at least one of $L_1$, $L_2$, and $L_3$ is an internucleoside linking group of Formula XVII; and at least one of $L_1$, $L_2$, and $L_3$ is a phosphorothioate or a phosphodiester internucleoside linking group, wherein independently for each internucleoside linking group having Formula XVII:

X is selected from O or S;

$R_1$ is selected from H, $C_1$-$C_6$ alkyl, and substituted $C_1$-$C_6$ alkyl; and T is $SO_2R_2$, wherein $R_2$ is selected from a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

9. The oligomeric compound of claim 8, wherein X is O, Riis H, and T is $SO_2Me$.

10. The oligomeric compound of claim 8, wherein the at least one region having the formula $(N_{g1})L_1(N_{g2})L_2(N_{g3})L_3$ is at the 3' end of the deoxy region.

11. The oligomeric compound of claim 8, wherein the at least one region having the formula $(N_{g1})L_1(N_{g2})L_2(N_{g3})L_3$ is at the 5' end of the deoxy region.

12. The oligomeric compound of claim 8, wherein a second region having the formula $(N_{g1})L_1(N_{g2})L_2(N_{g3})L_3$ is at the 5' end of the deoxy region.

13. The oligomeric compound of claim 8, wherein $L_1$ and $L_3$ are phosphorothioate internucleoside linking groups, and $L_2$ is an internucleoside linking group of formula XVII.

14. The oligomeric compound of claim 8, wherein $L_1$ is a phosphorothioate internucleoside linking group, and $L_2$ and $L_3$ are internucleoside linking groups of formula XVII.

15. The oligomeric compound of claim 8, wherein the deoxy region is flanked on the 5'-side by a 5'-region consisting of 1-6 linked 5'-region nucleosides, wherein each of the 5'-region nucleosides comprises a modified sugar moiety.

16. The oligomeric compound of claim 15, wherein each of the 5'-region nucleosides comprises a sugar moiety selected from 2'-MOE and cEt.

17. The oligomeric compound of claim 8, wherein the deoxy region is flanked on the on the 3' side by a 3'-region consisting of 1-6 linked 3'-region nucleosides; wherein each of the 3'-region nucleosides comprises a modified sugar moiety.

18. The oligomeric compound of claim 17, wherein each of the 3'-region nucleosides comprises a sugar moiety selected from 2'-MOE and cEt.

19. The oligomeric compound of claim 8, wherein each internucleoside linkage that is not an internucleoside linkage of Formula XVII is selected from a phosphorothioate internucleoside linkage and a phosphodiester internucleoside linkage.

20. The oligomeric compound of claim 1, wherein each nucleobase of the modified oligonucleotide is independently selected from thymine, uracil, guanine, cytosine, 5-methylcytosine, and adenine.

21. The oligomeric compound of claim 8, wherein each nucleobase of the modified oligonucleotide is independently selected from thymine, uracil, guanine, cytosine, 5-methylcytosine, and adenine.

* * * * *

SEQUENCE LISTING

```
Sequence total quantity: 93
SEQ ID NO: 1            moltype = DNA  length = 14836
FEATURE                 Location/Qualifiers
source                  1..14836
                        mol_type = genomic DNA
                        organism = Mus musculus
SEQUENCE: 1
cctcccccgt gtctccccac acccgggttg ggttgtttt ggttgaccag agtggaacac  60
aacgatctat tggcagggct gaacaccaat gggtctattt gtaaagcgcc aatgaccact  120
ttctgaagca gggttttagg gagcggggcc ttagggaact ctttggtcct ttttagaaca  180
ctggactttc ttctggaaag gcaggaaaca ctgaagttta agaagttgtt tccagcttcc  240
attaactgaa cacacattaa aaccaagcac agagaatcag gacgtttcgc gggagtgaga  300
cccagtcatt tctcctccgt ttccattctg cagggtgaga gttgtaatca cccacccact  360
attcgtacca tccacccacc cccagtcgag agaatagggg tacagagggg aggtggcaaa  420
gaaaattcac gatactgagt atctctggga gacctgtttg gtctctttgc tcggtagcgc  480
agccctacgt tagaatgcat cttcccggga atgactgtag tgagactttg gctgggaatc  540
caagttattc taactgtaga ttggtccacg ttgccctaag cctagcagtc cactgcggca  600
cagacaccct ggacatgagg tgggtcagct taagttcctg gcacgaaaga aagggtactc  660
tggcaacttt tggatgcggc gaaacagact gtttcgtctc tcaggttctt atttcacggc  720
ttgtgccttt gacagcccct tagtttctct atctgcagga tgggagcatt aagctctacg  780
acccagcctc tttacaattc aggtccaaag agcccgccca agttggggac tgggaagatc  840
aaaggtctca gcacccagcg gagccgcgga cactgagggc gccaagaagg gggtgggtag  900
gtagggaact ggaagggcgg ctgctccgca ggggatgcgc gtcagagacc ccagccacac  960
tccaggcccg cccccttgatg agccccgccc cgccccgcct ggttttcgcc tctaaagcgc  1020
ccagcgctcg cctcccgctg ccgcactttc actctcggtc cacctcggtg tcctcttgct  1080
gtccagctct gcagcctccg gcgcgccctc ccgcccacgc catggacgcc aaggtcgtcg  1140
ccgtgctggc cctggtgctg gccgcgctct gcatcagtga cggtgagtgc aatccgcggc  1200
cgggcccggg aaaggctcgc agctctgcgc cggagctcct tcgggtccgc ggttcctctg  1260
cccgcgccga agtcgcggag aaagaactcg gtcggcgccg ttcactacaa gcgaacttgg  1320
ggcagtccac tttgcagggc gcactcccac cgggtgccct ttcccgtgtc ccacgggtcg  1380
caccgaggtt ttgtgctctg cgaagtgcgg ccataggacc tagagagggc tgcaggggag  1440
gacccgcagg attgttgggc aagagtgggt tcggcgcgga atggaagcgt gggcgattgt  1500
gtccggggct tgggccccgg agcgcgccag ctgcactcag ctagtgtcta ccggcgccca  1560
gatgtttcca gaggcgaagg gcagcgcggt cccggagttg accgtgcaag aggttcactc  1620
gggtggtgcg tgtgtcagca aactctcaaa gaccggtcaa gtagctcgaa gtgcatggct  1680
```

-continued

```
tggctatagg ttcagtggtg aggctgagtt tcgtcccctg cgggtgtagc gtgttctctt  1740
acagcaccct cgaggggctc agggccacca gcagcgcagc gcagctcttg aactcgcgct  1800
gccagccagg gccgcgcttc tgcacagttc gttggtccgt agcgacgcgg acctgagcac  1860
gcgtctcttc actgcccctt tttcttctta cccgggtcac tagacaaagg ctcagcagtt  1920
acccaagcta tatgcacacc tctccccaac ccccaaacac acctgcaaac gggcgctttt  1980
gtagccagcc ccggagtcct cagctctgga atgagagctg cagcggagtt cagtctccca  2040
gacccagggt ggtgtcttct ttcactggga aagggctttc attttgtttt cttttttga  2100
cactgaagag aaaactctca gcgctgttac aagacaccgt tgctgcaaaa caaaacaaac  2160
cattgcctct gaacacaaaa caaaatccta ctagtcgatc ccctgccttc ctccgcagtg  2220
gtgtttcctg gagagaactg agggacagtc ggggctcttg gtgagactga gctctaaatg  2280
ctgcccaagt acaccaactc gttcgtttgg gttctttccc tgtgacaacg gggtacggga  2340
atggttggag ttgcctagtc cgagggaaat gttctgtaaa agaatagtca gttgctgatc  2400
ggagtagtaa aaaaaaagaa atgaaaggca gtttcgattt tttttttttt tttttttttt  2460
tttttgtta ccgagaacac ccgggaggct gagccttccc actggtcccc cagtgccccg  2520
tcatggagca cattgatttg ggcattaata attgaatgag ctggtgatgt tgcaagggtc  2580
acagcctctg gcaagttagg tatggggcaa gaatgtagga ctcaggtcct caaggttgga  2640
gtgcaattat ccagagtaaa agttgtctca ccctcaacat attctgaccc taggaagagt  2700
cggattgttg acagtgtctg gatcagacct gttctctagg caggacccca ttgtgctgcc  2760
cgaatgaact tttttacctc ctagtgcctg tgtgccctct gatcttacac agccctcaag  2820
ttgcagcacg gctaaccttg ctgtggttcc tgtcttttcc catcagctac tccaactcag  2880
aagctagata gtagacaccg gaggcttctt tggttaaacc cagagcagca ggcttgccag  2940
gcttgttaga ttgaatggac ccctggttcc ctaagccaag ctctctagat tcccaagtcc  3000
agggtggcag cagagctgga ttagactttg gtctgtacct gaagtctggt tttcctatgc  3060
tttagagtct aaagacacta cccttcctgg ggcatgcatc ccttagctaa ataatgcttg  3120
cagaagaaga taatcccatc atatatttaa ttcggtccac ttctccagct gcttcccaaa  3180
ggcagtgaac ttcagaatac ccagaagtct cctggaactc taaataagca aacttaaaat  3240
cctggggcta actattctca gtcatacttt taaactttgg tgaaaagacc cataaattga  3300
aacatttggg gatgctcagt agagctagga taaaaccctg ttgttggggg agcagctaca  3360
aatccagcag tcctcagggt ttgcaattct agacttaaag ggtggttctt aagggggggt  3420
tctaaaggag ccccttgcta atttacacta atgagtgtca attatagcat tttgcaaatt  3480
ggtgaattgg caaacaaagc tggtaatagg atccaggagg cctaggcatc caggtagtga  3540
ccataaaagc cacggttgac cccagctttt gggaaaagct ggatagaagg taaatccggg  3600
tcctcccctc tggattcttt tgtgatttcc agggcttagg atagggtgag tgggaggagg  3660
gaaaactgca ggtggtagaa gtgaagcccc ccacctccag gcctgcacca gagggccaca  3720
agggagccca gaactctgcc accccacttc tcctgggtcc ttttgtcctt tagaggctga  3780
gcccagtcag atctcactgt gatccctggc cgaggggatg gtctttgcaa gaaactttct  3840
gtaaccattc ctgctgatgt tcctgagtct tccccacaag agccaccaaa ccccctgcac  3900
caggcagata atgactggcc ccacttttct ctctacacct cctctaggta aaccagtcag  3960
cctgagctac cgatgcccct gccggttctt cgagagccac atcgccagag ccaacgtcaa  4020
gcatctgaaa atcctcaaca ctccaaactg tgcccttcag attgtgtaag tcctagccgc  4080
catcccccaa agaggagcat ggtatagaag cctcggactt ggcataacta ggggcagctg  4140
ttaccaccac caccacgggg acactgatat gccatcagac atgggtttca aaggatactt  4200
ttgttcccca gagccctgat gtcctcagtg tttctcactc ttgctttcca agctgtttct  4260
tgcagcacag tgggccgcct ctctacagaa aaagccatgg acttgatgga ggtcagccct  4320
cagctgacag ttgggtctgt cttgtcagtt tcaaggttct ggtgtccaaa gttaatcctt  4380
tctcacatag aaaaaaaaat tacaagaccc ggatggcacg gggggggggg gggttcagtt  4440
ttactcactt gcactcactt gctcagaggt catttttgtt ttagagtttt agagtttgct  4500
ggagtgtgat ggtagctgcc agtatttgat ttaaatttac ctgggaaata agaaaagccc  4560
aaaaaaggta taaatgatgt gaatatctca ctcagagtct ggtagacttg gcagagatgt  4620
gtcctgtgct agtctgtcct gctcactgcc ccccagcagg ggttcccatc ctcgggagac  4680
tcaacactaa caacagtata aggatgcagc agctggagca atgctagcct gacggctttg  4740
tcacccaacg gtgactgctt cagactttct gtgctcatca gccttcctct ccagcctccg  4800
ctgctgtgtt atgtacagta ggctttagag acctagatga tgaatattat ttttgctgtt  4860
ttgattaaaa tacaatactc tcccgagaaa gggattttaa agatgatgag tttacgtttg  4920
aataggctgt gctggtgcac tgtcccggga agggcccttg aacttagagg gtcaaataca  4980
actattgatt ctgggtgatc actaagttaa taaatggcag gatccagact gacacccctg  5040
atccctgttg aagttacatc cctctgaacg actggtcaac tgcagggcag cctgcttgaa  5100
gagggttacc tgtccctagg acactgaaca ggcatttgtt tttcctagaa gacagttcac  5160
cagctggaga ggagtcgtct cccgtagttt ctgtttggtt gcttttggtt tttgtttggt  5220
tttggttttt taattatctg gcatccagga cttgatggaa aataaccaga gctaagctca  5280
ccggttcatc tgcccattag gaagttctag ggatgggaga aagaacacgg cgtcaattaa  5340
caaatccaca aagctaagac cttgaagcat tctgtgaact tgtaaacgcg ctcaggcaac  5400
cattggacaa tttgtctaga ctgctccttg cccacctgaa ctgccctgtt cctccccttc  5460
tggactcctg ccgtcttcct ccagagctac ctttaaggtt gtcccatgta ctatcaaggt  5520
gctctgtcaa aagttcttag gctgcttctg gcactctcca gaattttcca agacctcccc  5580
cccaccatga tatcagtcat ccgcgccttc tgggtggttc ttcctccaca ccctttgggc  5640
actttgactc ctgtgggata ttcgtccttc cttttccttt agctttcctc acttgccaag  5700
ctccaacttg gccagaagct caaatgcctc cactgtggtc tcttctctgt gtcccctggg  5760
agacatcctt agcacgtccc taactctgcg gtggtggtcc caacacgatt caagtgctat  5820
gtcttccaaa actgaagctt ccgggagcag cagctgggcc ctgcagtgag gacctttagc  5880
tgggtgtgtt gggtgagccc acaggatcgc tttctcccgc ttggctgtac agcgtctctc  5940
cccttgtgtt ttggcagtgc acggctgaag aacaacaaca gacaagtgtg cattgacccg  6000
aaattaaagt ggatccaaga gtacctggag aaagctttaa acaagtaagc acaacagccc  6060
aaaggacttt ccagtagacc cccgaggaag gctgacatcc gtgggagatg caagggcagt  6120
ggtggggagg agggcctgaa ccctggccag gatggccggc gggacagcac tgactggggt  6180
catgctaagg tttgccagca taaagacact ccgccatagc atatggtacg atattgcagc  6240
ttatattcat ccctgccctc gcccgtgcac aatggagctt ttataactgg ggtttttcta  6300
aggaattgta ttaccctaac cagttagctt catccccatt ctcctcatcc tcatcttcat  6360
tttaaaaagc agtgattact tcaagggctg tattcagttt gctttggagc ttctctttgc  6420
```

```
cctggggcct ctgggcacag ttatagacgg tggctttgca gggagcccta gagagaaacc  6480
ttccaccaga gcagagtccg aggaacgctg cagggcttgt cctgcagggg gcgctcctcg  6540
acagatgcct tgtcctgagt caacacaaga tccggcagag ggaggctcct ttatccagtt  6600
cagtgccagg gtcgggaagc ttcctttaga agtgatccct gaagctgtgc tcagagaccc  6660
tttcctagcc gttcctgctc tctgcttgcc tccaaacgca tgcttcatct gacttccgct  6720
tctcacctct gtagcctgac ggaccaatgc tgcaatggaa gggaggagag tgatgtgggg  6780
tgccccctcc ctctcttccc tttgctttcc tctcacttgg gccctttgtg agatttttct  6840
ttggcctcct gtagaatgga gccagaccat cctggataat gtgagaacat gcctagattt  6900
acccacaaaa cacaagtctg agaattaatc ataaacggaa gtttaaatga ggatttggac  6960
tttggtaatt gtccctgagt cctatatatt tcaacagtgg ctctatgggc tctgatcgaa  7020
tatcagtgat gaaaataata ataataataa taataacgaa taagccagaa tcttgccatg  7080
aagccacagt ggggattctg ggttccaatc agaaatggag acaagataaa acttgcatac  7140
attcttatga tcacagacgg ccctggtggt ttttggtaac tatttacaag gcattttttt  7200
acatatattt ttgtgcactt tttatgtttc tttggaagac aaatgtattt cagaatatat  7260
ttgtagtcaa ttcatatatt tgaagtggag ccatagtaat gccagtagat atctctatga  7320
tcttgagcta ctggcaactt gtaaagaaat atatatgaca tataaatgta ttgtagcttt  7380
ccggtgtcag ccacggtgta tttttccact tggaatgaaa ttgtatcaac tgtgacatta  7440
tatgcactag caataaaatg ctaattgttt catgctgtaa acctcctacc gtatgtggga  7500
atttatttac ctgaaataaa atctactagt tgttagatgg agtgcacata catttctgaa  7560
gatggagaaa aacaggtgtg cctgctgatc aggtgctgtg ggctgccctg cagtcctggt  7620
gagcgacaga cactgaggca ggcttgtctc atgaacaggc tgcctctgca gtgaaagttt  7680
ttgtgtattt tttttaaccc aagctagttt tctaatgaat aatacttgac tcactaattt  7740
cccctcctcc tccttctcct cagttctcct aacatcctca tgtgatcccc agactcaact  7800
ccagtaatat caagctttcc tattttccca tgtaaaaaaa tcccatgact ctgggccatg  7860
ttaatatcag gcttttgtgg gaacaggtgg cctcacccca taaatcatta aataccattc  7920
agcttgaatc attttaatgt gacagtcaca aaccagttgc tctaataaaa actctgctaa  7980
ccatccttct ccttagctct ctagaacaat ctcagttatc cctagggatg ctccccagca  8040
tccagaaaag agaagtggga tcaatcatcc tgcctttctc cccctcctct cttggagggc  8100
tgcctgagcc cgtggcctcc acctcccctg ctttgtataa tttgaaatgc agatttgtag  8160
tgaaggcaga gttcacctct gcattgaaag ggaaggcagg cccagagctt ccttccctgc  8220
cctctgagat gtgcatttat gtctcaggat ggatgagctt tggtaggaat gctcaaaacc  8280
aggaccagcc agacaaactg gcagtccctg taagcggttc ccgggtcata gggttagggc  8340
acccctgttt aactttgggg tggggaaagt atctggtttt ctttgataaa ttgcttgtga  8400
accacatttg ccaagtggcc tccaggcctc aaactcaaag accgagctaa atcgactcgg  8460
aaggcaatgc tgaatgaaga ttgtgggaac tgagatagat acactcctct atgttgcaat  8520
gtgattaatg gttctactaa ttttatctaa gggggcgcag agaagaaaaa gtggggaaaa  8580
aagaaaagat aggaaaaaag aagcgacaga agaagagaaa ggctgcccag aaaaggaaaa  8640
actagttccc cgcttcctgc cgatggaccg cagtgcgctc tgctctggcg ctttgtaact  8700
cgctcctccc tcttcggggg cagaccccac actccgggca ggtgctcaaa cctgacggta  8760
aactcttccc tcttcggggg cagaccccat accccggggc gggtgcttag gctttcctgc  8820
cctggtggcc acaccagctg ctgtatttat gtgcttcata aggccctgct ctgtctgcta  8880
aagctatgaa gaaagatgtg cagagactgg ggtggagact aagccaaaga ggagctgcct  8940
agcctggcag cattgccccg agctgagccc ccttggccag gacttcacaa ggctcacacc  9000
tacaatccca tgaaggccag ggtggtctgc ttagccagga aagggcaagt gccttcccct  9060
cggccacact gccccttgtg gccttctcgg gacatgtggt aactgacttg ctctcaggcc  9120
cacccgcagc ttttccaaat acctgcagcc ttcagccctg ctgccctgcc tgtgggagca  9180
gctttgactc cagtccagaa gggtttctgc agactgtgtt gggtgagacg cagaaaggat  9240
gaaatctcag aacacatgtc agctgcttct caggaaatct tttctttgga caattcactt  9300
tagagtcttt aaacgggtct ctcgtgggga ggatagatgt gctctggaac tttctgaagg  9360
accagcagct tcagggactc ttagtctgtc cttccccact tttggtccca acatccctgg  9420
gatggtgtgc tgtctgggca ccacggtctc catcctcact cctgagagat ttctgccttc  9480
tgtgagttgg gttaaagctc tggaattatc tactatccca atccactacc ctcacctggc  9540
aatatttgtc tgtttttgtt tgtttgtttg tttgtttttg tcttttgcca gtttgaatta  9600
gaaggcaagg ctctgatttt agtagtgttt tggaaaagga ctttttcttt caccttcctc  9660
tttgcctcat gtgtacacac acacacacat cttgtacccc agacctctgg gtataatttt  9720
cataattggt gcagaaagaa gaaatgatct gaagatgtgt taaatggatt gcagggggaag  9780
gaaggcccag ggccctgtgt gtcatgccct cttgggttcc taagttctat gttccttaga  9840
ggttctagca ttaaacagat aaagcccttc atggtcctgg ctgaggaaga gtcttgctag  9900
ggggattcag ggaagacccg tgttaccagc tcttaccctt tatctggaca gctctcctac  9960
cctgtatctt ctcctcagat ctgaggatag caggctggac tattggtggg cacctttcaa  10020
gcccagggct actgtttgtc ctgtggcagc cggctacagt ctcgtctgag tggcctcatc  10080
tggacccttc ctgttattaa taaaacgctt ctggaggcca gatctgtgct caagccatag  10140
ttctgcttag aaagggatgc cccaccctta ccggacactg ggaagaactg ttggccccta  10200
gaaaccaaag gccaaactga ggctgccctg agttggaaga ccactttctg aaatgcccat  10260
ggactctgcc tcccaaccat tcgtctctca ctcctagcag agctgtctgt gcagactgtt  10320
tcttaggagg cacagcaagc tccagggaac cctctgtgct tatgaagctc gtctggtggg  10380
caaccccagc ccactggaca gagtcctcat ggaaatgcct gggaagctga tttcatctaa  10440
ggatgggttg aagtaggatg tgctcctgcg acttctcagg caggtgagag gggtagtcct  10500
tacactgtct agcataaacg ccttccggaa ggacctgcag ctccagagac cacctcctga  10560
gcaccaagac ctcttctggt ggtgtggaac cagccaagag atttcaagga agagtgatta  10620
tttgatgaat gctatgggaa tggcctcttc tcttggagtt ctgaggcctg gggatgccca  10680
ggaacactgg gcacctgctg ctgttagggc caatgcatag tctcagcacc ggtgtcctaa  10740
ggttaaggcg gtgcgccttg tcatgtgctc cttgtaccat gccatctgtg ccagtgtgtg  10800
tctgcctcac cctgtgcttg acatgttcac ccatcttctc tgcttcccgc caccatccag  10860
atcctcagcg gccgccccgg ctgtgccctt ccctgctctc ccgctctctc aggcctcgga  10920
aggaagatcg gtggctgcga gctgaactaa ggagtagggc ctgtggctca gcgctaggcc  10980
acgcacgcag catcccaggc atgtggtgag aaactgcctt aatgtgtctc ctctgttctt  11040
gtcaacagga ggctcaagat gtgagaggtg tgagtcagac gcccgaggaa cttacaggag  11100
gagcctaggt ctgaagtcag tgttagggaa gggcccatag ccacttcctc tgctcctgag  11160
```

-continued

```
cagggctgaa gccgtttgca agggacttgc tttgcacagt tttgctgtac tttcacattt  11220
tattatgtag caagatacat ggtgattttt tttttttca tttagcctga ttttccaacg  11280
tcattggtga caggccaagg ccactatgtt atttcctttg ttctggtatc cttcccttgg  11340
aggaccttct ctgagtagtg gctccccagg tttgtccttt gagctgaggc aggaggctca  11400
cccattcttc tgaataggaa ctgggtgttc ccacccccca aggactgcag ggctttccca  11460
agctgaggca ggaacgtgag gccagggaag agtgagcttc accctcatcc cacgctgtcc  11520
tcctcaaccc accatgctca tcattctgtc tcatccatcc atccatccat ccattcatcg  11580
ccatgtgtcc gcaagactgt ctccatgacc ctgaaaaagg actctcgaga tgaaatcctt  11640
tattcaaatg ggacagcaag aaggaaaagc caatgtctgg tgtctctccc cccgccccta  11700
ccctgcgcgc atctatgtct tgtttggaat attgtctctt caaccccctg ttcatgtcct  11760
tctcactcat gatcgatgtc ttgtctgtgc actgtctcta acccaaatgc aaaggctgag  11820
tgtgaggtga tggccccgag gtccaggttg tagtcatgga aagagccctg ctgtctccct  11880
tctcaggggg cccattttag acacacaaag cccaaagaaa ggtggtttgc aacagtgctt  11940
agctcgagcc tccatatttc cataactgtt agcttaaaac tgtggggttt taccttcctg  12000
gaaccaaatg cattcttctg ttgaggagta acaggtctca attcttttca attaatttta  12060
aaagtcaatc actaagagca tcggctttgg gccctgatgg gcaggcattt ccctggaaag  12120
ggggtgaact acctacctct cctcaagaca gccgaagggt gggattggtg ccgctctggg  12180
aagcgtggcc ccaggagttt tgtcctctgc agtttttaat gcaagttcac tgccactttg  12240
acaaaagccc aattagaagc cagtctctag ttccttaaac aaaacagaca gagtaaggaa  12300
aggaaggagg gtggcagcca gctggctgga cactcgagaa agacggggaa gtaagctaca  12360
gaaagatagt cttcaaaaac aggtgtttga gagtgaatac tctgtagaat tgttagtggg  12420
gtgtgtgtgg tggtggtggg gggatttcta caaaatagtc ctttaagttg agtttacagc  12480
agatgaaaaa tccaaccagc aaaattttga tcaaatttga acaaaaaccc aaaaacctaa  12540
aactgttgag caggttgcga tgaggagcac agggctagct gcagagctgg atcctcagga  12600
ggatagcgaa ttattttcaa ccctggaata gaaaccacac actggcttgc tgtgcaccag  12660
ccactttgca tctaatccaa gctttgaagg gtgttgcttg ggaggaaaca aatacagcct  12720
tccatcttca ctccagttag ggatcctttc aaagtctcct tcacagtgag gaaaaagaga  12780
agggtagaaa ctttagggag ccggatttgt gtatcaattc ctccgctgac agtcagtttc  12840
tagatggaga cagcctgctt aaagcaaatc cgaatttaaa taggacattt acatcggaaa  12900
agtctctccc taccttaatc ccccattctc ttgctttcaa aatacaagca cagcagtcct  12960
tgaatggctg ttgacccagg gcacctagct gtccctgctg gtcctggggc tgccagaatt  13020
cccttgggcg ccaagcaacc tgccaggtag ccagtccctc tgttacaagc ctttgcatct  13080
ggatagggaa aggggtggag acatacagtc tgctttgtgt tgaaacccag atttgtaccc  13140
tgtgtttata cactgctgct ggctcccgag gacagtggga ctttagcaag gaagtgcagc  13200
cgaggggtaa agagccctct ggttcattgc ctgatcggct ttgagagagg gtttggaggg  13260
caaggggctg cattcctctg agggacttgg cctgaggcct ttcgggcctc tccagtgggt  13320
tctgtttatc ctctcatggg tgattatctc agtggtgtca ccaggggctt cctcccagaa  13380
gtcagtcatc cccaggccgt gcaccctttt cagctggatg agagccaggg atgcattctc  13440
tccaaacagc taccctggcc cattttaagg taatctcatt cttcaaaatg ttccatagaa  13500
tcctccaaat tcccccagca gacttctacc ctcgccaagt tcccaaaacc cactcagcaa  13560
agttgccaac ctcgacgggc tagcagtgtc taagcagcga tgggttcagt gttgtgtgtg  13620
gtgaatactg tattttgttt cagttctgtc tcccagataa tgtgaaaacg gtccaggaga  13680
aggcagcttc ctatatgcag cgtgtgcttt cttattctta tttttaatat atgacagtta  13740
tttgagaagc catttctact ttgaagtcat tatcgatgaa agtgatgtat cttcacctac  13800
cattttccta ataaagttct gtattcaaat atagctgcca agcatcctca gtgaatgtta  13860
ccatgtggaa ttttccacac ttggttttac cccctcaaac ctgactctga ccgtgcagtc  13920
ttagcagaag agcttagcag gtcctagtgt tcactcttgg tctaactgct ggtgtcagaa  13980
gatctctaca gggagaggtg ttccattttc tccacatgac ctggattgct ccttagaggt  14040
cagacagcct tgcactgtac aaggcaatgg cttagggtaa agtcccagga gttttcccta  14100
cagtcccaag aatttggaag aggaaggccc acactacaca tgcaggtcat ggtggaaggt  14160
gacagaggaa ggactctgtc cctgtaagac agctggaaac cacaatattc tgcatgttcc  14220
tatcctgggt gaggacgcta atggaagtca aaggggaatt tgctaactgc tgttggccag  14280
cttcctccaa gaatcctgct tcccccaacag acagagcctt tgtctcttat agtttggtct  14340
tcagattctc tttatcccac attcagccat ttttgtaaaa gagaggctag caccagctcc  14400
aaatatccaa atctgcagtg tttgagatct cactgcgcct cctccatacc aacacatttg  14460
ccattactta tagggtagtt ttcatgtgag ttctaagttg attaacacac aagaattaga  14520
agggtgggag gctctaggaa aggcactgtg ggactatttg actgcatggg tgtgaaaatg  14580
taaggaacag gcaagagctt ggatcccatt ctctctgccc acattgtgac ttgagatata  14640
ctaattgctc ttgggggtct cagtcatata ccatccataa cagagttaaa ctgagagaga  14700
tacaggatca gctagaatga aaagcccacc ccatgcttcc agaaagtccc ctctttatac  14760
ctcctgtgat atgaactaga ggaaaagcaa ttgactttgc ttctcaaaca gcctacggca  14820
aagccctgtg agtttg                                                   14836

SEQ ID NO: 2            moltype = DNA  length = 20
FEATURE                 Location/Qualifiers
source                  1..20
                        mol_type = other DNA
                        organism = synthetic construct
SEQUENCE: 2
ccagagccaa cgtcaagcat                                               20

SEQ ID NO: 3            moltype = DNA  length = 20
FEATURE                 Location/Qualifiers
source                  1..20
                        mol_type = other DNA
                        organism = synthetic construct
SEQUENCE: 3
cagccgtgca acaatctgaa                                               20
```

```
SEQ ID NO: 4            moltype = DNA  length = 29
FEATURE                 Location/Qualifiers
source                  1..29
                        mol_type = other DNA
                        organism = synthetic construct
SEQUENCE: 4
tgaaaatcct caacactcca aactgtgcc                                  29

SEQ ID NO: 5            moltype = DNA  length = 16
FEATURE                 Location/Qualifiers
source                  1..16
                        mol_type = other DNA
                        organism = synthetic construct
SEQUENCE: 5
gcatgttctc acatta                                                16

SEQ ID NO: 6            moltype = RNA  length = 20
FEATURE                 Location/Qualifiers
source                  1..20
                        mol_type = other RNA
                        organism = synthetic construct
SEQUENCE: 6
gataatgtga gaacatgcct                                            20

SEQ ID NO: 7            moltype = DNA  length = 9001
FEATURE                 Location/Qualifiers
source                  1..9001
                        mol_type = genomic DNA
                        organism = Mus musculus
SEQUENCE: 7
ggcagatttc taagtttgag gccagcctgg tctacagagt gagttccagg acagtcaggg  60
ctacacagag aaaccctgtc tcgaaaaaaa aaaaaaaatc cctttctctg gctataagga  120
tggctcagtg gttaagagca ctgactgctc tgccagaggt cctgagttca agtcccagca  180
accatctgta atgggaaata atgcactctt ctagtgtgtg tctgaagaca gctgtagtgt  240
actcatataa ataaaaaata aatcctaaaa aaaaaaagaa ttcccttcct cttattgata  300
ccctttcttg tctctaggga ccccccatat atctttctag acatttctga gaactcatgt  360
aaatacatgc tgagccccct ctttgtagtt tgtaaccttt gctcattcca taccatttta  420
acaaatattt tccttgaaac actatttctc acccattgca tggaggtatc acataggact  480
ttatcaggca tcctgttctc cagtgtgtgg cttagagcca gtggaatgca cggcgtgtcc  540
gagaaccact tcacacaggg aagagaatac agatttttac tcagcaagta acaccagctg  600
ggaatggtgg ggcagacaag caatcctagt tactagggat gctgaggcag gaggatctta  660
aattcaagtt tagtccctat ctcaaaaatt aaaaaagaac ccctctaacc ccagcaactg  720
agaggcagag gccagggaga tctctgtgag ttcaaggtca gcctgtctgt tctacacaat  780
gagttccatg agagccaaag gtacacagtg tgatattttt aaaaaggtat gtgtgtcttt  840
tttttttca aattttatt attttcttca tttacatttc aaatgctatc tggggagtcc  900
cctataccac gccccccctgc tcccctcccc acccactccc acttcttggc cctggcattc  960
cactgtactg aggcatataa atttgcaaga ccaagggcct ctcctcccag tgattgtcga  1020
gttggccatc ttctgctaca tatgcagcta gaaacacgag ctccggaggt actgggtagt  1080
tcatattgtt gttccaccta tagggttgta gaccccttca gctccttggg tactttctct  1140
agctcctcca ttaggggccc tgtgttccat ccaatagatg actgtgaaca tccacttctg  1200
tatttgccag gcactggcaa agccttacac gagacagcta tatcagggtc ctttcagcaa  1260
aatcttgctg gcatacgcaa tagtgtctgc atttggtggc tgattatggc acggatctcc  1320
aggtggggca gtctctggat ggtccatcct tttgtctcag ctccaaactg tgtctctgta  1380
actccgtcca tgggtatttt gttcgttatt ttaaggagga atgaagtatc cacacgttgg  1440
tcttccttcc tcttgatttt cttgtgtttt gcgtgtgtgt gtgtgtgtgt gtgtgtgtgt  1500
gtgtgtctta actggcagag cacttgtctg tcatgcaggg ggcggggtgg ggggtgggga  1560
ctgtctaatc tccagctcta gtaacaaaaa taaaagaagt aaaaaataag taagaaacgg  1620
gggtgtgtct agagatagaa catgggcttt acacatttta gacatcatga gaaaataaag  1680
ctggaaatga cactgggcat ccatcttggc gcatctcaac tttcacactg caaccgaggc  1740
gcgctgtgca aagtcagtga caatccgcat ttccagacac agtgggttca gaccttccag  1800
gcgcgcacgc gggcctcgtg ttctcggttt ccgcggcgac tcggccgacg tcacagttag  1860
aagacaatag cgactttccc cgctcaggct cctcgggaac tttctcagtc cgcacgctcc  1920
aggagccgga gctaccctcc gccccgcccc cagcgtgccc cgcggccagg gagctccacg  1980
aagggcgggc ggaggccgcg ggtagcgatt ggttccgtgc caaggtgggc gtggtcagac  2040
tcaggcctat aaaagctccg tggcgccagg gcctcgtttt tttgcgcggt cctttcctgc  2100
ggcgccttcc gtccgtcggc ttctcgtctt gctctctctg gtccctccgg aggaggccgc  2160
cgcgcgtctc ccggggaagc atggcgatga aagcggtgtg cgtgctgaag ggcgacggtc  2220
cggtgcaggg aaccatccac ttcgagcaga aggcaaggcc cggggcgcgg ggcgcaggcc  2280
gcggtgacgc ggcgcacctg tgcgggagca cgccacgccc ccgccacggc ctgagcccgc  2340
taagtgctga gtcaccgtgg cctggggcag gggctgggcg ccgggaagcg aggcccgggg  2400
cgccgcgggg ccttccgggc gggcgggggc ctccccgcgc cccggagcgg ctgggcctgc  2460
ccgggagagc cggcttggca tccgttatcc ttctggggct gctgcttttc cggtgtccgt  2520
gtcccacagg ctcagagccc cgtggccacc ggctgcgatt gttgtaagaa tatttgaacc  2580
cggtggtgcc agaccggact aaggccgcag gacgcgtttg cggcacttta aagcaaagtc  2640
ctgggctgtt ctgtactagg tcagggtcgt gtcgcaaggc ggaaagaaag agatggcctt  2700
ggacagccgt cccttgcttt gcactccaga gagagacccg gctgtgggtt ttttctacca  2760
cagcgagttt ctgagcacat tttggaaaag tacatagaga tattttcgaa aatactgtga  2820
ccctgcaaaa acacatgcgt cacagggaag atgtgtgtgg taaggttgtg tccagagcct  2880
tagggaggtt accgttgttg tattcacctt aatcccgaga gaatatttga taaatgagcg  2940
```

-continued

```
ttatgtgctc tctgaagtgg tggacatacg tgtgagaagg cagacaccat agtgaatccc  3000
aagtgtttgg tttacgacga gaactgataa cggcaattta gagtttttcg taactagcct  3060
cgtttccagc agtttcttgg cattgaaatg cgttttgttg ttttcctgtg gaagtttttt  3120
gtttttgtct ttttctcctc cccacgtaat tcactgtgag aaagacgaag ttcggctggg  3180
tcttacccct gtgtgtgggt ttctgtcatc ttccaccatg ccatgccaga gcagctcgca  3240
ctatttttgt gacgctgcaa actacacatc gctggtgccc tttgtaccca atgaaacgat  3300
agttaagcat tccagattgg cagttgtaat caaagctggt tgatttaacc tgttgccaac  3360
ttttcagaat cagattttc tacccaaagt tcatattccc ttattctgtt gcaaaagttg  3420
gacatttaaa aaaaaaaaaa cctaaaaaat gattgtcctt gcttgttggt cggttgctct  3480
tacattttct ccctattgct acactttctg gagcagtact aatttgaatt ttgggtgttc  3540
ttttcttttt tgttaagtgg caaattttct agatttggat agctaatgag attttttttt  3600
taaggtagct ctggttagac ccaaatggat ctccacaggc agtaggacaa aggcattttc  3660
tgaccactaa ataaaaatag gggaactgat aaaatcactg aatgtggaga acagggttct  3720
cggcagccag tgttctgtaa gagtcaagtc tgacagtgca gtagccatct cttccccagg  3780
cctggcattc agtagcccct gtttgttcca cctggtgctt tctaaatgct gttcagtcca  3840
ggtgcctgca cacatggcat ctggcagcaa gtgttaggag aagtgtgaca gggagagaga  3900
ggcctagagc tgagcgtctc cagagccacc ctgtaggaag tgggtctact tggatctgaa  3960
cataggtttg attttcactg ttgtgtgttt tgacttgagc tttttactgt gcttggttag  4020
ggtgtaaccc agcaacagcc ctggtgcagg agtatttaca ctcaaacttg atgtcttcat  4080
ttttgtattt ttttaaatca aggcaagcgg tgaaccagtt gtgttgtcag gacaaattac  4140
aggattaact gaaggccagc atgggttcca cgtccatcag tatggggaca atacacaagg  4200
taggtcctag gctggctagt gaccagtgat ggaaaggaac tgagtcagga cccaattact  4260
aaccatttaa aactatctcg tttgttttct ttttctttta gataaagtta aaatgaccac  4320
ttaggtcaac cttggaaagt agccacaaaa gtattttatt tagtatcaag tattgcttgc  4380
ttccttaagt gtgggaaggt aaagaaggtg atttttcttc attgtaatta taattaagca  4440
gcaccttgct tattctgggt gtttattggg tgcttatttg ggtgtttgga gctgggcgtt  4500
gaggatggat gcattaggca gagtgtctaa ggacaaccat gccttagcat gagaggcata  4560
gcgggacaga agtgacaaaa actgaagatt caatataaat gcttaagtaa gatttatttt  4620
ctctatttgg gattagaatc aagtcagtaa aaagtagtgg cttaaattgc agttagtgaa  4680
cttttaccat attggagtaa tgatctgaat ttgcttaccg tcatttaaga gcctcatcca  4740
tgttgcgaga gccttttcct ttcctctcct tctcccctgc cttcttccct tctccacata  4800
gcccacggtg gcctggaatt tagtcttgtg tgtgctgtgt taaaggcatg taccatcaac  4860
ctgtgtgcta tgtgccataa tttgttctac agttacttag gattgggttt gacccattg   4920
ataattacta aagttacccc gagttgcctc tggcctggta gctttgattt gttaagctcc  4980
ttccagaatc ctgcccagtt cctattttct tggtctgagt aaacactgga agtcctgcat  5040
ataaaaggac ttgctgcatt gttgagctgt gccttgtgac tggcatccct tagcccacat  5100
gagtagtgtg gtacacctcc tggagttgag gacaccagcc ctggcccttg ggaacaagcc  5160
atctaacagt ctgcctgccc caagtaaaag ctagacaggt gagctgtttg gtggcacatg  5220
gtctagaaag ataagtattt ttatcatgaa gtatgctccc ttcttaaaag ccaaggtctt  5280
taaatgtggg actttaactt tagaagtgcc attaaagatc acatctgttc cagttacaag  5340
gaaggaacaa gagccaggca tgctgtcctg acactgccat ggccctaagg ctaaggtggg  5400
agggtcatag gtcgcagata tcctgagctg tagtagtgag acactgtctc aaaactcaaa  5460
agcaaacaaa aagaaaaatg tgacagtcta ggaaaaaaag gtagcctgag aatgtaaggc  5520
tatacagtgc agctacttac accagggcgc tgctgcctgt ttttatcgcc ccagcacata  5580
ccaggtcagt gtttgctatg ttggaggttg taagaatgcc tgtgttgtta catatagggg  5640
tttacttcat aatctgactg ctggtttctg gtaaataggc tgtaccagtg caggacctca  5700
ttttaatcct cactctaaga aacatggtgg cccggcggat gaagagaggt gagcagcacg  5760
ctctgtatgc atggtggagg agaggggtct gtggaggacc ccagtaagac agaactgcat  5820
ggcctcctgc ctctgctttt gtgtttgttt ccattcaccc aactcactcc cacaacccca  5880
cgtgctagaa tagcttctgt tgggtgaagg agctgacaaa tgtggactct taaagtgatt  5940
tggttttgta gcatttattg aagatgaact aatacaagtg ccaaaaggaa ccaatacaga  6000
aaatatcatg gataacagta ctgtcagtca ctggcaaagt aaatcattgt ataataggac  6060
gctaatgcag ataatgaaaa ctagttgaga ttccatttgt atgtgaaacc ttaggaaagt  6120
cctaaataaa gaagggctag cctgttttta gaatgggggc ctgggagcaa acctttgcta  6180
actcaggagc tggcatactt tactaaagcc ccagattatg actcttctca gagcactacc  6240
tttaaacttg aagaactgtc tgtcaaggta tcctgtagct acctgttttg aactttgtgt  6300
ttccagacct ttgccggtct ggaaaagcca tcatagttga taatgtatgt gtactttttc  6360
atccactcat acgtatttga cttagtcaga ttttaactta gttattgaac tctagtgatg  6420
tgaaatagac atcattgttc atccacctga tgctgtttta atgttaggca tgttggagac  6480
ctgggcaatg tgactgctgg aaaggacggt gtggccaatg tgtccattga agatcgtgtg  6540
atctcactct caggagagca ttccatcatt ggccgtacaa tggtggtaag tttttcatat  6600
aaggatatat acataggatt tcttctaaca tagttatgta ccttcccatg actttatggt  6660
ggttaaacta gtttctaaag agtcacataa attgttaaga gttcagggta ggaaaaaagt  6720
tcttttattg gctgtgatag taaagaatta atttgcctag gtcagttaag aacactgttg  6780
tgctgaaatg cagtagaaag cagttacatt tgatgagact ggatctgagt tgaggataca  6840
atagtcttta gtctaaaaca gccggatttt cttgccatga ttgccccccc ccttgcaaca  6900
tttcgttgag tctaaaatct gcgatggatg gcagtattca agtctgtagg ttatcgcttg  6960
gttaccatat gggagccgtc ttcccaagtt accctcggga gatgcatctg ggtcatgcag  7020
aacaccaagt agtaaaggct cttgcccacc tcgggcagct aacttttcag taggcacttc  7080
cttccttgca gttgaccctt tatccttaga atgctcttca gccctattgg tgaagcagaa  7140
cagtcattca taagtgttgt aaaataaagc tttagagtct tgttgctaag tagagatact  7200
tagaattgcc tcttatgtgt aggcctatag ttctttcaac atgagatttt gatagagaaa  7260
tttgtaagaa tgactactgt gtagttgggg aggagctaag atcagcatgt acctggtagt  7320
tacttgggtc ttagtatttc atctagaaat agccactagc aaggaaaaac ttagtggtct  7380
gctcttaact gctagtattt aagtctgtag tattgctggg aagaagtact agttacttga  7440
tcattcaaac ctaaatgttc ttcttttcaa aggtccatga gaaacaagat gacttgggca  7500
aaggtggaaa tgaagaaagt acaaagactg gaaatgctgg gagccgcttg gcctgtggag  7560
tgattgggat tgcgcagtaa acattccctg tgtggtctga gtctcagact catctgctac  7620
cctcaaacca ttaaactgta atctgaagag ttgtaactgt gtgactcctt tgactgggct  7680
```

-continued

```
aaggacagca atgacagctg atggagactg tgtacaactc actgaattca aatctgtttc  7740
tgtgcctttc catattttgc cagactacac aggtgataag ctgaaattct catttgagcc  7800
tgttagtaaa tatgtgtggc acttattttg agcctattaa tgtgtacaaa aaaaaatttt  7860
aagttagctc tatacattga gcatcaataa cagactcaat gatgctaact catagtattt  7920
cattttgaaa gtgttttatg tgataccatc aaaatggtgg gtggtagccc aaacaaaatt  7980
tgagcagaaa attttctgcc ccttatcaga gaaattattg aaagctctca agattcagag  8040
tacttaacct tatattttaa aattgtatta ggattagatg tcatgattta agaaaaagcc  8100
ctttagtaaa cttgtatcaa actcatagaa ggcaaacatg gagcctcagc tagctctact  8160
agccaagtga agttggtacc acccatcttt aaggttggca ctcagggaaa acacaatagc  8220
tcggggaatg acaccaagtt tgactggagg ttctggctaa atcgactttt atagccccag  8280
gtaatgaaat tgagtgcctt aatacccaag aaagagtgcc tttgaaagga aatattaaca  8340
ggcttgtgac tatctgaaat agttcaattg aagtatttc aacaaattgg gtgtaaacca  8400
tagttctcac tgatatactg aagtcactga agaagagaca actaaattgg aaaagcacat  8460
aatttggtgt ttccaacctt aaaattttta agtttagatt tccaatctaa gattgctcat  8520
aatgcttttt caagtagtta tgttgaagtt ccaggtaaat cctatgtaac tgatttcctt  8580
aatgtagttt tgatgtgggg gatgactcaa tgcggattaa cttggtaatc acaaaccatt  8640
tagtggctca cgtctcagta tttttagttg gaaagacaag ctgcaagtct gtccttggaa  8700
tctgacattg gatcatcgtc ggatgcatgt tttatgatac tctaataagg acttaaaagc  8760
ctaagtaggg tcaccagaaa gctgaagcct ggcaaagcta cagacacatt tcttccatca  8820
ttaggaagag ctcagatcta aatgtcaaat gggaacatac aaaaaggaac ttctaggtac  8880
gataaagcta agtttgacaa gttttttgtt taacctagca ccttgtagtt ttaaaaatca  8940
tttttagggt gtgtgcacta agaggaaaac aagttcatat tcttccacct tttattgtcc  9000
c                                                                  9001

SEQ ID NO: 8           moltype = DNA  length = 19
FEATURE                Location/Qualifiers
source                 1..19
                       mol_type = other DNA
                       organism = synthetic construct
SEQUENCE: 8
tttttgcgc ggtcctttc                                               19

SEQ ID NO: 9           moltype = DNA  length = 22
FEATURE                Location/Qualifiers
source                 1..22
                       mol_type = other DNA
                       organism = synthetic construct
SEQUENCE: 9
gagggaccag agagagcaag ac                                           22

SEQ ID NO: 10          moltype = DNA  length = 19
FEATURE                Location/Qualifiers
source                 1..19
                       mol_type = other DNA
                       organism = synthetic construct
SEQUENCE: 10
cgccttccgt ccgtcggct                                               19

SEQ ID NO: 11          moltype = DNA  length = 16
FEATURE                Location/Qualifiers
source                 1..16
                       mol_type = other DNA
                       organism = synthetic construct
SEQUENCE: 11
tgaggtcctg cactgg                                                  16

SEQ ID NO: 12          moltype = DNA  length = 33000
FEATURE                Location/Qualifiers
source                 1..33000
                       mol_type = genomic DNA
                       organism = Mus musculus
SEQUENCE: 12
caattggata ctgtcttagt tagggtttta ctgctgtgag caggcaccat gaccaaggca  60
actcttatga gaacaacatt taattgggac tggcttacag gttcagaggt tcagtccatt  120
atcatcaagg caggatcatg gcagcgtcca ggcaggtgtg atctaggaag agctgagagt  180
tctacatgtt catctgaagg ctgctaggcg aagactgact tccaggcagc taggatgagg  240
gtattaaacc catgcccaca gtgacacacc tactccagcc tcttccctga catttgaagt  300
taggttctac tgatgcaagg aataatagcg gctataatca ctcttatcaa aatggatatt  360
acatctcaaa tagcatctgc tcatatggtt taaatattat tccatgtgga ttatcttttt  420
tttttattgc tgagaactgt ggttttatta attggttttt tttttgtttg cgttttttgt  480
ttttgttttt gtttttttta atgtcaaatg gtaaattttc attttatttt atacttttta  540
aaaattaggt attttcttca tttacatttc aaatgctatc ccaaaagtcc cccatacct   600
ctcccccccca gtcccctacc cacccactcc cacttcttgg ccctggcatt cccctgtact  660
gaggcatata aaatttgcaa gaccaagggg tctctcttcc caatgatggc caactaggcc  720
atcttctgct acatatgcag ctagagacac gagctccggg ggtactggtt agttcatatt  780
gttgtttcac ctatagggtt gcagacccct ttagttcttt gggtattttc tctagctccc  840
catgtggatt atcttaagag ggtttcaata gtcacataag aaagtctctc attttagggg  900
tgaagaccac tttaaaaaaa ttcaaatggc ttgctgaaag ccacagacac tagagaaata  960
attatgttta gggtaaagtc ggcttgtcct cttgtgaaac tgtgtccaac ggagacaagc  1020
```

-continued

```
tgaggaatta tgggcaatga taacatgtta aatgttgagc taaatgtatt aaaaagcgca  1080
aaaaaacagg tgtggtgggg gaacagaggc tagaagtctc cctgaaaaaa atcaagtctt  1140
atttcctact tcccccgtgt ttggtctggg gaagaacaat agtgtttgct taagcatctc  1200
attctgtttt caaaaccttg catggttgac ttgggaactg atagagaaaa tgaagcaaac  1260
aatactctgt aatcaacatt aacatcaaag ctagctctct ccactgtggt ccctgaccca  1320
accacgttaa tctcccaggg tcttgttaaa actgtaggct tgggagagaa gtggttgtgg  1380
tgaggggtac cttggagtaa ttctaagtct cttggggtta agcctggaag attggtgctt  1440
tatgtattaa gagtcctggg gatccgaaag tagaaaaata atgatttttg ttagtgactc  1500
agtatggttc ttacttcaac acctcctctt aagggaggaa gtagtgtgtg catgtagctg  1560
gaattttaaa taataacagt tcaggtgtgt gagtatttca ttagacagtc agcttccatc  1620
ctttatgcat cctttaagca ggttggttta gacaggtgca caataaacgc caggctatta  1680
aacacaggga ctccaatatt taaaccaatt cttttgaatt gtctggctag aagcacatcc  1740
agtctgataa agtagacaaa gcacgtggag tcttgaaaag ttcgacaccc cttcggtcct  1800
cagatgacta ttatttagca attgagagca ctatactcct tcttttgccc acacctataa  1860
ggagatggac atggcacgta catcccagca cttttgacag ctttaaatgg tgtttattac  1920
gagcaggtat ggatgctggg aacagtgctt ataccgagtc ctggaaatgc ttattaaacc  1980
caggagatac aaggagtctg ccattaacct ctctgtaact caagagtagt tatcaggagc  2040
caatgaggga gaacaagaga attgaaacac gtgggaatat cggaccacca ggtagcgggt  2100
gtgtgtgtgg ggggaggcag ccctagggag ctctcaagcc gaggcccctc ggggtccccg  2160
cggcacgtgg cgggctcggg ccggagcgtc gcggcggtgg gggaggggag cggcatgagc  2220
cctggaggag gggtctagac tgcccgggat tcgtttgagc aggcgcggag tgcgcaggct  2280
cggcccaggc gcaaccagtg cgcgtaagac cgaggggtga acctcactgc tgcgcgtccg  2340
ggtctctgag caaggggcta aagtccgctt gtgcgcacct ccggactgtg tgtgactacc  2400
cgtagaaaca ctactgtcgc cctggccggt ggcgtccact ccgtcccggt cgctccctcc  2460
cgaccgtagt tgtggtgccc ccctccgcgc agccgcagtg gtcgctcccg cctcgcagcc  2520
ccgccgcccg gaggcctacc cctgccgagt gtcgcgcgtc ggcgccgctg cctatcccgc  2580
tctgtgccct acggccctcc cggcacccgc cgccgtcccg ctccgggctg cccttgctcc  2640
gagggctgca gcaccggccg tccccgtcag ccctcttgtc tggccgccgg gccgcggcgg  2700
gcgggagcag ccggaggagg agccgcagcc gggaggcggc ggcctgagcc catggcgtac  2760
agtcaaggag gcggcaagaa gaaagtgtgc tactactatg atggtgagtg gccgaggagc  2820
ctgcagccgg gatgcgggga gggcgcggcg gggtgtcggg ggtggcagcc cgcggggaca  2880
ccaacacggc ctacccagcg gtggcgtctc ggggacgccc gccttcgctc ctctcgggtc  2940
ctctcgggca cacgcaggtt tagggtgcac tgcctctgac cggtctcccg aggaacccca  3000
gttggcaccc tgggcctgac tgcacaaagc tggcgtcctg gagctccgcc ccacgtccct  3060
gtcccctccc ccgctctccc ggtccccccct tctcgccccc gatctgtccg cgctgcgctt  3120
ccagcctcac ccgggacccc ggcacccggg tggggctgcg gaggagttac tgctggccgg  3180
tggccaagtt cgcagagcgg cgctgtctcg ctggtgtttt gcgtggacta catccctcgc  3240
ctttgttcgc gttcttcgag ctccactttc tcagggttca aatggaaggg ctgcacttcc  3300
tcggtgacaa ttaaggggtt ttgagttgga agtaggtagg tcgttgggaa gtggtaggag  3360
agaggaagcg tgcagttgtt cttgtttagt gggtcctggc atgtctctat gggaggttat  3420
tacctccccc ttctttgttg ctctttgttc gatctgctat aataccctgc tctggggggt  3480
taggaaagaa caccggcatc ttgcttagga actcttctac tgtggtgaag accttgctgc  3540
aggaaacttt gagaagtgga ctaaatattc acaatgcagt gaacggtaca aggtgactgt  3600
aaggattttc taatttggag tataagtagt aatagtctct gggttcagtt acaccaaatg  3660
gaatggtgcc ctgcctatac agatttcacc caagacatca atagataaac cattgagaga  3720
agtaataagg aaatttgaca gaactttcga agctcattga ttgaacgctt gatctccaca  3780
aagcaatatg aaattgggag cgttttctgt agttgtattg aagtcacagt gtttggagag  3840
gtagattaga gaactaggct gaatgaaaca cttaaacttg ttaaaatagt cgtgcatttt  3900
cttggtttga cagaatcttt taatacaagc tttaaataaa atagccacct gtcattggct  3960
ggaaaaccaa aaaccttaca gaaagctagg ccaaaatgga aaaggctgtt ttgttttttg  4020
agacaggctc taagttgacc tggctgtcct gaaactcact gtgtaaatga ggctctaact  4080
catagagatc cacctgcctc tgcctcccag atcctgggat taaagatatg tgccaccatg  4140
gcctggctta attggaagtt tgagaggact caaactgtat tgcatgttta tttgaagtta  4200
caccatcatg gagagcagag atgggagagc atgtcggttt aaacatgagt tacattatga  4260
cgttggggtc atagcaaagc cctgacctgc attctctgat ccattggaaa ttacagcctt  4320
tctaaagtaa agtcctgctc ttgttagagt caggggaaag gttgagctgt tggggaacag  4380
ctcagtctct tcagctgtca gcttctgtca tcagtgatga actctaagtc ccattaactt  4440
tcaccaggcc tgatggagaa ccagagagga ctctctgtct tgaacagctc cttcctggct  4500
tcatgcgtag ggatgagcct ttgctgagga gtgggataga cattggtcat ggagataagg  4560
tgtggaggga ggcatttttc agtcatgtga ttttcgactt atgcccatgc agctgcttta  4620
cctagttgtg agtgaccaac tgtataattg atggtggaaa tctgctgagt tatctatctg  4680
tggttcttac ttgacttgtt tttagaatgt acttaactta tttttattct gactatttgc  4740
atttggggga cgctaacaaa aattgaagat atataaattg gtgtcatagt taagctaatt  4800
aacatgtcat agcatgctag actacagaga attctctgca gagaattccc ttcacgtctg  4860
acttgattac agaaaccctc ttcttgttag tttataaagg tagcagcaat ctttaattgt  4920
ctttattaaa ttctaaacaa gaggagcaag taaagtgact tttgtaccaa gaaagtgcat  4980
gactttcaga cgcatgcagg gttgggttgg tggagaaccc ggccagtagg attggggctc  5040
gaatagtata ctagtcttat gttagtgctt ttaacttggt tggtagggga ggagatcagg  5100
aaaggaggag gttaacgggg cactaggcac ccagagagcc tcttgacaac tcatgtgagt  5160
gttttcctgc taagactgtg tgcttagtga agaatacttc tgaagattga atatggtttt  5220
ctccgtgtgt gctgcagtct tcagaattgt acttgtaggg tctctgtgcc actgatctgt  5280
gaactttcag ataggagcgt atgaactatc cctaaacctc acaagagaaa tcagagttgt  5340
tcttagtgga ctgtgactac tgactggtca tcataactcc cagaaacaca tttcagaatg  5400
ttggctaatc tcttactaaa ctaaaagaca aagatcggta aatgatataa agctaattat  5460
gtgtctacac tgagatcctt tctgacctct ttcccgtttt tctcaaagtg taattgagca  5520
gatggggcta catttagttc taattgcaag gctcaggctt ttaatacttt atctagaaat  5580
ataaactttg cctggtttag agtgaagctt gggaccaatc atgtagtgcc ttctaatgta  5640
tagtgtataa cagaattgaa tgtatgcata atttatgtaa ttagacacca attgctttat  5700
gctttgttta ttttctctga tagagataat cagaatcaaa atgtttggag acatagtcca  5760
```

-continued

```
gaggaaagca cgtggcaaca aaaatataga atataacaat tactataatt atatttccca  5820
gtgtactcct aagtttctta acagatacaa gagtactaca gagtggccat cggttgtcag  5880
atttatttta ctttttattta aaatgtgtgt gcttcttgtg tatgcctggt gcccttgatg  5940
tttaggagtg gttgtgagct accacgtaga tgctggaaac caaatttggg tcttctggaa  6000
gagcaataaa tgctcttaag ctactctcca gcctgtccgt tcccactata acagtaggca  6060
ggaggatggt taggcttctg ccacttatag atgaaaacag gtggacactt catattctcc  6120
acatgggttt tctttcccca cataggtttc tgttttaatg tctaagaaag attcgtacct  6180
agaatacaaa gattttattt ttcttttgca gagttttgtt cttctgtccc taaaaaaatg  6240
tattaataat tggtttttttt cttagcaaaa ttaaatgtta gtaaattctt aaaacacatg  6300
gagttggtga acaaaaggaa aatttcttac attagcaaaa tgaaatgtga agtcattaag  6360
taacggtttg ggctttttta aggccgccat tgctatggat aatgacaccg agatttattt  6420
ctgtttagta ataaatgcct aggccttaag ctaggcctac tcccaactag ctcatcactc  6480
aattatctca tttatacttc tcagtttcct acaaccaact tcctccgagt ccgaataggg  6540
aataccccac gcctaattct gagttcctct ctcttccaga tgtcccacct tactatcctg  6600
ccttttgctg taagccatag gctttttatt ttaatctgtc aggaggtgcc ttaggcagtt  6660
ggggaaggat agagacacat cttcacacag tgtaccgaaa catcacccta acaccattac  6720
attgaagttc tactctcacc atgttggtta gtcggtctca ctctggtttc atggtttatg  6780
cttgtacatg aagtcagttt ggggttcaga aacataagat tgttttaagt ccctgctttg  6840
tcccatatag acaaagatta cttaagaagg aaatgggtgt ttgtaacaga gtaaaagagg  6900
aatggagtaa taaaacaagc atctctagga agcatatgcg ccagtcttaa aacagtcctc  6960
cctgtgaaac aacaaaggcc aagtccttgg aatgtgttgt acccaaaaga agggcaaccc  7020
agagataggg atgctgggct gagccccaag gggccaggca cagcaagctt ggttgaaaga  7080
gagtttgact cttagaggga gtgtcttgga gcttttaaag tggaggctag tcaataagag  7140
aattggtgag aagtagaatg taggctagag gaaagtgtta aagtgaaagg aaatggttgt  7200
ctttagatag aatcgggtac atttgagagt ggtttataaa ccaagaaaaa aatacatcaa  7260
aactacttgt tggtggcttg gacgagggat tagggctggg agttgtgatt tctggactgg  7320
tcatgagatg gacaacatac tgtccattga gattatatgg aatcaagggc tctatattgg  7380
ctattatgta tttgagatct tgatttagat caaatgaaaa tacttccaaa aattacctgg  7440
aacccaggga gaagtagtat ttcttagctg gtaagtgata aatactgacg tgtttgttga  7500
aggtaatggt atggagagac acagactccg gaaattgttc ctgagaagtc ataggatgaa  7560
gtcactcttg gtgtactgct tggccagtga caagctcttg acttatgagg aaagtgaaga  7620
aaagctgaga tttaaaaggt ttggaggaag tgagcttaga gaaggaacac aatggaggac  7680
agaattgtgg agatccagac tccacagtgt ttcaaggagg agggagggtc taacagtgtt  7740
aaaaccttca cagaactaat gttgtgtggc agacagaaat tgcacagtag tctttttatt  7800
cttgattttt tcccctccct cgagcccccc cacacacact acttttggca gcttctctat  7860
gtacagtgtg aaagtacatt tcacagtcct gaaatttaca atgatctgaa attttgttca  7920
ctcagaatca aaagcttatc ctgaaattaa cgaaattaca atttattgtc tttattccac  7980
taactgtgat aattacacat ttttgcttta gaaataccttt tgattataga atgttgtccc  8040
agttttagta cattatatat ttttatcttg agtcaaactt ttctggatat tcttaattgg  8100
taaaactata tttaagtatt tgaacaaaaa atgggatcac attttaaatg cccaaattat  8160
gtaactgaca gagactatag gtacatgaaa ttaagaaatt atgtaactga cagagactat  8220
aggtacatga aattaagaaa ttatgtaact gacagagact ataggtacat gaaattaaga  8280
aattatgtaa ctggcagaga ctataggtac atgaaattaa gaaattatgt aactgacaga  8340
gactataggt acatgaaatt aagaaaagaa gagcagtgtg aggtttgatc ttgctgtgca  8400
ttgcaatact aagtgcaggc cccaagatct ggagtctgca cacagacctg agtaacagta  8460
tgtggccttg ccttcaagtt atttctgact ggtaaataaa gatgcctaca gccaatagct  8520
gagcagaaga gttgtatgtg gggcttagga ttcctattgt aaatataaag gttgtgtgta  8580
tcttttatct ggaaactaaa tggtcaaagc cagggtagaa acgccaggtt gggattaagc  8640
gttttaacaa cagggctgga tggcttagca gtttaaaacc ctggctgctc tttcagagga  8700
cctgggttgg attcccagca ctcacagggt tgttcacagg ggtcattcac tacagccaca  8760
ggggatctga tgctgtctcc tgccctccat ggccaccaga cacagtcata tgtatggcaa  8820
aatcaccatg cacattaaat aaaatttaaa aagaatcagt tcagaaaaca ttttcttaaa  8880
aaagaaaaag gcagaaggtt ttttagtaag aaatagatga cttcaaagtc gccatgtata  8940
aaactaatag tgaacaggaa acattagaaa tgaagattct tccctctcct cctcccagaa  9000
tcacctaccc tctgctgcta gagtgctggt ttaaaggtgc cttgcccaca aaaatggttc  9060
ttgtttgttt ttgaaattat aatatgatca caccattttc ttccttcctt tactccctcc  9120
aacccctcct gtgtagcctt ccacctgctc tctttcaaat ccataccctt ggatttcttt  9180
aactgttgat acatataaat actcctaaat acataaatac agtgttacta tatgtttttta  9240
gagctggcta tttgttattg gataaccaat gggttggtca ttacctggag gagattcttt  9300
gtcctatcct tagtccttag ttgtctgtag ttctttgtct aggcttgagg cctcctgacc  9360
ttcactaacg tgtctgttaa tgaccttgtt caggtcatgt ttagccagtc atgttggtga  9420
gactttgtgg atgttgcttc tgacatgtct cactgacagg cttacagtaa actccttgtt  9480
cttcaagctc tttaaaccct ctctctcttc cccaatgccc tctgacccta aggtgtaggg  9540
gttgtattgt agatgtgtca cttggtactg ggctccaaaa ctctgcattt caattgtgct  9600
tttctgtaat ggtctctgct acaaggagaa cttttccttt atagggggtga ggactacagg  9660
ctcctgtgtt tacaaggaca attatgtaga atgtagatcg ggatgctgct gcttttgtaa  9720
agtagcaatt gcatatttta ttcaaagatg gatgacttca gtagtcttga gttggctagg  9780
tctccaatac taggcatgat ttccctcttg ctgaatggat ctgaaatcca attagaaagc  9840
tgttggttac tgtaaaggtc tgcgtgccac cactccacat ttatgctgcc atggtggttg  9900
ttactgtggt tcagaggtgt cataactgcg taggactatt ggttgcttcc ctcctctgga  9960
gccttgcatg actccttttt ataatatgaa gggtagtcct caagaaggat taggctctca  10020
gttctgtcca gctcaggggc ttcttgggcc ctgcatctca agtgcatgat gtcttcagca  10080
atatgcagtt acctctaggg ggcaaccaag ggcaatagcg tataagattt tgggagtctc  10140
ttggatagtc ctgaccagca actccaaaga cggctgcgta gttttttgtt tgtttgtttg  10200
tttgttttgt tttgttttgt ttttgtggat aatggctcct ggagggagcc tgtgtctatt  10260
tatacacagt cttatgtgta ttataggtac agtagggcaa tggcatgatt gtgcttgatc  10320
cttgagacat cctcactgtt cctctaccgt cctcattcct tgtcctgtat ttgtcttcct  10380
ccctagttag aagccccact ccattcccct tacatttcct ttccttcccc ttccttctcc  10440
ccctttgcgt tcccgtcgct cccctttttgt gcagaggaat taaaccaaaa gcttgtacat  10500
```

```
gctagagaaa tgttccacca ctgtatatct caagcctttg gagggattcg gaaaaattca  10560
tattatggct cagctgccct cgtgaatatg tgtcttttag gctaaatgaa tattcttact  10620
gagaataagg cctcaaaatt atgacagaag tttgtcgaaa gctgtatata ttaatataac  10680
gttaggagtc tcatagttag aaggtaactc ccttcataaa ttaggtaagc catccatttt  10740
gttcatattc gtcaaatgaa caaattcgat gctgagcaca agcatgtata ctgtattctt  10800
tcctcattcg ccattgtcct gctattacat tgctgtgcca gtgacaatac aaaagaatat  10860
tcactgcctg tgctctcttc ttcctaaatc tgaatgtagc tcctatctgc tagttgtata  10920
attttggcta cattatttaa catgcttctc ggcagttata aagttgtggt acatcctaga  10980
gttgagaaat aaaagctgat gctgagtact aggaaaatgt tcttgctgtt acttctcaaa  11040
cactacaact taaagttggc tgcataggga gaacatctgg aaggattagg ggaggggaaa  11100
ataggacaaa aatatattta aatttaaagt taaataataa tataataaag aaagtttcta  11160
cttaggtcaa caagatgtat tgttttctgg ttctgaagtt ttcatttacc tttgaaaaac  11220
tagttagcat tctgagtgct cctaaatttg taaatcattt tgtgaaaaaa ttgaactaaa  11280
taaatcagag gtactatacc aacagattca tactgtttga aggcaggttt tgtaaacctg  11340
aatgttcagc tgggtctggt ggcaaaagcc agtggtctct cagtggaatc atgaattcaa  11400
tgcctgcctg ggacacatag ctagaatttt gtctcaaggg ggaacaaaag caaatgtttt  11460
ctggattatt gtcaagtaga tagatagtat gaaaatttct ggatttttga ttgcccctat  11520
ataagtgaaa aggtactatg agaggagagt ttgaaatggg gatgtttgtg tttgagagct  11580
ggtcttgctg tgttgtctgg ccagcctgga gtcctgtttg caggtagata aggcttgcct  11640
tgatcttaca gagactcctg cttctgtttc cctcagtgtt agattaaagg tgtgcactac  11700
cataccctgc ttaagctttg tccttataag ggcagatata tgaagtgtgg gggctgtctt  11760
ttgttgtata aacctgtgct gaaacagtaa gatctgcagg ctgttaaagt caggtcaact  11820
gtcctaacaa attatgaata tttgatttta aactataaca ttaatagtaa tttctcattt  11880
cttgcttgat aaggccattg taaaattatt ccttataggg caggagaaat tactcagcag  11940
ttaaaagcat tggcagctcc tactaaggac ccagggttgt gttcctagca tatagccatc  12000
tgtaactcca tttccagggg atctgacaca tcgtgaccac cacaggcacc aggtgtcaat  12060
gcaggctgcc tatgtatata taggcaagct cgcaggcaca taaaagtaga tagtgtccct  12120
caccttagaa aaagtaatac ataagttttc taagcttgtt gacaagcttt cttattgtct  12180
aaaagtattt tgtggttgaa aatcagattt tggcattatt ctgtgtgttg ttttaagaca  12240
ttggcatctg tcttacttag tttgggtttt actgctgtga acagacacca tgacctaggc  12300
aactcttaca aatgcaaaca tttatttggg gctagcttag tttcagaggt ttagctcatt  12360
atcatggtgg gaagcatggc agcatgcagg tagacatagt gctggaagag ggttctacat  12420
ccttattcaa aggcagcagc aggagactcc ttcacaggca gccaggagga gggccttttc  12480
cataccaggt agagcctgag cataggaggc ctcaaaaccc acctccatag tgacacactt  12540
tctctaacaa ggccccacct cctaataatg ccacttccca tggccaagc atattcaaac  12600
caccacagca tctaagatgt tttaatgcac aggctactac tgtgtagtcc tgagaaatga  12660
agacaagagt gtctttatta ccctgaaaaa tgctgtgact ctcccacttg tggacactga  12720
acatttaagc ccttccataa ttccagctcg actgtaaggt atttctacag gattccaata  12780
agttatccaa gaagcactac tagctgacaa attagatcct actccgtact tcaagaatac  12840
ttcttatgta tctaaattta caaaatgaac aacaacaaca acaaaaatcc actaaaaatg  12900
gatttcacct taaggaacca aaccagggaa attggaaaac taaaagtcag aaaaactttc  12960
tctctccaca aagaatgtga atcctaggca tgtataaaat ctgcataata tattagattt  13020
ctaatgtaat ttgaatgtta caaaaacaac tcttgtttaa atataaattt tttgatgttg  13080
ggtacatgtc agtggtggta tttaataagc atcttttctc ttttaggtga tattggcaat  13140
tattattatg gccagggtca tcccatgaag cctcatagaa tccggatgac tcataacttg  13200
ctgctaaatt atggtttata ccgaaaaatg gaaatatatg taagtactag ttggcactgt  13260
gtttttaaac tggtatttga aagctcttct taggctgctg tgggagatgc atgtggtaga  13320
tgaaaagatc tgaacgaaca cagacaggtc ttgtggttgt gtccctcaga gaacgcttaa  13380
ggaattggag tagtcctctc ttccctctga tcatttcaaa caccaaatat ttttgtgaca  13440
atactgttaa gttgcctgtg ctgctagaaa caattgtcct ggggttggtg agatgactta  13500
ataggtagag gtgcttgcca ccaactggat ggcctgttta ccttccccag aactctcaca  13560
gtagaaggag agacctaatt cccccaaatt gttttctaat tccacgtggg catgaggaca  13620
cacctccaat aataagtaac cacagtgtaa ttttaaaaag aaataaaaga gaattgacct  13680
gaattattgc aagagtttgg tagaaaaatta atcataaata tttatttggt taacatacat  13740
atgaaatgtt gccaatgata acaaggtaag taaaaaatgg tgtaagatac acagccacct  13800
aaaaagtctt cgaaacatgg gcaggagcat acataaaaag tgcaaggtag gataaggctt  13860
aactaactac tccaggagaa gagggctaga cagtgttata ggaagcattt ctttaagata  13920
caggtatttt agagaaatgg gaagacttgt ggaagaagtc tgtggtaagt gaagctgagc  13980
tcttcagagc agaagttaga ataaacgaag gctaagggag atctcaagct ggtgttctta  14040
gaaacctttg atgaaagtca gtgggtagac agcagcgagg ctatgctggg aaagagcctg  14100
aacaaacagg agtagcctcg cttggagagg ggctgccggc tgcctgctgc ctgccacaaa  14160
tgtgtgcatt tgaattagca ttgtaacttg ctactcaggt ggatctggtt catttagaga  14220
gactgatcgt ggaaacttac acatatcatt tgataattct catttaacaa ctgatacttc  14280
caacatcctg gtgtttttct tttcagaggc ctcataaagc cactgctgaa gaaatgacta  14340
aataccacag cgatgagtat atcaagtttc tacgatcaat aagaccagat aatatgtctg  14400
agtacagtaa gcagatgcag agatgtacgt tataaataat tattttacta gtgctgaatg  14460
taaatgaatc tttttaaagt ttctgatcag agttgcctca ataggtattt ttcctcataa  14520
tttaaaatat taatataatt attaattcag aaggtcattg aaccaatatt aatgttactt  14580
tagaaaacaa acctatttaa atttgttctt ttacttttta ttttgcaccc atgaaaagtt  14640
tgggattggt agggagatca cagagttaca agagaaaaat atatttcttt cttttttttt  14700
ttttttaata atttttttga gacagggtct gactttgtaa ccagctgtcc tggagattgc  14760
taatgcagat caggctggcc tcaaactccc agagttccac ctgcttctct cttgcattaa  14820
caatcctcca tttcaccttc tgtgtactcc agtcacattg ttctgtaatg taaagatgtt  14880
gcctttttgtt ggcttctttg tgtttctttt tattcttcta catgtttttg attataggtg  14940
aaagtgtatt gttattggta gtcaattgta ttaactggta gtcaagtgta ttaaagaaat  15000
attgccaagt atcctgaaac tgtgggctgc tgtcttttga agcttaatac cggagcccat  15060
ttcctcagtg agaggtggat ttagttcagt gatgacgaat gataaggatt tctcaagttc  15120
actgaacacc atatttccct accgtatgtt atcgcatttg gttgactcaa gactggaata  15180
ggacggacgg atgctattac atctattgtt ttttgggttt tttatttggg atttacacag  15240
```

-continued

```
taatgggtag ccagcccttg ggtaaatgac aggatttgtt taaaccatta tagtgcttgt  15300
ttatattaaa ttctatttga gcataaaaaa ctaaaacttt ttttatagta tctgtaggtc  15360
tgtaaaaccc ctgccctctt gctaacgtgt gatctgagaa gtgaagaatg actagggatg  15420
ggccacacac acttctgttg tgttttttcc tctcagcaca gggagccaac catgtcatga  15480
ccaagtgaca tgtcatctgt cttatgttcc atgaaactga ttcattcatg gctgcttctg  15540
aagtcagtgt tagccacaga aaaaaaaacaa agtaacttaa tattttgata ctcactaaaa  15600
catgtttcgg agtcagggac actgtgtgtg agggtcagta agatgagtta gaaaggggtt  15660
gcagccactt aatctttaac tcactatcat atttaaagag aaaactagat ttgtgcctat  15720
tttcatatag gcttttgatt tatgttgttg gtgatggtgg tggttgggta gagtgacttc  15780
acaaatttcc taataagatt tggtaatgga attacataga taacaattta attatcttgt  15840
aaaataagca ttatattata aaattataac ttttataata ctacctacat tgaagtacta  15900
ctccctgtga attttaaaat tcataggtaa tattttaaaa ttacaaattt cacattgcta  15960
ccatgaaata ttatattatt acctatgatt gcctgaaaca aatattttta atagtttata  16020
agaaaaagcc ttcaatgact tgataataga ttgactttaa tgaagttcac cttccacagt  16080
taacgtcgga gaagattgtc cggtgtttga tggactcttt gagttttgtc agctctccac  16140
gggtggttca gttggtgagt atcctaaatc agtcagcctc aagaggatct gaaggggtta  16200
gagtgtctgt aggttttgtc taaagcggaa gttgtaatgg tagtaaggtt gtgttggctt  16260
gattttgctg tatcacccag gtgggcctcc gtctcagcca cctctgtggc tacctcccaa  16320
atgcttgctt acagacatgt gctatcattc caacttaatg agtacccaag ctgtcttgta  16380
gttcactgtg gggcccgggc tgaccttgat attgtggaaa tcctccccctg gagcctctca  16440
atcattggga ttagaggctt ggaatattat gatattgcta ttcactcttc tgttaatgta  16500
acaaaacctg cggtaacttt taaaagaatg gtttatcttg gttcacagtt tgggagctta  16560
actggccctg tccttgggga ctgtgatagc acattatggt atgtgcattt gggagaaggc  16620
cagtttacct catggccgct gaatggagaa aagaggattc cagtatccct ttcaagcaag  16680
atcagatctc cagtaaacta aaatcagatc ttggctctta gagagtccac ccccttccag  16740
tggtaccata ctggtgacta aatgttccct ggggttctta gaaggcattt caggttcaaa  16800
gtagcaagta taattgtctt taaaatgcca gtgtttaaca gtttttactt gaacacagtc  16860
tttaagcttg tgtcttttta ctcagagacc tttttctcct cttctttctt ccgccatttt  16920
tactaagact ttgcatgtgc actgtgattt agttgggtaa actgtaggaa aatggttatc  16980
tgaggaaagc ttaggctccg aagttataat cctttgcttt tgaatgccaa accttttgtg  17040
cttacacatg gcatatttaa tagggcttcg cttatatgta ttttgtgtaa cctgattttt  17100
taaaattctg agtattttat aaataacata gcatgtatct ccttcttagc tggggctgtg  17160
aaattaaacc ggcaacaaac tgatatggct gtcaattggg ctggaggact acatcatgcc  17220
aagaagtcag aagcatcagg gttctgctat gttaatgata ttgtgcttgc catcctcgaa  17280
ttacttaagt aagttaattc aaactgaatt ttccctgtga tcagatctct taattgaaag  17340
aaaaaaatga ttttaaagac tatcaaataa atggtaatag attaatgctg agtcttccag  17400
ggtttgttgt gagcccctgc agaagtgtga gaaatagacc actacagtgg gagagcgaga  17460
gggcagacag tgccgtgcct gagactgccg gtaaatggtc tctgctcatt taggtttgca  17520
gtcgtctaag ctgattaaaa atggctgcta gagatccgga aatgtgaatg ctaaagtaac  17580
ttgaagtcaa gcctttgcaa cttgtgttat aagaagtttg tctggccact tagtagcgtg  17640
gctgacccca gttctctcat ccatcctcta cacagacaca cagaacacat agataataga  17700
cacacagtga tgcccaactg ctgaaggggt tttggaagtt atccttcact gctttttcag  17760
aagtgtgaag gtccttagga gtgtggacac ttgtgaaact agcttatttt ccactgttag  17820
ctataatgct gcagtgagtt gtatttcagc tttgactgca gctgtgttct gtgggctttg  17880
agagtgatgc tcttgccccg catgtacatc ccaagagtta acttcctgac cttaaataaa  17940
cagcagctaa gtgctgtcag tgtaacatat ctgactcccc caaccgacag aaaccggaaa  18000
tctccttcat tgacttgaag cttcttccac tggcttcagt tctagagatc tgctgctttt  18060
tccttcatag cttagtcttg agtaagccca gttctgtaca gttcttcacc tggtaaatct  18120
gaacatgatt tgattggttt ggtaagcagc tctctttgct catctaaaca cattgggcat  18180
ttgatcatgt ttgattttga actttatgaa gaagttctgc tatgatgaag cccgctcgct  18240
gtttgcacta ttttagattt tcttagtgtt gcttttctgt gccttgagaa cataaatgcc  18300
tgggtttgat catgccagct tacgttgtat gagcacagtt acagcatctt taaataataa  18360
acaaaatgtt ttaagtcagc cacagtgaca agataatcat ttactacctt aaatggtgaa  18420
tttaaatttc attttgtatg tattggtgtt ttgcctgcgt gtgtgtctat gcaccacatg  18480
tgtgcagtgc ccatggagga cagaagaggc cggtagatcc ccaggaactg ctgtaagaga  18540
tggttgtgag tcaccatgtg ggtgctgggg atttaacctg gattctctag aaggcagcca  18600
gtgctcctaa ctactagtcc aactttccaa caccagtagc ttttttttaaa tacagttttt  18660
ttctatttgc actttgacat agggatggaa ctgatgtcat tctatggtgg agtgactaca  18720
gaagctcatt tgagtagttg ctgtgactgg tggtgtacag agcatcaggg aatgatgaag  18780
gcacttgtga tctgtcacag tcatgaggtc ttagtatgct gtagatgatg tgtaaaatgt  18840
gctcatctcg ctgtaaaagg tgtttatgga tatggacatt ggactgtctc agaactgtca  18900
tgttataaaa tactctgagt tttgttttat tcttggacca ttggaaaccg gggagtgggg  18960
tggcacaccg gcatgccaga ggcaggtagg tttgagatga gcctggatga gcagctatca  19020
aaataaccac agggaaaagg aaacaaccta tagttctgct cactccaaag ctgttgaaag  19080
aataaaaata ataacagcac tatgttggtt acagttgccc atagattatt ttataatgct  19140
gaaatttttt taattgattt attttcactt tatgtcattt gtgttttgtt tacacatgtg  19200
tctgtgtatg tgttggatta cctggaactg gagttacagg taactgtgag cctgctgtgt  19260
gggtgctggg gactgaacct gcggcctctg gaagagcagc cagtactgcc aactgttgag  19320
ccatctccag ccctccctcc ctccctccat gttgagttgt gttgtttgtt tgtttgagat  19380
agggttcctc tgtgtagcca tgggtctcct agaatttttct ctgtagacca ggctgacctc  19440
agactcaaga gacccacctg cctgtacctc ctgatggctg tgatgaaagg tgtatgtcac  19500
taagcccaac aattctgaaa ttgtgtaatg tagcccttgg catacccttt aggtgtgagt  19560
acatagataa tgtctgcccg tttttaaagt gtaaagacaa gggtagacct cagagtacag  19620
tactcgattg tcttggtagc ccgaggagac gtgacgtgct ggggtctgga tgctgagact  19680
gcgggggaag aagggtgagc attcgctgta agatgaagga cctgcttcca cattccggct  19740
tgcgctttcc tttcaggtat catcagagag tcttatatat tgacatagac atccaccatg  19800
gtgatggtgt tgaggaagct ttttatacaa cagatcgcgt gatgaccgtc tcattccata  19860
aatatgggga atactttcct ggaacaggag acttgagggt aagactgagt tctgtcagaa  19920
taaatataag aagagcatag gaggttgcta atttctggaa gagccatgtt gtcttagtca  19980
```

-continued

```
ttttgtttgt gtatttgtga tgggacctcg gcatctggtg tgtatggttt tttttgtttg  20040
tttccggaga tgtggcctca ccttagttga gcagttgttg ggatcattgc ttactgttag  20100
gatttgtcac atgtggaccc actgaatgct gcttgttgtt cagctgtgat tactttgaat  20160
atgtagaaac gagggatcag aagtggtctc aactcagtta ggtgtaagtg ctgatcctaa  20220
aaagtttgct gtcctctcca ggttgcatag gttgtcttgg gtagcagggg tggggtcaca  20280
atgggaatgg acagtgttct ataggtgtgg ggtacagatt atcacactgt cttgtggtag  20340
gttgggagag gtcaggcagt gtctttatct gagatcacag gcatagagtc ccagggtgtc  20400
ttattaggtg gtgttgaaga ctgattttgg gctccctacc tggggtgtgg ttctcaggac  20460
tccatgttgc cccagagtgg cgcagtggat gtagaagctc tgaggatccc tccctaccta  20520
tgggtctggg tcacagggct cctcactttg agaatggtgg ataagtgggc tctactttta  20580
catcttgtaa aattgtttca tgcctcaaac tgaggtttgt aagaactttt tagtttattt  20640
tgtgtggtgg ggaggagcac atgtgtgccc tgttacatgt gcaggagtcc tcctgccatg  20700
ggtggatcct ggggatcaaa ccgtggggat ctcacttgtt gggctttatc tacccaggta  20760
tttcgccagc ccaaactaca gtgcttgtgt gttatctaaa aactgcctta gagcttaaaa  20820
cgtacttcta caacctagaa tacccaagac acaatttaca aaactcatga aactcaagaa  20880
gaaggaagac caaagtgtgg acactttgtt ccttcttaga agggggaata aaatacccac  20940
ggaaagagtt tcagagacaa aattcagagc aaagactgaa ggcatggcca tccagagact  21000
gccccacctg gggatccatt ccataaacaa ccaccatacc cagacattat tacatatacc  21060
aacaagattt tgctgacagg accctgatat agctgtctcc tgtgaggcta tgccagtccc  21120
tggcaaatac agaagtggat gctcacagtc atctatagga tggaacacag ggccccccaat  21180
ggaggagcta gagaaagcac ccaaggagct gaaggggtct gcaactctat aggaggaaca  21240
acaatatgaa ctaaccagta cccccagagc tcgtgtctct agctgcatat gtagcagaag  21300
aaggcctagt cggccatcac tgggaggaga ggcccttggt cttgggaaga ttatatgccc  21360
cagtacaggg gaatgccagt gacaggaagc aggaaatggg agtgggtggg tagggaagca  21420
gagggagggg ggaggatata aggaattttt ggagaggaaa ctaggaaagg ggatagcatt  21480
tgaaatgtaa atgaagaaaa catttaattt tttcagaatt gtgtgttact tggtctttta  21540
atcattttaa aatatgtcag actttttgtt atgaaatagt cttctaagat ctacttttgt  21600
gttttaggat attggtgctg gaaagggaaa atactatgct gtcaattttc ccatgagaga  21660
tggtatagat gatgaatcat atggacaaat ttttaagcct gtaagtactg ctttcagaaa  21720
taaaatggga gttgtaaata tccttagata ctaatgtgtc ttattctgtg gctagatcat  21780
ctcaaaagtg atggagatgt accagcctag cgcggtggtg ctgcagtgtg gcgcagactc  21840
cctgtctggg gacaggcttg gttgtttcaa tctaactgtc aaaggtaagc agttcacgtt  21900
cccccctggtg tggtgtttct cctccccaag aacttcccat aaaagtttc attgctgagg  21960
gctggagaga tggttaagaa cacatgttcc ttttgtagaa gacttgggtt ggatcccagc  22020
tcctacatgt tggctcaaaa tctagcactc tcttctgatt tgcatgcatg tggtacgcac  22080
catacatgtt taaaaacata tttttaattt ctcattgtta ccttttgctt gccaactcga  22140
tgccaaactc tatatttgaa tttttagtgg atttttattt gttgttgttg tttgtttttg  22200
ttatgtggct gactagttaa tttagttccc caagtcttac atgttatcat atttatgttt  22260
atgtatttat ccatgagtag tttgttgcca tgtcagcgcc agcagttttt aatcagtttt  22320
ttcagaagac ctgtaccttg ttgtctgatt cagttgctgt tacagagtat gaggatttag  22380
cttggcgcac tttattctat catggttact ctcttcctta cccaacccta agaacttcgg  22440
tcgctgtggc tagtgctcag cagcagtggt ttttagctta gcagtcttct ctactggcaa  22500
gactcacttt tttttcttct ggattttttt gtttgcttag tttccatatt ccttattact  22560
aaactatgaa tttctaatgt attctgctca gctatctcag gtgctctgtc actgagctcc  22620
tcctgttcgg acttagtgtc ctcatgggtt taatgggaca gagagctctc tgcttctgct  22680
ttattatgtc tcctgatcag tgggcactgt atctaacttg ctggtggaac acataagtgt  22740
cttcatgagg aaagaagccc aagtgtaaat gtgtaaggtg gtgttgaaat tctcaagtcc  22800
ttacgaagag ccgaagtcca catgctgaat acaagtctca tattgctgtt atgggatgaa  22860
cttcgagggt ttcagaatga agcaaagttg catgtggcag cgcatgcttt tagactcagc  22920
attagaacag cagagatggg tccaggccag ctaaggcttt atatatagta aaaccttgtc  22980
tcataaagaa aaagataaat aaaataaatc tttttaataa agttaatgtt tggattagaa  23040
atgacttagc atgcacattg catgttttac tttagacttt ctgtgtgaac tttgaggtag  23100
taagtaacat cttgctttga gttctcttac agaactttta agataattaa atatagatgt  23160
taagaacttc tcatgattgt actctgcaga ccagcctcag cactgtggca tgctctggta  23220
ctctccttcg tatctagttg ggtcatacaa aattagttgg ccactctcct ggaggtcagc  23280
attcagttaa cagcactttc atgtgggcca tagaatgttc atagatatct cgtgtttccg  23340
agcagataag acttaaccgg aagtcatcag ccaccaggta gttcctttct ttttaggagc  23400
tatatactgt tagtgttctc ttttgtaact gaaagtttat aatgcttgta tttaaaagta  23460
gtagctttca ttataaactg catttgactc tttatagtac atctgcattg tgtttcaaca  23520
ggtagaagtt catttgtgaa tttgcaattc cattttcaga cttagaatac actgctgcga  23580
ctggcttcaa ctacattgtc tcaggcctag tgaagccaag cagccagctg ctgtccacct  23640
tgcctcctta attatttctt cttgtggtgt tcttttccgt gcttcctctt acgggttata  23700
gccttcattg tataaaaccc ctttgtagta atttttcctg ctgttgggtg gtagaatgct  23760
ggtcttgtct gggctctttc attgtactct gaagttaact tctgtcctta aaaatgtcca  23820
agagacactg ttgtagtaga agatgcctgg ttgataatgt acatgaagaa aacagagaag  23880
gcactataaa ctctcactag gtaatgagga tttttttttc ttttgtggca ttttcttttt  23940
ttccaaatat tttaagcttt gttatagaaa agttacaaaa acaaacaaca aaaataaaat  24000
cacacactga aattaaccag acccaaagat tcaatgactt ttgtgcttag agcagccagc  24060
gtctcaatac caggtgaaag cccactgcaa aaggaaatga ctttgttttt taaaaaaaaa  24120
aaaaatcttt tttttaataa ggctaaaatc catgaatctc tgctgtcatc attgagggac  24180
tttctttctt taatggttga attatgtgcc tgaatggcac cagaagttac tggaaacttg  24240
taacttgttc ctgtgtgagg cttgtaatct gttttgtttt ttttttgttt ttttttttt  24300
tttttttggt ttttcgagaa agggtttttc tgtgtagccc cggctgtcct ggaactcact  24360
ctgtagacca ggctggcctc gcactcagag atccgcctgc ctctgctggg tgctgggatt  24420
aaaggcggag gtttgtaatc ttaaataaat taagaaaatt atccacaata ccagcaataa  24480
ggatactctg tggtcaaact ttttggtatt gcttttcgaa attaagccac acatgtctgt  24540
gcgggagaaa caaaatttag catttgttta ttgtgttctc tcccttatgt gatctctcat  24600
gaacgtcttc tatggtagta aaatacatgt gtgcgtattt taacacttag tacaagttat  24660
tagttggata tacacccccc caggcccccc accctcgtca tcatcccctg tcattgttcc  24720
```

-continued

```
tccctgcccc ccccacccct accccccccc ccccaccttg tgttgaggtg cctgccttgt  24780
agtcatgctg tatagactgg cctcccaatt ctgatccacg taccttagcc tcccaagagc  24840
tgggattgct ggtatgtgcc actctgcctg gctgtctaca gacatttttt ggttgagtaa  24900
aattgtttgt atttatcctt tttaaggtcc tattttaaat tgctaaagaa tacatatttc  24960
attgttaccc aaatcttctt tgtctaaggt catgctaaat gtgtagaagt agtgaaaact  25020
tttaacttgc cattgctgat gctcggtgga ggaggctaca caatccggaa tgttgcccga  25080
tgttggacat atgagactgc agttgccctt gattgtgaaa ttcccaatgg taggtgttca  25140
ggttgcagta tctagaagaa catctgctat gtacaaatgg atgcatggga gagtctactg  25200
ccacacccct gaaatgtgtg atctcttctg atggatgagt ggttagattg caaatctgtg  25260
tgagagcatt ccatgtgcac tttcaagctt tcctttggga atagttcttt tatctggatt  25320
cggattatgt ttctgagatt atacggaagc taagctttta atgtgtaact tgttttttca  25380
ttgtttttaa tagagttgcc atataatgat tactttgagt attttggacc agacttcaaa  25440
ctgcatatta gtccttcaaa catgacaaac cagaacactc cagaatatat ggaaaagata  25500
aagtaagaaa tcacttcggc ttaatgaaac ttcaggaggc tatagaaggt caaataaagg  25560
aagttggttt agcatataca tcagatactt cctaacctta ggctattcct gtttttttaat  25620
ctcttatatt aatacaaata tgtaaccttt gtaaatagaa acattcttat tagatcaaat  25680
gctttatgtc tacagaatgt agaaacattg atcagaacgg gctgtgtcct ctctcccata  25740
gaccagttgt atgacattta taagtacacc tcattgtcaa atagaggtga aaaggtacat  25800
gtttgtgtgc tgtgggttca gtcagctaat atatgcagtg atctgatgct tagatagtgt  25860
cccattcagt ggttagtaaa tgaaagctcg ttcttgttta gttcctcctg tgtataacag  25920
aaactttaca tacagtggat tttgtctaat aaattgtgtc atttagacag cgtttatttg  25980
aaaatctacg tatgttacca catgcacctg gtgttcaaat gcaagctatt ccagaggatg  26040
ctgttcatga agacagtgga gatgaggatg gagaagaccc ggacaaaaga atttccagta  26100
agaaaaccct tgctatgtct tcttgcattt ttcttatgtg tcaaaataag acttaaaatt  26160
gaaggtacac agggaatggt tcacagcaca tgttgtgatt ttccttctct ccattttaat  26220
tacatataga tttagctccc tgatgtctca aagcctgaat taatatcacc agtttcattt  26280
tgtgtgacta cacagacatg gctgtgtcca gaaagtaggc acttgatata tctatctatc  26340
tatctgtctt acctatgcaa tgattgtaga acctgtggct attatcaaat ttataaaatc  26400
ttttgtgtat cagttcgagc atcagacaaa cggatagctt gcgatgaaga gttttcagat  26460
tctgaggatg aaggtgaagg aggtcgtagg aatgttgctg atcataagaa aggagcaaag  26520
aaggctagga ttgaagaaga caagaaggag acagaggaca agaagacagg tcggtttatg  26580
ttttggtgac catttcactt tccctactta agggttgcac tgtgtctctt agcgatcctg  26640
cagtcacacg tctcacttta ggcaggtaac ttttcctggt gtaagagata gttagttacc  26700
gctcatgctt actgtttagt gcttcagagc tgacttaaag gttttacagt tgtgctcaaa  26760
ttttctttgt ggtatagaaa ccttcctttt aataacatag tagtaaacgt tacatgtcat  26820
gggatggggt taaggggatg acagtagtta cagatgttgg gcctcagaac atttactgta  26880
gcttaggtgg acttagactc agtgctcttc tgccttgtcc tcttatatac tgggattgaa  26940
ggcatgccag tacacctggc taaaattcta aataatttat actggttaaa gctgacttca  27000
tgtagcaaaa gttaagctac atagtccttt gaaaagttac tttaagagtg aagactcttt  27060
aggaactgaa gaaactaaaa ctgaggaaag ataggaaggg gcagtttctg gtgtcttccg  27120
gtatttcatt cagagtgttt atttagcatg ccattacagc acctcgttag cactctcagg  27180
tttctcattg ctatgctgaa ctgtgcaggg gtaaggagtg ggcagtagcc tctttaaaca  27240
tgataatgct gcaagtttta gttgacctac tagtcaagtg aggctgcctg gctttactag  27300
gcctcactat atagacatgg ctgctccggc tacttactgg gtggccttgg attcacacca  27360
ttgtcctttc tcagatgcct gggtgctggg attacagaaa tgtgccacca cctccaactc  27420
agtttctttc tattttaaaa tatcttctgc attttctttt tttttccaa ataggaaagt  27480
gataaagtaa attgactctt ggtattttag acaaaatacc acaataatct atgggtcata  27540
acctcaaata agacccacca ccaccccctc ttggcactga gtaaaaattt agccagaatt  27600
atccaagaca ctaaaatgtg aaatctccat tgtcggcatg tagatttgta tgggaggtga  27660
cagcagtgcc ctgcagtgtc tgcattgccc aagcgtgctg ctgtccctgc acctctccat  27720
gaggccattg cttcataact aatttacaca gagaaaatac tctggctaat ctgggacatt  27780
tactttaatt actgtattta agttatgaag ttcagtttag tagtaattaa aaatttaagg  27840
ttagaacaat gggatattgt gggccagcaa ggtaaaggtg cttgctgcca agcctgatta  27900
catatgatct gcatgttgga ggaagactcc tgacttctac aagctgtctt ttgacctccc  27960
tatggaagtc atggtgtgga tgcccaaaca tacacacaca ctctgaataa ataaatgtta  28020
aaaacaaaaa acataatcta gcctcttgcc tttaggatca cgtccttctt acagtgcaga  28080
cacagttctc ttgagctcct tctgtcttac cactgcttcc gtgcctcagt ccttttacag  28140
ttttccctgg aagataccct ttcctcttac ctgagagttt gttcattctt tgggacccac  28200
attctagaga actgtgtctg cactgtaaga aggaagtgat cctaaaggca agaagctaaa  28260
ttattttttt gtttttaaca tttattatat atacactata tacatacata tatatattgt  28320
gtgtcttata tttcaaaata gacatcaata tttttcttct gtctttagat gttaaggaag  28380
aagacaaatc caaggacaat agtggtgaga aaacagaccc caaagggtga gcgatgcttg  28440
tgtctgtaga cgtcatgcat gtcttggggg ttgggcgggg gcatgcatac ttgagaaata  28500
ctggcacagc ctgagaacat acaatgagtg caggtctgcg tgtgggtaac gtgcttaggc  28560
tatttgaccg gtaactttta tgtatgcaat cgtgtttttc atgatgctca tattactgtg  28620
cttagaatac tttgatgtta ggagacaggc tagtttaagg aaaaaacatt gggctaagtg  28680
aaagcctatt ggagaatttt gttatcagaa tgcatgtatg gctaggtagg tgaagtgttg  28740
cggtaaatct ccaacccaaa tatgccctgg caatgaaaca caactcaatt aatatgaata  28800
catgctgtgt gcctagaatg ggcagatcta ccgctacact accatcgtca acaactgtga  28860
gagcccttag aacttgcagt ttctccaggc cacgtgcttc tgctccactt ttcttcttcc  28920
ccctcctctg catcctcacc ctcccctatt ttctcctctc tctccccacc ttcttctcca  28980
ccttcccttt atctgcccaa tcatcagctc tcctttattt tacaaattag gtgggaagca  29040
ggtttatggg aagtaaacct gagtgctgac tcattgcttg tttgtaggcc ctcactggag  29100
aaggaagtag catcaaatat aataagtaag ccccagggct atccacacct gtgaagaggc  29160
ttgagtctat aatctcagtc cactggagag gctgagccca gaggattgcc atgaatttaa  29220
atccacacta agctacatag tgatttttaa atcgtcactc tgggctgaag aatgagagtc  29280
tgtgttagaa gcaagcacgt gtgcttggtc acccagttgt ttgctaattt tgaaggataa  29340
cttagaatgc tcagttgtaa aacaactgga aagattaagg cttttattgc tcagaaaaaa  29400
aagaaaaaac aacaacaaca acaacagtga atagcttggt gtgaatctat aagactgtgc  29460
```

-continued

```
aagtagccag gtcagtgctc ctaaaccaag actattactt ttaatatttc atgatcctct  29520
ttcaacagag ccaagtcaga acaactcagc aacccttgaa tttgactctc caactttagg  29580
aacctcgaaa agtgagacga ttctgggata agaaaccttc cctgtttgag gacattggct  29640
tcattttata ctgttttggc atggactgta tttattttca aaatggcttg tttttgtttt  29700
tcttggcaag ttttattgtg agtttttcta attatgaagc aaattttttt ttccaccatg  29760
ctttatgtga ttgtatttaa attgatgtgt tattatgtca aaagccggat ctattaaaga  29820
aacaattggc ctttctgagc tgatttttcc atcttttgta attatcttta ttaaaaaatt  29880
gtacttggat cgttttctgt ctgtttatta tgaaagcttg tttccaagtc aatgacttga  29940
tggtcttaag actggaacat accaaaagga atgtcagtgt cagagaccat cactagatct  30000
acacagtgct tactggctct aacagctatt tcttacttca ggaaaaataa cagtgtcact  30060
ttgtgtcagg aagactggta tttcataaat tatttccaaa ttcataatct gtgcacttgg  30120
gatgaagcaa ttatttttga actgaatcaa atactcagaa attggaaatt gtgaattgaa  30180
aaaagaaacc tgtccaacca ataactggcc caacttaaga cccatcccat gagccagcac  30240
cagtccctga cacttaatga tactctgtta tacttgcaga ccggagccta gtgtggctgt  30300
cctctgagag gctccaccca gcagctgact aggacagatg cagataccca cagccaaaca  30360
gtggatggag cttggggact tttatggaat aggaggaagg atttcaggcc tccaaggaga  30420
taggaactct acaggaagac caactgagtc aactagcctg gacctttgtg gctctcagag  30480
actgaaccac taaccaaaga gcatacacgg gctggaccta ggtctaccca catagatgta  30540
gcagatgtgc agcttggtat ttgtgtgagt cccagacaac tggagaggag gctatgccaa  30600
aagcagttgc ctgtctggat cttccagctt ggctaccttg tctggcctca atgggaaagg  30660
atgtgcctag cctcagactt gatgtgtcag ggcatgtata caaaagattg taggcggtag  30720
aaacataccc ttttgtgatg tcagtgtaaa atgaaccagc tagcaaaacc tggttcttgc  30780
cctgtagttt gatcacaacc agggtttcta ctcaagaagt aaaacttaat atgctttggc  30840
attccgcatt cattgagtgt ctactcacct tttggtaata actgcagctg aatagaattt  30900
taagtgcttt cacctaaact tagattgtta ttgtagaaag cccacaaatg gagtttcctc  30960
tcccagtgtg tacaacagaa aaatgtttta ggaatttgcc aaagttggtg aaaccatcct  31020
acttgctaga atcaggttgc tgattttgag attaggagaa cagagtggta gaaaggaggc  31080
agtcgtggag aatgttctta cattgtcctg aggttcgaag gtttcatgtt catgggtttt  31140
ccccttttgc tatgtatttg ccaggagtcc atatccttta tgactaagga agcaggatcc  31200
cttcgctgca gagacttatt tagtgtgtaa ttttcatgaa acaaagtgta tcctttggat  31260
acttcatctg gtattgtgat ctgccttctg gcacatgtcg cataataatt acagtgtgtt  31320
aagttctggt ctatgaatct actagaatga tgtcccagat gccacagtga ttctccttgg  31380
ttggatctgg gaggttctgg tttcatagtt taaggctgtg aaactaagca gtttcagaac  31440
aggtgatttg ggacggtaaa aatacacaga taccagtaat ttgtaaagtc aaactacagc  31500
ccacattgtt tggaagaaca aaggctcctt ttgcatagca gtaatcacaa tttctacaaa  31560
tgtgtaaaac tgattctatg cataatgaat aagatgagtg ttaataatag cctgtcggga  31620
caagggttga aaatcaaaac aatgaggaaa taacaagaac caggtggagg gaggcgaagt  31680
tcatttttct gtcacaagag tgagatttat aaatagaaaa gacaacaaaa cagaacctgg  31740
taaaagccat gggaattttt caaaagtgaa ggccaaagct tgacaccgaa ccccacataa  31800
gttacatact taacagaagt tctctagacc agcaaaaaca agtaaaataa gatagggaac  31860
cccggcagtg gtggcgcact cctttaatcc cagcacttgg gaggcagagg caggtggatt  31920
cctgagtcta cagagtgagt tccaggacag cctggactgc acagagaaac cctgtctcgg  31980
aaaacccaaa aaaaaaaaaa aaaaaaaaag atatgggaac cataatggac ttgttccacc  32040
tcaaagaact ttatttcttt attttaaaaa taaagggtct ttgtttttgg ccaggggtag  32100
agagaaaatt cagtggttag gagtatttgc tgctcttaca cagggtccag gtttgattcc  32160
aaccacatgc tcacagccat ctgaggatct gacacccctt tctttgagta ccaggtatac  32220
atgtataaaa cacccataca tgttaactaa aaatagctta aaatttgac aagagttcaa  32280
tgaaacccat gaatgtagta tcttgttagg aagacacaat gtccaaggta attcttataa  32340
aggaaaacat ttaattgagg ctggctttcc atcgcatagg ttcagtccat tatcgtgatg  32400
ggaagcatgg cttgcagata gacatggtct tgatcagcag ggaacaggag gagactgttc  32460
cacactcggc cgaacttgag cataggagac ctcaaagcct gcccccacag tgacacactt  32520
cctctaacaa agccatacct acaacaagac cactaatagt gccactacct atgggccaaa  32580
catttaaaca catgtctagg ggtgggggtt agtacctatt caaaccacta cattccacct  32640
tctgggcccc atagtcttgt acctttacca taatgcaaaa tgaatttaat ttcaaaagtc  32700
cacatagttt agcacagttt cagcagtgtt taagtccaaa gtctcttctg agattcatgc  32760
actctttttt attagatatt ttcttcattt acatttcaaa tgctattctg aaagtaccca  32820
ataccctccc cccccaactc cccccccccc ccgccctgct ccccaaccca ctcacttctg  32880
cttcctggcc ctggcattac cctgtactgg ggcatataat ctttgtaaga ccaagggcct  32940
ctcctcccaa ttatggccga ctaggccatc ctctgctaca cattcatgta ctctcttaac  33000

SEQ ID NO: 13          moltype = DNA  length = 16
FEATURE                Location/Qualifiers
source                 1..16
                       mol_type = other DNA
                       organism = synthetic construct
SEQUENCE: 13
tagtctctgt cagtta                                                  16

SEQ ID NO: 14          moltype = DNA  length = 16
FEATURE                Location/Qualifiers
source                 1..16
                       mol_type = other DNA
                       organism = synthetic construct
SEQUENCE: 14
tcatgtacct atagtc                                                  16

SEQ ID NO: 15          moltype = DNA  length = 23
FEATURE                Location/Qualifiers
source                 1..23
```

```
                         mol_type = other DNA
                         organism = synthetic construct
SEQUENCE: 15
tgatggtgtt gaggaagctt ttt                                          23

SEQ ID NO: 16            moltype = DNA  length = 21
FEATURE                  Location/Qualifiers
source                   1..21
                         mol_type = other DNA
                         organism = synthetic construct
SEQUENCE: 16
tccctcaagt ctcctgttcc a                                            21

SEQ ID NO: 17            moltype = DNA  length = 26
FEATURE                  Location/Qualifiers
source                   1..26
                         mol_type = other DNA
                         organism = synthetic construct
SEQUENCE: 17
acaacagatc gcgtgatgac cgtctc                                       26

SEQ ID NO: 18            moltype = DNA  length = 16
FEATURE                  Location/Qualifiers
source                   1..16
                         mol_type = other DNA
                         organism = synthetic construct
SEQUENCE: 18
tgcagtgggg tgattt                                                  16

SEQ ID NO: 19            moltype = RNA  length = 5292
FEATURE                  Location/Qualifiers
source                   1..5292
                         mol_type = mRNA
                         organism = Homo sapiens
SEQUENCE: 19
ctcttgcagt gaggtgaaga catttgaaaa tcaccccact gcaaactcct cccccctgcta 60
gaaacctcac attgaaatgc tgtaaatgac gtgggccccg agtgcaatcg cgggaagcca  120
gggtttccag ctaggacaca gcaggtcgtg atccgggtcg ggacactgcc tggcagaggc  180
tgcgagcatg gggccctggg gctggaaatt gcgctggacc gtcgccttgc tcctcgccgc  240
ggcggggact gcagtgggcg acagatgcga aagaaacgag ttccagtgcc aagacgggaa  300
atgcatctcc tacaagtggg tctgcgatgg cagcgctgag tgccaggatg gctctgatga  360
gtcccaggag acgtgcttgt ctgtcacctg caaatccggg gacttcagct gtgggggccg  420
tgtcaaccgc tgcattcctc agttctggag gtgcgatggc caagtggact gcgacaacgg  480
ctcagacgag caaggctgtc cccccaagac gtgctcccag gacgagtttc gctgccacga  540
tgggaagtgc atctctcggc agttcgtctg tgactcagac cgggactgct tggacggctc  600
agacgaggcc tcctgcccgg tgctcacctg tggtcccgcc agcttccagt gcaacagctc  660
cacctgcatc ccccagctgt gggcctgcga caacgacccc gactgcgaag atggctcgga  720
tgagtggccg cagcgctgta ggggtcttta cgtgttccaa ggggacagta gcccctgctc  780
ggccttcgag ttccactgcc taagtggcga gtgcatccac tccagctggc gctgtgatgg  840
tggccccgac tgcaaggaca aatctgacga ggaaaactgc gctgtggcca cctgtcgccc  900
tgacgaattc cagtgctctg atggaaactg catccatggc agccggcagt gtgaccggga  960
atatgactgc aaggacatga gcgatgaagt tggctgcgtt aatgtgacac tctgcgaggg  1020
acccaacaag ttcaagtgtc acagcggcga atgcatcacc ctggacaaag tctgcaacat  1080
ggctagagac tgccgggact ggtcagatga acccatcaaa gagtgcggga ccaacgaatg  1140
cttggacaac aacggcggct gttcccacgt ctgcaatgac cttaagatcg gctacgagtg  1200
cctgtgcccc gacggcttcc agctggtggc ccagcgaaga tgcgaagata tcgatgagtg  1260
tcaggatccc gacacctgca gccagctctg cgtgaacctg gagggtggct acaagtgcca  1320
gtgtgaggaa ggcttccagc tggaccccca cacgaaggcc tgcaaggctg tgggctccat  1380
cgcctacctc ttcttcacca accggcacga ggtcaggaag atgacgctgg accggagcga  1440
gtacaccagc ctcatcccca acctgaggaa cgtggtcgct ctggacacgg aggtggccag  1500
caatagaatc tactggtctg acctgtccca gagaatgatc tgcagcaccc agcttgacag  1560
agcccacggc gtctcttcct atgacaccgt catcagcaga gacatccagg cccccgacgg  1620
gctggctgtg gactggatcc acagcaacat ctactggacc gactctgtcc tgggcactgt  1680
ctctgttgcg gataccaagg gcgtgaagag gaaaacgtta ttcagggaga acggctccaa  1740
gccaagggcc atcgtggtgg atcctgttca tggcttcatg tactggactg actggggaac  1800
tcccgccaag atcaagaaag gggcctgaa tggtgtggac atctactcgc tggtgactga   1860
aaacattcag tggcccaatg gcatcaccct agatctcctc agtggccgcc tctactgggt  1920
tgactccaaa cttcactcca tctcaagcat cgatgtcaac gggggcaacc ggaagaccat  1980
cttggaggat gaaaagaggc tggcccaccc cttctccttg gccgtctttg aggacaaagt  2040
attttggaca gatatcatca acgaagccat tttcagtgcc aaccgcctca caggttccga  2100
tgtcaacttg ttggctgaaa acctactgtc cccagaggat atggttctct tccacaacct  2160
cacccagcca agaggagtga actggtgtga gaggaccacc ctgagcaatg gcggctgcca  2220
gtatctgtgc ctccctgccc cgcagatcaa cccccactcg cccaagttta cctgcgcctg  2280
cccggacggc atgctgctgg ccagggacat gaggagctgc ctcacagagg ctgaggctgc  2340
agtggccacc caggagacat ccaccgtcag gctaaaggtc agctccacag ccgtaaggac  2400
acagcacaca accacccgac ctgttcccga cacctcccgg ctgcctgggg ccacccctgg  2460
gctcaccacg gtggagatag tgacaatgtc tcaccaagct ctgggcgacg ttgctggcag  2520
aggaaatgag aagaagccca gtagcgtgag ggctctgtcc attgtcctcc ccatcgtgct  2580
cctcgtcttc ctttgcctgg gggtcttcct tctatggaag aactggcggc ttaagaacat  2640
```

```
caacagcatc aactttgaca accccgtcta tcagaagacc acagaggatg aggtccacat  2700
ttgccacaac caggacggct acagctaccc ctcgagacag atggtcagtc tggaggatga  2760
cgtggcgtga acatctgcct ggagtcccgt ccctgcccag aacccttcct gagacctcgc  2820
cggccttgtt ttattcaaag acagagaaga ccaaagcatt gcctgccaga gctttgtttt  2880
atatatttat tcatctggga ggcagaacag gcttcggaca gtgcccatgc aatggcttgg  2940
gttgggattt tggtttcttc ctttcctcgt gaaggataag agaaacaggc ccgggggggac  3000
caggatgaca cctccatttc tctccaggaa gttttgagtt tctctccacc gtgacacaat  3060
cctcaaacat ggaagatgaa aggggagggg atgtcaggcc cagagaagca agtggctttc  3120
aacacacaac agcagatggc accaacggga ccccctggcc ctgcctcatc caccaatctc  3180
taagccaaac ccctaaactc aggagtcaac gtgtttacct cttctatgca agccttgcta  3240
gacagccagg ttagcctttg ccctgtcacc cccgaatcat gacccaccca gtgtctttcg  3300
aggtgggttt gtaccttcct taagccagga aagggattca tggcgtcgga aatgatctgg  3360
ctgaatccgt ggtggcaccg agaccaaact cattcaccaa atgatgccac ttcccagagg  3420
cagagcctga gtcactggtc acccttaata tttattaagt gcctgagaca cccggttacc  3480
ttggccgtga ggacacgtgg cctgcaccca ggtgtggctg tcaggacacc agcctggtgc  3540
ccatcctccc gacccctacc cacttccatt cccgtggtct ccttgcactt tctcagttca  3600
gagttgtaca ctgtgtacat ttggcatttg tgttattatt ttgcactgtt ttctgtcgtg  3660
tgtgttggga tgggatccca ggccagggaa agcccgtgtc aatgaatgcc ggggacagag  3720
aggggcaggt tgaccgggac ttcaaagccg tgatcgtgaa tatcgagaac tgccattgtc  3780
gtctttatgt ccgcccacct agtgcttcca cttctatgca aatgcctcca agccattcac  3840
ttccccaatc ttgtcgttga tgggtatgtg tttaaaacat gcacggtgag gccgggcgca  3900
gtggctcacg cctgtaatcc cagcactttg ggaggccgag gcgggtggat catgaggtca  3960
ggagatcgag accatcctgg ctaacacgtg aaaccccgtc tctactaaaa atacaaaaaa  4020
ttagccgggc gtggtggcgg gcacctgtag tcccagctac tcgggaggct gaggcaggag  4080
aatggtgtga acccgggaag cggagcttgc agtgagccga gattgcgcca ctgcagtccg  4140
cagtctggcc tgggcgacag agcgagactc cgtctcaaaa aaaaaaaaca aaaaaaaacc  4200
atgcatggtg catcagcagc ccatggcctc tggccaggca tggcgaggct gaggtgggag  4260
gatggtttga gctcaggcat ttgaggctgt cgtgagctat gattatgcca ctgctttcca  4320
gcctgggcaa catagtaaga ccccatctct taaaaaatga atttggccag acacaggtgc  4380
ctcacgcctg taatcccagc actttgggag gctgagctgg atcacttgag ttcaggagtt  4440
ggagaccagg cctgagcaac aaagcgagat cccatctcta caaaaaccaa aaagttaaaa  4500
atcagctggg tacggtggca cgtgcctgtg atcccagcta cttgggaggc tgaggcagga  4560
ggatcgcctg agcccaggag gtggaggttg cagtgagcca tgatcgagcc actgcactcc  4620
agcctgggca acagatgaag accctatttc agaaatacaa ctataaaaaa ataaataaat  4680
cctccagtct ggatcgtttg acgggacttc aggttctttc tgaaatcgcc gtgttactgt  4740
tgcactgatg tccggagaga cagtgacagc ctccgtcaga ctcccgcgtg aagatgtcac  4800
aagggattgg caattgtccc cagggacaaa acactgtgtc ccccccagtg cagggaaccg  4860
tgataagcct ttctggtttc ggagcacgta aatgcgtccc tgtacagata gtggggattt  4920
tttgttatgt ttgcactttg tatattggtt gaaactgtta tcacttatat atatatatat  4980
acacacatat atataaaatc tatttatttt tgcaaaccct ggttgctgta tttgttcagt  5040
gactattctc ggggccctgt gtaggggggt attgcctctg aaatgcctct tctttatgta  5100
caaagattat ttgcacgaac tggactgtgt gcaacgcttt ttgggagaat gatgtccccg  5160
ttgtatgtat gagtggcttc tgggagatgg gtgtcacttt ttaaaccact gtatagaagg  5220
tttttgtagc ctgaatgtct tactgtgatc aattaaattt cttaaatgaa ccaatttgtc  5280
taaaaaaaaa aa                                                      5292
```

```
SEQ ID NO: 20          moltype = RNA  length = 16
FEATURE                Location/Qualifiers
source                 1..16
                       mol_type = other RNA
                       organism = synthetic construct
SEQUENCE: 20
tgcagtgggg tgattt                                                  16

SEQ ID NO: 21          moltype = RNA  length = 23
FEATURE                Location/Qualifiers
source                 1..23
                       mol_type = other RNA
                       organism = synthetic construct
SEQUENCE: 21
ataaaatcta cagtcatagg aat                                          23

SEQ ID NO: 22          moltype = RNA  length = 1435
FEATURE                Location/Qualifiers
source                 1..1435
                       mol_type = mRNA
                       organism = Homo sapiens
SEQUENCE: 22
ggcggggcct gcttctcctc agcttcaggc ggctgcgacg agccctcagg cgaacctctc  60
ggctttcccg cgcggcgccg cctcttgctg cgcctccgcc tcctcctctg ctccgccacc  120
ggcttcctcc tcctgagcag tcagcccgcg cgccggccgg ctccgttatg gcgacccgca  180
gccctggcgt cgtgattagt gatgatgaac caggttatga ccttgattta ttttgcatac  240
ctaatcatta tgctgaggat ttggaaaggg tgtttattcc tcatggacta attatggaca  300
ggactgaacg tcttgctcga gatgtgatga aggagatggg aggccatcac attgtagccc  360
tctgtgtgct caagggggc tataaattct ttgctgacct gctggattac atcaaagcac  420
tgaatagaaa tagtgataga tccattccta tgactgtaga ttttatcaga ctgaagagct  480
attgtaatga ccagtcaaca ggggacataa aagtaattgg tggagatgat ctctcaactt  540
taactggaaa gaatgtcttg attgtggaag atataattga cactggcaaa acaatgcaga  600
ctttgctttc cttggtcagg cagtataatc caaagatggt caaggtcgca agcttgctgg  660
```

```
tgaaaaggac cccacgaagt gttggatata agccagactt tgttggattt gaaattccag  720
acaagtttgt tgtaggatat gcccttgact ataatgaata cttcagggat ttgaatcatg  780
tttgtgtcat tagtgaaact ggaaaagcaa aatacaaagc ctaagatgag agttcaagtt  840
gagtttggaa acatctggag tcctattgac atcgccagta aaattatcaa tgttctagtt  900
ctgtggccat ctgcttagta gagctttttg catgtatctt ctaagaattt tatctgtttt  960
gtactttaga aatgtcagtt gctgcattcc taaactgttt atttgcacta tgagcctata  1020
gactatcagt tccctttggg cggattgttg tttaacttgt aaatgaaaaa attctcttaa  1080
accacagcac tattgagtga aacattgaac tcatatctgt aagaaaataa gagaagatat  1140
attagttttt taattggtat tttaattttt atatatgcag gaaagaatag aagtgattga  1200
atattgttaa ttataccacc gtgtgttaga aaagtaagaa gcagtcaatt ttcacatcaa  1260
agacagcatc taagaagttt tgttctgtcc tggaattatt ttagtagtgt ttcagtaatg  1320
ttgactgtat tttccaactt gttcaaatta ttaccagtga atctttgtca gcagttccct  1380
tttaaatgca aatcaataaa ttcccaaaaa tttaaaaaaa aaaaaaaaaa aaaaa       1435

SEQ ID NO: 23          moltype = RNA  length = 21
FEATURE                Location/Qualifiers
source                 1..21
                       mol_type = other RNA
                       organism = synthetic construct
SEQUENCE: 23
tcctatgact gtagatttta t                                            21

SEQ ID NO: 24          moltype = RNA  length = 21
FEATURE                Location/Qualifiers
source                 1..21
                       mol_type = other RNA
                       organism = synthetic construct
modified_base          1
                       mod_base = OTHER
                       note = thymine
SEQUENCE: 24
ttatctataa tgatcaggta a                                            21

SEQ ID NO: 25          moltype = RNA  length = 19
FEATURE                Location/Qualifiers
source                 1..19
                       mol_type = other RNA
                       organism = synthetic construct
SEQUENCE: 25
acctgatcat tatagataa                                               19

SEQ ID NO: 26          moltype = RNA  length = 8515
FEATURE                Location/Qualifiers
source                 1..8515
                       mol_type = mRNA
                       organism = Homo sapiens
SEQUENCE: 26
gttctctcct ctcggaagct gcagccatga tggaagtttg agagttgagc cgctgtgagg  60
cgaggccggg ctcaggcgag ggagatgaga gacggcggcg gccgcggccc ggagcccctc  120
tcagcgcctg tgagcagccg cgggggcagc gccctcgggg agccggccgg cctgcggcgg  180
cggcagcggc ggcgtttctc gcctcctctt cgtcttttct aaccgtgcag cctcttcctc  240
ggcttctcct gaaagggaag gtggaagccg tgggctcggg cgggagccgg ctgaggcgcg  300
gcggcggcgg cggcacctcc cgctcctgga gcggggggga gaagcggcgg cggcggcggc  360
cgcggcggct gcagctccag ggagggggtc tgagtcgcct gtcaccattt ccagggctgg  420
gaacgccgga gagttggtct ctccccttct actgcctcca acacggcggc ggcggcggct  480
ggcacatcca gggacccggg ccggttttaa acctcccgtg cgccgccgcc gcacccccccg  540
tggcccgggc tccggaggcc gccggcggag gcagccgttc ggaggattat tcgtcttctc  600
cccattccgc tgccgccgct gccaggcctc tggctgctga ggagaagcag gcccagtcgc  660
tgcaaccatc cagcagccgc cgcagcagcc attacccggc tgcggtccag agccaagcgg  720
cggcagagcg aggggcatca gctaccgcca agtccagagc catttccatc ctgcagaaga  780
agccccgcca ccagcagctt ctgccatctc tctcctcctt tttcttcagc cacaggctcc  840
cagacatgac agccatcatc aaagagatcg ttagcagaaa caaaaggaga tatcaagagg  900
atggattcga cttagacttg acctatattt atccaaacat tattgctatg ggatttcctg  960
cagaaagact tgaaggcgta tacaggaaca atattgatga tgtagtaagg tttttggatt  1020
caaagcataa aaaccattac aagatataca atctttgtgc tgaaagacat tatgacaccg  1080
ccaaatttaa ttgcagagtt gcacaatatc cttttgaaga ccataaccca ccacagctag  1140
aacttatcaa acccttttgt gaagatcttg accaatggct aagtgaagat gacaatcatg  1200
ttgcagcaat tcactgtaaa gctggaaagg gacgaactgg tgtaatgata tgtgcatatt  1260
tattacatcg gggcaaattt ttaaaggcac aagaggccct agatttctat ggggaagtaa  1320
ggaccagaga caaaaaggga gtaactattc ccagtcagag gcgctatgtg tattattata  1380
gctacctgtt aaagaatcat ctggattata gaccagtggc actgttgttt cacaagatga  1440
tgtttgaaac tattccaatg ttcagtggcg gaacttgcaa tcctcagttt gtggtctgcc  1500
agctaaaggt gaagatatat tcctccaatt caggacccac acgacgggaa gacaagttca  1560
tgtactttga gttccctcag ccgttacctg tgtgtggtga tatcaaagta gagttcttcc  1620
acaaacagaa caagatgcta aaaaaggaca aaatgtttca cttttgggta aatacattct  1680
tcataccagg accagaggaa acctcagaaa aagtagaaaa tggaagtcta tgtgatcaag  1740
aaatcgatag catttgcagt atagagcgtg cagataatga caaggaatat ctagtactta  1800
ctttaacaaa aaatgatctt gacaaagcaa ataaagacaa agccaaccga tacttttctc  1860
caaattttaa ggtgaagctg tacttcacaa aaacagtaga ggagccgtca aatccagagg  1920
```

-continued

```
ctagcagttc aacttctgta acaccagatg ttagtgacaa tgaacctgat cattatagat  1980
attctgacac cactgactct gatccagaga atgaaccttt tgatgaagat cagcatacac  2040
aaattacaaa agtctgaatt tttttttatc aagagggata aaacaccatg aaaataaact  2100
tgaataaact gaaaatggac cttttttttt ttaatggcaa taggacattg tgtcagatta  2160
ccagttatag gaacaattct cttttcctga ccaatcttgt tttaccctat acatccacag  2220
ggttttgaca cttgttgtcc agttgaaaaa aggttgtgta gctgtgtcat gtatatacct  2280
ttttgtgtca aaaggacatt taaaattcaa ttaggattaa taaagatggc actttcccgt  2340
tttattccag ttttataaaa agtggagaca gactgatgtg tatacgtagg aatttttttcc  2400
ttttgtgttc tgtcaccaac tgaagtggct aaagagcttt gtgatatact ggttcacatc  2460
ctaccccttt gcacttgtgg caacagataa gtttgcagtt ggctaagaga ggtttccgaa  2520
gggttttgct acattctaat gcatgtattc gggttagggg aatggaggga atgctcagaa  2580
aggaaataat tttatgctgg actctggacc atataccatc tccagctatt tacacacacc  2640
tttctttagc atgctacagt tattaatctg gacattcgag gaattggccg ctgtcactgc  2700
ttgttgtttg cgcatttttt tttaaagcat attggtgcta gaaaaggcag ctaaaggaag  2760
tgaatctgta ttggggtaca ggaatgaacc ttctgcaaca tcttaagatc cacaaatgaa  2820
gggatataaa aataatgtca taggtaagaa acacagcaac aatgacttaa ccatataaat  2880
gtggaggcta tcaacaaaga atgggcttga aacattataa aaattgacaa tgatttatta  2940
aatatgtttt ctcaattgta acgacttctc catctcctgt gtaatcaagg ccagtgctaa  3000
aattcagatg ctgttagtac ctacatcagt caacaactta cacttatttt actagttttc  3060
aatcataata cctgctgtgg atgcttcatg tgctgcctgc aagcttcttt tttctcatta  3120
aatataaaat attttgtaat gctgcacaga aattttcaat ttgagattct acagtaagcg  3180
tttttttttct ttgaagattt atgatgcact tattcaatag ctgtcagccg ttccaccctt  3240
ttgaccttac acattctatt acaatgaatt ttgcagtttt gcacattttt taaatgtcat  3300
taactgttag ggaattttac ttgaatactg aatacatata atgtttatat taaaaaggac  3360
atttgtgtta aaaaggaaat tagagttgca gtaaactttc aatgctgcac acaaaaaaaa  3420
gacatttgat ttttcagtag aaattgtcct acatgtgctt tattgatttg ctattgaaag  3480
aatagggttt tttttttttt tttttttttt ttttttaaat gtgcagtgtt gaatcatttc  3540
ttcatagtgc tcccccgagt tggactaggg gcttcaattt cacttcttaa aaaaaatcat  3600
catatatttg atatgcccag actgcatacg attttaagcg gagtacaact actattgtaa  3660
agctaatgtg aagatattat taaaaaggtt ttttttttcca gaaatttggt gtcttcaaat  3720
tataccttca ccttgacatt tgaatatcca gccattttgt ttcttaatgg tataaaattc  3780
cattttcaat aacttattgg tgctgaaatt gttcactagc tgtggtctga cctagttaat  3840
ttacaaatac agattgaata ggacctacta gagcagcatt tatagagttt gatggcaaat  3900
agattaggca gaacttcatc taaaatattc ttagtaaata atgttgacac gttttccata  3960
ccttgtcagt ttcattcaac aatttttaaa tttttaacaa agctcttagg atttacacat  4020
ttatatttaa acattgatat atagagtatt gattgattgc tcataagtta aattggtaaa  4080
gttagagaca actattctaa cacctcacca ttgaaattta tatgccacct tgtctttcat  4140
aaaagctgaa aattgttacc taaaatgaaa atcaacttca tgttttgaag atagttataa  4200
atattgttct ttgttacaat ttcgggcacc gcatattaaa acgtaacttt attgttccaa  4260
tatgtaacat ggagggccag gtcataaata atgacattat aatgggcttt tgcactgtta  4320
ttatttttcc tttggaatgt gaaggtctga atgagggttt tgattttgaa tgtttcaatg  4380
tttttgagaa gccttgctta cattttatgg tgtagtcatt ggaaatggaa aaatggcatt  4440
atatatatta tatatataaa tatatattat acatactctc cttactttat ttcagttacc  4500
atccccatag aatttgacaa gaattgctat gactgaaagg ttttcgagtc ctaattaaaa  4560
ctttatttat ggcagtattc ataattagcc tgaaatgcat tctgtaggta atctctgagt  4620
ttctggaata ttttcttaga ctttttggat gtgcagcagc ttacatgtct gaagttactt  4680
gaaggcatca cttttaagaa agcttacagt tgggccctgt accatcccaa gtcctttgta  4740
gctcctcttg aacatgtttg ccatactttt aaaagggtag ttgaataaat agcatcacca  4800
ttctttgctg tggcacaggt tataaactta agtggagttt accggcagca tcaaatgttt  4860
cagctttaaa aaataaaagt agggtacaag tttaatgttt agttctagaa attttgtgca  4920
atatgttcat aacgatggct gtggttgcca caaagtgcct cgtttacctt taaatactgt  4980
taatgtgtca tgcatgcaga tggaaggggt ggaactgtgc actaaagtgg gggctttaac  5040
tgtagtattt ggcagagttg ccttctacct gccagttcaa aagttcaacc tgttttcata  5100
tagaatatat atactaaaaa atttcagtct gttaaacagc cttactctga ttcagcctct  5160
tcagatactc ttgtgctgtg cagcagtggc tctgtgtgta aatgctatgc actgaggata  5220
cacaaaaata ccaatatgat gtgtacagga taatgcctca tcccaatcag atgtccattt  5280
gttattgtgt ttgttaacaa ccctttatct cttagtgtta taaactccac ttaaaactga  5340
ttaaagtctc attcttgtca ttgtgtgggt gttttattaa atgagagttt ataattcaaa  5400
ttgcttaagt ccattgaagt tttaattaat gggcagccaa atgtgaatac aaagttttca  5460
gttttttttt ttcctgctgt ccttcaaagc ctactgttta aaaaaaaaaa aaaaaaaaaa  5520
catggcctga gagtagagta tctgtctact catgtttaat taaggaaaaa cacttatttt  5580
tagggcttta gtcatcactt cataaattgt ataagcacat taaatagcgt tctagtcctg  5640
aaaaagtcca agattcttag aaaattgtgc atatttttat tatgacagat gtttgaagat  5700
aattccccag aatggatttg atactttaga tttcaatttt gtggcttttg tctattattc  5760
tgtactctgc catcagcata tggaaagctt catttactca tcatgacttg tgccatataa  5820
aaattgatat ttcggaatag tctaaaggac tttttgtact tgaatttaat catgttgttt  5880
ctaatattct taaaagcttg aagactaaag catatccttt caacaaagca tagtaaggta  5940
ataagaaagt gtagtttgta caagtgttaa aaaaataaag tagacaatgt tacagtggga  6000
cttattattt caagtttaca ttttctccat gtaatttttt aaaaagtaaa tgaaaaaatg  6060
tgcaataatg taaaatatga agtgtatgtg tacacacatt ttatttttcg gtatcttggg  6120
tatacgtatg gttgaaaact atactggagt ctaaaagtat tctaatttat aagaagacat  6180
tttggtgatg tttgaaaaat agaaatgtgc tagttttgtt tttatatcat gtcctttgta  6240
cgttgtaata tgagctggct tggttcagta aatgccatca ccatttccat tgagaattta  6300
aaactcacca gtgtttaata tgcaggcttc caaaggctta tgaaaaaaat caagaccctt  6360
aaatctagtt aatttgctgc taacatgaaa ctctttggtt cttttatttt tgccagataa  6420
ttagacacac atctaaagct tagtcttaaa tggcttaagt gtagctattg attagtgctg  6480
ttgctagttc agaaagaaat gtttgtgaat ggaaacaaga atattcagtc caaactgttg  6540
taaggacagt acctgaaaac caggaaacag gataatggaa aaagtctttt aaagatgaaa  6600
tgttggagcc aactttctta tagaattaat tgtatgtggc tatagaaagc ctaatgattg  6660
```

-continued

```
ttgcttattt ttgagagcat attattcttt tatgaccata atcttgctgt ttttccatct  6720
tccaaaagat cttccttcta atatgtatat cagaatgtgg gtagccagtc agacaaattc  6780
atattggttg gtagctttaa aaagtttgta atgtgaagac aggaaaggac aaaatagttt  6840
gctttggtgg tagtactctg gttgttaagc taggtatttt gagactactt ccccatcaca  6900
acaacaataa aataatcact cataatccta tcacctggag acatagccat cgttaatatg  6960
ttagtgacta tacaatcatg ttttcttctg tatatccatg tatattcttt aaaaatgaaa  7020
tttatactgt acctgatctc aaagcttttt agcttagtat atctgtcatg aatttgtagg  7080
atgttccatt gcatcagaaa acggacagtg atttgattac tttctaatgc cacagatgca  7140
gattacatgt agttattgag aatcctttcg aattcagtgg cttaatcatg aatgtctaaa  7200
tattgttgac attaggatga tacatgtaaa ttaaagttac atttgtttag catagacaag  7260
cttaacattg tagatgtttc tcttcaaaaa tcatcttaaa catttgcatt tggaattgtg  7320
ttaaatagaa tgtgtgaaac actgtattag taaacttcat cacctttcta cttccttata  7380
gtttgaactt ttcagttttt gtagttccca aacagttgct caatttagag caaattaatt  7440
taacacctgc caaaaaaagg ctgctgttgg cttatcagtt gtctttaaat tcaaatgctc  7500
atgtgacttt tatcacatca aaaaatattt cattaatgat tcacctttag ctctgaaaat  7560
taccgcgttt agtaattata gtgggcttat aaaaacatgc aactcttttt gatagttatt  7620
tgagaatttt ggtgaaaaat atttagctga gggcagtata gaacttataa accaatatat  7680
tgatattttt aaaacatttt tacatataag taaactgcca tctttgagca taactacatt  7740
taaaaataaa gctgcatatt tttaaatcaa gtgtttaaca agaatttata tttttttattt  7800
tttaaaatta aaaataattt atatttcctc tgttgcatga ggattctcat ctgtgcttat  7860
aatggttaga gattttattt gtgtggaatg aagtgaggct tgtagtcatg gttctagtgt  7920
ttcagtttgc caagtctgtt tactgcagtg aaattcatca aatgtttcag tgtggttttc  7980
tgtagcctat catttactgg ctattttttt atgtacacct ttaggatttt ctgcctactc  8040
tatccagttg tccaaatgat atcctacatt ttacaaatgc cctttcagtt tctattttct  8100
ttttccatta aattgccctc atgtcctaat gtgcagtttg taagtgtgtg tgtgtgtgtc  8160
tgtgtgtgtg tgaatttgat tttcaagagt gctagacttc caatttgaga gattaaataa  8220
tttaattcag gcaaacattt ttcattggaa tttcacagtt cattgtaatg aaaatgttaa  8280
tcctggatga cctttgacat acagtaatga atcttggata ttaatgaatt tgttagtagc  8340
atcttgatgt gtgttttaat gagttatttt caaagttgtg cattaaacca aagttggcat  8400
actggaagtg tttatatcaa gttccatttg gctactgatg gacaaaaaat agaaatgcct  8460
tcctatggag agtatttttc ctttaaaaaa ttaaaaaggt taattatttt gacta       8515

SEQ ID NO: 27           moltype = DNA  length = 20
FEATURE                 Location/Qualifiers
source                  1..20
                        mol_type = other DNA
                        organism = synthetic construct
SEQUENCE: 27
tgcatggtgt agcccccctg                                             20

SEQ ID NO: 28           moltype = DNA  length = 20
FEATURE                 Location/Qualifiers
source                  1..20
                        mol_type = other DNA
                        organism = synthetic construct
SEQUENCE: 28
gttttcaaac acaccttcat                                             20

SEQ ID NO: 29           moltype =   length =
SEQUENCE: 29
000

SEQ ID NO: 30           moltype = RNA  length = 21
FEATURE                 Location/Qualifiers
source                  1..21
                        mol_type = other RNA
                        organism = synthetic construct
SEQUENCE: 30
cattttaatc ctcactctaa a                                           21

SEQ ID NO: 31           moltype = RNA  length = 23
FEATURE                 Location/Qualifiers
source                  1..23
                        mol_type = other RNA
                        organism = synthetic construct
SEQUENCE: 31
tttagagtga ggattaaaat gaa                                         23

SEQ ID NO: 32           moltype = DNA  length = 141001
FEATURE                 Location/Qualifiers
source                  1..141001
                        mol_type = genomic DNA
                        organism = Homo sapiens
SEQUENCE: 32
aatttataaa ggaaaaaggt ttaattgact cacagttcag catgtctggg gaagtgttag  60
gaaacttaca atcatggcag aagagaaagc aaaccatcct ttctcacatg gtgacaggaa  120
gagcaaagcg gggtaagccc cttacaaaac caccagatct catgagaact cactatcacg  180
agaacaccat ggaggtaact gcccccatga ttcaattacc tcccaccagg tccctcccac  240
gacatgtggg gattatgcga actccaactc aagatgagat ttgggtgggg acacagccaa  300
```

-continued

```
accatatcag aagcttaacc ttctttggag catgattatt cagttgaacc taagttcagt  360
agtcacccag ttatgctgtc ttcagctact attttccata tgtttctcaa acatctgata  420
tatcacactg gctagtgcac tttcttccac cagcatacca tctcaattta ccactttaac  480
aattggactg ccactttgtg tcagggacta tctgtgctcc aactactaca agtgataagg  540
tcctcactga cagccaggga gcaagtgatc cagctctaaa actcacctta tcatctgctt  600
tcctagacca ctcctaacaa ccaactattc tgggttgagt tctccaagag gcagagagtt  660
caggatacag aatgttgttt tgtttttgtt gttgttgctg ttgttgtttg tgtgtgtgtt  720
tgggcttttt tgagacggag tctcactctg ttgcccaggt agaagtgcag tggcatgatc  780
tcagctccct gcaacctcca cctcctgggt ttaagtgatt cccctgcctc cacctcctga  840
gtagctggga ctacaagtgt gcgccaccac acccagctaa tttttgtgtt tttagtagaa  900
atggggtttt accatgttgg ctaggctgct cccaaactcc tgacctccag tgatccacct  960
acctctgcct cccaaagtgc tgggattaca ggcgtgagcc accacaccca gcccagaatg  1020
tttattagaa tgcacaatta ataccagagg cagtggggaa ggaaggactg agcagaggag  1080
gaagttgagt tgtgattcaa cccaacaact gcctggctgg catggggagc tctggagtta  1140
aatagggcca tcagactttc ccagtgtggg gccaacatga ctgggtcttt ataccccccac  1200
ctctgtcagt cactcaacgt ggtctccctg caacaaggtg actcttgcag ccgagacaat  1260
ccctgaaggg acagagggct gaagcctgtc tgccaacagc actcccagtg gctggaacaa  1320
gtccttccct ataggggaat ctgggcggca cacctccatc tccatgtcca tcacatacga  1380
tatcacagac atttaaatat tttgataact gtacataaga gtttccttta taatcttata  1440
gatcttattt tatgcatttg aaaatattct tctgagacag ggcttttatc atattgccat  1500
agggtgccac gatataaaaa aggttaaata ctctctgatt cagaagtatc caatgatgac  1560
ttctctctca tgcatttaat tgaaaatctg gtttttctcc ttctctgcta gttctctacc  1620
tctctcccca cctcccacat catagcctat tcacatatgt ctgaatctca tgatagacaa  1680
gttcaggttc ttttcccagg ttctttttac cacatccccc cacccccaca taaaaagtat  1740
atatggcaca gcctaggttc cacccaaatc ctttctcctc ttcttcctgg gcccacaact  1800
ctcctacata cattggtata ccttgcgctt agggatggcc atgtgactaa gttctaacag  1860
tggaacatga tcagatgcca cttccagcct ctaagacagc cagtgtgttt cctccataag  1920
ctccttctct tcctcccaac tggagactct aaatgatgac cctgcctcaa gcaagcaaac  1980
aacaagtccc tcaggggtgg tgtaggctgc aaatggaagg agcttgagtc ccaaaccttc  2040
cacggagaag gctggctacc aacctggatc actcacccaa gactgctcga agagttggtt  2100
tgaaccattg tgttttgggg tctatttatt acaacagttt agcttgcttt gtgaatagat  2160
ttagtggcag agcctccaaa ttctatagat acattgatct cagtcctaac cgcatctgga  2220
acaccattaa ataaaggaat tgcaaaccca gagaaggtaa tgaatttgtc taaggtcata  2280
caagatggct aggatcagga cccaactctc cagttttctt tcttctctgc tattctgcct  2340
tctgtgatcc tacataagtg ggcatgattg tataacatat gcggccatga gatttctctt  2400
tcagcaagag aaagggacag gaagaaagag agggaatgca ttttcttggc ctgaattagt  2460
gtgagccatt agttacctac attgactaaa ttatctggaa tgaacattca actctacatc  2520
acatatagtt aaaatgacag atctgcttaa gattgtttct agcatacgtt atttcaattt  2580
aggcaaatgt gaccattcag tgtgagggga ccatactgtc attaggtccc tgtcagttct  2640
caattatact gttatcttag agggggaaaa atgtgaaatt tgaatgtaga cgagtgttga  2700
tttgactgct acagtttatt ttacgtatag aaataaaata atgtgtagca aaagcattat  2760
tacaaagatg ataatgaaat aactagtatt tataatagta taatagtata gtatttataa  2820
tagtatgata gtttaatgac tatttgtcag atgttgtgta agaaacttta tacacacaca  2880
cacacacacc tcatttaatt cctgtatcaa tcaggataca ggacgctgtg gtaacaactc  2940
ctcaaatctc ggtggcttgc acaacaaatg cttatttctt tttttttttt gacaccaagt  3000
cttgctctgt aacaggctgg agtgcaatgg tgcaatctcg gctcactgca gcctctgcct  3060
cctgggttca agcgattctc ctgcctcagt ctctcgagta gctgggaaca caggcacgcg  3120
ccaccacatc tggctaattt ttgtgatttt agtagagatg ggatttcacc atgttgctca  3180
ggctggcctt gaactcctga cctcaagcga tccacccacc tcagcctccc aaagtgctgg  3240
gattacaggc atgagccact gcgcccagcc ccaaatgttt atttcttgct catgtgacat  3300
gtacttcctc gagtttttcc ttcctgagat ctaagctgaa ggaacagctc tctggagcca  3360
cgccattctg gtggcggaaa ggaagagtaa aagtggtaga accttgcaat gctcttgaag  3420
cgcctatttg gaatgtctac atcatgtaaa tggtaatgga caagtatgta taatccccac  3480
accaaaaaaa ggggacacta ttggggacaa taaccacatt tcaatgctgc aagacggata  3540
ttgactgcac ccccttccca ctttcagaaa gaagaagagt aattttgctg aactccttct  3600
agagactgga aatgtccctt ccagttgggg tgattaggga aggctttggt aaaatttgag  3660
ctagagtttg aaggttaggt agactactgg tgggtgaaga aagaacaagg acctttgtag  3720
gcaaaggaaa acctcagaat tacagaggtg gaaaaagagt tctagtcaag ccacttcagc  3780
tggctacaga gtaggtggga aagaaaatgg gaggacaagg gctcagatga tggggggttg  3840
gggcattggg gggacacttg aaagctaaac taaggggttg aacttaattt aggaggcagt  3900
tagaagcttt tacatatttt tgagcaagag agtgacataa ttaaaatgat ctgggccagg  3960
tgtggtggct cacacctgta atcccagcac tttgggaggc tgaggagctt gggtcacctg  4020
aggtcaggag atcgagacca gcctggccaa catggtgaaa tcccgtccta ctaaaaatac  4080
aaaaattagc cgggagtggt ggcatatgcc tgtaatccca gtagctggga ggctgagaca  4140
ggaaaatcgc ttgaacccgg gaaacaggtt gcagtgagcc gagatcgtgc cactgcactc  4200
cagcctgggc aacagagcga gactccatct caaaaaaaca aaacaaacac acacaaaaaa  4260
ccaaaaataa ataaataaaa tgatcacttc tgaatactga tctaactagg ggttgcaggg  4320
tgggctgata tagggagaaa ctggagagca aggagatcac taaggtccct acatgtccag  4380
aaccaagata gaggtcttga actaggatgg tggcagttag aacaacaaca acaaaaagtc  4440
aattccaggc tgagtgcagt ggctcatgcc tgtaatccca acgctttggg aggctgaggt  4500
gggagttaga aagcagcctg ggcaacactg caagacctcc tctctaaaaa aaaaaaaaaa  4560
aaaaagttag ccaggtgtgg tggtgcccac ctgtagtccc agcaactcag aaggctgagg  4620
tgggaagatt gcttgagccc caggagttca agcttgccgt gagctacgat tgtgccactg  4680
cactccagcc tgagcaagac cttgtctcca aaaaaaggtc aattccactg actttctaa  4740
ggtgtacacc atcaaggggc agctccatct ccaggccatt ggctcatgag acattctgta  4800
gtcagaaggc tagggcagat tgctttgagc aagcccccat ggtggttctc actcctactt  4860
ctttgggtat atgcccctct gtttaaaaat aaagttaata tgcatttaaa aaaaaaaagg  4920
agaaaaaggt cagttccaga aactgtgtga ataaagcatt ttacttgctt tttctattaa  4980
tctataacat atgttgattt tttaaaaaga atataagagc tatgcaaatt ggagcttcaa  5040
```

-continued

```
gacaacttcc catctcccta ggaggagatg gctgccctaa accccctac atagaaatca 5100
tcccactgct tgggcttaaa cttgatgttg gggaaatgaa aaatccaagc taaggccgaa 5160
gcctggggcc tgggcgacca gcagaatgag gaccactggt cagtttcagg ctgaggtgcg 5220
tcttccaggg gacaatctct agctggccct taaacattca gacttcaagc tctatttaca 5280
gcataaaggt gtttcaaaag acgtgataca aataactgca aatgctctgc gatgtgttaa 5340
gcactgtttg aaattcgtct aatttaagat ttttttttct gacgtaacgg ttagattcac 5400
gtttcttttt ttttaagtac agttctactg tattgtaact gagttagctt gctttaagcc 5460
gatttgttaa ggaaaggatt caccttggtc agtaacaaaa aaggtgggaa aaaagcaagg 5520
agaaaggaag cagcctgggg gaaagagacc ttagccaggg gggcggtttc gggactacga 5580
agggtcgggg cggacggact cgagggccgg ccacgtggaa ggccgctcag gacttctgta 5640
ggagaggaca ccgccccagg ctgactgaaa gtaaagggca gcggacccag cggcggagcc 5700
actggccttg ccccgacccc gcatggcccg aaggaggaca cccacccccg caacgacaca 5760
aagactccaa ctacaggagg tggagaaagc gcgtgcgcca cggaacgcgc gtgcgcgctg 5820
cggtcagcgc cgcggcctga ggcgtagcgg gagggggacc gcgaaagggc agcgccgaga 5880
ggaacgagcc gggagacgcc ggacggccga gcggcagggc gctcgcgcgc gcccactagt 5940
ggccggagga gaaggctccc gcggaggccg cgctgcccgc cccctcccct ggggaggctc 6000
gcgttcccgc tgctcgcgcc tgcgccgccc gccggcctca ggaacgcgcc ctcttcgccg 6060
gcgcgcgccc tcgcagtcac cgccacccac cagctccggc accaacagca gcgccgctgc 6120
caccgcccac cttctgccgc cgccaccaca gccaccttct cctcctccgc tgtcctctcc 6180
cgtcctcgcc tctgtcgact atcaggtaag cgccgcggct ccgaaatctg cctcgccgtc 6240
cgcctctgtg caccectgcg ccgccgcccc tcgccctccc tctccgcaga ctggggcttc 6300
gtgcgccggg catcggtcgg ggccaccgca gggcccctcc ctgcctcccc tgctcggggg 6360
ctggggccag ggcggcctgg aaagggacct gagcaaggga tgcacgcacg cgtgagtgcg 6420
cgcgtgtgtg tgtgctggag ggtcttcacc accagattcg cgcagacccc aggtggaggc 6480
tgtgccggca gggtggggcg cggcggcggt gacttggggg agggggctgc ccttcactct 6540
cgactgcagc cttttgccgc aatgggcgtg tgtgtgtgtg tgtgtgtgtg tgtgtgtgtg 6600
tgtgtgtgtg gaggggtccg ataacgaccc ccgaaaccga atctgaaatc cgctgtccct 6660
gccgctgttc gccatcagct ctaagaaaga cgtggatcgg gttctagaaa agatgactcc 6720
ctgcacgccc ctccctgcac ctcccgagca gtgattccga cagggccttc actgcccctg 6780
atttaggcg ggggccggcc ccctcccctt ttcctccttc agaaacccgt aggggacatt 6840
tgggggctgg gagaaatcga ggagatgggg aggggtccac gcgctgtcac tttagttgcc 6900
cttccccctg cgcacgcctg gcacagagac gcgagcagcg ccgtgcctga gaacagtgcg 6960
cggatcccac tgtgcacgct cgcaaaggca gggttcacct ggcctggcga tgtggacgga 7020
ctcggcggcc gctggtcccc gttcgcgggc acgcacagcc gcagccacgc acggatgggc 7080
gcggggctgc aggtgcatct cggggcggat ttctttctca gcgctcggag cgcagggcgc 7140
ccggcgtgtg cgctccctgc cggaggcgcg gggctggcgc gcagggctcg cccctcactg 7200
cggcagtggg tgtggaccct ggtgggcgag gaagggggag gataggctgt gcctcctccc 7260
actcccgccc ccagcccccc tttttttccc cctcggaacg cgaggtgcca tctttttttcg 7320
gcgtgtcacg tctttacggt gccatgccaa accgggtggc cggcttcat aggacagggc 7380
ggggcctggc attaaaggga gggggacaat cagcgctgaa atcttggcgt tttgctgctg 7440
cgggcgtgag cactgggggc gttcgcccag caccttcttc gggggctctt tgctttgtct 7500
gtagaggtta cgtgatctgc gctcccagcc ctggtttctg gcttttattc tgagggtgtt 7560
cagtcaacct ccccccctacg cccatgcgcc tctctttcct ttttcgctcc tcatttccga 7620
gcccattgtt ggatctcgag gcttgctggg ttcgatgaac tcgagtcaac cccccgaccc 7680
ccggcacgca tggaacgggc gtgaccgcgc gcagcctcgt ctcggagtct gccggcgccg 7740
ggaagcttct gaagggatgg gattcgagtc tccgtgcgcg ctgcgggcgg cggcagaggg 7800
atctcgcccc tccctacacc ccaagtgtcc tgagggccac gccacaccag gttgcccagc 7860
gagggacgct ggctacccat ccggggatgg gtggggagcc ctggcggggc ctctccggct 7920
ttacgccctg ttgcttcgcc tggccggaga atgtgaggaa ggggcataag gttactggtg 7980
cttcggccac acccatcttt ctgagcccac tggactgggc gcagaggggg gattgccatg 8040
gaaaccacag gtgtccggag aggggatctt ggggctggcc tcaccccttc cctgcggaga 8100
ttggggaccc tggggtaggg ggagccgcgc ccagtcggcc tcctggagga cacgggagga 8160
agccccgaac ccccgcgcct gaggctgttt ctgattggcc cctggaggcc gcagacacgc 8220
agataggcgg ccctgggtgt atttttatta atattatgtc cgtactgatt aatattattt 8280
atcttaaata aatttcaccc gtgtccaagt tcaccgcgcc cccaaaaccg agtctggggc 8340
ggcaggggga actcctggcc aacgaatcca tgcctcgccc tcctgtgatg aacctggtac 8400
gcacggtttt ctggttaatt ctatcgctga aaactggtgc ggggggcgca cttctgagac 8460
ggaagagcat ctaggagctg aatcctccac gcgggtcgcc caggttgatc tgaatttctg 8520
gggaatggct tggctgcccg cccgggacca ggccgaccct ccttgacggt ggcgtagagg 8580
gctggagcct gggtactgcg aggctcctcg catggctggg cccgccgcga ggggttgcag 8640
agcggctcag ggatcgattc aagcatcgtc tctcctccct cgcccccaga cagagctggg 8700
cgcggggttc cccttccaga tggagcgagg gtctcggggt ggccccggaa aaggggagcc 8760
cgcggccacg gctacgtatt gccatctcgc gagcagagat gtcacctcct gcctttggag 8820
gaaagggagc ccggtgggga tgagcgcatt tagcccaatg ctgggaacaa agcgcactcc 8880
gcgcttctgc gatttcgctc cattttgaaa tgtgttggcg ctttggtggg gccgctgcgg 8940
tgggcaaggc cgggggcgct gttaatggag gaacctcagg gggacggtcc ttcgtaggaa 9000
actctatcct ggctctgcgc gcgctttaag gaaatggctt ccctccagga cctcgaggga 9060
tgcagctttt gcgcggatga cggtggggtg ctgaaccagc cggtgcgcct ctggaaatgt 9120
ctgggcacgg atcctggggc catcgacgac tcctccccat tcccagcagg cgggagctct 9180
tacattccga gcgagtgacc cctctcaccc tctggcgctc acacacctgt aactccaaac 9240
ctccgtctca gaatggtcca ggctggaagg gatgatgggg gctccgacag cgactgccta 9300
gctcacccct ctgcgtgctc aggctccagg ctcagcagga ccaatttgag ttctatctga 9360
tccccctcgg ccccttaact gacccatcct acaggagaca gggaaatgtc tttcctaccg 9420
cggttgattc tggggtgtca ttttgtgttt tgtgatggct gcttatattt actgtataag 9480
cattgtattt actgtataag cattgtatta taattactgt ataagctgct tatatttact 9540
gtataagcat ctccaaatcc tccctctacg taaacaaatt aatggataaa cagataagtg 9600
tatcccctgc ccccacccct gctacgcagg tccggagtga ctcttgaagc tcatacattc 9660
cttggccaag tttgcttctc taacagatgt ttatatagca ataacctggc ttggctcttg 9720
ggttcacctt tggacgattt ggggaagggg cttgttggct ttgctgggtt ttggatgagt 9780
```

-continued

```
gacagtccat gactgttcct gctggaaggg cgtgactttt aagtggtttc taatatcagg  9840
cattgctcct ccgacaggaa caaaagaaat ggatactgcc cataaattgt tagaaaactt  9900
agaatcgctt tgattgagga aaggttagat ttattccggt tggaaaaagt ggcctttcta  9960
ttaaacgtgc cctttgaccc tcatgccctt ggaggtcggt gccagcctgg agatgggata  10020
agattgtggt tttccttctg ccttttttaac atctgttgtt acagtccatt tgttgaaaat  10080
ttaaagaaac tgttttattc cactttccct cagcatttat gtgtgtggtt tcagtagctc  10140
tgtggctata tgtacgaaca cgtgttattt ttccaattgg acatgtgata attttccaac  10200
tggaccttgc cttctattga tgtatttatt tagcatcttc cttactccct ccttgaaaaa  10260
gaatcactca aaaacaaata aaaacagccg taggggccta atacagtgct agacatacaa  10320
gaggtattcg gtccatacca aatggatttt atccatgaag gataaatggg gaaatacagt  10380
gggaagcagg tgggaaactg cgtttgactc tgctctttcc tccaccacca ctttcctcat  10440
caccgtgttc agagaccccc aaagccccct cacactccca gaaacacccc cctggccact  10500
cctaacttgc catgcccagg agttaggtgc ttccactagt gacatggagc tggcgtttgg  10560
ggggcacctc agcaggtgac gggaagagaa gaccccagcc tcaccagctg ggctgcagca  10620
gggagaggag tcctcatgtt ccagcaggga ctctcagctg ttttcctgta aaaccatggt  10680
tctcaactgg gggccactga gatgtctaga gagatgtttt tgttttcaca actcggggag  10740
ggtgctactg acatcttgtg ggtagaggcc aggaatgctg ttaaacatcc tacaaggaag  10800
gcacaggaca gtctcctaca tcaaaaatatg acccagtccc aatgtcacca ctgctggggt  10860
tgacactggc actgctatct taattacatt cattgagtgt cttttaggag gccctattct  10920
aagtgcttgc taagattatc tcatttaatc ctcacaacac ttccgctatg tagcaggtgc  10980
tgttattatc tccgtgatgg ggaaactgaa gcacagagag ggttagtaac ttgctaaagg  11040
tcacagagcc agtgggtggt ggagctggtt gcctgacact agttccctcc cctctcagcc  11100
acatgtgggt ttacttggcc attgtggact agtctgggaa cccagatatg atctataaca  11160
ttgacccagt agaatattga ttccaaaacc actgtctcac aaatgaattt ttacaagagt  11220
ctgtaatcgg agcatgaccc agaataaggt tagggagatg tggagttaaa gctctcaatt  11280
tcttatctgg ccccgacaca gagagcaagg catttcactc tacattggtg ctctgtttat  11340
aaaacaaaga gcaaatatct cttcctaagg tccttaaacc tcttccccca atccagggtt  11400
tctggactgc tctgccatat gacggggcag ctggtttgat tgacccaggg aaggctggaa  11460
atcaagactg gggggatcaag acgtagattc agtgtggcca aggtcaagtc tctgaggttt  11520
agggacatca gatccccagc ttaggttctg tacctcggca aggtgaaagc gttggcgccc  11580
actgatgagg cctgctctga gattgtgggt gtgggttgag ttgggtgggc ataggcaagt  11640
cctcttgtaa gaatcttttg gcaaagatgg gcctgggagg cttttctcac ttcctggggc  11700
ccaggctttg caataagtat tccattatac tgtggtacct tggggctacc tgagaatcct  11760
ctgtctcgcc cctgttgcct tgccaaagag tttgctgtcc aagaattcct ttcctgtctc  11820
caggtgccat gctcctgcca cctctgccag gttccctgcc tgcccagatg gctcccaact  11880
gagtgtgagg aggaatttga gacaggtttt gagctttctg ggttctccag ttaggaaact  11940
ttctgtaagc atgcagatag aatgggcttc agcaaaatac aaactcgaac aacttccatg  12000
tatagtccct taattttctt tgcttttttc atatttcatc aggctccatg ctgagcccaa  12060
tcagggaccc gatagaaatc caaacaccat gtcagcgagt ccccaagaaa tgcattttgt  12120
gccaaggcta ttcaaggaag gtttgggagc agctcaaggg cagacactgt taccctcccc  12180
caggtcccca gtgcagggca gtgttctgca tgtggaggca gtttggccta atggttaagg  12240
aggtaggctc tgatcgggcc tcctgggcac aaatcccagc tccctgctca ctgtgagacc  12300
taagccatat tgtttagctg cttggagagt tttttgtcat ccacaacttg gagtatgatg  12360
gtacctgtct cacgggttgc catggggttc acacaagcta acccggtact cactagggcc  12420
aagcacatag taactgctca gtaaatggca tcatcggcgg tgtcctgtgg atgagtgctt  12480
gtgattggct gaatgaccag aggggtctaa agatcctggt gatggaatca gttgtacaga  12540
taaattgtta cactgagtag ggatcaagat aggaaaagtc ggcaactacc cagctcccct  12600
gcaccaaact gggcagaagt ggatcctctg aaaattgcac acacccatgt ttaaatgtac  12660
acacagaact cttgccacag gcaagcggag atttgtcatc tgctgtccct gcctcatctt  12720
cttcctgaaa tccactccat gccaggaata aactgcatgc tctccaccag cccaaactga  12780
cctgccttcc cgccagccat cccgggcagg gtgacctggc ttagtacatc gggttcagag  12840
atctttccag tttactcgtt gaataaaaag tgagggctga tcgagaaagt aatggcagtc  12900
agggaaggcg aaggaggtaa agaagagatt ttacaaatga agtaattcaa cagagtgctg  12960
acattggtaa actggcaaac agatttcagg gtggttggtt gagagtagag tagaaaagga  13020
ttaaataaag caaacttgtg gtgtactgaa tcttaggaat tccatgtatc caataagtat  13080
agtcatttat gaattaataa attcggccta agaagccttc ttatcgctta aatcaagact  13140
aagtaacaat atatcagttt taaaaagtca ttatatcaga aaatcattta aatgatacac  13200
atagatttcc aagattttac tttaaccgaa actatataaa tgtgaatttg ttcacccatc  13260
ttttgacaca gggctcaggt cttctcttgg tgtctggatc agccagttga aatttcttgt  13320
ctgttttgcc tatgccacat taataatgca ctgtctgggt cctccgattt cagtttggat  13380
tttgggttta cattgtggag tcatctgaat gcagaatcct tcagggattt tacttttttt  13440
ttttttttc atggtcttta ccatcccatt tgatagtaaa tattactcac ctttatgaag  13500
tctttccaaa acattcaact aaattttctt aaaatcattg aatgatttga agagcttatt  13560
cctcagcact tttactccat cagcttgcac cttatttttt aatctttttt tgagacggag  13620
tctcgctcta tcgcccaggc ttaagtgcaa tggcgcgatc ttggctcact gcgacctcca  13680
cctcctgggt tcaagcaatt ccgcctcagc ctccgccgta gccgggacta caggtacaca  13740
ccataatgct cggctgattt ttgtattttt gtagggatgg ggtatcgcca tgttggccag  13800
gctggtcccg aacttctgac ccaagtgatc cacccacctc ggcctcccaa agtgctggga  13860
ttacaggtgt gagccaccgc gcccggccag cttgcacctt atttaggata tgtgattatt  13920
atagcaagtc tggtgtacat acaagatttt gaatgggcac agatgacctt tagtaagtgc  13980
ttggctgtga taagaggcag tcctgactgc agatcaggct gtgtggaccc cagccttgca  14040
tgtttacaga ccttcatgtc ttattcttac agggtatcag aagaacacct actggggaaa  14100
cttataaatt agtaaaaggt gggcattctc cccgcccatc ttctgtctgt ctgccaggac  14160
tagcacagca ctttgaagtc attcacatag aatcccaact taagagggta aaatcctcct  14220
caacagactg aaaataagtt taaattccct ttgctatatt aactcccctg aggaaagagt  14280
cttagatcaa tgtccaacac taaaaacagt tttaaatcag caagtgagaa ttaaatctga  14340
agcaattgat aataatgttt cattcattcc tctcctttgg ccccgtccac cctactgcta  14400
aatccaggca tcaaagagaa gagggacata attatctcta gtcccagctg ctggtttcc  14460
ttccagccta tggcccagtt ttctgtttta ctgagaaggc tggtgatgtt atcttgggat  14520
```

-continued

```
ctaagtctgc agtttcacca caaaaagtcc agggatgcac tttcatgctt gtgtcctcct  14580
ccctgggata gcaaggatat tagaagaccc ctggctctgt aattgcttgt catgtgctct  14640
acagacgcca cagaatgcca agaacgaagt gctgggaagg acaaattcat ggaaccgtgg  14700
gacggtgctc ctcccccagc gtaaaggaca gctcctcctc ctgaattgga gccagcgttc  14760
taaatcatgt gtcaacagag ttgtcctgga tcggatccag ttctgccatt gatttgcagg  14820
tcatttcagt ggtacctgtt tccagttgtt cttaattgaa cagtggcacc aaactattgt  14880
cttgcctcat cccctcccca tggcctgtcc cccaaaaaga gacttcttgg gtaattaatc  14940
agggcaacat caggcagtct gggcgcggtg gctcacgcct gtaatcccag cactttggga  15000
ggccgaggcg ggcagatcat gaggttagga gattgagacc atcctggctt tgtgaaaccc  15060
cgtctctact aaaaatacaa aaaattagcc gggcgtggtg gcgggcgcct gtagtcccag  15120
ctactcgaga ggctgaggca ggggaatggc gtgaacccgg gaggtggagg ttgcagtgag  15180
ccgagatcgc accactgcac tctagcctgg gcgacagagc tagacttctt ctcaaaaaaa  15240
aaaaaaaaaa ggaatctctt tggttttata tatattttttt ttatatatat aatatatatt  15300
aaaatataat atatatattt atataatata atatataaat atattatata ttatatattt  15360
tatatattat atattatata tattatatat tatatattta tatatttata tattatatat  15420
atttatatat tatatattta tatatattat atatttatat ataatatata ttatatatta  15480
tatattatat attatatatt atatatttat atatattata tattatatat attatatatt  15540
atatatttat atattatata tttatatata ttatatatta tatattatat atttatatat  15600
tatatattta tatattatat atatttatat atattatata ttatatatta tatatgtata  15660
tattatatat gttatatatt atatatattt atatatataa tatattgtat atattatata  15720
tctaatatat tatatatatt atatatatta tatattataa tatatattat atattatata  15780
ttatatatat ttttatatat ataatatgta taatatataa tatatataaa aacatatata  15840
atatatatta tatattatat atatattata tatattatat atattaaata tattttatat  15900
atattatata tatatacaca tatatatata taaatgaggc caggctcggt ggctcacact  15960
tgtaatccca gcactgtggg aggatcactt gaagccagga gtctgagact agcctgggca  16020
acaaaacaag atcctgtctc tacaaaagga aactgtaaaa attagctggg catgatggca  16080
tgtgtctgta gccctagcta cttgggaggc cgaagcagga ggatcgcttg agcccaggag  16140
ttcaaggcta cagtgagcta tgattgtccc atagcactcc agcctgggta acacagcaag  16200
gccctgtctc taaacttttt ttttttaatt ctatttatat ttacatgtat ttaaatgtga  16260
atattcacta cctatttgtt gcatgcctgc attttttata ctgggcttgc caaaaacccg  16320
aacagctttc tactttgaca atgtatcaga atttaaatca gcaatatgtt aataagccaa  16380
gcaaaggtta tatatgcaaa taaaactgtt gtctataacc tcctgttaca ctggggcaca  16440
gcaaaagtca tggtgtagtc gcatgtgaac ctgtcccttt catagctgct cattgccagg  16500
aaacatcagg aatagccatt tggaagagtc atcagccctc ccaccatccg ttttctgtct  16560
tgtcttttcc ctatgagcag gggaaattcc acgctggccc caatccccag tgcagcggct  16620
cagcctctgc ctctgctgct ggtccccatg aggccagctt agaaacggag gattttgcag  16680
aacatcccta aatccgcttg aataatgaag tgatcattca taaactcacc tgaaccttat  16740
taaaacctat ttaatatttt tcctggataa tcctataggg ataacttgcc tcctgggctt  16800
ctctccaccg ggttcagttc ttcctttagt ggtgaagttc ctcccttctt agcatctcaa  16860
ctgtgcctga gaaaaggcca gtggcggctg cactctgttc cctgtggagt gttaataaag  16920
actgaataaa ttgaaataaa tccctttcaa tgtcattaag tgctataaat aatcatgaac  16980
caatgttcga tggctgatga gaaatgcaag aaaaaatttt taatcagtag gattcataag  17040
ttgacaatct gggccaagtt aaaaaaaata aaaataaaaa gacttttaaa aagatcttat  17100
cgtttgttac cagtaagact gaattccaga agcaagctac tccctcattt gtgggcccct  17160
gttatcactg gctgcttagg gttgccaagc cctgaattca tttgtcaact aagagatttt  17220
tggccaagat taagatttcc catgcctcca tatttccatc tgagaaatgg agattatact  17280
gtcttccccc tcagaatgga tgataatgtg gtctctcttc tgttcgcata gtcatagaac  17340
tgaaataaaa caacttaaga gaattccttt gagcttctca gaagtgctgc agggctgggg  17400
gatgcctccc aggagccgca gtcaggtgct gatctgaagt ctttggtggg ctgactttag  17460
cctgacctga aatagtatag ctgctgccac ctggctccct tagcgtcagt cagacggtgc  17520
agctggttcc taggggtgag ggctgagcca gcagggtccg tgcccaggag ggatgcatgg  17580
gtggccacag cccagcctgc actgatcttg tctgtcccct tctttggaag gaaggagccc  17640
caaaccaggg tgcaagacag tgggtggggg tgccttgagc atgacctcaa gtgatttcca  17700
gcccctgcca gtgctgactt ctctggggaa gggctgggac ttccttctgg gctcaagtca  17760
cgacccttgg atggaatttc ctgggagctt ttctgttttt tctggagttt tcagtttttt  17820
cctaaccaga cagggacttg gtacagaatc tcatattcta attatgccta ggagcagcct  17880
ctccccacca ctcacagtgt ttagcatgtg acaggaatcg attaaggcat gagtgattaa  17940
attaaagcca ggcattgact tggatggtgt aatattctga catctgtttg gtgtcaaagg  18000
cacggggcag gcgcgttaat tgaactgctt gcacctggca tttgaattga gccagagcgg  18060
ggctaaagtc agtttgcctt caccctgtaa atggagggtt tctccggagc gtggatggtg  18120
ggaggtattt cagggtgtat gcataacccc caccctgaca atggcccatc tcttctccag  18180
cgtggccagg tttgagtgcc agtcctgggt gtccagtggc cccatagcct tgcgttttag  18240
taaaatgctg cccccattac cacctggtct gtgcacttcg gtcactggaa tttgccatct  18300
tccagtcccg aatgtggcaa gccatggagc cttaagctct tctccctcca catcctggaa  18360
cagacccgcc agtttcttcc aggcattgcc tcagtttgcc cctctgtttc cagtcacact  18420
ctcaccagcg ataaaatgat tttagacctt atcatctcac cctcggatcc ttatggaaac  18480
aataatgagt tgttccctgt ttcaattcca aaattcatat ccaatccgtt ttgcatgcca  18540
ttgccaaatt cctcccagag caaccccgtc acctgccctg gccctctcca agtgtggtcc  18600
tgccatgggc atcgcctgct aagccaagct ggcctcgagc tgcctgcccg ggtccccaca  18660
ccttggctca cctccctgcc cagtcccgcc tcctgccagc ctgccctgtg gctccttcat  18720
agatgccgtg ctctttctgc cccttgctca cccatggcag ccttgcccct ctctccctgc  18780
cccacccccct atttaaattg acctgacctt cctcagtgtc catcttcccc gaagctttcc  18840
ccagccttgg cactcaaggt ccagaggcta cgcgtttcct ctcacctgtg gcagcgccgt  18900
gctccccagt gcctcacagt ttccttcttg cccccgcttc ctgtgtagga ctcatctgcc  18960
cacaggttgc acgtcctgtg agggcaagga ctgtgtctta tgtgactttc cttctccagt  19020
cacagagctg ggcacataga tagctcaaaa ccctctttat taacacagtt ggatgttgag  19080
aaatcaaaca ggccaatgtc aaatgagctc tccttattta aatcaagtca gttctccacc  19140
tcctagcact cagttccagt actctatata catggaaata ataaaaaaca catttccttt  19200
gaaacattct ataatcgttc ctttgcccta cttcagacca acttaacgca ctccccattg  19260
```

-continued

```
gtccaaatga gttttgctat acgaagatgc tgataataat agcagcagtg gattattctg  19320
ctaaaaccat tgcctcgtta atcctcagtc ccgaggtggg gattattatc ctcattttgc  19380
agagaagcaa actgagactc agagatttca cagctgggga gggagccagc tcatccctct  19440
gtccaggccc aagctctctc ccgcttgcct tcctgcctct gcaacctcag agcatccccc  19500
atctggttct actgcctgtg ctagtcgtgc aggagccaaa agacacgtct ttagtgctaa  19560
ggactggaga agccatgccc tccagcctct gtgaatgggt catatgtaac atgagcctgg  19620
agaaattatt tgaaaccaaa ggcaagcctc taaaccaggc tgctgcttca tggcgccggt  19680
gacggcagaa ccaaatttag tgctgtgggc aggtccacac ttatcaaata gagaagctca  19740
tttttcttcc ggctcacatc aagcatgaaa aatgttcaca catacccccc acacacacat  19800
gctttccgga ggggtccatg tggctagagg ctggaagatg tggatgagag gagcctggca  19860
ggtaagccca gggaagatga cattcagctt cccagacagc atctacaggg agaaatttaa  19920
ttaaaagtgg ggcggtttcc ctgagcaagg cagacaaagt cagccctcta ctgttaagaa  19980
aaagggtcac agtgagaggg gaggtgagga gactgagtct gtattttcta gtctgttggg  20040
ctacactacc tgatccccct tcctcaaaaa tccactttac tttccccatg tctacaccaa  20100
tgtggttcac actctgggac caggaaaagg gggagtgatg gggaacagag aagggaggag  20160
ctcacacagc tgaggctggg gttatgcata tcgaattact tagaatttgc aacctcacag  20220
ggtactttca tggcgttgaa atacacttcc cacagccacc ctccctctaa ctaaaagcaa  20280
gagtcatttc tcagttctgg tcttgcctcc cacgttctcc tccacattta agaaaatcca  20340
ccagctacaa agtgaagata ccatatgtga tatcccaccc tagtttctgt tttatcaggg  20400
tttggagcag gtggagcagg cagagggatc atttcagcct ataaattgta ttaagggtga  20460
gtactgagtc attcttcaag aaaagtttta gaagcatcca aaactgaagg gtggagccac  20520
ctggagacag tatcatcagt cctggccccg agcatggcct gcataggccc ccatggatcc  20580
cagcgggagc tgcagagtgc gggcaccttg gcacacagcc ctgagtgcaa aattaggagc  20640
tgggcagagg gcatctctct gtcgccattg ggcagcccag ggcacactgg tcatagcctt  20700
agaccacgaa caccctgtgc ccgggggaca gatgcaacca gtgtgccctg ggctgcccaa  20760
tggcaacaga gagatcgaca cctggacccc atgtcacggg gactccacta ctaaggctcc  20820
taagactgcc accttccagt gggataagcc ctgcctccta ctgggcccac aatgtgcaga  20880
gaacacttgg gactacctgg ctttctggat acacaaatat tgatccaatc tggactaatt  20940
agaaggtcag tcccaataac aaatcgaagt cagctgggcg tgatggctca ctcctataat  21000
cccagcactt tgggaggctg aggtgggcag atcatttgaa gccagaagtt caagaccagc  21060
ctgggcaaca tagcaaaacc ctgtctctac taaaaataca aataattagg ctgggtgtgg  21120
tggctcatgc ctgtaatccc aacagtttgg gaggctgagg caggtggtca cctgaggtca  21180
ggagtttgag accagcctgg ccaacagggt gaaaccccgt gtctactaaa aacataaaaa  21240
ttagccaagc atgatggcat gtgcctataa tcctggctac tagggaggct gagacaggag  21300
agaatcgctt gaatccagga ggtggttgca gtgagctgag atggtgccac tgcactccag  21360
cctggttgac agagcaagac tctgtctcaa aaaaaaaaaa aaaaaaaaaa aagccatgcc  21420
tggtggagca ctacgtgtaa tctcagctat ttgggaggct gaggcacgag aatcacttga  21480
acctgggagg cagtggttgc agtgagctga gatcgcgcca ctgcactcca gcctgggcga  21540
cagagtgagt gagactccat ttcaaaaaaa taataaatct gagtcacttt aatattgtta  21600
tttggatgtc aacctctagg tgtttgagac aggagagtga tatgggggca ctggaaacac  21660
acaggcacgg ggtgtcctca cacttgggta gcccacacga tgtgatttca gggtgctggg  21720
aggtcccccc actccccaaa ttactaacaa gtggatagta ctttacagtt tatatgatct  21780
catttgattc ttaacatgag cctgtgagtg aaaaattcct tcccctcttc tacagattag  21840
gacgttgaga ttcagggagg ttcagaggga ttcagggaag tcaagtggca cctggagtcc  21900
cgtggctaat ttgaggccgg taggggattc gaacccagga tttgtgcttc ttatgcctgg  21960
gcttctgctc cctggggcat ggtcttcccc ctagctttcc cattcactgc tttagcctag  22020
gggtcctacc ctttattaaa ctgccagtgc ctcactgctt ttctccccca aagacaaaaa  22080
aaaagtgttt ttgcttttgt tttgtttttc atgggcagag acctggaatt tcagcttgag  22140
aatttgtgcc atatgataaa taaatcaaca gatggctttt tccttaaaaa aaaaaaaaaa  22200
aaaaactaag atgtatttgc agtgaggcat aatttgtacc aaaaagtgct caccacactg  22260
tagtcatggg ggcaggaggc agccgcgggt gaagggagaa atcttggagt ccaggcagcc  22320
cccttctggg ctgaactggg gagctggggg tgctgccagc cctgccaggt tctcctagga  22380
ggcggcagct catatggctg tgggaggagg cagagggagc ctcatatgca cccacatttc  22440
cagggatcta gaagacagaa ggaggaaaac caccatcatg ttaaagcaga cagttaggta  22500
acacatcctg taatacaagt tattttttcc acatctaaag gctaaaaata gttgttagaa  22560
tttaaagata attggtaaat gagtttctat ccttctagtt tcacatcaaa tggaatcatg  22620
ctgccttcac atcactagtg cccgttattt gtgtttaatt tccacaatgt tgtctaattc  22680
cactctttgg gcttccccag ggatccagcc tccctcactc gcccatcgca gggagatgct  22740
ttattcatct ttgtgtcttc tgtgccgggc atagcgcatg gcacagaata agcactcagt  22800
aattgattca cgagtgaata aatggatgag tgggtgagtt caatattgac tacaaaaacc  22860
ctaaggccac actggtgagt ggctgcgcct gtagtcccag ctgctgggga atctgaggca  22920
ggaggatctc ttgagcccag gagtttgaaa ctagcctggg cgatatagcg agaacctgtc  22980
tcaaatgaca aaaacagggc caggtgcagt ggctcacgcc tggaatccca gcactttagg  23040
aggccaagat gggaggatca cttgaggcca ggagtccgag accagcctgg gcaacatagg  23100
gagaccctgt ctctacaaaa aatttttaa aaattagctg ggcatggcgg tgtgcgcttg  23160
tagtcccagc tactcaggag gctgaggcag gaggatcact tgagcccagg aaattgaggc  23220
tgcagcgagc catgatggca ccactgcact gcagcctggg cgtcagaacg agacctgctc  23280
tcaaaaaaac aaacaaacaa caaaaaaaaa ggctttctta aagagacttg agaacagaaa  23340
ggggaacaga tacataactt atatatttat ttgttcatct ttccaccttc ctggagggtg  23400
gaggggaaca ggtctgtatt tggagttttg aatgctaaaa gtgggaatac atgtactgtt  23460
tgccatgatc tgttcaaaag ttaagccaaa tgccttagat tctcctgaaa actggaatgc  23520
cactgtaaac tataagcccc acttcaaaga taaaagatct tgatgaacag ggctgggtct  23580
gtggactggg cctctcccca ccacacaagg aagggtggtg ccagttgaag gaaaatcact  23640
taaatccttg ctgtctccta ataaggtgtg gtcccaggta gggctgtcag aattagcaaa  23700
ttaaaacaca gggcatctgt gaaaattaga atttcagata acaacaaata attggcatag  23760
gctgcataat gtccctcaaa gatatcaggt cctaatctcc agaacctgta aatgtgatct  23820
tatttggaaa aggggtcttt gtagatgtgg ttaaattaag gattttgaga tgggggggatt  23880
atcctgtatt atctaggtag gtcctaaatg cagtcacact catccttgta agaggaagga  23940
agagagagat ggaaaacaca gaagagaaga caatgtggtg atggaggcag agattggagt  24000
```

```
gaggtggcca caagccaagg actgctggca gctaccagca gccagaaaag tccaggaacc  24060
aattctctct tggagctcca gagggagtgt ggccctgctg acaccttagc ttcaacctag  24120
tgatcctgat tttggacttt ggccttcaga agtgtgaggg aatgaatatc tgttgtttta  24180
agccaccaag tttatggtca tttcctacag cagccacagg aatcaaaaac agtaagtatg  24240
tcccatgcaa tgtttgtgac acacaccaaa aatattactt gttgttcacc tgaaattcaa  24300
atttaactgg gtctcctgta ttttatttgg ccaacctagt tcccaggccc aaagaaagag  24360
gcttttgaaa tttgcaagaa agctggttgg agctgtcaga aagtggactt tgtaaacaca  24420
gtaccaccga accaatttga actgtactac ctctagacaa aagagagggc agtcagacag  24480
ttgttcgtga tttcttcttt caacagtcat ttgagcactt actacaaaac agaagctatg  24540
tgtaagggtg gaggcgttag ctgttaatca ggacctccag gctaagtttc tgtattagtc  24600
cgttttcacg ctgctgataa agacataccc gagactgggg aatttacaaa agaaagaggt  24660
ttaattggac ttacagttcc aagtggctgg ggaagcctca caatcatggc agaaggcaag  24720
gaggagcaag ccacatctta catggatggc agcagacaga cagggagaga gagcttgtgc  24780
aggggaactc ctctttttaa aaccatcaga tctcgttaga cttattcact atcaagagaa  24840
cagcacagaa aagacctgcc cccatgattc agttacttcc caccagatcc ctcccacaac  24900
atgtgggaat tcaagatgag atttgttacc atatcagtta ccaacccttc cagataaatc  24960
acgtgaaata tcgccattaa cagagtgagc tcaggtggtt cttcagtgca tttctgatac  25020
ctgaaccttc cctgggaatt tcacagacca tcaggctctc caccctttga tagcaggata  25080
gcagggccca ggttctgcag gaggagatgt taccacaggc ctgaaaggga gggaggggca  25140
gatgctacag gaagatgctg gctctggatt cgctggagga gctttcaagg gaagtagata  25200
cacactgtct ccatcatttc atgtccatca cactctaaaa tgctttggac aagaagcaaa  25260
tgttaaagac aaatgtggcc cattttcctg tacaaagagg gctgctccca tgccaggcta  25320
ttggcactgg tgggcatgag gcttctctgc tgccctggcc gggggttct ctcactcacc  25380
attggctctc tgacacctgg agagaccacc acccttgggc tttcatgatg ctcacagaat  25440
ccacactgtt ggagctttaa ggagcctgga tcaactggaa caggcaggga gtactaggac  25500
agcccagcat tgccccaaaa tatccaggcc tgataaaaga gaaaaacagg tagctcacag  25560
gaaaaggata aaaaaaggag gagggattta acatgaaaag gtgcttgatc tccctcataa  25620
taaaaagact gctgattcca tccaggcaag tgacagaaaa aaaaaaatta atttaaaaag  25680
actgctgata aaaccacagc gagacactgc tgctcaggga tctgagggtg tgggcagcca  25740
ggctgccacg catcatgggt cggagaggaa gaccacaccc ctggagcaga gggcggctga  25800
tctgtcagat gccctttgac agcacctcag cttccaagaa ttaacccttt ctatgtgagc  25860
agaggcatcc atggggggac acactggtga atcatctgtt atgtagaagt ctggaaaaca  25920
tcaggatgga actggtgaaa taagtgtggc ctctgacgga atggagcggt ccgtctgcac  25980
tgctgcgggt gcccctcaga tcctgtgggt cagtgagaaa agcagtgagg aacaaggcag  26040
gtactgtgta ctgtcctctg cgtgcaagga aggccagcgc atgcaacaga gtccacacag  26100
acatagccta actctggaag gaagaatgag aatgcagttt cagtggtggc ctctggtggg  26160
gagaaactgg gtgaagggag atgtcatttc catttctcta ctattaattt tgtattacca  26220
tgcttaaatg ttacttttta cctttttttt tttttttgag acagggtctc tctctgttgc  26280
ccaggcagga gtgcagtggt acaatcatgg ttcactgcag cctgaacctc ccaggctcaa  26340
gcaatcctcc cacctcagcc tcctgagtag ctgggactat aggcacgcat accaccgtgc  26400
ccagctattt tttttaatca agatggagtt tttctatgtt gcccaggctg gtctcaagct  26460
cctggactca agcaatcctc ctgcctcagc ctcccaaagg gctgagatta aaacgtgagt  26520
caccctgccc agccaattgc tttttaaaaa agattaaatg catgtatacg ctcaggcatc  26580
agcacacttg gaaaggatga aaatatccgg aagaagggtt cttttaaaag gctcctcaag  26640
tgatgctggc aggcatgacg aatgtccctg gtcacaaaag ctctgatctg gcctaaccct  26700
gtcatgttag agactggagt gcgtgtgtgt gcgcgcaaag tgtgggggga tgggggtgag  26760
tgtgtgtggt gtgtaagcat gagtgtgtat gtgtgtggtg tgggggtgtg tgctgtgtga  26820
gcgtgtgtga gtctgtgtgt gtagtgtgtg tgtgaagtat gtggtgtgta tgtgtgacgt  26880
gaggtgtgtg tggtgtgtga gttgtgtatg gtgtgtgcat gagcatgtgt gtgggcatgt  26940
gatgtgtgtg tggtgtgtaa gcatgtgtga gtgtgtatgt ttgagcatgt gtggtgtgtt  27000
gtgatatgtg tgtggtgtgt gagcatgtgt gtgtgatgtg tctgtgtgtg gtgtgtgtga  27060
gcatgtgtgt tgtgtgtgtg gtgcatgtgt gtggcgtgtg agcgtgtgtg tgcattgtgt  27120
ctgtgagcat gtgtgagtgt gtgtgtgttc agcatatata aggcatgtaa ctgaacacag  27180
cactttagag ggctctcctg gagtcagagg gggtgggtag gaggagaagg gaggtgggct  27240
agtgtgctga agtatctact ccttgtcata gtctgtgaca acccagacta gcccatgagc  27300
caccctgttc cctgcatttc caatgagacc tcggtggaca tgttccctga ggtgaggctg  27360
actgatgtca tttgacgatc ttgatgccaa atccttttat atcaaaaaca accagaacac  27420
tctcttttct cttagtgctt tcacccagat gaccacattt catcctccca gccactctgg  27480
gccaggtggc actgctggtt tgaaagggag gtctcccctg gagtaacttc cgtgggcgga  27540
ttcacaccct gcccacagtc ctgtcccagt cagcccacca tggtggtctc cggttcctcc  27600
agaattcccg cttttcagct catccccaca ttcccggagg gactgagagc gcagccccag  27660
ggccctgctc tttgggggcc gtctctacac ccagagaagc agcaaggcat tcctaggttt  27720
ctctttcaga tgcagaactt cagtgttcag agatgttccc actggtcctg agagggctca  27780
gttcagcttt aatgactgcg ctgttgcgtg tgctctgcag agggcgggtg gcccagcgtg  27840
gctgactgca gttttcctga cgtggagccc gagcctgccc cgctgtttat taattaagga  27900
tcactctgct tgcagaaccc tgaactcccc agaactgtga ggtgggagaa ccccgagagg  27960
ccacctggcc ccacttccca cctgctgccc aaaccccctc tctgccttcc tgacagtcac  28020
cccaactccc agtgatcccc atcaaccatc tgacaagggg actgagaggg aagagaaagg  28080
aggggcccaa agaggaaggt aaaactgtcg ggaacagccc ccaaatgtgt gacagccttc  28140
agtggagttg cccactttcc cttttctcct ccctgcagga cctcccttct ccccagtcct  28200
ccccaacttc tgaggttaca ttgagaaaag tctgcagaga ggtgccagca tcacaaggtg  28260
ttaaggacca cgagtttggc attttaacag atgccagagc cacttgagaa atgtggtaac  28320
taagcccaga gaggtacagt taacctcccc agagtcacac agcaggttca tggcaaagct  28380
ggactagcac aggtgtcctt cccctgcaga tccccttctg tgccccacat cacctccctc  28440
cagtgtctgg gccacctgga gatgggccct cagactcacc cggccagagg tgccatctca  28500
tgggagaggt ctggccagga agcatcgata tttgagatcc caagaaatga agacttggcc  28560
tgtcagatga cagacttcgg tcatgggaac acgtgatctg ttttacacat gcgtcccctc  28620
agcagcagct ttccagaaca ttcccacttt cttctgtagt gagaagaact ctttccctgc  28680
agcctcctgc ccaactcctc cttcagtgtc tttgcttcag tgtctttgat aaaccattct  28740
```

-continued

```
gctttgcaga gtgcgagctc tgccttgcag ggttcgcatc tgcctgtgct gagtaaccaa  28800
cgctaaggtc gagtggtcgg tcacctctca taagagctag ggttgtctca tgctgatgac  28860
taggacttgc cctcaaggag aaaaataaat caaaacaaaa gcaaaaacag caaacatgca  28920
tctcttaaag aaggctctga gtccaggtaa atttccttcc actgaagcag ccaggctgaa  28980
ttcgaattat ctttgcccct gcttaaaaac taatgcaaat tttcctagag aatatccact  29040
aattcctgga gggggcatgg gcattcctga tgcccatgag aggaccattt gctcttccct  29100
cagtatgcta aataacagaa gcgacatttg ttgctggaaa gtatcagtga agttaataag  29160
gtttttcttg cccagggtga gggaacagtt cccaatgaca aatgctgtat gggaaggggc  29220
tgtagaactg ccagcccctt tggtccatcc gtaaagtgaa ctctgtggat cctggaggat  29280
tccagcgtct tttttttttt ttctttttttt ttaagacaga gccttgctgt cacccaggct  29340
ggagtgcagt ggcacgatct cagttcactg caacctccgc ctcccgggtt caagcgattc  29400
tcatgtctcg gcctcccgag cagcaagact acaggtgcgc accaccatgc ccgactaatt  29460
tttgtattat tagtagagac gggggtttca ctctgttggc caggctggtc tcaaactcct  29520
gacctcaggt gatccacccg cctcagcctc ccaaagtgct gggattacag gcatgagcca  29580
ccatgcccag ccagcatctt tcatttttct gtctgctttg gccctttcct ctctcactgt  29640
cttccttttc catttccaaa gtcagtccat ctcactatta gcacaaaaac tgctagagcg  29700
cttgtcattg gtcatctctc cctgcacctg gctggtctgt tcttggccac tgaagcgttt  29760
cccccagctg ttgctttaat cattttattg ttattatgcc ttacttaaga aatggatatg  29820
agatgcattt acctgtctct tcctgccact ctgcagagcc agtaagatgt ggtggaaagg  29880
gcccaggctt tggaggaggg ctggctgggg ttggatcttg gctgcccccct actagctgtg  29940
tgaccttggg taagtagctg gacctctctg agcctggttc ggaatcatag cacctctctt  30000
tcagggctgc tgtaaggaat agcagtggtg tgtataaagc agagcgcaca gccagcaact  30060
ggcccctagc cacactgctg agcacctact gtgataagct gccattgtgg tgtgtgaagc  30120
aaaggggaaa catgcctgct gtagtgagct tcctgtaggg caggttgtag aaccagaggt  30180
gggttccaag gttacaaagg gactcttagt gtattagtct gttctcacat tactataaag  30240
acctacctga gactggatca tttataaaga aaagaggttt aattggctca cattggctgg  30300
gtgcggtggc tcacgcctgt aatcccagca ttttgggagg ccaaggccgg cggatcactt  30360
gaggtcagga atttgagacc agcctggcca acatggtgaa accctgtctc ttctaaaata  30420
aaatacaaaa attagctggc catggtggtg tgcgcctgga atcccagcta ctcaggaggc  30480
tgaggtggaa gaattgcttg agcccgggag gtggaggttg cagtgagcca agatcgcccc  30540
actgcactct agcctgggca gcagactgag actctgtctc aataaaaaaa aaaaaaaaga  30600
aaagaaaaag aattgcaaga aataaattat tgtttatgag ctatatggtc tgtggtacct  30660
tgttgtggga ctgggagtct tggcgtctcc ctgaccctgc ctgttgctgc agcaccgctc  30720
agccctgcct gctccctacc tgcctcccct cggcctctcc tgcctccacc gggcccctgg  30780
tgcctcctct agagacagtc ctcctgggac cgattgtgtt ctcacttaca cgaggcatcc  30840
aggactacag ataaccagag gaaggggcgc cccccccgcc tgccctcctc cctggcatcc  30900
tcacgctgca gaggtcagag cctcatccca gccccttacc tgcccctact ctgtggagaa  30960
ccgtggtcag ttcgccaggc cggatccacg aacggccttg tggaagatgg tgagctcaca  31020
cccagagctg gctccgatga ccctgtctcc tttacatgtt tctaccttcc cctccctacc  31080
ttcccccact gctgggcgca gagtggagcc agatgaggtt taaagctcag aagggcttaa  31140
acgggttggg gcgcagtggc tcatgcctgt aatcccggca ctttgggagg ccaaggcaga  31200
ggatcacttg agcccaggag ttcgagacca acctgagcaa catagtgaga ccgcgtctct  31260
acaaaaaata aaataaataa aattagcttt gcagggtggc atgcacctgc agtccctgct  31320
actcagaagg ctgaggtggg aggatcgctt gtgcccagga gtttgaggct gcagtgagct  31380
atgctggcac cacagcactc cagcctgagt aacagaatga gatcctgtct caaaacaaac  31440
aaacaaacaa acaaaagaag gcttaaaggg ggctccaggt gggcttggca gcacaaagct  31500
atgaagttct atcttagaca caagttctgt tactgggcct ttgcaggctg gcctgggtac  31560
ctggctgcca tagacaggga accttccaga tgagctgcag gcgtggagca caggagccag  31620
ggtgctcttc ctgggctctg tccacaggca gaacgtacac agtctttgta cacgtccggc  31680
ggctctggtg cctattttg tttgtgtttt tcttttgttt ggggggatgg atttggtttc  31740
ccccgagccc tctgtcctcc tgtcacctgg ctggtgctcg gcaatgttga ccagctgcct  31800
ggctggagtt ggcagtggct aaggctgtga cagctaacat gttcctgagt cctctcattt  31860
cttcaccata atgccctgtt gagtttgcag atactgtctc tgtttttatc tcccggggaa  31920
actgaggctc agagtggcta ggccaccttc ccatggtccc tcagctcatg agggccacac  31980
agggcattgc ggtggccttc tcctcagcct tgaccctccg gccccagcat tgctgcctca  32040
aggggtctcc tctgctgagc cgtgcacctt ctgcctggca gctccaactc tgtggctgtg  32100
ttcagtggct cagcactgcc ccttgaccct ccctggcctt ctgcggatgc cagactggag  32160
cactctgaca aggtctgggg tggttgtatg ggtcctgtga cctctataca cctcccagtg  32220
cctgggaatc ctgcagatac accctcctta gccgtcccta accatagagg acatttctga  32280
ggtccccgag agagtggggc acccctgcag gatccaactg ctgggcccag gaaggatagc  32340
agcagcatga ggggttccat tagccacaaa ctcacggcat ggaaccttca cccacctcgc  32400
ccctcatctg ctgtttagca cctggcacgc cgtgtatact tactgattat tacattttaa  32460
tggcaaatta tagtggcaaa cgtatgcatc tttgcacaat tgttgtacag catgatgaac  32520
aagtcattaa tagtaaagaa taaatgtgaa agtgagaaaa atctgactgc caaagttttt  32580
actccttcct tccctcccca gacttttaaa tgaaagttta gggataatcc cttagttgtc  32640
ctgctagtag gacttgcaat taaaagaatt gggccaagaa cacttctacg cttctccttt  32700
taggtttggg tgtaaattcg gggtatttct cactgatgaa agcctggtgc agggcagacc  32760
gtgggaagct ttcatttccg gaatggacca tcaacatccc ttggagaaga attctcttct  32820
ccagacccag acctggtgtc ctggcaccca ttgggcaagt gggtcctaga agacaaacct  32880
ggtcagagcc tggaggctgc ttagcattcc ccacgcacat tagcagctcg gagagctcag  32940
gaagccgcag cccctccttg cctcaccagc ctggatcagg acagcatccc ctggaagaca  33000
cacagggcct ggcctctgat tacccagcct ggagggaaag ctcaatcgag catcatgtca  33060
cccggtgccc ccatgcaggg tggcactggt gagaccccca agccaatgat accacctcac  33120
aggagtgcag gcccattgtg gccagatcat cttgactttt caagataaat cagaaatcgt  33180
atttccatga gatatcccta tttgcaagtg atggtgacta aattagaagt ttttgaatat  33240
tgtaacatgt tcgtaggctg tttgtctggt ttaaactcta tctggaggaa ttcaagctag  33300
acttcaggaa taacttcttg aggcaaggat tttgagacct tagggaaaga aggacgtctt  33360
gggggtattc tgactgttgt cctcctggaa gggaagaaca gagaactaga agactgccct  33420
tagcgaagtt caaagcacct aagcccggga ccctcagcaa gtgttcttga gtcacagatt  33480
```

```
ctccctgagg cgcctctttc tggctccata gaatggctga ttctgtaact cggtgagttt  33540
gctttttttt tttcctccat cacccaggct ggagtgcagt gaagctggag tgccgtggag  33600
cgatcactgc aacctctgtc tcccaggttc aagcaattct ccttcctcag cctcccaagt  33660
agctgggatt acaagcatgc agcaccacac ctggctaatt tttgtgtttt taatagagac  33720
ggcccgaagt gctaggatta caggcatgag ccaccgcggc cagccataac tctgtgactc  33780
ttgttacaaa ggccttatat tttgctcttt gagggtggtt ttggtttgat gcctgttggt  33840
tgccatcttt taactaggga tgttttatca aaatgcccag ccaaagtgtc caaacaaatt  33900
ataccttaaa gtttgaaaat gtctggcact tctaattcaa tgcctgttgt gccaggcact  33960
gggctgctga ggaactgagt cccgtccctg caggctagct agagaacaca cacacacaca  34020
cacacacaca cacacacaga gtggtcttac aagtcagttt tatattctac ctatatgcaa  34080
taaaggtatt attatgttga ggtgccttga tataaaaatt tttcttaaag gagaggatgc  34140
ctaaaacagg cattacctga aacctcctct ctccagcatt ggttgtcttc tgtcatgact  34200
cagggttttc actgagaatg ggatggaaat gtggtctaaa gatagggcca atgttgggac  34260
tggatcccct ctgggaagtc agaccaggct agggcaggtc cttgaagcca tcaggaaaag  34320
cctctggagc cagaaacaaa acaaaaaaaa aatggtgtta actaaactca gtctcaaatc  34380
ctgaatagga ctcaagtcaa gcaaaataat taaaggagtt agcaaagggc aagtcagaga  34440
gaccgagcaa caccaatgtc ttccgggagc cctgtggcga gtgacagagc ctggactctg  34500
gagtagaact catcttgtgt cttcttctgc cactcgttag ctgggtgacc ttgagccaag  34560
ccccttaacc tcttggaccc tatgttctta tctctaagta ggggctggta atatcttccc  34620
ctttgaggaa tgccctctaa ggggtgttgt gaagattcgg taaggtggca ggggtaggac  34680
tcctggccag aaacaggcac ataataaatg ctaagtctct ccttctctcc acctgctgga  34740
tgctgtagat actaaggatt tcgatgtgaa tgagacaaaa cccctgcctt ccaggagcct  34800
ttgagaatca gagaactaga cccatttcca gaacaagggg atgcagggtc tggataaagt  34860
tttggggatc aatagagcag agggctccca gaggatccca tagggttgac tcctaactca  34920
agggcatgag acaaccccca ggaagggcac cctggaaggg gtccggctgt ccctgattta  34980
cttgtgggca ctgggggaat gcccggagcc atccagccct cagggctctg tgtgattctg  35040
ggttcctccc ataaaagata atcagattct ttcacgttaa tgtctttctc cacctcattg  35100
cacatcatgc agctattcat tgactcagca agtatcagct ttgcatgcga ccttggccta  35160
cccactttag cttttagtaa tagctccctt cttgaataat acaaccagtg gggaaacaga  35220
acctaactct tacctctggg aggcttattt gctttgagaa catatgtcct gcagttttgt  35280
tcatatggca gtgaagtttc gtgcacacac tctagagcca ggcagcctgg gttcaaagcg  35340
cagctctgcc aggtcctaac tgcatgaatt tgggcaagtc gctcaacctc tccatgcctg  35400
agtttcctca tctgtaagat tggagcaatg gtaatacctg ctttttaggg ttgagaagag  35460
aattaaatga attaagatgg gtaaagtgct tagagtggag ctttgcaagt agtaagtgct  35520
atgtaagtgt tcgatttaaa atgaaagacc cttaaataca ttctttgttc atttcacaag  35580
cccttcattt cacaacctta catttcacaa ccaagctctg tctcccctgg aatccagcca  35640
taactctgct cacaagtgtg agacaggccc cagcagagct gcacgaagag gagagaaggc  35700
agccccccag actcccaacc ccctgtccaa gatggcaaaa ccagaacaca gcctctgtac  35760
caccccagca ggtattcaga atctgcaatc tccaaagccc acttcaattg taaatgtaga  35820
gccacgtgcg ctttaagtca cctgtcactc tggaggctct tttgctcagt tcctcaccat  35880
tagcagggat gacagggagt gcaggagtgc ggtcgactcc cagatattgg agagcgctgg  35940
gctagctgcc cattctcccg gcctccactc ctctttgctg tccagccatc acttgctctt  36000
tgaaggcaaa caaaacagaa aacagtgcca aaagtatggg aagaaagcca gcttctcccc  36060
tggggtgcct gtgatgccat gcccaccctc cctgaccacg cagcccctgt ggaccctcag  36120
ggccccaagc ccccatttcc atcacatgcg tacacccatg tgtgtccata gccgcccatc  36180
tcagtcaata aggctgctcc tgcccacttg gaatagtggt gacaaccagg agtggcttat  36240
gggaactatc ccaatggcct gacagcatgt ccgctgcaaa ccgctgaggt aggacactgc  36300
cctcatgtct agctgatcag caagaggcgc agttgctttc ttaggtaaca ttgctgctgt  36360
gtcctggcca ttgctggggg gtggcactta atctacacca gaattttccc tcctgtatct  36420
tccaagctgc ttggatcttg gtgctgaatt aggttggact ttgtcttgtg gggaagggag  36480
gactatagac cctcaacgta agcaatggtc agactattct aagaaaactc gccgaattaa  36540
agcatgaggt aaatttagtt ctgacttctg tccaccccac tgccactgtc cccttttatc  36600
ccatgatccc ttgcttttct tttcctcctc tctccctatc tcttgtgttt gacgcatgat  36660
aggaattcag aaatatatgt ttgtggattt gtttattcac gtagcaaacc atttcttgag  36720
tgcctaccat gggccaggta gaatgggcgg ccccgggctg cagtggtttc ttcagcccct  36780
ctccagggtt tacactgtgc aagacggttt gtgatgggtc ctcccatcga ggaccacact  36840
cttctttctc tgtgcccctt ggtcctcagt ctctgacccc acttcaaagg cagcattcac  36900
tcagggaagc tcccatacaa tgctagtcag agtaaaagtt tggacaaatt gccaggaagc  36960
agcttgtcag tatgcataaa cagcctttaa aatattacta ctctttgacc cagaatttca  37020
cttctaggaa tctgtcctaa ggaagtagtc acatgcaaaa gatttatgta ccaagatgtt  37080
catcaaagtg ttgttttata acaggaagtc tcagaagctg gataaatatc caacctctgg  37140
aaatggttag atagaatagt atgtagccat tagaaaatta tgtctatggg gtttaaaatg  37200
tcatgggaaa acacttctga cataaaagag catgagaact gtatatttag cataatctta  37260
actatgtttt agaatgcaca ggaaaaaaat gtacaaacat attcatagtg atgtctctgg  37320
tggtaggatt atgatcagta agtacttctg tctcttcata ttttcctgta tttgataata  37380
catgcatatg ttgtttttaa aataagaaaa attttaagtt taaaattgga gctgaaaagt  37440
gtttttaggt caggcgaggt ggctcacacc tgtaatagca ccactttggg aggctgaggc  37500
agtcagatca cttgagccca ggagttcgag accagcctgg ccaacatggt gaaaccccat  37560
ctctactaaa aataaaaaaa ttagccatgt gtggtggcac acatctgtaa tcccagctac  37620
ttgggaggct gaggcatgag aattgcttga acccaggagg tggaggttgc agtgagccaa  37680
gatcgtgcca ctgcactcta gtctgggcaa cagagtaaga ctctatgtca aagaaaaaaa  37740
aaaaagaaaa gccttttttaa acagtagcag acataactat ataatcctta ctaagctgtc  37800
ggtcaaattt ttatttatat atttatttta ttcatttatt atttttagac agggtctcac  37860
tctgttgccc aggctggagt acagtggcgt gatcatggct ctcttcaaac ttgacctccc  37920
gggctcaagt gatcctccca tcttagcctc ccaagtagat gggaccacag gtgcatacca  37980
ccacacctgg ctaatttttt ttattttttta tttttagaga tggtgtttac tatgttgccc  38040
aggctagtct caaactcctg ggctcaagct atcctcccac ctcggcctcc cgaagtgctg  38100
gggttaccag catgagccac tgtacccagc cctcaaattt ttaaaaatct ataagagaca  38160
ttattggaca attagagaaa ttcacatatg gacttataat agtatcagag tgtgtggtgt  38220
```

-continued

```
gatggttctg gagggaatgg actttttctt tggagacagg cttttctatg cccacccttt  38280
tatcttgcta acttatcatc atccaggttc cagcagaaac attacttccc ccaggaaatt  38340
tcttaagggt gcagtatcat gatgtctgca gcaaattctc aaatagctca ggaaaaaagt  38400
acgtgtgtgg tatgagtgtg tgtatgtatg tgtgtatata tatacacata tatacacata  38460
tatatacata tatgtgtata tatatacata tatgtgtata tatatacaca cacatacaca  38520
tatatataca cacacacata catacatgta tttttatata attatatatg cagagagtgc  38580
aaatgttgcc aagttaaaga ttggtgagtc taggtgaagg gaatatggta tttattgtat  38640
tatttgtgca acttttctta agtttgaaaa ttttcaaaac aaaaaattgg aggaagaagg  38700
catgccagtc taccccaagc cctccattgg aatgctgaaa atctaaacaa tgtgatttgg  38760
caatttcatt tcttttctgt tgtgggccag tagtccttag atgttgggga agggggtagt  38820
cgctgaggtg tggttgactt aggatggaag aagcagaagt caagactccc agggtcaaag  38880
tggtttgctc tgctgaccca agtgtgggag gcccagagtc agcgtttcag gtgtgctaat  38940
tcagcatggt tctattcacg gccaaagtcc accctgggca cctctctggc agcaatcttg  39000
ggtgactcta ctaaggccag gcctccatga ccctatgtct ggatcccata tctccacctc  39060
tcccactgtc tcaggaacgg tgcttagctt tttcttttcc ctctcctgtc ttctttgcca  39120
gcatgtagaa agtttaaata attcccctct ttacaacaaa acaaaacata ccccccttcag  39180
tcaaccaccc tagctctctt ctccttttcc cagccagatt tttttaaaag catcctaggc  39240
caggcgcggt gactcacgcc tgtaattcca gcactttggg aggccaaggt gggtggatca  39300
caaggtcagg agatcgagac catcctggct aacatggtga aaccccatct ctactaaaaa  39360
tacaaaaaag tagccgggag tggtggcagg tgcctgtagt cccagctact cgggaggctg  39420
aggcaggaga atggcgtgaa cctggtaggc ggaggttgca gtgagccgag atggcgccac  39480
tgcactccag cctgggtgac agagtgagac tccgtctcag gaaaaaaaaa aaaaaaaaaa  39540
aaaaaagcat cctcagcact ttggcaactc catctcctcc caacatgtcc ctgttactgg  39600
aatccagcca ggactcagcc ccgatctttc tactctaacc agttgtctca gttaacaagg  39660
acaggtttat gctgcagtga caaacaagat cccaaattct tgtggcttca cacatctggc  39720
accacctcat cttccagcct taggagtcat cttttagttc cttgaaaact ctttacagtt  39780
ttctgttggg gccttgtcat atactattcc cctggaatgt tctttcctat cccctccctt  39840
tcaccttgct aacttgtgcc catccttcag gtctcagcag aaacatcact tccttgggga  39900
agttttctcc aacacccaca ctacacaggt gtcccatcta cactcctatg actttgtggt  39960
acttgtctca cttcattttc cactgccttc cccacaaggc acctgcacaa gggcaaggac  40020
cgtaccactg tacctatgtc actcattgct gtggtcacct gcactctggc tgcctacctt  40080
aactacacat tagaatcacc tgaggagctt ttaaagccac aatgcaagac tccaccctag  40140
gccaattgga tccaaatccc tggggtaggg ccagacatca gtggagttat atatacatat  40200
atatattttg tttgtttgtt tgtttgtttt ttgagacaga gttttgctct gtcacccagg  40260
ctggagtgca gtggcgcgat cttggctcac tgcaagctcc gcctctcggg ttcacaccat  40320
tctcctgcct cagcctcctg agtggctgga actacaagtg ctcgccacca cgcccagcta  40380
attttttttgt gtttttagta gagatggggt ttcaccgtgt tagccaggat ggtctcgatc  40440
tcctgacctc atgatctgcc tgcctcatca gcctcccaga gtgctgggat tacaggcatg  40500
agccactgca cccggccatc agtggatata tttttaaagc actgcagaga attctgttgc  40560
atcagcttga gaaccactga tctgccttgt gcttcacatt taaaactttt ttttaatgaa  40620
taaataaacc ccaaaaaatt aatctcccta agcctcccta gaagatagga tggtaaggat  40680
attttcctag gtaaaaatat gttaatttca tatttcatga aatttcatgt ttcatttcaa  40740
tcaagctctg tcatacacct tacatggggc aagcccagtg cctgggcagg gtgtaattat  40800
actcattaca caggcaagga aaagtcacat taggtgatgg agcacaaata ggcagttaat  40860
ggtttcaggg ctagttagga tatgtttgtc tttcaattgc aagtaataga agcccaaaga  40920
aattggttat ttatataata taattgattg gttcccaaat ttgaaaaatt caggaataga  40980
cccagcttag gtacagctgg atccagtcac tcaaacaatg tcacaaagaa ccctttgaca  41040
ggaatgtatc ctgtgttgac tctactttgc tctgagtagt ctttccccag gtgatgataa  41100
aaatggtcat catcgccagg cttgtgtcct gtttagtagg aatatacaag aagagctcag  41160
taaatgctgg ccccaccact aagcaaaaac aaaacttttg ttgttgttat tgttgtttta  41220
aataacagct tagacctttc ttctttcctt gttattctct ttcatctgta atccagtttt  41280
ctacttctga agtatagaat gttctgatga tttattcttc attacccaca acttgcacat  41340
gtttatttaa aaatgccagg attgcctggc cgttgtgtgc tgttaacctt tgtttgctgt  41400
tagtggatcc ctgaagttca ggctcccagg ggagcagata atgggtatcc agttcctgca  41460
atatccaccc tctggcaagc caagttcctt cctgggtaag gttttgccta cctgcattcc  41520
tagggaagtt tctgggcctg accaccaagc cagctctgag aaggggtgca taagccccac  41580
catgctttgg ctctgtccct atagaatatt ttatgttgtt actgaaaact aaaggaagat  41640
gggtgcggtg gctcatgcct gtaatcccag cactttggga ggccaagaca gattgatcac  41700
tcgatgccag gagttcaaga ccagcctggc caacatggtg aaaccttgtc tctacaaaaa  41760
caaaacaaaa caaaaattag ccgggtatgg tggcatgcac ctgtggtacc agctactcaa  41820
gaggctgagg cacaagaatc tcttgaacct gggaggtaga ggttgcagtg agccgagatc  41880
gcactactgc attccagcct gggtgacaga gcaagattct gtctccaaaa aaaaaaaaaa  41940
aaagaaaagg aaagctaaag gagagagact aaaatgatat caggttcctg gagaacaaac  42000
agacatgatt ttgcttcatg gcaggacagc cggaagaagt gggattatat cctcacatta  42060
caaataagaa aactgagact cagaatggtt aagtcacttg tcccaggcca cacagccagt  42120
aaattacaga aacagaattt gaacccaaat cttccagctc caaagcttgt gttcttttca  42180
ctacctcctg cttaattttt taatttctaa gattagaccc ttcatctatc catgacacct  42240
gcctgtcatc ccctgaaaaa aggtgaacgc cgttcagaaa tttttctagc ctgagctcac  42300
tcccagttca cttatttttg ctttgtcatg gctgcccagt ccccacttgt agaccaggaa  42360
taggtcatgg ctgcggggac tacacgctgt cgctgctgca agggccggcc tctgtttccg  42420
gggctgagtg ggggccagac ctgccaggag caccatcttc tgtgggtcct gcctggatgt  42480
cacatcccgg ccccaagaag tcactgcaaa ccttcgtatt attgagcttc acatcctaga  42540
atttgctgtc actgtggctg ctgcatgaag ttgtcctgag agaaacgggc attgtcatta  42600
acagggaaat tgatggtctg ggggaaaagt catcctcatt ctcttgcaga tctatgggtg  42660
attgagactg gctgatgttg aaggggtttc tcagccatcg tgtgccatgt tatggaacag  42720
tggtgtagcc agccatttga cacccagcgc tgacctttgt ttaacaacct cacctatata  42780
tgacaaaatg attgtcagaa ataatcgtgt aatgaaatga ctgtaataat ggccagaaaa  42840
gaaacgcaga tagtaaaatg tttctcttgt tgaactctgt acatataatt gcaccaggat  42900
tttttcaaa taaaaagtaa atattatact acaaaaaagg gaaaaagcac aagcatttat  42960
```

-continued

```
taaatagctt tctatatctt tctgagtttt gatcctttga ttgcagactg atgtaatatt  43020
ttatgtaaat cattgcttgg ttactaagtg aactttaaga aaagtgagac gtctgcagaa  43080
gttgcccata atttagcagc tactgtattg taccattgat gtacggcttt attttcttga  43140
ttaattattt aaacaatata attcacaatt ttaaaataat aaatttccac ttaaaatggt  43200
atttaaactc agcaaaatat atcatctatg agtaaaattt gtatttacca agcaaaaata  43260
ttacagtttg tggttcacat gctgtctcac tgttttaaat tttaaataca aaaactccaa  43320
gtaggctggg tgtggtggct cacacctgta atcccagtac tttgggaggc tgaggcaggc  43380
atatcgcttg agttcaggag ttcaagattt gcctgggcaa catagtgaga tcctgtctct  43440
actgaaaaca attagctggg tgtggtggca catgcctgcg gtcccagcta ctcaggaggc  43500
tgagatagga ggatcacttg aaccctgggg gacagaggtt gcagtgaggc aagattgcac  43560
cactgcactc cagcctgggt gacagattga gaccctgtct caaaaaaaga aaaaaaaaaa  43620
agaaacacaa aaactccagg tggtcgcaca gaatgacagg actgaagtaa cttagctcca  43680
atttctgtct tcataatcac tgtcctacca ttgtctgtgc ttagaatcta cttgcttaat  43740
gcaggaacat gtgttctcac agagatggaa aatgcaaatg gcgccagaag caagctggaa  43800
attctgaacc attaagaatt tactctctgc caggcacggt ggctcacgcc tgtaatccca  43860
ggactttggg aggctgaggc aggcagatca tctgaggtca ggagttcaag accagcctgg  43920
ccaacatggt gaaacttcat ctctacaaaa atacaaaaat tagccaggca tgatggtggg  43980
tgcctgtaat cccagctact cgggaggctg aggcaggaga atcgcttgca cctgagaggt  44040
ggaggttgca gtgagccgag atctatctgc accattgcac ttcagcctgg gagacagagt  44100
aagactccat ctcaaaaaaa aaaaaaaaaa aaaagaactt actctcaaaa taaatacgtg  44160
tggctgactc cacatatggt agggccaact gtataactag aagttctcca aataacttct  44220
gtggagaaaa aaaagtttat taaaggttaa ctttttaaa gtgctaacta gaacccttact  44280
aacactgaga tcgcaccaat tgtttataac ttagacaggg ccgggtgcag tggctcatgc  44340
ctataatccc aacactttgg gaggccgagg caggtggatc acttgatgtc aggagttcga  44400
gaccagccta accaacatga tgaaacccca tctctactaa aaatacaaaa attagccagg  44460
cacggtggta cacgcctgta atcccagcta ctggggaggg tgaggcagga gaatctcttg  44520
aacccaggag gcggagattg cagtgggcca agatcgcacc attgcactct agccccagca  44580
acaagagtga aactctgttt caaacaaaca aacaaaaaaa aaaacctctt ggaccaggaa  44640
aatatttttt aagggaggag tattttatca ctggcattgt ttaggattgc aggcacatga  44700
tgctaatgaa aagcagacta actattagtt ggttttatta ctgtttttga actctctctc  44760
tccctttttt tttttttga gacagagtct ctctctctgt cacccaggct ggaatgcagt  44820
gactgcagtc tcagctcact acatcctctg cctcctcagt tcaagtgatt ctcgtgcctc  44880
agcctcccga gtagctggga ttacagggca ccacaccagg ctaagttttt gtatttttag  44940
tagaggcagg gtttcaccat gttgcccagg ctggtctcaa actcctggcc tcaagcgatc  45000
tgcccatctt gacctcccaa agtgttggga ttacaggcgt gagccaccgt gcctagccct  45060
gtttttgaac tctctagaga cagtccagcc ccttattact tgtcctgagg cagctgctcc  45120
cttcacctgg ccccccgcat tgtgttccgg acccttgtcc tggtggtgct aaagaatatc  45180
tctgtcgatc ctttggggac tggggaaact gaggcccagt gccacgcgat gccatttgtt  45240
cagggaagat taggtcatct gctaggtccc cagtcacttg accttcttcc cagacaggaa  45300
gaagctgctc tgggtctctc agtgctccac gtgtctttgc acattgaaat gttttctgat  45360
ttttttttt ttttttgct gttacattta cttttaaaaa ataacaagca ataaaatgtt  45420
acatttgaga aggttgaaat gagaattgat ttgagttaaa ttctagcaga tttttcttag  45480
aagaatgata tcatcatctc cagctacctg caattgatct actctgaatt aagaaagaga  45540
cttccatttg ttgtttatat tttgcactct tgatgtgttt ctttaaatta tggtcatggg  45600
ccaggtgtag gagctcacac ctgtaatccc agcaccttgg gactctgagg agggaggatc  45660
actggaggcc aggagttcaa gacctcgtct gtacagtaaa ttttaaaaat tagccaggca  45720
tggtagcatt cacctgtagt cttagctact tgggaggctg agatgggagg attgcttgag  45780
ccagaacttt gaggctacag tgagttattt tcacgccact gccctctagc ctggctgaca  45840
gagcaagacc tgcctcaaaa aaataagtaa aaaataaatt aaatttcaat cattagcagt  45900
cattaggata tttaaataca gtatgttgaa tcaaagttac gcatgtgtgt attttttttt  45960
ccagagagtt gtttatcatg tgggttttaa tttaacttta aaaaaatgtt ggctggacag  46020
ttgcccaaat ggtatcatca gccatttggt tgagaacgta tgtcctgcgg gctcctctgt  46080
cactggagtt ttgctagctg acagccactg gctagttaga gactgcagtc agcacagatg  46140
caggcgtgga cttgcgcacg taaccatgtc aatgcaaagc catcacttct taaaaattct  46200
gaaccctgct gtctgagatg gtggtgcagc ggatagaact ctgctctaag aggcagtagc  46260
taattccatg tcttctttgc ccttgactag ctgagtgact ttgcacatgg ggcttgcctc  46320
tctgttgcct tgtctgcaaa gtggaatcat cttttccttg ctagacagaa ggtggaccct  46380
ggacctatgg cctttttgag tttccccccc gcttcttaga aggacctctg atcctactga  46440
gtttaatacc cacgggttaa taattgggaa aagcaaagga agcgcttctg tttaggtaat  46500
tatatgcatg tttttgtctt tttctggctg gaaagatatc caagccactg ggaaggtccg  46560
tggctaccca gggtagccct ctctggggag ggctgctata tccaagagcc cctcatgaga  46620
atttgaaaat cgaccatggt agggcctgct gacttttgac agctaatggt gtgctgagaa  46680
ttgtccctcc aaagatgcct ttccattccc tcgggagagt ctgggcagcc cctactgggg  46740
gctgggatgc tggctcttcc ctcagcctcc accccaactg ctctcttccc tcctcccctc  46800
cccagccccc taatttctct cacaaggctt tgttctgcag caacctttcc taatgcagtc  46860
ctggcctctt cgcagcttca ttacataacc ttccgtggac tcctggtcca aggatcaccc  46920
cagaaagcca gtcagaggta ggcacgcagc tggggtccat ttacttacct tccccacccc  46980
ctcggaactc agaggtggtg caggaatttg gactccaaga attaacagct ccaccaccat  47040
caccagagcc aaaactcagg atgcatgtgc ttcatctgct gcttatttcc agctgagagc  47100
cagtggtgcc atggttcctt agggagccgg tcccctgatg ccggctcctg gccccaaatc  47160
tctctgatcc gggctcttcc agaatgtctt gtctccacca tcgcctttga ccaatggtgt  47220
ccctttgcct ggtaatgtcc cctttgcctg atgatggccc tgtcactcct ctctttagca  47280
cagaggaggc tgtttcatcc cttcaagcct gccctccctt caagtcttag ctcaagttca  47340
ccttctccgc agagccttct ccaatcttct tgactacgtc tcctctcagc tccagcaacc  47400
tctgtctctg gcactgattc cttacttagc taagagaatc acagacactt ggggctcagg  47460
acaatctgct ttctcttctc ttacccatgg ccttggactg tgtgtacctc tttgtctcca  47520
ctcccaaacc caacccccag agggcagaga gcatgttgtc tgtccctttg ctcagcatga  47580
agccatgcgt gtggtagatc ggcagagttc cataacttgt gttgaccgag gggtcacttt  47640
gctctgaaat taccccctgtg tccttcagta tttgcacaga tagcttcctg gccagaccga  47700
```

-continued

```
atatatccaa gggcatggcc cacctctgct cctgtttcca ggtccctggt gggggttagt  47760
tcatgccttc ctcataatct gcccactggc ctggtcctca aggtcttccc aactgctcag  47820
ccagagttga gaaaatgggt cgctccatcc tgtttgtgtc gttctctcct tcctggccca  47880
ctctcctgcc cacaggtatc caggggctgc ctgtagcatt agaggacata catgcacatg  47940
cgtgggcatg ggacactcac gtagcctcca agcacagcat caataatgca ttctgtgctt  48000
tatagcatgg aaagctgctc taaactttat tacacagtgg acatgtctga agcagctccc  48060
aaatccaccc ctgagtgtgt tggaattggc aagcctatca cttgggagtc tagttttttt  48120
gttcgttaat aatagatgct tcctgtggcc ccagcttggc aattttgatt taaagtgatc  48180
ttaactgaag agactaatgg acgggtctga atttgtgcct tttaagcaca aagtattgct  48240
cttaattaac tggattctat cctttgagca ggcagaggcc ttcccccaag ggcgtcatta  48300
acgatccaca tctggacatc ttccaaagcc ttcttctgtt tcaggccaac cgcaggtgtg  48360
ttcctgaaca cccaggaggc tatgagagcc acatatgcct cccaaataca cacagtgtgc  48420
atgcccaggg acatagagca gtgtgcaaag tcccattcca tctctctcca cctgggagag  48480
gatggctctt ctgtctgatt catggctcaa agtggtaaag gagctcccca ctccccgtcc  48540
cacgcctact cagagtctgc aaatatgtat gcgatatgag agctcgtcag ttagctgtct  48600
tcagtgtggc gcacatttga ggagtctgac tcccctccag cacaggccaa tgtgcactgc  48660
tctcctatct ttgtaccccc actgttgcac tgtgcagagg ttggagccat agaagtacca  48720
gagctgtgaa aggagaggcc ccctctcacc tctgccctgg tctccatccc cactttctct  48780
aggaagctag taggtgctga caggggagag aagggagggg aggggtccag aaacagtggc  48840
tcatgcctgc aatcctagca ctttgggagg ctgaggcagg aggatcattt gaggtcagga  48900
gtttgagacc agcctgggca atgtagcaag accctatctc tacaaaaaga aaaaatgtaa  48960
ttagctgggt gtggtggtgg gcacctgtag tcctagctac ttgggaggat gaggtgggag  49020
gattgcttga gcccaagagt ttgaggttac agtaagctgt gattgcacca ctgcactcca  49080
gcctgggcaa cagagctgag accctatctc aaaaaaagaa aaaaaaaaag aaaggagaga  49140
gagagaaaga aaagaaaaga aaaaaaaaaa agaagggaag ggaaagccca gaagagtgtg  49200
gggagaggag gcggccgtca ttctggggcc ctcagtgtgc acaaccagat aacacatgct  49260
ctgtgggctt ttgtaccatt ttgcttgagc ataaagaaag gaaggctgcc cctaaataga  49320
aagcactctg gaggcaaaca aatctgactc caatcctggc cctgccactt tcccagctga  49380
ggacttagac aagcacccta gcctcttgga cattctcaga gccatctgct gcaagtgggt  49440
gctgccatac ccaccttact gggcaggctt gggggaccaa gggtggtaaa tggctcagtc  49500
tttcatgatg cggccacaca gcaggtgcgc catccaggtc catttctttc cttcctttcc  49560
cccaaatcaa gttgtcatta aagtactagt ccacattaat gaaatcaact gtattaattt  49620
tctatttgct gctataataa atcatcagaa atttagtggc ttaaaccaac acaaatgtat  49680
taccttacag ttctggaggc cagaagccct ccataggtgt cactgggctg aaatcaaggt  49740
tttggcaagg ttgcggtcct ttctggaggg tccaggggag aatccatttt cttccttttt  49800
ccagcttcta aaggtttcat gcattccttg gctcatgatc ttctatagct atagtcagaa  49860
aaattttcca tcaatcatct tcaaagccag caatggcagg atgagtcctc acatcacctt  49920
gctctgacac cagttctctg cctccctctt ccacatgtca ggaccctcat gattactttg  49980
ggctcactct gataatctgg gatgatctct ctattttaga gtcagctgac tgggaacctt  50040
aattccatct acaaccccaa ttcctctttg ccatgtacag tgacatattc acaggttctg  50100
gggattagga cgagcctgtc tctgaaaggc tactttacat gaaaattcat ttttttaatt  50160
aagatttttt tttcctcttg agacaaggtc tcactctatg gttcaggctg gagtgcagtg  50220
gtatgatcac agctcactgc agcctcgacg tctctgggct caggtgatcc tcccacctca  50280
gcttccctag tagctggaac tacaggggtg agcccccatg cccagctaat tttttttttt  50340
tttttttttt gagacagagt ctcactcagt cacccaggct ggtgtgcagt ggtgcaatct  50400
cagctcacag caacctccgc ctcctgggtt caagtgattc ttgtgcctca gcctcccaag  50460
gagctgggac tacaggtgtg caccaccacg cccgactaat ttttgtattt ttagtaaaga  50520
tggggtttca ccatgttggc caggctggtc tcaaactcct gatctcaagt gatccaccaa  50580
cctcagcctc tcaaagtgct gggattacag gtgtaagcca acatgcccgg ccccagctaa  50640
tttttaaata ttttttttgt agagatgggg ttttaccatt ttgtctaggc tggtcttgaa  50700
ctcctgggct caagcaaacc tcccaccttg gtctcccaaa gtgctgggat tacagcatga  50760
gccactgcac tcggccttaa gagaagattt aataattaat actttacaac aagatctgga  50820
agaggtggga tgagtaacta aatgaggata caagtaaccc gggtcatatt tgctaatacc  50880
cttggtcaca ttgaacttga tatcttatca gattttccta atcagctcct ttagcagcag  50940
tgttgcagca tcttatctca ttttgttttt tgttttttttg cctagcacat gcctgtaaat  51000
cactggattg aggtgtttag atgtttgttg tcctttggat gcttcttata aatccatatt  51060
tcatggctcc ctggaaagtg ctatgcaaat gataagctgc aaggatggaa aggaaattgc  51120
agtgctcctg aattgtaaat gggcttttac gaggaggttt ctaattactc gctctttctc  51180
ttgaactgag gagttgaagt gtaggtggca gatccataac agataatcat gtgtgtgatg  51240
tgacttcagc ctgagcgtcg aggaccaagt cacagagcag gaacagccac tctccagtgt  51300
ccttggggct acgtctgagg agaacctggg atttcatata tgacctgcac tggctggggg  51360
gctctcttga cgtaacgtgt tccctctgag catgttacag attctgacat tcttatgttc  51420
cttctgtgga gagacatgta cttagtgacc taactcactt tagcatattt ttgctcatcg  51480
tttgtgtagc ttaaaggaat cagataatta cccccctcccc actactttcg gaagcacaaa  51540
tgcaatgccc tagaattgta ctggggactc aaaaagaaaa gagagtagta aaatctatta  51600
aaggggacaa agacagccta tatactacaa gctttctatt tttatggcag agaatgccat  51660
tttctaagta aacagagaac tgcatttgac ctgcaatatc aaatgcatgg atttgatgct  51720
ttggaaagca actgttttct gcgttaatct gggtgtcttc cgtgaaatgt cctcctgcct  51780
ttggcttaaa cactagcttt gtctacagcc attccatcct gaacctgccc aatcttgtct  51840
gaatcctggt ttcaccactg acaagctgtg tgtccttggg caagttactt cacctgtctg  51900
tgcttcagag tcctcatctg tgagttgggg aatctggaca gaatctaccc catagggcgt  51960
agtgaggatg tgttgaatta tcccaagtgg ctacacagag taagcactca aatgatgtca  52020
tcgttgtcat gattgctgtt accagagcct agagttcatt ctgatactcg agtctgtggc  52080
ccatccagcc caggtaagga atagttggag gagttgggca tgttcagctt gaagaggaga  52140
cgacagggga tatgggatag ttgaatctgt gaagggcccc ctgggatgaa gaactggcat  52200
gttctgtgtg gctccagggc actgagcagg acccatttgc caaagtctca gggacacagt  52260
ttctagctat agacagaaaa attttctgtc actcagagga tgaaaataga atgagccccc  52320
ttaagaggta atgagctccc tgtcattgga aggattccag aagagctagg taaccacttt  52380
aggtgctatc aaggggcttt tttctttaaa gtcctttcca aaagcttctg agattgcata  52440
```

-continued

```
aacaatagga agccatcttg gtgctttaac acaaactctc cccagtgatg agggttgagc  52500
caaagccaga ttggcaagca gagaggagac ttgtgtacaa ggagttcctc gagtcaattg  52560
ctttttcctt gttctagcca gccagagggc tcctgttgga aaacaggaga ccggagaggc  52620
tgaggcctga ccaaaccagc ttctgcaggc cagctgggag gccacaactc ctacctacgg  52680
gaaaactgaa gggcatctct atttttagat tagcaaaaga aaataaattt aagtttgagt  52740
ctcctttgca actttttaaaa gacatcttta ttgagatgat cattcacatt ctataaaatt  52800
cccccacttt gagttacaat tcagtggttt tagtcttcct tgatgatttt gatggtcttt  52860
tcttaaggct cttggaagac ccagaagcct ctcagacaca ggtgggtgtg gagggcgtag  52920
cacagaggca gacttctcat ttcctgggtc tcccctttaa tgactctcag agacccctcc  52980
ttcccccctgc ccctggcttc taccccaggg gtgtagagtt ttgccatttt ccaagcagaa  53040
cttcatttcc tcttctgtgt ctacactctt tgtgcttctt tcttgccagc tttttctcct  53100
ttgcccgccc ttccttcctt ccttccctcc ctccccccctt ccctccttcc ctctttccct  53160
ccttcccccc ttccaccctt ccccccttcc cccctccct ccttccttcc ttccttcctg  53220
cctgccttcc ttccttcctt ccttccttcc ttccttcctt ccttccttcc ttcctggtat  53280
gtgactaatt tctgtttcag gacataaatg ttgtccaggc tgttctttgg tctttctgtt  53340
ggataatgga catttggcat tgagagaggc tgcttttttct gaaatcatgt tcttggggcc  53400
cagaacctag gtgtgtgctt ctgactttgt tttcttcctg atccaaattc tgatatgtcc  53460
atttaaattg atctagaccc acagggcact gtgggacaga tcctcagtgg aacatgactc  53520
tgtaacgaga gcattttgtt ttgtcaaaat gagaacatat tattgccttt catctgattg  53580
taaacataat acatgtttat aaaacagtat aatgagacaa aaatgtagac actaataagg  53640
gaaaatctcc ctaattgtat ttctcttcac agagaaagcc cctgttgggc atatatactc  53700
tagtttgttt atttgtttga ctacacatat atgtattctt ttcttatgta taaaaattct  53760
gaacatgcac atttctgcaa ctactgtttt cacttgatga tgcatggacc tctctagagt  53820
gtacgtttct tcttccttac aaagcagttg gcttcgccca gggtgcacca ggacacggtt  53880
ttggctctgt ccccagggtg tcacgggacc aggggatgat ctcacagggt ctgccatctg  53940
ccctgcctgg ccggaggctg catcgagagg gccaaggggc accacgtgtc gtgggtactg  54000
tcaaacaaga gccttcagag ccttccacag tctttctttt gcttcccagc attgcttccc  54060
cgctggtgga ctctgaatct agaactagct ccaggcgcct ctccaaattc agacgggagc  54120
tggggcacta ttataatgca aatctaggca aagccctccc aataccagga tccagaatgg  54180
ggtggggccc tttgccctga aaagctgttt agtttgaaaa tacaaacagg agacagaaaa  54240
gtttggctaa attaatggat aaagttttaa cgatggtaac catagtaggg ttcatcgaca  54300
gccagcgatg gttctgaaca cttgacatgt attaactcac ctaatcccca cattttacag  54360
acaatgcaaa ggaggctctg ggaggttgag tgacttgccc caaagtcgca cagctcctaa  54420
gtgaaggatt cggagtggac tccaggcagc ctggtctgac tccctgcact gcgctgtgct  54480
tatctctggc cccaatgccg ccatgcagaa gtgtctgggg gcactttgtc tctgtcagac  54540
agaattcgga gatgtgtatg cttgccctgg tatggcactt ctcttttttt gagacagaat  54600
ctcactctgt caccctggct ggagtgcagt ggcatgatct cagctcactg caacctccgc  54660
ctcccaggtt caagcaattc ttgtgcctca gcctcccaag tagctgggat tatagatgtg  54720
caccatcgtg cctagctaaa tttttgtact tttagtaaag atgttgtttt gctgtgttgg  54780
ccaagctgat ctcgaacttt tggcctcaag tgatctgcct acctcagcct cccaaagtgc  54840
tgggattaca ggcatgagcc accatgcctg gcagtgtggc acttcttacg tgtgttcagc  54900
ggacactgtt tatcttctgt ccctccaaga cggtgctgag ctcaggtcgt tcattactgg  54960
cagacaactg ctgatttcca acagaattgc catcctcttc tcccctgcga ctttcagagt  55020
gtgacctcag actcaaaaat tagaagtgaa aacatcttaa aaactatcac cttttcttcc  55080
taatcctcct ctcccctccc tgtcttcctt gttgtcccca tctaatgaac tatcatggca  55140
aaaagagccc atttctggtc attttctgtg gcctttcaaa ctcccaccta ccccactgct  55200
cctgggtgca ttacccgaaa gctgagactt cagtgcagaa agtgccaggc cctctgtccc  55260
cccagatcgc cttccttgtc ttccctgtgc ttgcctgtca cattgtgtgg gttccagcgc  55320
tggaaggaat gaggaacaga ttctctggtt ctccttttga agtttacctt cgctccacca  55380
cttctgagac cttcccggaa gttgcccctt gtttctctcc tctccagggc tgccccagag  55440
ctgcctctca cctcttcctg ctgtcacccc accaccatca gggcagaagt tgggacaaag  55500
cctctcctac tggctcctgc ttttctccct taggtccagc ctcctcttct ccatcttcag  55560
gagtctcctt ctccactcac acgtcatgac ttcagcacct cgcatcagtc cagaatatga  55620
ctgcttgttc aagtgccacc tttctcatgc atttttttct agtgacaatc acagccaccc  55680
tgtggggcag gagtgtcatc atccccatgt ttcaaatgaa gaattgcagt tcagagaggg  55740
caagtgactg gcccagcctc aacagctagc cagtggaccc caccagggct tctgactcca  55800
gtccgggttc cctttccacc caaatccatg gagggagctg agccgagaac aggtgtcctt  55860
caggaagacg tgaagccaaa gcctccacct ccaaactcag gggcccaggg agtccaggca  55920
cccatccact cacaaggctg gatatggtgc attccaggag aggggttggg ggcgagtggc  55980
ctctctgtgt acccgtgggg atagatgcgc aagtggcatc gccacatcgt gagtcctggc  56040
ttcatgggtg agctccaggt ccaacgagaa gccaagcagg gggcccttca agctcagctt  56100
tgggcccggg tcggggtaca gggtagagcg ggcctcccca gcccctgcca tgaggccaag  56160
gcagtgcatc gttcgcagcg tacattcaga aaccaaagcc taggagctgg ttatcattcc  56220
ggtttacagc tgatggaaga gcaggtgctt ccgagaaccc acagtgctct ttggccagtg  56280
acccaagggt gcctctgaga ggcctcgcag cacccggagg tgctgctgag gcaacgccct  56340
gactgtaaga aggaccattc atcctcagag agtggccgtg atgctgctgc gacagtccca  56400
ccatccctcc cgactctcac tcccaacaga cttcccactg taaagctgaa ctctccagca  56460
aatcacctct cgccagactc tctcctcact ctctctgggt ccactagagg ttcctcagcc  56520
tctctttgcc ttggttttcc cagctgtaaa atggagcaaa gagggcctat gtacccacaa  56580
aggtgtggtt ggagcgactc ctcctacatt agggcctcga gtggggcttc atgattggtt  56640
ggtggaggtc tccaaaccca cccagtgcca ccgaaggctg agactgcaga tgcaatgcca  56700
caggtgtcct tcctcagcct gggcagctga acatcatgtg taaaacgggg ataataagat  56760
aataacagcc ccttgcacct atgtggctgt gaggattaaa caagataaat gtgtaacagt  56820
gcctggctat agaaatattt actcttgtta ttaagggaag aatatgtgtg gctaaaaagg  56880
gatcgaagat gtaaaagcca atccctcccc ctctagcata tttaagggta atgttgagtt  56940
ggtttgtgga ccatttgctg cctgttagag ctggaaggta gggacccccct ctcaacagcg  57000
atgctacaaa ttatacccat tggaggtcaa ccaaaagaca aagcttattg gctggacatg  57060
gtggctcaca cctgtaatcc tagcactttg ggaggccaag gcaggcggat cacttgagat  57120
caggagttcg agaccagcct ggccaacatg gtgaaacccc atccctacta aaaatacaaa  57180
```

aattagctgg gcgtggtggt gcacacctgt aatcccagct actcaggagg ctgaggcagg 57240
agaatcacta gaacccagga ggtgaaggtt gcagtgagcc gagatcgcac cactgtactc 57300
aaaccgaggc aacagaggga gacgcaatct caaaaaaaaa gaaaaaaaga caaagcttgt 57360
taataccagc atattgttaa gggaataaag taggctgcag aacaactggt gtaatatggt 57420
gccatgtagg gaaaattaca tgtgtgcata ggagaggggt ctgcaaggtt gtgccctaag 57480
atgttagagt ggttcctttg cttttctctt ttataatttt gtatttgact tttaaataag 57540
gaccataaat cacttttata aaatacattc tctccagccc ctactactcc tttaaagaat 57600
aagagtggtt tgcccaagaa agacagtttt ttttgctctg gttttcttga ttctgacatc 57660
agaggaaact gcttctcatc cacttggggc tctgggttca ggggattcat ttcaggcaga 57720
ttaaagtggt gaccaggggc attcgtggac acagggaggg acaggagcac catcagtttg 57780
tctcacacaa ccactgtcat cctcactgaa ggctgttgcc tgatcaaaaa cagtattggg 57840
ccaggcacgg tggctcacac ctgtaatacc accactttgg gaggctgagg tgagtggatc 57900
acttgaggtc aggagttcga gatcaacctg gccaacatgg tgaaaccttg tctctactaa 57960
aagttcaaaa attagccagg cgtggtgggt gcctgtagtc ccagctactt gggaggctga 58020
ggcaggagaa ttgcttgaac ccgagaggta gaggttgcag tgagccgaga tggcaccacc 58080
acactccagc ctgggcgacc gagggggact ctgtcttaaa aaaaaaaaaa aaaaatatat 58140
atatatatat atatatatgt caaaaatggg gtagttttta gatctatagt agttctaaaa 58200
acaaaggcca tccaagcatg acagatttac aagcactatt ggctattcca gtagttacaa 58260
tggaggagag aagcttttag ttaaaacaaa caaacaacac aacaaaccca gaaaccttag 58320
gtcaaaacca aaattgtcct ctcagacaca atctgggaat tttctcatga cagtgggcat 58380
tagccaactg acatcagcag caaccatccg tgtgcacaca gtggcaccac ctcctcccaa 58440
aaagcagcct tcatctatgc cctcatacaa tcgttgatta ttctctttgg attgaggccc 58500
ggaattattt aagtttcttc ttgccagcat gagtctttcc tttctgtatg ctccttatct 58560
tctctcttta atttggcagt tctgcttgaa atctgggtct ttcattagta gtagttcaat 58620
ttggttccag aacattctgt ggtgtgatgc aatgtgacca gagctcacac ttcagagctc 58680
ttcaagggcc agtcttactg agcacctccc agtggctgcc tgtgtgctgg gcgccacttg 58740
tggtgggcag gagagaggag gggacacaaa aggagacaca gctccttctt agaagctcaa 58800
agttggggac cagctgccac agaagagtat gtttagcatc tgagacacca agatccagcg 58860
tcacaagggt gtttattaag cctcctcatc tctttctttt tcttttttttt tttttttttc 58920
ctcaggcagt cttactctgt cacccaggct ggagtgcagt ggcatgatct cggctcactg 58980
catgcaacca ccacctcccg ggtttaagca attctcctgc ctcagcctcc ccagtagctg 59040
ggattacagg tgcccaccac cacacccagc taatttttgt gtttttagta gagacagggt 59100
ttcaccatgt tggtcaggct ggtctcgaac tcctgacctc agatgattca cccacctcgg 59160
cctcccagtg tgctgggatt acaggtgtga gccaccgcgc ctggccttgc tgttgattca 59220
tctatagtat gtttgacttg atgacctcca gttaccttag acagaggttc tcatctaagc 59280
tccaactttc catttccttt gtcctcgtct ttccccttaa cccctccaca tttctctcaa 59340
aatcacccca cttctaaaaa atactgttta tttttctttt aaatttcaaa ttatctatac 59400
tcattgaaat aaatcaaaat agcatggaat aagcgaaaaa aatggatccc acccttcccc 59460
actcccattc cctagggcta accatagtta accatttaat gactaggttt ttttgttgtt 59520
gttatttttt atttatttat tttgagacag agtcttactc tgtcacccag gctggagtgc 59580
agtggtgtga tctcggctca ctgcaacctc tgcctcccag gttcaagcat tctcctgcct 59640
ctgcctcctg agtagctggg attacaggtg cctgccacca cacctggcta atttttgtac 59700
ttttggtaga gacagggttt ctcaatgtta gccaggctgg tctcgaactc ctggcctcaa 59760
gtgatctgcc caccttggcc ttccaaaata ctgggattaa ggtatgagcc accgcaccca 59820
gccctcctgg gctcttttcc tttagttgca ctcgctcccc gctcctggag tagagggatt 59880
tccgagagac tgtgggctcc agccttcacc taggcccagg actaggatgc ctgccctaac 59940
atttatcttt ataccttaaa gcaaaacagc tggaccataa gcattcaaga acaaactgtg 60000
aataaggaga aagttctccc aggaaacaag agctttagtt ctgttgggcc agcccttata 60060
ttccttagct gttaccagtc actgcttgat ttaatctcgg ctatcacttg gcctgacagg 60120
tctgctgctg gtgccaggat gtctgggttt tgaagcctgg ctccattaca tacttcctgt 60180
gtgaccttgg gcaacttact caacctgtct gttcctcagt ttccccagct gtattatgtc 60240
agcataatag tttgttgtgt gaattaaatg aggtaataac tggaaatgct tcaaacatgg 60300
ttcctatcat gagaaatcct gctttccgcc taaatgtgct ggaaaattcc tggtggtgca 60360
gaacaggaga ccagagcaaa ggaaagacag ggtgcagaag ccaaaaatta ccttggagaa 60420
caaagcgcat gttaaggtta tttttggatt ctaggtttat ctctgcttgg tcttcagtta 60480
cctgcaagag atccatttag gggatttttg tttgttttta acgatagctt tattgagata 60540
taattcatat gccataaaag tcactctttt aaaatgtttc cggtatattc acaaggctgt 60600
gcagccttcc ctgtccttga ttccagtctg agtttttaac tgaagggata aggaggacca 60660
cgctttcccc agaccagaac cgcgggccag ggggcgattc tgctgagtca ccgcgggcgc 60720
ctggtgcgcg gcggcggagc ccgggacctt ccttggctgc cccctagcga gggccgcagc 60780
gcagcctgag acacccgccg gggccgctcc acggccgtcg gatttagact ggaagctcgg 60840
tccaggtccc cagcttgatg cgcccgcggt gtaggagacc agcccgactc gggcttcccc 60900
tgagcccctg gactcttgac tccagcaggg cctgggtaat gaacgtcagc tccccttcc 60960
caaaggggtt gctctgttgg gaaggcaccc gtttgataca gtagcataga gatgggtttt 61020
agcatcaaaa tatcagaatt caagccttgc tctctgctta ctagctgtgt gaccctaaaa 61080
aggtttctga acgtctctga gcttcagttt cctcatcatt ccttctcacg gggtggttgt 61140
gagcattaca gagatcctct ctgtgaagcc cctgtgagtg gctcatcctg agggctgaaa 61200
taaacatgtt attaataatc caaaactggc aagggatgtt gactggtccc cctcccttgc 61260
ccaaggagct ttctagaacc tgagttatca ttaccaaact gtactgcctt gagtaagaaa 61320
gttagaagga atgggaagga tggtggcagg tggaggaagg cggattggtc atcacctcct 61380
tgcagcaaga aacagcccca gatcgtggga aacctacaga cctgctagac agactaggag 61440
caaaagctgg ggctttaaga atccccaggg aggttctcct gagagagtag ccagttggat 61500
tttgtaagca gagatttgtt tggggaggag gtgacaacgt agggagcaga ggggcaaagc 61560
tgtcgggaat cctgccttga gggcagggat gtgtgttggg gggagttggg tcactggggc 61620
tcggtggcct tgggcaagtt tctacctctc aggtccttta cccacctagg gtcgccatcc 61680
tgcccacctc acaggttaca gtgagcctgg atgcactgtc atgggcaggt gcccaggaaa 61740
atggcagaca tgttccaaac agcacgcagc attccccagt gatgcccagg gtcaccttgg 61800
aggtgggcga gatgcctggg gtttctcgtc caccccacaa cacctcaggg gacagccaaa 61860
gctgtccctt caggtaagct gcacagaaga tgtgaactct gctgcaaaga ctctattctt 61920

-continued

```
tgggagcaaa agggacccag ggtctcacct gcacatccct gtccctgagg gcctaggggt  61980
tcttggaggc cccagccttg gcaaaatgag gaagaaggtg aaggttgtct gggcccctgc  62040
caggctcctt cctcggccac gcactcccct tcctgcacac acacccttct ccctccaccc  62100
catctccatt gttgtcagaa aagtcacaat aaaaaggtcc atattgtcta gttcccatac  62160
ttttaatttt taaaatttta tttatttatt tatttatgta ttttttgaga cagagtctta  62220
acccaggctg gagttcagtg gcatgatcta ggctcactgc aacctctccc tcctgggttc  62280
aagtgattct catgcctcag cctcccgagt agctgagatt acagatatgt gccactatgc  62340
ccagctaatt tttgtatttt tagtagagac ggggtttcac catgttggcc aggctggtct  62400
cgaactcctg gcctcaagtg atctgcctgc ctgagcctcc ggaagtgctg ggatttcagg  62460
tgtgagccac cgcactcggc tccacacttt tcacttatta aaagactgtg gtgtccatca  62520
atggatgaat gaataaacca atgtggacta tccctcccat tacccaagga atgaagcacg  62580
gagccgtgcc aagatctgga ttcacagtga aagaagccag tcaccaaaag ccacgtgctg  62640
tgtgacttcc cttatacgaa atatccagaa gagatacatc catggtgaca gaaagtagat  62700
gagcagctgg ggactggcga aggggagaag ggggagcagc tgtctatgag gtccagcctt  62760
tcttctgggt ttggtgagaa tgttttggaa ctagatagag gtgatagttg tacaacattg  62820
tgaatgtact aaatgccact gaatcattca ttttaaatcg ttctttacgt tgcatgaatt  62880
ttaagtcaat caaaaacagt tgtttgaaaa gagaaaagcc tatgggtagc ggcagcagtg  62940
attggattta tgattcgatt ccatggctca tccctcccct gcctcacccc ctcgccctcc  63000
gacgtcttct tcttttactc tgaactgtta tctttgttct catctctctc tctctctctc  63060
aaccctgcag acacttttcc ctttctttgt ctgcccccac cctccagatt tccgtgtctc  63120
cagtgtctcc ctacgaggca tgaattgaga ctgggagggt gtgattctga agaaggcacc  63180
aacagtgact cagctagccc cttcccccac cccgccccc gggcctcaat ttagctaaaa  63240
aaccacaggg acggactcag gaggcaatac ctttccaagg gtccctaaaa aatgtcccat  63300
tttagtgtcc aggtttcact caactttagt gcctccccta aaatgtgttc cttacctccc  63360
accccactgc atctaagtca ctgcctgaga aaacaggatt gaggaaagga gaaaggaaga  63420
gagagagaga ggaggagaga gagagagagg gaggaaggct gatggattta gaaaagaaga  63480
aaacaagtgg tctgaggaaa acagccttgg tgtgtttatt ttcctgtctg tgtatcgctt  63540
ctcggccttt tggctaagat caagtgtatt ttcctgtctg tgtgtctcgc ttagattaca  63600
gggatctgtg ggtgatgaca cgtctggtcc aggctgcgta gtcacctcaa gggcatgctt  63660
attgatgtgt ttttcaattc actatctttg catgggagtc ccaggccaag aggcacagct  63720
gcgccatttg tctgttggtt tagatatcct ttatccagtt cttccagaga aatcatcctg  63780
cccttctgga ggaggtgggc agcaggggtc agagatggga gggaaaggaa ggagccaggt  63840
ccttggctag gatgccaggg tcccctgcct ctcacctggc ctgggctgga ggcctcctgc  63900
tgtcctgtca ctgatcacta ccccgcccca gcctcctgag ttagaagaca caggctaaag  63960
tagagtattt cttcattgaa aaacccatac aaaataaagg ttcataaaaa ataaaaattt  64020
agactgggtg ctgtggctca cacctgtgat cccagcactt tgggaggcca aggcaggtgg  64080
atcgcttgag ccctggggtt catgaccagc ctgggcaaca tagtgaaacc ccatctctac  64140
aaaaaataca aaaaattagc caggcatggt ggtgcatacc tgtggtccca gcttctcagc  64200
ctatggaccc acatagaata caatgtcagc ataagaaggg agccctgggg tcaccaaatg  64260
gtttgggcgg caaagaacct gaaggttgag agaagtggct tggttaccca gctgttggat  64320
gtgagacctg gccactgctt cttccatacc ctagacctgc accctgacat ctcaagtaaa  64380
aagttggggg atgttttatg gtccaggatg aaggaagggc agtgaggggc agcggagcat  64440
cactttgcat ttctgtctgc ctcttactgg ctgtgtgacc tggggcaggt aacttcccag  64500
actcctggga atcataacac ctatgatgat gatgatgatg atgatgatga tgacacctac  64560
ctcaaggatt gccctgaagg gtcacagaga tgcctgcaag gcacctgcat ggagcaagcg  64620
ccccttctct ggcaggtgct gggtgagcac tacctgctgc caggccctgg ggctatggca  64680
ctgcgtgacc ctgcaagtcc tacctggcga agctgtcgtt cttgtgctca gtcagtgttg  64740
gttgtaagac tgagaagagt cacttcattt tgctctccag ggacatcttt ctgggtccta  64800
ttttctgcct atgtcaagta gcgcctcaag gatgctcctg aaaatgggct tgtctttctt  64860
aacatggcag gtaggtccca aagcattagc atggggcagc tgacctagcc cagccaatgc  64920
agtgcagtga ctcttgcaac cgagtctaat cagaaggtcc atgaacctac gagcatttcc  64980
tgtcccagga tcagggtgga ggctgagcct ccctgcttag agattcttcc catgcattcc  65040
actttttttcc ccaaaagaaa atattgaccc ttgagaggca cacagtttat ttattttgca  65100
tagtaaatag tagcctgtat tttaaggatg agttgatttc tgcatcagcc cctgtaggtc  65160
atcagccttc tattggtgca tctgactctc tctagccctg cagggatggt ggagggggag  65220
gggaaggagg gatctttatt ggaaaccagg acagtgagac tcattgccct gtcatctgct  65280
ctgtggtgct gaatgaggca gcccaacaga gaaataccct gagcgagcat ccccagcctc  65340
caaaacagtg gcgcattgcc ctgagtcctg ggaatgacct ttgattctcc tgctcctgac  65400
ttggaaccca tggaaacctc tagaagcagc tgaggaaaac ccaacatgaa aagcagaact  65460
ccacactgag aatataggag gtgatcggaa catacaatga ttcttgctaa gaccgattca  65520
cagtttttct ttttttttcga tcgaagaaat actggagaag cctaaagaag gagtctaaaa  65580
actctggcac gtgggccaaa actgtccttg agctaagaat gattttcaca tttttaagtg  65640
gttgaaaaat gaaataaaat aagatgatgt tttgtgacac atgaaagcta tgggaaattc  65700
aaattctaat atctataaat agtgttttat cagaacacag tcatgctcat ttatttatgc  65760
tcgatggctg ctttcccgct acaattacgt tgagcagtta caacagagac cacgtggccc  65820
acaaagcctt acaatattta ctatctggcc ctttccagaa aaaaatgtgc cgactcttga  65880
ccttaacctc agcaatttgg gaggccgagg caggcggatc gcttgagctc tggagttcat  65940
gaccagcctg ggcaacatag taagactcca tctctacaaa aaatacaaaa cattagccag  66000
gcatggtggt gcacacctgt ggtcctagcc actcgggaga ctgaggtggg aggatcgcct  66060
gagcccagga agtcgaggct gcagtgagct gtgatggcac cactgcacct cagcctgggc  66120
gacagagcaa gaccttgtct ccaaataaat aaataatgca aagtaaaata aataaaacca  66180
tataaaaagg aatcaattta aaattataat gaaagctggc cgggcatggt ggctcacgcc  66240
tgtaatccca gcactttggg aggctgaggt gggtggatca cgaggccagg agatcgagac  66300
catcttggct aacacggtga aaccccgtct ctactaaaaa tacaaaaaaa aaattagccg  66360
ggcacagtgg cgggcgcctg tagtcccagc tactcgggag gctgaggcag gagaatgtct  66420
tgaacccggg aggtggagct tgcagtgagc cgagatcgtg ccacttgcag tccagcctgg  66480
gcgaaagagc gagactccgt ctcaaaaaca aaaacaaaaa caaaaacaaa aaaaaattat  66540
aatgaaagcc aaggggcata gtagaacaaa ttttctagag ctcattaagt caaatgagtc  66600
accagttagt aaaacgcagt cacggggaag agagggcagg attctttgaa gcagcggctc  66660
```

-continued

```
tcctaaaaac aacccaccct tgtccagctg ccttccctcc tgagggtgtt ccctttgact  66720
gtgtgacccc catcccctat ttcccaaccg tccaagccca cctctagcat aatacgagct  66780
tttaatccct ctccctgacc ccaacccgat tttgaagccc agtctagtat tttctcaaat  66840
acacttcttg gctccattcc ttcctttcca tcacctctgc cttttcactg catgcttgga  66900
ccactgcagt cagctcccta tgaacagttg ctctctaccc atccaatcgg ccccgcctgc  66960
tgctgccaaa ttcaccgagg gcacctctgt ggtgctgcct gtggacaaag tccaagccag  67020
ccacctcacc cacctacagg tgagtgggga gcagccagcg tgtccagtgg tttaccccat  67080
cgccacagac ttggtgatgt gtcgatgtgc agagaagggg tgttggcagc cacaacacaa  67140
gcaaccccgc cccatgtgag atctaagatg ggcgtgctgg gagccacctc tgagaatcca  67200
acagaaggca gaggggagaa cggctcacac ggcacaaaca ctccttcctt tttttttttt  67260
ctttttcctt tttgaaagga gtctcactct attgcccagg caggagtgca gtggtgcaat  67320
ctcagctcac tgcaacctcc gcctcctagg ttcaagcgat tctccagcct cagcttccca  67380
agtagctggg attacaggta cactccacca tgcccggcta atttttgtgt ttttagtaga  67440
gacggggttt ccctatgttg gccaggctgg tcttgagctc ctgacctcag gtgatctgcc  67500
tgccttggcc tcccaaagtg ctgggattac aggtgtgagc catggggcct agcctccttc  67560
catttaaatg tatgcctaat ttgcccattg agaacggctg agacgcattt taagtggcca  67620
gggtctactt agagttagtg ctcatgacca ggcccaggtc aagcctggct ggccagatgg  67680
tgcctttgac ctgctctgtc tctgtgcaaa ggaatgagct gaaggatggg ggtgcagtgt  67740
gtgggcagtg ggctggggct ggcaggactc agtgactaag ggaagagaac tttcctcact  67800
accagcctgt cttttcaggg caccgcgggg ggctttggga cttggtgatg aacacagcac  67860
agagagctgt ccagcatgcg ggtccctggc ttctcacact tcccaggctc cttcagaggc  67920
tctctccaaa gggagctgct ctctctagaa cccatgaatt tggaatatag gcaaccactg  67980
cattggggac cactgacctc aaacatagag accagagcaa atggggctca tcacgtgaaa  68040
ctcatctgga actctagcag gttcttttat atatatatat atatatatat atatatatat  68100
atatatatat atatatatat tttttattat tatactttaa gttctagggt acatgtgcac  68160
aacatgcagg tttgttacat atgtatacat gtgccatgtt ggtgtgctgc acccattaat  68220
tcatcattta cattaggtat atctcctaat gctatccctc cccactcccc ccaccccaca  68280
acaggcccca gtgtgtgatg ttccccttcc tgtgtccaag tgttctcatt gttcaattcc  68340
cacctacgag tgagaacatg ctgtgtttgg ttttttttgtc cttgcgatag tttgctgaga  68400
atgatggttt ccagcttcat ccatgtccct acaaaggaca tgaactcatc atttttttatg  68460
gctgcatagt attccatggt gtatatgtgc cacattttct taatccagtc tatcattgtt  68520
ggacatttgg gttggttcca agtctttgct attgtgaata gtgccgcaat aaacatacgt  68580
gtgcatgtgt ctttataaca gcatgattta tattcctttg gttatatacc cagtaatgag  68640
atggctgggt caaatggtat ttctagttct agatccctga ggaatcgcca cactgtcttc  68700
cacaatggtt gaactagttt acagtcctac caacagtgta aaagtgttcc tatttctcca  68760
catcctctcc agcagctgtt gtttcctgac tttttaatga tcgccattct aactggtgtg  68820
agatgttatc tcatggtggt tttgatttgc atttctctga tggccagtga tgatgagcat  68880
tttttcacgt gtctgttggc gaactctagc agcttctttt cacaagttca tggagagagg  68940
tttcccactg agggaatcac atctgtctga tcaaaagagg cttgggaaat ggctctcctg  69000
ttcattccct gaaaacctct gatggaacca ctgccactgt ggcagcccca gcactggcac  69060
cccagccatg attggtgccc cagccacatc tctgctgtga gccccagagc cctggttaat  69120
taatcatcca cgtgttgatg gggagaggcc cattcacaaa agcgacataa agcccaggga  69180
gacgtggccg tggcaagaag ggtgtgggac tacattccgc cccaactga gagattcaga  69240
aaccagaaaa aaatggaaaa acatactgtg ctcttgggtg ggaaaactaa atatcatgaa  69300
gggagcaatt tttatagttt tggcctataa tacaattcca gccgaaatcc cagtggaact  69360
ttgagaattt gcaggaaaaa aaaaaatgtc taaagtacat ctggaagaca aacttacaag  69420
aaggtcaaat aattttgaaa aagaaaatga tatctaagcc cacctagaga ataagacttg  69480
agatccaaag ctaaatcagg aggctctagc aaaattgaca gataagcagg acagagtgca  69540
tggtgcattc acctggggaa gagggcagat tggtctacaa ataggcctgg gtccactgac  69600
tttagctgtt atatttgggg agaaactttt caacctcact ccatcttaaa cctaaaaata  69660
ttccagatga attaataaat ataaaaaatt agaccactaa aaatgtagaa gaaaatggat  69720
gatctttcta taccatagag caatggaata aatcacaaag gaaaacagat ttgactatat  69780
aaaacttaaa ccctgcccat caaaaaccat cagaaaccaa aataaaaggc aaccaactgg  69840
agaagatagt tgccacaaat atgatcaagg gttaatgtta ttcataaatt aagagcccac  69900
acaagtcatt agaataagca ctgagacctg aacagacaag caaaaagaat gagagtgggt  69960
cggcgcggcg gctcatgcct gtaatcccag cactttggaa ggctgaagca ggcggatcac  70020
ttgatcccag gagttccaac accagcctga gcaacatggt gaaaccctgc ctctacaaaa  70080
gtcataaata ttagccgggt gtgatggcac acgcctgtag tcccagctac tcaggaggct  70140
gaggtgggtg gatcacttga gcccgggagg tagagtctgc agtgagccaa gatcacaccg  70200
ctgcactcca gctggagcaa cagagtgaga ccctgactta aaagaaaaaa aaaaaaaaag  70260
aggagaaaaa tgctgatctc actagtaatt aaaacatcag gccaggcgca gtggctcaca  70320
cctttaatcc cagcactctg ggaggctgag gcaggcagat cacttgagat caggagttct  70380
agaccagctt ggccaacatg gtgaaatccc gtctctacaa aaaatacaaa aattcgccaa  70440
gcgtggtggc acatgcctgt gatcccagct actcgggagg ctgagacagg agaattgctt  70500
gaacacggga ggcagaggtt gcagtaagct gagatcgtac cattccagtc cagcctgggc  70560
tacagagcga gactctgtcc cagaaaaaat taaaacatca catatttaaa caactctagg  70620
atatcattta aaaaaacatt aatagactgt tttttagagc acttttaggt tcacagtgaa  70680
actgagtgga aggtacagag acttcccgta tgttccctgc cctccacgta cagcctcccc  70740
cactgccaac gtcctgcacc agagtggtac acttgttaca accaatgaat cctcattaac  70800
atatcattat cacccaagtt catagtttac attagtaaaa catcatcttt catctataag  70860
cacaaaaatt ttttggcatt tatttaggtg tatgattaac tcagtgttga caagactcac  70920
acttcatacc cacttgcact gcatctgaga agcaattggt gtctacagcc gctacaccct  70980
caacaagccc gatcttgttt gaaaagcaat tggtgatgct tctcaaaatt ctatggacaa  71040
agtcagccgg gcatggtggc tcatgcctgt aatccctaaa ctttgggagg ccgaggcagg  71100
cagatcacct gaggtctggt gaaaccctgt ctctactaaa aatgcaaaaa ttacccaggc  71160
atggtggctg gggcctgtaa tcccagctac tcgggaggct gaggcaggag aatcgcttga  71220
agcaaggagg cggaggtttc agtgagccaa gattgcacca ctgcactcca gcctgggtga  71280
caagagtgaa actccatcta aaaaaaaaaa attatggaca aagtttttca aaaagatatt  71340
taatgcaact ttatttgtaa tattggaaca tctgaggcca tttcagtgct aactattagg  71400
```

```
ggatggttag gaaaatatgg tacatatgtg gaaaggaaca tttggtagtt agtgcccctg  71460
atgtttacaa aggcttttag tgaccaacaa atgctcatgc tataatctta tgtgaaaaaa  71520
gcaagtagca taattgcaac tatattttta atgcatagaa taaaaggcta gaaggaaata  71580
tcacagatcc ttgacataca ttcccaaacc tttgtaaatc cgcggattca tgaaaacaga  71640
cacatttgca caagtgcctg atcttttctg ttatacattc attagaagtc aagccctggt  71700
gccacaaagt atctgccttt tcaaatgtga tcagaatgtt ctcttttgct tcaaggccat  71760
ttttcacgaa gcagtggcat ttttgcctct tcatcagagt caccgtgtgc cctggaggac  71820
tgagaacagc agagccgttt taggatggga cagggcagcc aggaggattg ggctcactcc  71880
ctactgagtg cctcactccc gtacagcccc catagaggaa gaggggttca aatttattcc  71940
tcagccagat ggcatgtgcc gcctgtcctg gaatttcaca tcacttatga tggaccaaaa  72000
ttccaaaagc tgaatccatg attgtcaaag tctggtatgg caggatgtca acagtaatcg  72060
tttctgggca gagggatgat tttctcttcc catcttgctt tgtataaata cattttctat  72120
aataaggttg tattactttt ctcatcaaga aatagcaaag tactgtttta ctcaaaatat  72180
gaatagagcc aggcatggtg gcagcttatg cctgtaatcc caacactttg agaggcggat  72240
atgggaggat cactttagcc caggagtttg agaccagcct gggcaacata gtgagacccc  72300
cgtccccact cccccaaaga aaacccacaa agcatttatc ctggattatt cacaggggcc  72360
aaaaaaaaaa aaaaaaattc aggcctccta tagccatgag ctacgaatat gaaaatatgc  72420
aaatgtgtaa gaaaagccag cacatccgat ttttactttt actttcacac ctctgtccac  72480
catgttccaa gagaagaaac ttggtcattg aaaggaatag atcaaatcca aagaacaaaa  72540
ccactgtgct cattaaactt cttagtgttc acaaagcttt agctgcaggt tgaatggggc  72600
aacccgaatt ggctggctca cctgggctgc agggagcaga gatcgcgaca ctgcactcca  72660
gcctgggcaa caaagcgaga ctctatctca aaaaaaaaaa agttcataaa ttcaaagtta  72720
tgaattattt ttaaaataat aataatttac aataaagatg aggacaaagt gtgagtaaat  72780
ggtggtttct atccagctct gttgagctga agtggcatct ccctgctggg gcttttgggg  72840
aagaagggtg tgtgttgctc ttcagatccc aagcctcatg cccctactgg gccctgtggg  72900
gtgcttctca gcccaccagg agagccaccg ttggaacaca cacgtggggg acctggtggg  72960
tgccggtgtg gtgaatgggg gccacagcct gactccagga agccagcaaa ctcggagctg  73020
gaggagtcag gacacccccg atgagtcaag agttggtttt gctgccagtt gacatctgat  73080
tgaaccatct cttcacttct ccgtgcctca ctttccttac cagacaggct ctgctgatgc  73140
tgtccctctc ctgttcagtc gtgccctcac cgttaaagag aaagagcaaa ctgctgggca  73200
gcagcattga ttttttaat gaagtggaaa gagagctggg aataacaagt cgggcccacc  73260
tcacctgcct cacctggtgg gtttatttgt tttgtttttt tttttttgtt ttgagacaga  73320
gtttcaccct gtcacccagg ctggagtgca gtggtgtaat ctcagctcac tgcaacctcc  73380
acctgccagg ttcaattgat tctcctgcct cagcctcccc agtagctggg attacaggca  73440
cctgccacat gcctggctaa ttattgtatt tttagtagag atggggtttt accatgttgg  73500
ccaggctggt ctcgatcccc tgacctcagg tgatccaccc acctcggcct cccaaagtgc  73560
tgagatcaca ggcgtgagcc accatgcctg gccgtcacct ggtggtgttg aatatgaact  73620
gctgcggtgt tggtaaatta agcaagcaga tagatgtaaa taacgcttgg gcaggaatat  73680
ggagcacggg atgaggatgg gcggccaact gttagagagg gtagcaggga ggctgagatc  73740
tgcctgccat gaactgggag gagaggctcc tctctctctt cacccccact ctgccccccca  73800
acactcctca gaacttatcc tctcctcttc tttccccagg tgaactttga accaggatgg  73860
ctgagccccg ccaggagttc gaagtgatgg aagatcacgc tgggacgtac gggttggggg  73920
acaggaaaga tcaggggggc tacaccatgc accaagacca agagggtgac acggacgctg  73980
gcctgaaagg ttagtggaca gccatgcaca gcaggcccag atcactgcaa gccaaggggt  74040
ggcgggaaca gtttgcatcc agaattgcaa agaaatttta aatacattat tgtcttagac  74100
tgtcagtaaa gtaaagcctc attaatttga gtgggccaag ataactcaag cagtgagata  74160
atggccagac acggtggctc acgcctgtaa tcccagcact ttggaaggcc caggcaggag  74220
gatcccttga ggccaggaat ttgagaccgg cctgggcaac atagcaagac cccgtctcta  74280
aaataattta aaaattagcc aggtgttgtg gtgcatgtct atagtcctag ctactcagga  74340
tgctgaggca gaaggatcac ttgagcccag gagttcaagg ttgcagtaag ctgtgattat  74400
aaaactgcac tccagcctga gcaacagagc aagaccctgt caaaaaaaaa agaaaagaaa  74460
aaagaaagaa agaaatttac cttgagttac ccacatgagt gaatgtaggg acagagattt  74520
tagggcctta acaatctctc aaatacaggg tactttttga ggcattagcc acacctgtta  74580
gcttataaat cagtggtatt gattagcatg taaaatatgt gactttaaac attgcttttt  74640
atctcttact tagatcaggc ctgagtggcc tctctttagc aagagttggt tagccctggg  74700
attcttactg tagccacatt aataaacaac atcgacttct aaacattcta taataccatc  74760
ttttggccaa attgacttcg cctcttcctc tctctttcca aatgaaatgt gtttcatttc  74820
actgtcagac cacatggttg gggaccccac agagcacaca gccctccctc tgccttccca  74880
tgctggccct tcacccactg ctggagtgcc aggttggtcc aagggttgga ccaagttgtc  74940
tgaggttgtc tcaaggttgg tcgaggctgt ctccgcgctg ggttgtgcta caaggagccc  75000
ttctttccat gggtgtggct ggcagtgagt gctcacagca acagcccaca gtgcagcccg  75060
agggcaggat ggactcagtc cctgcctcca tacccatttc taaggaggca aaatggcaaa  75120
cactctactt ttctctttta atgctaaaaa taagaaaaca ccttgcagcc cagggtatgg  75180
gtagtgcatg gaagccgtgg agttgtgagg tgggaagtga cctctgctgg atatgtctat  75240
tcaggaagat tgctggagtg ggtggggtct ctgggaggtc ccctgagtgt gggaagctgg  75300
gaccaccagc tttctcgcac agggagtggc catcccagct tggagaggtt ccaggactgg  75360
ttgggaggca cgtttcagat ttctatctgt tgaatcagcg aagatattgg attatgagga  75420
atttgggaat taggaaagtg ggtgcaggtg ggttgggggt aggtgaagga agacatgggc  75480
gtattggggg agcaggggct gctcagaggt gttccagaag ctctgggtga ggaggtgaga  75540
gggaccgggg aatgcagctc ggcccagcct ccctgcctga ggtcagccat cacgtggtga  75600
tggcaagatg gaaatgtgct ttctgactgc tccagccagt gctgccagat tcagctcccc  75660
agggagggca cctgagaggc tccaagccag gagatctgtt ttctcctttg ttttgttttt  75720
ttttgttttg ttttgtttta ttatacttta agttctaggg tacatgtgca caacgtgcag  75780
gtttgttaca tatgtataca tgtgccatgt tggtgtgctg cacccatcaa cttgtcattt  75840
acattaggta tatctcctaa tgctatccct ccccccctccc cccaccccct gttttctcct  75900
ttgaatcctt cttagaggcc gggcgcggtg gctcacgcct gtaatcccag cactttggga  75960
ggctgcggca ggaggattgc ttgagcccag gagttccaga ccagcctggg caacatagtg  76020
agacctcgtc tctacagata ataattttaa aaattatccg ggcatagtgg catgcaccta  76080
tagtcccagc tactcaagag gcagaggcag gaggatcact tgagcccagg aggcggaggt  76140
```

-continued

```
tgccgtgagc caagatccca ccactgcact ccagcctggg cgacagagac ccccatgtca  76200
aataataata ataataaata aatccttctc agtcccttcc tcactgtgtc cccctccact  76260
gaatttttcc acctcctctc ccacttcccc cactcccgct ttccctctcc ttctctcccc  76320
actccatctt tttctttctc tgctgtttct cgtccctccc tcctctccat cccacaacac  76380
tgcctaccct gtccctgccc caccctggtg ctcaggatgt gtgaagtgag gggtggtagc  76440
ccccaagacc tcaaccccga aggttagcct gttgaaacca ctttctccca gctgccccc  76500
tggcagttgg tgctgctggg ggaaactggg attgggggcc agattttgcc tcttttcctg  76560
acaaagagag atgaagagtt ctctcaccag gtgcctggga ctggggtgtg ggtgtcccag  76620
cctatcccag cgcatctgtt ctgcatcatg attaatagtg ctgctttcag ccgggcgcgg  76680
tggctcacac ctgtaatccc agcactttgg gaggctaagg tgggcagatc acaaggtcag  76740
gagttcgaga ccagcctggc caacatggtg aaacctcgtc tctactaaaa atacaaaaat  76800
taaccaggtg tggtggtggg tgcctgtagt cccagctact tgggaggctg aggcaggaga  76860
atcacttgaa tctgggaagc agaggttgca gtgagccaag atcgtgccac tgcactccag  76920
cctgggtgac agagtgagac tccgtcctaa aaaaaaagga gttttgctct gtcgcccagg  76980
ctggagtgta gtggcgccat ctcggctcac cgcaacctgc gcctcccggg tgcaagcgat  77040
tctcctgcct cagcctccca agtagctagg attacaggcg cctaccacca cgcctggcca  77100
gttcttgtat ttttagaaga gacggggttt caccctgttg gccaggctcg tctgggactc  77160
ctgacctcag gtaatccgcc cacctcagcc tcccaaagtg ctgggattgc aggcatgagc  77220
caccgtgccc agtcaactcc ttctcaaaaa aaaaaaaata gtgctgcttt ctctttcaag  77280
tgtcctgatt tgggtgatag taaatgccac tctacttata agggatctac ctcagaatgc  77340
taattgggac atttttgtag cactctactg ttggcagcag gtgatgctca caacagcccg  77400
tgagggtgga tgacgtccgc ttcacagatg acaaaggagc ctcatgctca gaccgtgggc  77460
tgccagagca ggtccatggc tgcagcccca catggaccat atttccccct tgtcactctt  77520
tccaccaagc tcccttggaa cttcagttat taagctctct tgggtggaat ccaagttaga  77580
atcacaacat gtgcctcata tggattgtgc cagtgaaaaa tgacattcta tttagaggca  77640
gggcagcctg gcttagagtc agtttaaaat atgtattatg ctgcaacaaa tgtaccatga  77700
tcctgtaaga tgttcacaac aagggaactg gatgtggggt atactgtctg tactaacttc  77760
acaagttttc tgtaaatcta aaactgttcc aaaataacaa gttcgtttaa aattaactcc  77820
aggagaccag gtacggtagc taatgcctat aatcccagca cttcggaagg ctgaggcagg  77880
tggattgctt gagcccagga gtttgagaca agcctgggca acatggtgaa atcctgtctc  77940
taaaaaaaat cacaaaaatt agccaggtgt ggtggcgcat tcctgtagtc ccagctactt  78000
gcggggctga ggtgggagaa tcatctgagc ccaggagttt gaggctgcag tgagctgtga  78060
ttgtaccact gcactccaac ctgggcaaca gagcaagacc ctgtctcaaa aaacaaaaat  78120
gaaataaagt ccaggaaaga agtaggtttt accactctta ttttctgaag agaaaactaa  78180
atttaatgtg taaagtgagg acaagttcac caagttagtg tttgagttgc ctaaaatatg  78240
tttgctaaaa ctattcaaag ctttcacata aaacatgatc agaagttcta tgccaaaaca  78300
tatgtgtgtg tatatatata tgcactatat atactgtata taaaaatgca aaatctaaat  78360
tgccaacctt ttagaaattg ctctgaaagg aaagcatttc aagataattt gcttacccaa  78420
agaatatact ttccaagaaa gcaagtaata cttaaggtgt tcataatcct catcaaatta  78480
attcttgcta ctgaaagctt acaaggagct gttttgatgt cgggtgtgac aggtttgact  78540
tggcagaagg tgtcacttta ctaacaacat tttaaataag tgacagaaga caagaaacta  78600
cacgttaaat gccagaacaa agagtgtcta agtggatgct aagagttgaa atatggctgg  78660
atacctgccc aagagagctg aaaagtagat gaaagttggt tacctataaa ctagtgcacc  78720
ctaatgaatt aaaaggtgtt gatgagttaa cttgttatgc cttccagata agacatgcaa  78780
atggggcttc ttcctccttc actacttcca agggatttaa caaggagacc aatgcaaatg  78840
ataaggactg tagggctcaa gctggggaca gattggggaa agggggacca tcatgcccat  78900
atagatgtcc ctgtgccctg gcagtcaagg ctgctgaaaa ataacaaaac ccagaagtct  78960
gcgtgatgct gcctctccat ttgtccaaag ccttcttgcg gcagtttgca ggcttttgca  79020
aaagctccag gaccaaggag ctatgttcat gctggaagct tgttcaggat tagctgttct  79080
ttgtgggatg ggtgcagcca gggccaggtg tccagggaca gtgttttaac aaagggcatg  79140
aggtgtctga tctcacagtg gaactccact tgcctttttt tcatcttctc attctgcttc  79200
atgcacagaa ccagccccat cctgaaactg actctaaatt actcccgccc caggtggagt  79260
gcctttctcg gagttcaaca gagccttcct gtcgcccaag ggacaactcc actgaatgcc  79320
caagccacac ccaaaaccta acaagtaaaa accaaattct gtgctccccc atcctgggcc  79380
attcctggtt tctctactgc tgttggtgat accaccatca gcttgtccat catgaccctg  79440
gccagttcct cccacaaccc tccacagcac ccagggacct cacctccatt ccatccgaca  79500
cagatctcct caccacaaac cttggttttg caacagcagc catgagacct ttacaccctc  79560
cgccccttcat cctgtccccc actgaggccc cagagccatt ccttaaagca gcgcgccaca  79620
aactataacc cacaagccaa ttctggtacc cagcctgttt tgcacagcca gtgaactgac  79680
aatgatcttt tcatacagcc agaaaaacaa aacaaaacaa aaaacaacaa aaaaaaaccc  79740
caccattctg agcatgtgac ttccatgttc aagatgtctc atgttcagaa aggcccctgg  79800
aaaaggagga aggggagctg ggcacaaagg gagaccctct cagctgagct cctcccatcc  79860
agacattttc ctggacttcc tatccaatga cttcccttag cttcttatca gccaccccctg  79920
tctgcccagg aggctggaag atgtggcctt ttaactgggc acagctctgt cctctatcat  79980
atcagggctc tgttcccaag gagggtagag agaatggaca ccaggtggac cctcagcagt  80040
ctgtgccaca gagggagtgt ttgcaatttc cagactaaaa gtccccatgt gcttgacggg  80100
gtatgtgact acaacgtgat gcttgacttt tcctcatatg accagagcca ctttgtccat  80160
ctggtacaat gtcagctatc tgctaggggc cctccaggat tcccagtcaa ttccatatct  80220
gcatcaccac cattggcact aaataaaata aaatactcaa gttcctgctg gtgagcatga  80280
gcagtgctac actgggccct tcaaccaagg tgacatgata atgactgaaa ataatcactg  80340
ccacttattg gggacgtctc atctgccagg catggtacaa agtgctttaa ataagcattc  80400
aacaatttca tgctgacaga agccctgtga gccagtggag ctactactat gcccattata  80460
caggggagaa aactgaggca gagagaggtt aggtaattcg ctcagcctca cacaaccaat  80520
aggtggtgga gccaggattt gggccccatc tgcctgactc tctagaggct ctatcttcca  80580
gtcttccaga gttgagtcta agccatgaat aggacaatta gacagcagag gaaacccatt  80640
cagccaccat gtgcatgaag agtaaggaat ttctgtcata cagaggggag tgaattcact  80700
gagctgagag ctgaggaacc attgatctga tggctgagac accactggga agactggaga  80760
ggcttttctg ggcatgcagt gccaggcaca ggaggagctg agggaagatg actaagaggt  80820
actggcaaag aattcagaaa ttctgatgga agctttacat gttaccatca catccatcca  80880
```

```
tctatccacc catccatcca cccatatctt cctccctcca cccaatcatg catacatcca  80940
gtcatctata caccacccac ccacccatcc atccatccat ccatcccttc atccatccca  81000
tcatccatcc aattatacat acatccaatc atatatctgt acataatcca ttcttccctc  81060
ggttcatcca tccatccatt catccatcca tccacccatc ccttccttca tccttcctat  81120
catccatcca atcatatatc tgtacataat ccattcttcc ctcggttcat ccatccatcc  81180
attcatccat ccatccaccc atcccttcct tcatccttcc tatcatccat ccaatcatac  81240
atatatccaa tcatacatct gcacatcacc agctcatcca tctatccatt tatccatcca  81300
tccttccttc catccatcat tcatccatca tacatacatc taaccataca tctctacatc  81360
attcattctt ccatcgattc atccaattat ccatcattcc ttcctccatc catcccatta  81420
tccatttgat catacatata tcatctatac atcatccatt catccatcca tccatccatc  81480
cacccatatc ttcatccaat caatcataca tacatcgaat catctacaca tcacccatcc  81540
atccatccat ccattcatct atccacccat ccatccatcc atccatccat tcatctatcc  81600
acccatccat ccatccatcc atccatccat ccatgtaacc atccagtcat atatccaatt  81660
acacatccat ccagttatac attcatacat gcatctaatc attcaattat acatacacac  81720
atccatataa ttctacatcc aattatacct ccatccaatt acacattcat acacccacct  81780
aataaattat taattcatat atccatccat ataattatac atcaattata catccatcta  81840
atcattcagt aattcaccca ccatccagtc atctatccaa taatacattc atccaatcat  81900
ccatccatcc atccacccat tcatccatcc atccgtccgt ccacccatca tggtatgagc  81960
catgatttac cacgatggtc ccctgtggac agcccaggtg gggcagaact gaagggaagc  82020
ccagggctgc ccccataaac atttgcctcc tttacatgga tgagaactag atccacatgt  82080
ataaatcctc atgatttgaa ggtgctttta ccaacattca ctcatgggat tctcccagga  82140
gctctaggag gaggcaggta gagttgaggt catctcacgc attttacaga tgaggaaacg  82200
gaggccctga gaggcaggtc caaggccacc tgaccagaaa gaagtggaac tgggacttga  82260
acccagccat cttgcccctt ggtcccatgc tctctagcct gtaactcctg cttcctggtg  82320
gggcatctcc aggaggaccc tatcggctgg ccatgggcct gccctggagt cttttgctct  82380
gtgtggccat ccttcctccc tcaggagagt gtgtgctccc agagcacagg ctgtatcttc  82440
tgagcatttt gtcccttccc agtacctagc actcagctct gtatacattg ggctctcaag  82500
aattctcaac cttccagagt gtaaggcctt gacctgctca gccctggata ctgcatgatg  82560
cattgataag cccataaaat aaccagggca gattgactcc cagtggccaa agtgccacag  82620
ggaagggaca attcagccct tctaggagga ggaggaggta gttttctcat ttctattaag  82680
gcaacaaaag ctgccttact aaggacattc ttggtggagg gcgtgactgt caaccactgt  82740
gatcatttgg gcctctcttg cccaggcttc ccattctgaa aggacagttt tattgtaggt  82800
acacatggct gccatttcaa atgtaactca cagcttgtcc atcagtcctt ggaggtcttt  82860
ctatgaaagg agcttggtgg cgtccaaaca ccacccaatg tccacttaga agtaagcacc  82920
gtgtctgccc tgagctgact ccttttccaa ggaagggggtt ggatcgctga gtgtttttcc  82980
aggtgtctac ttgttgttaa ttaatagcaa tgacaaagca gaaggttcat gcgtagctcg  83040
gctttctggt atttgctgcc cgttgaccaa tggaagataa acctttgcct caggtggcac  83100
cactagctgg ttaagaggca ctttgtcctt tcacccagga gcaaacgcac atcacctgtg  83160
tcctcatctg atggccctgg tgtggggcac agtcgtgttg gcagggaggg aggtggggtt  83220
ggtccccttt gtgggtttgt tgcgaggccg tgttccagct gtttccacag ggagcgattt  83280
tcagctccac aggacactgc tccccagttc ctcctgagaa caaaaggggg cgctggggag  83340
aggccaccgt tctgagggct cactgtatgt gttccagaat ctcccctgca gacccccact  83400
gaggacggat ctgaggaacc gggctctgaa acctctgatg ctaagagcac tccaacagcg  83460
gaaggtgggc ccccccttcag acgccccctc catgcctcca gcctgtgctt agccgtgctt  83520
tgagcctccc tcctggctgc atctgctgct cccccctggct gagagatgtg ctcactcctt  83580
cggtgctttg caggacagcg tggtgggagc tgagccttgc gtcgatgcct tgcttgctgg  83640
tgctgagtgt gggcaccttc atcccgtgtg tgctctggag gcagccaccc ttggacagtc  83700
ccgcgcacag ctccacaaag ccccgctcca tacgattgtc ctcccacacc cccttcaaaa  83760
gccccctcct ctctctttct tcagggggcca gtaggtccca gagcagccat ttggctgagg  83820
gaaggggcag gtcagtggac atctgatctt ggtttagtat ccttcatttt gggggctctg  83880
ggtgtggcct gggcctctgg actttggcca cggtgtttgt tccagccctt ctcctaacct  83940
gtcctttcca gacactcggc atctaggtta ttagcacctc gcatactttc tgacatgctc  84000
ctcagtcctg attttgacca tcttctcttg cttcccatct gtgtcagtca agactgcatt  84060
tggctgtaag aaacagaaac cccaactaac tgtggcattt acatgaagag gtttactttt  84120
ctcacataat cagatgtcta gacttggcca gcacctcaag ggtcattgat gctctcctgt  84180
ctttattttc tgtcatcttt agtggttgga ttgttgcctc atggttacaa agtggctgct  84240
gcacttccag gcatcacatc tgcctttgaa gcaggaacaa gttgcaaagt aaagtggcca  84300
aaagggccct gaaactaaat gtgtcccctt aggaaagcag gagttttctt gcaagtggca  84360
atcttctgct tatgtctcat tggccagagc tgggtcttac ggccacccct tgctgcgagc  84420
aaggctggga cattgagcat tttgccgtcc aacctcttta gcagaataaa ccaaggggga  84480
agaacgttaa tagtggcttt tgagtcacta gttggcagta tctgcccctc tatctttcca  84540
tcctccccat ggagtttcaa ggttcctttc tcagtacttc ttcaggctct gcacgttcat  84600
ttggatcttg tgtcttgggg tgaaaaactg gcccaagtgt ctccccaagc atccaccttt  84660
ggattaattt ggaaaatggc tgtcaagtgc ccgcctcttg cttggtataa tgctacagct  84720
ttagaggacg cagcaggcat gggccttgcc gctgaggttc ttagcctcat gagaatatcc  84780
agatcagatt ctcttggctc cttcttagag ccagtgatgc aagacacttc ctgctcatct  84840
tgtcgggacg gttttacaag ttgcctgcca tcctgagaaa gtctacaaaa cgatgccaga  84900
cctcatgcca gcttcccaag ccttgactct cagtgctccc tcaacaggat tctggaagaa  84960
tctcccaaac aagtcgcaat gccctctgga ccctgtgcag gcatgagact caagagcatt  85020
ggctcccacc cctggtggag ggaacactgc tggggctggg atcttgcctg gttgctccgc  85080
ctgcacccaa gacaaccata attaaaatgt ccttcattga acttggaaag ccttcaaagc  85140
tgacaactcc ttatgtgtac ccggaaaggc ctgggagtgt gccagggcat tgctcgggag  85200
ggacgctgat ttggaagcat ttacctgatg agagactgac agcagctcct ggtagccgag  85260
ctttccctcc tgcctctgct gtgaaggtgg acccatccaa cagtcaaatg cctgactctg  85320
gacaggagcg gacctattta ttgccatgca agggactctg cacttttgaa ttgtgggtca  85380
tgggcttgga tttaggggtt agagctggga gaagtcttgg aagtcaccta gagatgacac  85440
tgccattttg cagatgagga aaccgtccaa tcaaaatgga ccaaggactt gcccaaagcc  85500
tcacagcaaa accataggcc cccgcactaa ccccagagtc cctgtgctgt cttaaggatc  85560
atatagttgt aagcaatcat ctggttttca gtatttcttc ttttaaaatg cctggggcca  85620
```

```
tgcccagcag tctgtttcac tgcagcgttt acacagggct gccgggcttt cctggtggat  85680
gagctgggcg gttcatgagc cagaaccact cagcagcatg tcagtgtgct tcctggggag  85740
ctggtagcag gggctccggg ccctacttca gggctgcttt ctggcatatg gctgatcccc  85800
tcctcactcc tcctccctgc attgctcctg cgcaagaagc aaaggtgagg ggctgggtat  85860
ggctcgtcct ggcccctcta aggtggatct cggtggtttc tagatgtgac agcaccctta  85920
gtggatgagg gagctcccgg caagcaggct gccgcgcagc cccacacgga gatcccagaa  85980
ggaaccacag gtgagggtaa gccccagaga cccccaggca gtcaaggccc tgctgggtgc  86040
cccagctgac ctgtgacaga agtgagggag ctttgcgtgt ttatcctcct gtggggcagg  86100
aacatgggtg gattctggct cctgggaatc ttgggttgtg agtagctcga tgccttggtg  86160
ctcagttacc tccctggctg cctgccagcc tctcagagca tttagggcct tctggacttc  86220
tagatgctcc tcatcttgcc tcagtcagcg cgtcagttcc agagacttct ctgcagggtt  86280
ttctggggca ggtggtggca gacccgtgcc ttcttgacac ctgaggtcag tccaccctcc  86340
tgctcagact gcccagcaca gggtcacctc ccaaggggtg gaccccaaga tcacctgagc  86400
gcacagaggg tgcagatgac tggaccacac cttttggtga tcttaatgag gtggtcccag  86460
aggagctcag acatgcaatc tagcatccag ttctgggact ctgtctcctt ttcaaacgta  86520
ttcatgtaga acaggcatga cgagaatgcc ttgtcaacat gggtgatggg gaatcaatca  86580
gacagggcgc cgggctcaag gctgcagtca cccaagagtg gctcagccca ccaggcccta  86640
ggaaacgcct gcacagcctg gagctcctgg agtcatttcc ttcatgtctt cttcactgca  86700
cttacgtaaa gatgccagcc attggtttgg tgatttggag ggtgcccagt tgcccaacaa  86760
gaaatgcaga agaggcctag ccaggatttc accagcagtg gagagtagag aagatgtggc  86820
cagaaaagag tttcctttcc ctcctaaaga tggtactccc tgcagctact ggggaagcct  86880
gcagcattct ctagggctct gtgtgttgag agcagcccca ccctggcccc ttctgagtgc  86940
atttctgctt tgtgacttga tccgtgaagt cccctgagat gggcagaggg gatgtcctcg  87000
aagctggggc agagcctcat ccttgaacgt gaaggacgtt tgaagactgt ggcatgatca  87060
caggatgaga tcacagggaa cttgagtttc tctcctcctc tcccttcaca gttatttcac  87120
tgagggaaat ccctcccctg cccagaatga aaactctagc caactcttga cttttccatc  87180
actccaaagt agttgaaagt acattagtct ccacagtggc aaaacagtgt gcaaaagcta  87240
aataattaga acagccagtc ccatgtgaca gtcaaagctt ctaactccat tcaaagttgc  87300
agccattccc ctcgagggct ggcagggagg ggaggggtaa gagaaacagg aaggttctta  87360
ctgagttggt cctggtgtga gctgcgtcac actccctgca gaggtttcaa ggagactctc  87420
tctctctctg tctccatggg gaccttattt gaattcttct actcttaccc cagcctgcca  87480
tctccagcta tcctcccctg aagagccctt ctgctgcgct ggattctggt ggccatgtca  87540
tctcctcggc cccgtgggag tctgaagatc tggctgcagc ctcacctctg aggtcctgct  87600
agttgccacc tcttaaacat gatctgaggc tcccatgcac tctgacctgt gcccacatgg  87660
ggcccacggg aaacacgctg gcaagcaaac tgtgggtgtg cagacggttc tcagggctgc  87720
agcacctgtc ctttgctctg cccccaaagc aaggccagcc catcttccat cctctagtgt  87780
tccttggtgg ggccctgacc acagtccacc aggtccctaa ccagagggga cacacaccag  87840
gtgtcctcaa tgtattgcct tgaaacagtt gtgctgggac tgtgatgggg ggtggccatg  87900
tagccacccc caccaccccc aagccactct ctccaaggaa atcctcctaa agatcccttt  87960
acatcctcca tgtggtgggg aggttctaga gttgggtgca tgtgtcttca gctactgaca  88020
atgcagacct tagttggcac ctcgctctgg cctatcctgt ttgctgttct tggcgctcca  88080
gtgaaactcc ccatgggcca tccagttggg gtgcagtgtg gccaccccct tgcaggttcc  88140
tgccttgctg gagagcacag ggccctcctg gctcttgtaa aacactcccc atggtacaga  88200
gaggccagca gtgatgtgag gcccaacctc cctccatggt gttcccaagc agctcccttt  88260
ctggggtcaa ggggtggcaa agacagtgca gcgtccaatt tctgactcaa gccgggcctg  88320
gctatcgcag ctctgcactg tgtgtgacag caaggcaact cacccagtgc cgtggcagtg  88380
accgtgtccg aggaagcctc ctcacaccct ctgtctcaag gactctggca tttagctgga  88440
cttgctgtag ctctgagcct ttctgccatt gccatcacct tgtcagaaac tcaggccgaa  88500
tctgcactca gagttgtgcc caggcagttg agccaacact tgctcagcga tattgtcaca  88560
tgacaaggca ctgtcaccac tgggcatcgt gggtagcgca gtgtcggctg gatggacccg  88620
gagggtgtct gtgtcatgct agtgctagtg atgggagccc cgtgagccca ttgcccgccc  88680
tcccatgccc tcagcagctg cctggggaca gccaatggcc tgggtgtttc tgaggctacc  88740
acatggcttc caggaaactc gagaaccttt ctctcccttg cctacactct tcacacaggc  88800
ctgtgctggc cagcggtggg gatccggcat tcctatctta ggtgcagaga gtgactgact  88860
cattgcaggc ctgggagata agactgatgg cccagccagc aagatgtatg gatttctcag  88920
aggcagtggc ctctgtcatt gtcctcagga aatgctggtg attctggtgg cctgaggtca  88980
atgcatgtca acgtggccaa cttgccttat aaactttttt tctggacaat tgcgtgcact  89040
gtcctgtaac agtgtcctgt tgtttatgat gcagaaatag gtgtttttaa agcctattga  89100
ttttggtact attaatgtgg tcaggaactt tctcagtctt tcttgtttgg ggtgagctgt  89160
ggcttcctaa acaggaaccc aagacacccc caaaagctgc tcaccagcac tgccagcctc  89220
cctcttacca agtagcaccc gttcaggaca ttctgcgaaa ggcatttgcc cagaagttgg  89280
gaggaaggaa atgtaacatt ttggggcacc taccatatgc caggcaccag gctaaacgtg  89340
ttcacacaaa ttctcttact aaccctcacc atccttctac aagacaaact agtatcttca  89400
tcttggggtt caagatgagg aaatggaggc tcagagaggt tgaatgaatg ccggtgcctg  89460
gatatgaacc ccatctgcct gactccgcaa cccaggcaaa gtctttcctt gaacttccca  89520
gcagccactg cttagacaca gcctccacaa ccatggctca gcagcaaatt gcttctctga  89580
cctcactcag cctgtgtgtc cttgttgagt gaggcattca ggaccctggt cccaaagtgg  89640
agaaagtctt tcctactagg tcatagctac acctgcatgt gggtgctgtg ccttttgttt  89700
agtgaacttt tatcaccagc atcctcagca atgacattgg cagagaagcc agagctgagg  89760
caccttggta ttcttgggat gtgactttcc tgaatgttta agggaaaatg cccgaaggta  89820
cagagagctt ggtttctagt aaacaataac tgtcttgctt ttacccccct tcatttgctg  89880
acacatacac cagctgaaga agcaggcatt ggagacaccc ccagcctgga agacgaagct  89940
gctggtcacg tgacccaagg tcagtgaact ggaattgcct gccatgactt gggggttggg  90000
gggagggaca tggggtgggc tctgccctga aaagatcatt tggacctgag ctctaattca  90060
caagtccagg agattttagg gagttggttc ttatcaaagg ttggctactc agatatagaa  90120
agagccctag tggttttttt ctaataccat ttctgggtaa ttcctaaggc atttagtgtt  90180
ctgaaagatg ctagccttgt ccagcctggg agttgagaat gaatgtctaa cagaaactct  90240
aggccgggcc tggtggctca cgcctctaat cccagcacta tgggagaccc aggtgggcag  90300
atcacctgag gtcaggagtt tgagaccagc ctggccaaca tgtgaaatcc tgtctcacta  90360
```

-continued

```
caaataaaaa aattagccgg gtgtggtggt aggtgcctat aatcccagct actcaggagg  90420
ctgaggcagg acaatcgctc gaacccagga ggtggacgtt gcagtgagcc gagatcgcat  90480
cattgcactc cagcctgggc aacaaaagca aaactccgtc tcaaaaaaaa aaaagaaact  90540
caaatatgtg tgacaggcga ttctcactgc aggctgccct gtggctgatc caggagcaag  90600
gccttaacca tgtcatcccc aagcgattgc ttgtaaactt tcttctgtgc agccttcaac  90660
ccttattatg attttcttct caggaaccaa actgctgtat tcaagaaagg cagctttgtg  90720
taatcattta tcataaatat cttaagaaaa atcctagaga ttcctaattt taggaaatgg  90780
gagacctatg gtactgatat aatgtgggct gggcttgttt tctgtcattt gctagataaa  90840
tgaacttgag agcctactgt aaaatgtgga agcttctaga ttgcagaagg gctggaaaga  90900
cactgttctt ttctcccgag tgatgggatc tgtccagtat ttagagctgc ctctgaggcc  90960
atctgattct aggagactct gcctcgttga ggatattttg aggcctaact acacattcct  91020
gcccccagag aggtcacagc ctatagcagg ctgatgtttc tcatgtcaca tggcacagaa  91080
aggcacattt tcgttctcag gctaacaaag agcttcaaaa actattagaa gggacagtgg  91140
ctataagaga agaacctcag tcaatgtgtg aaattaacta ggaacctggc tcctgtttct  91200
tttaggtcat gtttttcagc ttaggtaaaa ctagaggctt tgataaagca tgacctctag  91260
aaatcattgc ttttcataaa tggaagtggg tttgagtttt ttctactgat tgttagtgca  91320
ggtgatgtct acatgccccc agaacatatt ccatgcaaca aaaaaagccc aggtcaccgt  91380
ctttgctggg aacttgactt ttgtgctcac tgaattttaa gctttctgac agcagcctgg  91440
aatcatggag ggataaagta cctattagta agatggaaaa aggtgtttca ggttggagct  91500
gcagtctgtt gagagtaagc tatgggaagg cctgtatacg aggggtggac ttttcttctg  91560
taagtgtcca gagaccaggc ctcctgaaga gggcatgggg gcttaactta cctggactac  91620
tgtgtttaca atactcattt atcttgaact cctcctaacc cctgagaatt gctacattta  91680
gtatttgctg agtacttcct agcatcctag ggaatcaata gaacattctc ccaaccaggc  91740
tgggtgcggt ggctcatgtc tgtaatccca gcactttggg aggccaaggt aggcagatcc  91800
cttgaggcca ggagtgcaag actagcctgg ctgacatggt gaaaccccgt ctttactaaa  91860
aatacaaaag ttagccaggc atggtggtac acacctgtaa tcccagctac atgggaggag  91920
taggaggcag gagaattgct tgaacctggg aggtggaggt tgctgtgagc cgagatcatg  91980
ccactgcact ccagcctggg cgacagagtg agtgagactc tgtttaaaaa aaaaaaaaaa  92040
aagaacattc tcctaacctg gcttcttcct ccaggggtgt aattaatcat gtcagtttcc  92100
tcattgatac acacacacac acactacaat cctgtatcca ttacttttca aggtacattt  92160
actatttacg tttggggtcc ttgtctcttt tttaatagtg tttcttaaag tcttgtatta  92220
tatcagagta cagtaacatc ccagtcaaga gcactctagt aagctctagg aggaaagcga  92280
cttccggaag gcagtggaga cctgtcctgt tggggcagca taggggcagc ccctgcctct  92340
ggtcagttct ggcgctcagg ctcagggttg cctctgggct gttcttccca gagactgaca  92400
aagggctccc ataaggcacc tgcagagcct gtgagaagct gaagtcaatg ttttcctgac  92460
accagttgat ctgtgcagga tccattgatt taaccacctg ctgtgtggca tgcactgtgg  92520
tcgatgccag gaacaggaat tggaggggcc catgagcatg gccagtatca caggctggag  92580
gtgctgctgc gctctgaccg ggcctcttgg ggatgagccc atgtcaacca ccttgcctcc  92640
gatggggtcg ggcccacagg ttacctttgt gtgtccatga ccacaccttc ctccccgacc  92700
tcatccaaat ctctttcttt tccaagcccc tgaatccttc agggctgcag gttttgttta  92760
aagcagagct ggtgagttgc ataggttgtt gcattgggac tagatggggt gttcaaagag  92820
ttgggagtta aaaaacataa agggtattta ttaggagaac caaggagtgt aattctcctg  92880
ttcttaatat gcggccaggt taatgaatgt cacgtgaatg aaccagaaaa aaatgaagtg  92940
tgcccttgat cagctgggtt ggtgtgcagc aagctgtgtg accaggggac agcagtggtc  93000
ctgagggccg tcactgtctg ccgtgcagag cccttcctcc cacgggggcc tacctcacct  93060
gtgccaaggg cttgtctgtg gtcagtgacc tggatagatc tgaatggggc ttctttttcg  93120
aggagtctta tggcaggtct ctcagtaaag actccattct tgatgatcac acattttgga  93180
ttttccaaat ctgtcagaga atgggcttga ggcggggttt gtgggcacta gtttcactgg  93240
tttcatttac caaaaagggg agcagaagtc aagtatggtg gctcatccct gtaatcccag  93300
aggcaagaga attgcttgag cccaggagtt cgagaccagc ctgagcaaca taaggagacc  93360
ccgtctccac aaaaatgaaa aataacattt tagtcagacg tggtggcatg catctgtggt  93420
cccagctgct tgggagggtg agatgggagg gttgtttgag ccctggagtt aaagttgcaa  93480
tgagctgtga ttgcaccact gcactctagc ctgggtgaca gaacgagacc ctgtctcaaa  93540
aaaaaaaaaa aagaaagaaa gaaaggaaaa aaaaaactca tgcctgtaat cccagcactt  93600
tggggaccgg ggtgggcaga tcacgaggtc aggagatcaa gactatcctg gccaacatgg  93660
tgaaaccccg tttctactaa aaatacaaaa attagccagg tgtggtggca cgtgcctgta  93720
atcccagtta ctcgggaggc tgaggcagga gaatcgcttg aaccagggag tcagaggttg  93780
cagtgagctg agatcgtgcc actgtactcc agcctgggcg acagagtgag actctgtctc  93840
aaaccaaaaa aaaggggtgg ggggcggggg caggagaaca gtgagaggta gggagaggaa  93900
aggggattct cgctacaccc aaaccagata ccatctagag gctagaatct ttgggaggct  93960
caaattccct agaaagcagg agaagcttct gtagccctcc cgctttccca gtagattaag  94020
cccagggcgg ctccagatgt gtgacatgct ctgtgcccaa ccagagccca tcataggcag  94080
aggaataaca cccacaccag aagggccctc ggaggtcacc acgtccaaga accctcttta  94140
cagatgagga aactgaggcc cagagagggg agagccacct agcgagctgg tggcggctag  94200
accaggagag ctgtcattcc aagcaagcaa aggcaacgag acgagcccag agctgtgctc  94260
ccatctcttt gttagggggc ctgggatgcc ctctcagtgt cattttgtcc aggatgatgc  94320
tccctctctt aagcgattaa tgcgcccttg ctaacctttt gctatcgctg cctcttcaaa  94380
ccagaggagt tgagagttcc gggccggcag aggaaggcgc ctgaaaggcc cctggccaat  94440
gagattagcg cccacgtcca gcctggaccc tgcggagagg cctctggggt ctctgggccg  94500
tgcctcgggg agaaagagcc agaagctccc gtcccgctga ccgcgagcct tcctcagcac  94560
cgtcccgttt gcccagcgcc tcctccaaca ggaggccctc aggagccctc cctggagtgg  94620
ggacaaaaag gcggggactg ggccgagaag ggtccggcct ttccgaagcc cgccaccact  94680
gcgtatctcc acacagagcc tgaaagtggt aaggtggtcc aggaaggctt cctccgagag  94740
ccaggccccc caggtctgag ccaccagctc atgtccggca tgcctggggc tcccctcctg  94800
cctgagggcc ccagagaggc cacacgccaa ccttcgggga caggacctga ggacacagag  94860
ggcggccgcc acgcccctga gctgctcaag caccagcttc taggagacct gcaccaggag  94920
gggccgccgc tgaagggggc agggggcaaa gagaggccgg ggagcaagga ggaggtggat  94980
gaagaccgcg acgtcgatga gtcctccccc caagactccc ctccctccaa ggcctcccca  95040
gcccaagatg ggcggcctcc ccagacagcc gccagagaag ccaccagcat cccaggcttc  95100
```

-continued

```
ccagcggagg gtgccatccc cctccctgtg gatttcctct ccaaagtttc cacagagatc  95160
ccagcctcag agcccgacgg gcccagtgta gggcgggcca aagggcagga tgccccccctg  95220
gagttcacgt ttcacgtgga aatcacaccc aacgtgcaga aggagcaggc gcactcggag  95280
gagcatttgg gaagggctgc atttccaggg gcccctggag aggggccaga ggcccggggc  95340
ccctctttgg gagaggacac aaaagaggct gaccttccag agccctctga aaagcagcct  95400
gctgctgctc cgcgggggaa gcccgtcagc cgggtccctc aactcaaagg tctgtgtctt  95460
gagcttcttc gctccttccc tggggacctc ccaggcctcc caggctgcgg gcactgccac  95520
tgagcttcca ggcctcccga ctcctgctgc ttctgacgtt cctaggacgc cactaaatcg  95580
acacctgggt gcagctgctc cactccctcg gcctcctccc gtgctcaggc tgtggccgca  95640
cgcgcccctc acgcttgccc gccactctgc atgtcaccag cacccccgct ccgtgctacc  95700
caccttgttt gactctctgg ccacttgatt tgtccacaac ggcccatcag cccacaggag  95760
gtttggtggg tgccttccac cgacaggatg acgggtgccc tcatggtgtc tagaactctc  95820
caaccctccc atgtaggcat aagcagcccc actttgcaga tgaggaaacg gaggctcaga  95880
gaagtacagt aacttgccga aggccaatga gtagtaagtg acagagccag gtttgggatc  95940
caggtaggtt gtctctgaaa gacacgcctg tcctgcatcc cacaacgcct cccaggaggt  96000
gctggagtgt ggacgcctaa cacagagatg tgcagggcac acacagcagg tgacacacac  96060
agcatccaga ggtggcccag agctcatgct gtgcctttgg cccagtgccc tgcccccacc  96120
cactctgcct tgtggcagga agacaaggag cagacacaag atctccctgg tccacatgcc  96180
accacctccc tctgcagagg acaaggggat cctcatgctg gcattggagg gggttgagca  96240
gggcccacct tgagccctca ggagcacgac cacagcagcc ctgcagggag ggattggtgg  96300
gaggagagtc ccaagtatca gggagaggag agttggtgtc ccacaggaga cctcagagcc  96360
acaaggcgag cttgttcata aatttgggac ccttagcatt tcacagttat ttgcagagcc  96420
cagaaatgga tgttactgaa gctcacagtt gcaagcatct gttaaatttt tattagattt  96480
tacttttagg gaaaactttg aaatgctata aagaagcctg tgtttaaaag ttaagacaga  96540
ggctgggggc gatggctcac gcctgtaatc tcagcacttt gggaggccaa ggcaggtgga  96600
tcatttgagg ttaggagttc gagaccagcc tggccaacat ggtgagaccc tgtctctact  96660
aaaattacaa aaaattagct gggcgtggtg gcgggcacct gtagtcccag ctactgggga  96720
ggctgaagca ggataagtgc ttgaacccag gaggcagagg ttacagtgag ccaagatcac  96780
accactgtac cctaagcctg ggcgacagag tgagactctg tctcaaaaaa taaaataaaa  96840
taaagttaag agagaaaaaa atatatccta tatcctttgt taaattccaa aacagtaggg  96900
gacaaataac tgacttgaca ggttactaca atatttcctg aaatgatgtt ttcttgaata  96960
ctggcctact agaggttcat aggtgtgttt ggattaaaaa agagttccat ggcccagtga  97020
ctgggggaaa aaaataaaag actaaagtaa gttaaacagg cttttctgct gcaggacttg  97080
tcagagcctt taatgtacta atggccattg tgaccctctg agaaggtcac agagtgggtt  97140
tcccaaactt acttgattct acctgctaac atttcctgga ggaagtttgg gaaatgccga  97200
tttagcagat tcttttgttg tgccgtggat ggtgctggtt gatgtgggca aaacaaagaa  97260
cacgtgagtc agatccgcct ggggctctta ctaaagtgca ggttcccagg tgccacttta  97320
ggcttacaga cccagttgtg gggtaagcct gggagtcttt tagcaggtga ttctgccaca  97380
tagtatagtt ggaaaacctc tgggcatact cattgctggt ccctctagaa atccaggtga  97440
caatagccaa tgagaagctc caagagaccc agttgtccat ggggtagagg gaatgtgata  97500
ttgaaaccaa agaagaaaat ctatgatcag ttttcagcag tgactgtcaa gagaaggaga  97560
agggtgagtt agcgctgatg ctggctgaca ggtcagcggg ttggtttcac caaggagtgt  97620
gatgaaggct gatgttgtct gtgggaatgt atgatggtaa ctggtttgta gctaatttgg  97680
ggaagcagtg agaattcgtg ccctttgaag accagtaagt ggcaagaaac ccaccaggcc  97740
tggctcaggg ctgggctggg cttggctcgt ctcagagcag ctggggctgg tggccaaagc  97800
caccattagt gaggggcagg ccctggggt acaaccagca actaggggac aaagacaacc  97860
ctgccagcct ctcctattct ggaggcgtgt gaccagaaat ggagatgggt tggtcagcat  97920
aagatggcca ggaaggtgga aatcaggact gctggcaatc tagccacatg ggcaggggag  97980
ccgggtggtt ccaggcagtt tccaaggcca agagggtgag caggcacctc acagggaatc  98040
agggccaagc ctggctgcag tgtggagaca atgcacccac ccccatcctt ggatcttgca  98100
ggaggctggg tcctcactga gctaccaaca tccatggccc tgaggctttt aaaacaccca  98160
tccatggagt ggggctggtc ccagtggggt gaggctgacc ctggcagaaa cagggcagga  98220
gcctgtgggt tagggagact gcaccttcct tagatagcct ccatgccatc atgtccccgt  98280
gacagtttct gctgcgtccc ctctgcatgg tcccaccctc ggccagcctg ctgccccctc  98340
ttgccaggtt gcgctaatca gtgaccccag tgtgctgtgt tgatactaac aatgcgaggc  98400
ctagcagatt caagggaaaa gagaaccaac tgggtttcca ccagacccaa ctaaacaaac  98460
atggacctat cccagagaaa tccagcttca ccacagctgg ctttctgtga acagtgaaaa  98520
tggagtgtga caagcattct tattttatat tttatcagct cgcatggtca gtaaaagcaa  98580
agacgggact ggaagcgatg acaaaaaagc caaggtaagc tgacgatgcc acggagctct  98640
gcagctggtc aagtttacag agaagctgtg ctttatgtct gattcattct catatataat  98700
gtggggagta tttgtcacta aagtacagct gtcatttaaa gtgctttgta ttttggggca  98760
ggcttttaaa aagtccagca tttattagtt ttgatactta ccccagggaa gagcagttgg  98820
caggttcatg aagtcatgct cctaattcca gctttcttag tgtactttca gtgagaccct  98880
gacagtaaat gaaggtgtgt ttgaaaacca aacccaggac agtaaatgaa ggtgtgtttg  98940
aaaaccagcc ctaggacagt aaatgaagcc atcttctcac tgcataaact gcacccagat  99000
cttcgcccat ccttctcagt atttcacttc acccattgtt tactgtctca atgactgggg  99060
aaatgtctgg ggaaatgctc ccgtaattgc acagtggcgt ttttcctgga aaatcccacc  99120
atggctctag ataagaccta tttttcttaa aggtatctaa aatttccagc ataaattctg  99180
tctgaaacac ctgaatttta atcagtactg gagcccggag ggcatctcca gttgccacat  99240
agctctgagc attcagtggt gtgttgaggg ctgctcccgg aagtgcctgc agagtcaggg  99300
ctccccagcc tcatctagtg aggcagtgga agggcctgtg gggatttgga gagctggcct  99360
gggtctctga agtgatagtg acagctgctt gtcaatcacg gtgcacattt agtgctgggg  99420
gcagggggca gggaatacca gcctcatgca tgcatgcatt catttgttcc ttccttcatt  99480
cattcattca gtacacatgg gtacaacatc cctgccctgg agttgcccag agtctaggga  99540
ggggaaagat ctattaccct gggcctcggc cagctgggga gtgctgctgg tggagagggg  99600
ccgtgtgcag cgagggaagg aggagtcgtc aataccccca ccccagcttt gctttcttgt  99660
catcagcccc agggccccag cctgtgtccc tcctctccca ttgctacttc atctcctggg  99720
tcctccttac caagcctgac cacacagagg gccttggccg cttccatggg gaattggaaa  99780
gcaataagat agcatcccct agaagcccag tgaagtctgg gacaggaccc ttctctgagc  99840
```

-continued

```
tctgacttgc tcttggaaac acttcgaggc ttagcctccc cactttgttt cccgagagtg  99900
tgacctgttc ccctccaaac acccccttct cctccagggc catgcccacc cgtcaaaatc  99960
ccccacgggc aggacgaact gtgggtgtca gtcaccatct atcctgcatc ctggttccag  100020
ggcccccccc agccccgcct ccatagggac aggcgtgcag acacccgtcc ctggctgctt  100080
cctcttgtgg aatgggttca aaagtaagca gtgttgttta cactgacaaa ctgaaaaaaa  100140
aagaaaaaga gataacattg gaggcttggc acagtggctc atgcctgtaa tcccagcact  100200
ttgggaggct aaggtgggag gatgtcccca gcccaagagt tctagaccag cctgggcaac  100260
atagcaagac cccatctcaa aaaaaaaatt taattggcca ggcagaggtg ggaggatcac  100320
ttgaacccaa agggtggagg ctgcagtgag ccgtgatggc accactgcac tccagccagg  100380
gcaacagagg gagaccctgt ctctaaaaca aacaaacaaa caaacaaaca aaagagttaa  100440
cattggccag attaggattc accagatagt gttaatatta gtttgatttg agactttaat  100500
cagaaagcac atgtgtggtg ggggtgggtg taacctaagt caggtagaat ctttccaact  100560
tggggggggc acactcctga ttgtagccat atgagtctgt cagtgtggtg gaagaggcca  100620
tgggttaatg ggcaggtaaa aaagcacctt gcctggaatt gagtagaaag taaggccctt  100680
cagaccccgt gacacacttg gggacatttt cttgagtaac atcctaagat tcatgtacct  100740
tgatgatctc catcaactta ctcatgtgaa gcacctttaa accagtcgtc tccaaattca  100800
ggggcacagt aacatccaac aggctggaga aagaacgtac tagaacttcc attccttttt  100860
catgtcctct tctaaaagct ttgtcagggc caggcgcggt ggctcacgcc tgtaatccca  100920
gcactttggg aggccgagac gggtggatca cgaggtcagg agatcgagac catcctggct  100980
aacacagtga aaccccatct ctactaaaaa tacaaaaaaa cgagccgggc gtggtggtgg  101040
gcgcctgtag tcccagctac tcgggaggct gaggcaggag aatggcgtga acccaggagg  101100
cagagcttgc agtgagccga gattgcacca ctgcagtcca gcctgggcga cagagcgaga  101160
ctccgtctca aaaaagaaaa agaaaaagaa aaagaactgt gattggggag gacggtcact  101220
ttcctgttct tactgatcag aagggatatt aagggtacct gattcaaaca gcctggagat  101280
cactgctttc aaccattacc tgccttattt atttttagtt actgtccttt tttcagtttg  101340
tttccctcct ccatgtgctg acttttattt tgattttatt tatgtttatg tttaagacat  101400
ccacacgttc ctctgctaaa accttgaaaa ataggccttg ccttagcccc aaacacccca  101460
ctcctggtag ctcagaccct ctgatccaac cctccagccc tgctgtgtgc ccagagccac  101520
cttcctctcc taaatacgtc tcttctgtca cttcccgaac tggcagttct ggagcaaagg  101580
agatgaaact caaggtaagg aaaccacctt tgaaaagaac caggctgctc tgctgtggtt  101640
tgcaaatgtg gggtttgttt atttgttttt tagcctcaaa gacctttctt caaatgagtt  101700
ctggcataga agcaccgtgt aaaatagtta gaattctggg caaaggggaa aagagagctg  101760
ggggccatcc ctctcagcac cccacaggct ctcatagcag cagctcctaa gacacctggt  101820
gggaccttgg tttcgaaatc gctactctaa ggctgggcac ggtggctcac acctgtaatc  101880
ccagctcttt aggaggccga ggagggtgga tcacctgaga tcaggagttc gagaccagcc  101940
tggctaacat ggcaaaaccc tgtctctact aaaaatacaa aaattagccg ggcgtggtgg  102000
tatgcgtggt ggtaatcgca gctactcggg aggctgaggc acaaggattg cttgaacccc  102060
agaggcagag gttgtagtta gctccagctt gggcgacaga gcaagaccct gtcgcaaaaa  102120
ttgtttaaaa aacaaaccca aaattgctac tctcattggg ttcctttgcc cattcctgat  102180
tttggcaaga gaaatgcttc cagattgccc tgatctgggt aggacagcat cacgccatag  102240
caacactgcc ccgtgagctc actgccccct caactagctt gtggtccttg gttaatgtca  102300
gtttcttttt tgagtttgtg ttatgtctaa gggtcatctg ctgggtaacg gaacccaggg  102360
actgccctag tccctagact gtgccatgcc cgactctgcc agctttgtca gtgatgctgg  102420
tgctcgcctc ctcgggtgct cgcctggtct gagcacaccc aaggagttct tgaggcctta  102480
gggttgtttg cgagagaatg aaagaacacg acctagctct ctttagcatc cttggtcagg  102540
ttcaacactg cccccagggg cctctggtgg agccaaccac catcagccaa ataaatccat  102600
aattagagtc agaaaatgga tgtctgcata tgtgtagtgc actaatgtcc tgccgatgat  102660
tgacatggag tggagagtga cctgatcatt gctgtgagct ctgctggcct tggcacaact  102720
catgctgata actaatgcac acagttcctc tgggaggaaa tgtcctcagg gaacttggag  102780
tttgggtggg gatgtgggtt tgtgtgccca gcaagccctt gtggttgtag cagacactag  102840
tggcatctag gaggcaaagg gtcaccccag tcttagccac gttttgagtc aaggtggcgg  102900
agtggggctg gtgttgactc ttggtggcag taacttttcc caatggtgaa aaaccccctct  102960
atcatgtttc atttacaggg ggctgatggt aaaacgaaga tcgccacacc gcggggagca  103020
gcccctccag gccagaaggg ccaggccaac gccaccagga ttccagcaaa aaccccgccc  103080
gctccaaaga caccacccag ctctggtaag aagaacgttc tcttgaatct tagaggaagc  103140
tgaagctctc agaggtacag ccttcatttt aggaggcctt aggccactga gaatgaataa  103200
cccctggcag ctggtcagca gcttgcagtt tactaagcac tggagtcttc attgccttct  103260
cagtcctttt gatttctgag gcaaatgttg aatccctacc ttttttttt tttttctttt  103320
gagacagagt ttcgctttg ttatccaggc cggagtgcag tggtgtgatc tcagctcact  103380
gcatcctcca cctcccaggt tcaagcgatt ctcctacctc agcctcccta gtagctggga  103440
ttacaggcac ctgccactat gcccggctaa tttttgtat ttttagtaga gacagggttt  103500
caccatgttg gccaggctgg tctcgaacgc ctgacctcag gtgatccacc tgcctcggcc  103560
tcccaaagtg ctgggattac aggcatgagc caccactccc agcctgaatc ctcacttttt  103620
atcaatgaag aaattgaggc tgattctgca gcatgataaa aaaaaataca gaaaaaggaa  103680
aaaaaagaaa gaaatcgagc ctctgagagt ttgcttgact gagtctaacc agctcatttt  103740
aaacccgagg aaaatgcagt cacatgacta ctaagtggca gctctcggag cctctctggc  103800
cccaagtcca gggttccata gaggcagccc cagcatggca tgttttcagt ccccaaatga  103860
gactctggag acaaatgtct ctggagacag agcagcagcc tggataagtc acaatgggtg  103920
acgtcactca gggctcaacc cctgggcagc ttaacttgct agggacgtta ggagtctgct  103980
gcaaaacctg agggtcttag ctgagcagtc acaggctggg cccgttgccc tgggctcctg  104040
tgagtaaaac ccagtcaatt ttgagtaccc agtaaggcat ccattgagtt attttgcagc  104100
caggagtgct attaagaaca gtcgcggctg ggcgtggtgg ctcatgcctg taatcccagc  104160
actttgggag gccaaggtgg gcggatcacc tgaggtcagg agttcgagac cagcttggcc  104220
aacatggcaa aaccccgtct ctaataaaaa tacaaaataa ttagctgggc gtggtggcgg  104280
gcgcctgtaa tcccagcttc tcaggagggt gaggaaggag aatcacttga acccaggagg  104340
cagaggttgc agtgagctga gatcgcacca ttgcactcca gcctggatga caaaagtgag  104400
attccttctc aaaaaaaaaa aaaaaaaaac agtcgtcctc tttggggatt agggacagcc  104460
tgcctgcctg cccgagcact tctctcttcc attgccccag tgaagtattc caggcccctg  104520
ggtttagact ctgcaccatg taggggtgtc tgacctgcac ttgctccttg gtggcacggg  104580
```

-continued

```
cagcctatgg cacttgctgc gggctgtgac caaagcctgg cctggatctt ggatcttggt  104640
gactctgctt ctccctggcc tgagggagct gcccagagcc tgcccaccac ctgctgcgtg  104700
tctttgcggt ggcatttctc gcacacatgc cgtgcagtgg cacccccaag gatggccatt  104760
cactaaggcc cattgttttt gtcttttcgc ttcgtgtttt ctggcctggt gtttttctca  104820
tatacatgtg atccagggat aattcccaga attttgacag gattttaagt agcgtttgga  104880
tcctgctgtt ttttttcac ttaacatcgg gccagttgac tcacactctg ttttttgttg  104940
ttgttttttt gagacggagt ctcactgtgt cacccaggct gaagtgcagt ggcacaatct  105000
tggcatactg caacctctgc ttcccaaatt caagcagttt tcctgcctca gcctcctgag  105060
tagctgggac tacaggcaca ggccaccacg ccctgctaat ttttgtattt ttagtaaaga  105120
cagggtttca ccattttggc cagcctagtc tcgaactcct gacctcaagt gatccgccca  105180
cctcggcctc ccaaagtgct gggattacag gggactcaca ctttgtaaca acctgaaaca  105240
acgtgatgca tttccctttg ggtcttacct gctcttcggt ggctgcctgc aggtggagag  105300
accctccccc ttgggcccct cgaccttgtt tcagaatggg gcccctgctg ggccagctgt  105360
gggtgcctgc cacgtgaagg actcattaag gccctgttta agcctgatga taataaggct  105420
ttcgtggatt tttctcttta agcgactaag caagtccaga gaagaccacc ccctgcaggg  105480
cccagatctg agagaggtac tcgggagcct acttcgctgg gagcagcctc cctttgcgtg  105540
tgtggccatt cactggcttg tgtttctaga gccgggagga ccctttctg caatgcaggg  105600
ttcacacagg gttcgcagcc tgaagatgga gcagtccgaa ttctcttccc tgtgcagttt  105660
gcgcagctgt gtttgtctga tggctttct aatcctgtgt gctctccttg acttcaggga  105720
caatggcatt acaggcatga gccaccatgc ctggctgtct ccctatgttt cagatgaaga  105780
cataggctta aggaggtcag gtgacttgcc cacgaccact ctgtaaataa gaggcatgaa  105840
aagtatttgg agccaccacc accaagccca ctggtcaccc tgggtctctg aagtcaggga  105900
ggcaggagga tgggaggtct gaggaggcag agaggctgag cctggaggcc ctggaggccg  105960
aggccccatc tgttgtttcc ttatgtggaa aataagaggc ttcgtttgtc ctattgccac  106020
agagcgtact acttcaggaa catccaagac atggaaatcc gcagggcacg gtggctcacg  106080
tctataatcc cggcactttg ggaggttgag gtgggagaat cgcttgaggc cagaagttca  106140
agaccagcct gagcaacata gtcagacccc gtctctataa aaaacattat ttttaaaaaa  106200
gacatggaag tcaaattcta aaaactggtg ctggctgggt gcggtggctc atgcctataa  106260
tcccagcact ttgggaggcc gaggcgggtg gatcacctga ggtcaggagt tcaagaccag  106320
cctggccaac atggtaaaac ctctactaaa gaaatcttta ctgaaaatac aaaaatccag  106380
tctctactaa aataagtctc tactaaaaat acaaaaatta gccaggcgtg gtgctgcaca  106440
cctgtaatat cagctactcg ggaggctgag gcaggagact cgcttgatcc catgcagcgg  106500
aggttgcagt gagccgagat cacgccattg cactccagcc tgggcatcag aataagactc  106560
cgtctcaaaa aaaaaaccac aaaaaaaaca aacaacaaca aaagaaaact agtgcttatt  106620
cgtcactggc caagctgccc attggctaca tgggtgcttc aaagagctgc ccttctccag  106680
gtctggccag caggtatgtg ttacagcaaa tgcctggggc agcggcaggg gcattgctgc  106740
gggaagcttc tggacttgca ggaaagctaa gttctcagac tgcaggggag ctaagcacac  106800
ctcggcacag ggtgaggcct gcggttctca gacttcagtc tttgtggagc ttgagaaaaa  106860
tgaggctttg caggtcccac ccctagagat tctgctctat ccactcttga aggggatcga  106920
gaaatttgca ttttgcaact cccactttcc tccttgaaag ctccggagat tctgacgcag  106980
ggttccgtgg gccacacttt ggaaaataca gacccatgag atagaatacc agactgttga  107040
agtgtaacgg gggcctggga agtgcagtaa cagaagcaag tttgagggta aaggacaccc  107100
agaggaggga gggacagcat ctgcatggag aggagaagag accccccagc agcttccagg  107160
gtgttggaag ggtgcgctag taactgctat gcatggcagg tggggaactg tacgtcaggg  107220
cacagcagca tgaagcggta tggctcgtgt ggacagctag ggacaggcag gcgtggagca  107280
ggcatcctgt tctgaaggcc aaatcccaca gaggagccag ggtgctggca ggagccctga  107340
actagccgaa cagctgaaca gctgaacatt caccctgtgg ggaaagggtc agaagcgtcc  107400
aggcttgagg gcacagctgg gtctcgtcac tgcatcaccc ttatttagga taaaggccct  107460
gaagaattgt attagaggtt ggcaaagcat atctaccacc tcctggagcc acgctggccg  107520
cagggattat aattatttcc attttcaaat taaggcctct gagctcagag aggggaagtt  107580
acttgtctga ggccacacag cttgttggag cccatctctt gacccaaaga ctgtggagcc  107640
gagttggcca cctctctggg agcgggtatt ggatggtggt tgatggtttt ccattgcttt  107700
cctgggaaag gggtgtctct gtccctaagc aaaaaggcag ggaggaagag atgcttcccc  107760
agggcagccg tctgctgtag ctgcgcttcc aacctggctt ccacctgcct aacccagtgg  107820
tgagcctggg aatggaccca cgggacaggc agcccccagg gccttttctg accccaccca  107880
ctcgagtcct ggcttcactc ccttccttcc ttcccaggtg aacctccaaa atcaggggat  107940
cgcagcggct acagcagccc cggctcccca ggcactcccg gcagccgctc ccgcaccccg  108000
tcccttccaa ccccacccac ccgggagccc aagaaggtgg cagtggtccg tactccaccc  108060
aagtcgccgt cttccgccaa gagccgcctg cagacagccc ccgtgcccat gccagacctg  108120
aagaatgtca agtccaagat cggctccact gagaacctga agcaccagcc gggaggcggg  108180
aaggtgagag tggctggctg cgcgtggagg tgtgggggc tgcgcctgga ggggtagggc  108240
tgtgcctgga agggtagggc tgcgcctgga ggtgcgcggt tgagcgtgga gtcgtgggac  108300
tgtgcatgga ggtgtggggc tccccgcacc tgagcacccc cgcataacac cccagtcccc  108360
tctggaccct cttcaaggaa gttcagttct ttattgggct ctccactaca ctgtgagtgc  108420
cctcctcagg cgagagaacg ttctggctct tctcttgccc cttcagcccc tgttaatcgg  108480
acagagatgg cagggctgtg tctccacggc cggaggctct catagtcagg gcacccacag  108540
cggttcccca cctgccttct gggcagaata cactgccacc cataggtcag catctccact  108600
cgtgggccat ctgcttaggt tgggttcctc tggattctgg ggagattggg ggttctgttt  108660
tgatcagctg attcttctgg gagcaagtgg gtgctcgcga gctctccagc ttcctaaagg  108720
tggagaagca cagacttcgg gggcctggcc tggatccctt tccccattcc tgtccctgtg  108780
cccctcgtct gggtgcgtta gggctgacat acaaagcacc acagtgaaag aacagcagta  108840
tgcctcctca ctagccaggt gtgggcgggt gggtttcttc caaggcctct ctgtggccgt  108900
gggtagccac ctctgtcctg caccgctgca gtcttccctc tgtgtgtgct cctggtagct  108960
ctgcgcatgc tcatcttctt ataagaacac catggcagct gggcgtagtg gctcacgcct  109020
ataatcccag cactttggga ggctgaggca ggcagatcac gaggtcagga gttcgagacc  109080
aacctgacca acagggtgaa acctcgtctc tactaaaaat acaaaaatac ctgggcgtgg  109140
tggtggtgcg cgcctataat cccagctact caggaggctg aggcaggaga atcgcttgaa  109200
cccaggaggc agaggttgca gtgagccgag atagtgccac tgcactccag tttgagcaac  109260
agagcgagac tctgtctcaa aacaaaataa aacaaaccaa aaaaacccac catggcttag  109320
```

-continued

```
ggcccagcct gatgacctca tttttcactt agtcacctct ctaaaggccc tgtctccaaa  109380
tagagtcaca ttctaaggta cgggggtgtt ggggaggggg gttagggctt caacatgtga  109440
atttgcgggg accacaattc agcccaggac cccgctcccg ccacccagca ctggggagct  109500
ggggaagggt gaagaggagg ctgggggtga gaaggaccac agctcactct gaggctgcag  109560
atgtgctggg ccttctgggc actgggcctc ggggagctag gggcctttct ggaaccctgg  109620
gcctgcgtgt cagcttgcct cccccacgca ggcgctctcc acaccattga agttcttatc  109680
acttgggtct gagcctgggg catttggacg gagggtggcc accagtgcac atgggcacct  109740
tgcctcaaac cctgccacct ccccccaccc aggatccccc ctgcccccga acaagcttgt  109800
gagtgcagtg tcacatccca tcgggatgga aatggacggt cgggttaaaa gggacgcatg  109860
tgtagaccct gcctctgtgc atcaggcctc ttttgagagt ccctgcgtgc caggcggtgc  109920
acagaggtgg agaagactcg gctgtgcccc agagcacctc ctctcatcga ggaaaggaca  109980
gacagtggct cccctgtggc tgtggggaca agggcagagc tccctggaac acaggaggga  110040
gggaaggaag agaacatctc agaatctccc tcctgatggc aaacgatccg ggttaaatta  110100
aggtccggcc ttttcctgct caggcatgtg gagcttgtag tggaagaggc tctctggacc  110160
ctcatccacc acagtggcct ggttagagac cttggggaaa taactcacag gtgacccagg  110220
gcctctgtcc tgtaccgcag ctgagggaaa ctgtcctgcg cttccactgg ggacaatgcg  110280
ctccctcgtc tccagacttt ccagtcctca ttcggttctc gaaagtcgcc tccagaagcc  110340
ccatcttggg accaccgtga ctttcattct ccagggtgcc tggccttggt gctgcccaag  110400
accccagagg ggccctcact ggcctttcct gccttttctc ccattgccca cccatgcacc  110460
cccatcctgc tccagcaccc agactgccat ccaggatctc ctcaagtcac ataacaagca  110520
gcacccacaa ggtgctccct tcccccctagc ctgaatctgc tgctccccgt ctggggttcc  110580
ccgcccatgc acctctgggg gcccctgggt tctgccatac cctgccctgt gtcccatggt  110640
ggggaatgtc cttctctcct tatctcttcc cttcccttaa atccaagttc agttgccatc  110700
tcctccagga agtcttcctg gattcccctc tctcttctta aagcccctgt aaactctgac  110760
cacactgagc atgtgtctgc tgctccctag tctgggccat gagtgagggt ggaggccaag  110820
tctcatgcat ttttgcagcc cccacaagac tgtgcaggtg gccggccctc attgaatgcg  110880
gggttaattt aactcagcct ctgtgtgagt ggatgattca ggttgccaga gacagaaccc  110940
tcagcttagc atgggaagta gcttccctgt tgaccctgag ttcatctgag gttggcttgg  111000
aaggtgtggg caccatttgg cccagttctt acagctctga agagagcagc aggaatgggg  111060
ctgagcaggg aagacaactt tccattgaag gccccttca gggccagaac tgtccctccc  111120
accctgcagc tgccctgcct ctgcccatga ggggtgagag tcaggcgacc tcatgccaag  111180
tgtagaaagg ggcagatggg agccccaggt tatgacgtca ccatgctggg tggaggcagc  111240
acgtccaaat ctactaaagg gttaaaggag aaagggtgac ttgacttttc ttgagatatt  111300
ttgggggacg aagtgtggaa aagtggcaga ggacacagtc acagcctccc ttaaatgcca  111360
ggaaagccta gaaaaattgt ctgaaactaa acctcagcca taacaaagac caacacatga  111420
atctccagga aaaaagaaaa agaaaaatgt catacagggt ccatgcacaa gagcctttaa  111480
aatgacccgc tgaagggtgt caggcctcct cctcctggac tggcctgaag gctccacgag  111540
cttttgctga gacctttggg tccctgtggc ctcatgtagt acccagtatg cagtaagtgc  111600
tcaataaatg tttggctaca aaagaggcaa agctggcgga gtctgaagaa tccctcaacc  111660
gtgccggaac agatgctaac accaaaggga aaagagcagg agccaagtca cgtttgggaa  111720
cctgcagagg ctgaaaactg ccgcagattg ctgcaaatca ttgggggaaa aacggaaaac  111780
gtctgttttc ccctttgtgc ttttctctgt tttcttcttt gtgcttttct ctgttttcag  111840
gatttgctac agtgaacata gattgctttg gggccccaaa tggaattatt ttgaaaggaa  111900
aatgcagata atcaggtggc cgcactggag caccagctgg gtaggggtag agattgcagg  111960
caaggaggag gagctgggtg gggtgccagg caggaagagc ccgtaggccc cgccgatctt  112020
gtgggagtcg tgggtggcag tgttccctcc agactgtaaa agggagcacc tggcgggaag  112080
agggaattct tttaaacatc attccagtgc ccgagcctcc tggacctgtt gtcatcttga  112140
ggtgggcctc ccctgggtga ctctagtgtg cagcctggct gagactcagt ggccctgggt  112200
tcttactgct gacacctacc ctcaacctca accactgcgg cctcctgtgc accctgatcc  112260
agtggctcat tttccacttt cagtcccagc tctatcccta tttgcagttt ccaagtgcct  112320
ggtcctcagt cagctcagac ccagccaggc cagcccctgg ttcccacatc cccttttgcca  112380
agctcatccc cgccctgttt ggcctgcggg agtgggagtg tgtccagaca cagagacaaa  112440
ggaccagctt ttaaaacatt ttgttggggc caggtgtggt ggctcacacc taatcccaac  112500
acctggggag gccaaggcag aaggatcact tgagtccagg agttcaagac cagcctgggc  112560
aacataggga gaccctgtct ctacaatttt ttttttaatt agctgggcct gttggcactc  112620
tcctgtagtt ccagctactc tagaggctga ggtgggagga ctgcttgagc ctgggaggtc  112680
agggctgcaa tgagccatgt tcacaccact gaacgccagc ctgggcgaga ccctgtatca  112740
aaaaagtaaa gtaaaatgaa tcctgtacgt tatattaagg tgccccaaat tgtacttaga  112800
aggatttcat agttttaaat acttttgtta tttaaaaaat taaatgactg cagcatataa  112860
attaggttct taatggaggg gaaaaagagt acaagaaaag aaataagaat ctagaaacaa  112920
agataagagc agaaataaac cagaaaacac aaccttgcac tcctaactta aaaaaaaaaa  112980
tgaagaaaac acaaccagta aaacaacata taacagcatt aagagctggc tcctggctgg  113040
gcgcggtggc gcatgcctgt aatcccaaca ctttgggagg ccgatgctgg aggatcactt  113100
gagaccagga gttcaaggtt gcagtgagct atgatcatac cactacaccc tagcctgggc  113160
aacacagtga gactgagact ctattaaaaa aaaaatgctg gttccttcct tatttcattc  113220
ctttattcat tcattcagac aacatttatg gggcacttct gagcaccagg ctctgtgcta  113280
agagcttttg cccccagggt ccaggccagg ggacaggggc aggtgagcag agaaacaggg  113340
ccagtcacag cagcaggagg aatgtaggat ggagagcttg gccaggcaag gacatgcagg  113400
gggagcagcc tgcacaagtc agcaagccag agaagacagg cagacccttg tttgggacct  113460
gttcagtggc ctttgaaagg acagccccca cccggagtgc tgggtgcagg agctgaagga  113520
ggatagtgga acactgcaac gtggagctct tcagagcaaa agcaaaataa acaactggag  113580
gcagctgggg cagcagaggg tgtgtgttca gcactaaggg gtgtgaagct tgagcgctag  113640
gagagttcac actggcagaa gagaggttgg ggcagctgca agcctctgga catcgcccga  113700
caggacagag ggtggtggac ggtggccctg aagagaggct cagttcagct ggcagtggcc  113760
gtgggagtgc tgaagcaggc aggctgtcgg catctgctgg ggacggttaa gcaggggtga  113820
gggcccagcc tcagcagccc ttcttggggg gtcgctggga aacatagagg agaactgaag  113880
aagcagggag tcccagggtc catgcagggc gagagagaag ttgctcatgt ggggcccagg  113940
ctgcaggatc aggagaactg gggaccctgt gactgccagc ggggagaagg gggtgtgcag  114000
gatcatgccc agggaagggc ccaggggccc aagcatgggg gggcctggtt ggctctgaga  114060
```

-continued

```
agatggagct aaagtcactt tctcggagga tgtccaggcc aatagttggg atgtgaagac  114120
gtgaagcagc acagagcctg gaagcccagg atggacagaa acctacctga gcagtggggc  114180
tttgaaagcc ttggggcggg gggtgcaata ttcaagatgg ccacaagatg gcaatagaat  114240
gctgtaactt tcttggttct gggccgcagc ctgggtggct gcttccttcc ctgtgtgtat  114300
tgatttgttt ctcttttttg agacagagtc ttgctgggtt gcccaggctg gagtgcagtg  114360
gtgcgatcat agctcactgc agccttgaag tcctgagctc aagagatcct tccacctcag  114420
cctcctgagt agttgggacc acaggcttgc accacagtgc ccaactaatt tcttatattt  114480
tttgtagaga tggggtttca ctgtgtcgcc caggatggtc ttgaactcct gggctcaagt  114540
gatcctcctg cctcagcctc gcaaattgct gggattacag gtgtgagcca ccatgcccga  114600
ccttctcttt ttaagggcgt gtgtgtgtgt gtgtgtgtgt gggcgcactc tcgtcttcac  114660
cttcccccag ccttgctctg tctctaccca gtcacctctg cccatctctc cgatctgttt  114720
ctctctcctt ttacccctct ttcctccctc ctcatacacc actgaccatt atagagaact  114780
gagtattcta aaaatacatt ttatttattt attttgagac agagtctcac tctgtcaccc  114840
aggctggagt gcagtggtgc aatctcggct cactgcaacc tccgcctccc aggttgaagc  114900
aactctcctg cctcagcctc cctagtagct gggattacaa gcacacacca ccatgcctag  114960
caaattttta tatttttagt agaggagggg tgtcaccatg tttgccaagc tggtctcaaa  115020
ctcctggcct caggtgatct gcctaccttg gtctcccaaa gtgctgggat tacaggtgtg  115080
agccaccacg cctgccctta aaaatacatt atatttaata gcaaagcccc agttgtcact  115140
ttaaaaagca tctatgtaga acatttatgt ggaataaata cagtgaattt gtacgtggaa  115200
tcgtttgcct ctcctcaatc agggccaggg atgcaggtga gcttgggctg agatgtcaga  115260
ccccacagta agtggggggc agagccaggc tgggaccctc ctctaggaca gctctgtaac  115320
tctgagaccc tccaggcatc ttttcctgta cctcagtgct tctgaaaaat ctgtgtgaat  115380
caaatcattt taaaggagct tgggttcatc actgtttaaa ggacagtgta aataattctg  115440
aaggtgactc taccctgtta tttgatctct tctttggcca gctgacttaa caggacatag  115500
acaggttttc ctgtgtcagt tcctaagctg atcaccttgg acttgaagag gaggcttgtg  115560
tgggcatcca gtgcccaccc cgggttaaac tcccagcaga gtattgcact gggcttgctg  115620
agcctggtga ggcaaagcac agcacagcga gcaccaggca gtgctggaga caggccaagt  115680
ctgggccagc ctgggagcca actgtgaggc acggacgggg ctgtggggct gtggggctgc  115740
aggcttgggg ccagggaggg agggctgggc tctttggaac agccttgaga gaactgaacc  115800
caaacaaaac cagatcaagg tctagtgaga gcttagggct gctttgggtg ctccaggaaa  115860
ttgattaaac caagtggaca cacaccccca gccccacctc accacagcct ctccttcagg  115920
gtcaaactct gaccacagac atttctcccc tgactaggag ttccctggat caaaattggg  115980
agcttgcaac acatcgttct ctcccttgat ggtttttgtc agtgtctatc cagagctgaa  116040
gtgtaatata tatgttactg tagctgagaa attaaatttc aggattctga tttcataatg  116100
acaaccattc ctcttttctc tcccttctgt aaatctaaga ttctataaac ggtgttgact  116160
taatgtgaca attggcagta gttcaggtct gctttgtaaa taccccttgtg tctattgtaa  116220
aatctcacaa aggcttgttg ccttttttgt ggggttagaa caagaaaaag ccacatggaa  116280
aaaaaatttc tttttgtttt ttttgtttgc ttgttttttt gagacagagt ttcactctgt  116340
cgcccaggct ggagtgcagt ggtgcgatct ccgcccactg caagctccac ctcccgggtt  116400
catgctattc tcctgtctca gcctcccaag tagctgggac tgcaggtgcc cgccaccaca  116460
cctggctaat ttttttgtat ttttagtaga gacggggttt caccgtgtta gccaggatgg  116520
tctcaatctc ctgacctcgt catctgcctg cctcggcctc ccaaagtgct gagattacag  116580
gcgtgagcca ccgtgcccgg ccagaaaaaa acatttctaa gtatgtggca gatactgaat  116640
tattgcttaa tgtcctttga ttcatttgtt taatttcttt aatggattag tacagaaaac  116700
aaagttctct tccttgaaaa actggtaagt tttctttgtc agataaggag agttaaataa  116760
cccatgacat ttcccttttt gcctcggctt ccaggaagct caaagttaaa tgtaatgatc  116820
actcttgtaa ttatcagtgt tgatgccctt cccttcttct aatgttactc tttacatttt  116880
cctgctttat tattgtgtgt gttttctaat tctaagctgt tcccactcct ttctgaaagc  116940
aggcaaatct tctaagcctt atccactgaa aagttatgaa taaaaaatga tcgtcaagcc  117000
tacaggtgct gaggctactc cagaggctga ggccagagga ccacttgagc ccaggaattt  117060
gagacctggg ctgggcagca tagcaagact ctatctccat taaaactatt tttttttatt  117120
taaaaaataa tccgcaaaga aggagtttat gtgggattcc ttaaaatcgg agggtggcat  117180
gaattgattc aaagacttgt gcagagggcg acagtgactc cttgagaagc agtgtgagaa  117240
agcctgtccc acctccttcc gcagctccag cctgggctga ggcactgtca cagtgtctcc  117300
ttgctggcag gagagaattt caacattcac caaaaagtag tattgttttt attaggttta  117360
tgaggctgta gccttgagga cagcccagga caactttgtt gtcacataga tagcctgtgg  117420
ctacaaactc tgagatctag attcttctgt ggctgcttct gacctgagaa agttgcggaa  117480
cctcagcgag cctcacatgg cctccttgtc cttaacgtgg ggacggtggg caagaaaggt  117540
gatgtggcac tagagattta tccatctcta aaggaggagt ggattgtaca ttgaaacacc  117600
agagaaggaa ttacaaagga agaatttgag tatctaaaaa tgtaggtcag gcgctcctgt  117660
gttgattgca gggctattca caatagccaa gatttggaag caacccaagt gtccatcaac  117720
agacaaatgg ataaagaaaa tgtggtgcat atacacaatg gaatactatt cagccatgaa  117780
aaagaatgag aatctgtcat ttgaaacaac atggatggaa ctggaggaca ttatgttaag  117840
tgaaataagc cagacagaag gacagacttc acatgttctc acacatttgt gggagctaaa  117900
aattaaactc atggagatag agagtagaag gatggttacc agaggctgag gagggtggag  117960
gggagcaggg agaaagtagg gatggttaat gggtacaaaa acgtagttag catgcataga  118020
tctagtattg gatagcacag cagggtgacg acagccaaca gtaatttata gtacatttaa  118080
aaacaactaa aagagtgtaa ttggactggc taacatggtg aaaccccgtc tctactaaaa  118140
atacaaaaat tagctgggca tggtggctca cgcctgtaat cccagcactt tgggaggccg  118200
aggcgggccg atcacgaggt caggagatcg agaccatcct agctaacatg gtgaaacccc  118260
gtctctacta caaatacaaa aaaaagaaaa aattagccgg gcatggtggt gggcgcctgt  118320
agtcccagct actcgggagg ctgaggcagg agaatggcgt gaacccggga ggcggagctt  118380
gcagtgagcc gagatcgcgc cactgcactc cagcctgggc gacaaggcaa gattctatct  118440
caaaaaaata aaaataaaat aaaataaaat aataaaataa aataaaataa aataaaataa  118500
ataaaataaa ataaaatgta taattggaat gtttataaca caagaaatga taaatgcttg  118560
aggtgataga taccccattc accgtgatgt gattattgca caatgtatgt ctgtatctaa  118620
atatctcatg taccccacaa gtatatacac ctactatgta cccatataaa tttaaaatta  118680
aaaaattata aaacaaaaat aaataagtaa attaaaatgt aggctggaca ccgtggttca  118740
cgcctgtaat cccagtgctt tgtgaggctg aggtgagaga atcacttgag cccaggagtt  118800
```

-continued

```
tgagaccggc ctgggtgaca tagcgagacc ccatcatcac aaagaatttt taaaaattag  118860
ctgggcgtgg tagcacatac cggtagttcc agctacttgg gagaccgagg caggaggatt  118920
gcttgagccc aggagtttaa ggctgcagtg agctacgatg gcgccactgc attccagcct  118980
gggtgacaga gtgagagctt gtctctattt taaaaataat aaaaagaata aataaaaata  119040
aattaaaatg taaatatgtg catgttagaa aaaatacacc catcagcaaa aagggggtaa  119100
aggagcgatt tcagtcataa ttggagagat gcagaataag ccagcaatgc agtttctttt  119160
attttggtca aaaaaaataa gcaaaacaat gttgtaaaca cccagtgctg gcagcaatgt  119220
ggtgaggctg gctctctcac cagggctcac agggaaaact catgcaaccc ttttagaaag  119280
ccatgtggag agttgtaccg agaggtttta gaatatttat aactttgacc cagaaattct  119340
attctaggac tctgtgttat gaaaataacc catcatatgg aaaaagctcc tttcagaaag  119400
aggttcatgg gaggctgttt gtattttttt tttctttgca tcaaatccag ctcctgcagg  119460
actgtttgta ttattgaagt acaaagtgga atcaatacaa atgttggata gcaggggaac  119520
aatattcaca aaatggaatg ggacatagta ttaaacatag tgcttctgat gaccgtagac  119580
catagacaat gcttaggata tgatatcact tcttttgttg ttttttgtat tttgagacga  119640
agtctcattc tgtcacccag gctggagttc agtggcgcca tctcagctca ctgcaacctc  119700
catctcccgg gttcaagcta ttctccttcc tcaacctccc gagtagctgg gttgcgcacc  119760
accatgcctg gctaactttt gtatttttag tacagacggg gtttcaccac gttggccagg  119820
ctgctcttga actcctgacg tcaggtgatc caccagcctt gacctcccaa agtgctagga  119880
ttacaggagc cactgtaccc agcctaggat atgatatcac ttcttagagc aagatacaaa  119940
attgcatgtg cacaataatt ctaccaagta taggtataca ggggtagtta tatataaatg  120000
agacttcaag gaaatacaac aaaatgcaat cgtgattgtg ttagggtggt aagaaaacgg  120060
tttttgcttt gatgagctct gttttttaaa atcgttatat tttctaataa aaatacatag  120120
tcttttgaag gaacataaaa gattatgaag aaatgagtta gatattgatt cctattgaag  120180
attcagacaa gtaaaattaa ggggaaaaaa aacgggatga accagaagtc aggctggagt  120240
tccaacccca gatccgacag cccaggctga tggggcctcc agggcagtgg tttccaccca  120300
gcattctcaa aagagccact gaggtctcag tgccattttc aagatttcgg aagcggcctg  120360
ggcacggctg gtccttcact gggatcacca cttggcaatt atttacacct gagacgaata  120420
aaaaccagag tgctgagatt acaggcatgg tggcttacgc ttgtaatcgg ctttgggaag  120480
ccgaggtggg ctgattgctt gagcccagga gtttcaaact atcctggaca acatagcatg  120540
acctcgtctc tacaaaaaat acaaaaaatt tgccaggtgt ggtggcatgt gcctgtggtc  120600
ccagctactt gggaggctga agtaggagaa tcccctgagc cctgggaagt cgaggctgca  120660
ctgagccgtg atggtgtcac tgcactccag cctgggtgac aaagtgagac cctatctcac  120720
aaagaaaaaa aacaaaacaa aaaacccaaa gcacactgtt tccactgttt ccagagttcc  120780
tgagaggaaa ggtcaccggg tgaggaagac gttctcactg atctggcaga gaaaatgtcc  120840
agtttttcca actccctaaa ccatggtttt ctatttcata gttcttaggc aaattggtaa  120900
aaatcatttc tcatcaaaac gctgatattt tcacacctcc ctggtgtctg cagaaagaac  120960
cttccagaaa tgcagtcgtg ggagacccat ccaggccacc cctgcttatg gaagagctga  121020
gaaaaagccc cacgggagca tttgctcagc ttccgttacg cacctagtgg cattgtgggt  121080
gggagagggc tggtgggtgg atggaaggag aaggcacagc cccccttgc agggacagag  121140
ccctcgtaca gaagggacac cccacatttg tcttccccac aaagcggcct gtgtcctgcc  121200
tacggggtca gggcttctca aacctggctg tgtgtcagaa tcaccagggg aacttttcaa  121260
aactagagag actgaagcca gactcctaga ttctaattct aggtcagggc taggggctga  121320
gattgtaaaa atccacaggt gattctgatg cccggcaggc ttgagaacag ccgcagggag  121380
ttctctggga atgtgccggt gggtctagcc aggtgtgagt ggagatgccg gggaacttcc  121440
tattactcac tcgtcagtgt ggccgaacac atttttcact tgacctcagg ctggtgaacg  121500
ctcccctctg gggttcaggc ctcacgatgc catcctttttg tgaagtgagg acctgcaatc  121560
ccagcttcgt aaagcccgct ggaaatcact cacacttctg ggatgccttc agagcagccc  121620
tctatccctt cagctcccct gggatgtgac tcaacctccc gtcactcccc agactgcctc  121680
tgccaagtcc gaaagtggag gcatccttgc gagcaagtag gcgggtccag ggtggcgcat  121740
gtcactcatc gaaagtggag gcgtccttgc gagcaagcag gcgggtccag ggtggcgtgt  121800
cactcatcct tttttctggc taccaaaggt gcagataatt aataagaagc tggatcttag  121860
caacgtccag tccaagtgtg gctcaaagga taatatcaaa cacgtcccgg gaggcggcag  121920
tgtgagtacc ttcacacgtc ccatgcgccg tgctgtggct tgaattatta ggaagtggtg  121980
tgagtgcgta cacttgcgag acactgcata gaataaatcc ttcttgggct ctcaggatct  122040
ggctgcgacc tctgggtgaa tgtagcccgg ctccccacat tcccccacac ggtccactgt  122100
tcccagaagc cccttcctca tattctagga gggggtgtcc cagcatttct gggtccccca  122160
gcctgcgcag gctgtgtgga cagaataggg cagatgacgg accctctctc cggaccctgc  122220
ctgggaagct gagaataccc atcaaagtct ccttccactc atgcccagcc ctgtccccag  122280
gagccccata gcccattgga agttgggctg aaggtggtgg cacctgagac tgggctgccg  122340
cctcctcccc cgacacctgg gcaggttgac gttgagtggc tccactgtgg acaggtgacc  122400
cgtttgttct gatgagcgga caccaaggtc ttactgtcct gctcagctgc tgctcctaca  122460
cgttcaaggc aggagccgat tcctaagcct ccagcttatg cttagcctgc gccaccctct  122520
ggcagagact ccagatgcaa agagccaaac caaagtgcga caggtccctc tgcccagcgt  122580
tgaggtgtgg cagagaaatg ctgcttttgg ccctttttaga tttggctgcc tcttgccagg  122640
agtggtggct cgtgcctgta attccagcac tttgggagac taaggcggga ggttcgcttg  122700
agcccaggag ttcaagacca gcctgggcaa caatgagacc cctgtgtcta caaaaagaat  122760
taaaattagc caggtgtggt ggcacgcacc tgtagtccca gctacttggg aggctgaggt  122820
gggaggattg cctgagtccg ggaggcggaa gttgcaagga gccatgatcg cgccactgca  122880
cttcaaccta ggcaacagag tgagactttg tctcaaaaaa caatcatata ataattttaa  122940
aataaataga tttggcttcc tctaaatgtc cccggggact ccgtgcatct tctgtggagt  123000
gtctccgtga gattcgggac tcagatcctc aagtgcaact gacccacccg ataagctgag  123060
gcttcatcat cccctggccg gtctatgtcg actgggcacc cgaggctcct ctcccaccag  123120
ctctcttggt cagctgaaag caaactgtta acaccctggg gagctggacg tatgagaccc  123180
ttggggtggg aggcgttgat ttttgagagc aatcacctgg ccctggctgg cagtaccggg  123240
acactgctgt ggctccgggg tgggctgtct ccagaaaatg cctggcctga ggcagccacc  123300
cgcatccagc ccagagggtt tattcttgca atgtgctgct gcttcctgcc ctgagcacct  123360
ggatcccggc ttctgccctg aggccccttg agtcccacag gtagcaagcg cttgccctgc  123420
ggctgctgca tggggctaac taacgcttcc tcaccagtgt ctgctaagtg tctcctctgt  123480
ctcccacgcc ctgctctcct gtccccccag tttgtctgct gtgaggggac agaagaggtg  123540
```

tgtgccgccc ccacccctgc ccgggccctt gttcctggga ttgctgtttt cagctgtttg 123600
agctttgatc ctggttctct ggcttcctca aagtgagctc ggccagagga ggaaggccat 123660
gtgctttctg gttgaagtca agtctggtgc cctggtggag gctgtgctgc tgaggcggag 123720
ctggggagag agtgcacacg ggctgcgtgg ccaacccctc tgggtagctg atgcccaaag 123780
acgctgcagt gcccaggaca tctgggacct ccctggggcc cgcccgtgtg tcccgcgctg 123840
tgttcatctg cgggctagcc tgtgacccgc gctgtgctcg tctgcgggct agcctgtgtc 123900
ccgcgctctg cttgtctgcg gtctagcctg tgacctggca gagagccacc agatgtcccg 123960
ggctgagcac tgccctctga gcaccttcac aggaagccct tctcctggtg agaagagatg 124020
ccagcccctg gcatctgggg gcactggatc cctggcctga gccctagcct ctccccagcc 124080
tgggggcccc ttcccagcag gctggccctg ctccttctct acctgggacc cttctgcctc 124140
ctggctggac cctggaagct ctgcagggcc tgctgtcccc ctccctgccc tccaggtatc 124200
ctgaccaccg gccctggctc ccactgccat ccactcctct cctttctggc cgttccctgg 124260
tccctgtccc agccccctc cccctctcac gagttacctc acccaggcca gagggaagag 124320
ggaaggaggc cctggtcata ccagcacgtc ctcccacctc cctcggccct ggtccacccc 124380
ctcagtgctg gcctcagagc acagctctct ccaagccagg ccgcgcgcca tccatcctcc 124440
ctgtccccca acgtccttgc cacagatcat gtccgccctg acacacatgg gtctcagcca 124500
tctctgcccc agttaactcc ccatccataa agagcacatg ccagctgaca ccaaaataat 124560
tcgggatggt tccagtttag acctaagtgg aaggagaaac caccacctgc cctgcacctt 124620
gtttttggt gaccttgata aaccatcttc agccatgaag ccagctgtct cccaggaagc 124680
tccagggcgg tgcttcctcg ggagctgact gataggtggg aggtggctgc cccccttgcac 124740
cctcaggtga ccccacacaa ggccactgct ggaggccctg gggactccag gaatgtcaat 124800
cagtgacctg ccccccaggc cccacacagc catggctgca tagaggcctg cctccaaggg 124860
acctgtctgt ctgccactgt ggagtcccta cagcgtgccc cccacagggg agctggttct 124920
ttgactgaga tcagctggca gctcagggtc atcattccca gagggagcgg tgccctggag 124980
gccacaggcc tcctcatgtg tgtctgcgtc cgctcgagct tactgagaca ctaaatctgt 125040
tggtttctgc tgtgccacct acccaccctg ttggtgttgc tttgttccta ttgctaaaga 125100
caggaatgtc caggacactg agtgtgcagg tgcctgctgg ttctcacgtc cgagctgctg 125160
aactccgctg ggtcctgctt actgatggtc tttgctctag tgctttccag ggtccgtgga 125220
agcttttcct ggaataaagc ccacgcatcg accctcacag cgcctcccct ctttgaggcc 125280
cagcagatac cccactcctg cctttccagc aagatttttc agatgctgtg catactcatc 125340
atattgatca cttttttctt catgcctgat tgtgatctgt caatttcatg tcaggaaagg 125400
gagtgacatt tttacactta agcgtttgct gagcaaatgt ctgggtcttg cacaatgaca 125460
atgggtccct gtttttccca gaggctcttt tgttctgcag ggattgaaga cactccagtc 125520
ccacagtccc cagctcccct ggggcagggt tggcagaatt tcgacaacac atttttccac 125580
cctgactagg atgtgctcct catggcagct gggaaccact gtccaataag ggcctgggct 125640
tacacagctg cttctcattg agttacaccc ttaataaaat aatcccattt tatccttttt 125700
gtctctctgt cttcctctct ctctgccttt cctcttctct ctcctcctct ctcatctcca 125760
ggtgcaaata gtctacaaac cagttgacct gagcaaggtg acctccaagt gtggctcatt 125820
aggcaacatc catcataaac caggtagccc tgtggaaggt gagggttggg acgggagggt 125880
gcagggggtg gaggagtcct ggtgaggctg gaactgctcc agacttcaga aggggctgga 125940
aaggatattt taggtagacc tacatcaagg aaagtgttga gtgtgaaact tgcgggagcc 126000
caggaggcgt ggtggctcca gctcgctcct gcccaggcca tgctgcccaa gacaaggtga 126060
ggcgggagtg aagtgaaata aggcaggcac agaaagaaag cacatattct cggccgggcg 126120
ctgtggctca cgcctgtaat tccagcactt tgggaggcca aggtgggtgg atcatgaggt 126180
caggagattg agaccatcct ggctaacaca gtgaaacccc gtctctacta aaaatacaaa 126240
aaattagccg ggcgtggtgg tgggcgcctg tagtcccagc tactccggag gctgaggcag 126300
gaaaatggcg tgaacccgga aggcggagct tgcagtgagc ggagtgagca gagatcgcgc 126360
cactgcactc cagcctgggc gacagagcga gactccgtct caaaaaaaaa aagcacatgt 126420
tctcgcttct ttgtgggatc caggagatag agaatagaag gatggttacc agaggctggg 126480
aagggtagtg aggggatggt gggggatgg tcaatgggta caaaaaaaat agaataagac 126540
ctagtatttg atagtgcaac agggtgacta tagtcaataa taatttaatt gtacatttaa 126600
aaataactaa aagatagccg ggtgcagtgg cttacgtctg taatcccagt actttgggag 126660
gctgaggtgg gcgtttgaga ccagcctggc caacatggtg aaaccccatc tctactaaaa 126720
atacaaaaat tagccaggca tggtggcggg cgcctgtaat cccagctact cgggaggctg 126780
aggcaggaga atcacttgaa cctgggaggc agaggttgca gtgagccgag atcttgccac 126840
tgcactccag cctgggtgac agtgaaactc cgtctcaaaa ataaaaataa aaatacagct 126900
gggcacggtg gctcacgcct gtaatcccag cactttggga ggccgaggcg agcggatcac 126960
aaggtcagga gatatagacc atcctggcta acacggtgaa acccggtctc tactaaaaat 127020
acaaaaaatt agccaggcgt ggtggcaggt gcctatagtc ccagctactc acaaggctga 127080
ggcaggagaa tggcatgaac ctgggaggcg gagcttgcag tgagccgaga ttgtgccact 127140
gcactccagc ctgggcgaga gagtgagact ccgtctcaaa acaaaaacaa aaacaaaaac 127200
aaaaacaaac acacaacaaa aacctaaaag aatataaatg gattgtttgt aacacaaagg 127260
acaaatgttt gaggggatgg atacccatt ttccatgatg tgattattat acattgtgtg 127320
tctgtatcaa aacatctcat gagccccata aatatataca cctaactatg tacccacaaa 127380
aattaaaaaa atatattttt taaggtgaag agggaggcga gatgctggcc ttaaccccta 127440
acccgttgtt ctccctgcaa gctgtccaca gggcctctca gactcgaggt tcagctatat 127500
ggatgcatga gcttggtccc cagccaacat gggagacact tcaccatcgg cagcagctac 127560
agcacaggaa ccctgggtca ctgccatgtc ccctctgtga ctttgtttaa acagaaaatg 127620
atgctctggg ccggctgtgg tggcccacac ctataatccc agcaccttgg gaggcggggg 127680
tgggcagatt gcctgaggtc aggagttgga gatcagcctg gccgacatgg cgaaacccca 127740
tgtctactaa aaatacaaaa actagccagg catggtggca catgcctgta atcccagcta 127800
cttgggaggc tgaagcagga gaatcacttg aacccaggag gcagaggctg agtgagccaa 127860
gatcgtgcca atgcactcca gcttgggtga gggagtgaga ctccgtctca aaaaaaaaaa 127920
aaaagaaaga aaaagaaaag aaagtgatcc tactggaacc atgcttactc ccctccccac 127980
ctcacactgt gtagaaatta gtgctgtcgg ccaggcgcgg tggctcatgc ctgtaatcgc 128040
agcactttgg gaggccaagg caggcggatc acgaggtcag gagatcaaga ccatcctggc 128100
taacacagtg aaaccctgtc tctactaaaa atacaaaaaa ttagccgggc atggtggcag 128160
gcacctgtag tcccaactac ttgggaggct gaggcaggag aatggcatga acctgggagg 128220
cggagcttgc agtgagccaa gatcgcgcca ctgcatacca gcctaggtga cagagtgaga 128280

```
ctcagcaaaa aaagaaagaa agaaagaaag aaatcagtgc tgtctatact tctttctgca  128340
gtgatggaaa tattctgtat ctgtgctgtc cagtatagta gccactagct acatgtggca  128400
cttgaaacat ggctggtaca gttgaggaag agtggctgcc atatcggacg acacagctat  128460
agattctgtc accccacccc gagagtccag agcggggact tctgccttag gccctattca  128520
gggctgattt ttacttgaac ccttactgtg ggaagagaag gccatgagaa gttcagtcta  128580
gaatgtgact ccttattttc tggctccctt ggacactttg tgggatttag tctccctgtg  128640
gaaagtattc cacaagtggt gccaccaccc cagctgtgag agcagctggg agctgctttt  128700
gtcatctttc cctggaaagt cctgtgggct gtctcttcct catgccttgt cccatgcttg  128760
ggcatggtgt caagcgtcag gagggagaaa gggtccttat ttatttattt agagagggac  128820
ccttcttctg ttcccaggct ggagtgcagt ggtgcgatct cggctcactg caacctccgc  128880
ctcctgggtt caagtgattc tcctgcctca gcctcctgag tagctgagat tacaggcaca  128940
tgccaacatg cctggctaat tttttttttt tttttttttt tttttttttg agatggagtt  129000
gtactctcat tgcccaggct ggaatgtaat ggcacaatct cggctcactg caacctccac  129060
ctcctggatt caagcaattc tcctgtctca gcttcccaag tagctgggat tacaggtgcc  129120
cgccaccatg ctcaactaat ttttgtattt tttttttagt agagacgagg tttcaccatg  129180
ttggtcagac tggtctcaaa ctcctgacct caggtgatcc acctgcctcg gcctcccaaa  129240
gtgctaggat tacaggcatg agccaccacg cccggcctga aagggttctt atttagtgtg  129300
cattttgaca ttcaatttaa ttccaaggtc ttgtggggtc atggtttaca ggatgttgat  129360
atagaaaaga cttcacttaa tggccgggc gcagtggctc atgcctgtaa tcccagcact  129420
ttgggaggcc gaggcaggca gatcaggagg tcaggagatt gagaccatcc tggctaacac  129480
agtgaaaccc catctctact gaaaatacaa aaaattagct gggcgtggtg gcaggcacct  129540
gtagtcccag ccactcggtt ggctgaggca ggagaatggc atgaacccgg gaggcggagc  129600
ttgcagtgag cagagaccat gccactgcac tccagcctgg gcgacagagc aagactctgt  129660
ctcaagaaaa aaaaaaaaaa aacagacttt acttactgga agccaaccaa tgtatattta  129720
gagtaatttt tcctgggctg agctgtcatt tacttttgca gtatctcaag aagaagagtt  129780
tacagtgtaa atatttgatg cacactttga ttatatagat gaagcaaact attttcaaga  129840
gctttgcaag gacttacttg tatccaaaca ccattctaaa ggagtcttac ctacttctaa  129900
aggctggtct ctacttggaa ccacttgctt ggccctggtt caagtcctgc tgcaaacctg  129960
gaagtcctgt cattgtcttc ttccctccag agcagtggca cccaatctaa tttttgctgt  130020
gccccagcag cccctggcac tttgccctgt agactgcaga cctcatgtaa tgtatgttaa  130080
gtccacagaa ccacagaaga tgatggcaag atgctcttgt gtgtgttgtg ttctaggagg  130140
tggccaggtg gaagtaaaat ctgagaagct tgacttcaag gacagagtcc agtcgaagat  130200
tgggtccctg gacaatatca cccacgtccc tggcggagga aataaaaagg taaagggggt  130260
agggtgggtt ggatgctgcc cttgggtata tgggcattaa tcaagttgag tggacaaagg  130320
ctggtccagt tcccagagga ggaaaacaga ggcttctgtg ttgactggct ggatgtgggc  130380
cctcagcagc atccagtggg tctccactgc ctgtctcaat cacctggagc tttagcacgt  130440
ttcacacctg ggccccaacc tggagaggct gaccaatggg tctcaggggc agctcggttg  130500
ctggagtttt tgtttttatt tatttttatg tatttaaggc agggtctctg tattagtcca  130560
ttctcacact gctaataaag acatacccaa gactgggtaa tttataaagg aaagaggttt  130620
aatggactca cagttccaca tggctggggga ggcctcaaaa tcatggcgga aggcaaagga  130680
gaagcaaagg catttcttac atggcgacag gcaagagagc gtgtgcaggg gaactcccat  130740
ttataaaacc atcagacctc atgagattta ttcactatca tgagaacagc atgggaaaga  130800
cccgccccca tgattcagtt acctcccact gggtccctcc catgacacat ggaattatgg  130860
gagctacaat tcaagatgag atttgggtgg ggacacagcc aaaccatatc agtctccctc  130920
tgtcatccag gctggagtgc actggcatga tctcggctca ctgcagcctc tacctccctg  130980
ggtcaggtga tcttcccacc tcagcctccc aggtagctgg aactacaggt acctgccact  131040
atgcctggct aaatattttg tatttcctgt ggagacgagg ttttgccacg ttgcccaggc  131100
tggtcttgaa ctcctgaggt caagcaatat gcccacctcg gcctcccaag gtgctgggat  131160
tacaggtgtg agccacagtg ctcggcctaa gtcactgcag tttttaaagc tcccaggtga  131220
ttcttcagtg cagtcaaaag tgagaactgg ctgggtgcgg tggctcatgc ctgtaatccc  131280
agcaccttgg gaggcgaagg tgggcagatg gcttgaggtc aggagttcaa gaccagcctg  131340
gccaacatgg taaaacccca tctctactaa aaatacaaaa gttagctggg tgtggtggtg  131400
cgtgcctgta atcccagcta cttgggaggc tgaggcatga gaattgcttg aacccagggg  131460
acagaggttg tagtgagccg agatcgtgcc actgcactcc agcctgggca acagagtgag  131520
attccatctc acaaaaaaaa aaaaaaaagc gagaaccact gtcctaggcc ctgatgtttg  131580
caggcaacta aaaaaggaag tggacatccc cagtcagctg tggcgcacca agaacaagtc  131640
atgggaacat aacctaattt tctaaatggg ttactaggca cttagagcaa aacaatgatg  131700
ccgaaatcct gatttcagca aagcctctgc ctgcctgtct tggaagtatc cacatgaggc  131760
tgctggggcc ttggtgtccc cagcagtttc tagtctctag gtcttgctgt gggtgtctgt  131820
gcagtgaggg tgtgtgtggc gctgggtgag ctctgtctag gcctggcaca ggatgcggtc  131880
tggtagctgc tgcttctctt ctgcagaagc gcagccaagc accctctggg gtttcaggcc  131940
cacacccagc ctgaagttct gggagtggct cactttccaa ccttcagggt ctcccagcag  132000
ctgactgggg agtggtggag ggaaaaggga ttgtattagt ccgttttcac gccgctgatg  132060
aagacatacc cgatactggg cagtctaaaa gatagaggtc tgatggactc acagttccac  132120
gtgactgggg aggcctgaca atcatggtgg aaggtgaaag gcttgtctca cacggtggca  132180
gacaagagaa aagagcttgt gcaggggaac tcccctttat aaaaccatca gatctcggga  132240
gacttattca ctatcatgag aacagcacgg gaaagaccct cctctatgat tcaattacct  132300
cccaccaggt ccctcccaca acatgtagga attgtgggaa ctacaattca agatgacatt  132360
tgggtgggga cacagccaaa ccatatcagg gcgtcccaga aagggtatag ggtctgagac  132420
ccaagtcagc atgagaaagt atgcttctca tggtggccca gttgggtgga agtggcagcc  132480
gggccgtctt tccaccaggc cactcaagta gcagctgaga gacccctgcc ctggccagtc  132540
cccgccctcc cctcttgcca ctgcctctgg ttctgaacag atgggcaccc tcatcttgta  132600
tttgtgatta atgtctaaca atgtagtttt gtgagaaggg tttgctgata cagccttgct  132660
gcagatgctg cgaactgtgg cctggggcag accttacctc cagacacgcc ctgaggcagg  132720
ggagggcact ggcccgtagc tggccgagag ctctcgggtt gcgcgacagg gatacttttc  132780
agcggctggg tcgctatcca aagtgagaaa acgaggaggg accaggaggc tgtccgcctc  132840
aagagatgtg ggggccaggt ccagttatct ggggaagcag taagcttctc tgctgtttct  132900
aaccccaggc ctcccctggt ctaaggcagg gcctcccagc ctcggggcac tttaaagata  132960
tctgggcctg gccccatccc cacagtctga ctgagtgggt ctggataggg cctgagcatt  133020
```

```
ggtgatttcc tgggtgaaag gaggcccctc acagtctctg gaagcttctc tgtgttagga  133080
aaagctctgg gcttgactct gctttgaaag tcaagatccg caaatcctct cagcctcagt  133140
ttctccttca gcaagatgaa atggaaatgc tgtacctacg tcccggggtg gttgtgagac  133200
ccaaaaaaga caatgttctg gaaggttcct ggtgcgttgc agtcctctaa gaacctgagt  133260
tagagccacg ctgagtctca gcttcttggc tccttctgtt tcaaactcgt ccatgtgata  133320
gctcaggaag ggtaggcagg gccctgcccc ctactcagaa aacaccatcc tggtcctggg  133380
gatccccgca gcattagtcc cctgttttcc cagtgtattg agaaaaattg ctaacaagca  133440
gtggggcaca ccaccagcct cctgggttcc tttcagtttg gggatttttg gacattccca  133500
ggaatgtctt aaaaaacact tcaaaaaaca ttaacataaa tatttttatc aaagcctgta  133560
ttaaatggtc tttcaagaaa atacagtaac aggtcaggca tggtggctca tgcctgtaac  133620
cccagcactt tgggaggcca aggcaggcag atcacctgaa atcaggagtt caagaccaac  133680
ctggccaaca cagccaaatc ccatctctac aaaaaataca aaaattagct gggtgtggtg  133740
gcacacacct gtagtcccag ctacttggga ggccgaggca ggagaattgc ttgatcccgg  133800
aggcggaggt tgcagtgagc tgagatcgtg ccactgcact ccagcgtggg tgacaaggtg  133860
aatctttgtc tcaaaaaaaa aaaaaaaaaa aagataaaat acagtataca gtaatagaga  133920
acaatccttt tttcaaagta gtgaccccaa atgaacaaaa tatgcatcta gcttaaatgc  133980
gaacctggtt ttctctacgc ccattcaagc ccctgcaata ggggcccttc accccgcatc  134040
catggactcc taaaattata tggaaaatgg ctgtgtgtga gtgtggatgg acatgtgcac  134100
acatattttt ggctttacca gatgctcaaa gagcctagga cccaaaaagg gctgagaatg  134160
accgtgtcgg ccacttcagg gtcatcagga attgctgtgc actgctcact tctccagtga  134220
acactttctg cttctgtgtt tcctggtatc ctttgggact cctggctagg tcatgtgttt  134280
ctctactttc aaaagggctt cagccaggca cgatggcatg agcctgtagt cccagttgct  134340
ctggaggtta aggtgggaag attgcttgag cccaggaatt tgaggccagc ctgggcaagt  134400
agataggtag atgattgata gatagataga tagataaata gatggataga taagtcgcta  134460
gacagtcatc catccaccca tccacacata aaaaggcctt tgtcatgtca tgttttgtgg  134520
cccacctgcc agtgttgccc acagttgctg cccctccaaa ctcatcagtc actggcaaac  134580
aggaggaatg tgtggctcat gtctgggcat cagtggctgt gggagacatc cttgatcttc  134640
tccagcttct ccttccacat tttcctttgc aatctggcaa tatctattaa aataaaatgt  134700
gcatgccttt tgacctaaga gcttcacttc taggacccac ttacacgtgt gtgacatgat  134760
gttcatacgg gtttatttat ctgaggttgt tcatacacac cattgcctgt aatcactaaa  134820
ggcgggagca gcctacacat ccatcccacag aggagtagat gccttttggt acatccgtgg  134880
cgacggaata ctaagcagcc tgtgtatcta tacactcaca cgtgtttgtt tatgtgtgga  134940
atatctctgg agggtacaca agaaacttaa aatgatcact gtctctgggg agggtacctg  135000
ggtgcctggg aggcaggtca gggaaggagt gggcacaggt attaccaatt ggaagacaat  135060
aaaaacaaca gctcctggcc aggcgcagtg gctcacgcct gtaatggcag cactctgaga  135120
ggctgaggcg ggcagattgc ttgcgtccag gagttcaaga ccagcctggg caacatagca  135180
aaaccccgtt tctattaaaa atacaaaaaa ttagccaggt gtggtggcat gcacctgtaa  135240
tcccagctac tcgggaggct gaggtgggag aatcacctga gcctgggagg tcaaggctgc  135300
agtgaggtga gattgtgcca ccgcactcta gcctgggcga tagagcaaga ccctgtctca  135360
aaaacaaaca aaaaacagtc cctggcactc tgggccaggc ctggcagggc agttggcagg  135420
gctggtcttt ctctggcact tcatctcacc ctccctccct tcctcttctt gcagattgaa  135480
acccacaagc tgaccttccg cgagaacgcc aaagccaaga cagaccacgg ggcggagatc  135540
gtgtacaagt cgccagtggt gtctggggac acgtctccac ggcatctcag caatgtctcc  135600
tccaccggca gcatcgacat ggtagactcg ccccagctcg ccacgctagc tgacgaggtg  135660
tctgcctccc tggccaagca gggtttgtga tcaggcccct ggggcggtca ataattgtgg  135720
agaggagaga atgagagagt gtggaaaaaa aaagaataat gacccggccc ccgccctctg  135780
cccccagctg ctcctcgcag ttcggttaat tggttaatca cttaacctgc ttttgtcact  135840
cggctttggc tcgggacttc aaaatcagtg atgggagtaa gagcaaattt catctttcca  135900
aattgatggg tgggctagta ataaaatatt taaaaaaaaa cattcaaaaa catggccaca  135960
tccaacattt cctcaggcaa ttccttttga ttcttttttc ttccccctcc atgtagaaga  136020
gggagaagga gaggctctga aagctgcttc tgggggattt caagggactg ggggtgccaa  136080
ccacctctgg ccctgttgtg ggggtgtcac agaggcagtg gcagcaacaa aggatttgaa  136140
acttggtgtg ttcgtggagc cacaggcaga cgatgtcaac cttgtgtgag tgtgacgggg  136200
gttggggtgg ggcgggaggc cacgggggag gccgaggcag gggctgggca gaggggagag  136260
gaagcacaag aagtgggagt gggagaggaa gccacgtgct ggagagtaga catccccctc  136320
cttgccgctg ggagagccaa ggcctatgcc acctgcagcg tctgagcggc cgcctgtcct  136380
tggtggccgg gggtgggggc ctgctgtggg tcagtgtgcc accctctgca gggcagcctg  136440
tgggagaagg gacagcgggt aaaaagagaa ggcaagctgg caggagggtg gcacttcgtg  136500
gatgacctcc ttagaaaaga ctgaccttga tgtcttgaga gcgctggcct cttcctccct  136560
ccctgcaggg tagggggcct gagttgaggg gcttccctct gctccacaga aaccctgttt  136620
tattgagttc tgaaggttgg aactgctgcc atgattttgg ccactttgca gacctgggac  136680
tttagggcta accagttctc tttgtaagga cttgtgcctc ttgggagacg tccacccgtt  136740
tccaagcctg ggccactggc atctctggag tgtgtggggg tctgggaggc aggtcccgag  136800
ccccctgtcc ttcccacggc cactgcagtc accccgtctg cgccgctgtg ctgttgtctg  136860
ccgtgagagc ccaatcactg cctataccc tcatcacacg tcacaatgtc ccgaattccc  136920
agcctcacca ccccttctca gtaatgaccc tggttggttg caggaggtac ctactccata  136980
ctgagggtga aattaaggga aggcaaagtc caggcacaag agtgggaccc cagcctctca  137040
ctctcagttc cactcatcca actgggaccc tcaccacgaa tctcatgatc tgattcggtt  137100
ccctgtctcc tcctcccgtc acagatgtga gccagggcac tgctcagctg tgaccctagg  137160
tgtttctgcc ttgttgacat ggagagagcc ctttcccctg agaaggcctg gcccctttcct  137220
gtgctgagcc cacagcagca ggctgggtgt cttggttgtc agtggtggca ccaggatgga  137280
agggcaaggc acccagggca ggcccacagt cccgctgtcc cccacttgca ccctagcttg  137340
tagctgccaa cctcccagac agcccagccc gctgctcagc tccacatgca tagtatcagc  137400
cctccacacc cgacaaaggg gaacacaccc ccttggaaat ggttcttttc ccccagtccc  137460
agctggaagc catgctgtct gttctgctgg agcagctgaa catatacata gatgttgccc  137520
tgccctcccc atctgcaccc tgttgagttg tagttggatt tgtctgttta tgcttggatt  137580
caccagagtg actatgatag tgaaaagaaa aaaaaaaaaa aaaaaggacg catgtatctt  137640
gaaatgcttg taaagaggtt tctaacccac cctcacgagg tgtctctcac ccccacactg  137700
ggactcgtgt ggcctgtgtg gtgccaccct gctggggcct cccaagtttt gaaaggcttt  137760
```

-continued

```
cctcagcacc tgggacccaa cagagaccag cttctagcag ctaaggaggc cgttcagctg  137820
tgacgaaggc ctgaagcaca ggattaggac tgaagcgatg atgtcccctt ccctacttcc  137880
ccttggggct ccctgtgtca gggcacagac taggtcttgt ggctggtctg gcttgcggcg  137940
cgaggatggt tctctctggt catagcccga agtctcatgg cagtcccaaa ggaggcttac  138000
aactcctgca tcacaagaaa aaggaagcca ctgccagctg gggggatctg cagctcccag  138060
aagctccgtg agcctcagcc acccctcaga ctgggttcct ctccaagctc gccctctgga  138120
ggggcagcgc agcctcccac caagggccct gcgaccacag cagggattgg gatgaattgc  138180
ctgtcctgga tctgctctag aggcccaagc tgcctgcctg aggaaggatg acttgacaag  138240
tcaggagaca ctgttcccaa agccttgacc agagcacctc agcccgctga ccttgcacaa  138300
actccatctg ctgccatgag aaaagggaag ccgcctttgc aaaacattgc tgcctaaaga  138360
aactcagcag cctcaggccc aattctgcca cttctggttt gggtacagtt aaaggcaacc  138420
ctgagggact tggcagtaga aatccagggc ctcccctggg gctggcagct tcgtgtgcag  138480
ctagagcttt acctgaaagg aagtctctgg gcccagaact ctccaccaag agcctccctg  138540
ccgttcgctg agtcccagca attctcctaa gttgaaggga tctgagaagg agaaggaaat  138600
gtggggtaga tttggtggtg gttagagata tgccccccctc attactgcca acagtttcgg  138660
ctgcatttct tcacgcacct cggttcctct tcctgaagtt cttgtgccct gctcttcagc  138720
accatgggcc ttcttatacg gaaggctctg ggatctcccc cttgtggggc aggctcttgg  138780
ggccagccta agatcatggt ttagggtgat cagtgctggc agataaattg aaaaggcacg  138840
ctggcttgtg atcttaaatg aggacaatcc ccccagggct gggcactcct cccctcccct  138900
cacttctccc acctgcagag ccagtgtcct tgggtgggct agataggata tactgtatgc  138960
cggctccttc aagctgctga ctcactttat caatagttcc atttaaattg acttcagtgg  139020
tgagactgta tcctgtttgc tattgcttgt tgtgctatgg ggggaggggg gaggaatgtg  139080
taagatagtt aacatgggca aagggagatc ttggggtgca gcacttaaac tgcctcgtaa  139140
ccctttttcat gatttcaacc acatttgcta gagggaggga gcagccacgg agttagaggc  139200
ccttggggtt tctcttttcc actgacaggc tttcccaggc agctggctag ttcattccct  139260
ccccagccag gtgcaggcgt aggaatatgg acatctggtt gctttggcct gctgccctct  139320
ttcaggggtc ctaagcccac aatcatgcct ccctaagacc ttggcatcct tccctctaag  139380
ccgttggcac ctctgtgcca cctctcacac tggctccaga cacacagcct gtgcttttgg  139440
agctgagatc actcgcttca ccctcctcat ctttgttctc caagtaaagc cacgaggtcg  139500
gggcgagggc agaggtgatc acctgcgtgt cccatctaca gacctgcagc ttcataaaac  139560
ttctgatttc tcttcagctt tgaaaagggt taccctgggc actggcctag agcctcacct  139620
cctaatagac ttagccccat gagtttgcca tgttgagcag gactatttct ggcacttgca  139680
agtcccatga tttcttcggt aattctgagg gtggggggag ggacatgaaa tcatcttagc  139740
ttagctttct gtctgtgaat gtctatatag tgtattgtgt gttttaacaa atgatttaca  139800
ctgactgttg ctgtaaaagt gaatttggaa ataaagttat tactctgatt aaataaggtc  139860
tccattcatg gattccaagg acaagaaagt catatagaat gtctattttt taagttcttt  139920
cccacgcacc cttagataat ttagctcaga acaggaaatg atagtattaa taaaagctgg  139980
acatcaggat taacagctct ctctggggcc ctgaaggtga gagttctcag acttgctcat  140040
ttgcagttgc ttctttgtga tgctggcaaa ccatcctagt cccattcaaa gggcaataca  140100
aagccttgtg gctgacctca cgatgcagca ctcagtttgc aagaccggca ccagtgtatg  140160
caaacctgag aaggttgggg atgaggatat gggatctttc atccctggaa atttagtcca  140220
gaggcctggg gctggagcag aacaccaagc caatcagctt aatgaatggc ttagattcct  140280
gctaggtttg cagagctgcc ttctttcctt tggtacctta ttatagattg aggagtattt  140340
ctgctaaacc aagataggga taaccagata gcatcttcat agcaatgcca caaaggaaaa  140400
caaaaacaaa acagtaatcc atcatattat tccttagtaa ctatgccaag gtcatgatac  140460
tgaatcctta gattgtttca aaatactact tttctttgct cttcctgatg tgtttgccac  140520
cgcaggcaga tgtttaagta aaacagattt taactgcagc tacaaaagca gcaacaggcc  140580
agcaaaagag aagtgctatc tcagagagca tggctttcag agccacaaga gacagcctca  140640
ctggctgttt cagcttgact gccatgcaaa gaagagagca gagggagaac cagccccacc  140700
cacttattca tcttgtacaa aaaaaaagca cctaccagcc taggctacat agtgagacac  140760
tatctccaca aaaaacccac gaaaactagc tgggtatggt ggcacatgcc tacagtccca  140820
gctactggta aggctgtggt gggaggatct cttgaggcca ggaaggagat ccaggctgca  140880
gtgagccaag attgcaccac tgcactccag tctggacaat cgagcaagat cccatctcaa  140940
acaataaaaa aaaaaagcgt gtaacctcct cagaagaaag atgttataat ctcaggcagc  141000
a                                                                  141001
```

```
SEQ ID NO: 33          moltype = RNA  length = 22
FEATURE                Location/Qualifiers
source                 1..22
                       mol_type = other RNA
                       organism = synthetic construct
SEQUENCE: 33
ttagagtgag gattaaaatg ag                                           22
```

```
SEQ ID NO: 34          moltype = DNA  length = 12001
FEATURE                Location/Qualifiers
source                 1..12001
                       mol_type = genomic DNA
                       organism = Rattus norvegicus
SEQUENCE: 34
aggacaggtg aggtcctagg tggaggtacg tttttgggct tcatggggca gatgctgccc  60
taggaagggt acaagacttc tatagccctg ctggggaccc cattgtcctg gaaggcggcc  120
caactctcta ctcctgtgga atgggaagcc cttgcttggc tttccagcct ccaaacaaga  180
taccactgca gctcagtttg agcgcttcaa gagtagtaat cattgtctga gggaggccct  240
ttgtacccat ggcctgcttt ctcggcaggt ttacaatgga ctgaaatcca actctctaac  300
ttcctggaac ccaaagaaag tctggctttg gacaaaggcc ctttggctgg gatttgtgct  360
tatgtaattc ttccgtatgc atgcaagtca tctggagaat actagtgaga ataaggacaa  420
ccacagatat gtaagccttt taccttacat agacgtattt aacaatggtc taatacggcc  480
ttaagtgtga tcagtaagga agcggcaggg tacgtatctg aaagatgaca aaacgtgact  540
```

-continued

```
ggagtgcctc aagaaaaaat gtgaactgtg tatctctcac agaagacaca cctgggccgg  600
ctatgtgcct gtttccttca gttggatatg tgaccatcac tgcctagcga gttgtaagag  660
tgacttctac tcccaggccc tcacaatatc cgaccaacta acatttaccc aggaggccct  720
accctctctg aaggcatgca agtggttagc aattgctgag agatgaggct cttctgtggt  780
gtagtgtctg tgtccaccta tgctccccta agtaacccaa ataaacttgt ttatctgcca  840
tactgaattt gggcagaatt gtcatttctt cagtttgttc agtacctttt ctgtctgtgg  900
taaatagaag taagactccc agggctggag agatggctca gcggttaaga acactgactg  960
gtcttccaga ggtcctggag ttcaattccc agcaaccaca tggtggctca caatcatctg  1020
tgatgggatc cgatgccctc ttctggtgtg tctgaagaca tatttaaaag aaaagaaaga  1080
aataagactc tccaggatag tcatagagca gagcccaggg gtctacataa gtaactgtat  1140
cccagtgtag ccaatcagtt cctcctgttt ctctggccta gagttaggtt tcggtatttt  1200
gccatcctca gaattaaatc ctgcctcctg agtgtagcag aacatgcagt tttatgcatg  1260
agctcttggg agaccacaga gatttcaatt ttaaaaagag acagttttct tttttagttg  1320
agaaacaact ttaacggtcc ccagctccgg aaaaaaaaaa aaaaagaaag aaacaacttt  1380
aaaaagagac aattctgttt ttagttaaga attctctctc ttactgatac cctttcttgg  1440
ctccagggac tccccatata tctttctaga catttctgag aactcaagta aatatatggt  1500
gatgtctccc caccttttt tgtagtttgt accttttgct cattccatac cgtcttagaa  1560
aatatcttcc ttgaagcact atgtctcacc cagtgcatgg aggtttcaca aatgacttca  1620
tcaggcatct tgttctccag cgcatggctg tctgagaacc acttcaaaca ggcaagagga  1680
tacagaatgt tactatgcaa gtaacaccag ctggggatgg tggggcagac gagcaattct  1740
agttattggg gatgctgaga caggaggatc tcaaatggaa gtttagtccc tatctctaaa  1800
gttaaaagaa agccaggtac acgcctctaa ccccagcaac tgggaggcag aggcagaggc  1860
agggagagcc ctgtgagttt gaggtcagcc tggtctgcat aatgagttct gtgatagcca  1920
aaggtataca cggtgtgata tttttaaaag gaggtgtgtc taactggcag agcacatgtc  1980
tgtcacgagg ggtgtgtgta tgtcaaatcc ccagtaccag taacaaaaac attagtgaag  2040
aataagtaac gtggtatgtg cccaggaatt agaaacctgc agagaggggt tggggattta  2100
gctcagtggt agagcgcttg cctaggaagc gcaaggccct gggttcgatt ccccagctcc  2160
gaaaaaaaga acccccccc aaaaaaaaag aaacctgcag agaaaaaaaa aaaacctgca  2220
gagacacaga ggtgtgtctg gagatagaac atgggcctta cacatattac accgagcatc  2280
catcttggct caccccaact ttcacacagc aactgcggcg cgctgcaaag tcagtcgcaa  2340
tccgcatttc tagacagagc ggcttcagac cttccaggcg cgcacgcagg cctcgccgag  2400
gttctcggtt tccgccgcga ctcggccgac gtcacagtta gaagacaata gcgactttcc  2460
cagctctgtc tcgattctgg aactttctca gtccgcaagc tcctgaagct ggcgctcccc  2520
tcagccccgc ccccaacgtg ccccgcggcc agggaacttc aggaagggta ggcagagacc  2580
gcggctagcg attggttccc tgccaaggtg ggagtggcca ggcgcaggca tataaaagct  2640
ccgcggcgct gggccctcgt tttgcacctt cgtttcctgc ggcggcttct gtcgtctcct  2700
tgctttttgc tctcccaggt tccgaggccg ccgcgcgtct cccggggaag catggcgatg  2760
aaggccgtgt gcgtgctgaa gggcgacggt ccggtgcagg gcgtcattca cttcgagcag  2820
aaggcaaggc ccggggcgct gggcgcaggc cgcggtgacg cggggcacct gtgcgggagc  2880
acgccacgcc cccgccgcgg cctgagcccg ttaaatgctg agtcaccgcg gccttgaggc  2940
aggggccggg cgcgggagag ggaggccggg gcgccgcggg gccttccggg cgggtccctc  3000
ttcgcgcccc cgagtggccg ggccggcccg agagagcggg cttggcatcc gctatccctc  3060
tggggctgct gcttttccgg tgtccctgtc ccacaggggc tcagaccctt gtggccaccg  3120
gctgcatttg ttgtaagaat atttgaacct ggtggtgcca aaccggacta acgcagcaag  3180
cagaacgcat ttgtggcatt ttaaagccaa gccctggcta tattaggtca gggtcgtgcc  3240
gcaaggggga aagaaaagag atggccttgg gcagttgttt tgccaccaag agctccaaga  3300
aagagacctg actctggttg ttgtctacga cagcgagtct ctgagcacaa tttgaaaagt  3360
atacagaaat attttcgaaa ctactgcagt tctgcaaaaa cacatgcgtc acaaggaaga  3420
tatttgtgtg gttaagagcg tgttcagagc cttagggggt taacattgta ctccttttaa  3480
tcccgagaga aatatttgat aaatgagcgt tatgtactct ctaaagtggt ttacataaat  3540
gtgaggagac cgacaccata gtgaatccaa gtgtttcctt tatgaggaga actgataacg  3600
ggaatttaga gtttttcata actagtctca gtttcttggc atttaaatgt attttgttgt  3660
tttcctgtgt aaattttttg tttttgtctt tctcttcttc ccacataatt cactgtgaga  3720
cagggctttt cccccaccct gagaaagctg aagactagct aggtctaccc cagtgtccac  3780
cttcccagag cagcttgcag cattctttgg tgacgctgcc ctttgtaccc gatcaaacga  3840
tagttaagca ttccaggttg gcagctgtaa caacttgact atcaaaactg tttgatttaa  3900
actgttgcca acttttcaaa atcagttttt ttctactcaa agttcctagt cccttatttt  3960
gttgaaaacg ttggagagtt aaagtagaaa ggtccggtat gagtgtcctt gtttgttgca  4020
gttggttgcg tcttgccttt tctccctgtt gctacaattt ctgaagtaat actaaatttg  4080
aattttggat gttcttttct tttttgttaa gtagcaaatt ctctagattt ggatgcctaa  4140
tgagactttt ttaaaaagta gctctggtta gacccaaatg gatccccaca ggcagtagga  4200
cacaattatt ttctggctac tggataaaat tatgggaact gataaacatc actgaatgtg  4260
gagtagaggt ttctgggcag ccaatgttct gaaagaatca agcctgacac agtgcagtag  4320
ccatccattc cctagttctg acattgagct gccccctttt gttcctctgg gtgcttttca  4380
agtgctgttg agtccaggtg tctgcacacg tgcatctgga aacaagtgtt agggaagatg  4440
ggtagggagg gagaggccta gagctaagca gctctagagt caccctggag gaaatgggtc  4500
tacttggatt tggacatagg tttgattttg ttttgttttt tgacttgtgc cttttactgt  4560
gattcagaag tattaacaca aacttgatgt cttaattttt gtattttttt aaataaaggc  4620
aagcggtgaa ccagttgtgg tgtcaggaca gattacagga ttaactgaag gcgagcatgg  4680
gttccatgtc catcaatatg gggacaatac acaaggtaag tcttaatcta tctctacctg  4740
gctgactagt gagatgaatg ggactgagtc aggaccaatt actaaccatt taaaaccatc  4800
aattttttc tttttcttt agattaagtt aaaataacca cttaggtcaa cctcggaaaa  4860
tagccacaaa agtattttag ttagtatcga gtatttcttg actccttaag tgggaaggtg  4920
agggtaaatt ttcttaaatg tgattattat agcttgactt taatatacag aaacaaatac  4980
gcaccttcct tattttggat aatcctttga ggtgtttgga gctgggggtt gagggtgggt  5040
gctttaggca cagtgtctaa ggacagctat gcacgagagg catagtggga cagaagtgac  5100
aaaaactgaa gattcaatat aaatgcttag agtaaaattt tttatatttg ggattggaat  5160
caagtcagaa aatatagtgg cttacattgc atttagtgaa cttttaccat attggagtaa  5220
tgatctgtgt ttgtttataa tcttttaaga gcctcattca tgttgctaga gccttttctt  5280
```

```
cctttccctc ttctcccctg ctttcccctc cccacatagt gcatgctagc ctggaatctg  5340
tgctggagct taaaccattt agtcttagat gtgcagggtt aaaggccatc aacctgtgtg  5400
caatgtacag taatttggcc tacagttact tatgtttgtg tttgacccat tcggataatt  5460
actaaagttc aatcaagttg ctttgcctct ggcctggtag ctttggtttg ttaagttcct  5520
tccagaatcc tgccctgtac ctatttcttg gtctgggtag aaattgtaaa ctatgtaagt  5580
cctatttcct gagttgttgt tgctgttgag atgtcccttg tgaatgatgt ccccttagccc  5640
acatgtacac ctctaatgct gtttacacct ggagttgaga agcacagcag ccttgacacg  5700
tggggataat ctaaaaatct gtctgcccca agtaaaagcc agatggctga gctgtttggt  5760
ggtgtaaggt cttgaaagat aagtgttttt atcatgatct taaaagcaaa gatctttaaa  5820
tgtgggactt taactttaga agtgccacta aaggtcgctt ctgttccagt agaggaagga  5880
accagagcta gacatgctgt gacactacca tgctcctggc acttggaagg ctaaggtagg  5940
agggtcatta actgcagata tcatgggctg tggtagtgag accctgtctc aaatctcaaa  6000
acaaacaaac atgacagtct agtgaaaaag cgggtagctt gaaaatgcaa ggccatatag  6060
tccagctatt tgtaccaggg tgctgcttcc tgtttgtatc actccagcac ataccagctc  6120
catgtttgct gtgttggaag ttgtaagaat tccgatgtca ttgcatacag aggtttactt  6180
cataatctga ctgctggttt ctggtaaata ggctgtacca ctgcaggacc tcattttaat  6240
cctcactcta agaaacatgg cggtccagcg gatgaagaga ggtgagcagc attctctcta  6300
tgcatggtgg tggagagggg tctgtggaaa acacctgaag acagaactga gtggtctcac  6360
tgccttttct tttgtatgtt tccattcacc caactcccac atccccaagt actggaatag  6420
tttatattgg gtgaaggagc tgacaaatgt ggactcttaa gtgatttagt tttgtagcat  6480
ttattgaaga tgaactaata caagtgccaa aaggaaccaa tacagaaaat atcatggata  6540
acagtactat cagtcactag caaagtaaat cattgtataa tatactaatg cagataataa  6600
aaactagttg agattccgtt tgtatgtgaa accttaggaa agtcctacat ttaaagaggg  6660
gctagcttgc ttttggaatg gaggcctggg agcaaacctt tgctaatcag gagctgacat  6720
ccttttcgaa agtcctagac tgtggctctc tcctttaaac tggaagagct atgtgtcaag  6780
gtatcctggc tacctgtttt gaaatttgtg tttccagacc tttgtctgga aaagccatca  6840
tatttgatag tgtatgtgca ctctttaatc cactcatagc atttgacttc gatgtgaatt  6900
tagctattga actctattga tgtgaaatag atatcattgc ttatccacct ggtgctgttt  6960
taatgttagg catgttggag acctgggcaa tgtggctgct ggaaaggacg gtgtggccaa  7020
tgtgtccatt gaagatcgtg tgatctcact ctcaggagag cattccatca ttggccgtac  7080
tatggtggta agtttccata tagtagtaga tgtaggattt cttctaacat agttatgtac  7140
ctttccatga cttcgtggtg gtggttaaac tagttcctaa aagatcacat aaattggtaa  7200
gagttcagaa taggaaaaaa tattatttta ttggatgtaa tagtaaagaa ttaatttgcc  7260
taggtcagtt aagaacgctg ttctgctgaa gtgcggtaga aagctggtta catttgatca  7320
gactggatct gagttgagga tacaatagtc tttagtttaa aacagctgga ttttcttgcc  7380
atgattgccc ccttacagtt aatcatttcg ttgagcttaa aatctgcgat ggatgtcagt  7440
attcaagtct gcaggttatc gcttggttac catatgggag ccgtcttccc aagttaccct  7500
cgggagatga atctggttca tgcagaacac caagtagtaa aagctcttgc ccacttcggg  7560
cagctaactt ttcagtaggc acttcctttc agttgaccct ttatccttag aatttttcttc  7620
agccctattg gtgaagcaga acaatcattc ataaatgttc taaaaataaa atttaaaatc  7680
ttgttgctaa gtaaagatat ttagaattgc ctcttatgtg taggcctata gttcactcac  7740
caagagattt tgatagagaa atttgtaaga atgactactg tacagtgggg tgagggtgag  7800
ggctaagatc agcatgtgcc tggtagttat ttgggtcctt agtattcatc tagaaatagc  7860
cacgagcaag gaaacactta gtagtctgct tttagctgat agcataaaaa ttagcttatt  7920
gatttactaa tagatttgaa cattttctaa tatacatggt cctttgaagt attgctggga  7980
agaagtgcta attacttgat caccgaaacc taaatgttct taattctttt caaaggtcca  8040
cgagaaacaa gatgacttgg gcaaaggtgg aaatgaagaa agtacaaaga ctggaaatgc  8100
tggaagccgc ttggcttgtg gtgtgattgg gattgcccaa taaacattcc ctatgtggtc  8160
tgagtctcag actcatctgc tgtcctgcta aactgtagaa aaaaaccaaa ccattaaact  8220
gtaatcttaa cagttgttaa ctgtgtgact cctttgactt gctctaagga cttgcagtga  8280
gaggtgactg acgatgtttg gaggatgtgt agaacttcct gaatgtgtac aactcattga  8340
actaaaatct gttgtttctg tgccagacct cactggtgtt aagctgaaat tctcattcaa  8400
gcctctctct ctctctgtgt gtgtctgtgt gtgtgtgtgt gtgtgtgtgt gtgtgtgtgt  8460
gtgtgtgtgt gtgtgtgtgt gtgtgtgaga gagactgaga cttatttaga gcctcgagag  8520
atagagactt atttcaagcc tattaatgta taccaaaaag acctaagctc tatacactga  8580
gcatcaacaa cagactcaat gaggctctca tagtatttaa ttttgaaagt gtttcatgtg  8640
ataccatcaa aatgacgtgt ggtagcccaa accggatttg atcttagaaa attttctgcc  8700
ctttgttatc atcagaaatt actgaaagct ctctttaaga ttcagagtac ctaaccttat  8760
tttaaaatcg tattagagtt agaagccatg atttagata aagcccttta gtaaacttgt  8820
ataaaactca taaaaggcaa ataggtagcc tcagctagcc aagtttaata cctcctctac  8880
ctgccaagtg aagttggtac cacctgcttt tttaaggttg gcactcagga aatacatagc  8940
actgggagat gagaccaagt ggttctggcg gttgtggcta aatcgacttt tacagcctca  9000
gttaatgaaa ctgagtacct taataaatac atcccaagaa agagagcttt gtaagggaaa  9060
tattaaccta aaaggctcgt gactatttgg aacagttcaa ctgaaatatt tctgacaaat  9120
ttggtgtaaa ccatagtcct cttaattttt caaatacaaa acactgaaaa ttggaaaaaa  9180
ataagtgttt ccaggtttaa aaattttaag tttaaatttc caatttaaga ttgcttataa  9240
ggaatgcatc cgtatgtagt tctgttgaag tttcaggtaa atcatacata acttatttcc  9300
ttaatgaagt tttgatgggg tgtgtgtgtg tgcgtgcgtg tgtgtgcgcc tgactcaatg  9360
cagactaact tgggaagcat ctggtggaat cacaaaccag tgtttatcag ctcatttctc  9420
ggtattttta gttggaaata caagctgcaa gtctgtcctt ggaatctggc tttgaatagt  9480
caggtgcatg ttttagcatc ttcccagaaa tattctagta gggacttaaa aagcccaagt  9540
agggtcacca taaaaccaga acctggcata gctacagaca catttcttac catcattagg  9600
aagatcttaa agagttaaat gtcaagtggg agcatcaaaa aggagcttct cagtactcta  9660
aggtctgatg aattattttt gtttagccta gcactttgta gttttaaaat cacattttca  9720
ggatgtgtgc aagagaggaa aacaagttca tgttcttcca cctgttttgt ccctgggatc  9780
acacaggcca tcaggattgg cagaaagtgt ctttactggc caagtcatct tgtctttcaa  9840
atgtaatttg atgaaaggaa cttccagact gtaaataaga ggtgctcaac ctgtgggtta  9900
caaccccttt ggaacttata tcattctgct tatcagatat ttacaatcca taatagccaa  9960
aattagttgt aaaataacaa aaataatttt atggttagcg gttggcacag catgaactat  10020
```

```
attagagagt cacagcattg ggaaggctga gaaccactgc tgtaaataaa tacctagcat  10080
taagtccctg actctagaca acactacccc accttcttgg gttttttttgt ttttttgttt  10140
tttgtttttt tttgtttttt ttttttgaca ggatttctct gtgtatagct tttactgtcc  10200
tggaattcac tgtgtagacc aggctggcct tgtctcacaa aagatccacc ctgcctttgc  10260
ctcctggggg ctgggattaa aggtgtgtac caccacctgg caaaatttgt ttgggtaaac  10320
tttttttggt ttcttgagac agggtctgtg tagccctggc tgtcctgaac ttgctctgta  10380
gaccaagctg gtcttgaatt cagagatgca cctgcctgtg ccttcgctgg gattaaaggt  10440
gtgcactacg acgacccact gggctcggac aacactttta tgtcagtgct tccaataaat  10500
actattagag tcttggtttg gcttcacaag tagcagcaaa ggttcagtgt acttcttggg  10560
ctattgaaga tggtaaagac aacaggcaaa gcttacaaga aatgtcatac tgtacttaag  10620
tctataaaaa gctttctggt tgcatatgtt aacacgggcc tcattttaca ccttggaaat  10680
ttcaatggga tgattataaa cacgtcaacc ttctaaataa gtaatgccca agcaatcagg  10740
taatttatag tataatgtat aatgttggga atccaattat ttcccctaac aaatctttac  10800
aaattaatta gggcaacatt accacaaagc caagagggaa aaaagaactg acctgcagac  10860
acaaatttct tagttgaact ttaagatcac taacctttac cttatggtca aaatactaaa  10920
agtcaaaaga ataaaactcc aagcactggc aaatactacg taagtgtctt tctttcccca  10980
tcaaagaagt ctaatttaga ctccaacaat tattaacagc tcaatctttg atggttaaca  11040
tctgtccaat cttaatgcag tgtatgaaga atagcacaca ttaaagtttg ttacgaaaat  11100
agagtttatt aaaaacatcc ctattgtttg aggagctttt caccgttacc ttttcttaaa  11160
ttaaaaaaaa aaaatagaga gcacttctaa ttaggatttg taaactttta aaagtcaaaa  11220
cttttaaaaa gttacagcaa aaaaaggggt aatatatctt cagtattttt tgttattttg  11280
tggctatttt taaatagaag gaaagcaatc aaattgctca caatccccac caactactgt  11340
ggagtgatgt agcaggagcg aatattatac agcatctgta cacctcacgt tctacaccca  11400
agtgtcactg tcacattctg tcaaatccag tctctagcga ggagcctctg ctgctgagcc  11460
agaatccttc tcaggttcaa cggatgaggt agcctcagca ggtgactctt caggttttac  11520
cactgtggcc atggcctccc ccttattaag ttctgaaaca gtgtctgtgt ttcccacttg  11580
gctaagggga gcttcgacag ctttgttacc acctgccctg tctgccacct cgtgcttctc  11640
ctttcctcta ctttcttcct tctctctacg ggactctcta tctctagaat ccctgtctct  11700
gtcccgatgc ccactagagc gtctacttct ctcttccaag tctctgtgtc tgtcccgctc  11760
agggctcctc cttccccact ctctcctttc acggttgcta ttatctctct catcactacg  11820
gctcccatac cgctcccggt cattttccac cctacttcca aaagatcttc ttccaaacct  11880
ttcttggtct ctacctgagt tgaactgctg cctgttatca tttctaaact gctgtggctg  11940
ctgctgagct ggcgctggct gctgggatgg cgctggctgc tgctgtgtct gtgactgctg  12000
t                                                                 12001

SEQ ID NO: 35          moltype = DNA  length = 21
FEATURE                Location/Qualifiers
source                 1..21
                       mol_type = other DNA
                       organism = synthetic construct
SEQUENCE: 35
cggatgaaga gaggcatgtt g                                           21

SEQ ID NO: 36          moltype = DNA  length = 18
FEATURE                Location/Qualifiers
source                 1..18
                       mol_type = other DNA
                       organism = synthetic construct
SEQUENCE: 36
ttggccacac cgtccttt                                               18

SEQ ID NO: 37          moltype = DNA  length = 23
FEATURE                Location/Qualifiers
source                 1..23
                       mol_type = other DNA
                       organism = synthetic construct
SEQUENCE: 37
agacctgggc aatgtggctg ctg                                         23

SEQ ID NO: 38          moltype = DNA  length = 25001
FEATURE                Location/Qualifiers
source                 1..25001
                       mol_type = genomic DNA
                       organism = Mus musculus
SEQUENCE: 38
aagggtttct ttggcttaca cttttcttat tgttgttcat tattgaagga agtcaggaca  60
ggaattcaaa caagtcagga tcaaggaggc aggagctgat gcagaggcca tggagggatg  120
ttacttacta gcttacaccc cccccccccc cccggcttgc tcagctttct tttttttttt  180
tttttttttt tttttttag atattttcta atttacattt caaatgctac cctgaaagtc  240
ccctatacca tccccccaca ctgctcccca acccacccac tcctgcttcc tggccctggc  300
attcctctgt attgttgctc agctttctta tagaacccag gaccaccagc ccaggaatga  360
caccacccat agtaggctgt gccttcctcc actgatcacc aacggagaaa tatgggcaac  420
agcttgccca taggatgggt cactagttgg gttggttact gttgggccat tccctcagtc  480
tctgctccat cccccatctc tacatttctt gtagacagaa tcaattttgg gtcaaaagtt  540
ttgcaggcag gttgttgtcc ctcttacatt tctcatggag gcatttcctc aacttatttc  600
ctctctctga tgtctccagc tcatgtcaag ttgacacagt tgttcgggac ccacatgaag  660
accaagctgt tcatctgcta catgtgtggg gaggcctagg tccaacccgt gtatgctgtg  720
gtagttcagt ctctgagagc caaaacagtc caggttagtt gactctattg atcttccttt  780
ggagttccat ccccttttggg gccctcaatc cttcccacaa ctctaccatc agagtcccca  840
```

```
agcttcatcc actgtttggc tgtgggtctc tgcatccgtc tgagtcagct gctgggtgga  900
gcctctcaga ggacaggctt tctagactcc tgtctgcaag catagcatta atagcatcag  960
ggattggtgc ttgcccatag gatggatcac tagttgggtt ggttactgtt ggccattccc  1020
tcagtctctg ctccatcccc catctctaca tttcttatag acagaatcaa ttttgggtca  1080
aaagttttgc aggcaggttg ttgtccctct tgctccactg aggttcctgc ctagctacat  1140
gaggtagcct ctttaggttt gatatcctca atgctgtgaa tcccaactaa gatcaccccc  1200
cattcattcc tggtgtctcc cctatctcag gtctcagata tgccttcaag atgccccccc  1260
cccacctctc cacctctgcc agctgcagat ttccattcat tctcatggcc atctggctat  1320
ctctcctgtt cctccccata cctggtcctg aaccccttc accccactcc ccatcccctc  1380
tcccacccag ttcctttcct ccatcttcct cctatgactc ttttattccc tcttctaaat  1440
aagattcaag catcctcgct tggacattcc ttcttattta gcttctttgg gtctgtggag  1500
tggagcgtga gtattccaac ttctaaggca cacagacaac ctcagattct ccagcccttt  1560
gtgtgtgttg cttatttgaa caaacgggtg aaagaaaaca cacaaagttg gcgtgttgaa  1620
agagttagtc gatcttctgg ggtaggtttc agtacagaga ccaaagggac attctcagac  1680
actagacaca ctatgcaaag acaggatgtc acatgacaaa ggataacggc acaagtaaac  1740
atttaagcaa cagtgttcca taccggctca cgtagaaaaa ggacaagact ataggaaaga  1800
aagcaaacac tccgccgagg actacagcaa agacagaaag tatctgcagg tacggcttca  1860
aaaggagcat ttctctcagc aacttatatc tgttaatgcc ctgtcttctg gaataagggc  1920
ttagttttta tcagtagaga gagattgatt tttaagatgt atctgatttt acattgtaga  1980
tctccttagt cacccccctgt agtaaactaa ggaaaacttc cgtggaggga gaggggaaga  2040
ttagtaactc gtagtgagta agaattctct ttcaagaaaa agattcaaga gcaatacaag  2100
gcctagatat gaaggtgtgt gtgtgtgtgt gtgtgtgtgt gtgtgtgtgt cttaacagcc  2160
tgttcagaat ttagtaggtc acatacactt acaagtaatg aagacaatat attaatgaat  2220
ttgcagtaat tttttgtttt agaaatagaa actgttgtaa ggaggataat cattcagagc  2280
tctttgatat gtatcactca cattcacata catgcataca cacagagaga gagaaagaga  2340
gatacagaga tagacagaga gagaacccaa aaatgtaaag agaggaaatg agttgaaaga  2400
aaaaatggga aactgggtta gggaggggtt cagatgacag tgactggggg ctttcagagt  2460
tgggagtgag gcagcgatgg agagagggca gggaggaggg agtgtccatt gtgacctctg  2520
cagaactctg actagactga gcagctcaca ccgtgttgga gctgtcctaa cactaccaag  2580
gggacggggg agaccccatg aacaccacct agggagttgc tcctttcatt ctgtgtaaag  2640
tctgatgtct tcaaacttgt tgtaaattta tactctgttc taaaaacagt gacattcttc  2700
tctttgtagg atgacctcat tacatcaggt gttatatttt atcttttttg cctcagtttc  2760
tagtggtaag ttgctgtatt tattttcccc taacataata tttttatta cttgagagtt  2820
tcatacaatg caccctgatc acactcactt tccattcctt ctaagttcac cctcccactc  2880
ttgagccctg ccagctcact ccccccttct tgaaaaaaaa tcatcaagtc aatcaatttg  2940
tgttgagaat atatactcgt tgggaatgtg atcaaactcc caatggtcag ccccttaaag  3000
aaaagtgagt ctttttcctc ccccacttct ctccccactc ccttacccag ttggaagcca  3060
tcaactgtga agagttatac ttcagcatct ttactacaat tttaaaggac tctcttcagt  3120
atttaagtat ggcttagaaa tagctcattc cttgacctgt aatgtaggaa acagcctaag  3180
tccacaaaaa gaaattacac ttcagacccc atatattgtg gaataattcc atgctgtgaa  3240
ctccagggaa ggaaatagag tcgtttattt tccagtgaaa gctccccttt aatacatcaa  3300
agaaagaaag agatttaaat atagaattac aaagagtctt cacctatatc atctgaatgc  3360
tagtaatatc tgtctataga gttgcatctc tatctaccta cacaacacat tgccatgatt  3420
cctaggagca agattagaaa gagaagactc gactcacctc attgattatt attccataag  3480
ggattcagtc tagtatctct ctctgtctct gtctctctgt ctctgtctct gtctctctct  3540
gtctccgtct ctctctctct ctctttctct ctctctctct ctctctcacg cacacacaca  3600
cacacacaca cacacacaca cacactcacc aattcctgac tgaaaatgtt atagaaaaat  3660
taatgtgtgg cttacacatt tggttaattt accccttgca attatgcttc cattctacat  3720
tacatccagt aaatacattg cttaccattc agtagaatga aatgggaagt tacctcacca  3780
atactgatct taacaactta gtgtaagcac ttcttaaaat aatttattta tgttatattg  3840
aatgcctgag actgccattg acatattaag catagttagt tctttttggt gtgacacatg  3900
tgaacagtag cagatctaaa ataaaataaa catatgtaac atattaaatt atacagatta  3960
tagcttaatt tttctttgtg attagattga ttttcaggtt attccttcat tatcaatgtt  4020
ttgaaatccc attgttattt gtactgtctt gttcagtact gttttgacat gttgttgttg  4080
ttgttgttgt tgttgttgtt tgacacagag tttctatgtg tagccctggc tgtcctggag  4140
cttgatttgt agaccaagct gacctcaaac tcagagatct gcctgcctct acctccaagg  4200
gctgggattg aaggtgtgca ccatcatcgc tcggcagcct gtcttaacat cttaaacact  4260
gagttcaata actgtgtcga ttcacaagga cattctgaga attataagac ttttttgctt  4320
atgaatatat atatgcaaat gtaactgaca aaatattatc cattgtggtt gtatcacact  4380
taaaaatctc agagccgaga aagttggggc aagatgatta aaagttcgag gacaggatgg  4440
gctacataac aaggttctgt ctcaaattgg ctataccaaa ccgtccaaca catattttaa  4500
agaaaaataa atgggaggct agagagatgg ctcagtagtt aagagcactt agtgctcttg  4560
catgggatca gttcaattct cagcgcccat gttagatagt tcacaacttc ctatgactct  4620
aacttccagg aatacagcac cctcttctgg cttctgtagg tacacacaca cacacacaca  4680
cacagacggc atacgtacat acatacatac atacatacat acatacatac atgcctacat  4740
acacatgtac atgcatacac aataaaaaag tttttaaaat cttttttttt aaagaaagaa  4800
aattaaaaga ccaattacat tggcatattt tggccaagtt tgcttaattc taggaacaag  4860
gagttacttt aatctaagaa aaacaatcaa tggatgcaat gtagatccaa aggaagtgaa  4920
agaagagagt cctacagaga tttgtcattt gtcttcctgc tatcgggcag agaaccagca  4980
agagagaaac gtgggcattt gaagcccact cagccgtgtc atagcacaag ttgggtcttc  5040
accaatggac agaaggttaa acaaaatata atatcacagt atgcacatgc aacacaaaac  5100
aggatattac tcagcgtgtg aggaagaaaa ttctccctca tactggggca tagctgagcc  5160
ttcgtggttt tatactcaac gaaatgagtc atttacaaat gaacacatga ctgaacccct  5220
aacgtttggt tcccagagat gccgatttca ggaaaacaaa agaccgaaga gaactgacca  5280
ggggctaatg ctaatgacta tttaatgggt acaagtttc agttggaaaa gctgaaggaa  5340
ttctagaata gtggtggaaa ttgtacctaa ggtacatact tcattccaca actctagaga  5400
cctgaaaagg gccggagtga caaactttat gtcatatata ttttgccata gaagaacaaa  5460
attaaaataa tctaacacat cgaagatttt aaagattttc ataataaaat agtttagcaa  5520
actcagaact ttcccaatga ctaagtagta ctgtaaaaca acaacaacta gaaaaacatt  5580
```

```
caaaccaaaa gttttcaaga aatctcatat gtaatggtga ctgaaatagt gtttccctga  5640
ggtactgggg taaggcagga gtatccacaa cttggctcct gtgaatagga aacaaggaac  5700
agagagatgc aagcatcttc aaaaagttgt cataggatcc atcatggaca ttccaggagg  5760
ggttcagttc tacttttagt tttctgtgac atctcattac aggttttgat tttttccccc  5820
catagcttcg ccagcatgga aatttattca caagtaccaa gtcagggagt ctgcctatgt  5880
gtccatcaat agatgaatgc aaagagcaaa cactggatgt aggcacagtg caggggggcag  5940
ggaggggtgg catgttctgc atttagctaa aatggttgtt ttagtttttta ctaattcttc  6000
aagaatgcca tataccatat tttgctaatt tttacctcga ctccccaaac tccatccaga  6060
accccccatt ctgtacccac ctaactctgt gttctccctg tttcatttgg ccacagtgag  6120
gaatgaaatc gtgccatttg tgtaacaatg gctgtgactg ggcatcatca ttattcagtg  6180
agataagtca gattgaagaa gataaatatc ccattttctc aaatttgtgg attctagacc  6240
ttatatggat acataaaatc cagtgtgtgt gtgtgtgtgt gtgtgtgtgt gtgtgtgtgt  6300
gtgtgtgtgc ttgagtgaca cactctaggc tccagagtct aggggaatga cagagactag  6360
aaggaaagag ggaaacgaaa agatatgaag aataaatata gtcgaagcac atgatacatg  6420
cctatgatat tatgatgtat acacacctat gcaggtgtcc catgaagccc cctgctatgc  6480
aacgaatacg tgtcaataaa tgtgttgaga gactatctac tgtcacttcc cttaaacatt  6540
atattagaga tcctgtgtag cacagtaggg aaggtcgaag gacctaagag tcaggagaaa  6600
gatggaaatt aactgactct tcccataaat gtggttatgt acatagaaaa attcaaagta  6660
atgaatgcac tgattatttc aggcagatca gcaaggagtt tacaaactcg atggaccccc  6720
gggagtggag gcacacactt gtaatctcat gactcaggag gcagagggca catcagagac  6780
cctaactcca gctcttccgt tcaaaatctt caatatacaa acagtagcca actctcgcca  6840
gtactaggaa ctgtactgag attatgaaag tcaatattat aggttaaatg attcaagtag  6900
tggctacatc ctaatcaaaa ctgcacattt attaatcctt taaaaatcaa ttcaacttat  6960
caaatcctgg tgttgtgctt gataagaaca ttttaatgtg ttatgatggc ttaatagtaa  7020
aatgttgcat ttcttagagt taacaggtaa actgtgaggt gggaatagac tgccaattag  7080
ctggaaacag acgcagtatg gtttggtggg agacaacact gaacttggaa aaagaagtcg  7140
gatctctatg tagctcctgg gatacttgcc tgtagtggag aaaaccatgt tccctaccaa  7200
gtctctgctg aattttggaa atggatctgt agtgaggttg ctcttcctcc ccacaaatcc  7260
cttccgaggc cccatggacg cagcggagcc tatccttgga ataacttttc taaaggcatg  7320
gactaaaaat atataggggtt gctggggaaa ttaattatat tgaaatatga gtagctaaag  7380
tggaaaatac tcagtacaga attagttgtg gctcggagtt aacaccttac atgacattag  7440
tggcatgccc aaaactgaat agaaataacc aacaaattat cgacaaatca taatgatgtt  7500
atatctcatc atcacataca tgacaaatac taatcatgtt aattgattac attaataata  7560
caggtatgta tgtaccacat tttggttagg gaatcaatga aaaaccacat gaggtttttt  7620
tgagctcgtt ggttatctag gtcctacaag cctcatagga gggtttttgag actgctatgc  7680
acctacaatc ctctcaagac atgactgatg gctgttacag tagtctatat ttgagttaaa  7740
ttttattctt ctggaagtac ttccacgtga gtctggtaat gttttcaagt tataaagaga  7800
aatgggctag caacacctct ccatgggcat gtatggctgc atgaagtaat cttttattca  7860
gtcactaggc aacctactgt gtgaattatt agctatctct tctagcaaca gagcactttt  7920
gaatttttat gcattttggc tttttaaaaa ctaaagctga tgtaaggttt tcgctaaata  7980
gaactcagta agttttccct ggtaaatgtt ggtcatgaga ccatttttaa tgttcgcatg  8040
acatcataca agggcccctc agtcttggct tttagtttgt ggtagtgtca aaacaataaa  8100
tgaacgtaaa cacagcacac ccttgctgac cccctagagg ggtttcatgg ggaccgtgtt  8160
cttcttgccg gtcaacagct gagaaatcac tgagttgctc ctgcagcctt cccaagacaa  8220
tcactcataa atgtgacaac acggagggcc cccatgttgt ttgtgattta tagttccatc  8280
tggggctgtt cactgaagag cgttgcccga tctgatgtcc gaggtcaggc atatttagca  8340
ctgacttttt aacaaaccat gtaacgaggt aagtgcccac caacatctgc agtaatgtgc  8400
gcccgcgtgt ttttttcttc acagaatgcg ttactaaggt cttcaaagac atcagctttc  8460
aaggaggtga cctgagtact gttttcacac cgagcgccac atactgccgc ttggtctgca  8520
ctcaccaccc acggtgcttg ctcttcacgt tcatggctga gtcatcttcg gatgatccta  8580
ccaaatggta acagtttctg tttctctgaa gaggaactga tttccagtgc cagttactca  8640
ccaatgcaga ttaccttaca accccacttt tgtcatttta caaaagggga tgttagtggc  8700
tggaaagtga gtttccttcc acggaaatac taaatattac aggaaggata gcgcttaggc  8760
atattggtgg aaaaccgtaa taactcctgg gacctcaatc ttaaagtcac gtttttgctc  8820
ttcatccatg gtttgtctta cattcttttt ctgtcgtggc tattggctaa caatggtggg  8880
gttatctaga gcttccttct aacctttcaa ttagggggaa aatgtttaaa aagctacttt  8940
aaaaattatt acaacaattt tctacccct ccaatatcct gtcatattat gtggctttct  9000
cggctcccat cagtggttca ataaggcatg cagactttta tataaaactt aaggcccttc  9060
attggggcag gcagactctc agctctcttc tctaatctta gatcgtctgc caagtagcta  9120
atgatttatc tcgtttccat tcctttccct atctgcctct gaatctccca cctctgcttt  9180
agttctctct ctctctctct ctctctctct ctctctctct ctctctctcc ctctctctct  9240
ctctctctct ctctctctct ctctctctcc ccctctctct gtcccacccc cagaagtccc  9300
acccttgtac ttcccgtccc actttaggca atatgagtgg gtgaggaagg acaagcactt  9360
acaaatcaga agctggtgat gggccataga catgacgata ccaaacatct gccagaactt  9420
agctctttgc cagtacagta atcaacaatt gcacaattga aagtacagag acacgcctta  9480
atacaatata aggaaggtca tcgcaacact gtcatatttg ctttacctac ctgtatatgg  9540
tcacagataa atactgaaag tgagtttaaa atatcatcga cctgcatatc taaatacttc  9600
aacatgaatt tcccaataag gaaactgtaa gaagcccaac aaagttaaac atacttgaaa  9660
tgttaatttt agctgttaat taaattctca tcaaatttca caggttccta tggctgtttt  9720
tccctctcta tcttattttt aaaatattgc atccatttct gtctctatgc taagcttgaa  9780
attttaatat ataaccttta atgcaaaatt aagctgccaa tatctttgtt attgctgttt  9840
tctcagatgg ttacatattg ctgtcaacat taaatattct tctgaaatct agaacagaga  9900
tcggcaagac aggaataaaa ctttaggctt tgttgaacca aatgcaaaaa gaacattctg  9960
tgtttctaac actgttttag aatgtaacca tgtgtgggct ggagggattg ctcagtggtt  10020
aagtttgctg gctgctcttc taaagggccc taggtttgtt accccaactt acagagattt  10080
gcaatcattg gtaactccag ctctagatgc catcttctgc ctttctcatg catgtgatca  10140
cacacacaca cacacacaca cacacacaca cagagagaga gagagagaga gagagagaga  10200
gagagagaga gagacagaga gagacagaga cagagacaga gacagagaca gagacagagg  10260
cagaggcaga gagagagaca gagagaggca gaggcacaga ctgagagaga gtgtgtgttt  10320
```

-continued

```
aaaatttaaa atgtagccat gtaaaaaata gaaaaccatt tctatctcaa ggataacaca  10380
aaaatggcag attttaagca acattttagc aataggttaa agtccttcca ttcttattca  10440
tgtcctgttg gaaaggaggg ccgtgtgtgt tcttttagat gtagggatgt tgtaataaaa  10500
aacaaagtca aatcttgcta attaaacatt tgttttggca ggaaacccag tcgtttgtct  10560
ccttctcttt gaccttagga tcccctcttt gaaagcatga attcctgctg aataatgtta  10620
ttttcatttt attttactat tttatttttt aaaaaagaac aggtttgcct gcatcctgaa  10680
ggacagcgtc acagaaatat tgccaatggt aaacatgaca ggcgcgatct ctggatattc  10740
cttcaagcaa tgccctcagc aattaagtag taagattttt tttatcaaat acaattaaaa  10800
ctagccatta gagtatatac gtgtaatcgt ttcagataca ggtttgtggc tataaaataa  10860
aatactacca cctaggacta aacttcccac caaggaacca tcttcctatg tagagtagag  10920
gacacagttt tctcccttcc tctccccata agcacactgt ctcgctttac catttcttag  10980
cctcataaag gcatgtcagc acctcagttc ttattattgc acacgaaagc cctcgttata  11040
aaagctaatt caaatcaaga ggagaaatgc agactgaagt ggcacatgtt ttaatagtgg  11100
aacgggcact tttcagtaag ttaaggggtg aaccagttgg tcagtgcggt ttgaggtcag  11160
aaagtcaaaa ttcaaattca caagctttct atttgttaaa aaaatttttt atttatttta  11220
tatgcattgg tgttttgcct ccatgtgtgt ttgcgtgagc gtgtcagatc ccctgaaact  11280
agagttacac acagttgtga gctgccatgt gggtgttggg aattggaccc aggacctctg  11340
gtagagcagc cagtggtttg aatcgctgag tcccctctcc agtctcaaat gtacaagctt  11400
aaagcggttc cagtctaaga ggcacattgg cttcctcgga atacctccta gtggaagtgg  11460
gaatcacagc tgagtgaaac aaaacataga acttccacgg gagagtgggc gagaagcgag  11520
cagtttccac gcgagagggc cagcagcgaa agcagcgtac tgtagttgcc cctcgcttct  11580
ggtgacgcct agattctccg cctttatttc cagcttgcag caaagatgtg tacgtgaacc  11640
tagacatgaa gggcatgaac tataacagct ctgtcgtgaa gaatgctcga gaatgccagg  11700
agagatgcac agacgatgcc cactgccagt ttttcacata cgcaacaggg tatttcccca  11760
gtgtggacca tcggtgagtg agcgggagtc cgagccgctg gatataagcc tgcccaggga  11820
aagaaaaccg ctggttccgt aggtattttc atcaatttga agcctaaact tctttttttta  11880
aaccccaaga tatttgcata acaacaatca ctgttttgtc atgaaaaggt catagcgtgt  11940
ctaacacaca tttacgacat attcaaattt cagaactgga ggatggctcg gtgggtgcgt  12000
aaacacactg cttatgcagg gaccctgagt ttggatccca gcatgcacat aaaagccaga  12060
tatgggtgtg tatgccttta accccagtgc ttgggacatg ggcacgggac agagggagga  12120
tggttggagc tcactggtta gctccaggcc tttattatta ttattattat taaatattgt  12180
ctttatttac atttcaaatg ttatctcctt tccctgcccc ccccccaacc ccctctccca  12240
tccccctccc atttctacta ggttgtttac ccacacacca acccactcct gcctccctgc  12300
cctggcattc ccctacactg gggcatagag ccttcacagg accaagggac tctcctccca  12360
ttgatgcctg acaagaacat tctctttagc tccaggctta gggagagatc ctgtctggag  12420
gggaaaagac agagaggtca tagggcagga actctaacac cccccccccca cttggacttc  12480
ctattctcac ttgcataccc acacccccac accccacaca caccatatac aatacataca  12540
gcgtggcctc acagattctg tgtatgttgt aaagcataca caagcttacc ctatctaact  12600
tcaaaaggca ttacattttc acgcttgtgg ttctgagagc tcggtttgct tggccatgct  12660
cttcccagtc taacaaatgt cctaacctaa aaatcatcaa aacttaaagt ttgtttctct  12720
atctacctac atgtacagtt ctgtccctta cccaagacga agtcattgga acccatgtgc  12780
aaagttttct cctgtttgat gtgggattcc aaactcctcc aaggaagaaa tctgttatat  12840
aaactaacga gagggaatga ctaaatctgc atcttcagtt taaattgttg ttagaaaagt  12900
atatgacttg ttcttttaca aacattttaa ttttgtgtgt gtgtgtgtat gtttatgtat  12960
gtgtgtgcct gtgcgtttag acacacacgt gtgcagataa ctatatagcc agaagagaca  13020
tctctcaatc tctcaaggtt catttttaga cttaggaatc tttgacatta tctagatttg  13080
cacagtaaac aacaggtatg tggtagttgg attttaacat tggctattcc tacttcactt  13140
tccataattc tggggggggaa aagatgaatg ggaagtgaaa cattaaagat gtcttttaga  13200
atgaataata aaaaaatgga aagtagcctt ctatggctct ctttagctct cctcagagga  13260
catgttttat gtcttagact tcacagaatg ccaactgcag gctaggaaaa tgttcctagg  13320
gcttacacaa aagcgtattt ggagggctaa cgtgaacccg ttcacacaac cacctcacac  13380
cacatcaggt cttctgtgtt gtcctctcac tgatgagata acattattcc tgagtccaca  13440
gagcctccct gtggttagaa gagctgccag gactcatgca gccacctggc tctgcaggtg  13500
aacactcctg ggcagttcct ctgttattac agtcatttcc cccctgcgga ccgtaacttc  13560
ttatcctctc gtgtttttat acacttggaa agaacaatat tttgccattt ttgtttgtat  13620
tcagtaaaat gtgtcttttg aagtacaccc gaacggggac gccaaccaca ataacgaagc  13680
tcaatggcgt ggtatctgga ttttcactga agtcctgtgg actttcaaac ttgggtaact  13740
atcatttttc tcaatgagat attggtacca ttaagcctga gtgaagcaga gactatgtgc  13800
aatgggtcta actttaaaaa cagctgatgg ttatacatga agcgaaccca gtaacctttt  13860
actgtcttca aagtgaaatg gttcactatg tcctggaaag catttccttc ttaaatttca  13920
aatttgttct ttttataaac aacaacaaca acaacaacaa cagcataaat aaataaataa  13980
ataaataaat aaataaataa ataaataaat aaataaggtc ttcggatgaa ctttccattt  14040
ataatacaat ttacaaaccc tgtctgggat gtctatgatt ttgctggtgc ccctgccttc  14100
ctaacacagt ttcttccctt ggacagcttg tatcagggac attttcccta acacggtgct  14160
ggcagacctt aacattgaca gcgtggtggc cccagatgct tttgtctgtc gtcgcatctg  14220
cacgcatcac cccacttgtt tgttcttcac attcttttcc caagcatggc cgaaagaatc  14280
tcagaggtaa ggcgttgtca ttaagggtca tctggtcttt ttaaaaaaac ggccaataaa  14340
aatgtgctgc acaatcaaga taggaaacgt ctaggcagca ggacacttct ggactccttg  14400
agatagattt gaattgcgga aaggaatggt accagcagga ggaaagactg ggaccacgga  14460
caatagggca aggttcaaaa gtgttttgaa aagttcttag tgacattaca atttacagaa  14520
cgcgacttgg tgattcaaga agcaatgtta ggatgaggtt gctattaaat gcttctctga  14580
gctaccttta tttgctatac ttgtaccaag tggtctttct ctttgctata ttttatctga  14640
tttattcata cactcccttt ggtcctttag acatctttgt ctccttaaaa cctctgaaag  14700
tggattacca agcacacgca ttacaaagag ccacgccctt tcgggcttca gtctccagca  14760
ctgcaggcac agtgtcccag gtaaacaatg caggctgtcc ctctctctga gctccacagc  14820
cccaaggaac tggatggctg tgaaggctac acacttcaaa cctggcgtgt gctttgttgt  14880
ctagtattct gccatccgtc cttttacaac gacactgatt tcttgggaga agagctggac  14940
atcgtcgatg tgaaaggcca agaaacctgt cagaaaacgt gtaccaataa cgcccgctgc  15000
cagttcttta cctactatcc atcgcacaga ctgtgcaatg agaggaagta aggcacaagt  15060
```

```
taggtggatg ctcttggagc atctccttgt aggatgagtt ttgcttacag agttttgttt  15120
tcagccgcag gggcagatgt tacctaaagc tttcctccaa tggatctcca acgagaatac  15180
ttcatgggag gggaggcatc tctggatact cactgaggct gtgcaaaatg gataatggtg  15240
aatacttgaa aaaatacaac tgaaggggaa tagtcaacct aacgttgcta gtctactaca  15300
cgaggctagt ctacaacaac catagagaga tggagacagc agcacaagga ggttgaggca  15360
ggagaatcag aaatttaata ccagattgga ttaaaaggca aaatcctgta taaaaaatga  15420
caacaaaata gacatggaag agagaacaaa gttaacaaat ttggaggttt tcccttacat  15480
atatgtatgt catatatata tatatactta tatatatatg tatatgtgta tgaatatgta  15540
tatgtatata tgtcatttca agtggcattt cctgtagaga cagacccaga gggccaattt  15600
ttgttttcaa gaagtgtttt ttttaattat cagagattaa actattaaac agtccattaa  15660
ataaattatt cattttcttc ccacttaata tttcagtgag ccatgattag atgctatgat  15720
atatgatatg atatatacac acacacatat atataatatc tctcatatat atatatatat  15780
atatatatat atatatatat atatatatat acatacacat acatacacac atgcatatat  15840
ataattccag atgttaagct atcctgtaaa ttgtgatgag atttcatcaa taaagtgtga  15900
ccctaattac tcctcgtgaa agtttcaaaa gtataaaacc tttttcatca gatcatttgc  15960
tattctagaa ggtgactcta tccttagttt cagaggacct gatttacagc acattgagat  16020
gttttatccc aacaactgca gtgccctaaa cagaaaacat gccttcctag aattcactgg  16080
tttgatagca atctctgggt ggcctgagcc tcttaagaca gttaattaag ttatagttca  16140
tacacactgt gttttgctca tgataaactt acctaataag aaggaacatt caagacaagt  16200
attgtcttaa ttctacttct tcatggtaga aggggcaact agaaagacgg ctaagtcatg  16260
tgagcatgct ttaaaaactg ggatccagaa cagatagctt gatacactga agattacatt  16320
tctcacccac ttctgccttc attatgtttg tctctgttga atttatagcc tggtctgtac  16380
aggtgacaga atggatcagt tgtagattga cagaagagaa aatgtggagg gtaataaacc  16440
tgtctgcctt ctcatgcata gagaagtggt tacactgtac aatattgggc tacaatactt  16500
acctttatgc aagagagaag atcgaactca gttgtttttc gtatttactc tgttgttggt  16560
ctctaatgta acttgacttc ctaaagacac ctagcaatgg acaccactaa aagaagtatt  16620
tcttcatccc caatgcaaag ttgagcacta taagttttca gcattctgtt caagttgatg  16680
gagcagacat cgagatagaa ctttttctga aggcttgcat tgggcttact gataatgtgt  16740
cctacttact gcttgcctgt taactttcta aaggttacct ttctgctgat ggactgaaag  16800
gtttctgagg gatttctcag aagcctttca ggacgaggga cattgaagcc taggtaactg  16860
ctaaccacac tctctctgtt gtagtgtgca caactaaaat caaccccaga gtggtaggag  16920
gagctgcgtc tgttcacggt gagtggccat ggcaggtgac tctgcacatc agccagggac  16980
acctgtgtgg aggctccatc attggaaacc aatggatact gacagcagct cattgtttct  17040
ctgggtgagt attattgcta ttctcctggg attgccatca tgaaggtgaa atctgggact  17100
atcataagag tcaataaaca ctttgaaaat gtaaatgatc ctgtttccta aattaattct  17160
ctctgtgtgg gcagggacga tggtgtagaa gagaccagtc ctcatcattt ggccacaata  17220
gaacaggggc aggagcagag cagattgccc acctctgcct tttcattcaa acgcaaatta  17280
tttccattgt cttcctgatg gtgcctggtg gcgaagcaca gggccagagt gaagcttaca  17340
atcctcagct ctctgaatcc tggttaccct agtctctctt tctctgcctc cgaatgctta  17400
gagttcagca cacaccatca gaccagatcc ccgcacttag cattgctttt cgatattggc  17460
caaatgtgaa catcttagcc ggggaagtgt gtatctcgag gaaattcggt tgagtgaaac  17520
ctttctgtgc tacttttagt gcctctgttg cttccagaca caggtttaga ggctaatcgt  17580
tttgttaatt tttttccatg catggatgca ttatgcacat aattcaatgc tacacttgag  17640
atcaatagtc ccctttgcaa gcacatatga aaaaacacag aaagtcccag tgacttttct  17700
ttaaattctg cccaagacaa ggttgagact aatacccaac tctcctgagc ttggagatgt  17760
gctggggagt agaaagacca tttatttaaa gtgtccaata ttagtgcaag aactaatcca  17820
gtgatttcac tgtagaggaa atatgtgact aaaagttttg agaataaaat cactttttttt  17880
accacctaaa ggtagaaaca gacacagagt ataaataact gtgaaacaca aatatttgga  17940
aattgcctag tgatagattt ttttttccat tctgtttgtt ccttaggata gagacaccta  18000
aaaagctgcg tgtctacggt ggcattgtaa atcaatcaga aataaatgaa gggactgctt  18060
tcttcagggt tcaagaaatg ataattcatg atcagtatac gacagcagaa agtgggtatg  18120
atattgccct gttaaaactg gaatcagcca tgaattacac aggtatatat atagagagag  18180
agagttttag gtgacctaga taaaacattc acgttaggag actcacagtc tcatctatgg  18240
ggtctaatca acagacagac aaggaaggtc tgaaaagatg gcctcactct gttgagacag  18300
agagtttgcc ttagaatact agattagcga tccatactta tctccttgta ctaaggtcaa  18360
atctaagtgg atcaaggaac ttcacataaa accagagaca ctgaaactta tagaggagaa  18420
agtggggaaa agccttgaag atatgggcac aggggaaaaa ttcctgaaca gaacagcaat  18480
ggcttgtgct gtaagattga gaattgacaa atgggaccta atgaaactcc aaagtttctg  18540
caaggcaaaa gataccgtca ataagacaaa aagaccacca acagattggg aaaggatctt  18600
tacctatccc aaatcagata ggggactaat atccaacata tataaagaac tcaagaaggt  18660
ggacttcaga aaatcaaata accccattaa aaaatggggc tcagaactga acaaagaatt  18720
ctcacctgag gaataccgaa tggcagagaa gcacctgaaa aaatgttcaa catccttaat  18780
catcagggaa atgcaaatca aaacaaccct gagattccac ctcacaccag tcagaatggc  18840
taagatcaaa aattcaggtg acagcagatg ctgtcgtgga tgtggagaaa gaggaacact  18900
cctccattgt tggtgggatt gcaggcttgt acaaccactc tggaaatcag tctggcggtt  18960
cctcagaaaa ttggacatag tactaccgga ggatccagca atacctctcc tgggcatata  19020
tccagaagat gccccaactg gtaagaagga cacgtgctcc actatgttca tagcagcctt  19080
atttataata gccagaagct ggaaagaacc cagatgcccc tcaacagagg aatggataca  19140
gaaaatgtgg tacatctaca caatggagta ctactcagct attaaaaaga atgaatttat  19200
gaaattccta ggcaaatgga tggacctgga gggcatcatc ctgagtgagg taacacattc  19260
acaaaggaac tcacacaata tgtactcact gataagtgga tattagccca aaacctagga  19320
tacccaagat ataagataca acttgctaaa cacatgaaac tcaagaaaaa tgaagactga  19380
agtgtggaca ctatgcccct ccttagaagt gggaacaaaa cacccatgga aggagctaca  19440
gagacaaagt ttggagctga gacgaaagga tagaccatgt agagactgcc atatccaggg  19500
atccacccca taatcagcat ccaaacgctg acacctttgc atacactagc aagattttat  19560
cgaaaggacc cagatgtagc tgtctcttgt gagactatgt cggggcctag caaacacaga  19620
agtggatgct cacagtcagc taatggatgg atcacagggc tctcaatgga ggagctagag  19680
aaagtaccca aggagctaaa gggatctgca acccaatagg tggaacaaca ttatgaacta  19740
accagtaccc tggagctctt gactctagct gcatatgtat caaaagatag cctagtcggc  19800
```

```
catcactgga aagagaggcc cattggacat gcaaacttta tatgccccag ttcaggggaa  19860
cgccagggcc aaaaaggagg agagggtggg taggggagtg ggggtgggtg ggtatggggg  19920
acttttggta tagcattgga aatgtaaatg agctaaatac ctaataaaaa tggaaaaaaa  19980
attaaaaaaa aagaatacta gattagactt tgagagtgca gacggagaga cttgccttca  20040
ggcttcttca ggtacataga atgacatcgt tttataaaat accgaagcaa taagaataat  20100
gattgatatt ttgctttagt aacaaagggc ttgacagcac agttgagcaa atgctacaga  20160
atattaaacc acattaaaaa tgaaaggtgg tgtaaagagg gcctgtctta ccctttccct  20220
tgtcccttct gcttgggaca tttcatatgt gccactgaac acatgacatg aaacacatga  20280
gaaaaagata acgaatatca taaagaaaga gagcatgatt aatgtcaggt gagataacac  20340
ccctttctgg gacaaatgat tggctttctt tctgcttcgg tcagcttttc gctactgtga  20400
caaaatgcct gatgtaacca ccctgtaaga aagaaaggtg atatgggctc tcttgatgtc  20460
agaggcttca gcctgcagtt gtgtgtgtgt gtgtgggggg ggggggtcca ctgctttgta  20520
gcccttggta agaaatgtgc agaggagcaa attttcacct cctggatgct gggaagcatt  20580
aatgaaggga cggggctcct gatagcccct tcaaaggccc accctcaatg acgtcacttc  20640
cttcctacac cttccccccc aacacacaca cacacacaca cacacacaca cacacacaca  20700
cacattctcc attatctcta agtagtgtca caggctggga tggagtcttt gaacatgggc  20760
ctttggggag acacctcaga tccaaaccgt agtggcctct gatgactaaa ctgtgatttt  20820
caaaattaga ttttcagcgg ccaatatgcc tgccttccaa aggagataga aacgcagtgc  20880
acacagaatg ctgggtgact ggatgggggt acacagcact aagaggtaac aaaccatgcc  20940
ttctatctct gctttattct gaagtcaaag aacagagctt aaccattgcc tctgttttct  21000
atctagtcat atggcccaaa cgtgagtcaa gtcacctact caataacagg aagactgata  21060
acaaagatca atacatctga tcagaaacgt taaatatgat taaacccctc taaagaccat  21120
tttaactgga gacttttagt ttgggaccta acactctatg taaaagttct agcctggttt  21180
ctaattattt tgtctgaaaa gaaattctac ttagtgtcag ttaattttga acttaataac  21240
attaatgaaa ttatgtacac aatagtagaa acaatgtctt ctttatactc catacttaca  21300
aaaattactt atgaatcaag cttagtaata ccacccccccc ccaggatttg tatgtacaat  21360
tttggctttt aaatataatt gtatataaac ctatagtaat tattcctcta aaacactaat  21420
atgacccttt tcaggtgaag tacaaagtac tcttcagaaa gccaaggttc cattggtgtc  21480
aaatgaagaa tgtcagacaa gatacagaag acacaaaata accaataaga tgatctgtgc  21540
aggctacaaa gaaggaggga aggatacgtg caaggtaagg cagtctcaag caatcagtca  21600
tgccagattg aagtgagagc ttaatgcatt tgtacaaacc actgtaccat tgagcagtgt  21660
ccgagtgtgc ttcctgttgc tgtgataaaa cactgaccaa acacaactca gggaaggaaa  21720
gggtttatca agcttacagg ttacacagtc caccatagcg gaaagtcaag gtaggcagga  21780
actgcagtag agacggtgga ggagtgctac ttcctggctt ctgtttagtc ttgtgttccc  21840
tacttttctt ttgtgacaat gtggttaaca attagcagtg gagaaagttc cccacagtcc  21900
aggctgatgg cagaggtgcc tcagctgtgt tccctcttcc caggtgtgtg aggttgacaa  21960
ctcagattag ccatcgcaag cagatcactt ggtgggttta ttttaggtaa actaaactct  22020
acaggaggaa ggaaagctgg ataaaggaga acaattggat gtttggatgc ttgtgagagg  22080
gccagaatat tatgtaaaat tgctgtgagc aatacttact taactcagga aatgcctacc  22140
atgatcccgg catgtgtctt ctttttctcc ccctttgaca gggagattct ggagggcccc  22200
tgtcctgcaa atacaatggg gtctggcact tggtgggcat cacaagctgg ggtgaaggct  22260
gtggtcagaa ggagagaccg ggggtctaca cgaacgtggc caagtacgtg gactggattc  22320
tggagaaaac tcaaacagtc tgaaagagtt caactggtat cactttgtgg ccctggaaga  22380
ttattccata gaaatgagct tgacgtctct gatgaagaca ctgggatact gactcttcca  22440
ctgtaaccaa ttgaatggcc ttgatgtacg taagaacacc cagaaagaaa actattattt  22500
tcagaattcc tgatctggga gaaccactgg ttgttttctg catccagcta ctactcaagg  22560
aaacaaatac agcaaggaga ttttaaaaat aaaaacacat cagatatata aggaaaatat  22620
caagtaaggg tgctgtctgc ctttttagtc tctgtgacaa atacctaaag tagttcacaa  22680
aaggaaaaat ttcttttgca cacctttcct caggtttcag cctacgatct ggttggctgg  22740
ccccattgct ttagcctgag gtgaggcaga accatatatc cataggaggc tgtggagaag  22800
gagtctgctc agttcatggt aggcaggaag caaatggaaa caggaatgta ttggggacac  22860
gaatggtcct tcaagaatat actgtcaatc atttacttct tccagagaca tcctgctccc  22920
taacctccct ttccttccca gataacacct ctgtcctagc tggccccaag agatcaggta  22980
gaaaggcaga ggaaaccata taaagagttg ttaagtgcaa aatcaaaacc agaaggaatg  23040
cagacaggag ctcaaaatgt ccatttataa gaatcttttt ttttctctgc ctatatgaat  23100
ccccctcctg tataaaggac tgactcaatt cagtgatggg ttttgagaag tctgtttgtg  23160
tgtgtgtgtg tgtgtgtgcg cgcgcgcgtg tgtgtgtgtc tgtctgtctg tgcacattca  23220
tgtttaggta tgtgcaggta cctggtgggg gcgatcaacc ttgcattatt tctcatgtgc  23280
catctaccct agcttttcaa agacagagtg tcttactggg attggagact tgggctaagc  23340
tagctatcta gcaagtccag ggaccattct gtctctacct ccccaaactg aaattaagaa  23400
gacatgccat ggtgcttaat ttaaacctct ctctgtcttt gtctctgtct ctgtctctgt  23460
ctctgtctct gtctctgtct cgctctctct ccttcctcct tctctccctc ccactctctc  23520
tttgggtgtg cacgtgcgca tgtgcaagtc atagtgtgtg tgcagggcag tggaccatct  23580
tcaggagtca atgctctcct tccatcatgt aaggtccagg gatggacatt aggtgttcag  23640
atttggtgac aaatgtctgt accttcttag ccacgtcaca agccagctgt tccgatttcc  23700
tacagatgct gggaatcaaa tctgagtcct cggggttgcc tggcaagcat cattactgac  23760
tgagctctcc agtggccttg tcagtcttct ctctgcattt tcccaaactg gcttggacaa  23820
gcaccattgc aggtgttaag tgcacacttc ctaatttcca catgggccga gtataggagg  23880
agcaattttc caggaagtgg tcccttgaag acacaccgta ctgatttgct tgcctcggaa  23940
agtatctcag cgtagcctgc actctttttg cagtgttagg ggaaagtaca ggtggatgga  24000
gataaggaag acaagccaaa acctaccaag atctgccagt gagtgggagt ttacaaagct  24060
gagtaatgaa tgtgctggac ggaaatgtgt gttgaaatcg tacatactac gggggggggg  24120
gggggggtgg ataatttggg agcaaatgtg gtttcaatag aggctgcagc ctcctcaaac  24180
agttctctgt attctgagta cctgactttt gtcctcacat ggggcaataa tgtagtattt  24240
ggactttgtc cccgtacttt tcagtcagcg ttgataacta tacaagttgt ccaaatgaaa  24300
agtatttatt gtgcccaatt atgtcagagt gtcttgttga gcttggggaa ctgaagcgcc  24360
agccaataaa ttatgaaggt ttcataaggt tttctgttga tttagtacga accgaagaga  24420
ggagctgcac aaaatctata ctttcaaaca aagatgacca tgacacaaag ggttctaaga  24480
aatgacaacg aagaagagtt agcagaagct aagagagtgg catggaaagg aagtggcccc  24540
```

```
aagcaagaca aagcaaagac agcaaacaag caaaagccag agatcgatgt cactgaaatg  24600
gcacgagcag gctggattca aaatgcttct agagtaagac agaattgaca tcaaatgggg  24660
tcacaacttc acaacccatg aacaagcagc gccttttata acctatttat tacatttcac  24720
ataggaaatc ttttataacc tatttattac atttcacata ggaaattgag gaggcattgc  24780
tgtcttctct gagaagtatt taaggaatgt tttcgtctta attttttttc agaacaagtg  24840
caacatctta attctgaata tctagtacct agaaaatgct atgagctata aggaataaga  24900
aattacgctg agcagattca catctccaca ccaacaagct gcgaatctgt atactttctg  24960
gcacttttct cacttaatct tctctctcct ggagctagct c                      25001

SEQ ID NO: 39          moltype = DNA  length = 16
FEATURE                Location/Qualifiers
source                 1..16
                       mol_type = other DNA
                       organism = synthetic construct
SEQUENCE: 39
ctgtttgagt tttctc                                                  16

SEQ ID NO: 40          moltype = DNA  length = 16
FEATURE                Location/Qualifiers
source                 1..16
                       mol_type = other DNA
                       organism = synthetic construct
modified_base          5
                       mod_base = OTHER
                       note = uracil
SEQUENCE: 40
ctgtttgagt tttctc                                                  16

SEQ ID NO: 41          moltype = DNA  length = 20
FEATURE                Location/Qualifiers
source                 1..20
                       mol_type = other DNA
                       organism = synthetic construct
SEQUENCE: 41
acatgacagg cgcgatctct                                              20

SEQ ID NO: 42          moltype = DNA  length = 25
FEATURE                Location/Qualifiers
source                 1..25
                       mol_type = other DNA
                       organism = synthetic construct
SEQUENCE: 42
tctaggttca cgtacacatc tttgc                                        25

SEQ ID NO: 43          moltype = DNA  length = 26
FEATURE                Location/Qualifiers
source                 1..26
                       mol_type = other DNA
                       organism = synthetic construct
SEQUENCE: 43
ttccttcaag caatgccctc agcaat                                       26

SEQ ID NO: 44          moltype = DNA  length = 34001
FEATURE                Location/Qualifiers
source                 1..34001
                       mol_type = genomic DNA
                       organism = Mus musculus
SEQUENCE: 44
tgcagctaga gacacgagct ccgggggtac tggttagttc atattgttgt ttcacctata  60
gggttgcaga cccctttagt tctttgggta ttttctctag ctccccatgt ggattatctt  120
aagagggttt caatagtcac ataagaaagt ctctcatttt aggggtgaag accactttaa  180
aaaaattcaa atggcttgct gaaagccaca gacactagag aaataattat gtttagggta  240
aagtcggctt gtcctcttgt gaaactgtgt ccaacggaga caagctgagg aattatgggc  300
aatgataaca tgttaaatgt tgagctaaat gtattaaaaa gcgcaaaaaa acaggtgtgg  360
tgggggaaca gaggctagaa gtctccctga aaaaaatcaa gtcttatttc ctacttcccc  420
cgtgtttggt ctggggaaga acaatagtgt ttgcttaagc atctcattct gttttcaaaa  480
ccttgcatgg ttgacttggg aactgataga gaaaatgaag caaacaatac tctgtaatca  540
acattaacat caaagctagc tctctccact gtggtccctg acccaaccac gttaatctcc  600
cagggtcttg ttaaaactgt aggcttggga gagaagtggt tgtggtgagg ggtaccttgg  660
agtaattcta agtctcttgg ggttaagcct ggaagattgg tgctttatgt attaagagtc  720
ctggggatcc gaaagtagaa aaataatgat ttttgttagt gactcagtat ggttcttact  780
tcaacacctc ctcttaaggg aggaagtagt gtgtgcatgt agctggaatt ttaaataata  840
acagttcagg tgtgtgagta tttcattaga cagtcagctt ccatccttta tgcatccttt  900
aagcaggttg gtttagacag gtgcacaata aacgccaggc tattaaacac agggactcca  960
atatttaaac caattctttt gaattgtctg gctagaagca catccagtct gataaagtag  1020
acaaagcacg tggagtcttg aaaagttcga cacccccttcg gtcctcagat gactattatt  1080
tagcaattga gagcactata ctccttcttt tgcccacacc tataaggaga tggacatggc  1140
acgtacatcc cagcactttt gacagcttta aatggtgttt attacgagca ggtatggatg  1200
ctgggaacag tgcttatacc gagtcctgga aatgcttatt aaacccagga gatacaagga  1260
```

-continued

```
gtctgccatt aacctctctg taactcaaga gtagttatca ggagccaatg agggagaaca  1320
agagaattga aacacgtggg aatatcggac caccaggtag cgggtgtgtg tgtgggggga  1380
ggcagcccta gggagctctc aagccgaggc ccctcggggt ccccgcggca cgtggcgggc  1440
tcgggccgga gcgtcgcggc ggtgggggag gggagcggca tgagccctgg aggaggggtc  1500
tagactgccc gggattcgtt tgagcaggcg cggagtgcgc aggctcggcc caggcgcaac  1560
cagtgcgcgt aagaccgagg ggtgaacctc actgctgcgc gtccgggtct ctgagcaagg  1620
ggctaaagtc cgcttgtgcg cacctccgga ctgtgtgtga ctacccgtag aaacactact  1680
gtcgccctgg ccggtggcgt ccactccgtc ccggtcgctc cctcccgacc gtagttgtgg  1740
tgcccccctc cgcgcagccg cagtggtcgc tcccgcctcg cagccccgcc gcccggaggc  1800
ctacccctgc cgagtgtcgc gcgtcggcgc cgctgcctat cccgctctgt gccctacggc  1860
cctcccggca cccgccgccg tcccgctccg ggctgccctt gctccgaggg ctgcagcacc  1920
ggccgtcccc gtcagccctc ttgtctggcc gccgggccgc ggcgggcggg agcagccgga  1980
ggaggagccg cagccgggag gcggcggcct gagcccatgg cgtacagtca aggaggcggc  2040
aagaagaaag tgtgctacta ctatgatggt gagtggccga ggagcctgca gccgggatgc  2100
ggggagggcg cggcggggtg tcgggggtgg cagcccgcgg ggacaccaac acggcctacc  2160
cagcggtggc gtctcgggga cgcccgcctt cgctcctctc gggtcctctc gggcacacgc  2220
aggtttaggg tgcactgcct ctgaccggtc tcccgaggaa ccccagttgg caccctgggc  2280
ctgactgcac aaagctggcg tcctggagct ccgccccacg tccctgtccc ctcccccgct  2340
ctcccggtcc ccccttctcg cccccgatct gtccgcgctg cgcttccagc ctcacccggg  2400
accccggcac ccgggtgggg ctgcggagga gttactgctg gccggtggcc aagttcgcag  2460
agcggcgctg tctcgctggt gttttgcgtg gactacatcc ctcgcctttg ttcgcgttct  2520
tcgagctcca ctttctcagg gttcaaatgg aagggctgca cttcctcggt gacaattaag  2580
gggttttgag ttggaagtag gtaggtcgtt gggaagtggt aggagagagg aagcgtgcag  2640
ttgttcttgt ttgatgggtc ctggcatgtc tctatgggag gttattacct ccccccttctt  2700
tgttgctctt tgttcgatct gctataatac cctgctctgg ggggttagga aagaacaccg  2760
gcatcttgct taggaactct tctactgtgg tgaagacctt gctgcaggaa actttgagaa  2820
gtggactaaa tattcacaat gcagtgaacg gtacaaggtg actgtaagga ttttctaatt  2880
tggagtataa gtagtaatag tctctgggtt cagttacacc aaatggaatg gtgccctgcc  2940
tatacagatt tcacccaaga catcaataga taaaccattg agagaagtaa taaggaaatt  3000
tgacagaact ttcgaagctc attgattgaa cgcttgatct ccacaaagca atatgaaatt  3060
gggagcgttt tctgtagttg tattgaagtc acagtgtttg gagaggtaga ttagagaact  3120
aggctgaatg aaacacttaa acttgttaaa atagtcgtgc attttcttgg tttgacagaa  3180
tcttttaata caagctttaa ataaaatagc cacctgtcat tggctggaaa accaaaaacc  3240
ttacagaaag ctaggccaaa atggaaaagg ctgttttgtt ttttgagaca ggctctaagt  3300
tgacctggct gtcctgaaac tcactgtgta aatgaggctc taactcatag agatccacct  3360
gcctctgcct cccagatcct gggattaaag atatgtgcca ccatggcctg gcttaattgg  3420
aagtttgaga ggactcaaac tgtattgcat gtttatttga agttacacca tcatggagag  3480
cagagatggg agagcatgtc ggtttaaaca tgagttacat tatgacgttg gggtcatagc  3540
aaagccctga cctgcattct ctgatccatt ggaaattaca gcctttctaa agtaaagtcc  3600
tgctcttgtt agagtcaggg gaaaggttga gctgttgggg aacagctcag tctcttcagc  3660
tgtcagcttc tgtcatcagt gatgaactct aagtcccatt aactttcacc aggcctgatg  3720
gagaaccaga gaggactctc tgtcttgaac agctccttcc tggcttcatg cgtagggatg  3780
agcctttgct gaggagtggg atagacattg gtcatggaga taaggtgtgg agggaggcat  3840
ttttcagtca tgtgattttc gacttatgcc catgcagctg ctttacctag ttgtgagtga  3900
ccaactgtat aattgatggt ggaaatctgc tgagttatct atctgtggtt cttacttgac  3960
ttgtttttag aatgtactta acttattttt attctgacta tttgcatttg ggggacgcta  4020
acaaaaattg aagatatata aattggtgtc atagttaagc taattaacat gtcatagcat  4080
gctagactac agagaattct ctgcagagaa ttcccttcac gtctgacttg attacagaaa  4140
ccctcttctt gttagtttat aaaggtagca gcaatcttta attgtcttta ttaaattcta  4200
aacaagagga gcaagtaaag tgacttttgt accaagaaag tgcatgactt tcagacgcat  4260
gcagggttgg gttggtggag aacccggcca gtaggattgg ggctcgaata gtatactagt  4320
cttatgttag tgcttttaac ttggttggta ggggaggaga tcaggaaagg aggaggttaa  4380
cggggcacta ggcacccaga gagcctcttg acaactcatg tgagtgtttt cctgctaaga  4440
ctgtgtgctt agtgaagaat acttctgaag attgaatatg gttttctccg tgtgtgctgc  4500
agtcttcaga attgtacttg tagggtctct gtgccactga tctgtgaact ttcagatagg  4560
agcgtatgaa ctatccctaa acctcacaag agaaatcaga gttgttctta gtggactgtg  4620
actactgact ggtcatcata actcccagaa acacatttca gaatgttggc taatctctta  4680
ctaaactaaa agacaaagat cggtaaatga tataaagcta attatgtgtc tacactgaga  4740
tcctttctga cctctttccc gtttttctca aagtgtaatt gagcagatgg ggctacattt  4800
agttctaatt gcaaggctca ggcttttaat actttatcta gaaatataaa ctttgcctgg  4860
tttagagtga agcttgggac caatcatgta gtgccttcta atgtatagtg tataacagaa  4920
ttgaatgtat gcataattta tgtaattaga caccaattgc tttatgcttt gtttattttc  4980
tctgatagag ataatcagaa tcaaaatgtt tggagacata gtccagagga aagcacgtgg  5040
caacaaaaat atagaatata acaattacta taattatatt tcccagtgta ctcctaagtt  5100
tcttaacaga tacaagagta ctacagagtg gccatcggtt gtcagattta ttttactttt  5160
atttaaaatg tgtgtgcttc ttgtgtatgc ctggtgccct tgatgtttag gagtggttgt  5220
gagctaccac gtagatgctg gaaaccaaat ttgggtcttc tggaagagca ataaatgctc  5280
ttaagctact ctccagcctg tccgttccca ctataacagt aggcaggagg atggttaggc  5340
ttctgccact tatagatgaa aacaggtgga cacttcatat tctccacatg ggtttctttt  5400
ccccacatag gtttctgttt taatgtctaa gaaagattcg tacctagaat acaaagattt  5460
tatttttctt ttgcagagtt ttgttcttct gtccctaaaa aaatgtatta ataattggtt  5520
tttttcttag caaaattaaa tgttagtaaa ttcttaaaac acatggagtt ggtgaacaaa  5580
aggaaaattt cttacattag caaaatgaaa tgtgaagtca ttaagtaacg gtttgggctt  5640
ttttaaggcc gccattgcta tggataatga caccgagatt tatttctgtt tagtaataaa  5700
tgcctaggcc ttaagctagg cctactccca actagctcat cactcaatta tctcatttat  5760
acttctcagt ttcctacaac caacttcctc cgagtccgaa tagggaatac cccacgccta  5820
attctgagtt cctctctctt ccagatgtcc caccttacta tcctgccttt tgctgtaagc  5880
cataggcttt ttattttaat ctgtcaggag gtgccttagg cagttgggga aggatagaga  5940
cacatcttca cacagtgtac cgaaacatca ccctaacacc attacattga agttctactc  6000
```

-continued

```
tcaccatgtt ggttagtcgg tctcactctg gtttcatggt ttatgcttgt acatgaagtc  6060
agtttggggt tcagaaacat aagattgttt taagtccctg ctttgtccca tatagacaaa  6120
gattacttaa gaaggaaatg ggtgtttgta acagagtaaa agaggaatgg agtaataaaa  6180
caagcatctc taggaagcat atgcgccagt cttaaaacag tcctccctgt gaaacaacaa  6240
aggccaagtc cttggaatgt gttgtaccca aaagaagggc aacccagaga tagggatgct  6300
gggctgagcc ccaaggggcc aggcacagca agcttggttg aaagagagtt tgactcttag  6360
agggagtgtc ttggagcttt taaagtggag gctagtcaat aagagaattg gtgagaagta  6420
gaatgtaggc tagaggaaag tgttaaagtg aaaggaaatg gttgtcttta gatagaatcg  6480
ggtacatttg agagtggttt ataaaccaag aaaaaaatac atcaaaacta cttgttggtg  6540
gcttggacga gggattaggg ctgggagttg tgatttctgg actggtcatg agatggacaa  6600
catactgtcc attgagatta tatggaatca agggctctat attggctatt atgtatttga  6660
gatcttgatt tagatcaaat gaaaatactt ccaaaaatta cctggaaccc agggagaagt  6720
agtatttctt agctggtaag tgataaatac tgacgtgttt gttgaaggta atggtatgga  6780
gagacacaga ctccggaaat tgttcctgag aagtcatagg atgaagtcac tcttggtgta  6840
ctgcttggcc agtgacaagc tcttgactta tgaggaaagt gaagaaaagc tgagatttaa  6900
aaggtttgga ggaagtgagc ttagagaagg aacacaatgg aggacagaat tgtggagatc  6960
cagactccac agtgtttcaa ggaggaggga gggtctaaca gtgttaaaac cttcacagaa  7020
ctaatgttgt gtggcagaca gaaattgcac agtagtcttt ttattcttga ttttttcccc  7080
tccctcgagc ccccccacac acactacttt tggcagcttc tctatgtaca gtgtgaaagt  7140
acatttcaca gtcctgaaat ttacaatgat ctgaaatttt gttcactcag aatcaaaagc  7200
ttatcctgaa attaacgaaa ttacaattta ttgtctttat tccactaact gtgataatta  7260
cacatttttg ctttagaaat acctttgatt atagaatgtt gtcccagttt tagtacatta  7320
tatattttta tcttgagtca aacttttctg gatattctta attggtaaaa ctatatttaa  7380
gtatttgaac aaaaaatggg atcacatttt aaatgcccaa attatgtaac tgacagagac  7440
tataggtaca tgaaattaag aaattatgta actgacagag actataggta catgaaatta  7500
agaaattatg taactgacag agactatagg tacatgaaat taagaaatta tgtaactggc  7560
agagactata ggtacatgaa attaagaaat tatgtaactg acagagacta taggtacatg  7620
aaattaagaa aagaagagca gtgtgaggtt tgatcttgct gtgcattgca atactaagtg  7680
caggccccaa gatctggagt ctgcacacag acctgagtaa cagtatgtgg ccttgccttc  7740
aagttatttc tgactggtaa ataaagatgc ctacagccaa tagctgagca gaagagttgt  7800
atgtggggct taggattcct attgtaaata taaaggttgt gtgtatcttt tatctggaaa  7860
ctaaatggtc aaagccaggg tagaaacgcc aggttgggat taagcgtttt aacaacaggg  7920
ctggatggct tagcagttta aaaccctggc tgctctttca gaggacctgg gttggattcc  7980
cagcactcac agggttgttc acaggggtca ttcactacag ccacagggga tctgatgctg  8040
tctcctgccc tccatggcca ccagacacag tcatatgtat ggcaaaatca ccatgcacat  8100
taaataaaat ttaaaaagaa tcagttcaga aaacattttc ttaaaaaaga aaaaggcaga  8160
aggtttttta gtaagaaata gatgacttca aagtcgccat gtataaaact aatagtgaac  8220
aggaaacatt agaaatgaag attcttccct ctcctcctcc cagaatcacc taccctctgc  8280
tgctagagtg ctggtttaaa ggtgccttgc ccacaaaaat ggttcttgtt tgtttttgaa  8340
attataatat gatcacacca ttttcttcct tcctttactc cctccaaccc ctcctgtgta  8400
gccttccacc tgctctcttt caaatccata cccttggatt tctttaactg ttgatacata  8460
taaatactcc taaatacata aatacagtgt tactatatgt ttttagagct ggctatttgt  8520
tattggataa ccaatgggtt ggtcattacc tggaggagat tctttgtcct atccttagtc  8580
cttagttgtc tgtagttctt tgtctaggct tgaggcctcc tgaccttcac taacgtgtct  8640
gttaatgacc ttgttcaggt catgtttagc cagtcatgtt ggtgagactt tgtggatgtt  8700
gcttctgaca tgtctcactg acaggcttac agtaaactcc ttgttcttca agctctttaa  8760
accctctctc tcttccccaa tgccctctga ccctaaggtg taggggtgt attgtagatg  8820
tgtcacttgg tactgggctc caaaactctg catttcaatt gtgcttttct gtaatggtct  8880
ctgctacaag gagaactttt cctttatagg ggtgaggact acaggctcct gtgtttacaa  8940
ggacaattat gtagaatgta gatcgggatg ctgctgcttt tgtaaagtag caattgcata  9000
ttttattcaa agatggatga cttcagtagt cttgagttgg ctaggtctcc aatactaggc  9060
atgatttccc tcttgctgaa tggatctgaa atccaattag aaagctgttg gttactgtaa  9120
aggtctgcgt gccaccactc cacatttatg ctgccatggt ggttgttact gtggttcaga  9180
ggtgtcataa ctgcgtagga ctattggttg cttccctcct ctggagcctt gcatgactcc  9240
tttttataat atgaagggta gtcctcaaga aggattaggc tctcagttct gtccagctca  9300
ggggcttctt gggccctgca tctcaagtgc atgatgtctt cagcaatatg cagttacctc  9360
tagggggcaa ccaagggcaa tagcgtataa gattttggga gtctcttgga tagtcctgac  9420
cagcaactcc aaagacggct gcgtagtttt ttgtttgttt gtttgtttgt tttgttttgt  9480
tttgtttttg tggataatgg ctcctggagg gagcctgtgt ctatttatac acagtcttat  9540
gtgtattata ggtacagtag ggcaatggca tgattgtgct tgatccttga gacatcctca  9600
ctgttcctct accgtcctca ttccttgtcc tgtatttgtc ttcctcccta gttagaagcc  9660
ccactccatt cccccttacat ttcctttcct tccccttcct tctccccctt tgcgttcccg  9720
tcgctcccct tttgtgcaga ggaattaaac caaaagcttg tacatgctag agaaatgttc  9780
caccactgta tatctcaagc ctttggaggg attcggaaaa attcatatta tggctcagct  9840
gccctcgtga atatgtgtct tttaggctaa atgaatattc ttactgagaa taaggcctca  9900
aaattatgac agaagtttgt cgaaagctgt atatattaat ataacgttag gagtctcata  9960
gttagaaggt aactcccttc ataaattagg taagccatcc attttgttca tattcgtcaa  10020
atgaacaaat tcgatgctga gcacaagcat gtatactgta ttctttcctc attcgccatt  10080
gtcctgctat tacattgctg tgccagtgac aatacaaaag aatattcact gcctgtgctc  10140
tcttcttcct aaatctgaat gtagctccta tctgctagtt gtataatttt ggctacatta  10200
tttaacatgc ttctcggcag ttataaagtt gtggtacatc ctagagttga gaaataaaag  10260
ctgatgctga gtactaggaa aatgttcttg ctgttacttc tcaaacacta caacttaaag  10320
ttggctgcat agggagaaca tctggaagga ttaggggagg ggaaaatagg acaaaaatat  10380
atttaaattt aaagttaaat aataatataa taaagaaagt ttctacttag gtcaacaaga  10440
tgtattgttt tctggttctg aagttttcat ttacctttga aaaactagtt agcattctga  10500
gtgctcctaa atttgtaaat cattttgtga aaaaattgaa ctaaataaat cagaggtact  10560
ataccaacag attcatactg tttgaaggca ggttttgtaa acctgaatgt tcagctgggt  10620
ctggtggcaa aagccagtgg tctctcagtg gaatcatgaa ttcaatgcct gcctgggaca  10680
catagctaga attttgtctc aagggggaac aaaagcaaat gttttctgga ttattgtcaa  10740
```

-continued

```
gtagatagat agtatgaaaa tttctggatt tttgattgcc cctatataag tgaaaaggta  10800
ctatgagagg agagtttgaa atggggatgt ttgtgtttga gagctggtct tgctgtgttg  10860
tctggccagc ctggagtcct gtttgcaggt agataaggct tgccttgatc ttacagagac  10920
tcctgcttct gtttccctca gtgttagatt aaaggtgtgc actaccatac cctgcttaag  10980
ctttgtcctt ataagggcag atatatgaag tgtggggggct gtcttttgtt gtataaacct  11040
gtgctgaaac agtaagatct gcaggctgtt aaagtcaggt caactgtcct aacaaattat  11100
gaatatttga ttttaaacta taacattaat agtaatttct catttcttgc ttgataaggc  11160
cattgtaaaa ttattcctta tagggcagga gaaattactc agcagttaaa agcattggca  11220
gctcctacta aggacccagg gttgtgttcc tagcatatag ccatctgtaa ctccatttcc  11280
aggggatctg acacatcgtg accaccacag gcaccaggtg tcaatgcagg ctgcctatgt  11340
atatataggc aagctcgcag gcacataaaa gtagatagtg tccctcacct tagaaaaagt  11400
aatacataag ttttctaagc ttgttgacaa gctttcttat tgtctaaaag tattttgtgg  11460
ttgaaaatca gattttggca ttattctgtg tgttgtttta agacattggc atctgtctta  11520
cttagtttgg gttttactgc tgtgaacaga caccatgacc taggcaactc ttacaaatgc  11580
aaacatttat ttggggctag cttagtttca gaggtttagc tcattatcat ggtgggaagc  11640
atggcagcat gcaggtagac atagtgctgg aagagggttc tacatcctta ttcaaaggca  11700
gcagcaggag actccttcac aggcagccag gaggagggcc ttttccatac caggtagagc  11760
ctgagcatag gaggcctcaa aacccacctc catagtgaca cactttctct aacaaggccc  11820
cacctcctaa taatgccact tcccatgggc caagcatatt caaaccacca cagcatctaa  11880
gatgttttaa tgcacaggct actactgtgt agtcctgaga aatgaagaca agagtgtctt  11940
tattaccctg aaaaatgctg tgactctccc acttgtggac actgaacatt taagcccttc  12000
cataattcca gctcgactgt aaggtatttc tacaggattc caataagtta tccaagaagc  12060
actactagct gacaaattag atcctactcc gtacttcaag aatacttctt atgtatctaa  12120
atttacaaaa tgaacaacaa caacaacaaa aatccactaa aaatggattt caccttaagg  12180
aaccaaacca gggaaattgg aaaactaaaa gtcagaaaaa ctttctctct ccacaaagaa  12240
tgtgaatcct aggcatgtat aaaatctgca taatatatta gatttctaat gtaatttgaa  12300
tgttacaaaa acaactcttg tttaaatata aattttttga tgttgggtac atgtcagtgg  12360
tggtatttaa taagcatctt ttctctttta ggtgatattg gcaattatta ttatggccag  12420
ggtcatccca tgaagcctca tagaatccgg atgactcata acttgctgct aaattatggt  12480
ttataccgaa aaatggaaat atatgtaagt actagttggc actgtgtttt taaactggta  12540
tttgaaagct cttcttaggc tgctgtggga gatgcatgtg gtagatgaaa agatctgaac  12600
gaacacagac aggtcttgtg gttgtgtccc tcagagaacg cttaaggaat tggagtagtc  12660
ctctcttccc tctgatcatt tcaaacacca aatattttg tgacaatact gttaagttgc  12720
ctgtgctgct agaaacaatt gtcctggggt tggtgagatg acttaatagg tagaggtgct  12780
tgccaccaac tggatggcct gtttaccttc cccagaactc tcacagtaga aggagagacc  12840
taattccccc aaattgtttt ctaattccac gtgggcatga ggacacacct ccaataataa  12900
gtaaccacag tgtaatttta aaaagaaata aaagagaatt gacctgaatt attgcaagag  12960
tttggtagaa aattaatcat aaatatttat ttggttaaca tacatatgaa atgttgccaa  13020
tgataacaag gtaagtaaaa aatggtgtaa gatacacagc cacctaaaaa gtcttcgaaa  13080
catgggcagg agcatacata aaaagtgcaa ggtaggataa ggcttaacta actactccag  13140
gagaagaggg ctagacagtg ttataggaag catttcttta agatacaggt attttagaga  13200
aatgggaaga cttgtggaag aagtctgtgg taagtgaagc tgagctcttc agagcagaag  13260
ttagaataaa cgaaggctaa gggagatctc aagctggtgt tcttagaaac ctttgatgaa  13320
agtcagtggg tagacagcag cgaggctatg ctgggaaaga gcctgaacaa acaggagtag  13380
cctcgcttgg agaggggctg ccggctgcct gctgcctgcc acaaatgtgt gcatttgaat  13440
tagcattgta acttgctact caggtggatc tggttcattt agagagactg atcgtggaaa  13500
cttacacata tcatttgata attctcattt aacaactgat acttccaaca tcctggtgtt  13560
tttcttttca gaggcctcat aaagccactg ctgaagaaat gactaaatac cacagcgatg  13620
agtatatcaa gtttctacga tcaataagac cagataatat gtctgagtac agtaagcaga  13680
tgcagagatg tacgttataa ataattattt tactagtgct gaatgtaaat gaatcttttt  13740
aaagtttctg atcagagttg cctcaatagg tatttttcct cataatttaa aatattaata  13800
taattattaa ttcagaaggt cattgaacca atattaatgt tactttagaa aacaaaccta  13860
tttaaatttg ttcttttact ttttattttg cacccatgaa aagtttggga ttggtaggga  13920
gatcacagag ttacaagaga aaaatatatt tctttctttt tttttttttt taataatttt  13980
tttgagacag ggtctgactt tgtaaccagc tgtcctggag attgctaatg cagatcaggc  14040
tggcctcaaa ctcccagagt tccacctgct tctctcttgc attaacaatc ctccatttca  14100
ccttctgtgt actccagtca cattgttctg taatgtaaag atgttgcctt ttgttggctt  14160
ctttgtgttt ctttttattc ttctacatgt ttttgattat aggtgaaagt gtattgttat  14220
tggtagtcaa ttgtattaac tggtagtcaa gtgtattaaa gaaatattgc caagtatcct  14280
gaaactgtgg gctgctgtct tttgaagctt aataccggag cccatttcct cagtgagagg  14340
tggatttagt tcagtgatga cgaatgataa ggatttctca agttcactga acaccatatt  14400
tccctaccgt atgttatcgc atttggttga ctcaagactg gaataggacg gacggatgct  14460
attacatcta ttgttttttg ggtttttat ttgggattta cacagtaatg ggtagccagc  14520
ccttgggtaa atgacaggat ttgtttaaac cattatagtg cttgtttata ttaaattcta  14580
tttgagcata aaaaactaaa actttttta tagtatctgt aggtctgtaa aacccctgcc  14640
ctcttgctaa cgtgtgatct gagaagtgaa gaatgactag ggatgggcca cacacacttc  14700
tgttgtgttt tttcctctca gcacagggag ccaaccatgt catgaccaag tgacatgtca  14760
tctgtcttat gttccatgaa actgattcat tcatggctgc ttctgaagtc agtgttagcc  14820
acagaaaaaa aacaaagtaa cttaatattt tgatactcac taaaacatgt ttcggagtca  14880
gggacactgt gtgtgagggt cagtaagatg agttagaaag gggttgcagc cacttaatct  14940
ttaactcact atcatattta aagagaaaac tagatttgtg cctattttca tataggcttt  15000
tgatttatgt tgttggtgat ggtggtggtt gggtagagtg acttcacaaa tttcctaata  15060
agatttggta atggaattac atagataaca atttaattat cttgtaaaat aagcattata  15120
ttataaaatt ataactttta taatactacc tacattgaag tactactccc tgtgaatttt  15180
aaaattcata ggtaatattt taaaattaca aatttcacat tgctaccatg aaatattata  15240
ttattaccta tgattgcctg aaacaaatat ttttaatagt ttataagaaa aagccttcaa  15300
tgacttgata atagattgac tttaatgaag ttcaccttcc acagttaacg tcggagaaga  15360
ttgtccggtg tttgatggac tctttgagtt ttgtcagctc tccacgggtg gttcagttgg  15420
tgagtatcct aaatcagtca gcctcaagag gatctgaagg ggttagagtg tctgtaggtt  15480
```

-continued

```
ttgtctaaag cggaagttgt aatggtagta aggttgtgtt ggcttgattt tgctgtatca  15540
cccaggtggg cctccgtctc agccacctct gtggctacct cccaaatgct tgcttacaga  15600
catgtgctat cattccaact taatgagtac ccaagctgtc ttgtagttca ctgtggggcc  15660
cgggctgacc ttgatattgt ggaaatcctc ccctggagcc tctcaatcat tgggattaga  15720
ggcttggaat attatgatat tgctattcac tcttctgtta atgtaacaaa acctgcggta  15780
acttttaaaa gaatggttta tcttggttca cagtttggga gcttaactgg ccctgtcctt  15840
ggggactgtg atagcacatt atggtatgtg catttgggag aaggccagtt tacctcatgg  15900
ccgctgaatg gagaaaagag gattccagta tccctttcaa gcaagatcag atctccagta  15960
aactaaaatc agatcttggc tcttagagag tccacccccct tccagtggta ccatactggt  16020
gactaaatgt tccctggggt tcttagaagg catttcaggt tcaaagtagc aagtataatt  16080
gtctttaaaa tgccagtgtt taacagtttt tacttgaaca cagtctttaa gcttgtgtct  16140
ttttactcag agaccttttt ctcctcttct ttcttccgcc atttttacta agactttgca  16200
tgtgcactgt gatttagttg ggtaaactgt aggaaaatgg ttatctgagg aaagcttagg  16260
ctccgaagtt ataatccttt gcttttgaat gccaaacctt ttgtgcttac acatggcata  16320
tttaataggg cttcgcttat atgtattttg tgtaacctga ttttttaaaa ttctgagtat  16380
tttataaata acatagcatg tatctccttc ttagctgggg ctgtgaaatt aaaccggcaa  16440
caaactgata tggctgtcaa ttgggctgga ggactacatc atgccaagaa gtcagaagca  16500
tcagggttct gctatgttaa tgatattgtg cttgccatcc tcgaattact taagtaagtt  16560
aattcaaact gaattttccc tgtgatcaga tctcttaatt gaaagaaaaa aatgatttta  16620
aagactatca aataaatggt aatagattaa tgctgagtct tccagggttt gttgtgagcc  16680
cctgcagaag tgtgagaaat agaccactac agtgggagag cgagagggca gacagtgccg  16740
tgcctgagac tgccggtaaa tggtctctgc tcatttaggt ttgcagtcgt ctaagctgat  16800
taaaaatggc tgctagagat ccggaaatgt gaatgctaaa gtaacttgaa gtcaagcctt  16860
tgcaacttgt gttataagaa gtttgtctgg ccacttagta gcgtggctga ccccagttct  16920
ctcatccatc ctctacacag acacacagaa cacatagata atagacacac agtgatgccc  16980
aactgctgaa ggggttttgg aagttatcct tcactgcttt ttcagaagtg tgaaggtcct  17040
taggagtgtg gacacttgtg aaactagctt attttccact gttagctata atgctgcagt  17100
gagttgtatt tcagctttga ctgcagctgt gttctgtggg ctttgagagt gatgctcttg  17160
ccccgcatgt acatcccaag agttaacttc ctgaccttaa ataaacagca gctaagtgct  17220
gtcagtgtaa catatctgac tcccccaacc gacagaaacc ggaaatctcc ttcattgact  17280
tgaagcttct tccactggct tcagttctag agatctgctg ctttttcctt catagcttag  17340
tcttgagtaa gcccagttct gtacagttct tcacctggta aatctgaaca tgatttgatt  17400
ggtttggtaa gcagctctct ttgctcatct aaacacattg ggcatttgat catgtttgat  17460
tttgaacttt atgaagaagt tctgctatga tgaagcccgc tcgctgtttg cactatttta  17520
gattttctta gtgttgcttt tctgtgcctt gagaacataa atgcctgggt ttgatcatgc  17580
cagcttacgt tgtatgagca cagttacagc atctttaaat aataaacaaa atgttttaag  17640
tcagccacag tgacaagata atcatttact accttaaatg gtgaatttaa atttcatttt  17700
gtatgtattg gtgttttgcc tgcgtgtgtg tctatgcacc acatgtgtgc agtgcccatg  17760
gaggacagaa gaggccggta gatccccagg aactgctgta agagatggtt gtgagtcacc  17820
atgtgggtgc tggggattta acctggattc tctagaaggc agccagtgct cctaactact  17880
agtccaactt tccaacacca gtagcttttt ttaaatacag ttttttttcta tttgcacttt  17940
gacataggga tggaactgat gtcattctat ggtggagtga ctacagaagc tcatttgagt  18000
agttgctgtg actggtggtg tacagagcat cagggaatga tgaaggcact tgtgatctgt  18060
cacagtcatg aggtcttagt atgctgtaga tgatgtgtaa aatgtgctca tctcgctgta  18120
aaaggtgttt atggatatgg acattggact gtctcagaac tgtcatgtta taaaatactc  18180
tgagttttgt tttattcttg gaccattgga aaccggggag tggggtggca caccggcatg  18240
ccagaggcag gtaggtttga gatgagcctg gatgagcagc tatcaaaata accacaggga  18300
aaaggaaaca acctatagtt ctgctcactc caaagctgtt gaaagaataa aaataataac  18360
agcactatgt tggttacagt tgcccataga ttattttata atgctgaaat ttttttaatt  18420
gatttatttt cactttatgt catttgtgtt ttgtttacac atgtgtctgt gtatgtgttg  18480
gattacctgg aactggagtt acaggtaact gtgagcctgc tgtgtgggtg ctggggactg  18540
aacctgcggc ctctggaaga gcagccagta ctgccaactg ttgagccatc tccagccctc  18600
cctccctccc tccatgttga gttgtgttgt ttgtttgttt gagataggggt tcctctgtgt  18660
agccatgggt ctcctagaat tttctctgta gaccaggctg acctcagact caagagaccc  18720
acctgcctgt acctcctgat ggctgtgatg aaaggtgtat gtcactaagc ccaacaattc  18780
tgaaattgtg taatgtagcc cttggcatac cctttaggtg tgagtacata gataatgtct  18840
gcccgttttt aaagtgtaaa gacaagggta gacctcagag tacagtactc gattgtcttg  18900
gtagcccgag gagacgtgac gtgctggggt ctggatgctg agactgcggg ggaagaaggg  18960
tgagcattcg ctgtaagatg aaggacctgc ttccacattc cggcttgcgc tttcctttca  19020
ggtatcatca gagagtctta tatattgaca tagacatcca ccatggtgat ggtgttgagg  19080
aagcttttta tacaacagat cgcgtgatga ccgtctcatt ccataaatat ggggaatact  19140
ttcctggaac aggagacttg agggtaagac tgagttctgt cagaataaat ataagaagag  19200
cataggaggt tgctaatttc tggaagagcc atgttgtctt agtcattttg tttgtgtatt  19260
tgtgatggga cctcggcatc tggtgtgtat ggttttttttt gtttgtttcc ggagatgtgg  19320
cctcacctta gttgagcagt tgttgggatc attgcttact gttaggattt gtcacatgtg  19380
gacccactga atgctgcttg ttgttcagct gtgattactt tgaatatgta gaaacgaggg  19440
atcagaagtg gtctcaactc agttaggtgt aagtgctgat cctaaaaagt ttgctgtcct  19500
ctccaggttg cataggttgt cttgggtagc aggggtgggg tcacaatggg aatggacagt  19560
gttctatagg tgtggggtac agattatcac actgtcttgt ggtaggttgg gagaggtcag  19620
gcagtgtctt tatctgagat cacaggcata gagtcccagg gtgtcttatt aggtggtgtt  19680
gaagactgat tttgggctcc ctacctgggg ttgtgttctc aggactccat gttgccccag  19740
agtggcgcag tggatgtaga agctctgagg atccctccct acctatgggt ctgggtcaca  19800
gggctcctca ctttgagaat ggtggataag tgggctctac ttttacatct tgtaaaattg  19860
tttcatgcct caaactgagg tttgtaagaa ctttttagtt tattttgtgt ggtggggagg  19920
agcacatgtg tgccctgtta catgtgcagg agtcctcctg ccatgggtgg atcctgggga  19980
tcaaaccgtg gggatctcac ttgttgggct ttatctaccc aggtatttcg ccagcccaaa  20040
ctacagtgct tgtgtgttat ctaaaaactg ccttagagct taaaacgtac ttctacaacc  20100
tagaataccc aagacacaat ttacaaaact catgaaactc aagaagaagg aagaccaaag  20160
tgtggacact ttgttccttc ttagaagggg gaataaaata cccacggaaa gagtttcaga  20220
```

-continued

```
gacaaaattc agagcaaaga ctgaaggcat ggccatccag agactgcccc acctggggat  20280
ccattccata aacaaccacc atacccagac attattacat ataccaacaa gattttgctg  20340
acaggaccct gatatagctg tctcctgtga ggctatgcca gtccctggca aatacagaag  20400
tggatgctca cagtcatcta taggatggaa cacagggccc ccaatggagg agctagagaa  20460
agcacccaag gagctgaagg ggtctgcaac tctataggag gaacaacaat atgaactaac  20520
cagtaccccc agagctcgtg tctctagctg catatgtagc agaagaaggc ctagtcggcc  20580
atcactggga ggagaggccc ttggtcttgg gaagattata tgccccagta caggggaatg  20640
ccagtgacag gaagcaggaa atgggagtgg gtgggtaggg aagcagaggg agggggaggg  20700
atataaggaa tttttggaga ggaaactagg aaaggggata gcatttgaaa tgtaaatgaa  20760
gaaaacattt aattttttca gaattgtgtg ttacttggtc ttttaatcat tttaaaatat  20820
gtcagacttt ttgttatgaa atagtcttct aagatctact tttgtgtttt aggatattgg  20880
tgctggaaag ggaaaatact atgctgtcaa ttttcccatg agagatggta tagatgatga  20940
atcatatgga caaatttttta agcctgtaag tactgctttc agaaataaaa tgggagttgt  21000
aaatatcctt agatactaat gtgtcttatt ctgtggctag atcatctcaa aagtgatgga  21060
gatgtaccag cctagcgcgg tggtgctgca gtgtggcgca gactccctgt ctggggacag  21120
gcttggttgt ttcaatctaa ctgtcaaagg taagcagttc acgttccccc tggtgtggtg  21180
tttctcctcc ccaagaactt cccataaaag ttttcattgc tgagggctgg agagatggtt  21240
aagaacacat gttccttttg tagaagactt gggttggatc ccagctccta catgttggct  21300
caaaatctag cactctcttc tgatttgcat gcatgtggta cgcaccatac atgtttaaaa  21360
acatattttt aatttctcat tgttaccttt tgcttgccaa ctcgatgcca aactctatat  21420
ttgaattttt agtggatttt tatttgttgt tgttgtttgt ttttgttatg tggctgacta  21480
gttaatttag ttccccaagt cttacatgtt atcatattta tgtttatgta tttatccatg  21540
agtagtttgt tgccatgtca gcgccagcag tttttaatca gttttttcag aagacctgta  21600
ccttgttgtc tgattcagtt gctgttacag agtatgagga tttagcttgg cgcactttat  21660
tctatcatgg ttactctctt ccttacccaa ccctaagaac ttcggtcgct gtggctagtg  21720
ctcagcagca gtggttttta gcttagcagt cttctctact ggcaagactc actttttttt  21780
cttctggatt tttttgtttg cttagtttcc atattcctta ttactaaact atgaatttct  21840
aatgtattct gctcagctat ctcaggtgct ctgtcactga gctcctcctg ttcggactta  21900
gtgtcctcat gggtttaatg ggacagagag ctctctgctt ctgctttatt atgtctcctg  21960
atcagtgggc actgtatcta acttgctggt ggaacacata agtgtcttca tgaggaaaga  22020
agcccaagtg taaatgtgta aggtggtgtt gaaattctca agtccttacg aagagccgaa  22080
gtccacatgc tgaatacaag tctcatattg ctgttatggg atgaacttcg agggtttcag  22140
aatgaagcaa agttgcatgt ggcagcgcat gcttttagac tcagcattag aacagcagag  22200
atgggtccag gccagctaag gctttatata tagtaaaacc ttgtctcata aagaaaaaga  22260
taaataaaat aaatcttttt aataaagtta atgtttggat tagaaatgac ttagcatgca  22320
cattgcatgt tttactttag actttctgtg tgaactttga ggtagtaagt aacatcttgc  22380
tttgagttct cttacagaac ttttaagata attaaatata gatgttaaga acttctcatg  22440
attgtactct gcagaccagc ctcagcactg tggcatgctc tggtactctc cttcgtatct  22500
agttgggtca tacaaaatta gttggccact ctcctggagg tcagcattca gttaacagca  22560
ctttcatgtg ggccatagaa tgttcataga tatctcgtgt ttccgagcag ataagactta  22620
accggaagtc atcagccacc aggtagttcc tttcttttta ggagctatat actgttagtg  22680
ttctcttttg taactgaaag tttataatgc ttgtatttaa aagtagtagc tttcattata  22740
aactgcattt gactctttat agtacatctg cattgtgttt caacaggtag aagttcattt  22800
gtgaatttgc aattccattt tcagacttag aatacactgc tgcgactggc ttcaactaca  22860
ttgtctcagg cctagtgaag ccaagcagcc agctgctgtc caccttgcct ccttaattat  22920
ttcttcttgt ggtgttcttt tccgtgcttc ctcttacggg ttatagcctt cattgtataa  22980
aaccccttttg tagtaatttt tcctgctgtt gggtggtaga atgctggtct tgtctgggct  23040
ctttcattgt actctgaagt taacttctgt ccttaaaaat gtccaagaga cactgttgta  23100
gtagaagatg cctggttgat aatgtacatg aagaaaacag agaaggcact ataaactctc  23160
actaggtaat gaggattttt ttttcttttg tggcattttc tttttttcca aatattttaa  23220
gctttgttat agaaaagtta caaaaacaaa caacaaaaat aaaatcacac actgaaatta  23280
accagaccca aagattcaat gacttttgtg cttagagcag ccagcgtctc aataccaggt  23340
gaaagcccac tgcaaaagga aatgactttg ttttttaaaa aaaaaaaaaa tcttttttttt  23400
aataaggcta aaatccatga atctctgctg tcatcattga gggactttct ttctttaatg  23460
gttgaattat gtgcctgaat ggcaccagaa gttactggaa acttgtaact tgttcctgtg  23520
tgaggcttgt aatctgtttt gttttttttt tgtttttttt tttttttttt ttggtttttc  23580
gagaaagggt ttttctgtgt agccccggct gtcctggaac tcactctgta gaccaggctg  23640
gcctcgcact cagagatccg cctgcctctg ctgggtgctg ggattaaagg cggaggtttg  23700
taatcttaaa taaattaaga aaattatcca caataccagc aataaggata ctctgtggtc  23760
aaactttttg gtattgcttt tcgaaattaa gccacacatg tctgtgcggg agaaacaaaa  23820
tttagcattt gtttattgtg ttctctccct tatgtgatct ctcatgaacg tcttctatgg  23880
tagtaaaata catgtgtgcg tattttaaca cttagtacaa gttattagtt ggatatacac  23940
ccccccaggc cccccaccct cgtcatcatc ccctgtcatt gttcctccct gcccccccca  24000
cccctacccc cccccccccca ccttgtgttg aggtgcctgc cttgtagtca tgctgtatag  24060
actggcctcc caattctgat ccacgtacct tagcctccca agagctggga ttgctggtat  24120
gtgccactct gcctggctgt ctacagacat tttttggttg agtaaaattg tttgtattta  24180
tccttttttaa ggtcctattt taaattgcta aagaatacat atttcattgt tacccaaatc  24240
ttctttgtct aaggtcatgc taaatgtgta gaagtagtga aaacttttaa cttgccattg  24300
ctgatgctcg gtggaggagg ctacacaatc cggaatgttg cccgatgttg gacatatgag  24360
actgcagttg cccttgattg tgaaattccc aatggtaggt gttcaggttg cagtatctag  24420
aagaacatct gctatgtaca aatggatgca tgggagagtc tactgccaca cccctgaaat  24480
gtgtgatctc ttctgatgga tgagtggtta gattgcaaat ctgtgtgaga gcattccatg  24540
tgcactttca agctttcctt tgggaatagt tcttttatct ggattcggat tatgtttctg  24600
agattatacg gaagctaagc ttttaatgtg taacttgttt tttcattgtt tttaatagag  24660
ttgccatata atgattactt tgagtatttt ggaccagact tcaaactgca tattagtcct  24720
tcaaacatga caaaccagaa cactccagaa tatatggaaa agataaagta agaaatcact  24780
tcggcttaat gaaacttcag gaggctatag aaggtcaaat aaaggaagtt ggtttagcat  24840
atacatcaga tacttcctaa ccttaggcta ttcctgtttt ttaatctctt atattaatac  24900
aaatatgtaa cctttgtaaa tagaaacatt cttattagat caaatgcttt atgtctacag  24960
```

-continued

```
aatgtagaaa cattgatcag aacgggctgt gtcctctctc ccatagacca gttgtatgac  25020
atttataagt acacctcatt gtcaaataga ggtgaaaagg tacatgtttg tgtgctgtgg  25080
gttcagtcag ctaatatatg cagtgatctg atgcttagat agtgtcccat tcagtggtta  25140
gtaaatgaaa gctcgttctt gtttagttcc tcctgtgtat aacagaaact ttacatacag  25200
tggattttgt ctaataaatt gtgtcattta gacagcgttt atttgaaaat ctacgtatgt  25260
taccacatgc acctggtgtt caaatgcaag ctattccaga ggatgctgtt catgaagaca  25320
gtggagatga ggatggagaa gacccggaca aaagaatttc cagtaagaaa acccttgcta  25380
tgtcttcttg catttttctt atgtgtcaaa ataagactta aaattgaagg tacacaggga  25440
atggttcaca gcacatgttg tgattttcct tctctccatt ttaattacat atagatttag  25500
ctccctgatg tctcaaagcc tgaattaata tcaccagttt cattttgtgt gactacacag  25560
acatggctgt gtccagaaag taggcacttg atatatctat ctatctatct gtcttaccta  25620
tgcaatgatt gtagaacctg tggctattat caaatttata aaatcttttg tgtatcagtt  25680
cgagcatcag acaaacggat agcttgcgat gaagagtttt cagattctga ggatgaaggt  25740
gaaggaggtc gtaggaatgt tgctgatcat aagaaaggag caaagaaggc taggattgaa  25800
gaagacaaga aggagacaga ggacaagaag acaggtcggt ttatgttttg gtgaccattt  25860
cactttccct acttaagggt tgcactgtgt ctcttagcga tcctgcagtc acacgtctca  25920
ctttaggcag gtaactttc ctggtgtaag agatagttag ttaccgctca tgcttactgt  25980
ttagtgcttc agagctgact taaaggtttt acagttgtgc tcaaattttc tttgtggtat  26040
agaaaccttc cttttaataa catagtagta aacgttacat gtcatgggat ggggttaagg  26100
ggatgacagt agttacagat gttgggcctc agaacattta ctgtagctta ggtggactta  26160
gactcagtgc tcttctgcct tgtcctctta tatactggga ttgaaggcat gccagtacac  26220
ctggctaaaa ttctaaataa tttatactgg ttaaagctga cttcatgtag caaaagttaa  26280
gctacatagt cctttgaaaa gttactttaa gagtgaagac tctttaggaa ctgaagaaac  26340
taaaactgag gaaagatagg aaggggcagt ttctggtgtc ttccggtatt tcattcagag  26400
tgtttattta gcatgccatt acagcacctc gttagcactc tcaggtttct cattgctatg  26460
ctgaactgtg caggggtaag gagtgggcag tagcctcttt aaacatgata atgctgcaag  26520
ttttagttga cctactagtc aagtgaggct gcctggcttt actaggcctc actatataga  26580
catggctgct ccggctactt actgggtggc cttggattca caccattgtc ctttctcaga  26640
tgcctgggtg ctgggattac agaaatgtgc caccacctcc aactcagttt ctttctattt  26700
taaaatatct tctgcatttt cttttttttt tccaaatagg aaagtgataa agtaaattga  26760
ctcttggtat tttagacaaa ataccacaat aatctatggg tcataacctc aaataagacc  26820
caccaccacc ccctcttggc actgagtaaa aatttagcca gaattatcca agacactaaa  26880
atgtgaaatc tccattgtcg gcatgtagat ttgtatggga ggtgacagca gtgccctgca  26940
gtgtctgcat tgcccaagcg tgctgctgtc cctgcacctc tccatgaggc cattgcttca  27000
taactaattt acacagagaa aatactctgg ctaatctggg acatttactt taattactgt  27060
atttaagtta tgaagttcag tttagtagta attaaaaatt taaggttaga acaatgggat  27120
attgtgggcc agcaaggtaa aggtgcttgc tgccaagcct gattacatat gatctgcatg  27180
ttggaggaag actcctgact tctacaagct gtcttttgac ctccctatgg aagtcatggt  27240
gtggatgccc aaacatacac acacactctg aataaataaa tgttaaaaac aaaaaacata  27300
atctagcctc ttgcctttag gatcacgtcc ttcttacagt gcagacacag ttctcttgag  27360
ctccttctgt cttaccactg cttccgtgcc tcagtccttt tacagtttc cctggaagat  27420
acccttcct cttacctgag agtttgttca ttctttggga cccacattct agagaactgt  27480
gtctgcactg taagaaggaa gtgatcctaa aggcaagaag ctaaattatt tttttgtttt  27540
taacatttat tatatataca ctatatacat acatatatat attgtgtgtc ttatatttca  27600
aaatagacat caatattttt cttctgtctt tagatgttaa ggaagaagac aaatccaagg  27660
acaatagtgg tgagaaaaca gaccccaaag ggtgagcgat gcttgtgtct gtagacgtca  27720
tgcatgtctt gggggttggg cgggggcatg catacttgag aaatactggc acagcctgag  27780
aacatacaat gagtgcaggt ctgcgtgtgg gtaacgtgct taggctattt gaccggtaac  27840
ttttatgtat gcaatcgtgt ttttcatgat gctcatatta ctgtgcttag aatactttga  27900
tgttaggaga caggctagtt taaggaaaaa acattgggct aagtgaaagc ctattggaga  27960
attttgttat cagaatgcat gtatggctag gtaggtgaag tgttgcggta aatctccaac  28020
ccaaatatgc cctggcaatg aaacacaact caattaatat gaatacatgc tgtgtgccta  28080
gaatgggcag atctaccgct acactaccat cgtcaacaac tgtgagagcc cttagaactt  28140
gcagtttctc caggccacgt gcttctgctc cacttttctt cttccccctc ctctgcatcc  28200
tcaccctccc ctattttctc ctctctctcc ccaccttctt ctccaccttc cctttatctg  28260
cccaatcatc agctctcctt tattttacaa attaggtggg aagcaggttt atgggaagta  28320
aacctgagtg ctgactcatt gcttgtttgt aggccctcac tggagaagga agtagcatca  28380
aatataataa gtaagcccca gggctatcca cacctgtgaa gaggcttgag tctataatct  28440
cagtccactg gagaggctga gcccagagga ttgccatgaa tttaaatcca cactaagcta  28500
catagtgatt tttaaatcgt cactctgggc tgaagaatga gagtctgtgt tagaagcaag  28560
cacgtgtgct tggtcaccca gttgtttgct aattttgaag gataacttag aatgctcagt  28620
tgtaaaacaa ctggaaagat taaggctttt attgctcaga aaaaaaagaa aaaacaacaa  28680
caacaacaac agtgaatagc ttggtgtgaa tctataagac tgtgcaagta gccaggtcag  28740
tgctcctaaa ccaagactat tacttttaat atttcatgat cctctttcaa cagagccaag  28800
tcagaacaac tcagcaaccc ttgaatttga ctctccaact ttaggaacct cgaaaagtga  28860
gacgattctg ggataagaaa ccttccctgt ttgaggacat tggcttcatt ttatactgtt  28920
ttggcatgga ctgtatttat tttcaaaatg gcttgttttt gtttttcttg gcaagtttta  28980
ttgtgagttt ttctaattat gaagcaaatt tttttttcca ccatgcttta tgtgattgta  29040
tttaaattga tgtgttatta tgtcaaaagc cggatctatt aaagaaacaa ttggcctttc  29100
tgagctgatt tttccatctt ttgtaattat ctttattaaa aaattgtact tggatcgttt  29160
tctgtctgtt tattatgaaa gcttgtttcc aagtcaatga cttgatggtc ttaagactgg  29220
aacataccaa aaggaatgtc agtgtcagag accatcacta gatctacaca gtgcttactg  29280
gctctaacag ctatttctta cttcaggaaa aataacagtg tcactttgtg tcaggaagac  29340
tggtatttca taaattattt ccaaattcat aatctgtgca cttgggatga agcaattatt  29400
tttgaactga atcaaatact cagaaattgg aaattgtgaa ttgaaaaaag aaacctgtcc  29460
aaccaataac tggcccaact taagacccat cccatgagcc agcaccagtc cctgacactt  29520
aatgatactc tgttatactt gcagaccgga gcctagtgtg gctgtcctct gagaggctcc  29580
acccagcagc tgactaggac agatgcagat acccacagcc aaacagtgga tggagcttgg  29640
ggacttttat ggaataggag gaaggatttc aggcctccaa ggagatagga actctacagg  29700
```

-continued

```
aagaccaact gagtcaacta gcctggacct ttgtggctct cagagactga accactaacc  29760
aaagagcata cacgggctgg acctaggtct acccacatag atgtagcaga tgtgcagctt  29820
ggtatttgtg tgagtcccag acaactggag aggaggctat gccaaaagca gttgcctgtc  29880
tggatcttcc agcttggcta ccttgtctgg cctcaatggg aaaggatgtg cctagcctca  29940
gacttgatgt gtcagggcat gtatacaaaa gattgtaggc ggtagaaaca taccctttttg  30000
tgatgtcagt gtaaaatgaa ccagctagca aaacctggtt cttgccctgt agtttgatca  30060
caaccagggt ttctactcaa gaagtaaaac ttaatatgct ttggcattcc gcattcattg  30120
agtgtctact caccttttgg taataactgc agctgaatag aattttaagt gctttcacct  30180
aaacttagat tgttattgta gaaagcccac aaatggagtt tcctctccca gtgtgtacaa  30240
cagaaaaatg ttttaggaat ttgccaaagt tggtgaaacc atcctacttg ctagaatcag  30300
gttgctgatt ttgagattag gagaacagag tggtagaaag gaggcagtcg tggagaatgt  30360
tcttacattg tcctgaggtt cgaaggtttc atgttcatgg gttttcccct tttgctatgt  30420
atttgccagg agtccatatc ctttatgact aaggaagcag gatcccttcg ctgcagagac  30480
ttatttagtg tgtaattttc atgaaacaaa gtgtatcctt tggatacttc atctggtatt  30540
gtgatctgcc ttctggcaca tgtcgcataa taattacagt gtgttaagtt ctggtctatg  30600
aatctactag aatgatgtcc cagatgccac agtgattctc cttggttgga tctgggaggt  30660
tctggtttca tagtttaagg ctgtgaaact aagcagtttc agaacaggtg atttgggacg  30720
gtaaaaatac acagatacca gtaatttgta aagtcaaact acagcccaca ttgtttggaa  30780
gaacaaaggc tccttttgca tagcagtaat cacaatttct acaaatgtgt aaaactgatt  30840
ctatgcataa tgaataagat gagtgttaat aatagcctgt cgggacaagg gttgaaaatc  30900
aaaacaatga ggaaataaca agaaccaggt ggagggaggc gaagttcatt tttctgtcac  30960
aagagtgaga tttataaata gaaaagacaa caaaacagaa cctggtaaaa gccatgggaa  31020
tttttcaaaa gtgaaggcca aagcttgaca ccgaacccca cataagttac atacttaaca  31080
gaagttctct agaccagcaa aaacaagtaa aataagatag ggaaccccgg cagtggtggc  31140
gcactccttt aatcccagca cttgggaggc agaggcaggt ggattcctga gtctacagag  31200
tgagttccag gacagcctgg actgcacaga gaaaccctgt ctcggaaaac ccaaaaaaaa  31260
aaaaaaaaaa aaaagatatg ggaaccataa tggacttgtt ccacctcaaa gaactttatt  31320
tctttatttt aaaaataaag ggtctttgtt tttggccagg ggtagagaga aaattcagtg  31380
gttaggagta tttgctgctc ttacacaggg tccaggtttg attccaacca catgctcaca  31440
gccatctgag gatctgacac ccctttcttt gagtaccagg tatacatgta taaaacaccc  31500
atacatgtta actaaaaata gcttaaaaat ttgacaagag ttcaatgaaa cccatgaatg  31560
tagtatcttg ttaggaagac acaatgtcca aggtaattct tataaaggaa aacatttaat  31620
tgaggctggc tttccatcgc ataggttcag tccattatcg tgatgggaag catggcttgc  31680
agatagacat ggtcttgatc agcagggaac aggaggagac tgttccacac tcggccgaac  31740
ttgagcatag gagacctcaa agcctgcccc cacagtgaca cacttcctct aacaaagcca  31800
tacctacaac aagaccacta atagtgccac tacctatggg ccaaacattt aaacacatgt  31860
ctaggggtgg gggttagtac ctattcaaac cactacattc caccttctgg gccccatagt  31920
cttgtacctt taccataatg caaaatgaat ttaatttcaa aagtccacat agtttagcac  31980
agtttcagca gtgtttaagt ccaaagtctc ttctgagatt catgcactct tttttattag  32040
atattttctt catttacatt tcaaatgcta ttctgaaagt acccaatacc ctcccccccc  32100
aactcccccc cccccccgcc ctgctcccca acccactcac ttctgcttcc tggccctggc  32160
attaccctgt actggggcat ataatctttg taagaccaag ggcctctcct cccaattatg  32220
gccgactagg ccatcctctg ctacacattc atgtactctc ttaactttaa ttccttataa  32280
aatcaaaacc aaatcacatg cttccaacat acagtggcac aggagataca ttaccactac  32340
aaaacaggga ggggaacatg atgcggaaat aattaaccaa agcaagactg aaaaccagct  32400
gagtaaactc caaactctgt atctcgatgt ctgacgtcaa aatgctctac agatctccaa  32460
ctcctttcag ctttattaac tgcaaggcgt ttcttttcct ggtctagttc cgttccctgt  32520
tagcagcttt ccttgacagg tatcctatgg ctcagatatc tctagatttt tggggtctac  32580
agggcaatcc aggcttcacc ttcacagctt cacagagtgg cctctctggg cctccatgaa  32640
gagacacccc tgacacattc ccagtctcaa cagctttcct taattgtaga gggaaattcc  32700
aatatccttt tcttctatcc ttgattctaa tgccagaacc caatggtcaa atctgtcaag  32760
ttctgctgct gctggtttga gctggaatat gccccccccc cccccctgttc aattacaagt  32820
tcaacagctt tctgttttcc atggtttctt tcactgccta agcttagctg acatggaact  32880
tggtctatag accagctggc cttgaactca gagatcacat gcctctgtct cctaaatgct  32940
gggattaaag ggtgtgtaca tgcctggacc taagcttttc tttaattcca ttttacaagg  33000
tggaagatta gctgggtggg atcttgccgc aagatcacca ctcacttaat tccactaaat  33060
atctttaatc tgtttatctc cttgaacaaa gagttgggct ttgttccact tcctggttcc  33120
cctttaaccc ttgaaccata cgatttctat ttttcctttc taagcttgat gaaaacactc  33180
cttacaagag tggatcacaa cacaaagtct aaattaggct tttctgagat ttcttttgcc  33240
agtgcaagga aagtaatcta aatctcttga acttagcctc aggcagactc tttggacaga  33300
gggcaaaaaa cacccacatt tgtcaccaaa atatcacaag tacaatctct aggcaacata  33360
ctaaaattct cctctgaaac ctcaatcttg agccaggcct tcacagttca aagaatgctc  33420
agagccatgt tcttactact gtggcccatt aagcagcttt taaagcattc tactgctttc  33480
ctaatacaga gtccccaaat ccacgtccct gcaaagggtc agtcttatca cagcagtacc  33540
ctagtccctg gtaccaactt cttagttagg gtatcattgc tatgaagaga caccatgacc  33600
aaagcaactc ttataaagga aaacatttaa ttggggctgg cttacagtgt cagaggttca  33660
gtccattatc atcattatgt gtaggcagac atggtactgg aggacctgag agttctacat  33720
cttgatctat aggcagcaga atgagacttt cacactagca tatcttgagt ttaggagacc  33780
tcaaaacctg cccccacagt gacacacttc ctccaacaag gctatactta ctccatcaag  33840
gccagacctc ttaatagtgc agctcttcat gggctaagca ttcaaacaca aatgtcttac  33900
acagagtcat tacctacaca aaccaccaca gatagattaa aataatctct tgtacttaat  33960
tttacattgt taagattact aaaaggattc agcacttcat t                       34001
```

SEQ ID NO: 45 moltype = DNA length = 16
FEATURE Location/Qualifiers
source 1..16
mol_type = other DNA
organism = synthetic construct
modified_base 5

```
                        mod_base = OTHER
                        note = uracil
SEQUENCE: 45
accctcaagt ctcctg                                                16

SEQ ID NO: 46           moltype = DNA  length = 16
FEATURE                 Location/Qualifiers
source                  1..16
                        mol_type = other DNA
                        organism = synthetic construct
SEQUENCE: 46
accctcaagt ctcctg                                                16

SEQ ID NO: 47           moltype = DNA  length = 89000
FEATURE                 Location/Qualifiers
source                  1..89000
                        mol_type = genomic DNA
                        organism = Mus musculus
SEQUENCE: 47
attccttttc ttcctttgtt ttttttgttt tgttttgttt ttgtttttaa agatcagggt  60
ctccctctgt catcttcttg ctcacagctt cggtgcgacc cctgtaccac ctcctgtcag  120
ctgctttcca gagtgtacat tcctgctgcc tccttactgg gcttattcaa gcacatgtgt  180
gcccagaagc attaaattat tactgattta ataattatta ttattaattg ttccacccgg  240
gcaattggcg gcatggccaa aatcctatgt tcaagagact gggggaagag gactgggagt  300
tgcaggcccg cctgggatac acagtaaggg tcgtcctatg ctagacagac tgtgtctcag  360
gtaaacacag ccctcctaaa aggaaacaaa tacagaacaa atgctgggac ctggccatga  420
aaagaagctc tgagttcttg atacactggg tgtggtggct cctgcctgta agagttagag  480
gcagaaggat tgaagtttaa gaccatcctt ggctacacag ccttgagtca aggctctgtg  540
aaatgaggct ctgtcaaagg taaacaccac catcttcccc cttcccccaa atgtgcttcc  600
agaacctcca gttttgcctg caaagtagtg tattctccca tcttgcgtta gggagtgaat  660
ctccacattg cacttggcag ttaaaaggat gtaggatgtg gtaaagctga agtaacatgg  720
aaacagctgc aatactggct tctgccttac aatggcttgg gtggtgggtg gatggggcac  780
ctggagagat ggtggcctag atccccagga ccctcataaa aagtcaagca tggtggtgag  840
cgtgtgcagt tccggctgct ggctaacctt ctcagctgaa ctgaccagct cttggctgag  900
aaatcctgtt tcaaaaacta agagaagtga caaggcctaa tgtcaagctg tgacctccgt  960
atgcacatgc acagggcagc ataccacagc cacacaaatg agaaaaaatg gaggctggag  1020
gagtggttta gagtgctgct gttggagggg actatagttt ggttctcagc acccataatc  1080
agatgactga caactgctct taacttccac ttcaaggaat tccatgtcct cttctcatct  1140
catgtgccta tatcacaccc aacataaaca cataattaaa ataaaggggc tggagtcgtg  1200
gtggtttagc agtttagagc acttgttgct cctgtagagg aggtgggttc agttctgagc  1260
acccatatag cagcttgtaa ctgtacctcc agttctgaga ggatctgatg ccctcttttg  1320
gttttcttgg tcctgcatga ctctggtgaa caaaatattc ctgcaagacc aaacaccatg  1380
catgcaaaag aaaagtttgg ggttagagag acagctcagt ggttaagaac agttgttgtt  1440
cccagcaccc acacatttaa aatctcatat aaaaccatcc agaactccag ttctagggaa  1500
tctgatcctt cctgacttct gtgggcaccg ggcacagatc tggtgcgcat aaaaataaaa  1560
taaatcttta aaacttttta actgttattt tatgtaaatt aaaaaaaattg tacatggatt  1620
ttttttttt ttgcctgcat gtcggtatgt gcattatgtc tgtgtctgtt tctagtggag  1680
gccagacgag ggtgtcagat tcctggaact ggaatcactg atggttgtgt gagttgtcat  1740
gcaggtgctg ggaaccaaat ttgagtcggc tcccaaggca gcaagtactg agccattggt  1800
ctaggagaaa aaaaaaatta aagtaaaaat aaacctacag ttgtagccat ccgcaaaaca  1860
cttgcttggc ttaatggaac tgtagacttg accctctgta acgtacagaa ataagcacga  1920
gagggtgaga acgcctttat gaggcagaag tgtcgactca tctttcactg gcactgggat  1980
tcttccagag ttgggatctg cgatgctttc tgctttgttt tgttttttttg tttttttgtt  2040
ttagtttttt tgttttgttt tgttttgttt tgtttttcga gacagtgttt ctctgtatag  2100
ccctggctgt catggaactc actctgtaga ccaggctggc cttgaactca gaaatctgcc  2160
tgcctctgcc tcccgagtac tggggattaaa ggcacgcgac accacgcccg actgcgatgc  2220
tttctaaaat atgggtttc actacagcct aagaattcag gtgtaacagc cactgaacct  2280
taccacggtg tgcttccctg agcactgtgg cctttgcttt aaaaagaata tcacaaagtg  2340
atagcaaatg ccaggaagtt ggaagaactt ttatgacaca gttgtcagtg aggattggga  2400
aggtagtagc gtgtatccta gcaggaggga ggctgagaca ggaggaacat caagagtctg  2460
tagccagcat acaaaactat agaaactata gaaaaagatt gcggctctct ttcctcttac  2520
tggttggagt agagaagtga tatttatatc agccaatgag aaatttttac ggaattaact  2580
agtgtcaagt gacaatccag tgttgaagaa tggatccctt acacccttgg caggttgacg  2640
tttctgcgac caataagcca acccgaatca acctagtgag ctgaggcctc agtgtctttt  2700
ccagagaccc cgccttcccg gtctgacaac ccggtttgac ttctattggc tttcacttaa  2760
gagtgacagt tttattaccc agtgaatttg tgagattagc ccttcctcgt gcctttttta  2820
ttggctcacg ttcttgagtg gcagtgcttt gaaccaattg gatatagcag tagggttgcg  2880
gactccgccc cggaggccgg gagggttgtt cgctcgggtc gggtgtcgcc tgagaaccgg  2940
atgaggcggc gactctgagg ccgagccggg agcgggcgtc gcggcgaagg ggagaccggg  3000
cgggccggca gagcagagca ggaggaagca acggccacag acacatcgga accgagagtc  3060
ttagtcgggg gatccgcgcg gcggaggcgg acaccatggg caaccgcggg atggaagagc  3120
tcatcccgct ggttaacaag ctgcaggacg ccttcagctc catcggtcag agctgccacc  3180
tggacctgcc gcagatcgcc gtggtgggcg gccagagcgc cggcaaaagt tcggtgctcg  3240
agaacttcgt gggccggtga gcgagcgcgc cggcggcggt tctggggctc cggccgggag  3300
ggcgggcggc ggcctagggc gcggagggcg ggcggggaat ggcggaactg cggctcgcgg  3360
acgccgcagc accggtggca gtggataagg tctggggcaa gagtctccat ggctttccgc  3420
agggactgga gatgcagatc caagtctggg actagtcgat gatagtgggc ggtgtttggg  3480
gcaagacggt cagtgccgac ccctcttggt gcttctagtt ccggctatgg ctgggcaact  3540
ctgacatcgc tttacctgta gtccgggata gatccactcc tctttccttc tgctacctgg  3600
```

-continued

```
aaatcttagt gtgtgtgcta agatgttgaa gataacactt gccacttagc catccatggg  3660
gaatgacccc tggggtctgt ctggccagtt attttctgga gcctgctctc ttgcctggtt  3720
agctggttat ctgttctaga caggcttcct accggcacca tttggttgtc ccatctgtcc  3780
aaactcactc tgaagtccac cgttgtctgg ctagccatct aaggtgacct ctcgtgtgca  3840
aatgcccatc tgtgcccctt atttacgtga gttggcctct gccatctgac tggctgaact  3900
ttgggagcct cctgttatct ggttctcttg ggccgactgg ctctttgaat ccatccatta  3960
gtctgttctc cattcccacc caggcatccc tgcctgtcca tcctctctga gtgacagagg  4020
ttggagaact tgggaagaaa cattctttag gattctttct tgggctagga tcccctaacc  4080
tagagcttcc cagttggaat gctctctaga tagctctggg agcctcagct tgttccatct  4140
gtccagtggg caaattccac ttgcagctgt ttgtaggatc caggaagtga gtgaaggagg  4200
gatgttgatt tactcctgtc ccctccccct ctgcctctcc ccgcagcagc acttctccat  4260
tccaggaagt gttccatgta tgatgctgca gtgtgtgcct acccagtgtt aacatttgct  4320
ttgctgtgga cattatcatt gtgtgtgtgt gtgtgtgtgt gtgtgtgtgt ccaagtgtgt  4380
gccagagtgc atttgtggaa gtcagagggc ataatctttg tgaagtcctt caaaatttat  4440
gtggggatta aacaccgggc cgcagactta tatagcaagt cctagtatcc attgagctat  4500
gtcattgtcc ttccatctta aattgtagag acatggtctc tcactgacca tgcagctcac  4560
cgatctcatt gggtctctct ctctctctct ctctctctct ctctctctct cacacacaca  4620
cacacacaca cacacacaca caccatgcag ctaactgatc tcactcagct attctcgctg  4680
gccagtgagc tccagggatc cacctctctc tgtctcaccc tatcattggg tcacacacac  4740
acactcacac acacaccctc tgttattgtt gttaccagtc ttttgtggag gcagaacatc  4800
tctaaatttg aggctagctc actctacata gagtagagtt ctagggcagc tagggctaca  4860
tattgagacc cagtctcaaa aaaacctcaa aagttgattc aagactgcag ggactgggta  4920
cttggaagtg tacatttagg ttgaattagc tgcacctgtg atcttaggat tttgggagtc  4980
tgaggcagga gatttcttga gtttgagttc aacatgggct ccattgttag tcctgtctcc  5040
aaaaaaaaaa aaaaaagcca tgagagggct gtgtggtgac gctcgggcat ggagtacttg  5100
cctagcatga ataagaccca ggggtcagtt cccagcacca aactaataag aaatattgtt  5160
gatatttatg ttctctttga ttgcattcat actcaaaaac acctatggct tttaggtaat  5220
gaaataaaaa ttttatgtat atgtatatac acatatccct gtttgtttgt ttgtttgttc  5280
gtttatttat ctatttgttt tttggttttt ttgagacagt gtttctctga gtaacagagc  5340
ctggctgtcc tggagccacc tttataggcc aggctggcct ctaactgaga gacttgcctc  5400
tacctctcaa gtgatgagat taaaggcaag tccaccaagc ctagctattg atcaatgttt  5460
taaaaagcat ctcagaatgt agacaggctg gccttgaaca tacagggatg cacctagttc  5520
tacctcctga gtgctgggat caaaggcata cagcaccgtt cctgggtggg ggttattttg  5580
gtttttttgtt ttttaatttt aaaaaaaattt ttgtttgttt attttgaaac agtctcatac  5640
tgtagtccag gctgacctgg aacttactat agcataggtt ggcctccaga attgtagcag  5700
cagttgtccg atttcatttt ctaagtgctg gggtcacaag cacacaccac tatggcatta  5760
agttcatttt actctagaat gcataacgta cctgtgttgc aggactttgc caagaggccc  5820
actcaatccc attctttatt tcctgctatg gactttatta aacagagtca gaactatgag  5880
tctgtctgac ccttgtgctg tttctttcct ctgctgttct tgaatatcca tccaggggca  5940
tctggttgtc agccaggagc aaaggagagt gtgccaaggg cttgggccag cccagcacct  6000
agggacagct caaaatgctt cctgtcaggg ctgccttaga tttttctaag aacattagtg  6060
tacactagga cagctcagtg ggcccagccc cttgccgaga cttgcatgca gattgctagc  6120
cctggaggcc aagggcttga aatgtaacag gtttcacatg aggtccagat ttctacagag  6180
cctgaaacta ccctgaaggt tttagtaata atgaggtaga ggcctgaggc cccaagcatg  6240
ggtctaccaa agctgtgact ttagtcaagg gcattgattg ggcattctag gccccaggtt  6300
cctgagtgtg tgtctgtgca caagtgtctg aatatgagtg tgtggggtca gagggcagcc  6360
ttaatcatgg ttcctcagga gccgtcgtct ttgtgggttt gagtcacttg tagtctaggc  6420
tgactggcca gcgagcccca gggatctctc tgcctggacc attacagtgc tgtgatgaca  6480
ggcgtgcata gtgatgcctg gcgttttacc tgagcgccaa tgattgaatc ttggctgaca  6540
ttgaaatggc tatagagctg aggctaacct agaactctgg atctcctacc tttaccttct  6600
gagttctggc attgcaggag tgcaccacca tgtttgggtt tatgtagtac tggggatgga  6660
actgagaact ttgtgcatgg taggtgaggc agccagaccc caggtttctc tgctctaaga  6720
cagagctgta tgtaatctgg gcagagtggc agtggtataa tgtctgctcc cccagaagtg  6780
aaaaagtaag actgagaccc tcaccctggg gtgagctgac ttcacgggta actcactgga  6840
tcttctaacc aggactgctt ttaccatttt agaagcgtta gcatttgaaa ccagcatctg  6900
agccagccag ctttgtgagc tagctatggc tctcaggagg gcttggtttc tacctaatcg  6960
ttgctattta attgagggac tggcaaagag gctagctggg ctttttttccc ctaccccacc  7020
cccatttgga caggaaccca ggaagttggg gttccagcct ggaaagcgga ggctagactc  7080
cttcctgtga atgtattgcc tttctgaatc ggaatctcag aaggaagtgg ggttacagtt  7140
tgttccttga gtgtttgact gccttacagc gttacctggt gcatgtcact gaggccgagt  7200
cccacttgtc tatgactttc acgaaggctg gcaagatggc tcagtaggga aaggggtttg  7260
ccaccaagcc tgatgacctg ggttgatttc tgaactccaa tggtagaagc agagaagcaa  7320
tttctgtgtg atgtatgcac acggagacac aagcccaaag aggatacata aatgaaatgt  7380
tcgggaaaaa aattttttta aagaaaaaca aaaagggagc ccaatactgc agctcagttg  7440
gcaagtgctt agcatgagtg ggggttccac acccagcagc acagaaaccg ggtgcttgga  7500
aagtggaggc agaagatcag gaattcaagg tgtgcttcgc agcagagctg gttctgctag  7560
cctgggctac atgagatcct gcttccctga aaaaataaaa tagagttcca gcctcaggcc  7620
tagaacccag gactcagcta acctgggtgg gctctgttgg gaattaaata aataggtgtg  7680
tgtgtgtgta tgtgtgtgtg tgtgagtgtg tgtgagagag tgtgtgtgtg tgagtgtgtg  7740
tgtgtgagtg tgtgtgtgta agggggggg gagaaaacgt gtaatagcaa taactcttcc  7800
ataggccaag tgagtgttca ctggacagtg ttttccagtg cttagcacaa ctttgcctca  7860
tgcctagggt tatggccttg agccaaataa ccttccagca gagactagat gaagacactg  7920
gtgccgtcca atagcgctgg gaaacggaga ggggaagagg cagggagaag ttgggaaaga  7980
taccctgaag attggagaag catcccagga tgtggaaata gccagtacag gttctgagct  8040
gacagcgcac ctgagagtgt caggaagctg aactgtggag tgaggtttaa aagggatggc  8100
tgtggggctt ggcacaggcc acttctctcc tggggaggca cattccctgc ctctggctgg  8160
acgcttgggt gggctgttcc acatggtcag ttttctcttt acgcatttcg cctgttcaga  8220
ccttctccca ttttccttgg atcaggaggc acgggtggca gtgtgcacag gtacatttgg  8280
acatgtgttc atatgtgtgt gggtatcaga ggttgtgtgt ggtaggtaca gtgcatgtgg  8340
```

-continued

```
tggtcagagg acagcttgta ggagttgttc ctctcctttg tgggtcccat agagccaact  8400
caagtcatca ggcttggcag caggtgtctt tatccagtga gcatctcacc aggatagtgg  8460
tggtggtggt ggttgttgtt ttgtgttttg aaacagggtt tctctatgta accctggctg  8520
ttctggaact ctgtagatca gggtggcctt gaactcatag agaccagtct gcctctgcct  8580
cctgagtgct aggattaaag gtttaatctg ccatcactac ctggcttttc ttctgttttt  8640
aatacacaat gtttttttata cgtaccccag gctggtccca agcttgtgat cctcccccac  8700
tttcccagtg ctgcaatggc agccggttct accaccctgg actcgattga gcatttccag  8760
tgctgggtaa gagctggcca ccgaagggac gcccgttgct ctcactcttg cagttgcttg  8820
gagctgcagc tggtctaggc tgtgccaggt ttgaatacaa atgctgaaat gacaggctcc  8880
ttggttgctg ggagaaactt gggcatctgc tgaaccctaa tttacagggg aggggccaag  8940
tgctagctgt aattaggccc ttattaaagt gtcaatgttt ttggagaaaa tacagtcagt  9000
aatgagctgc tcacatggcc tctctgcaag ctgagcgaat ggaggacgtt gtcatgcctc  9060
ctgagccaga tgctacacta aggaagtctg cttccatgtg tggtagaggt ttctgggagg  9120
ccagccttaa ctttagccag aggctaggag ggcactttgc ttccgtgtag tttctcttta  9180
aggtctactt cctctctctc tctctctctc tgtgcatgct tccatgagtt tatgtgcacc  9240
acacatgtgc agtgcccttg aaggctggaa ctggagctgc agacagttgt gagctgccat  9300
gtggtcctct gcaagagcag taagtgctca tgactgccaa gtgtcttcct cacacctcct  9360
gtttcttttg agatggggcc tcatgaagcc caggctagcc tagaatttcc taagtagctg  9420
agggtgacct taaactccca gtctttcctg tgtctgtgtg ctggaattcc agatgtgtac  9480
catcattctg gtttattcct tgctgggatg gaacccaggg cttgttgcct gctaggcaac  9540
tgaaccagtc taccagctgc atcccaccca agtttttggg agatagttgc tgcttttata  9600
cttttctcag ttacagttac aggttgggaa acagactgga gagggaggtg acatttgtca  9660
tgaaagccag atttctttaa ggttgtcagg tgtgcgtctt cactgtcaag ccttagttgg  9720
gcctaatgga ccaggtgctg gagacttgac agggacccag aactaactag acagaaaaat  9780
gggtgggcag gtaactaaac aacattctgg aagaatgaga aatctggtga tagatagcat  9840
ggagtcagaa gtgagactgg ttttagcatc cactgtcaca tggctgcccc tcagttgaac  9900
tggagactgg tgggacagaa cagtatccac acagaaggac caacaggtag agtgccctgc  9960
acatacctgg ttagctgatg gcccgatgca gatttggcat agcctgggat acatggggct  10020
caggacagta cctgtcagtt tttaattaca agagcagagt gggcacagta gcagacccag  10080
gccgtccagc ttcccggccc ctctggagtc ccgctctcag cggagggtgc ctgctgttct  10140
taggccaccc cttgtcttcc ccacagagca ccctgatcac tctgcttaga ttgctggaca  10200
gctgctttcc ctagctgagt gtgggagctc acgcctgtaa gcacagcgtt tgagaggctg  10260
aagcattagc catagttcaa ggtcagtttg gggcacagag tcagaccttg cctcaggaaa  10320
caaacaagca aacaaacaag caccagaaca ataacacgaa gaaaagctgg ctgtaatccc  10380
agcacctgag aggtgcagga ggagagagaa gtttaaggtg tgcctcttct actcagacaa  10440
gtggaggcta gcctgagcta cagaagacct gtctcaaaaa tcccaaacaa actgaaggga  10500
aaaatggtat aacaacaaag tccacaaaaa caatcttcct ttttcctttt cttttttttt  10560
ttcagatgta tatggtatgc atgtatgtat atgtgtgttt tcatgtgtga gcatgagtgc  10620
ccaaggaggc ctggtatctc ccactgcatc cattgagtca gggcctctca atcaaactct  10680
gagctcactg atccagctag tctggctagc tcattgatcc attgcctttc taggttggac  10740
tcagaagcgg gctacaaaat ccgcctagca tatatgtggg ttctaggaat ccagactctg  10800
gatttcttgt gtagcactta accgctgagc ccacagctgg tttgtggttt gtttgtttgt  10860
ttgttggtgg tgtttttttt ttttttttc ctttttgga tttttgagac agggtttctc  10920
tgtatagccc tggctgtcct ggaactcact ttgtagacca ggctggcctt gaactcagaa  10980
atccgcctgc ctctgcctcc caagtgctgg gactaaaggc gtgtgccacc accgccaggc  11040
ttgttttttt tgttttctgt ttttttttta atgtattttt aatgtacact ggtgatttga  11100
ctgcttgcag gtctgtgtga gacagtgttg gattccctgg agcaggagtt tttggaaagt  11160
tgtcagctgc catatgggta ctaggaattg aacctggatc ctctggaaga gtagtagcca  11220
gtgctcttaa cctctgagcc atttcaccag ccctctacaa ctagctttct ggcctgggca  11280
cttctagaaa tctttccacg tcagtttcca gttgtagctt ggagcatcct gaccgctgag  11340
tgaggcgggc aggagcagca gttggggctg aggtagtcgt gctgttgaga gcagcagctc  11400
tctcggtggg ctgttagcta cagccttgat gatgtgctta ccacaccagg aggcctgtgt  11460
gctccctctc actagcaaaa atcccttgga gtgggtatta tgaagccaac ctcttggctt  11520
ctctcctggg ccttacccag aggcttgtcc ctgtagattc ccctaactga gatttcccag  11580
tcttcctcct gagcctggaa taaagtcttt ggcaaacttc ccaggtgcca aggtccggag  11640
ttctgtgtgt ggaggctttg ggtgggcttc acttaaggct ctccaggtgc ctgtgtgtag  11700
gaggctggag cggcaggcat gcagaacatc ttggaggagg cagctgtctt cttgctgagg  11760
tgaagcagtg gaatgacttg ctgacctgtg ctttgtgcct gtgtggctgt gaagtgcgct  11820
gtggcttatg tgtggacctt ttggtgacag acatcaaagc tcttttgccc tcattgttcc  11880
aggactctaa atgcacttca tggaaggagc cttgtagagt gtagtgtgaa tggggaaggc  11940
tacgtgccct cccccttggcg gtggcagcca cttcacagtt ggagttggat acatgccttc  12000
ggactctctt agaggcctcc ctcctgtccc tatgtcccat gtgccaccta tctgctcaga  12060
gccactcagc ttccacttgt agaacaaaac cagcgactcc caagaacctg ccgatcctgg  12120
caccacactg cttgcgcctc ctcctcttcc tccccgtggg ttcttagcca cctcgctctc  12180
accatatccc ctctctcaag actgtgcctt atgtaatgta tggcactgtg gtcttgagtt  12240
ccacatgtaa ctgggagtga ccttgaactc tgcatctggg gctggagaga tggctcagca  12300
gttaagagct ctgactgctc ttccgaaggt cctgagttca aatcccagca accacatggt  12360
ggctcacaac cattcgtaat gagatctgac tccttctgga gtgtctaaag acaactacag  12420
tgtacttaca tataataaat aaataaatct taaaaaaaaa gaactctgca tcttcatatg  12480
tctatctgag tgctgggatt acaagcactc aatacctgct ttgtgtgcag ctaggcatgg  12540
aactcaggct tgatgcacac taggcaaacc ctcaactggc atatggccag cctgtttcca  12600
gtcctgttat tatcattgct atattggtat tcgtgggtgt atctatatgt gcgcctgtgt  12660
ggaggggagt gatggaggcc aaggactatt ttcacttaaa aacttttttt tttaaatgtg  12720
tatgagtatt tctttctgtt tcatgtacat gtcacccaag gaagaggaca ttggatcccc  12780
tggagatgga gttacacatg gttgtgatcc atcttgtggt tactgggaat tgaaccctgt  12840
ttctctgcaa gagcagcctg tgctcttagc tactgagcca tctctccaga cccttaatta  12900
taattttttg agctagcgtc tcactcagag cctggtctca ttgtctgtcc ttccccttct  12960
ctggagttag gatcacaggc acatatgccg tgctcaggct tttctttttt ttttttttt  13020
ttttttttta agatttattt atttattata tgtaagtaca ctgtagctgt cttcagacac  13080
```

-continued

```
tccagaagag ggcgtcagat cttgttacag atggttgtga gccaccatgt ggttgctggg  13140
atttgaactc cggaccttcg gaagagcagt cgggtgctct tacccactga gccatctcac  13200
caggcttttc tgttttagga agtgaactca tgtttggcca gcaagtgctt tatccatggt  13260
gatgatctcc ctagcctatg atttgtttgt ttattttatt tttgatacag agttttgcta  13320
tacagctcag ctggattcaa acctgaaaag tccttgcctt agcctcccta atgctggggt  13380
tataggcagt gtcactgtac cttggtcctc tgctgccttt ctctagaaaa gctgaggtga  13440
ggtctgactg tgatccacgg gtatgtaagc aaggccagca aggctacctg ggaatatccc  13500
tactccctgg tgaagaagga ggcacccgag agcctgctcc taacgcatgt tcccagactc  13560
tgatggcttg gagagcaggc aggcattgtc ctactgtgat gctgcttacc gaggatacac  13620
cccagcacac agaggccatt cccatcgaaa gccccagagg tggcctcagt acacaactct  13680
gtcctggctc agggcctctg tcttttgtac tgatagatga ggtttttcta gagttgttgt  13740
tctcaatctt ctttagatga cccaaccata aaatgacttt tgttgttact tcaaaactgt  13800
aatttttgtt actgttaaga attgtagtat aaatatctga tatgcaggct atctggtatg  13860
tgacccctgt gaaagggttg tttgacctcc aaagtgttgt gactcacaga ttgagaactg  13920
ctgttctaga ggatggtagc tttctggtct ggaatgcctg ccccagcatc cttagctgca  13980
gggaaccagc cagtggtgag agtgaccttg aattcctgag ccttctgcat ccactattag  14040
tgctggcatt cagagtgtgc cactgtactg agaggacatc atggttgcta gaatcctcat  14100
ggctacccag tgaaggctgg tagagatcaa gtccaggagc ctgtggccgg tatctggagc  14160
cctgctcagc tcagtcttcc tgtgctttag gtccccttgg ccatcatttt gcaatgttga  14220
cttcccactc agccaagcgg aaggaagcct ggcttctgta gcctttgcct aggtggcact  14280
gccaggggac actgtcttgc ataggctgtc aaggatttgg gtataagttg ttttctaggg  14340
aagggcctac atggggtttg ccctggcatg tggtgaaaac tgagtcttaa acttttcttt  14400
tctttgaagt tttcttgagg tctcatgtca cattgctaac ctcaaactaa gttaaatgca  14460
cagccagggc ggggcttgtg cttctgtact tcctgctgtc gcctccctgt gccgacgtta  14520
ctacaccagg cctagatgct gttttttttcc ctccgacaac ctgcttcaac ctcaagtact  14580
gggattgtag gcctttccac cacagtcatg cctggatttt taaaaagttg gtagttttat  14640
gtaatctagg ctgggcctca aacttctgtc acttctgggc tcctgatctt cctgctctgc  14700
tgcctgagtg ctgggattgt cagcagatgc catcacatca ggctttaagg tttctcatgg  14760
cactggggat cgctcccagg gctctaccac tgagttacct cttcttcttt aagaccacat  14820
tagagttatt aatgtaatta ttttgggtat tagagatggt gttctcctgt gtagccctgg  14880
ctgtctatag accaggctgg ctccggattc agagatctgc ctgcctctgt ctcctgagtg  14940
ctgggagtaa ggtaaaggtg tgcactggct acagcagagt tataaagaga ggggctgggc  15000
tcaatgggag aaaggtgctt ggtgccaagc ctaatgacct gaggtgcatc cctgagacct  15060
gtatagtgga agagagcaga ctcctgaaag ttgtcctccc atcaggacca tagcaattcc  15120
acctccaagc agagaaacat caataagatg caatttaaaa acatttaggg catgttgccc  15180
atgtctgcct tccttggcct ctccctactg caggctctgt taagactgtc actgttgatg  15240
gaaggcccct gtcacatggc tgccgttgcc ctcctaacac aggatcgcat gtcccctgct  15300
tccctcctct gctctaggct ctcaggctgt ccgtcctagg ctctcatgac cttggacttt  15360
gatagaacac aaacaacagt aacttctccc agcttatctg gcttgttctc acagctgact  15420
gtgagttttt tcattttggg taaggaacta ctttaggtcc gctttgtgca tcttgtagga  15480
ctccataatg tgggccagca ggacattccc agggagaggg catctgccat gtttccttac  15540
ttgaaagtta ctgggtttgg ttttgcatat cttatccttt gtaagtatcc aggccctaaa  15600
ggttttatgc atgaggacgc aagtgtatgt gtgagtttgt gtgcatgtgt gggttcttgc  15660
gtgaaggaca aagattggtg tccaatgtct cccttaagta ctgtggaaga atctctcact  15720
tacacaaagc ttgtctaaat ctgctaatct ggctagccag catgttctgg ggatctcctg  15780
tctctgccca caaacactgg cattacaggc agataccaca agagcttggc gctacgttag  15840
tcctcaagtt tgcatgtaag tgctttgcct gctgagccgc taagccgact ttccaacctt  15900
cattttgatt tttctaggtc tggggatgca actcatggcc tcatgtatac taggaaaggc  15960
ctctacccct gaaccagacc cctattctct ctccatggga ttctagtcag gggttctacc  16020
actgagccac gccctcagtg cctcactgag ggattctagg caggagttcc acctttaaat  16080
aatacccta gtttctcact gatggatttc aggcaagtgc cctcctgctg agtcggcttt  16140
ccagcccta attagggggt agaggggcag agccacacct ccaacccctc attggggcat  16200
tctagataag cactctactg ttgaagcccg tttcctagct gtctcttgca ttttatatag  16260
attataaagt gtaagttgaa aagttgaaga gttgttttat atttttcttt tgcaaagcat  16320
tgtacaatct tgtatttcat tggatggctt ttgtcagatg ggcacagtct cttttggatg  16380
ctgctggagc actgcccagc agttcccaca tctgcacaag ccacatctgt ttatgagtgc  16440
agctctctgc ttagtgttga aatcaggcgc cttgaggacg ctttgttctt tttctcaatt  16500
gttttgaatg ttctaagtcc tttaaacatt aattttgttt ctatttgttt gtctttttga  16560
gaattctatt tttgtttgtt tggtttggtt ttggtttggg ggggttttggt ttgtttgttt  16620
gtttttgttt tttgagacag ggtttctctg tgtagctctg gctgtcctgg agttcgctct  16680
gtagaacagg ctggtctcga actcagaaat ccgcctgtct ctgcctcctg agtgctggga  16740
ttaaaggtgt gcgccaccac gcccggcaag aattcttact ttgtttctca cactgacctg  16800
gagcttgagc cccttctgcc ttggcttgtg cgtgctggta ttagaggtgc agcaccatgc  16860
ccagctctga atgcccattt tacagttagc ttgtggatcg cttgctctgt ctgtctgtca  16920
ggctatccat ctatcaccca tcttagagtt tcactaagca attctgcttg tcttggaact  16980
cactgtgtac acaaggctgg ctttgaacat cagcctccaa gtactgggct taaagatgtg  17040
ggtccccaac cccagttacg ttgtggattt ctactaaaca aaataaaaag ctaagacacg  17100
atagctcagg gatggagacc tagtcaactg tagaccatgt ttctatctat agcaccaaaa  17160
aaggaaataa aaaaggctgt ttataaagac ccgtcgaagc ctatcctgtc ctaggctggc  17220
ttcagaatca tcatgtatct gagggtgacc ttggactccc ggtgctcttg actttacctc  17280
ccaggtgtta gcatgacaag catgcaacca gcacttaagt ctgtgtgatg ctgaggacag  17340
agctcaggac tgtgtatgcc aggcaagcac ttgaccaagt gagccttagg cccagggagg  17400
gtagggtttt acggtattca tttttctgct tcatgtgcac tgtttgtaga tgtaggtatc  17460
agaggatata gttgcaggtg tgggtaaggt gtaggttctg gccgtcacct tgttggagat  17520
gttcagtgct gtgaatgaca gacatatcag gtggccccag tggggaattc tgtctgtgca  17580
caccaaactc ctattagttt tgattgctgt gctatttcat cagctgtcca cgcccctgca  17640
ttgcctgctg cctcactctt gttcatttga ctccccctcc ctgctcccca tagtaggagc  17700
ctgtccaaaa cccaggagca catggtggtg caggcctgtg ctccagccct gatgctggaa  17760
atgttggaaa cgtgttaagt atattggtta gaaaatagcc actcagaaaa catcagtaat  17820
```

```
tgtgtaccac aaatgcaatt gtatattttt tctttttttat ttttctatgt agacggggct  17880
gttctcagac tcattacaga ggtccacatg cctctgcctt ccaacatgtg agactaaaag  17940
gtgtgtggca tcacatccag ccttaacaac gtgaaatgcg catgaggggg agtgtgtgtg  18000
tgagtgtgtg taagtgtgtg agagtgtgtg tgtgtgtaag agtgtgtgaa agagtgtgtg  18060
tgtgtgtgtg agtgggtatg tatgagagtg tgagtgtgtg tttgtgtgag tgtgtatatg  18120
agtgtgtgtg ttggtgatga gaggacaact tctaagactt gcttctctcc ttcctctctc  18180
tgtcttcaag atttgacaga cagcacctgc tgctgagcca tcatagcccc cttctttatt  18240
ctattccagc cccaccaagc cttgataatc atccccctga tcagcctgaa cctgtctgca  18300
cttcctgacc accgttgtcc ctcaggccgc tctgtcactt cctgcctcct tcaggcttcc  18360
agggaaatgt ctcttcccca gggcaatccc aagaccctat gctactgtac cattggcccc  18420
cttgtaattt cttttagaaa catttatact ccctctttgt ttgacctaag gtttcttcct  18480
cttcctgggt gtgttcctgc tttgcaggta cctgggccat ctccctgtgt caccttacac  18540
ccacctttgc tttagtcacc aagagtcact cagcaaagga gaaaggtgtg ccctttgcca  18600
cactgtgacc tgggccccac ccagctggac caaaacaatt tgtttagtgc tctgtggagc  18660
tggatctcat tgagacactg cacctacata cagcaaaagg aggggacaag gcctgcctgg  18720
gctttgtgtg gacagcaatt ggtttttttg agacagggtc ccatgttgcc cagacaggcc  18780
tcaaacctag aagaggctgg ccttaaactt ctgatctttc tgcctttact ttcccagtgc  18840
tgggatgacc tagcaccaac cacatctgct ttatgggggc tgaagatgga acctggggct  18900
cctatgtact aggcaagccc agtgccaacc atagtcgtag agtttatgcc gagacagcaa  18960
gtcatgagtg tgtgtgaggc acgagaaaca agccaataca agtgtagagg catgaagact  19020
agtgtgggga atggaatcaa tgtctaatac tcatatatga aaacacaatg tcatgtacgt  19080
gaaggccttt ttaaaattgt aaaagcaagt aagcaacaac aacaagccac caaaaaccaa  19140
tagaaagaca gacaggagaa gccagccaca gaagccacac gaatctactt ggaagccaca  19200
cgaatccaca ggctagctcc ccgagacaga gtggagttgt gcttccagga ggtggcaagg  19260
gagggagtga gtgagcgcgt gggggacgta gagcttgggg agattcaaat gtcctgaaat  19320
cattgagaat ggtttcacaa tctgaatcca caaaacccct agcagccact taaaactggt  19380
ggatctaaaa gcctgtgacg cactttcctg aaagacagtg aagccagagg cagaaagcaa  19440
ctctcccatc cccctgcctt acgcctacaa aagaatgaat gccttgaaga caaaactcag  19500
tgctgaggca gggtcactgg agacaggagc attgccaaga gttcaacctg ggctaaggtg  19560
tgagagaccc tctctcaaaa acagtaggag ccatagataa gagaagcata gattgttctt  19620
ctgagatgga cttagccact tcatggggag ctccagccgg ctccagcctt gcgagtgcct  19680
taggtcctgt gcgcgcacgc acgcacgcac gcacgccagc cactccttcc cctgagtttg  19740
ggcacctcgg ctcatcccac aaccaagctc ttgtggtact gtgtctgtgt gtgtggtttg  19800
gactcccagg agctgcctgt ttggcttcct ctcctaatgg tttcaggagt ccactgtctc  19860
ctgtgctgtg ccaagctccg ggcatttacc aattttactt acttattttt ggggattgga  19920
gattgacctg ctcgcatgtt cgacaagcca ctctggcact gactccatcc taagccctcc  19980
tgtgttttgg gatggaatct catcatgtag tctaatccag cctggcctgg gtcagcgagt  20040
gtactgagaa tagtaaaaga tgccttttag acaggtagaa atagctcagt caggatccca  20100
ctacacccaa ggctgcacct gatagccaga acccagtgac atcactcact ccgaataacc  20160
acagtgctag aaccccatga tacccactgt acagtatata agcgaccaag agcagtgctc  20220
tgctctgcac atctggagag atgacacctt gatccgtcat gtggctggag agtctcccca  20280
aggatcctga cccttgaatc agatttccat tagacattag acctgaccct cagctaaata  20340
tgatatgtcg cacaggtgag ttaccttagg gagataggct tagaaagaac ataggaattt  20400
agaaccttgt gtgatgacca tcagcaaaat aaaatataac ttttgttata ttaactacac  20460
atactccacc ctcttgctca aaacactttg gggtgggctt taaggtttca aaagctcaca  20520
ccattcccag ttagttctca ttctctgcct cttgcttgca gatcagatgt aagttctcag  20580
cctacaccag atgtactact ccagtgctat ggctgcctgt ctgctgcagt gttccccacc  20640
atgctggtca tagcctaact accttacctc tctggtactg tgagtccagc tcaaatgctt  20700
ccttttacaa gttgcctttc tttttggttt ttcgagacag ggtttctctg tgtagccctg  20760
gctgtcctgg aactcactct gtagaccagg ctggcctcga actcagaaat ctgcctgcct  20820
ctgcctcctg agtgctggga ctaaaggcat gcgccaccac tgcccggctt ataaattgct  20880
tttctcatgg tgttctgtca tggcaataga caagtaggga agagttgggt gtgtggtaca  20940
tgactttaat acgaccactc cagaggtaga ggctggcaga tctttatgag ttcaaggcca  21000
gcctgatcta cataatgagt tacaggatag ccaaagtatg aagaaagacc tgtttcagaa  21060
aaaaaaaaaa aaagaagaag acattagctg aggcatcttt ttcccctccc ctctgcccct  21120
cctctcctcc cactgattta gttatggttg cttgcaaaag gtgtgtatgt gtgcctgtat  21180
gtgtgtacct gtacgtgtgt gtgtgtgtgt gtgtgtgtgt gtgtgtgtct tactgctcat  21240
gacactgcct ctcagagccc tttcactgcc tgtagcccct gggtgagggg atgaggctca  21300
tggccccttc ctctgagcat aatgaaatgc tggcaggctg gatcctgcac agggcgcagg  21360
gctgcatgta gctgcaggtg tgccctgtcc agaagacagt ttctcagcat tcctccttgt  21420
cattatttta tttgctattt atttatttgt ttgtttgttt aagtttttca aggcagggat  21480
tcttttgtac ccttacctgt cctggaactt gctctgtaga tcagattaaa ggcatgcacc  21540
acaacacatg gcgttgttgt tgttgttttt tgttttgttt tgtttttttta tatacagtct  21600
ctctatatag atttggctgt tctagaactc cctgtatagg cctcacagag atctacctgc  21660
ctcttgagtg ctgggattag aggcgtatgc ctggcttctt agtatctttc tttttgtgt  21720
tttggttttt ggtttttggt ttttttttt ttttttttt ttttggtttt tcaagacagg  21780
gtttctctgt atagccctgg ctgtcctgga actcactctg tagaccaggc tggccgtgaa  21840
ctcagaaatc tgcctgcctc tgcctcccga gtgctgggat taaagacgtg caccactacg  21900
cctggccctc ttaacagctt tctgttcctg attccaaatg tttcttgaaa cattggaagc  21960
attgatacag ctgtcctgtt cagatctgtc ccgagcaccc tgcggtcact cttccatatt  22020
gatcatgtcc acatgaagtg ttgctcactg cagaggcttt tctgagagag attgagagca  22080
gcctgaatca atagttataa actttagcac ttagaacagt ttgtcagtta acaggggtag  22140
gttcagctgg gcatggcgga gcatgccttt aatccccaca ctcaggagac agacacgaga  22200
tctctgagtt catggccacc ctgattacaa ttaccgttcc agtactacat agagagaccc  22260
tatttaaaca aagaaacatg ctgggctatg gtggtgcaca tctttaatcc cagcacttgg  22320
gaggcagagg caggcggatt tctgagttcg aggccagcct ggtctacaaa gtgagttcag  22380
cacagccatg gcaacacaga gaaaccctgt cttgaaaaaa caaaaacaaa ccaaaaacaa  22440
tcaaacaaac aaacaaacag aaaccaaaga aacaaacaac caacccctcc ccccaaaaca  22500
aacaaacaga caaaaaacct gtagtcaatt ctcccgcaaa tcctggagct ctctaaccac  22560
```

-continued

```
cagcttttgg ccagctttac agaaccagca ttgagtttct tcctgtagag tggatgtcct  22620
gtggttagtt taccccagta ataatcctga tatcattgct gtgccagtgg acatctcttt  22680
ccagacaggt tgttctggtg gcctgtgggc cacagccaga aggaccactg atggctttct  22740
tttctcagag gcaacagctg tccattagag tgtggtgtct tcagaggtgg ggctaaccct  22800
ttagctctgc tgggtgacca agtgcagcag ccatagcctg tgatatgccc cgggcctccc  22860
tgtctcctct ggcacaaaac tcccttttac gctcacagct tccaggagga agggaactgt  22920
ttgatgcttc cgtctgactt cctgagtcgg gtgaagaatg ctggccttgc agggtgagct  22980
cagaagtgtg ccctccagtc cattctgtgg gagagtctct gaagagctga tgctccttct  23040
cttcagggtc tcttacaatc taccatgaag ttgctgcctc tgggcttttt ggagggaagc  23100
ttttttagta attttttttg tttgtttgtt ttttcgagac agggtttctc tctgtagcct  23160
tggctgtcct ggaactcact ttgtagacca gactggcctt gaactcagaa atctgcctgc  23220
ctctgcctcc ggagtgctaa gattaaagac agcgccacca ccgccctctg cagggaagct  23280
tttgaacact taattcaggc cctttattcc ctttacgcct ccagagactt caccatgttc  23340
agccttttgg tttctttgta attttttcc tccagggttt tcaatttcgc ccatgctgtc  23400
cttttagtct ttttcagata atattttatg agactgaaga gatggttaat ggcacttgtt  23460
ctttaagagg acctggttct cttcccacca cccagttggc agctcacagt cctctgtaac  23520
tctagttcct ggagatctga caccctcatg tggtctctga gggcactgca tacatatggt  23580
gcacattcat acatgcaggc aaactctctt gcacataaaa taaaaataca acagatctta  23640
gctgggtgtg atggagtcag agacaggtag atctctgtga gttcaagatg aacctggtct  23700
acatagtggc tccagactag gtaggctaca gagtgaggcc ttgtctcaaa aatatacaaa  23760
tgtttacaaa tattagttca ttcattcatg atttgtgtgt gtgctagtgt gtgagtgcgt  23820
gtgtgcgtat gtgtgtgtga gtgtgctatg tgtaggagtg tatgtacatg gaggacagag  23880
ggcagcttta gagttagctc tccatcttta tattgcttct ggatcacact caggtttctg  23940
acttgcacag caagcttgct tacctactga gctgtcttga cagcccctct tccttttttt  24000
ttttccattt ggttgtgata ttactacatt tattccaaat cttagcaatc tgagtctttt  24060
ttctttggga aattttggat ctttcctctc ctctcagcgc cccaagcccc cccgccccca  24120
ctttttaaaa aacagaacca agttgacctc caattcaatg tctatgcaaa gatgaccttg  24180
aactcctgcc tcccctacct ctactcccct gtgcagtgct gggattgcag gtgtgcactg  24240
ccctgcctgg cttaggtggg gcgagggata ggacccaggg cttcctgtat cctagggggg  24300
cattttacct ttggaacccc aggccttgag gctttggtct gtttgctttt aattcttctg  24360
tagccatcag gcatagcact gctgacgctg gccacattta ttggcatttc ctcaattccc  24420
tctgtcttag ttcttcctta gctttctgct gaggctaggg aacacatttc cctcccctcg  24480
agcccgccgc tctctgccac agctgagcac gcagtctctt ttggagaatg ttctctgtgc  24540
ctttgagggt tgggaagatg tccgagtggg caaggactag tttggtgtgt gaaaggccct  24600
gaattctagc ccatcttgaa gggaaaggag gaaaagtaga caaagcccag agagtgggct  24660
gctgcttctg gatttgggca caaggctttc tttctgcctt gttgctttgg gtggtattca  24720
ctctgaatac tcttgatgtc tactcatccg tcattccagt ttctttcctc tttattgcca  24780
gggagtgggg gatagacagg gtctcactgc ttccctctgg ctggcctgga actcacagag  24840
atctacctgt ctatgttttt tgagtgctat gataaaggtg tgtgccaacc tcatttgttt  24900
ctttaaagga aaaaaaaatt tgttaagctg ggcagtggtg gcacttgcct ttaatcacag  24960
cactcgggag gcagaggcag gcggatctat gagtttgagg acaacctcgt ctatgaagag  25020
agttccagga cagccagggc tacacagaga atccctgtct tgaaccccac tccctccaaa  25080
acaggatttt aaaattttgt gtatatgagt ttttgcctgc atatgtgtat gtatagcaca  25140
tgcatgtccg tgtctgagga gaccaataga gtgtgctggg tgtccttgga actagagtta  25200
caggtggtat gggtgctgtg aatcaaaccc ggctcctctt aactgctgag ctagctctcc  25260
agcctaatcc cacccacctt ttgtgtgtgt gtgtgtgggg gggggtagta gtcaggctgt  25320
ctctctatat aacctaggct aatctggact taaactattt ttgccatatt cctctggaat  25380
acaggcatcc taggtgtgtg ttactcttcc tggccatttg tcaattactg aaaagattgt  25440
cattgtccat gcaagccaga ggagcagact ttgggccttc agagcttgca tgaatatctg  25500
cgtaggtgta gttgcctgct ttcattagga gggacacgca ggtaggaagt ccctgaagac  25560
gctgactggc tagatgagca gacctacaat ctctgtattc aggagagaca gacacctcct  25620
cagtaaatac ggtggagggc agtggaggaa gacaccgacc tcagcctgag tccgtgtgct  25680
caggtacaca cgtgcactct cacatcaccc acacacaagc aaaagacatc cacaccgatt  25740
gcattaccta attccctggc cagttctttg acatatcaca tggcattcct tgactttgcc  25800
tcacccacta tctctcatca ctgtcttacc tggacttctg gttgttcttg gttgtcattc  25860
tcctgacagt gcctgagggt caccagactt gtgtgagctg aaggacctga aggaagcagg  25920
tgacagttga ggaggaagca ggtttaaggt ggtgttgagt cacctgacag gaaaggctgt  25980
gctgatgtcc tcacaggggt gccaaggaga agggcatgtg cttcttgtgg ttcttggagt  26040
tgacatcccc ccccagcccc cacaccattc attgcctttg tgacagcacc ctgcacatgg  26100
ccgacaccac acctcgattc ctgtgccacc tctgcctgct tctactggtg tcctaaggac  26160
atggtcacat gttaggaccc catctgcagg tggagacact gtgacagtga tgtccttgtg  26220
caggtcacac atggagagcc tgtgactgaa acatcaggct ttagactcta cccgtggcca  26280
cccatattct taattggtgt caggaggaag cggcaatggc ctcctgtgtt cagagttcac  26340
tggcgtcttc ttaccctggc tcccagatgt gctggggatc agcagacagt gctcaaaagc  26400
tgagggcagg gttgcagcag tttagctggg ggtctcagtg ctcggggttt ttacctgtgg  26460
ctttggtctg agttacttta acctgaagct tcagattcct tatctaccag atgtgagtag  26520
agaaagccgt tatgtgccgt tctagtacag aataccaagt caggggggatt cagggttcag  26580
atcagctgga gctacatttt gagactttag acaaccaaaa gacaaaatgg ggacaggata  26640
agcctcttgg gagtacagca agagtccctt gttcatagtc aggccagctc ctgtggggtg  26700
tgtgtaccct atacaggcca tttattagca ggtgtttgtt tgttttttgt tttggaatgg  26760
gttcatgtag cctaggttgg tctcaaactc agtttgtagc taaggatgac gactactgat  26820
cttcttgtct ccatctgagt gctgggatga aatgcgtgtg ctgccatact tattttatga  26880
agttctggtg atggaactca ggcaaacaca ttgcccgctg agtgccagac agtactggga  26940
catggttccc tgtccttgtg gaactgacag gtaggttact tcagaactgg gaggcaagaa  27000
ggacgtgtga ttgctactgg aggacaaaaa tccagagaca agggggggggg ggagcagggc  27060
agctgtcaga ggagcgtctg caaaggggtc agcctgtgag gtgaatggct atggaatgtt  27120
ctggtggtcc tccctaggga acagttgaac ccatagagtt gggaatccac atccaccagc  27180
catctaacac agaagctgcc acagaaatgg cgatcgctct cagttcctcc cttacgctgc  27240
cttttacaca gcacagcacc tggcccacga tacaaaagtc ttctgccaag gacacagggc  27300
```

```
agggctagac atggacacag ctcttccacg agcaggtctg agacatcaag ggccctgaaa  27360
gggcggagtt gagagccatg gcgccacagg tcagacagct tccctgtcat tctgtaaaat  27420
gtttttagct attcgataca actggatgat gacaggtcag atatttgcct gttataaagt  27480
tataaattga tctgcaatca cctggaattc gcatcacctt ggagactgca acataacttt  27540
tgttttgttt gagatagagt ctcatacagc ccaggctggt ctttaactaa cagtaatcct  27600
gcctcctgag tgcaagaaat ttcagatata tacaaccact ctgttttctc atattttttt  27660
aaggcagggt tttgtggagc ccagctggcc tcaggcttac tgtgtaactg aggataacct  27720
tgaactccag atctaccggc caccagtgag tggtggcatc acatgagggc caccacaccc  27780
agggaagcag gtgctgtgtt atcctgagtc catgtgccag ctgtctccct gaagaaagga  27840
tgcaagcaga tgacctcccc cgaggctggc ttagtggcta tcatgcttac ctggcatgca  27900
caaatctctg ggctccatct gccagccaga cacagtgctg cacacctgtg atcttagcac  27960
ttgcagaggc aggagatcag gagtgcaggc tcttactcag cttcagagag gcttcaaagc  28020
ctaggctgca tgagatccta cctcaagata aagaaagcaa accatcaaac acaaaaacat  28080
cccaagtatg gagaagactt cctccataca gagcgtactc tatgctccac atactggagg  28140
gtgccaggcc ctggactatt tctcagaccg gttgccttag cctctcctgc tgggtggaca  28200
tataggtcat tagtggcttt ctcttggaca tcttgctatc tgtcatggtt acctcatgtt  28260
agcagtgact ggtctttgac tgtggtgtct atgtcctgga tcagtgtgct ggggagcaga  28320
tctctgagga gaggggcctc atctcctgtc tattctggag gtgttcatgt tctgctgcag  28380
ctgatcatct gacaaagtga ggaaaaagaa atctggcagg gcccggtggg tgttggctca  28440
ccaggaagca gctagacctc tctgaggaag ggacaaccta gctgagccct tagtgtacac  28500
aggaaactag agctgtcata agaaaggtca ctgtgtgagg ataaacagag gccctgaggc  28560
aggaagatgc tgtgctcttc ctcctctcaa cccagctcca gggaatcgat gggggagtag  28620
tggctgatcg ttgagtaata ccaaggcctc caaggccctt ggggggcagg tggaaccccc  28680
tgaaagttac aagcagagga gtggttacag gttgctccaa gtttactttg gttgtatagg  28740
atggatgctg tcatgggtgt gggtgtgcct gccagaaatg gatgatgggt ttcttttgct  28800
gtattgtcta ccataggttt ttagactggg gactttactg agtctggatg gagttcatca  28860
ctttgggctc ggctaatgag tcccataaac cccaggggtc tttctccatg ccccaagtgc  28920
tgggaggtgg gcatgactgc ttgactttgt gtgggtactg gggatcctca cctgctcctt  28980
cctcacgatt gtttggtgga cacttagtga ccaagccatc tccctagccc caagaatgat  29040
gtatttttag atagtatggc aaaaacttgg taatcctaac ttccctttgg ggcaggtgtc  29100
attgtgcctg cttaaccaac aagaaagctg cgggagggct ggtgagatgg ctcagtgggt  29160
aagagcaccc gactgctctt ccgaaggtct ggagttcaaa tcccagcaac cacatggtgg  29220
ctcacaacca tccataatga gatctgactc cctcttctgg agtgtctgaa gacagcgaca  29280
gtgtacttac atataatcaa taaataaatc tttaaaaaag aaagaaagaa agaaagaaag  29340
aaagaaagaa agaaagaaag aaagaaagaa agaaagaaag aaagaaagca agcaagctgc  29400
gggagctaga ggtggcccaa ctgaccagat tgtccaggaa cgttctagaa gtaatccagt  29460
tctggattac atctgggcct tgaggagttc tggagtcaca gccaccaaga cactctagct  29520
atttcctgtc cttgttcccc gcccaggctg gctctcggat gtgactgtga gcaggtggca  29580
ctaggcctga gtgccaaggg tgggactgat ttgggtcctg ccggattcct ggctagggag  29640
ggactgctgg gcagaagctg ggtggtacgt ggtaagcagc gccagaactg aactcacatg  29700
gccaggcagg tgccgggttg ccactaccac cacctgagct tcagtgtcct tgtctgtgaa  29760
atggcagagt cagtccttca tcccacctgt tttgttccca attctgggtc agtagaaggg  29820
gagattgggg agagcaggct tggtcctgcc atgatgtggc cgctgctggg atagaagcat  29880
ggtgtaggga cagacaggta gggaggaaga ggcttaaggg gcttacagtc agatttggcc  29940
tgtaatgggg gaagactgag cctgtgtggg caggcaggga tggcgttgat aggagcaggc  30000
tgtgcgtgca gagtttagca ggcaacagga aggcttcacc ctgtcacttg agaagagaca  30060
cacccacctt caccagaggc cctggtcagt ttgccagaga tagcaggtgg agcttatgcg  30120
gcatgacctc taatctcatg gcttcaggct ccgaggtctc cggaattacg gagacgggga  30180
agggtctcca cgcaggacct ttacctacat cctgccaggt ttctcaagca atggctgact  30240
catccttcct tgcttctgtt tggcttccct ccctggaggc ctggagaccc acctccagct  30300
gttggttcac atagctgtct ctaccttctc cactctctct gtacagaaaa aaataaacag  30360
acctgggttt tggatcagcc gttgtgctac ctctttttg tcccctccca ggagcccttt  30420
tcatcctcca aggggcctaa ggcttagagc cctagaggct ctgaggagga aaagctgttt  30480
acaatggtcc ctgtcactag tcctgtgaac ggggatgtcc tcctatgcca taactgagcc  30540
actgcccaga gagggcctga taaagagccc tctctgggca gtggctcaga tgccttctgt  30600
ctcttcaata acattgaatc ctagcagccg acactgattt ataaggcact gttcaagctg  30660
ctggtgactt gaccaaatgc aggagctctg atctgttaca gaaccaacta ccatctgtct  30720
gaggctgaac tagcaggagt gggaaggaag gaaggatagg ctctcaatac agcctctgac  30780
tattactagg tgggcagtcc cctagggaag ggtggcttgg cagaaacccc tgcaaaggtc  30840
aatggtttgt ggcgagagcc actagtgaac ctagatagtc tggagacccg gactgtattg  30900
gtccagctct gagtggacac aagacctttg tagaaaagct ttctgaatat ctgtgttggg  30960
gaaggggtat ttgtgtgtgt gacttattaa catactggcc tagcattcgt gtaaagcctc  31020
aagtccatca gcactacata aacatggtga tgcacatgtg taatcctggc acttgggaag  31080
tagagaccgg gaaggttagg agttacaaac catcctctgc tccatagggt ttgaggccag  31140
cctgggctgc atgagtcact ctgccaaaga aaaaagggaa ggaaacagaa ggaggcagct  31200
ccttttcgga atgagaaatg atgcaacact ttacacttaa ctgaccacct accatgtgct  31260
gtccctgtac caggcctaga gaaatgatct tacgtttacg tatcgaggtg tggatgtctt  31320
tgagccagag ttctcgacat cccccacaaa tttgttgcca tccctcacag ttggcagagt  31380
tttactaacc aggaaaccca gacctgagag agaaggaagc agacccacgt cgcatagcac  31440
agaactggct aagtgggact agaacgttag ggcagccagg acacacagga aaggtcatag  31500
caacagctaa gaaaagtact caggcctgtg gaggcaggtg gcctggggaa ggaagaacta  31560
gatagctgga ggctattgct gctgccagct aaggacagtt ggcatttgta ggagagctgt  31620
ctgggaagcc atagtgtgtg ctctgctgca ctgcccagga aatactcttt aaaaaaaaag  31680
aagaagaaga agggctggag agatggctca gcagttaaga gcactgactg ctcttccaga  31740
ggtcctgagt tcaattccca acaaccacat ggtgacatgc aaccatctgc actgggattc  31800
gatgcactct tctagtgtgt gtctgaagac agctgcattg tactcatata aataaaaaaa  31860
taaacacatc cttaaaaaaa gaattttttta ttttatgtat gaaagtgttt tgcctgtgtg  31920
tgtgtgtgtg tgtgtgtgtt tatgtatcat gcctggtgct tgagatcaga aggtgatgga  31980
ttccctaagt tagagatggc tgttagtcac catgttgggt gctgggaatt gaacctgggt  32040
```

-continued

```
cctctggaag agcaactagt gctcttaact gctgagccat tgctccaact acacacacac  32100
acacacacac acacacacac acacacccca cccttttaaa aatagatttc tttttattta  32160
tgtgtatgag tgctatatct gtaggatgcc agaagagaga atcagacccc attatatatg  32220
gttgtgagcc accatgtggt tgctgggaat tgaactcaga ctcaggacct ctggaagagc  32280
agccagtgtt cttaacggct gagccatctc tctagcctct tctcttctct tttctctctc  32340
atttcctttc cttttctttt cctttctttt ctatgaaaaa cacgcacaca cacttttttt  32400
ttagactaag ctggccttga atttaaagag atctgcctgc ctctgcctcc cagttgctgg  32460
gattaaaggt gtgcactgcc accccccacc tgtatcagac acccattttt ttaaaacagg  32520
agaaagaaaa tgttagattt ttattttacc tatcttatct agatgtctag tgtgtgtgtg  32580
tgtgtgtgtg tgtgtgtgtg tgtgtgtgtg tgtagaggga tagtcttggc atggaagcag  32640
tggagtctaa aggacaactt tccagagctc tgtccttctt ctttgtgaaa cttaagtctt  32700
caaacttggc agcagatgcc tttacccccct tagccatttc actttgctta gtcccagggt  32760
tcagggaaac tgcatgacgt cagctctggc tgccggctcc cagtctgccc agtgacatga  32820
ctgctgtctc ttacttggct tctgccttct ctgttgtctt cccgattgac caccaaggcc  32880
ccagtctttc cttgtgagaa ctggagcttg ttctgggcat cacagccgtc accattgaaa  32940
ctctctatat cccttgtctg ggacagaggc tggtgatgtc tgaggcgtca ccattgtcct  33000
caggctgcct gacatctcag attgaccaaa tgtaaagtca ctgcactgct gtgttatgtg  33060
ttactggtcc tggagagggg gggggggtgt tcagggacag attcaccctc tgagaggctg  33120
cattgtagac tagaagctga gattctggga cctgctgatc agggtcttca gatggacctc  33180
ttgtgattca gtctgagttg ctgccattgc tggtgcaccg cagccttggg cagggcccag  33240
tctctgcacc tcactcagtt ctctgagaag aggcagctga gctacctggg atctccctgc  33300
tgtgctgtta aatccacaca gtgctctact tcctgcttgt cacacctgtg ctactgctcc  33360
acagtgccta cagagtattt gactaaatta gtgaattgat ttagtttagg acttttgaga  33420
cagggtctca actcaggctg gtctataact ctctgtagcc aggtatgacc ttgaactcac  33480
tgaccataac tgtttacaga tttacaacag ccatcattgt tgaggaagag ggtgtctcct  33540
ccctctcatg cctcgctcct tgggctctat tgtagttcag tggtgtttc tttaagatca  33600
aaacaaatcc tccttacttg gtccacccag gaggaagttc cttcgagaag ataaaagact  33660
ctttttcttt tatgtggctg actgcctaag cttttggatg ggtgttagta ttgacctaca  33720
ccccccaccc cccactaatg tcggatgggc cttcaatatt gacctacacc actcccccta  33780
cacctttcct cctgtcggat ggcccatcag cacacacaca cacacacaca cccgctgagc  33840
tgtgaagctt ttaacaggtc atgcctcttt tatttagtgt gtgtgcacac atatgtatca  33900
gtgctcctgt gtatatcgtg gtgcatgtgt ggaggtcaga ggaccacttg tgggttggct  33960
ctctctttcc accatctcag tcctgggcat taagctcagg catcagcctt gctggcagtg  34020
gactttcttc ctcccctctc ctgtctttca ttcctttgca gtgttgggga tggtgccatt  34080
agctgcccat gctagcctgg tgctgtgctg ctgagctgta gccctagttg atgaggctga  34140
cctggcacct gtgttgtagc caaagtcaac cttgacattc tgagtctcct acttccgagt  34200
tccctcctgc ccctcagatt gtcacttgtg tctctggaag ccactcagcc agagttcttc  34260
ctgagcctgg gattcacaga cactctgtat ctatttgcaa attcttcccc cccccccca  34320
cagggtttct ctgtgtagcc ctttgtagac caggctggcc tagaactcag aaatccgcct  34380
gcctctgcct cccgagtact gggattaaag gcatgcacca ccacgccccg gcagtaatga  34440
actttttgac cctcctatct cctatgccct gctagtgacc tttcttgaga gacacaatta  34500
agtatgcatc gtaaatacac accctgattg ttctgataac tttaaatcaa aacaaaacaa  34560
aaactgctga tcaccgtaca gatcagcatt gaggctaatt tttgcctccc aagaaagttc  34620
agttgtgtgt cttcctgcct gttcctccaa ggaaaagcct ttgccctgat tcctatcaca  34680
aaagatcagc tttgcctgtt caggttcaag tctatctctg tggtagcttg taacctgggc  34740
cacatgtctg agaagatgtg catggctcca agacagccat actcttctct ccctcttctc  34800
ccctcccccc tctgcctttg tagaccaggc tggcctggaa ctcacacctg cctctgcctc  34860
tgagtgctgg gaataaaggc ctgcgccacc aatgcctggc agctatacta atttttacac  34920
ctagttaggg agaccacaca gggataactg tgggccagcc atgcagcagt gctgatggtg  34980
acctaacttg ggatttttgg cctctacatt agctggtata ggcattagcc accatggcca  35040
ttttcttccg tgctgggaat cctgctgggg aagctctcta ccaactgagc cacaccccag  35100
cccttgtttt attttgagac agcttcttgc tgtgtagtcc tgtctggcct gcctcagctt  35160
ccagggtact ggggtgactg gcggttgttt gttcggttgg ctttgaactt gatccttccc  35220
cagtctttct tgtggctctt ttgccatggg caagattgtc tgaaatacaa tgcaaggagg  35280
gcttagtgga agtgctagag cagattgtgt gtacacagct ctgtgtcttc ctacttagtt  35340
caggtcccct gcagaccttg ggctgcagag cctcggtagc cgagggcttt ccaggaacgc  35400
agctggggtt ggtgcgtttg ttaaaacttg caggaaacag ttgcctagtg cctgtggtca  35460
ccagcagcac tgagtcattt ctgctgcttt ctcttctccc agggacttcc ttccacgagg  35520
atcaggaatt gtcacccgga ggcctctcat tctgcagctc atcttttcca aaacaggtat  35580
gagaaataga aattcaggga ctggagagat ggctcggtgg ttaagagcac tgactgctct  35640
tccagaggtc ctgagttcaa ttcccagcaa ccacatggtg gctcacaacc atctgtaatg  35700
ggatccgttg ccctcttctg gtgtgtctga agacagcaac agtgtactca catacataaa  35760
ataagtaaat ctgtaaaaaa aaaatttaaa aaaagaaaag agaaatagaa attcaaaacc  35820
aagacaaagt agaaataata agtaaagcga gggacgcaga ggtagcagct cgtggacagc  35880
tccctggcat gtcggaagcc ctgctttcac caccaccacc accaccacca ccaccaccac  35940
cccccaccac cacccccacc cccccacccc ccccaccccc cccgcccagc agaatgaacc  36000
tggcctgaag gtgcatagct gtaagcccag caccgggaat gtgagaaggg ctagacgctc  36060
caggtcatcc tgtgatgcat agagagctca gggccacctt gggctacgga agagcatgtc  36120
ttcaaacagc agcaataaat tgaagaacac ccttctacaa ccctgagtcc ccaggcagga  36180
ccaggctacc tggtgcccac agttactttc tgatttattt attttagttt attttatttt  36240
tttgagaagt cttgcctggc aaccagaatt gctgccttgt actttctgta tggtcataga  36300
ccagccccaa ctggaaggac cactgtgcct ggtatttgag gcttgatcca tagtctcatg  36360
ctgccagttg ctcccagtat ggcatgttaa tgaatttaca gatgggaact gaggcccagc  36420
caggttacct gcgtttttag ggggccactg gcctgggatc ctcagccaat ccagtgcggc  36480
ctgacattcc agggccctgc agttgttctc ctgattctac cagttaggcg tggaggggag  36540
gctccagcgt aagctgctgg tttggtgtgc caaccacagg atgggctgct gcctcttcca  36600
tcaggcttgt gctcagctct gctgccatag gccctgacct ctatccctgt gcttgctttc  36660
atcgccttca ggggttccac ctcaccttag aaatccctat tttgcacttt ttccttttgg  36720
ctttttgagg caaggtttct ctgtggctgg cctggaactc actctgtaga ccaggctagc  36780
```

```
ctcgaactca cagtgatcca cctgcctctg cctccaagtg ctggcattaa agctgtgcac  36840
caccactgca tggcttactt ttgtactttt tcatggaaca tcagctgcca ctgttgctgc  36900
tcctggtccc tggccaccct gggaaagcct gcatggctgc agagaaggga gccaggcttt  36960
cccgggctcc tgtcttccct ttgtaggtgc ctgcaaagtg cagacaattg gaagacttgg  37020
ttgtgtgcca ggcttgttat acctgcaggt tggctgctcg tcagggcagc tggtgcccgg  37080
gttagcctct ggttctcttg gacctgagtg ctaggataac agtgctaatg agccactgta  37140
tgtgacttta ttgtagtttt atttatttg aaaattttta tatattttta attgtatgag  37200
tgttttccct acatttctct ctgttcccat gtgtgtgcct ggtccctgta gaggtcagaa  37260
gagggtatca gatcctcagg ccttgcacat ggtaggcaag tgctctgaca tacatcccta  37320
gcctgttgct tgcttgcttg cttgtttgta cttgttagct caggctgacc tccacttgta  37380
tctgggggtg accttgagct cctgatcttc ctgccttcca ggtgctgggt gctgggatta  37440
taagtatgta ctgctctgcc tggttcatgg ggtgctgggg atggaacccc agaattcatg  37500
cagactagat gagcactctg agccatagcc tgtcccacca actgtgtatt ttcacttctt  37560
ttgagacaga gtctcacttt gcagctaggc aggatttgaa ctcattgtat tccagatggg  37620
ccttgaactt ttgattctct atatgaacct cctgagtagc ggggacagca tacccagggc  37680
ctgactggca tgtacaggga acactggggt gctggtggct agcagacctg ttgtgttttg  37740
agattccttc attgccagag tctactggaa tcctgaggtc tagggtaggg ctggggagaa  37800
gaccatgaaa ggaacacctg cccagagctg gcctgcataa aggatcaagt cagtccctga  37860
ctttctccat cttcaaggga acacaaacgt cccacctctg cctgagttta ctacttagat  37920
ctttgttgga acttaccttg gggataagac cagacctgta tagctatggt aagaagggac  37980
cttagactag tgccaaagtg ggtcacatgg gaggaggcat ggctgcttag ggcaaggtga  38040
cagttatagg ggcatagttg gatctttttg ggctgagagg acaggtgtgt ctctcaggtg  38100
tgttctgtcc tgtgtcccct aagcttgaat gcctctgacc ctttgcctaa tggtggcatt  38160
gcccatatta tgcacagcct tggtgggaca ttggaaagca gccctgtgtt tctgtcacat  38220
gtgttatgtt gtcaccaggc tgccccactt ccccacctct ggcctaatag atgctgcaga  38280
catgcattca ccacactcct ctggctgaaa agagtgtatc tgggctgttt agagagcagt  38340
agtgtgtgca gaggtagaga ggccagagag ggaggtatag ctgagcccca gagatcatga  38400
gttcctcaca ctgaagcttg ggacctaagc tacagagcca gggatttggg cagacagctg  38460
ttcactcctg aaaggttcag gagtctaaag atgaggcttg tgaggccaag cgtggtcttc  38520
cccttcagta ctttagacac ccaagtgctt gggagcttct tgttcagact ggtctgttga  38580
gccttgagta gtagctggta ctgtttaaaa attacctaag agcacaggca ccaggaagct  38640
tagtggccca tggatgaacc ctgcccttac ccagaatcat cctgctaaac tctgggtaca  38700
gggcttttct ctcccatcct cagccttcgc cttgacctgg cttggtctat gatcgatggg  38760
ccataaaaga gatgtcagta catagcctgt gcttgccaga gcccagcctg tcttgctctc  38820
caaacacagc catggctcct caccatgttc cacagggtca cttgttagat aaaactgtgc  38880
tttcttgagt tgaattttgt ttaagactga atctcatgta gctcaggctg gacttgaatt  38940
tgcttatacc tgaagctagg gtctaagaaa aaactgagct tggagcaggt gtgactcaag  39000
ttgggggcta gttgtaataa ctgcttcttg taatcatagt agcagtacat cttagacaag  39060
gtgacagtcc ctactggtct caaatctgaa gaagctatag gctaaacagg agtagtgaat  39120
gtgtgctaac gctcctgtgt aaggctctga aaaatccttc atgcacaaat cctttagact  39180
gttctgtttg tttgtttgat ttttgagtca gagtgttggg taggccagcc tcaaactcaa  39240
tgtgtagctg atggtgagct tgagcctctg ccccatcctg ctgcagtcac atgagcatgc  39300
cgccacatgg ggttcatgtg ctgctggcat caaaaggttc tctaccaaac tgagtcctat  39360
cccgtcgtgt ttttcagatc tattgttgta aggtgcatgc gtgtggatgc gtgtagagtc  39420
cgtggtgttg gatcctcctg agctggagct gctggtgtca tgagcctcct gacaagggtg  39480
ctgagcacca ggcagtttcc ctcaggagca gtagtcagtc atgactgtcg ggccaactct  39540
ccagcctcct tgtggtttgt ttgagactgg aacttatggc cttcattcga accctcaagg  39600
ttcacagaag gttcacagat cctatttggt tgttggttgt gtccgagggt ctttaacatg  39660
tgtctgagca cccaggcatt cttgtccaga catgcatgcc aataccaaat ctgaagaagg  39720
cagaccttgt gggcgtgggc atcaggagcc tgtcaccatg gtttcctctt tggtgggctg  39780
tgattaagtc ctgatccttg tgcttccatc ttccaacacc tacatacatg cttaagaagc  39840
agaagcaggt gctggccagt gtagtgagtc aagcccagcc cgttatagtc acacccatgc  39900
aggcaggtag aagctcctta gaaaccccct tcccagttca tttcctgggc acacagtgat  39960
gctgcccttg gggaactctg gcaagaaggc tggctggccc accaggctta gcagaatgtc  40020
tgctgacccc ggctcacctt tggtttcttc ctttatccct gctgtgtacc aggccctggg  40080
ctgaggcctg tgtagcctgc taagaggccc caggggagaa cctaactggt tcactgtgca  40140
gggaagggca gggagaatcc actctgctgc cagtggggat gtggctatca gaatgctgca  40200
gtgctggccc aggggccagt ggaacatggg gacctggatg agcagagctg tcaatgacat  40260
agaggtatgg cctgggctac tgatgaccaa ctggcaggca gctgaatcca gcacactttt  40320
ttttttcttt gagatagggt ttctctgtat agccctggct gaccgggaac tcactttgta  40380
gaccaggctg gcctcgaact cagaaatcca cctgcctctg cctcccgagt gctgggatta  40440
aaggcatgtg ccaccactgc ccggatcaca cttttttata taacatttga gcacatgtat  40500
taacaggggt atttttggaa gcagggtctc tttctgcctt ggaattatgt ttaaagtggg  40560
ctgactggtc tgtgagtccc atgtgtcttc ccagcactag gtgacaaaca ttcactccca  40620
catctgtctt atttttgtga gttctgtaaa ccaaatgcag gttctcagga ttgcatagca  40680
agcactttac cgactgagcc gtcagccttg agagcttctt ttcaaggcaa ggctttgctc  40740
tatagcccag gctggcctct aactcataat gctgcctttg gcttccgact gctcctgcag  40800
gtatgagctg ctccagcgag cttaaagcgg gcatttatgt taggacctgc caaaggtatt  40860
gtgtggcttg tatcagtggc atgccctctc tggattctct cttgtgttaa gagagggaga  40920
tgacacagcc ttttacccca gcatttccac attgcacctt ggggctctct gctcattaat  40980
ggcagagatg ttggctgcct ctcttctctg tcttcacaca catttgtttg tctgttctgc  41040
tgatcaaggc agttgaggtg aaggtagggc cctccagagc taattacgct aacaattgta  41100
gcaaacactg ggtgcctgcg agctgctgct gctgctgctc tgctgccagg ttccagcccc  41160
acaaacagaa tgcagatgat aaaggaggcc aaggcagaat gagtggcaag cagggagagg  41220
gagaagggaa ggagccagcc cagccctggc cttggtcctg gctctgctac cttaccctgc  41280
caccatctca catttgctga ctgccttgat ccggaagaga actgaagttc tgtgggggct  41340
gggtgactga tccattttta gtggcagctg caggaagagt atttccgctt gtctcctgga  41400
aggccagagc acggctgccc ttgggaagtg ggtcagctga ttgtgtgtgg gctgaggggg  41460
agtcccagag cctcctgtcc acaccctcac tggccctgct tctagcaccc atgctagaca  41520
```

```
gagccggtcc tgctgaggtc atcgggtttg agagtcactt cctctacaag gtgtctgacc  41580
tacccagtcc cagcaccacc ccatgtcctc ctgagcctca gatgccatgt ctgtgtgtct  41640
ctgtgagtgt atgctatttg tgctgatgtg cacctgcctg ctgcagagcc tggagaaggg  41700
aggatgtcag gtgccctctt catccctctc cacttgttcc tgttttgttt aaatcagtat  41760
aaccttggcc tgccttgaat tcatagcaat tctccttgcc tctgcctcct gagtagtagg  41820
attaaaggtg tgcaccacca tgctgggact tggaaaccag caagccccag tgagccgcct  41880
cttccccatg ccctttgggg ctgagggtta tgtacgtttg tgggatgcct ggttgtgggt  41940
gctgggatcc acatttctac ccttgagttt gcacaacaaa cttctgagtc atctctagcc  42000
acatgctttg tagttcttaa gtcagggtct cacagtagcc caaactggtg cctgccagtc  42060
tcacattcct aaaccctctg cctccacatc cctagatctg gaattacagg cctggattac  42120
aggcccttgt taccatactg ctgtatgcca tgctgggtgc ccaggctcc ttgcatgact  42180
gccaaggccc tgcttgtgga gagtctttcc tgccaggcat tctggccctg agctctttgc  42240
attctctctc tttccagcag ctggccctgt ggtcctgtac tccggatggc caggtgactg  42300
tttcttagat gccccacaca gcactcatcc tggctccttc tccctgcagg agaccttgct  42360
gcctcagagt gtcaaccaga gtgtgttctt gcaacctttg agacaagact tggcacctcc  42420
ccagccttta actgagcaaa tttaagcatc tagatcccag cctggcagct gatgccttca  42480
gttcaaacac aaactcctgc tcatcttttt gtcttttgtc agacagattt cctgtgtggc  42540
ccagttttgt ttgttttttt tttttttctg agacagggtt tctctgtgta gccctggctg  42600
tcctggaact cactctgtag accaggctgg ccttgaactc agaaatccgc ctgcctctgc  42660
ctcccgggtg ctgggactaa aggcgtgcgc caccatgccc agctctgtgt gacccagttt  42720
atctcacgct ccttcctcgg cctcttaagt atgaggtttg caggtgcatg ctgcagtacc  42780
cagctcttct cactgaggtg atggggtctc aagtgtcact ccatcccgga ccacacactg  42840
agctccactc tagcctggga ccaaatccct ttatcaaaaa gaaaagaagc tgtcagtaaa  42900
gagttagtca caaagtatga ctcagtactc ttataacagg ttggttgttg gggtgcacac  42960
ttgtaacccc agcgctgggg tggttgagat ggaccggctg ccagccagcc tgggcaagct  43020
aacgagctta ggctctgttc agaggcactg tcacaaaagc aatagaggaa ggctgtgagg  43080
ctgactctgg ccaccacagg cctgtgtgct tgtgtgcatg aacacgtcat gcacagaagc  43140
agagcagaac cggtagtaca cacttttttt ttctcgattt ttttcgaggc agggtttctc  43200
tgtgtagccc tggctgtcct ggaactcact ctgtagacca ggctggcctc gaactcagaa  43260
atctgcctgc ctctgcctcc caagtgctgg gactaaaggc gtgcgccatc atgcccagct  43320
aatgcacact tttaatccta gcaaagatga acaaaggagt gcaaggccgg agctgcttac  43380
acagtgagac tatctcaaaa tataaaccaa cccaataaaa taagagaaag aatgaacgcc  43440
gtgttcctca agttctgcag gactgaagtg gttgcatttc ttcctctgcc tggcacatgc  43500
ctggcacatg catgacactg catgtccttg tgtattctcc tttccctcct tctcaccttg  43560
aacatctttt tcccataaca gaatatgcgg aatttttgca ctgcaagtcc aaaaaattta  43620
cagactttga tgaagtccgg caggagatcg aagcagagac tgaccgggtc acaggcacca  43680
acaaaggcat ctcccctgtg cccatcaacc ttcgggtcta ctcaccacac ggtaaaggcg  43740
gggttgggat agagggaagc tggtactctg ttcctgtcca gtagggtctt cctgagcatt  43800
tgagaagagc atcctggact aggaaggctt ggacatggtg ggcaagagtg ggcataggca  43860
catgcctata accccagctc tggggaggtg aaggacagag gacagaggaa gaccccatct  43920
ccaacaaaag caaaaaacat tagacccagg ctcagtggtc aggcacttgt gtagcatgca  43980
tggaatcaac ccccaggacc acatttaaca taaaaatgaa ccatgagtgg tgttgtgtat  44040
accactaatc ccagcattca gtagacataa agactgtatt tgaaactaat ctcctctaaa  44100
cttttgtaaa aagttttgtt ttaatttttt ttaaatttta ctttatgtga gtgtactttg  44160
cctggatgtc tgtatacata ccagtcacat gcctggggtg cctgaggaag tcagagaggg  44220
agtcagaccc ttggagctgg acttatcagt ggttagaagc caccatgtgg gtgctgggag  44280
ttgaagccag gtcctctggt aaccactcag ctgcattctc tttactgtag ttctttacat  44340
tttcttttct ttgtgtgcat atgtggtgtc acattatgtg gtgcacatgt ggaggtcaga  44400
ggacaacttg aagaagtcaa ttctctcctc cttccatgta ggtcccagta atggaactca  44460
ggtcgtcagg cttagtggaa ggaatcttta cccactgaac tctatcactg accctattta  44520
ttttctgtct ctccctttct ttcaaaacac agctatgtag cccagactag cctcgaactg  44580
cttctatggt ccagttgacc ttgaattcct cgtcgccccc cccccccccc gttcctacct  44640
ccccagtgct gcacttatag acctgtgcac ccagacatgg tctctgctgt gctaggaatg  44700
caaagcagag ctttgtggat gatgggtggg tcctggacca cctgggctta tagcctgagc  44760
tacatggtga gttccaggcc agtctgggct acataccgaa cccctgcctc agaaatgaag  44820
aaggtatgat gggaagacac gtggcttggg aagtagagtg cttgctacac aagggaaagg  44880
cttgcattct cctatagcag ccatgcagaa cgcagcactg cactgcactg cacgtcttta  44940
attacggaac tctgcaggtc tgggcagatg gtccatccct ggtgctcagt agctacccag  45000
tgtagctctg ggctcagtga ggaaaccctt tctcaaaaga agccagcaag atagctcaat  45060
ggtaaagaca ccttctggca agcctggtga ccaagtttag ttcccagaac ccacatggta  45120
aggagacagc tgactaccat ggatcctctg acttctactt cttgatacac aaacacactc  45180
acacatactg acacaaatgc acacttacac acatgcgcac gcacacacac actctccttc  45240
tctctctttc tctaaaaata tattaaattt ttaaaaagta taaatatggt agagaacaat  45300
tgtggaagat atttgtgtga cctctgacct ccacacacgt gtacgcatga gggtactcac  45360
ccaacacaga aagtacacag tgaaatgtgt tctagtagga gtgttaggag tgaccccagg  45420
tgtgactccc cttgggaact tgctggtgtc cactgggttt ctacaggctg tgtgtaggct  45480
ctgaactcta aatggggctc tcaccacctt gcctgttgat ttccccctca gtgttgaact  45540
tgaccctcat cgacctccca ggcatcacta aggtgccggt gggggaccag ccgccagaca  45600
tcgagtacca gatcaaggac atgatcctgc agttcatcag ccgcgagagc agcctcattc  45660
ttgccgtcac acctgccaac atggacttgg ccaactcaga cgccctcaag ctggccaagg  45720
aggtggaccc ccaaggtaac cgcccgcact gggcagcagc cagtagtgct gggtcccctc  45780
cctgaggtgc tttctgtcac agttgtgtta gaagcctcct gagattcagc attccctgta  45840
accacatcac tataaccaac actgtgacag agccaccgtc ttttttttt tcttttttttt  45900
cctttttttt ttaattaggt attttcctca tttacatttc caatgctatc ccaaaagtcc  45960
cccatacccct cccccccact accctcccca cccactccca cgttttggcc ctggcgttcc  46020
cctgcactga ggcatataaa gtttgcgtgt ccaatgggcc tctctttcca atgatggccg  46080
actaggccat cttctgatac atatgcagct agagtcaaga gctccggggt actggttagt  46140
tcatattgtt gttccacctg tagggttgca gttcccttta gctccttggg tactttctct  46200
agctcctccc ttgggagccc tgtgatccat ccattagctg actgtgagca tccacttctg  46260
```

-continued

```
tgtttgctag gccctggaga gtcactgtct tttaaagagc atacagggtt agttaggctc  46320
ctggtttcag agtgtcctct tgtgattggt ggtttgttgc tgctgggcct gtgagcagat  46380
aacactttcc tgtgcacgtg gggagcaaca tggaataaga aaaggtcaag ggaggcagag  46440
gcaggtggat ttctgaattt gaggccagcc tggtctacaa agtgagttcc aggacagcca  46500
gggctacaca gagaaaccct gtctcgaaaa aacaaaacaa aacaaaacaa aaaaaagaag  46560
aaaaagacaa gggatccctt taagtgtgat gcttcaagtg accccagcga cctacaagct  46620
tcaaggagac ctcacttcac cacctctcag tggctctcct ctacagacag cttagcacac  46680
gggcctttga gagacattta agacccacat tttagtctgc agatttaacc ccagtgaggg  46740
gttgtccgtt cagaggtgcc cagcttgaat gattatctgg gtttgatcag aggtgcccag  46800
aatgaatgat tatctgggtt tgatctgaga atctgttaag agtactttct gctggacatg  46860
gtagcacacg cctttaatcc cagaacttga taggcagtgg caggtggatc cccttgagtt  46920
caagtctagc cagggcttca cagtgaaacc ctgtctagaa agggcttggt ggatggcact  46980
taactgttct ttttattttt ttggtttttc gagacagggt ttctctgtat agccctggct  47040
gtcctggagc tcactttgta gaccaggctg gcctcgaact cagaaatccg cctgcctctg  47100
cctcccgagt gctgggatta aaggcatgtg ccaccacgcc cggctggcac ttaactgttc  47160
ttgcagagaa catgggttcg gtccccgcac ccatacgatg cccacaacaa tctgtggttt  47220
caattcctgg gatctgatgc cctcttctgg cctctgcagg tacaacatgg tacacaaata  47280
tacatgcaca ccaaacactc atacacacac acataactta gttgacctaa tggcatatat  47340
aaatcaataa gacccagtct ttagcagagc cctcccagga cacagttata attccaggca  47400
catctgtctg cattgtgcag ttgtatctgg tgagatgaga acgtctgggc ctggagtagc  47460
tctgttggtg tgtgcctgtc aagcaggcag gatcccagca ctctgtgacg ctggtgtggt  47520
gccgcacact agaggtgaag gcagggggat caagatttca tcatctgcta cactgagagg  47580
ccagcctggg ctacaggaga acctctctca aaaaacaaga agaaataaaa cctggaaaag  47640
tagagaaggg cgcacacacc ctgggagagt ccgggtgggg ttttgagcag aggaggcctg  47700
tgaggccgca gaatgagctg caggtagggc tgtgtgccct cgtcaggagc ttcttagccc  47760
atccagccgt gctgtccgct gtccacacac agtgggcgtg gccatggcaa acattagcag  47820
ggcagtgcag gcggtcacca tttgtgagca catttttctt ttctttttttt cttttttctt  47880
ttcttttttt ttttttttt ttttttttt ttttttttt tttttttgcc tttgaaaata  47940
ctcatggttt ttacagaaaa gttaccatgg aaaaatcagg agcctgcaaa gctccctttt  48000
tccatgtaga tagcgctggc cacagttcct ttcaaagttt ttcttacacg taaacttatt  48060
ttttaagagg acagtctctc cttatttctg tctgtgcctc tgtggtcatt gcttttgttg  48120
attgcaactt ttctttgttt atttttcaat catggtttca gaatgtagcc ctggcttacc  48180
tgtacttcac tgtgtagacc aaggcagtct cagtatcaga ttctacctgc ctccccctcc  48240
caaatattaa gattacagca agccaccatg ccttgcccta ctttatatta tagtgatagt  48300
gtgttactct gtgggcaggc cccattgtac agttaccctc tcctcaccct cactgtctct  48360
cttctcagca gctggcttcc tgggcaacca tggctcaggc ccctctccac tcatttctct  48420
ccatagtgtg gcctcttccc tatcaactat gaattcttat aggtgtaccc acttcacaat  48480
agtgccagct aaggtagtca cctgtgatgg ccaagttgat cccagtcttc tgtgggcctc  48540
cattagcctc tgtgtgtctt gcacacatgg aacatacagg caacacattc acaggtgtgt  48600
ccaagccggt gcctgggttc cttatgtatc aggtggttct tgttagttag gcaggatctt  48660
ctgtggtcca gattggcttc aaactctgtt tagtgggaga tgaccttaaa cttgtgatcc  48720
tcctgagtct acctcccgag ggctgaggtc acgggtgcac accttgcagg ctcagtgtaa  48780
ccagatgttt aggaaagagc ccaggctcct tggcaagtgc tccgcacctc acctggcaca  48840
gggtcgacct agggtttctg aatgctaagg caagtccatg gagtacatgg gcttctaccc  48900
tggcttggaa gctcagctta taaactgctc gggtgaaccg tggtcaggac cccaaactag  48960
ggatccggga gcaagggagg ctgagaagca cagtggattt atttggtggt gtggctttgc  49020
tgtgggatgt gctaactctg gttgacttgg ggagaacttt gatgggctgg tccttggagt  49080
agtaattggg ccaggttgct caggttcaaa tgtgatgttg agaatgggca gggggggattc  49140
tagtttccgt gatgttcatt ggttctgctg gggtcttgtt atgcgcttac cagtgttctg  49200
tcactagagc agtaactgtc attttatact ctgccaacag ttgtccaggc aaaagatacc  49260
atggcttgtc cctgtctctt ggactgtaga gggccccaag ggcccttgat catgatccct  49320
tctgacctct ggactctttc aggcctacgg accatcggtg tcatcaccaa gctagacttg  49380
atggatgaag gcacagacgc cagggatgtc ctggaaaaca agctactgcc cttgagaaga  49440
ggtatgtaca cagggctggg gtgggccaca gatcaggggt gtatcttttg tggttctcct  49500
ctggacacag tgtttctaca ttacagctgt tttctggaac actaagaagc aggtatgcag  49560
ccacactcgt gctcggtact tgctgtaatc ccagcactct ggaggtgggg ttggggtcag  49620
gaattccagg tcatcttggg ctacatagaa agttctctgt cagcctgggc tacatgagac  49680
cttgtttcaa acaaacaaat acagaatgtt tcatcagaaa tagattgagt tactggaaat  49740
gagtctcagt ggttgtatta ctcagggttc tctagagtca cagaacttat agatagtctc  49800
tatagagtaa aggaatttat tgatgactta cagtctgcag tccaattccc aacaatcgtt  49860
cagtagtagc tgtgaatgga agtccaagga cctagcagtt gttcagcccc acatggcaag  49920
caggcgaaag agcaagagtg agactccctt cttccaatat ccttatatgg tctccagcag  49980
aaggtgtagc caagtttaaa ggtgtgttcc accacacctt taatcccaga tgaccttgaa  50040
ctcccagtct tctggaatcc atagccacta tgcctcaaga tctccatacc aagattcaga  50100
tcagaaactt ctatctccca gcctccaaat tagggtcact ggtgagcctt ccaattctgg  50160
attgtagttc attccagata tagtcaagtt gacaaccagg aatagccact acagtggtat  50220
agcccttgct cagcacatgc aaggaaccag gctcattccc cagcttccca aacaaagcat  50280
aacaaagaga cactgctgct gcttgagtct tccctagcta gtggaggctg gggggatgaaa  50340
tgcaggacca gaaagggagt caactacatg gggcagtccc tgttgaactg cacctccagc  50400
ccactcatac ctgcccttga agttcacgat gctttcctca gctaccttcc atgccattca  50460
cacccttggt ggggctcagt gctgccctgt gcccgctctc gtgagtgatt tttggaccag  50520
tctgtttcta gtctccacct ggccagctca gcacaaagcc atagcaccat gtccttcctg  50580
gcgtaacgca taccttgacc ttctttcttc aggctatatc ggcgtggtta accgaagcca  50640
gaaagacatc gagggcaaaa aggacatccg ggctgctctg gcagccgaga ggaaattctt  50700
cctctcccac ccagcctacc ggcacatggc tgaccgcatg ggcaccccac acttgcagaa  50760
aaccctgaac caggtatagc ggaggtttga ggccaccaag ggctggtaac tacagctaaa  50820
tgggaggttg ctgtagtctg gactcctgca atctaaccct gtgcagcctt tgagcacaaa  50880
tcctggcctg gctttcccat gccttctttc tcttgtccat cttgccctta tatttcctag  50940
ggtaggggtc tgtgaggcca tgtgtgtcca ggacaaggta catgccttgt gtgacaggat  51000
```

-continued

```
acagtaaaca gtatccaccc actgctctgt gcctcacgcc tccttactca cagtgacgac  51060
acagtgagaa aactggagcg cctgcctaga accccctagt gagggtgtgg gggtgtggct  51120
tggtggcaga gcacctgttt agaaccccac agtgggagtg ttacttagca atagagtgca  51180
ggcctaggat gtggaagccc tgggcttcat ctccagtacc gaataaatcc agtgtggtgg  51240
tgctactgta atcccagcac tcaggagctc agaaagccaa agtcattctc agctatgtga  51300
tgtgggataa gtgagagtct acctgagtca aaaaacaaca gcaaagacct ctttgctcat  51360
agattgggac ctgaagagag agccattgtc cttagggaat gtccactgga aagccagctg  51420
gtaaacgagc caccagatga attcctcaag tgttagctgt ggctggaggt tagtgcagaa  51480
tgaagctgag agcagcatcc ctagagcagg tgcagcaggc attgggcagt gtgtcttgta  51540
ggaagggata aagggggctg gagagatggc tcagtggtta agactgctct tccagaggtc  51600
ctgagttcaa ttcccagcaa ccacgtgtaa tgggatctga caccctcttc tggtgggtct  51660
gaagacagtg acagtgtact catgtacaaa aaaataaata aatctttaaa aaaaaaaaaa  51720
aggaagggct aaaagcagag accactggac ctggccaaag tgtggagggg caggaaggaa  51780
aaccctccac agagcctggg gctattgaga accagaggtg tatagcttgg ctggcccccc  51840
tgaattaaga ggtgctctgt ggagcattga ttgtttgtga gctcagcgat gtggtccata  51900
gcagccacct gctgctcagg cctgaggact tcatttcagt ccccaaacta aaggaacggt  51960
agaaggagac agtagactcc atgttctctg acctccaccc aggcacccta acatgtacac  52020
ttacccccca acacacgtac tcacagaagt aaataagaat tctaaaaggc ccacagaaca  52080
acctggctcc cacagacttg gggctcgtca caggccggag cctctgcact gctctcctct  52140
agcattggtg tgttcagaat ctttcttttc cctgctggga atccacctgc tatgcagtgg  52200
ggctcttgct ctgtccctcc cctccctcag tctcccgcag atgtggcccc acgtcctgct  52260
caaagcatat acctttgagt cttagttaga gggccatccc aggcctgcac actggtccca  52320
ccatccccat ccttgggtgt caactgacat ctgctacagg ctctctgctc cacttgttcc  52380
agcttctgtc cccgtctcaa tgatttgtct gtaggtttgt ggctctcttt ggattgcacc  52440
caagactgag tattctggcc tgagggtgga ttgtgttctt tcctggcctc tgggcctgtg  52500
gtaccctgtc tgacccttac cttttctata gcaactgacc aaccacatcc gagagtcact  52560
gccgacccct cgcagcaagc tgcagagcca actgctgtcc ctggagaagg aagtggaaga  52620
gtacaagaat ttccggcctg atgaccccac gcgcaagacc aaagccctgc tgcagtgcgt  52680
actcactccc cttccccttg cctggcccag tcatcctgct ctccattcag gcccttgtcc  52740
taccctgccc ctgcgagtgt ggggtccagt ctctggacat ttaacatgac actgtcattt  52800
gtagggttca tgtcctgaaa ctgtgtacct gcattacaaa aaaacaggga aaagtcacat  52860
tgtttcaaca agttaccatt gtgtgctaat cccagcattt tagtaagttg ccattgtgtg  52920
ttaatcacag tgttttagta agttgacatt gtgtgttaat cacagtgttt tagtaagttg  52980
tcattgtgtg ttgtgcctca ttcgttgctg tagtcctgtg gcctgtggca ctcaagttgg  53040
acacagctga acaaggtatg ttatctaagc ctgtcatcct gggccttagg aggtggtggc  53100
aggaagataa atcaaaactt gctgagctga gaacgtggat gagcaagtta aagtcgaggg  53160
cctgagctcc atctcctgac ctagtgcaag gagagaaacc cttcctccaa gcctgagggc  53220
gtgcacccgt gatcccgtgg gtcatgggga gatccagtct ggggagacag actgagctcc  53280
gccttcaggg agaaattcag taaagtagag agagatttaa agacagtgga cagtcacttc  53340
tttcctgcgc acgtgcacac acacacacac acacacacac acacacgaaa gagagagaga  53400
aaacaagaca ctgtttaaat gaaaaaaaaa gaaaaaggag agagcaagca aatataccat  53460
gatcaactgg gtgtggtggc ctggtgcaaa cttcagccac ttggtaggca tttgggagtc  53520
ccttccttcc ttgcatcatt tagttccaag aggtcaaaca ctgtggccct cagactcagt  53580
gagaagtacc tttacacact gagccatccc aggaccacac ctacccccaa aatatgttct  53640
ttttcgtttt cctttttttt tttatgctta catgaactgt tgatgccttg tgtggttgcc  53700
aagttctccg gtgctcaccc tgtcacctgc tctgcacaga tacaagctga gcctcacagt  53760
gcagagccac ttagtcaaga tttcccagcc taccatgttg tcgctcctgt gggaccgagg  53820
tagagaggta gcggaaagta aagatgctcc tcagccggtc tggagcagct gccttgacag  53880
acagccatgc agtcaatcat gggacctggg gaaggactgc atagctgtgc cctcagaatt  53940
ccatctagaa ttttagtatt aacagatcta ttgaggtctt gagaacaacc aggatagtgc  54000
ccagcactta ccaaagtagc gttgatactt tacacattgg ctgttaaaca gtgatattga  54060
aaaagaaaga aaaatggcca aacatggtgg catacatgcc tgtaatgcta gcatggaagg  54120
cccagacaga agggtctgta gttgaaagcc agttggggtt acacagcaat acctgtattc  54180
acatacaaca atcccatgaa aatgagccac aggactgaca aggtggctca gcgggtaaac  54240
aggcttgctg ccaagatagc ctgagtttta tccccaagac gtacctggta gcaggagaga  54300
actgagtccc ataagtctcc tctgacccca ctcatagact gtggcatgcc tccttccaat  54360
acacaaatgt aacttaaagc ctttgtaaga gcagagctta tctcttgatt catgtaatta  54420
cagggccgtg cagaaaactc tgtcttaacc ttttgccttt tctttcgtga aggatggttc  54480
agcagtttgg agtggacttt gagaagcgaa ttgaaggctc gggagatcaa gtagacacac  54540
tagagttgtc tggtggagcc cgcatcaatc gtatctttca tgagcgcttt ccctttgaac  54600
tggtaaaggt aggtgttcag cctggagtta agtcagacac tctcatgctt ggtctttgtc  54660
ttggccttaa aaattcttac aaaccatgat gttacaagct cctgcatcat gtcagaggct  54720
gctgtcagca aacttggtct gaaggacatg tccccatctt cccagatctc ataatttaga  54780
agctctgagc tgaacaggag gaaagtccat gtttcttcca ctggtggagg gaagaaagat  54840
acatgggggc caacgagata gcccagcagg taccctctgc tctgcccgac tgcctgagtg  54900
tgatctgcag gcagaagcac agaaccaact gcaggttgtc ctctgacctc cacacacaca  54960
ggcactgaca acacacacaa atgtgcacag agggctgaag agatggctca gtggttaaga  55020
gcaactgctg ctcttccgaa agtcctgagt tcgaatccca gcaaccacat ggtggctcac  55080
gaccatctgt aatgagatct gacgccctct tctgatgcat ctgaagaccg ctacagtgta  55140
cttaaataaa tctttaaaaa aaaaaaaaaa aaaagtgcac aatgctaggc ttacaccagt  55200
aactgcagag ttgtgtgagt tgaggcagga ggagactgag tttgaagata acatggcctg  55260
caaaagaccc tgtctcaaaa actgaaacaa aaacaaaaca gaaaagtaaa gcaaactgtc  55320
tttgtgtcct tttcctttga ggccgtagct ctcacctcat aggtgtgtgt atgctagtgt  55380
ggagatcaga gaacagcctg cagtgtcccc taattggttt ctctgtgtta gccctggttg  55440
tcctggaact cactctgtag accaggctgg cctcaaacct agagactgct tgcctgtgcc  55500
tcctgagtgc tgagagtaaa ggtgtgcact gcctctgcca cctagccact acgcacttat  55560
ttttaaatca aggtctcatt gtaactcata tttggctgtg tagtcatgct tgatcttgac  55620
cctctacccc ttatggtagg attacaggct agtgaatgtc agcacatcca gtttgcctgt  55680
gttgtagata gggcccagag ctccacacat atgtggcaag catccggcga gcatgagaac  55740
```

-continued

```
cgcagcctgg cttagcctta ttttcttaga caggatgtct cacctacctg gaacggtacc  55800
agtaggttag gtctgctggc tggaaagttt agtgttttac ttatgtttat gaacattttg  55860
cctagtgtat gctgtgtgta ccatgtacat gcccaattgc ctacaatgac cacaagaagg  55920
cgccagatcc cagggaatgg agttattgat ttagtgagcc attatgtgag tgctgggaac  55980
tgaacctggg tcctttgcaa aagcagccgg tgctcttaac tgctaagcca tctctgcagt  56040
ccagtatgcc cagatacagc catctctgca gaccagtaca cccagatgca ctcaggtctg  56100
caggcttagt ggcaggtacg ctaacctact gagccatctc tgtgaccttc agttgtttgt  56160
aagtttgagc ttgctacatc atctttgtga gatacactgg tgaatagaaa cagagctagc  56220
cactgttcct gctgtgaggt gccctggacg tggctccatg tgtggttggt ttcttctcag  56280
atggagtttg atgagaaaga tctacgaaga gagatcagct atgctattaa gaacatccac  56340
ggagtcaggc aagttccatg gggaattccc atgttctctt cctgtccatt catgtgggcc  56400
ccccaacctt ctgagtccct ggctagtgag gcctttagaa ggttcatgga tagtttccag  56460
aactgtataa acatcttagt cttcaaggac agagaaagtg cgtgtgtttt ggctgtgact  56520
gtcctaggtc tcttgattac ttgtgtcccc taggatacat gaccttgttc tgtgagatct  56580
atagtgacca gaggttgggt ggaaccagac ttgaatcatg cccacaggcc ccatgtcatc  56640
atgggtcact tgtgggcctc ctggtgtccc ctccttaatt gcaatcaatg aagtataccc  56700
tgttctctag cgtcccaaga tccttgggtt accctgaggg ctccccagtt ggggactctc  56760
tggtatccta cccccagctt taatgggata gttttccttg tcagggacct agccatgctt  56820
agaaagttgc tgaccacacc ctttgtttct ctctgactta tctctccctg cttccccact  56880
gggtctggac gtttttagaa ctgggctctt cacgccggat ttggcgttcg aggccattgt  56940
gaaaaagcag gtggtcaagc tgaaagagcc ctgtctgaaa tgcgtggacc tggttatcca  57000
ggagctaatc agtacagtta ggcagtgcac cagcaaggta ccacacctgc ggacgcgggg  57060
ccgcaggctt ggtatcaggc cccaggttac ctcacttcca agaatcctac agggatggga  57120
ctgtgtcagt ctggacccac tcaggagggg gtgggggaat gctgggcttc ttagaaccag  57180
ctagactggt gacaggtctc ctgggatcct gataccaagc ccagcatgcg tatggtggaa  57240
tggggatgtc atctggctgt gttgctttgc tgcttgcgag ggaagcagat cgggtattcc  57300
tcttcagctg ttggaggcca aggctcccga agcttcactg ttatcccccct tgaaaaatga  57360
caaatgcctg cttctttgga gtgggtcact tctctgttcc catggcactg ggaagaacat  57420
aaacactggt ggcatactga gagctcagtg cccagcttca cagagctact tgggttccac  57480
agtggctctg ccagccttca ctgtgccctg tgctgccctt gttccatccc cacccctccc  57540
aggtaactcc acactcagtc ctcatggtct tcaatgagga ctcatgccca ctcttcatgg  57600
gcaactgcct ccatttggcc caaaccacca ggctcctctg ggaggactgt atcctgggac  57660
agcacgctcc tgccaagcag cgggagtgct tgaggggaag gagagggcgt ctgctagtgc  57720
aacctcgaca ttgtcagctc tgaaagggca gagagcacct gcttcagctg cctgtcctac  57780
tggagcaaag tccccatttg cttcctcagc ttctccagtg ggaaacagag caaaataagc  57840
cagccaagca agggctgggg ttagcgttag ggtgagtttg tagagtgctt ggctggctgc  57900
acaaagcttg gggttccatc cttagcatcc catagaccag atgtggtggc tcatacctgt  57960
gatcccagaa ctggatccag gagttggaag taggaagtta gaagttcaag gtcatcctca  58020
gtatatatac taagttggag gctagcctgt gctacaaggc catttcaaaa actgaagccc  58080
agaggggctg ctgattgaca ccctctggtc ccttatcaca gacgtgatga tttaagattc  58140
ctcacatgcc tttggcccta tgctgagtgt cctgtagcac ttagccttga gctgtaggcc  58200
agcctatgct cccccaggcc ttgcttatcc caagctgctt ccaggacaga tgtgggtgca  58260
ggcttttctg cgtatgcact aaccagctca ttctcctttc ttctctttct ctctttatct  58320
cccgtcctat gtgtgcattt gtgcgtgtgg cctgcactac ccctgggtgt ctctcaacct  58380
cgtcccgccc tcctccgcat gaccaggacg gggctcttca cccccgacat ggcctttgaa  58440
gccatcgtga aaaaacagct tgtaaaactc aaagagccga gtttgaagtg tgttgacctg  58500
gtggtgtcgg agctagccac ggtcattaaa aagtgtgctg agaaggtaac aggtcttgct  58560
cctcctgtcc ctcatcaatt cccacctatc atctcttcat tggtgtcagc cctgagcatc  58620
gggacaacct tgcctacagg ggacccctgc tgggcacagt gccatctgga actttgcgtg  58680
gcaggctgag tgggggaggt acagcgcaca cgtcccaccc tctcagtttt ggggtccagt  58740
tgggaaacct ttgccatgtc caagcacagt cacatctgtg aaaccattct cacttctaga  58800
tgtcacccct tgccaccact gtgtcctcct gtgtgttcct gcattggggt gcgtttagca  58860
gcatctttcc tctcctgggg aaagtgtggc tcgggtcact cactacccca gataaaaaga  58920
agggagtctg aggattggcc acatggctgc caaattcaca gagatcaggg aatattttcc  58980
agcaaagggt tccctgagct cagcgacccc gacgctgtgc cttttatcct ggagcagggc  59040
actatgctca ttcgaatgcc cagtgagggc catcagtttg tcctgcctgc acctagtgct  59100
gggcgggagg gggctgcctg gcacctctgg gtagtaagtg tcattcaccc tctctgccac  59160
tttccacctc caatcgctgg ctttgcaagc ggctctcagc atgcacggca ccctcttgcc  59220
tttcccactc cacatgcccc tgactggcct gcccttgtct cccggctccc ctcccctccc  59280
ctggcctggc catgaagacc ttgtcagctc agcccttgtg cttgctcccc agctgagttc  59340
ctacccccgg ctgcgagagg agaccgagcg aattgtcacc acctacatca gggagcgaga  59400
agggagaacc aaggaccagg tattgtacca gttctctgtt tcctctttgt tcatgtctag  59460
caaattttga gaatttagtt ttgtgaagtg ataatatttt tctttaactc aacctggctt  59520
ccaaataaat tagtcagaga ctctaagatg tacttaatca agctatatga cacaatagct  59580
aagtagttat taatctgttc taatccttga agctaatctg gcgacctccc agccatagtc  59640
tccaaggtac ttgtatcttg tgtctggctc tctgctccaa tatgttccta tatgttccaa  59700
tatgttccta tggtgagcat cacagagatt cctctctttc tttaccctcc cctggctgag  59760
gtcagaagtc cagccataca ctctccagtg ctcagccatt ggcagatcag cttttattga  59820
gaaaacagag aataaaccaa caactgtata cacaacattg agacaagaga tacttagaat  59880
agacaacagt accatgtcca gattgccacc agatatgggg acagaaatca gcatttgaat  59940
aagataagga tatttattta tttatttatt tatttattta tttttgtttg gttgtttggt  60000
ttttcgagac agggtttctc tgtatagccc tggtgatcct ggaactcagt gtatagacca  60060
ggcttgcctt gaactcagaa atctacctgc ctctgccttc caagtgctgg gattaaaggc  60120
gtgcaccaaa catgcttaca ctgtgaggtt ttggttttgg ttttggtttt ggtttttttt  60180
tttttttaga tattttcttt atttacattt caaatttctt agtttcttct gaaaatcccc  60240
tatcccctcc tcctccccct gatccccaac ccatccattc ctgcttcctg gccctggcat  60300
tcccctatac ttttgcatag aacccttcaca agaccaaggg cctcttctcc cattgatggc  60360
ccactaggcc atcctatgct atatatgcag ctagagccac aagttccacc atgtgttttc  60420
tttgattggt ggtttacagc tgtttatctc gcctgtgttt tccatagcat gcacgtggag  60480
```

-continued

```
gctggaggac atctctgagg agggttcttg ccttctcttt atgcagaggt tctgggggtg  60540
atgtgggggg gtcgaactta gttcaccagg cttccaaggc aagtgtcttt atctgcggag  60600
ccatcctaac agctccagat ccattctgag gcctaggacc atgatgcggc taatatagca  60660
cttgcctagc atgcgaagcc ctagtttcca cctccagcac cctgtcagga tgtggtgagg  60720
cacaattgtc atcctaactt gggagcagag ttaggaagat ccgaaactcg gtgtcatccc  60780
ttgactacat aactgagttc aaggccagcc tgggctacag gagactgtgt cgcctaccac  60840
accttcccaa aaaaaagaga gaaaggaaaa aacgaattat tactatctgt ggccaccaac  60900
ctgtatcctg gcctccccat aatgcattga gaagtcttcc accatgattg ttcaggtggc  60960
attaatgtct ttgtgcaact acagattaga ttgttctata catgcaacta aatctttgtt  61020
cattttctca agaccaaggt gttctgttct ttgccgggcc tttccatagt gcttcgggga  61080
gactgtgatt tccaactctg acccagtgtt gagggccatg tgtcacctat ggtggcagtg  61140
gttgactttc tccattgttg ggacattttc tactgtgaat ctactgtatc gttttagagc  61200
tgcccctacc tgctggagaa atgctagggc atctggagcc ttgcacttcc ataccctgag  61260
ctgtcattaa cccttcagga ggggagctgg agccatgcct cctcagtgga cctcgattgt  61320
gttcccagca ctcccatgtt tactcacaat catctatgac tccagttcca ggagctccca  61380
tactcctagt gttgcaagcg ctaggcacgc acagtgtgat cagtcatata tgtaggcctt  61440
gtacatatag aataaaaata atctaattat ggggtctcat tacaggtgct taaatctaaa  61500
ttactgcaag tgttcatatt gggcctgtca tggtgaaaaa actggctcct ttgactttaa  61560
gccagcattt agtactggac ctcttagaca ctctgtaacc ccatggctta ggagatatgg  61620
ctttgatgaa ggggcctgtc atcacagtat ggagtcatca cagtatggag agactgaaat  61680
aggatgagca agaattcaag gctggacaga ctgggttata ttatgagact gtctcaaaat  61740
aaaacaagga cagaatgctt ctgtcataca catagccctg ggttctattc ccagcacctc  61800
aggaacctta cactgatggt gcacttgaga ttgctcagga ggtggaggca ggaggatcgg  61860
gagttgaagg tctttctcag ctgtgtgtta aattagaggt catcctgggc tctgggaaac  61920
cctgtcccca gaaaacaaac agaaagtcaa aacaatacac caccgaaata caccatgaac  61980
acttctgctt gtttccatca ctgctcctga ggctgctgct gctcttcctg tgcacacagc  62040
ctctgggatc cactgtggac actaccaggc ttcacagcag agctgtggga agacagtgtt  62100
caggccttac agagccagct tcagggactc tgcacaacac cccgccctcc ccaacaacct  62160
cctaggtctg tgtatattgt cttggttatc actgaggagc taaagacaca gtgaccaggg  62220
agtgtctggc cttgagccag cagaaacctt tgccagcgga accagagccc ctctgccagg  62280
cagcctggcc tgttgttaat aggaactagg gtagaaagct gcctgagtca gtacagtcca  62340
tggagcgact tcagcctttg caaactagga ccattagcat cctagcagac agggctgtaa  62400
tgaggttggc agtggactat agcggcatct ctgtctgcca gatttgagaa tgcagctgtc  62460
tcaggtatgg gcatgtacac acatgctggg cacctgcaga ggtgattggg cttttagtgc  62520
gtgtggtact gagttccatc tttttttttt tttttttttt tttaagattt attagccaag  62580
catacaagca tagtggtgca cacctttgat cccagcactc aggagggcag aagcaggtgg  62640
accatatgta ggtatatggt ctacagagca agttccagta tagccagagc tacacagaga  62700
agacccatat gggaatgaat attttgtctg catgtaatgt gtgtgtgcta catgcatatc  62760
aggtgcttgt agaggccaga agagagcatc tatcccttgg aaccagagtt cgagacaggt  62820
gggagccacc atgtgagaac tgagaattga actcaggccc tctctccagc cctcagccat  62880
actcttaatt ttacattagt atgtttgaaa acagagccac acataagcca agcatgttgg  62940
tgcacatcat taatcccagc acttgggagg cagaggcagg cggatctctg agttcaagga  63000
tagccagggc tacacagaga aatcctgtct caaaaaaaaa ggaggaaaga aaagaaagcc  63060
acacatgggc tgatgctggc ttgaactcgg agtgcagctg tgagagtatc tgtataacat  63120
acacacatgt tgtcacgtgg gtgtgcgtgc atgtgaactg atgagatccc agaggcgagt  63180
ctgacgtcag atgcgctgtg atttgaagct ggctcaggag cagcgtggtg gtaaaacact  63240
ctcctaacat ttataaatcc tgactcccaa caatggcagt atcaataaaa gagaaaaaga  63300
aagagaagag aatgaattcc aatccacttc cataacttaa taacattagg ccccaggtca  63360
caggtcaggc cgtggcccaa ggaagacagc ccacaaggca gtacccatgc ccaccacatt  63420
gagctaccag gcactgtccc cttatcccag ccttcctgtg tggctctttt ccacctgcag  63480
atctcccctt gtcctggtga tttagcctgc ccgctacacc ctgtcgggga gagcaggggg  63540
ggggggggatg caccagttat gtctgctgcc ctctgctgtg tgtgtgtgtg tgtactgtgc  63600
cttccttgct gttctgtaca ctgtagtcac acacccctac tttcctctag attcttcttc  63660
tgattgacat tgagcagtcg tacatcaaca caaaccatga agacttcatt ggatttgcca  63720
agtacgtata cagccattgt cagaggggca gcaccaagac cagagtggtc atccatctgc  63780
tggggatgct gggcaaaggg tagagccatt tgagagtgcc ttggagcttt ctgtgctgtg  63840
acttctgtca cagtgtcctc acctagcatg ttgtctatgg acatctcagg gacaaggtgt  63900
gtactctgtg gccattctca gggaagagga ggccagccag gttcatactc tgcatgactt  63960
cttagagctt ttcacagctg gagcaccatg tgggctctgc ctttcacaca ctgtacacag  64020
atacatacgc actgtagact taaaaccaga accttggggt gggatgtttc cattgttagc  64080
acttggctag catgcacaag acctggatta gaccacaggg ccaaaacaac agataccaca  64140
cctgattgta ttggtcctgg gtcagccata agctctggac cagctgggca aacttgggtg  64200
ccacgggggg gggggggggg ggtgtgttct ggtggctcat gcagattttc ttagctttag  64260
acaataggat accaccaggc accaaaagac agacccttgt gtccatctat actactgatg  64320
tactttcgtg ccagatccct tgctggagca gtacacaatc taggccaggt ccacctgtcc  64380
acaggaagtc catgtgttaa gacacagtcc acttgccggg cggtggtggc gcacgccttt  64440
aatcccagca cttgggaggc agagacaggc agatttctga gttcaaggcc atcctggtct  64500
acaaagtgag ttccaggaca gccaagacta tacagagaaa ccctgtctcg aaaaaccaaa  64560
aaaaaaaaaa aaaaaagaca cagtccgctc aaggctcttg gagtccagag ggtggctatg  64620
gggcttttag agctcgggtt ttagagacgt gctaagtggg agggcacaag gctgaactgt  64680
ctattgtctc tgggcagaac tggtggacca tgagctctga gcgggcacat ggtggatgaa  64740
tgaagcgaat gactgactgg tcgatcagaa gccctccctg agcacgtgta gcctagggcc  64800
cttagctggg tgatttcttc cctggggtgg gctgcattgg gggctgggca aggcagcctg  64860
tttaagccct gctcttccag ccgtgcatgg gcagcagagt agcccccatt ggttgctttc  64920
agtttcctca cctcaatgtg tctgcttctc acacttcatc cacagttcct tctcacaatc  64980
tctcctgttt ttcctttgac cactccactt ctttctctgg attccggggc cttcccactt  65040
acccagctgt ttctatactg aggagctggt cacagggtgg gtattgcctg ctgtgtgcct  65100
ttttccctgg tgtgtgaccc ggggcgtcct ccctggggag cctcaaacct gtgggggatg  65160
ttccagaagc ccttgaatta caacagccat tctctcaacc agggccccag ccaggccttg  65220
```

-continued

```
tgaagaggac tctgggtaag acaccataga gcctgccgta tagggcgcac agactgggga  65280
gtcgtggaca gtggcacagc agcctgaggg atgagcactg gggagaccgt cgcagagaaa  65340
tcatgcagtg gctgacaggg gactgcaggg agctggtact ggacagggag atcaataggc  65400
aggacaccag ccagtgaggc aggatggaga caacagctgg tgaccacgcc cctcatcagg  65460
gagaccctgc catggcaccc agtgtctcta gttagggcca tcaccatctt ggctcctgtt  65520
tgagggagct atgtagcaca taatacataa gtagcacatc tggccccttg tcactatact  65580
gttgagtgat ggcttagctt agtctcacct tcttcaggat ggctcattat agacagggcc  65640
taaaggaaac accctgtgat ggctgctgcc gtggcacagt tggtagagca cttgcttagc  65700
atgcatgaag tctagcacca aatcaaaggg gtgtgatagc ccactggaag agagagagag  65760
aaacagcaca attggtccaa agttatcttt ggttatatat ctgaagtaga agccagtcag  65820
gaacacagga gaccctccct ccctcaaaaa aaaaaaaagg ccagtaagat gatttagcag  65880
gtaaaggtgc ttgctgtcta agctgcatga ctagttagat ccctgtgtgc acaatgctgt  65940
gccctccaaa aaaaataaag ataaaaagcc gagccctggg agagtggtgt cagaagagca  66000
ctaaatgggc atctgtgtgg gtccttacca gtctagaata aagagcccat ctcctccaaa  66060
cactcactgc ctttctagca actgactgaa gctttgttgc tgctccctag tctctgttta  66120
ggctacttga actcctgagg tagcccagcc taggcacaga ctcctcctac cttagcctcc  66180
actggggccc ctggcttgta cgctcactta acaactttaa attgagtttc ccaattgaaa  66240
ctcagctggt ttgagctgta ggcagaatct cagagcagcc agccggtggt gaaaccaagt  66300
gtgttgctat ttgtgtcctt ctgcagagga cctgggttct gttcccagaa cccacatcag  66360
gtagctcaca accacctgct actccaggct tccagtgccc tctggcctcc atgcacacct  66420
cacatgtgtg gtgcacataa gctcatgcag gcaggcacac acagtgacat acatacacat  66480
gtacatcttt tttttttttt tttttttttt aaagatttat ttatttatta tatgtaagta  66540
cactgtagct gtcttcagac actccagaag agggcgccag atcttgttag ggatggttgt  66600
gagccaccat gtggttgctg ggaattgaac tcaggacctt cagaagaaca gtcgggtgct  66660
cttatctgtt gagccatctc accagcccac acatgtacat ctttataaaa aaaaaaaaag  66720
aaaagaaaac tataacagat gagtgacagg acacggtttc tttcagatgg ttatattact  66780
gttagaatat gcatcagaat cagtaaggag agtggtgggt agctacagga agtgtagtgt  66840
ggtctgtcta cagcgccact gcatgcagag cacctggcat acacaaagct ctgttttcgt  66900
ccccagcact tcacatactg catatggagg cagcctggag aacttgaagc ccaacaatcc  66960
cagcacttgg gggggctgag gaaggcagat ctctttcagt aactgtccag cctggtctac  67020
atgagatcta agatagccag ggctacatag tgagaacctg gagagacaga gagagagaga  67080
gagagagaga gagagagaga gagagagaga gagagaggaa gagagagagg aagagagaga  67140
ggaagagaga gaggaagaga gagaggaaga gggagctaga gttgctgcgg gtctgtgaag  67200
gggagcacac acgaggcctt gtatttggtc tgctgcattc ccttctcaaa gctgaaggtg  67260
caagaacctc ccatagtggg tttgggcaag tccttctagc agccatttgg ccagtgtaag  67320
ccctagaact atcagggctg gtgatgggag ccacttgtag actgatgaag ggtcagtggt  67380
gggaagagaa tgtaaagaag ccccaggtac gttgtgctca gggtcccctg gaaccagctt  67440
cctgtcccag tcccctgcat cttacacctc ttctttgaag ctctaacttc tagtgacttg  67500
tgggaaatag ctggtgcttc tggagtggcc atgagaaggt tctagaagcc agggttagcc  67560
agatacactt ttctcatttc atgtgctcta gttgttctct atgttcagga gccatggcct  67620
tgcctctgcc cttagtgggt cagtgggccc ctagggaagg cacctcagcc cgggccgcca  67680
gggcatctct ttacctccct cccatgtctc atctgaatat gccttctctg cttctgttac  67740
agtgcccagc agaggagcac gcagctgaac aagaagaggg ccatacccaa tcaggtagct  67800
ccccagtctc tgctgtcact cccttctgaa gacaggagca tacttagctc atcatagcat  67860
ttgatatggg aaccgactcc ttagtactag gctgctctgt cagcttctgg gtcatgtagc  67920
tgttagaact aaggcttcca caggaccttg gggcaaattg caaacaccca aaggcctcat  67980
ctgacatcta atgtgaaagt tacaacttga ccctcaaagc aggagatgtg ttacagtgac  68040
cccgaggtgt atgttttcta actcttggcc ccaggaatga aggcaggtag gtagaaacca  68100
tggaaagtgc cacaggcaac tcagggaaga tggggatggt ttgaatgcca cggctggaga  68160
accccaggcc tcctttataa tcccacccca gcttcagagg cttcgcatac ttacagatgg  68220
cttcagagat gccagtatta cgtgtctggt tgggcttgtt tttctgtcca gtttctgcac  68280
tgtcccccaa ttcccttccc atgtcagact ggggtgggga tggggcgctg tgctgtttta  68340
tcttgcacga tttagagcca gatggggaga aatgtaacaa atgcatgatt ttgagttttc  68400
tttttgtatg tgtgcttgcc ataggtagta catatgttgt tgcttttttt tgttttgatg  68460
aagataatga attaaatatt aacaccatga atataattaa tagcatgtaa ttttttttctt  68520
ttgctgtttt tttgttcctc tgatcttcct tctcctaccc ttgtgctttc cctgcgttct  68580
ctctgtccct acacgcccct tccatctctc ctgctctccc ttgattgacc cacaacccta  68640
actttacatt ctcaaagggg gagatcttgg taagtacctg cttagtgtgg tagctaactt  68700
agagacctag cagtaaagga ggcctgcctt caccctctgc tcaaaaaaact aaaacgtgca  68760
ctaacccggg agctacacgt caccgctgtc actggacctc gcgctgtcct ggggatctgt  68820
tgctctcaca aaaatactaa cccaattgca gctctctggg agacacgccc ctctgctcag  68880
tcctagcagg ttctcttggt gtcctgtagt tcaaagatgg caaatatgca ttcacacatt  68940
gcctccggcc ccacctcagc ttcctagaca tgcagatttt gctcaggacc tgctggaatt  69000
catttctttt tttttttttt tttgtttttt tggttttgtt tttttttttg gttttgtttt  69060
tttgtttttt ttcgagacag ggtttctctg tatagccctg gctgtcctgg acctcacttt  69120
gtagaccatc ctggcctcga actcagaaat ctgcctgcct ctgctgggat taaaggcctg  69180
cgccaccacg cccagcttgg aattcattct tgctgccagg ccttatcctc tttctcttcc  69240
tgcagacatc actgactgac cagaccatgg cttaccacat gaggagattt gcctttctgt  69300
gcctgtggca ggcatgacta aatgatccaa cactctttcc tgtgattttc ctccacagtg  69360
aacccagggc agacactgct aatcaaccct ggcattcttt cttaatatgc acaccattga  69420
ctccccattc tgtagctatt gtgactgatt attttttttt ccattttttta ttaggtattt  69480
aactcattta catttccaat gctataccaa aagtccccca tatccaccca ccgattattt  69540
tttttttaat tttccatatg atatcctact cctttactca cataggcata aataatcagg  69600
ttccctctag cctgctgcct tcatagcagc tggatggtca gttccacttt cccacttttc  69660
ttatccattg cctgggacag atatcacaga gtgatcccag caccttttct gctgtgctca  69720
gaattgttgc catagactac tcctaccagt cagttggtgt gcattgtatt tgccatccta  69780
actgtgggca actcatcttc cttttgctca agggctggga gctggggttg tcagaagggt  69840
gtgaggccca gccctgctga aagctgagtc tgtgtggagg tgctccccgc aagcagcttg  69900
gcctcaagcc ctgacagacc cctttctcca ggatattctc ctgctgccac caccattctc  69960
```

```
tgcagggata ttcttggagt tttgactttt gcaaaggttg agccacttct gtgtgtaagt  70020
ggtgggtcct tgttgcacct gggtcctggc aaaagcaggc tgggtcaaag tcgaaacctg  70080
ggccagtgtt agagaagagg ggtctaggac cagattagcc tcaggcctgg agcaaagcag  70140
tcaagtagca cttctaggtg gtcattgttc ctaccttgtt ccattctcct ggccacaaaa  70200
gcacacacag cctggagatc ctgagcgtgg ccggccgtag cctcgggtgc cttggccatg  70260
cttggtcttc caagtgatct tcacccagag aggaaaccat catggctcct gccgagctcg  70320
ccttgctact acttgctgct caagcccctg ggatgggtcc tttctgtcct gcatgcctgc  70380
atgccgttac tgtgccccag gaatggccat cctagctgcc tctgctcttg ccacacctcc  70440
cctagctcct tctcacccag ttccttacag ccgtgaccct aggttccaaa tctaccttgg  70500
agataaggag gcacagcctt cgctgttccc tggaatcagt ctgtctgtac ttgtgggatc  70560
ggtgttatct ggggctacat tggggtaccc acatgggcgg ggggctggaa ggaaagggtg  70620
ctcacacagg caggggcag agaaggaagg gtgcccacac aggtgggggg agtggggagc  70680
ggggagggaa gggcgtctac agaggcaggg ggtgggaggg gcgggggcg ctttggggat  70740
tttgccagct catgtatcct tagtggaggc agctaggcta gacctccaag ggacagagtg  70800
acacagctgt tacacagtag tacagagacc ccactatgtt ggattaatct tcttggggta  70860
cagtggtagc ttgggcctaa gtttctctcc cttggttgac atgtggtgac taagttcaat  70920
aagctcttac gctgggctaa gactgactga aaggaccctg ccacccatcc ctggcaggac  70980
agaacttggc tacaggaccc caggctgggt gagttccagg attaagcagt cagcctacaa  71040
gcctcaccag ccagcctagg tggtctagaa ttgaggttcc tggaatgctg aaaagcctcg  71100
tagctaagcc caggctgttt tggaatgaat ctgtataagt cagtaactct gtttctagca  71160
cgaacactat gccctcctgg ggctccaggc atctctagga gtctgagatc tcttgacttc  71220
ccagggaggg agagattctt gccctcagct ttgatgaggg atgtcaagtg gaagcttatg  71280
ttgttcttgg cccaagaagg gacttaagta ggctggaggg attcctgaac ctttcatagc  71340
tgctttggcc ttcatggcct gctgcttgga acccaaacac acccactgta gcagggtagg  71400
tgggcacagg ccctgtttag gtttggcaac tctagagcca aacaggacag gatagggaaa  71460
ggggaacctc aactctaggg ccccagacac cctattttgg attcttctgc cccatcctac  71520
ctgagaaacc caaacgcagc ctccccacct gtccatagct atacatgtca catgctctgc  71580
agcctggccc atctgttgct gccttggtcc caggcatccc tgttgtcacc tctgcatgct  71640
tcctgctgtc cccagagtac ccaggtcagg gggtgggagg ctcaggtcta catgtgcctc  71700
cgtgtcccag ggatcatggg aatctgaaaa cgtggccccc tcaggctgcc tgtacctagc  71760
agtcaggtga gtccccaggc tgacctggcc tctgttcccc atcagataac agctatggcc  71820
caacgagccc tttccatggt gtgtctctca accgagaccc ctgagttgtt actcatagaa  71880
aagtgtgccc actgggcttc cagctagctg aaacacagtc ccactctggt ggacccttca  71940
gggtctctag tggtcctctg gccagccctc tgggtgggac tgtctcccta gctctggtca  72000
cctacacaca gaagagcttg tgtgagtgag acacctttgt gggtcagtcc atgaaagagg  72060
tcacagctgt cccctgctgt gggttctcca gtgagtcatc tctgcctacc ttgtgcagat  72120
ccccagtgtc acattctgca cagtctggcc ccagccctag ccctggcctc ctggcctaag  72180
ccctttgtta ctcctaggac gtgcattttt gtttcctgtg tcatttacat cactgtaacc  72240
cccaagggc ttctggggcc ctggcttgcc attctgtccc tgagctagag atgtgccctc  72300
cgactgtctg catccgtccc cacagcggtc ccggctccct gtctgattcc tagctgggaa  72360
tgcttggctt gacatggaac taggatcctg gctggggtgg aggtattgct gccacagagc  72420
caggcttcta tccttactgg ggaggagggg gtgggtggag cagcagggct gtcctccctg  72480
ctaagctgag gcctctccac caggtgatcc gcaggggctg gttgaccatc aacaatatca  72540
gcttgatgaa gggtggctcc aaggagtact ggttcgtgct gacagctgag tcattgtctt  72600
ggtacaagga tgaggaggta agcagctggg gacaagggtg gcctgataag gtaggcaagg  72660
gaggtggtcc ccagactgat taccccattc ccccagtcac ttgagaaagg gagtttacag  72720
tcaggcatgc tgacgtgctg agacccagca ccagtggtaa ggtccaggcc tgtccaagtt  72780
atgtaggaag tgcccctgtc agacagtcca gctggtaaca tgcttatcct gccacgggag  72840
ctctgactca tcccagaacc taagagaaaa gggaggcgtg aagggcgctc gtattcccag  72900
caggctccgc aggcagtgcc tgctggccag ccaggcttgc ctccttgaca ggctccaggc  72960
aaataagaga cctgactcaa aaagccagag cgcagcgcct gagagatgac acctcaagtg  73020
gttctctgtc ttccagatcc acttgcatga gtatgtgcct acacacaaac ttgagtatac  73080
acccacacaa aagaagaaac aggaaagcaa gccaggggcc gtggtggtgt agcttagcat  73140
gcacggaacc tttggtccca tccccactta gcatcgcatg cgtgcctgcg atgcccacac  73200
tcagcaggct ccttcactaa catagctcgt tcaagggcag cctgcattac agtgaggttt  73260
tatcaggagg acttccgtct gaaggagaga ccctggcctc agttctctgc tgctggatgg  73320
gaactgaggg ggcatcctag tcagggccag gctcccaaca tgtgctctgg tggcctgtac  73380
cagcagtcac ctctgtaggg tgttccagcc accatgtagg agagacccac acacacacca  73440
gtgcaccaaa gggacacaag gactcagtgt ggtaccatat gtgacctgtc catgcacatt  73500
ccattcccat cttaggagct ggccagcacc ctggccctga agtggtgtaa gtgtcacccc  73560
aaggccagac ttccctggtc tagtttctgc tgttgttggt tttttggttt gttggtttgt  73620
tttggttttg gttttggttt tttgagacag ggtttctctg agtagccctg gctgtcctgg  73680
aacttacttt gtagaccagg ctggcctcaa actcagaaat cagcctgcct ctgcctccca  73740
agtgctggga ttaaaggtat gcgccaccat gcctggctct gacctggcca tattttttag  73800
cataacaaag actctgggat tatcccccag aatgaggcac ccagtgttga gtttccagct  73860
ccagctgtaa gaaaagtaac ctgaaagctg ggcagactct gtgtgtgtgt gtgtgtgtgt  73920
gtgtgtgtgt gtgtgttttc aaggttcatt gcagaggagc gtagccctgg gcctagctga  73980
caagcttctt cctttggact gggaatgacc attccaattc ccctcatctg gagacagaaa  74040
gcaggcactt gggcctcact gtagacaagg cctgtagcag ggccacacca ccaccaagag  74100
gtatgaaagg agccctctgt atgtatgcca aagatgaagc tcactgagat ctaggggctg  74160
tggagaccct gacaccttta atggtcctgg taagggacct aagtatccca ggtagcagcc  74220
atccctgaga cccagaccac tcttgtagac aagcccaaga taaagaccag caggggactt  74280
ttctttattt taggagtaaa ccagaagata acagtgtcgt tggaaataag gagaaaggcc  74340
cagttcacct gaggacatcc ctccccaccc cagcgctcgc tcagtcctgg gcctactttt  74400
tccaccctcc tcccagaatc ttccccagtg gagagaggta gcactcacct taggtggtct  74460
ggaagttccc actgttgctg ctggcccaag cccagcctaa ccaatgtgca gactactgta  74520
catgtcccag cctcctgaac aggtagtctg aacactggga tggcggggat ggctgttcag  74580
ttcctcagcg tggccatggt acaggccagg gagtctgctc ctcccaagat cctccattca  74640
gttcatccac gcaccctgaa ctcttctgac gtggcaaggc caaggccact tgctcacatc  74700
```

-continued

```
tggagaaagt tgagattttc aggaaatccg aaagcaggct ggaggagggc ttgggtcgat  74760
ggcccgtgcc gcagaaggag gtccttgtgc agttgcatac tttgcgagca agcgcatgcg  74820
tatgctcgtg tgtgtgtgtg tgtgtgtgtg tgtgtgtgtg tgtgtgtgtg tgtgtgcgtg  74880
cgtgtgagag aaagagagag agagagagat ggcagccacc cgatcctggg cagaatcaca  74940
cataaacagt tccagatgtg gcaagcctag atgtctgtga ctcatttact tggccctggc  75000
ctgctggcag gaagctttct gtctcgtgac accatagggt aggggccaca gagttgcttc  75060
tgggaactta ccctcctctg gaaacagagg ctcctttggg gatccccaaa atcccaggtt  75120
tgtttcttat aacaagacag acttcaggcc gccttccctg tctggagctc tcggtatgca  75180
gtgtgtgtgt gtgtgtgtgt gtgtgcgcgc gcgcacgcgc gtgcgcgtgt gtgcgagtgt  75240
tccacactcc ctgctcacag cctctccgcc tgtgcttcat tcaggcagtc agacctggtg  75300
aggttgactg ggagccagtc catgaattgg ctggaaactg gggccacaac tgtgccaccc  75360
tccccaagag taacactcat cattcctcag acagatgggg atcgggaacg cagaggagaa  75420
gcagtgtgtt caaaggcaga gcaaagcttg aacacagcag ttcctcatac agtgttcaga  75480
ctggccccat tctgcactag agctacgggg gaattcagaa ttgtattcca caaagctgct  75540
ttctgggact ttctgttcgt gcagtggaca gaaacatgag aaagagtcat gaaggatctc  75600
cagtgagcct ggagagagtg ctctgtgggg aagagtactt acgcacctgc gcacccatgg  75660
gtgctgtgag tgcctgggac ttcagcacta ggtgtgcaaa gaggaggagg ctggggcttg  75720
ctggctccag gtttagtaaa agcacttgtc tcacagaagt aaacatcatc ttccccatga  75780
aggcctcttg gttctcctca gtgtgttgca catgacacac acaggaggac atgtccaggt  75840
gatgggctga ggcccagctc agttgttgga gcttttccta gtgcttcatg aactgggtgt  75900
gactcatggc tcaagcggta actccttaca gcattggtga gcaagatgcg agaggatcag  75960
gaattcagct catcttcagc tgaataggga attgaatgct accctgggct ataggagact  76020
ttattctgga aaaaaaaaaa aaagtctgtg tggtgcagaa aatccccagt gagctgttgt  76080
catctacaac cattcttagg ttagttacac agtgtccctg ctctgtgctg gacagacagc  76140
ttcctaatct gagcagacag aaggaaaagt gccccccccc caaaaaaagc tgggcagtgg  76200
tggcacatgc ctttaatccc agcacttggg aggcagaggc aggcagattt ctgagttcga  76260
ggccagcctg gtctacagag tgagttccag gacagtcgga gtatacagag aaaccctgtc  76320
tcagaaaacc aaaaatagaa gaggaaggaa aagtgtcaca ggcctattgt tatggctcct  76380
tgggaggcag gaggaacaca acttcatgga aggcctgtct caaaagcagg aggaggagga  76440
gtgttgcctg cacggccagc atcgtgcttg cctgagagag accctgggtt ccgtccccgg  76500
cttgggtcgc tagagcgctt gtcaggcatg catggagtag caaagccact gacgctcctg  76560
tgacagtggt gcccaggcat cagtttccca ggcctggcgt ctgaaatagc ctcctgcgcg  76620
ccagtctccc tccctgtgag tgattgccgc cataactcag ataatgggga gagccacctg  76680
ggaaggcatg aagttagggc tgtgaggtct gagtgaccac tgcatgtgtg ttctctggat  76740
caaaaacaaa gctgacagcc ttcctttctg gcaactgctg gaccagccag gtggtaggca  76800
gtcatcatag catctgtagt agggtggcat gaggtcagcc ctgagggacc ttctgcatat  76860
agacctagga aggccaggag gggggcagta cagggtgtag ggacaagaac agtctggacg  76920
gggtcggtcc gtacacaggt cctgggatga gagagaatgt taagggaacg tttgaccaaa  76980
aaatcaaaaa cagcacctgg gaggcagagg cagacgaatt tctgagttcg aggacagcct  77040
ggtctacaga gttgagttcc agaatagcca gggctatata gagaaaccct gtctcgaaaa  77100
aaacaaaaaa caaacaaaaa acaacaaggg gacgtttgag taaatgtggg gtgacagagc  77160
tctcagcaca ccaagtgccg ggtgttggca gtggctgtca gattgttgct ggctctgccc  77220
cggcagctca ggtgagaccc ctgccctctc tcctcaggag aaagaaaaga agtacatgct  77280
gccactggac aacctcaaga tccgggacgt ggaaaagggc ttcatgtcca acaagcacgt  77340
gtttgccatc ttcaacacag agcagaggtg aggaagagcc agcccagcag gccctttgcc  77400
agggtcttgc ctagcacaga gctatcccag ggacattcct gtgtggtgtg ggcggagcaa  77460
catggacaga caactgacat ggatgcagta agcatgaggg cctcagtgca accctcacac  77520
acatacaact ctcatacaca caacaaccct cacacacaat cctcacacac acatagccct  77580
cacacaaaca cacaaccctc acacacataa tcctcacaaa aacatagcct tcacacacac  77640
agtcttcaca cacacacaca caaaaccctc acacgataca atcctcacac acatacaacc  77700
ttcacacaca caaccctcac atacacacaa cactcacaca cagtacaagg aaacgtctgg  77760
cagggtgctg gggaggcaga aagcaggatc ctcggtgccc gctaaacctg ctgaccggtc  77820
taggcaagtc tgtgagcttc gggccagtga gacagaccct gtctaaaaga gtgaggtgct  77880
cagataaagt gaggaagggc gtctggtgct gacctctgac ctctgcatgc acatacaccc  77940
atgcacttac tcagggctcg acagtgcaga cagtgtaggc tgagtctatt cctgctgcta  78000
taggatattc tggtagacat tgttgctgtg gtcttcctta caaacacctc agtgtctcca  78060
cacctcagtg ggcgatccaa agccagagct ggactgtgtg cggtacttgg tgctatagta  78120
tacctggcag acacacccag aaacctctta acaaactagg gaaggtacta gaaccacctt  78180
cgtacccaga tcaggcagag agcccccaga gcccatggtc ttagtggcca gtcaagtccc  78240
tctaccactc actccaggaa tgtctacaag gaccttcgac agattgaact ggcttgtgac  78300
tcccaggaag atgtggacag ctggaaggct tcgttcctgc gcgctggggt ctacccagag  78360
aaggaccagg tgagggggtt cctgcgcgct ggggtctacc cagagaagga ccaggtgagg  78420
ggttcctgcg cgctggggtc tacccagaga aggaccaggt gaggggttcc tgtgtgctgg  78480
ggtctaccca gagaaggacc aggtgagggg ttcctgtgtg ctggggtcta cccagagaag  78540
gaaaaggtga gggggttcct gtgtgctggg gtctacccag agaaggaaaa ggtgaggggt  78600
tcctgtgtgc tggggtctac ccagagaagg accaggtgag gggttcctg cgcgctgggg  78660
tctacccaga gaaggaccag gtgaggggtt cctgtgtgct ggggtctacc cagagaagga  78720
ccaggtgagg ggttcctgtg tgctggggtc tacccagaga aggaaaaggt gagggggttc  78780
ctgtgtgctg gggtctaccc agagaaggaa aaggtgaggg gttcctgtgt gctggggtct  78840
acccagagaa ggaccaggtg agggggttcc tgcacgctgg ggtctaccca gagaaggacc  78900
aggtgagggg ttcctgcgcg ctggggtcta cccagagaag gaccaggtga gggggttcct  78960
gtgtgctggg gtctacccag agaaggaaaa ggtgaggggt tcctgcgcgc tggggtctac  79020
ccagagaagg accaggtgag gggttcctgt gtgctggggt ctacccagag aaggaaaagg  79080
tgaggggttc ctgtgtgctg gggtctaccc agagaaggaa aaggtgaggg gttcctgcgc  79140
gctggggtct acccagagaa ggaccaggtg agggggttcc tgtgtgctgg ggtctaccca  79200
gagaaggaaa aggtgagggg ttcctgcgcg ctggggtcta cccagagaag gaccaggtga  79260
ggggttcctg tgtgctgggg tctacccaga gaaggaaaag gtgaggggtt cctgtgtgct  79320
ggggtctacc cagagaagga aaaggtgagg ggttcctatg tgctggggtc tacccagaga  79380
aggaccaggt gagggggttc ctgcgtgctg gggtctaccc agagaaggaa aaggtgaggg  79440
```

```
ggttcctgcg cgctggggtc tacccagaga aggaccaggt gaggggttcc tgtgtgctgg  79500
ggtctaccca gagaaggaaa aggtgagggg ttcctgtgtg ctggggtcta cccagagaag  79560
gaccaggtga gggggttcct gtgtgctggg gtctacccag agaaggaaaa ggtgaggggt  79620
tcctgtgtgc tggggtctac ccagagaagg aaaaggtgag gggttcctgc gtgctggggt  79680
ctacccagag aaggaccagg tgaggggggtt cctgtgtgct ggggtctacc cagagaagga  79740
ccaggtgagg ggttcctgtg tgctggggtc tacccagaga aggaccaggt gaagtgttcc  79800
tgtatgctgg ggtctaccca gagaaggacc aggtgagggg gttcctgcgc gctggggtct  79860
acccagagaa ggaaaaggtg aagggacacc ttccctgctg accctgcatg gaggaaggga  79920
cccgtgattt ctaggccaag cgtgtcaagt cagcttttct ttgctatgga gatggcttag  79980
gtgatagcat gaggcctgaa tgttagccct agaactcagt caggagctat gtgtggtggt  80040
gcacactggg gctcaggagc cagccagcca tagcacagca gagatctcca ggtcctagtg  80100
agaggccccg actcaaaagt caatctaaaa gaacactaat aacaagccag acacagcaga  80160
tagcgtatgt gcctatagtt gttgcagagt ctggcaaagt ggacacactt ggggtgaaaa  80220
ggggagtatg gatccctaac gcccacttac cagacagcct agaaaaacct acaaactcca  80280
gattcagtga gagtccctgt ctcaaaatgt attgtgtttt gtttttaggg tgtgtctctg  80340
actagcctat agtttagtct gtagaccagg ctggccttaa actcagatct atctgctcct  80400
gcctcctgaa tgctacaagg cctgggatac aatgtaataa caggtcctgg tatgttgatg  80460
cacaccttta atcccatttc aagaccagct ttgactctat agtgagctct aggatagcca  80520
ggactatgta gaacctgtca ttcattcata gacagacaga cagacagaca gacagacaga  80580
cagacagaca gagtaaacat aaaagttctg aggcactgag ttgggataga ctacatgcac  80640
acaatgtgta agggtgatat gcacataagg tacatacatg aaacacaagt gaataaatac  80700
ctgctacaca ccaagggaaa gaaatgttca gtttggctcc caatgttaga gggctcagtc  80760
catggctgca tggtcccatg tgtataggct gtctcatggc agtggtattg aggtgcggaa  80820
gcgagaagca gaggggaagg catgaaaggg ctggggccaa ggtatccctg gggatacaca  80880
cctagtggcc tacttccccc agcctgaagt tttcagagct tcacaagtaa cagtagtatg  80940
gttctaaaag gacggctttg cagacagaag ccatggctac tcctcaaagg atccaagttc  81000
agtccccacc acccacatga cagttgacag ctgtctgtgg cctctggaca cctgcacaca  81060
cacactgcat atacacatac cataccaatg tacacataaa aatcagaagt acagtactgt  81120
cagctgagac tcaagggacc aacacctgag ccctagggac atcccatatt caaaccatag  81180
cagcatactt cagacctcag agggcaccaa gctggtaccc actgagtcaa gcgaagcgga  81240
ggaggcatgg gttgtcatca gggtccagaa gttctccaga aggggttctc catggtgagg  81300
acggcaagag cacttagggt tcatccacct tgttgtcttt tccctcttgt ccttggggtg  81360
aagtcactac agaccctggc catccaaagg gaggctgtgt tctcatcccc cggctctaac  81420
cagtgttacc ccagtgcaga ctacaaggtc taccagggcc atctggaaca cactcaggtg  81480
gggcatttgt cagcagggta ggcccagcac agtgaaccat ccccctctgt gtcctctgca  81540
ggcagagaat gaggatggag cacaagagaa caccttctcc atggacccgc agctggagcg  81600
acaggtggag accatccgta acctggtgga ctcctacgtg gccatcatca acaagtccat  81660
ccgtgacctt atgccaaaga ccatcatgca cctcatgatc aacaacgtga gtgacagctt  81720
ccaagtcacc aaagatccta gccgcatgcc agtcagccca gcaccagcag gtggaagcag  81780
gagagtcaca agtccaccat cctctcagat actcagccgg tgtagggggc tttcactgtg  81840
agaccttgtc tcagcaatga caactgggga agacgggggg aggggtgggg ggtcagaagg  81900
taaaggcgcg cgtgcacgtg cacacacaca cacagtcaat acatactgtt aacttaaaag  81960
caaacctaat tttaaaaagc tgtgcaaagt tagaacaagt tggtttgttt agtagctttt  82020
tggggttttg gtgtgttggt tggttgggtg ggtgggtggg tgggtggttg gtgtgtaggt  82080
tggttggttg gtgtgttggt gggctgcttg gtgtgttggt gggctgcttg gtgtgttggt  82140
gggttgcttg gtgtgttggt gggttgcttg gtgtgttggt gggttgcttg gttggtttgg  82200
ttggttggtt tttgtggtat tggagattga acccaaggca tggtgattct taggcaagca  82260
ctgaatgact gagcacctca gctccttccc tgggagattc taggcagaag ctttacagct  82320
aaacttgact ctcactcagt ctgtgatgga tgctttccca atctcaacag gcttctgagt  82380
tattggctaa tataggggtc tgacctttcc ttcccaccac tgtcctcaga caaaggcctt  82440
catccaccat gagctgctgg cttacctgta ttcatcagca gaccagagca gcctcatgga  82500
agagtcagcc gagcaggctc agcggcggga cgacatgctg cgcatgtacc acgcactgaa  82560
ggaggccctc aacattattg gggacatcag caccagcacc gtgtccacac ccgtgccccc  82620
accggtcgat gacacgtggc tccaaaacac cagcggccac aggtctggac agcagtttgt  82680
cccccaatgt gcatatacaa gttcaagccc cacccttcct attccttctg tcccattagg  82740
aaatagttca cagctgaagt ttggaaaggg acaagagtct taagtgaatg gcacaacacc  82800
tgttctgctt aaagccacag gggagccatg gcttccaggt gccaacctga gctagatctc  82860
tggaggagaa aaccgcacac cccaattctc caccaactct tgcatcttct agtgctttct  82920
ccgtgggtcc aagtagaaag caaaagcaag aagcccagga gacagttacc cgaggttggc  82980
ctcttagaac atagagacgg tacagaacac gttttagaag gcctgtagaa cctagaactc  83040
cattggcctc gagatgggaa agatgggcca gagacactac ggtagtcaca gtccaagtgc  83100
taaagtggca gtcaagggaa tgtcagtaca ggggacccac tacggaccct gtggagccct  83160
caggaaaagg aagagcccaa acctggcaag attcagtccc taggtccagt ggggagcagg  83220
gcaggcagat atgtagaggc agaggtgata catcaggact ggggctgggc tctaagtgga  83280
tcagaaggtc aagtgcagtc tgcacacctg tcccttggag gtttactgtc aggtacacag  83340
gagcctcagc aacatggaat ggtgtggctc aggctggtgg gtgcctctac ccccacctca  83400
gtcacttgtg gtagatgttc acaatatcct tcctccagat tacagccttt ccttcctcca  83460
tagccccact ccacagcgcc gacctgtgtc cagtgtgcac ccaccaggcc ggccacctgc  83520
agtgcggggt cctacaccgg ggcctcccct gattcctatg cctgtggggg ccacatcctc  83580
cttctcagca cctcccatcc catcccggcc tggaccacag agtgtgtttg ccaacaacga  83640
ccccttctct gcgccacctc agataccatc tcggccagca cggattcccc ctggtatccc  83700
tccaggagtg cccaggtaag gcccacgacc tgcatcctag gctccctttg tggtatcttt  83760
cacctttccc cccttctgat ggcttccagt gtagccccaa caggacatag aacagcacag  83820
gcatccctgc ttgtgtcctg agacattgag ccctaaaggg gccaacccct gctcagccag  83880
tgccacagag cagtggacca gctgatgcca gggttcctgc ctgtcctcta agcagcaggt  83940
gacatgtctc actagccctg ggcaccatac cactgttgac cctgctgaag tcagcaatgc  84000
ctggtgagcc aggttctggt ctccacttct gagatcagtg aggcaggcaa gatggcacaa  84060
gtgcttgcta ccaagcctga tgacttgagt tcagtctcta ggaccctctg atggagggag  84120
aggactagct cttcccaagg ctgagaactt gcctataaaa cccaggcaaa ctagtgacat  84180
```

-continued

```
ggggatacta ggaaagtatc tggacttgac atagtccctt gtacccccaa tctgggagcc  84240
cctcgggtgg gctggaaggg ctgggtcccc atcctcaccc tgcttctgcc ctcactaccc  84300
tccacctccc cgtatcttta ctttctttgc agcagaagag cgcccgctgc gcccagccgg  84360
cccaccatta tccgcccagc cgagccgtcc ctgctcgact aggctgcagg gggcaatgtt  84420
ctggggggt cctcgtgcac ccacagtgta ggacagtttt ggtggtctgg gccctgctac  84480
ttgccctcca tgctgggacc aggctccccg tgggcaagcc ctgccctttc cctcctcgcc  84540
ctagtggaca tgacaatgaa gggtgaggag gcccacagca cagcacatgg gggctttgca  84600
ctttgggatg aggaggagct ctggctagca gaacaggaac tgcatccttg ggaccatcag  84660
gaaaaaaagg tccaggctag tgtgggggga ctcttctgga gctcctccag agcctttgtt  84720
ctttctgggg tccaggaact gcccaccttt cctaaggact cctcaggagt gagccaggcc  84780
cagcaggtcc agtgctgacc cacctggctc aagttgtata tatagagctc ctttggccat  84840
attaaccaca caagctgagc ccagcccagg ctccgcaccc agaggtgcct ttgtgccttc  84900
ctcaggcctg gagggcctca gctctggcca ccctcactct cctcagcccc ggttgtggtt  84960
tgggctgtat gaactgggga gacatcagag gcctcttggc tcccaaccag atgtccccac  85020
agggtgggcc ctgggtgcct ctgcagcctc ggctcccacc gcctggattg accactgtta  85080
agtgcctgcc tctgtatatc ctattaataa actaaaataa agggaagccc tactggtggc  85140
tacgtgtgtg ggccttttgt gtgtgtccca gctcaggaga ttgagcaccc cctcatgagg  85200
ctgcccacac tcatttacac gcgtgagtct tgtgtcatct gttctgagcc cctcttgtcc  85260
ccatccgtac caggcctcac acacagtgct catgggaaac aggaattcta tccacctctg  85320
tgcgatgctg tggccaagcc ctcctcccag ccccgccagc caccgggacc aggggactca  85380
gttcattcag ccatggttta tggtcttttt ctttcgtgcc aggcgaccac ctccattggc  85440
tcctgcccga cctttcttct gagcttcgtg ggagtgtccc cccttcctgg ctgccctggc  85500
ttgaggctag gtctgtccca agctgacatc cctaagccca gtcaccaggc actattaact  85560
ttctgaccat aatttattga ctccagtgcc caggacaaat gccctctgtt ccttgaggct  85620
catgggccag ccttctctga ggccctgcac ccagagagaa ggaaggggcc tctcccaaac  85680
cacctactag ctggctcccc tctgggccaa ggggccaggg ctccttcctt tcaaataaaa  85740
gtgactgtcc tggcaagaac tctgcagatg tgtctccttc ccagacccta gtgaagtagg  85800
cttaccccag gaggagagca gagacattgc agttggggtg tctagttgga gggtgggggg  85860
cagcaccaca gcttcacccc atcctgatag ctgcaagact gaagctaagg cacgatttca  85920
ggagaaagcc agggcatcca agagcagtgt ccccacactg ctgcgcccag cacttccacc  85980
ctccaaggaa caggcacagt cgctgagccc tccccttcc gaggggtctg tgagccattg  86040
gcactccctg gtcactgagg aagggagaca catggggcca ctgctaagga cccaactatg  86100
tagtgtctca tctgagtctg ggaggtgtcc agcaagtcac acacccgctg ccctcatcct  86160
ctgtggcagg ggctacgtgg gtacagggcg cttgtcatgg aagaagcgct tgagtgtgca  86220
gacttgcagg acagccacca gcagcaacac agccacattg gcagctgacc agaagttgac  86280
ccgctccagg ttgtcttctt gaagatttcg atcacgagcc tcaaaggctc ggagcagagt  86340
gagcatctgg atgctccgtt ccagccgggt cctcatggtc tctatggatt cctgccaggg  86400
cacaaaggaa cgggtcaggc tgcttaagtc agaatgccta cctaccccac cacgcacggc  86460
tctggctatc cgttcacctg cctcacgtct tctctagaaa ctgaggggtt ttccccttgg  86520
tgttttttttt tttgtttttt gggtgggtgt gagacttttc tttttaagag ggattggggc  86580
acacgtgcat ggcagacgac cccaggtagc caggcttggt gcagttgcct ttgcctatca  86640
agccacttca ccaaactctg ctagtctgtg caagccaagg atgaccttga acttgtgatc  86700
ctcaggacca agagaaccat acccagtgtg tgcagtgctg ggtgtggggg ctcagctgtg  86760
ggagcgtcct aggtaagtgc tctgccaact caattattcc cggccctttc tgttggtttt  86820
gtgagacggg agcttgctat gtaaataagg ttggtcttga actcactggc atcctgcctc  86880
agcctcctca gaactgggat tctaagcatg caccatcata cccagctcac cttgatgtct  86940
tccattttga catcaagcat ctcttctggc tccacagcct ccgcccaacc ttctacctcc  87000
tcctcatctt ggaagctgtc aaagatgagc tcaaagaaca caagcttttc tgagatggtg  87060
ctgaaggagt tgtcaaagca cagcctgtag tctccggcct cagtaggctc caccctgggc  87120
agacagatga gacatagacg tgaccctgga gtgaccagcc agctggtctg tggaaccagt  87180
aggatggtaa cctgaggcca ctggggagct gcagggctgt aactgaacca aggcagggca  87240
ggacttcact cacgtgtgta ccccatcagc ctttcgagac tcactgacca acagcacacc  87300
ctgagggctc tccaaggtga agtccacgtc cagcccagca cctccgatca cctgaagagc  87360
aggtaagaat tggggaactg gcagctttgt gcaagcctat ctgccacaga aagcctgggt  87420
taaaccgaac cgggaaagac ccatgtaaga tcaccaagaa cctatcttta agaagaaaaa  87480
agaacaacca caaatcccag gtatttgctt gagatagagg agtagcgcct gtggagggag  87540
attagtcaga gctgcacttc taccatagag ttaggaaact cggtcgtcg tagtttagca  87600
gcaagcggtt tttgttttgt tttgttttgt tttaacccag caagctattt ggattcccc  87660
aagggcctat ctgaagacca acatccatcc acacctacaa ggtttcttcc cagtccctaa  87720
gatggataca tccacgtgag gtcttttatc aaccaccctg ccaacgccct tgagtagtct  87780
aaggtggctg tctacctgac cgctaactta atcgtaacct acccaacagc cgccaggaac  87840
ttccctagaa cccaacccaa agagctctga gcagagcatg ccccttctct gcaagactat  87900
tagcgttctg gccacacctc tgccccgccc ctcccgcctg ttggccacgc ccccagccct  87960
gctctattcc gagcccggga ccccctctct cacctggtac tcggtctcaa gactagcatt  88020
ggccggtgcg gactgataga aacactgctt tctcccggcg ggaagcagaa atgtgaactc  88080
gccgtcctgg ataggcggcg gccctgcctc tcccactcct actgctggca ggagtagcca  88140
cagggccagt gctacggccg cgccggccgc catcatccgg gtcaccctct actcacgggg  88200
cgtggaccct ttaaggattt gtcctgccca cctcttattt cggcaaagct cattggcttc  88260
ggcttctgtt cgaccccaaa gccgcggaat gctgactgaa gggccccagg atggggagct  88320
gccctggtaa ttgcctaatc tgctagaaag catactaacg ctactgcgaa cttcgtgaaa  88380
cctacccaag tctgatatca accactgcat ttggtggggg cactgacaaa tctaaaaatg  88440
gtgaagcact tctttacagg caacaattaa gatgactaaa cggggaggtt tgcaggtcct  88500
cccttggcac cgcccgctct ctgccttccc caattcaagg tgcttttgcc cattggtcaa  88560
tcaagtgtag gcgtagccct ccgaggacgg cggctttgtt ggattctgat ctcaacttgt  88620
gtgacgggtg cgacaggcag atatgccagg tgctagtatt ccaatattgg agttctggcg  88680
atgttagttc agtgagcatg gcctcccccg actgcttttc ctttacacct tataccatcc  88740
ctaagggggt ggtggaatgt ttgttggtga gtagaatact gcctcagcct gcgtacaata  88800
catctcaaac ctttgggtca gcaggtccac gtgcatctgt gctgacacat gcagtattcc  88860
agtacttgaa aggctgagtc gggaggtgga aggagttcga ggccatcctc tcgaactggt  88920
```

```
atggaactac atagttccag accagcaaaa aaatcaagga atctattttg ggctttgaat  88980
ggctcagaga acacaggcgc                                              89000

SEQ ID NO: 48          moltype = DNA  length = 16
FEATURE                Location/Qualifiers
source                 1..16
                       mol_type = other DNA
                       organism = synthetic construct
modified_base          5
                       mod_base = OTHER
                       note = uracil
SEQUENCE: 48
agactctcgg ttccga                                                  16

SEQ ID NO: 49          moltype = DNA  length = 16
FEATURE                Location/Qualifiers
source                 1..16
                       mol_type = other DNA
                       organism = synthetic construct
SEQUENCE: 49
agactctcgg ttccga                                                  16

SEQ ID NO: 50          moltype = DNA  length = 18
FEATURE                Location/Qualifiers
source                 1..18
                       mol_type = other DNA
                       organism = synthetic construct
SEQUENCE: 50
agaggagacc gagcgaat                                                18

SEQ ID NO: 51          moltype = DNA  length = 23
FEATURE                Location/Qualifiers
source                 1..23
                       mol_type = other DNA
                       organism = synthetic construct
SEQUENCE: 51
catggtttgt gttgatgtac gac                                          23

SEQ ID NO: 52          moltype = DNA  length = 24
FEATURE                Location/Qualifiers
source                 1..24
                       mol_type = other DNA
                       organism = synthetic construct
SEQUENCE: 52
cctacatcag ggagcgagaa ggga                                         24

SEQ ID NO: 53          moltype = DNA  length = 16
FEATURE                Location/Qualifiers
source                 1..16
                       mol_type = other DNA
                       organism = synthetic construct
SEQUENCE: 53
agcactttat tgagtt                                                  16

SEQ ID NO: 54          moltype = DNA  length = 15000
FEATURE                Location/Qualifiers
source                 1..15000
                       mol_type = genomic DNA
                       organism = Mus musculus
SEQUENCE: 54
tctcagggga aaggtatcct ggattcagta accaaggaac atcacaatgt cacattgcac  60
aacaaacctc acacaagaga tttattggga gagatacaag aaggtggctg cctttccttg  120
gtggagaaac agcaggaaac ggagtgggag gcaagctttc ttggtggtgg agttttccag  180
ggtggaaatt tctagggagg ggattggtaa ggtttggtga gttttcaaac cctgaggtgt  240
gtgcttggac cttacaccct acacatgcac ctcatgatac aacgcccact tcccatacgg  300
agccctgtgc tcaccacagt ccttcttgga ctggctgaat ttaggctcct gcataacctt  360
gtagcccttc cctcctttcc tactgcaaaa ccctcttagc ttgctgtggt aaatacactt  420
ctgtaattcc cgtaattagg aggtggaggc agggaaatag caaagttagg tcactctaga  480
tcaagtccct cttgcaaaaa caaagaaaaa aaccacgccc tctatggtac aaaccagttc  540
ctcttcccta gagttctggc ccctccccgg gaggatgtgg tcatagggtc aggtcctggg  600
gccaaggtct gtcctggtac aacccccggac tgaccggttt ctttcacttt ggtcggctct  660
gctatgtggc tcggccttgc ttttgtgatg gctaacgtta tgatggcagt taattttatg  720
tttaaaagtt taaaatgtct gtgcttaaga aaactataaa gcgttaagag tggttaaggc  780
ttagaatttg tttttacaac tattttggtt tctataaatg agcttgtttt gctccagagg  840
accctctgct tggcccagaa caaattgtaa ctttgtattc cttgccttta taaacccttg  900
actgaggtag ctgggtgctg cattagggaa tcccaacttg caaatacgga cctggatgga  960
gccagtatct gaataaaagc ctcttctttg ttagaatgta ttaatggtca gactggcgag  1020
tctctgaatg accccagacc cataacactg tcttcacgtc ctagtggcaa tcaccaaaag  1080
tccttttga aaccaaaagt tgaataagtg tcccgttgtt cctccggtct tgcaaggcct  1140
```

-continued

```
tgcaaagctg atcacagcct tcctctcttc ctggagcacc aggaacctgt tatagtctgc  1200
ctttattgtc tataaaatga aatcacctat gaagattccc caccctctct tccctggttg  1260
cttggctttt tcttctcaga ctgtcccaga ccagtgatag atgcccacca acccggatca  1320
gtggtagatg cccactaaca atcccagacc ctagtaaggg agggtaaggg ggtgggggtg  1380
ggggttgggg ctggtggcac ttgcctttaa tccctgcatt caggaggcag acgaaagctt  1440
atttctcagt tgtagtctag agatgccatg ctctggctct tgaactaaga aggtaccact  1500
ggcaactctg gaagcccagg agggagggag ggagggaggg aggaagggag ggagggaggg  1560
aggaagggag ggagggaggg agggagggag ggagggaggg agggagggag ggttggttcc  1620
tactgagcaa aataaatgct gggtagaaaa agccacagtg tcctgctccc caccttctgc  1680
ccagcacttc agctgtaaga caaggcaatg ccctttgatt tagcacttca ctctggaaag  1740
agtacaattc tgagatgaca gcgagatcat catccctgtg tatttctgcc tgctcccagt  1800
gacccaagtt gaccgtgatt gaggttattt tgtaaaatat ttccttgagg caccgggaat  1860
caaggccatg catcctaggc gagcattctg ccactgagtc tcatgcttcc accgaggagc  1920
cacatcccca gtccttttgt aagagaattt gccgatgtag gtggccatgg tggcacagga  1980
aattagggag gctgaagcag gcaggagaat cacaattaag tcaacctgag aaacatagtg  2040
tctccagagg aaaagaattt gcaactgtga ttaagggccc atattgagtc tggctacaca  2100
gccctgacta accagaactc actgtgtaga cagctggctg gcctcgaact catacagacc  2160
tacctgcctt tgcatcatgg cagtaaaatc atgtaccgcc atggactctc actctgtggg  2220
agtatccttg atgggcctga cccaatcgga tgagccctga aaagggacca gaagtttcct  2280
ggcaaagcag acacagtgtg aagcaattca atgcagggac attctctgct ccaccctctg  2340
ttttattgct tttaattctt aaaattaatt tatttattct atgtacaatg ttttccctca  2400
tgcatgccca tgcaccatgt gcatgcctga tacctgcaga gtccagaaga ggcaatcaga  2460
acccctggaa ttggagttat agacagctct gagccctcct gtaggtagat gggaatagag  2520
cctggatcct ttggatctaa agtccatacc tgctgagcga cacctccagc cctgacactg  2580
gctttaaagt tagaggaagt aggtggccag aaatgtagaa atcacacgta gccgtggtcg  2640
acagctgaga agaagctggg acatctgtcc tgcagccaca tggaagtgag ttctgaccag  2700
gacctggggg gggatctcac tttagaggct ccagagactt cagcttgaac ctcagcgttc  2760
tgatgatctg ggcagaaact ctaactatgc agcaccaagt gtttacccat gggtctgtgc  2820
atccgtaaaa gtagttttgg ggggcattgt tttagggtgc tcagagtgtg gtaattggtc  2880
acacagcaga aggaagctgc atgaaggaag gtcacataag cattctgtaa gattctgaaa  2940
gcaggttttg tcccatcatt cttaccttac cctcaacagg acctggaaca ccatcctagt  3000
aaagtcagga aaatggaggg caggaaccta actcttcagt ccgctactcc caccagtgac  3060
tccctgctca aaacacttct acagcgctgt tctgctgggt ctcccatgaa gcccttgctc  3120
ctcagaccca ggagcaagct tgaccaatct ctacctctga agcttctgag acctttgccc  3180
gcatctattg atcctcactc ctgggcaggc agcggggcca tcggcagacg ccatgacggc  3240
tctgttgttc ctggggtctc tgctgatgag tctggatctg acactttcgg tgaggacggt  3300
ggacactggg attgagccag agtggcagtg aggggtccct gttccggatt tagcctctgc  3360
ctgtcacctg ctagttcagg tgactgagag acttgtggtg ggggtggggg ttgggggaag  3420
gcacagctag cccagaagat ccaaacaaag gaggtagcag cccatgctgg tggatgtgag  3480
gacacaggct acttttgtgg gggagtcaat gagaagagaa aggaaggcta cactttgtga  3540
ggaaatcctg tactttggcg aggtggcagg aggttgaggc ctataggatc aagggaagtc  3600
taacattgtg ggcaatgttc ctgccttctc tctcctatag gctccaccat ggaaagactc  3660
caagaaattt aaggacgcac ctgatgggcc cacagtgggt aagtgatctg gcctcttttc  3720
ctaatctact ctgtggggat ggctgtgctt tagcctgcgt ggtctcaggc ctctggagca  3780
aggagggatc ctgagccaag ctgttccgtt gacatttaaa cctgggtgcc tacagattca  3840
gatgtgtgcc cggagtgcca ggcttgggct gtcctggatg cctgtgttag agcctggcag  3900
gtactctgta gtgttggaga tgatgtcatc tgatgatgtc atcacacctg cacaccaaca  3960
agtgctcgcc agtttcccca tcttcctccc tttcctttca acactcctgg agaatgtcag  4020
acataaccgg tagagttcag agcttcagtg ggcgatggga gccagaacag agctttagac  4080
tcacccaaga tcacagacac cccaagttgt ctccaaaccc taactttctc acttgtgagt  4140
ttactctctg cttcattttt ccctgtctga aaagttagac gggttgctga ggagaaaggg  4200
ttcctcattg ttgtagatgc tgctgccagg aaaatgccct aacatgttag ctcttaggct  4260
agggcatagc tcactggcag agcacttgcc caacatgcac gcacacacac ctgggtttgg  4320
tctgcagcac tgtgaggga aaaaattcct tttttttta attttaaaga aaaaattctt  4380
tcttaagctg gagagataac tcagaggtta agagcactgg ctgctcttcc agaggtcctg  4440
agttcaattc ccaacaacca catggtggct cacaaccatc tatctgtact gggatctgat  4500
gccttttttct ggtctgtctg aagacagcaa cacatatagt aaataattaa ttaattaaag  4560
aaagaacaat tctttttttaa agatttattt atttatttta tgtatgagtg ttctatctgc  4620
atgtacacct gtatgccaga agagggtatc agatctcatt acagatagct gtgagccacc  4680
atgtggttgc tgggagttga actcaggacc tctacaagaa cagacagtag atctcaaatg  4740
ctgagccatt tttccagccc aagaaaaaaa atcttaactt ttagtaaatt tgacttaggt  4800
gaagggttcc acccccatcc tgccccaaac cctgctatag gacttgtgag tacagaactc  4860
taccacagtg agccttgtct gtggggtcaa gctgaggctt gtagtgtgat gtctctcact  4920
gaagcccaac tcagtgtgac cctccaggct tctgtcctaa ccactctaag ccaatcagct  4980
gctgtccctt tcaacctgac ccaccatggc cccctgtctc caagttctag gacccttccc  5040
tctctctatc accctgttgc taaattgcca ctaaaaggag aaaagaagaa gaagaagaag  5100
aagaagaaga agaagaagaa gaagaagaag aagaagaaga ggaagaaaca aaacacattt  5160
gttgagcacc tactgagtcc tggactcaat gtcccaagca ttgccactaa gcctcacggt  5220
gttcccctga agtagacagt gatttctttt tcattttctc tttgagatta taatataatt  5280
acatcactgg gcagtggtgg cacatgcctt taatcctagc acttgggagg cagaggcagg  5340
cagatttctg agttcgaggc cagcctgctc tacacagtga gttccaggac agccagggct  5400
acacagagaa accctgtctc gaaaacaaaa acaatatata tatatatata tatatatata  5460
tatatataca catatatatg tgtgtgtgtg tgtgtatacg tatatatata tatacacata  5520
tatatataca catatatata tacatatata taatcatatc atccccctcc ctttcttccc  5580
tccaaaccct cccatagccc caataattat ttcttttttt ttttaagatt tatttattta  5640
ttatatgtaa gtacactgta gctgtcctca gatactccag aagagggcat cagattttgt  5700
tacggatggt tgtgagccac catgtggttg ctgggatttg aactcgggac cttcggaaga  5760
gcagtcggcg ctcttaacca ctgagccatc tcgccagccc caataattat ttcttatgat  5820
taactatact tttctcagct accatgaaca tcaagttcac aaattcagtg attccgttca  5880
```

-continued

```
caaattaggt tccgtgagcc tctggctatg acattttcac caatcattag catgtaatct  5940
tgttacatct ggattctgtt taaagacatt attcagtgtg catgttgttg atcccttaaa  6000
cactaatcta atggccgatg ccactattac tgcctgcctg acaaggtgtc cctgacacgt  6060
tttcttcata aggcgcatac aacttcttgt gttcttgcaa gtaggagcct caggtaacac  6120
ttgggcatac acatagaacc actctgtctc cctgaagtac tgaggatcga acctagagcc  6180
ttgtgtatgc caggcaaatg cttggccact gagttaaaac tctggccctc tttaaaaaga  6240
agtgtgtgtg tatgtgtgtg tgcaagtgca tgtgtgtatg tgtatgtaca tatgtgtgtg  6300
tgtttgtgtg tgtgtatgtg tgtatatgtg tgcgtgtgtg tgtgcaagta catgtgtgtg  6360
tatgtgtgtg tgttcgagca tctttcactg acccattcaa ttccataaag atcatgaagg  6420
cactgtgaac gttggcagtt tctttggctt tctttggcct tgtgctgact tgtgagcaag  6480
cactacacga ctgacctata tcctcagcct gagtcacaag tattgggttg gagggggctt  6540
acaaataaat gtttacaaag caggcagggg cagtggtggg ggggtgcctt taatcccagc  6600
acttggcagg cagaggcagg tgaatttctg agtttgaggc cagcctggtc tacacagtga  6660
gttccaggac agccagggct acacaaagaa accctgtctt gggggtgggg gtgggggaac  6720
aaaacaaaaa acaaaacaaa acaaagcagg caggttcaca aatataaagt cagtgaggat  6780
tggcagttgc attactgttg ccagtttact aagccaaaaa tggccaaggg acctaagtgt  6840
ttgtttgttt gtttgtttgt ttgtttgttt gtttgtttgt tttgtagaca ggctatctct  6900
gtgtaataga cctggctgtc ctggaactca ttctgtagac caggctggcc ttgaactcac  6960
agagatccgc ctgcctcagc ctcccaaatt ctgggatgaa aggcgtgtga cctaaatctt  7020
taatgagctc aactttgtga catgcacctg tgtttcagac ttgctcaggg tcagatatct  7080
attccagctg tctgactcta gaagcctact ttctaagcag gatgcagtct tgaatgcata  7140
gctgaccttt ttccaaatca ggccctgtga ggcagagggt gggcagctgg gtctcagggc  7200
agggctctga ggtgtggtgt tcctacagtt ctcactgtgg atgggaggct ctgccatttt  7260
ccctttcagt accaccgtca gctacaccac aaatgcatcc acaaaaggcg gccaggctcc  7320
cgcccctggt aagacatttt ctaatagggg ttgggggagg gggctggatg aaatggactc  7380
tgtctagcta tctaagcatc gtgtttggtc aaaaggtgtg tgtgtgtgtg tgtgtgtgtg  7440
tgtgtgtgtg tttgtgtgtg tgtgtgaagc aaggctagcc tagccagcct caggcactgc  7500
agggaaacct catctatccc ccaggtgtgc taccaccccc aactttgatg aagatcagca  7560
atggggatac tgcttggagc ccaagaaagt gaaaggtatg tatggcatgc aggccccggg  7620
tggctcaagg ctgtgtgtgt cttgctgctc actccgttcc cacacaccta ctcacctact  7680
aagcatcatc agatgccaaa cacttgggat tctgggcccc gccctttttcc ttctcttaca  7740
gcattctttc aaaagtcaga ggaagaattc tggggaaaga ggccaccatt gtccagatga  7800
gcttgagggt ctagaagctt ggggttctat ggtttgatga caagcaggtg caggcagggt  7860
attggtccct acatatgtcc ttccgactcc ggaagtgctt cgctcttgtt atctacctct  7920
cagaccattg cagcaaacac aacccgtgcc acaaaggagg gacatgtatc aacaccccca  7980
atgggccaca ctgtctctgc cctgaacacc tcactgggaa acattgccag aaaggtaaga  8040
ggaactgcct cccagcaaga tgtccctgga gacccggtgc tttgccatgg tcccattgac  8100
ttccttgtgt ccccagagaa atgctttgag cctcagcttc tcaagttctt ccacgagaat  8160
gagctatggt ttagaacggg gccaggaggt gtggccaggt gcgagtgcaa aggttctgag  8220
gctcactgca agccggtggc cagccagggt aagtgggtgt gcagggactg tggggaggag  8280
ggcagagagt caggaacccc tggtagaagg ctgggtgcaa tgatgtacac aggtaaggct  8340
cagtttgcac ctctccccac cccaccccca gcctgcagca tcaatccgtg ccttaatggg  8400
ggcagctgcc tcctcgtgga ggaccaccca ctgtgccgtt gccctacagg ctacactgga  8460
tatttttgcg acttgggtga gtaagacccc gtgtggaaag gcttgcggag gtggatagag  8520
agaatggaag tgaaccagag ggctccaaca gactcatccg ccgactgcag ggagccatct  8580
ctctttctct agacctttgg gcgacctgct atgaaggcag gggctcagc taccggggcc  8640
aggctggaac tacgcaatcg ggtgcgccat gtcagcggtg gaccgtggag gccacctacc  8700
ggaacatgac tgagaagcaa gcgctaagct ggggcctggg ccaccacgca ttttgccggt  8760
tcgcgagaag ggaccgggca ggggaacttg ctttctctta gggtcctcga gggcctcccc  8820
acgttctaac agtgctccct cttgagattg caggaaccca gataatgaca cacgtccatg  8880
gtgcttcgtc tggagtggcg acaggctgag ctgggactat tgcggcctgg agcagtgcca  8940
gacgccaacg tttgcacctc tagttgtccc tgagagtcag gaggagtccc cgtcccaggc  9000
accatctctg tcccatgcac caaatggtta ggcagaggag ggggtcccgg cgcagaggac  9060
atgggtctct cttattcctg gcagcccgtg ccaggtatcc atggcctcag ccagtctctc  9120
cttccacaga ctcgaccgat catcagactt ctctgtccaa gaccaacacg atgggctgcg  9180
gacagaggtt ccgcaaggga ctgtcctcgt tcatgcgcgt ggtgggcgga ctagtggctc  9240
tgcctgggtc gcacccctac atcgctgcac tgtactgggg taacaacttc tgcgcgggca  9300
gtctcatcgc cccctgttgg gtgctgaccg cggctcactg cctgcagaat cggcaagtgc  9360
caccctcggt gacccccctag accgctccta ccgtacccgc accctactct ttccctgccc  9420
gccattcttg agctccctcg aggggttgga aactaaggca cccccagagc atttgtagcc  9480
ggtctgagcc tgctgcctgt cccccacccg actgcaggcc agcgcccgag gaactgacag  9540
tggtacttgg tcaagatcgc cacaaccaga gctgcgagtg gtgccagact ctggctgtgc  9600
gctcctaccg ccttcacgag ggcttctcct ccatcaccta ccagcacgac ttgggtgggg  9660
tggccctaca gggataggga gaaaggatgg cggagggctg gggccctatg tcgccatcta  9720
acctttgcct ctcggggtag ctctgctgcg cctgcaggaa agcaaaacca acagttgcgc  9780
gatcctgtca cctcacgttc agcctgtgtg tctacccagc ggcgcggccc caccctctga  9840
gacagtgctc tgcgaggtgg ccggctgggg tcaccagttc gagggtaggc acaactgttg  9900
ggcgctggtt ggagactttt ggttatctag gagcgcagtt ggtacgcccc gatgaatctg  9960
ggggacaagt ttcactgaca tgacagttgt aaaaaacgca cagagccctt gtctctgtag  10020
cgtgactttc ccagattcta gaattctctg tcgagattcc agagcccctt gaggtttgtt  10080
ctagtttttt gccttctatt gtggcgttaa acaccatgac caaatccagc ttaggcagga  10140
aaggttttat ttggcttccg aggttgcagg gtttcttgct gtccaccatt gaggaagcca  10200
caacagggag tggaggcagg aactgaggca ggaaacggaa agggacactc cttgctgcct  10260
ttctcttcat ggcttgttca gctttctttt taaaaaattc acttattttt attttatgtg  10320
catgtgagtc tgcctacaag catatgtgtg caccatatgt acatctggta caggggaagc  10380
cagatctgta atacaggtta aaaaccacgg tgtgggggct gggaacggaa ccaaggccct  10440
ctgcaagaac agcaagagct cttaacctct gagctagccc ccaacacctt gcggcttgct  10500
tactttgctt tgcttttctc ttttcctctt cctcttcctc ttcctcttcc tcctcctcct  10560
ctttctcccc ctcttcctct tgttttgttt ttgtttttttg ttttgaaggc agggtttctc  10620
```

-continued

```
tgtgtagtcc cagctgtccg ggagctgtcc aggagctgtc cagctctgta gaccaggctg  10680
ccttcaacct taagcactcc atctgccttt gcctcccaag tgctgggatt aaaggcttgc  10740
acctttctgg ctcagtttct ttcttacaca atccaggccc acctgttcag ggcggcatca  10800
ctcacagtgg gcggggccct ttcacatcaa ccattaatca agaaaatgcc cggggctggt  10860
gagatggctc agtgggtaag agcacccgac tgctcttccg aaggtccaga gttcaaatcc  10920
cagcaaccac atggtggctc acaaccatct gtaacgagat ctggcgcctt cttctggagt  10980
gtctgaagac agctacagtg tacttacata taattaataa ataaatcttt aaaaaaaaaa  11040
aaaaagaaaa tgccctacag atattgccct aggccaatct tctggaggca tctcttcggg  11100
tgaggttcct tcccccccta gatgactctt gagtgcgtca aattgacaga cagtaaccca  11160
gcacaaggat tacagggaga cttgaactgt cttgtgcttc ttttgggctc caaattataa  11220
aggcttaacc aggactttgt ccccatgctg gagcaatgga gacaatggag agaactattc  11280
tgggagccag gttctgagcc actgtgtgga agaggatagg aagtgcttcc tgtgttttaa  11340
gccctgctct tctctgggct tcagtgtcct tgccatgaaa tacttattgg caggtcccta  11400
tcactcaggc ttgctgtgag ggagcaaagc ggagtaggtg gggaattgtc tggtagcctg  11460
gcccacgcag caagctcagg tcctcccctc tgatttgcag gggctgaaga atactccacc  11520
ttcctgcagg aggcacaggt tccctttatc gccctggatc gctgctccaa ctctaacgtg  11580
cacggagacg ccattctccc tgggatgctt tgcgctggct tcttggaggg aggcaccgat  11640
gcctgccagg tcagccctgg ggtcctggta ggtaccttgg tccctgcctg tcaagcataa  11700
ggcaagaacc acgtgctgcc tgttccccac ccagggtgac tccgggggcc ctctggtgtg  11760
tgaggaagga actgcagaac atcagctcac cctgcgcgga gtcatcagct ggggctccgg  11820
ctgtggtgac cgcaacaagc ccggagtcta cacagacgtg gccaactacc tggcttggat  11880
ccagaagcat attgcttcat aactaaccag gctttatcct tccctccttg tgtgctcctt  11940
gggatgggac gatgaatgtg gcatgctggg tcacagtgaa gctagtgccc cgacactggg  12000
ggcacagaaa ctcaataaag tgctttgaaa acgttcctca gaattctgtc ttgaaacgtc  12060
aagtgggagc acaggtaagc caactccctc gttgcctgga caaggcaact agccagatgt  12120
cagcataaga ggcgtagact cttgtccgga ccaccatatt ttctcatcct tactttgggt  12180
gagcttttgc cgcccatgtt caagtccacc tgaggtcaat taactggact ctagggagaa  12240
ggcagtcttg gcatattttt aaaacgctac gggtgattcc ttatgcaata gaggttggga  12300
actgtagtta agagtgttcc agacgggaat cgtggtgcgg atagtagctg ctgagcatgt  12360
gtgagaggcc ctgggttaga tcccagcacc accattaaaa gaagggggag gggttgtgtt  12420
gggttgtgtg ggttttgttt gtttgttttg aactttaagc ctggcatggt ggtgcaagtt  12480
ggtgtcaagg aaaatctgag gctgcatctg atgcctctaa gtacaagctg ggttaggagc  12540
cagccagcca gagccttcgg ggatgcggtg actccaaagc gaggtttgta gttcccttgc  12600
aggagaggag cctagttgtc cagatgagta catttcttgc ttttaaaaat gtccttctgt  12660
ttattgattt attgagatat ctgtcgtcct aatgccgaaa ttataggcct atacaatcac  12720
ccagtttatg tggtgcaggg ggatcaatcc caaaactttg ttcttggtct agccaggccc  12780
tctgtcaact gcactgtact gactgcgcta cactccccgt ccttacaccc atctttgcac  12840
agcatcttac tgcatagctt ttgtctggcc tgtgacttgc taggtagcct tgaacttgta  12900
cagatcccct tgcttcatga gtgacaggtt taagtacaag ccaccatgtc tggctttttt  12960
tttttttttt aattaagaaa aaaaaatggg gctggtgaga tggctcagtg ggtaagagca  13020
cccaactgct cttctgaagg tctggagttc aaatcccagc aaccacatgg tggctcacaa  13080
ccatccgtaa tgagatctga tgccctcttc tggagcgtct gaagacagct acagtgtact  13140
tacatgtaat aaataaataa ataaataaat aaatcttaaa aaaaaaaaga aaaaaatgtg  13200
gtttgtgtta tgagtgtgtc acagtgtggt gtgaaggtca gagcacaact ctgtggagcc  13260
agttctctcc ttctgccttt gtgggggctc tggtgataaa actcaggcca ccaggcttat  13320
aagacaatgc acccttactg tctgagcctt tttttttttt ttttatggtt tttcgagaca  13380
ggctttctct gtgtagccct ggctgtcctg gaactcactt tgtagaccag gctggcctcg  13440
aactcagaaa tccgcccgcc tctgcctcct gaatgctggg attaaaggcg tgcaccacca  13500
tgcctggcac tttttttaata attaaaaacc tgagaatttg ggctggagag agaatgactc  13560
agtggttaag agcacggact gctcttccag aggtcctgag ttcaattccc agcaatcaca  13620
tgatggctca caaccatctg taatgggatc caatgccctc ttctggtatg tctgaagaca  13680
gcgacattgt actcatatac ataaaataaa tacatttctt ttattatatc taagtacact  13740
gtagctgtct tcagatgcac cggaagagag cgtcagagct cattaaggat ggttgtgagc  13800
caccatgtgg ttgctgggat ttgaactcag gaccttcaga agagcagtca gtgctcttaa  13860
ccactgagcc atctctccag tcctaaatgt gtctttaaaa aaaaaaaagt taaaatttca  13920
agacttttga gctggtgaga tggctcagtg ggtaagagca cccgactgct cttccgaagg  13980
tccgaagttc aaatcccagc aaccacatgg tggctcacaa ccacccgtaa tgagatctga  14040
tgccctcttc tggtgtgtct gaagacagct acagtgtact tacatataat aaataaatct  14100
taaaaaaatt ttttcaagac ttttaaattg ctgggcagtg gtggcgcatg cctttaatcc  14160
cagcactcgg aggaagaggc aggcggattt ctgagttcga ggccagcctg gtctacaaag  14220
tgagttccag gacagccagg gctatacaga gaaaaaacaa aaaacaaaac aaaaacaaaa  14280
aaaatcaaga cttttatgtg tttctgtgga catgagtgca ggtgcccaag caagccagat  14340
gcactgcttt acctgggtgc tgggaattga actctggtcc tctgaaaatg gcactcagtt  14400
gcgggacctt tttttattta tttttttatt ttattttatt ttaaatcatg tgtgtgtttg  14460
tgtgtgagct tgcctcagga gttgtcagat ctctcgagtg ggagttacag gctttgtagg  14520
ccaaaagagg tgatgctggg aacggaactc aggctctgtg taatgaatgc tctttcttaa  14580
cgctgagcca cctttccagc ctctcatcca tcttcttcca tttcctccta catgctactt  14640
ttagaaccgc ccccgaaccc ccaccaactc taccgccctc tccttctcct cctagttaga  14700
tgttctgtga cgtttgcctt acgtcacagc cccgccctgc gaacttcggg catgctgcca  14760
gtgttcttag ctctgaatgc agccggccac cccccctaat gcaagcacaa gttgctggga  14820
ctgactgagc ggagatgagt gactggaagg gctacatcag tgcagtgctg cgggatcagc  14880
ggatcgatga cgtggctatc gtgggccact cggacaatcg ctgtgtgtgg gcatcacggc  14940
ctgggggtct gctggctgcc atctccccgc aggaggtggg tgtgctcacc gggccagacc  15000
```

```
SEQ ID NO: 55          moltype = RNA  length = 23
FEATURE                Location/Qualifiers
source                 1..23
                       mol_type = other RNA
                       organism = synthetic construct
```

```
SEQUENCE: 55
taaagcactt tattgagttt ctg                                          23

SEQ ID NO: 56          moltype = RNA  length = 23
FEATURE                Location/Qualifiers
source                 1..23
                       mol_type = other RNA
                       organism = synthetic construct
modified_base          1
                       mod_base = OTHER
                       note = thymine
SEQUENCE: 56
taaagcactt tattgagttt ctg                                          23

SEQ ID NO: 57          moltype = RNA  length = 22
FEATURE                Location/Qualifiers
source                 1..22
                       mol_type = other RNA
                       organism = synthetic construct
SEQUENCE: 57
aaagcacttt attgagtttc tg                                           22

SEQ ID NO: 58          moltype = RNA  length = 21
FEATURE                Location/Qualifiers
source                 1..21
                       mol_type = other RNA
                       organism = synthetic construct
SEQUENCE: 58
gaaactcaat aaagtgcttt a                                            21

SEQ ID NO: 59          moltype = RNA  length = 21
FEATURE                Location/Qualifiers
source                 1..21
                       mol_type = other RNA
                       organism = synthetic construct
SEQUENCE: 59
aactcaataa agtgctttga a                                            21

SEQ ID NO: 60          moltype = RNA  length = 23
FEATURE                Location/Qualifiers
source                 1..23
                       mol_type = other RNA
                       organism = synthetic construct
modified_base          1
                       mod_base = OTHER
                       note = thymine
modified_base          22..23
                       mod_base = OTHER
                       note = thymine
SEQUENCE: 60
ttaaaatcta cagtcatagg att                                          23

SEQ ID NO: 61          moltype = RNA  length = 23
FEATURE                Location/Qualifiers
source                 1..23
                       mol_type = other RNA
                       organism = synthetic construct
modified_base          22..23
                       mod_base = OTHER
                       note = thymine
SEQUENCE: 61
ttaaaatcta cagtcatagg att                                          23

SEQ ID NO: 62          moltype = RNA  length = 20
FEATURE                Location/Qualifiers
source                 1..20
                       mol_type = other RNA
                       organism = synthetic construct
SEQUENCE: 62
taaaatctac agtcatagga                                              20

SEQ ID NO: 63          moltype = DNA  length = 22
FEATURE                Location/Qualifiers
source                 1..22
                       mol_type = other DNA
                       organism = synthetic construct
SEQUENCE: 63
ttgttgtagg atatgccctt ga                                           22
```

```
SEQ ID NO: 64          moltype = DNA  length = 21
FEATURE                Location/Qualifiers
source                 1..21
                       mol_type = other DNA
                       organism = synthetic construct
SEQUENCE: 64
gcgatgtcaa taggactcca g                                            21

SEQ ID NO: 65          moltype = DNA  length = 31
FEATURE                Location/Qualifiers
source                 1..31
                       mol_type = other DNA
                       organism = synthetic construct
SEQUENCE: 65
agcctaagat gagagttcaa gttgagtttg g                                 31

SEQ ID NO: 66          moltype = DNA  length = 20
FEATURE                Location/Qualifiers
source                 1..20
                       mol_type = other DNA
                       organism = synthetic construct
SEQUENCE: 66
gctgattaga gagaggtccc                                              20

SEQ ID NO: 67          moltype = DNA  length = 20
FEATURE                Location/Qualifiers
source                 1..20
                       mol_type = other DNA
                       organism = synthetic construct
SEQUENCE: 67
tcccatttca ggagacctgg                                              20

SEQ ID NO: 68          moltype = DNA  length = 16
FEATURE                Location/Qualifiers
source                 1..16
                       mol_type = other DNA
                       organism = synthetic construct
SEQUENCE: 68
ttcaaggtga actgtt                                                  16

SEQ ID NO: 69          moltype = DNA  length = 16
FEATURE                Location/Qualifiers
source                 1..16
                       mol_type = other DNA
                       organism = synthetic construct
SEQUENCE: 69
tatttctgct ccaggt                                                  16

SEQ ID NO: 70          moltype =   length =
SEQUENCE: 70
000

SEQ ID NO: 71          moltype = DNA  length = 12
FEATURE                Location/Qualifiers
source                 1..12
                       mol_type = other DNA
                       organism = synthetic construct
SEQUENCE: 71
tttttttttt tt                                                      12

SEQ ID NO: 72          moltype = DNA  length = 20
FEATURE                Location/Qualifiers
source                 1..20
                       mol_type = other DNA
                       organism = synthetic construct
SEQUENCE: 72
gccaggctgg ttatgactca                                              20

SEQ ID NO: 73          moltype = DNA  length = 13000
FEATURE                Location/Qualifiers
source                 1..13000
                       mol_type = genomic DNA
                       organism = Mus musculus
SEQUENCE: 73
actgcacagt gagacccttc tatacaaagt aaaagacagt taggcatgca gctcagaggt  60
aggttgtcta cctagcaagc ttgaggtctt gagttcaatc tttttttttt tttttttttt  120
ttttggtttt ctgagacagg gtttctctgt gtagccctgg ctgtcctgga actcactctg  180
tagaccaggc tggcctcgaa ctcagaaatc cgcctgcctc tgcctcccga gtgctgggat  240
taaaggcgtg cgccaccacg cctggccgag ttcaatcttt taactttgga aaagacccac  300
```

-continued

```
gaaacaaaag aggatgagaa tcagagtggt ttggaaatta ccaaagcctg tttgtgaagt  360
aaaataaaag ttaagaaggg ggaagacagt gggcatttgg gccctagcaa taagaaaagg  420
taatccagaa tgttctctag aaatattccc gtggcgttca ctgggaactc ccttgctgcc  480
ttcataaacc atgtcttttg gtagtttctg gagtgaccct gctgcctgtt tctctctcca  540
aaccctggga gttgcccagt gccgcacagc cattccaaaa gcaaggaaaa gtttgtatga  600
tgtgtgaagg aatcaagaag atggacttac agacaagcac tttagggggc gagggaagga  660
agggggaaag gcttgcctag tttcccttat ctgcagggtt tctaaaacaa caacaacaac  720
aacaacaaaa caaatctcca tagtttatgc cagaagtgag ccccgccttt aatcccagca  780
ctcagaaggt agatcctgac agatctgagt ttccaggcca gccagggata cagttttagg  840
acaatatggc agtgagactc tgtctcaaaa catgtcaccc tatacacttt atcatttttt  900
ttaattccag acagggtttc tctgtgtatc tctggctgtc ctggaactca ctctgtagac  960
caggctggcc ttgaactcag aaatctgcct gcccctgcct cccaagtgtg ccaccactgc  1020
ctggtgactt tatttttatt ttattttttta aagaaacaac aacaaagcgt ggggtctcct  1080
atctgtcttg gctcacctgg aaccctctat gtagaacagc cggccccgaa cttgcagaga  1140
tccagcccta ccattttaaa gattggtttc atttccctgg cctccagaac ggtcttagac  1200
cctccccccca gcagaagcaa agcagaaaca gaaggtcggg ggaggagagg gaggtgggta  1260
ggttaagagg aacgatgaag aacaccttct gctagttaac tttgcctaat tatagatgaa  1320
tcacagatgc ccgacactca gatcaccgcc cataatttag gtgactcaag tttttgtcct  1380
ttcagaacta aaattctaaa aaatttccag gcccaaagca tccatcaagt gtgcctctag  1440
agaggaaccg tttgcactca gtaacattcc attctttagg gcttcttaca gacagaaaaa  1500
gagaaaagta gggcagtttt gcaagggtca cctgaaagct gcttaaacaa gccccaggct  1560
tggtacacac agctttaatc cagcacttgt gtaaggacct gagtttgagg ccagcctggt  1620
ccagaaaccc tgtctcagga aaaataaata aggaagaaag aaaaagctta aactggccat  1680
tgggatggga agggaggcaa tggtctaaca ctggacctcc agctttgcta gagccccacc  1740
tcagtctaag ggtgcctctc tcctttagtt ttataataga atattcatgt aattttatgt  1800
ccttagtgac tatcagcctg tatggtcatt aagttctgtc taccctggga aagcctctgc  1860
ccaaacctcc ctattcacag gtcctagaac gtagaggtgg ggagcaggac ggtgccgcca  1920
ggccgtgtgc gatcgcgagc tctggatctc aatgcgcccc ggggcgctgt ttcccacgac  1980
tccagcagct tttctaaaaa tccaggcagc ctccagttta cgggatcaac ccgagactcg  2040
cttccctttg aaaattctag agtataaagt aaacgtacga gcaaagtatg tgtcttaaca  2100
cttaatggat gacatagaga ccaaaaaagc catgtccgtg ggcccagtag gccgcaataa  2160
ggggcgacca ggaaactgca gcacagcccc ccgcagccgc cctgctccca caccagtcat  2220
tccagcaccg tggtgaaggc gcttggggc ggggcggggc gcgcctgcgc agcgaggctc  2280
tgcagcagaa actttgccta gaccggctgg aaccggttag aaccggtcga acccggccgg  2340
ctgccagccc tcgattcagc agctcacaaa gggaggcggc gactcacgac ccgcgtatcc  2400
ttgcgcctct ccccaccccc tttgtcctcg cgacgggttc cgcggtcctc cccgccctcc  2460
ctggcgcggc ccccgctttc tgcgcccagt gacgctttct ccatggtcct gggagaaaga  2520
gaaaaacatc ctttcccctc cgtcgtagtt ttaggaagcg atgagataga cctggggacc  2580
ttgccgccac gggccgggct ctgacggtta ttagcgcagt gcgggtggtg ctcggcatgg  2640
ccgccaaggt cgccgtgccc tcacctgcag cgaccatggc cttgctgggc tgagaccgca  2700
gcctaacatg gcggacgtag gcaagcacca aagcgctcgt gtacccgggc tcggaaaagt  2760
ggccccgaga gcagccggag gctgcaggtc gtccctacag gagcattccc agtataaacc  2820
agtacaaagt gtcaccacct cagaagccac tcgcagggcc ggtcactttc cgagagacct  2880
ccatcttgtt tcgcatgaaa tggcagccgc tcggggagtt acaaaatggg aagtggaagc  2940
tgaagctgtg ggaaagcctg ttttaacact tgcaacatac gctataccct ctgtcctccc  3000
aggaaaacgc aaaaggtgtt gaaacatctg aaaaacttgg ggctcccatt tttaatagct  3060
attagttcat gttttttctc cttgtgacca gaaattttaa acctatttgt acctatttag  3120
ctggtacaag ctaaacattt ctctgtatta gcaaggtcca agaggcccac acgacgtcaa  3180
gaaaaatcta gaaacttgga agtcaggatc tatttttaac tctctgagga actatttttc  3240
ttccttcacc aaggtggtgg agggttacta ggttccggtg gagtgacgtg tccctttgca  3300
ataaataccg gcgctccggg ctctgcgtca ggcattcagg cagcgagagc agagcagcgt  3360
agagcagcac agctgagctc gtgaggcagg agactcagcc cgaggaaatc gcagataagt  3420
ttttaattaa aaagattgag cagtaaaaag aattagaact ctaaacttaa gctaatagag  3480
tagcttatcg aaatattact tagtcttaat aatctaagaa gatcttaaga gataacatga  3540
aggcttattt aaacagtttg aaaaaggaaa tgaggagaaa agtatttgta ctgtataatg  3600
gaggctgacc agagcagttt aggagattgt aaagggaggt tttgtgaagt tctaaaaggt  3660
tctagtttga aggtcggcct tgtagattaa aacgaaggtt acctaaatag aatctaagtg  3720
gcatttaaaa cagtaaagtt gtagagaata gtttgaaaat gaggtgtagt tttaaaagat  3780
tgagaaaagt aggttaagtt gacggccgtt ataaaaatcc ttcgactggc gcatgtacgt  3840
ttgaaggcat gagttggaaa cagggaagat ggaagtgtta ggctagccgg gcgatggtgg  3900
cgcacgcctt taatcctagc acttgggagg cagaggcagg cggatttctg agttcgaggc  3960
cagcctggtc tacagagtga gttccaggac agccagggct acacagagaa accctgtctt  4020
gaaaaaacaa aaaggttagg ctagtatttg gagaaagaag attagaaaat ggaagtgaaa  4080
gacgaagaag acatacagga aggtgaagaa aaagctgtta gagaagatag gaaaatagaa  4140
gacaaagcat ctttagaaga cagaaaaggt acttaaaggc acaggtagta ggaagccgaa  4200
gaatagaaga tagaaagaag caagatagaa aaacaaaatg gaagttaaga caactttgga  4260
tgccagcatt caagataggc aaagaagata agattgaggc caaaaggttg gataagatat  4320
aaagtcagaa ggaaattatc tttaaagcca taagttcaaa tttctgatgg agcgagcagt  4380
ttagaagagt ctttagacag ccacatacaa gattgaagct agcaatcaaa gctactagga  4440
ctgaagtaaa aagttaaggc agaatgcctt tgaagagtta gaagaatatt aaaagcctta  4500
acttgtagct taattttgct tgatgacaaa aggacttttg ataacagttt caagattgtc  4560
agcattttgc attggacttg agctgaggtg cttttaaaat cctaacgact agcattggca  4620
gctgacccag gtctacacag aagtgcattc agtgaactag gaagacagga gcggcagaca  4680
ggagtcccga agccagtttg gtgaagctag gaaggactga ggagccagca gcagcagtgc  4740
atggtgaaga tagcccagga aagagtgcgg ttcggtggag gaagctagga agaaggagcc  4800
atacggatgt ggtggtgaag ctgggaaagg gttccaggat ggtggagcga gagcgagttg  4860
gtgatgaagc tagctggcgg cttggcttgt caactgcgcg gaggaggcga gcaggcattg  4920
tggagaggat agatagcggc tcctagacca gcatgccagt gtgcaagaaa ggctgcaggg  4980
agagcatgcg gtgcggtaac attccttgag gtcggcaaca tggtggtggt tttctgtaac  5040
```

-continued

```
ttggatggta acttgtttac tttgtcttaa tagttatggg ggagttgtag gcttctgtgt  5100
aaagagatat atctggggct gtatgtaggc ctttgcgggt gttgtaggtt tttctttttc  5160
agggttatgt cctcttgcat cttgtcagaa gcttttgagg gctgactgcc aaggcccaga  5220
aagaagaatg gtagatggca agttgtcttt aaccgctcag aggggaatga atggtagagc  5280
cagcacaacc tcccagtttt gtaagacgtt gtagtttgaa cagatgacct accacaagcc  5340
tcactcctgt gtaggggagg taattgggca aagtgctttt gggggaatgg gggcaaaata  5400
tattttgagt tcttttcccc ttaggtctgt ctagaatcct aaaggcagat gactcaaggg  5460
aaccagaaaa aaggaaatcc actctcagga taagcagagc tcgccaggtt tacagtttgt  5520
aggaagtaga ggatggatgc tagctttcac actgagtgtg gaggagctgg ccatggcgga  5580
attgctggta gtttactctt tccccctccc ttaatgagat ttgtaaaatc ctaaacactt  5640
ttacttgaaa tatttgggag tggtcttaac agggaggagt gggtggggga aacgtttttt  5700
ttctaagatt ttccacagat gctatagttg tgttgacaca ctgggttaga gaaggcgtgt  5760
actgctatgc tgttggcacg acaccttcag ggactggagc tgccttttgt ccttggaaga  5820
gttttcccag ttgccgctga agtcagcaca gtgcggcttt ggttcacagt cacctcagga  5880
gaacctcagg agcttggcta ggccagaggt tgaagttaag ttttacagca ccgtgattta  5940
aaatatttca ttaaagggga ggggtaaaac ttagttggct gtggccttgt gtttgggtgg  6000
gtgggggtgt taggtaattg tttagtttat gatttcagat aatcatacca gagaacttaa  6060
atatttggaa aaacaggaaa tctcagcttt caagttggca agtaactccc aatccagttt  6120
ttgcttcttt tttccttttt cttttttga ggcgggcagc taaggaaggt tggttcctct  6180
gccggtccct cgaaagcgta gggcttgggg gttggtctgg tccactggga tgatgtgatg  6240
ctacagtggg gactcttctg aagctgttgg atgaatatag attgtagtgt gtggttctct  6300
tttgaaattt ttttcaggtg acttaatgta tcttaataac tactatagga acaaaggaag  6360
tggctttaat gaccctgaag gaatttcttc tggtgatagc ttttatatta tcaagtaaga  6420
gatactatct cagttttgta taagcaagtc tttttcctag tgtaggagaa atgattttcc  6480
ttgtgactaa acaagatgta aaggtatgct ttttttcttc ttgtgcattg tatacttgtg  6540
tttatttgta acttataatt taagaattat gataattcag cctgaatgtc ttttagaggg  6600
tgggcttttg ttgatgaggg aggggaaacc tttttttttc tgtagacctt tttcagataa  6660
caccatctga gtcataacca gcctggcagt gtgatgacgt agatgcagag ggagcagctc  6720
cttggtgaat gagtgataag taaaggcaga aaaaataatg tcatgtctcc atggggaatg  6780
agcatgagcc agagattgtt cctactgatg aaaagctgca tatgcaaaaa tttaagcaaa  6840
tgaaagcaac cagtataaag ttatggcaat acctttaaaa gttatggctt atctaccaag  6900
ctttatccac aaaagtaaag aattgatgaa aaacagtgaa gatcaaatgt tcatctcaaa  6960
actgctttta caaaagcaga atagaaatga agtgaaaatg ctgcattaag cctggagtaa  7020
aaagaagctg agcttgttga gatgagtggg atcgagcggc tgcgaggcgg tgcagtgtgc  7080
caatgtttcg tttgcctcag acaggtttct cttcataagc agaagagttg cttcattcca  7140
tctcggagca ggaaacagca gactgctgtt gacagataag tgtaacttgg atctgcagta  7200
ttgcatgtta gggatagata agtgcctttt ttctcttttt ccaaaaagac ctgtagagct  7260
gttgaatgtt tgcagctggc cctcttaggg cagttcagaa ttttgagtag ttttcccatc  7320
cagcctctta aaaattccta agccttgcac cgatgggctt tcatgatggg atagctaata  7380
ggcttttgca tcgtaaactt caacacaaaa gcctacatga ttaatgccta ctttaattac  7440
attgcttaca agattaagga atctttatct tgaagacccc atgaaaggga tcattatgtg  7500
ctgaaaatta gatgttcata ttgctaaaat ttaaatgtgc tccaatgtac ttgtgcttaa  7560
aatcattaaa ttatacaaat taataaaata cttcactaga gaatgtatgt atttagaagg  7620
ctgtctcctt atttaaataa agtcttgttt gttgtctgta gttagtgtgg gcaattttgg  7680
ggggatgttc ttctctaatc ttttcagaaa cttgacttcg aacacttaag tggaccagat  7740
caggatttga gccagaagac cgaaattaac tttaaggcag gaaagacaaa ttttattctc  7800
catgcagtga tgagcattta ataattgcag gcctggcata gaggccgtct aactaaggac  7860
taagtacctt aggcaggtgg gagatgatgg tcagagtaaa aggtaactac atattttgtt  7920
tccagaaagt caggggtcta atttgaccat ggctaaacat ctagggtaag acacttttcc  7980
cccacatttc caaatatgca tgttgagttt aaatgcttac gatcatctca tccactttag  8040
ccttttgtca cctcacttga gccacgagtg gggtcaggca tgtgggttta aagagttttc  8100
ctttgcagag cctcatttca tccttcatgg agctgctcag gactttgcat ataagcgctt  8160
gcctctgtct tctgttctgc tagtgagtgt gtgatgtgag accttgcagt gagtttgttt  8220
ttcctggaat gtggagggag ggggggatgg ggcttacttg ttctagcttt ttttttacag  8280
accacacaga atgcaggtgt cttgacttca ggtcatgtct gttctttggc aagtaatatg  8340
tgcagtactg ttccaatctg ctgctattag aatgcattgt gacgcgactg gagtatgatt  8400
aaagaaagtt gtgtttcccc aagtgtttgg agtagtggtt gttggaggaa aagccatgag  8460
taacaggctg agtgttgagg aaatggctct ctgcagcttt aagtaacccg tgtttgtgat  8520
tggagccgag tccctttgct gtgctgcctt aggtaaatgt ttttgttcat ttctggtgag  8580
gggggttggg agcactgaag ccttttagtct cttccagatt caacttaaaa tctgacaaga  8640
aataaatcag acaagcaaca ttcttgaaga aattttaact ggcaagtgga aatgttttga  8700
acagttccgt ggtctttagt gcattatctt tgtgtaggtg ttctctctcc cctcccttgg  8760
tcttaattct tacatgcagg aacattgaca acagcagaca tctatctatt caaggggcca  8820
gagaatccag acccagtaag gaaaaatagc ccatttactt taaatcgata agtgaagcag  8880
acatgccatt ttcagtgtgg ggattgggaa gccctagttc tttcagatgt acttcagact  8940
gtagaaggag cttccagttg aattgaaatt caccagtgga caaaatgagg acaacaggtg  9000
aacgagcctt ttcttgttta agattagcta ctggtaatct agtgttgaat cctctccagc  9060
ttcatgctgg agcagctagc atgtgatgta atgttggcct tggggtggag gggtgaggtg  9120
ggcgctaagc cttttttaa gattttcag gtacccctca ctaaaggcac tgaaggctta  9180
atgtaggaca gcggagcctt cctgtgtggc aagaatcaag caagcagtat tgtatcgaga  9240
ccaaagtggt atcatggtcg gttttgatta gcagtgggga ctaccctacc gtaacacctt  9300
gttggaattg aagcatccaa agaaaatact tgagaggccc tgggcttgtt ttaacatctg  9360
gaaaaaaggc tgtttttata gcagcggtta ccagcccaaa cctcaagttg tgcttgcagg  9420
ggagggaaaa gggggaaagc gggcaaccag tttccccagc ttttccagaa tcctgttaca  9480
aggtctcccc acaagtgatt tctctgccac atcgccacca tgggcctttg gcctaatcac  9540
agacccttca cccctcacct tgatgcagcc agtagctgga tccttgaggt cacgttgcat  9600
atcggtttca aggtaaccat ggtgccaagg tcctgtgggt tgcaccagaa aaggccatca  9660
attttcccct tgcctgtaat ttaacattaa aaccatagct aagatgtttt atacatagca  9720
cctatgcaga gtaaacaaac cagtatgggt atagtatgtt tgataccagt gctgggtggg  9780
```

-continued

```
aatgtaggaa gtcggatgaa aagcaagcct ttgtaggaag ttgttggggt gggattgcaa  9840
aaattctctg ctaagacttt ttcaggtgga cataacagac ttggccaagc tagcatctta  9900
gtggaagcag attcgtcagt agggttgtaa aggtttttct tttcctgaga aaacaacctt  9960
ttgttttctc aggttttgct ttttggcctt tccctagctt taaaaaaaaa aaagcaaaag  10020
acgctggtgg ctggcactcc tggtttccag gacggggttc aagtccctgc ggtgtctttg  10080
cttgactctt atatcatgag gccattacat ttttcttgga gggttctaaa ggctctgggt  10140
atggtagctg atatcactgg aacactcccc agcctcagtg ttgaactctt gataattaac  10200
tgcattgtct ttcaggttat gcccaattcg tcttattacc tctgagtcga cacacctcct  10260
actatttatt gaatactttg attttatgaa ataaaaacta aatatctctc attgtgtgct  10320
tctttgtgca taaaacacag gcttatttta agcctaaaga gaccaaatgt ctgatctacc  10380
tcagcttctc cgattagtga ggccttccct gtttccttgg gctgcatggc tctttcatgc  10440
agatggctct aaagttgggc ttgggtccta ggtggccact cttgcacctc aggaacacaa  10500
ggcctttccc tgctgttcag gctctcctcc ctgagaaaac attctggatt gtctatgagg  10560
aagttgggaa aagatggtgt cgaaaagagg tggtgtgcat tgctcctctg ttcctaacac  10620
tggatggaag actagtttc atgtagttta gggaaatagt tatacatggt ctaaaggccc  10680
aaaaacattc ccagagtgta tgcaatactg tgtgtaagtg tgcactgcgt gtgtttggag  10740
gtcagaactt ctctgaggtt ctagagatga agcaagtcct cagccatggc ccaagaatgg  10800
gaaggaactg ggtcctgctg taccacttcc cattccttaa ggaacagttt ggcccggtgt  10860
ggtgcaagca tggtcggtca ctgaaaaaag aaaacccact taggtttcac aggcttgaag  10920
agctgcatgt catccagcaa attactggct gctgtaagga caggccccta ggtcccagtc  10980
ccaggtgccc ttcctgccac tcaatcaagc cttacaccct gggcaaaaac atcctgcgtt  11040
gaaggttcag ctcccagggc tggaaacttg tgctggcatc taccccagtt caaaggggct  11100
cagcacattg acaactaaaa ctaagccctc aggtgagcaa aatggtctcc ttaaggcaat  11160
catggtcatt ggtgttcctg cagtaaagga cagcatcaca gctgatgtct gtgtactggc  11220
tagttttgta tcaacttgac acagctggaa ttatcacaga gaaagcttca gttggggaag  11280
tgcctccaag agatcctcca cgagatcctg ctctaaggca ttttctcaat tagtgatcaa  11340
gggggaaaga ccccttgtgt gtgggaccat ctctgggctg gtagtcttgg ttcagttcta  11400
taagagagca ggctgagcaa gccaggggaa gcaagccagt aaagaacatc cctccatggc  11460
ctctgcatca gctcctgctt cctgacctgc ttgagttcca gtcctgactt ccttggtgat  11520
gaacagcagt atggaagtgt aagccgaata aaccctgtcc tccccaactt gcttcttggt  11580
catgtttgtg caggaataga aaccctgact aagacagtct gagacctgac agatctgtgc  11640
taaagtctgg taccaactga gctagaccct gccacacacc tcagtaatgg cccattctga  11700
attcacccag agctgaggct ttgccgaggt gaggcacaaa gacttcactg gagagcagga  11760
gatatgaaca gaggttgggg ctcacacttc ctgattgggg gccaggactg ggggcaagat  11820
gaaggaacgg taggcatgct tgtaaatttc ccaaagggtt agatccagat cttagctttc  11880
agtgtgtagg ccagggtgac tctgaatttg ggtccttgga cctcaacttt ggaagttgca  11940
gggatgagcc actgggctct gtacagtctt gtgctgccca catgctctag ttgtacaaag  12000
gatactccct caaacaagct ctccccaaat aggcctttga cgtctggacc cagccaccgg  12060
cccaaaagcc gattagtaca gggccagcag catagcatcc ttctactacg gcatgaaatt  12120
aggagaggaa gggtttgaag agagagagtg gaagatgtgg tttttatttt ttatttattt  12180
tatgtatgtg agtacactgt agctgtacag atggttgtga accttcatgt ggttgttggg  12240
agttcacttt taggacctct gctcactcca gtcatctccc ctcgctcagt ccctgctcac  12300
tccagcccaa agatttattt attattatac ataagtacac tgtagctgtc ttcagacaca  12360
ccagaagagg gcgtcagatc tcattacaga tggttgtgag ccaccatgtg ggtgctgaga  12420
tttgaactcc ggaccttcag aaaagcagtc agtgctctta actgctgagc catctctcca  12480
gcctgtgatt tttatatttt aggtagggcc atagtatcac cagacaggta ttccttgtat  12540
ggctcaggat ggtaaaatta aagttgtgcc tcaggctcct gagtgggact gcatggctgc  12600
tccagtatac ctggccacct ggattgttga ctctgaagct caggtcttag tttctgcctc  12660
tgatcagttg acaaacttga tacctgccca gctcacaatg caacctttgc atgcatcctg  12720
gacttagcct tgacaagggt agataggcaa ctgagtagga cgtgactgga cttcgctgcc  12780
atctagtgtg caaatgtagt gcatgcaatg tccttgaact ttttcttgcc atgcctattt  12840
tgttgtttta tttgtttgtt tttggtttat taattttttg taggatctct ctaatctgac  12900
ttcttggaat ttgctatata aactgggctg gccttgaact cacagcagtc ctcctgcctt  12960
tgcctcctca gcaaatcctg ccagcctata tacctccatg                        13000
```

```
SEQ ID NO: 74          moltype = DNA  length = 21
FEATURE                Location/Qualifiers
source                 1..21
                       mol_type = other DNA
                       organism = synthetic construct
SEQUENCE: 74
cggatgaaga gaggcatgtt g                                            21

SEQ ID NO: 75          moltype = DNA  length = 18
FEATURE                Location/Qualifiers
source                 1..18
                       mol_type = other DNA
                       organism = synthetic construct
SEQUENCE: 75
ttggccacac cgtccttt                                                18

SEQ ID NO: 76          moltype = DNA  length = 23
FEATURE                Location/Qualifiers
source                 1..23
                       mol_type = other DNA
                       organism = synthetic construct
SEQUENCE: 76
agacctgggc aatgtggctg ctg                                          23
```

-continued

```
SEQ ID NO: 77          moltype = DNA  length = 20
FEATURE                Location/Qualifiers
source                 1..20
                       mol_type = other DNA
                       organism = synthetic construct
SEQUENCE: 77
ctcctcagac cgctttttgc                                              20

SEQ ID NO: 78          moltype = DNA  length = 24
FEATURE                Location/Qualifiers
source                 1..24
                       mol_type = other DNA
                       organism = synthetic construct
SEQUENCE: 78
taacctggtt catcatcgct aatc                                         24

SEQ ID NO: 79          moltype = DNA  length = 20
FEATURE                Location/Qualifiers
source                 1..20
                       mol_type = other DNA
                       organism = synthetic construct
SEQUENCE: 79
ccgtcatgcc gacccgcagt                                              20

SEQ ID NO: 80          moltype = DNA  length = 52000
FEATURE                Location/Qualifiers
source                 1..52000
                       mol_type = genomic DNA
                       organism = Mus musculus
SEQUENCE: 80
ttgcagtgac tcagcctacc tccttcttac gcaacatttt tttttctttg tccaaccttt  60
actccttcct tatttctccc ctgcaataca cagggccagg agtctcctag accccagttc  120
aaatctgagc tctaaatgcc tacacagtga gttccaggcc actcaagggt acatactgag  180
accttgtctc aacatacacc ctcataaaaa gagaagacag ccacaggatt ctatttatat  240
ggaatactat actgagggct gagagagatg gcacacagcc aagcctgatg acttgagttt  300
gattccaaac ccacgtggta gaggggaaga actgactcct acaagtggtc ctctgacccc  360
cgcacagatg ctgtgcatgc cccacaaccc taggaacaaa tacaatcata gaaaataaat  420
gtccagagca agcaaagcca caaatgcagg gagctggtgg cagggatatt aacaagatcc  480
cttttccagg ataatggaat gtcttggagc tagagaggtc ataactgaga atatattaag  540
tggcactgaa ttgcaaacat caaaatctca aatatgtaca tttatataat ataaattata  600
cctcaactta aaaataatca agaatcaggt gtggtggtgc acagtgcatg agcataggag  660
acctcaaaaa tggccccaca gtgacacact tcctcaaacc aacaaggcca catctcctaa  720
tggtgccact ccttatgaac caaacactca aatacatgaa taggaagcta ttcctattca  780
agccaccaca ctgcgcttgg cagcacatgc ctacagtctc agtattaggg agttggaggt  840
atattcaaga tctcaaggtc agtccggact acactgtgag ttcaagggga gtccgagctg  900
cattcaaaga ccctgtgtca aaacaagggg agtggctgat ttggtagagt agttggtcaa  960
catgctcaag gccctaggca tcatcacagc actgcaaaat aaataaacag aatattgaga  1020
taagaggaag aaaacgtcac caactcagcc taagccgtga aagtttaata ccaccgatac  1080
taggaaaaga tggcaggtac cctgataata tgccctggga aggatacggg gattctgcca  1140
aagacgcata aagttaatct tgtagaactc gcaggtcatt gcaggtccaa gaggcactct  1200
ttcaaacaac tgacctcaaa ctaaggctga ggtgaagatc tgggatccag tcttcggtcc  1260
acaaagaagc tataagggat gttattcgga ataaccataa aactttgagt agaaacttgg  1320
gtgaggactg gagatgtggt tacatggtag agtgtctccc ttacacactg gaaaccccag  1380
gttctggccc cagcatcaca aaaatcaggc atggaagctc ataccettaa tcctagcact  1440
gggaggcaaa gccaggaaga ctgggacttc taggtcattc tggtttcagt aagttcaagg  1500
ccagtctggg ttgcacgaga ctctgcctga aaaggagaag cccccaaagt aggacaacaa  1560
cgaagtgggc ctgaaagact gttcagttgt taagagagca gcagcagcag caggaggatc  1620
tgatttcaga ttccagttgt ctcatgtaac aagctggcta ttccacaaat gaccataact  1680
ccagctttga ggggtgcagt gccttccctg gtctctgcat atgcaggtac tcacactagt  1740
gcacacacac acacacacac acacacacac acacacacac acacacacag agaaacacac  1800
acacacaaat aaatctttaa aaagtgtatc cgtgactgtc ctggaatttg ctaggtagac  1860
caggctggct ttgaattcac agatctatct gcctttgcct ctggagaccg tgtgaaccat  1920
gacatcttcc ccaattaaca aaaatacact tatttattat gtagccagtt gggggggggg  1980
gcgcggcagg gaggggagat gggccctcta caatgtagag atcagaggac aacttgtgga  2040
agttgttctc tcctcccact acaggagtgt ctgtgtatgc ccttccagga ttatatgggt  2100
cctctgtttc agtcctttgg tctcctagtg atggagatgt tcaagaacgg cacccttcac  2160
ccgactcctg agatttcccc tgaatgcacc tctagagctt ccattctcac ttcacacaga  2220
gggagtgttc agagcctttg caggtctcct ggatgtaaaa ctcagtgaat ggcaacgaaa  2280
tgataggcct catggtaaaa ccatgtagag tgtgggatgt gctaggagct ggtgtggatt  2340
tttttttacaa agtattttat cttatttctt gcgcacataa gcgtgtgtgt gtgtgtgtgt  2400
gtgtgtgtgt gtgcgcgcgc gtgcgtgcaa gcattcgagc acagtgtgtg taggagtgca  2460
tgtgtatcac ggggtacatg tggcagtcag aagacaatgt atgtgttggt ttttttattt  2520
tagcatggga ggcccaggaa ttgaactcgg gtgtctgtga ttggcagcaa gcacctttcc  2580
ctcttcggta gacctttgtg atcttcacat tgtaggagag ctgcacacag gtacatgaga  2640
ctcatatcca cgaaacccct ggccagattg taaatgctgc ccgcccgggt ttgtggcgca  2700
gttggagcct gagttttgag gtgattgatg tttagtgtcc ccatgaaact tctatatggt  2760
ttgcatgggt gcggctactt ttgttcattg gcctctctac acccaggttt agagggtttg  2820
gagtcagggg tgtttgcgtt tgtgtcatga ctgtgtgtgt gagccctggc tttggttgtg  2880
tgctggagga taaggatgga tgtgctcacg agctggatac ctgtcacgtc acgcaggtta  2940
```

-continued

```
agcccgcatc tcttgtggca gacctgagtg taccgaggtc tgcaagtccc aggcttggcg  3000
ggtagaaggg tcggacccca ggaggccggg caggggggcgg gggcgctcag agccggcccc  3060
ggggcggggc gagccgccca ggcctggggg cggggcagcc cgacagcctc acttcggcga  3120
agttggcggc gcggaggctg gcccgggacg tgcccggagc cctgggaaag agggaggagg  3180
gaggagggag ggtcgtggcc ggccgccatg gggctggggg cccggggccg ccgccgccgt  3240
cgtcgcctga tggccttgcc accgccacca ccgcccatgc gggcgctgcc cctgctgctg  3300
ctgctagcgg ggctgggggc tgcaggtgag ggatcaggga ctcggagggt gggactgggg  3360
ttgcaggggc ggggaagcaa aaaaaaaaaa gtatatatat atatatatat attctcctaa  3420
gtttggaatt tagaggacct gcccccccag gattaaagcc ggggcagaga tgcagcagct  3480
gggggtgtgt atcagtcatg gggttcgcac agattcatga tgggaaggca ggatcctaga  3540
ggcccaagga atcgagaccc ttgaatgaat caagagtcca agagtaggag ctggagttgt  3600
gggaatctgg ggctgaaatt cggaagcgag gtgtaccaaa agtttcaggc tcaccccatc  3660
ctacttctgc ctggagtcct gggaaggtta ggatgggggc tcaaggaccc cccaaggcct  3720
aggacccctt gcacaaaagc gcctccccta tcccgggcgg gccgtgaagg gggggggggg  3780
acaaggaggg ggcgcggagt tctcggagct ctgaactcgg agaaaacgtc tcatgttgga  3840
gagctgcaag acccggcgct ggagcgcgag aagcaggagc tggagccctt gcgaagcccg  3900
cgccccctcc cccgcgtgcc gcccgatccc tcttcaggcc gccgggatcc cgtagtctcg  3960
ggaccccgtc tctgtgccgg gaggagaagg ggcgaggtcc acgtgctcat ctccagcttc  4020
tgggccccca tccctgtggc cgcagcccct ccccagcatg cctgggcccc cctcccctct  4080
tcctccactc tgagctcccc tcccccgctc gggacaatgg cttcgccgtc tagacacccc  4140
ctccccccgg ccggcctcac gctttctttg ccagacaaag cgggacccac gaagggccag  4200
agcggggact gagggggcgc ccccacccct gccccgggag gcctgatcag cgggggaggg  4260
gcataggcag ttggctgtgg ccaggggttc tagggctcct atggtgggac tcagtgctgg  4320
gccgggtgag agttgcatag agagtggctt agcctctagg ctctactagg caggactggg  4380
caggagccac cgcccccgcg gggccagtgc agactcatgg cctgtcacac atagaaaggg  4440
aaaaaaatgc atgtgcacag gtttagtaca gccatagatg cacacttggc acacacaaga  4500
cacacctatg tgtttgctgc tcacatgttg atgtgcattc aggcataggt cacccaagac  4560
ctgctaggca ttcatgttca aggtcacatt tatagctgcc aatccatgac ccagacaagc  4620
acaccagtgg ccacacagct gtatgcttga atactgctgt tcatatagat ggatgcacag  4680
tgcatgcagc tcgtgtgcac atggtgtaca aggctatgct gtttgaagat accagcatgg  4740
taccaagcac atgcactatt agtcactatt agtaatatag tggcctaata cacagactgt  4800
cacacaaact cacaggcata tgtacacaca cacacacaca cacacagagc tcacatggtt  4860
gtgttctccc cccccccat acagcttcta gtgtgatgtc acaaaattga ataggtcctt  4920
cattcttaac tcatcctttt actgtctctg ttttttttt ttttttttt ttttttttt  4980
ttttggttgg tttctccttt cagtttctgt ctgtccctat ttctcaattc tcccccaatc  5040
tcctttcctt ctctctctga ggaacaaaac ttctacaggg gcccacacct gtctgagcac  5100
ataattctcc accagctcag acctggccac acctctcacc atctggcaag actgccacac  5160
ccaaagtggg atacaaccct gagggatggg gacactggac agggcagcac atatcttgca  5220
ccagttctct cccttacact ccatagccta tccatctagt acccaaaacc acctctctat  5280
ggctgctgtt ggttcctcct aggtgtacgc tttgcctact ctttcaagag ctagcaggga  5340
ctacagtaga cacaggctca acactgcctg ccttctccat ctacccaaga catgggcttg  5400
aagctgcaga tccccttta cactcagcat ctttacttcc tactctgtgc cttttctctg  5460
ttgtgcacat cctagtcaag gcaacttcct gagcccacac atctggcaca agtcaactcc  5520
tccttctcac ccctgccttg tggttcccag ggcttgagct ggcagggaca gctgcagccc  5580
caacagctgg ggctggggtg gggggccgtg ggaactgtag atagggggcc tcttagtacc  5640
cacacagata ccctcctagc ccagtgcagc tgttgcctgg cagacaggag gggagggtct  5700
gatttggggt tctgtgtgcc tgtctgacct ccccaccttc ttttgccccc acacagcacc  5760
cccttgtctg gatggaagcc catgtgcaaa tggaggtcgg tgcacccacc agcagccctc  5820
cctggaggct gcttgcctgt gagtgtctgg cccagcgcca tcagtgggcc ctgtgtgggg  5880
agggaatagg tcctctgcct ctgagtctcc tgggggatgc tggtatcact tcctccatgt  5940
gtgtggcttc ggtaacctct tgtgtttccc catagggaat cagacagctt taagagcaga  6000
agctctggtg tctctctggc ttgggttcaa atcccgcatc atcttgctaa gtgtctgaga  6060
cttaaccagt tcgttaagtc acagtgctct ggaataaaag attgatttcc aaggccaatg  6120
acagtggctt gacagtgaca aggacgtcca tgccctccca tatgtcagaa tacaggaggc  6180
acccaggaga cctattttag agccctgttt tattttgttc tagtttgtat gacctttggt  6240
tagtcatttc tcttttctga acctcacggc atctgtgaag caggagtgct ttccctggcc  6300
tgtgactgtg caggaaggga cccaagaatt atttgggaaa tgcagaaagt tagagaagag  6360
gaggagggtt tgggagctac cagaggcagg cagaactcta gattctggga catctcgagc  6420
aagtgctggg gaccttccca gccactttg catctacaat ggcttttctt tcatgaggtt  6480
gactgtaaag atttgaaaag gacctttaac tgggcttacg cttgtatttc ccagcagaag  6540
caggaggtca ttccgtacag ttccagggca gtctgggctc tcacagagtg agcttgtctc  6600
aatgttttgt tttctaaagg gggctggggc agctgagagc ttagtaggta aaggcacttg  6660
ctgccaaact ggacaacctg agttaagtcc tggggaccca aaagatggaa agagagaact  6720
aatctcggca agttgttctc tggcctctgc atgaatacat acacacacag ataatgtaat  6780
aaaaatcaaa actatattaa aaataagaga aacttttgaa accttttgac gactggagat  6840
ttcaatggtg tttgcccagt acatacaaag ccctgggttg gagggaaagg acctcaaggt  6900
ctgtgggctt attggtttg ttttcttttt aatagtaata gcattccatt cagcagctat  6960
taattagttc gttcatcagt gtgttcattt cctcaatact gtgtgggcta gccagtggat  7020
cagcctcaag ctaggtgggg ccaggatgac ttccgatata gaaaaacaaa aacctttaaa  7080
attcaatggc tggaatctca tttagcttta ttgggggtca ctggccgagg ggcatcctga  7140
ggctgagggt tgggagggtc cttacttgga agcagtcgct tggaagggag gctgaggcgt  7200
ggggcggggc gcctgcgcag tagaactaca cgcctggaca gctgccgaca ggtgaatacg  7260
cctgaggctg ccccgcccct cgacaggtga atcaccggct cacgcggcct ccgggagccc  7320
ggatcgcgcg gagtggagct cgcttaaggc tccagaatag agatttgggg gggacctcag  7380
cctatgttct tctcatccca acccactctt tcaggcttct caaatcctgc tgtctcctta  7440
ggagtgaccg ccccctcccc aatgacactt tctcccccac ttctccccag tcttccgacc  7500
gggagaaggc ttcggagttc tccgtcgctt ggtccttgtc tgtcttgcta gtccgttccc  7560
tccttggaag ctgctccccc gccccctcc cgctccgcta cgtctcccct aaagctaagg  7620
cggcgaggcg ggtccggggc tggaaccggc cggaccggtc ggcgggggcg cgaggtgcag  7680
```

-continued

```
agcgtgggaa cccgcccgcg gcgcagggag ggtgccgcgc ccagcttggc gatgataccc  7740
gtggtcccca gtgctctgca cgcagcgccc cctcctggcg tgtcatcgtc gccgccttgc  7800
aggactgggt agggggttga gagcatcacc tccaaggttc gaatgtccac cacacccttg  7860
cagggttgag cttcgacagg gttgagcttc gacacgttta tctaggaacg gaattcgggg  7920
tgggggtatt gtagggtgac gctaagaaat gagtcacctg ctttgagttc tgcccttggt  7980
gtttgagaca agactgagct aggggatcct cgctgggagc cggaagggta gggtagagga  8040
gaggagggtt gaggtagggg tgatgtacgt tgtgtcattg catagttgca tagccaggat  8100
tgtttgacta ctccagtccc cttccttagc cctcctcacc tctgtccgta gaaaggttac  8160
aaacttaagt cgtcttttag tttttatttt ctagcactca ggacttagat tttttcgaga  8220
cagggtttct ctgtgtagcc ctggctgttc tggaactcac tctatagacc aggctggcct  8280
cgaactcaga aacccgcctg cctctgcctc ccaagtgctg ggattaaagg cgtgtggcac  8340
ccctgtccca ctactcagga ctatcttgat gggtttgggg aaggggcgc aggccttggt  8400
ccagattgag ggctgaggtg cccatgccaa gccccaccga tccatgagag gaggattgca  8460
tgctcttggg agaaaggagt ttatgatttg tggctatctt cctgcctctc catatgagtg  8520
agagtttccc atattcgtgt gggaggctgt ggcttcttgt ctgtgtatgc caggccagta  8580
tgcccagttg tatgtgtctg tgcggtttct gggtctttct gggtgtgtct gcctcctgga  8640
gtctgaggct tttcatttgt tgttcccagt acctggaatg cccttcccca catcaccctt  8700
tggctcaccc attttttttgc cgtttttttgt tgtttgaaaa tataacaccc actcattcta  8760
tcacccttag gctgcttgtg agtttcctgt ggttgctgta ccagattacc acaaacaggg  8820
tggcttaaaa caacagaaat gtactctgga aaatcctgga ggccggaagt ctgaaattaa  8880
ggcgttgcca gaactggctt tctttactga ccatccaggg ggagaagact ttcttatgtc  8940
ttgtccagtt tctgattggc tcaggcttat ggctgcccca ccctactctc tgcctttgtc  9000
tgcacatgac ctttcttctc tctttagttt ctatctgtct ctctcccgtg tcctgggaaa  9060
ggaacctagg cccctgcaca taccatacaa gaactaccac tgtgtcatgt ccctggcttt  9120
tctcttgtaa agatactgtg tgttggggct ggtggcacga ctcagtagtt tagagcagag  9180
tttggtcccc agctctcatt ggttactcac ctgtaactcc agctccaggg gttttggcct  9240
ctgaggaagg acactgtact caggtgcaca catactcaca cacaaccaca catgcataca  9300
ataaataggg gctgaaaatg gctccacagt taagagcgtg tattattttc tcagaggact  9360
tggatttgat ccctggaatc cgcatgataa ctcataacca tccttaatgc caacgccctc  9420
ttcagacctc catgggcatc aggcacgcac agcatgcacg tacatacatg cgtggaaaac  9480
acttatccac atcaaagtaa aataaatctt ttaaaaattg gcttgaaata caaagtgaac  9540
ttgtcttggt attcttcaca attacattgg caaaaattct tcttcccttt ctttttcttg  9600
tgctgagaat tgaatctagg gctttatgca tcctaggcaa gtgcagtacc actgagctat  9660
attccaaatc ctcttgttat ttgtttaaaa tatatgtatt gatcttgaga cagcgtctca  9720
tgcagtcaag gctagcctca aacttgctat gtggccaagg ctgaccttga actcctcatc  9780
ctcctgcttt ttcctcggaa tgccaggttt gtgtgaacca ccttgcctgg cacatctcct  9840
ttaaaaagaa ataaagtgat agtcacagct tctgggacat gggcgtgttc ttcagtgtac  9900
cacgtccttt gtgagcttgt ggcatgtaca agctgttttt ggtatgttcg tattaatgtg  9960
ttacctgtct atgttttctt tgcctgacct ggctatgagg accaaaaggg taagagtcac  10020
ttttattttg cttgctgctg tgttttagta tgtagtaggt gtcaataata tttgttgtca  10080
gaataaatga ggatggctgg gaatggtggc acttgccttt aaacccagtg ctagaggcag  10140
agaggcagag gggcagaggg gcagaggcag aagagaggca gagaggcaga gaggcagaga  10200
ggcagagagg cagaggcaga gaggcagaga ggcagagagg cagagaggca gagaggcaga  10260
ggcagaagag aggcagagag gcagagaggc agaggcagaa gagaggcaga ggcagaggca  10320
gaggggcaga ggcagagagg cagaggggca gagggacaga ggcagaggca gagaggcaga  10380
gaggcagagg cagagaggca gaggcagaga ggcagagagg cagagaggca gaggcagagg  10440
cagaggggca gaggcagaga ggcagagagg cagaggcaga ggcagagggg cagaggcaga  10500
gaggcagagg ggcagagagg cagaggcaga ggcagaggca aaagagaggc agaggcagag  10560
aggcagaggg acagagaggc agaggcagag aggcagagag gcagaggcag aggcagaggg  10620
gcagaggcag aagagaggca gagaggcaga ggcagaggca gaggcagaga ggcagagagg  10680
cagagaggca gagaggcaga gaggcagaga ggcagagagg cagaggggca gaggcagagg  10740
aagagaggca gagaggcaga gaggcagaga agcagagagg cagaggcaga gacagagaga  10800
cagaggcagg taaattactg tgaattccag tctagccagc gatatgtagt gagaccctgc  10860
ctaaaatata ttaaaaaaaa aaaaaaaaag ggaaggaaga gtaaatggat ttgtctgata  10920
gtctgtctgg cacgagtgtt gtttgataaa cgcatcttgt gttatctgtc tggcattgcc  10980
atgcttttat accgtcccga ccacacatct tcccacaggt gcctgccagg ctgggtgggt  11040
gagcggtgcc agctggaaga cccttgccac tcaggccctt gtgctggccg aggcgtttgc  11100
cagagttcag tggtggcggg caccgcccga ttctcctgtc gttgtctccg tggcttccaa  11160
ggtgaagggg tgtgtctgga cgggaaccct tggtaggcga gaatgtagtc agacccaagc  11220
tcaccctctc ctggttcttc caggcccaga ctgctcccag ccagacccct gcgtcagcag  11280
gccctgtgtt catggtgccc cctgctcagt ggggccggat ggccgatttg cctgtgcctg  11340
cccacctggc taccagggtc aaagctgcca aagtgacata gatgagtgcc gatctggtac  11400
aacttgccgt catggtggta cctgtctcaa tacacctgga tccttccgct gccagtgtcc  11460
tcttggttat acagggctgc tgtgtgagaa ccccgtagtg ccctgtgccc cttccccgtg  11520
tcgtaatggt ggcacctgta ggcagagcag tgatgtcaca tatgactgtg cttgccttcc  11580
tggtaagtaa gttgtgccca gggaaggcag ctggggacaa taggctagcc tcttagtgac  11640
cattgtcacc ttgtcctccc ctacgaggct tcgagggcca gaactgtgaa gtcaacgtgg  11700
atgactgtcc tggacatcgg tgtctcaatg gggaacgtg tgtagacggt gtcaatactt  11760
acaactgcca gtgccctccg gagtggacag gtgggcatca gggctgcaga gaaccagggt  11820
ggctgacctc aggtgggcac acgggcaact tagactagca catctttgtg ccctaggcca  11880
gttctgtaca gaagatgtgg atgagtgtca gctgcagccc aatgcctgcc acaatggggg  11940
tacctgcttc aacctactgg gtggccacag ctgtgtatgt gtcaatggct ggacgggtga  12000
gagctgcagt cagaatatcg atgactgtgc tacagccgtg tgtttccatg ggccacctg  12060
ccatgaccgt gtggcctctt tctactgtgc ctgccctatg ggaagacag gtgagtggcc  12120
cttttctttg taggcaacag aatggtttca gcatgaaagg taaaaacaga ctctgagttg  12180
agcgttagaa agattggggg ctggggatgt ttcttcctgg cagagtgtgt gcttagtgtg  12240
cacaggctct gagtttaatc cttagcgtga aggaagacaa gaaggaggag ggaaggtgga  12300
agaaagaaag gaaagaggga ggaagggttt gctggaccct gggtttggaa agaagcctga  12360
gcctctgtcc tatgaggtgc atagtccaag gcagagactg ttggaattgg ggaactattg  12420
```

-continued

```
agaggtctaa ctgggaaaaa ggcaggaact atggaagtca caaaggtctg tttgtccctt  12480
acatcttatt ttggtggggg gtggtcagac tctggttgtc aggctaggtg gcaagtacct  12540
tgagtttatt gttgttgttg atgcgttgag acatggtgtc actatttgta catcaggcta  12600
gcctcaaact tgcaagaaag gatccttggg cttctgtgtt ctgagtggtg ggattaagga  12660
attttgttgc tatgcctgaa tagggtcttg atttatcatc ttttaaaata ttaaaaaaag  12720
tgtgtgtgtg tgtgttttgg ctgcatttat gtatgttata ttatgtcatg ctacacgcat  12780
gactggtacg ctgagaggcc agaaaaattc atcagctctc ctgagattgg agttactgat  12840
ggtggtgagc tgccgtgtag gtgtgttggg aatgaaacgt aggtcttctg gaagagcagc  12900
caggattctt agccgctgag cacctctttg ggccccggtg ccttgtttgt aaaatgtttc  12960
taagttattt tcaaatggta tcgaagaagc agattaacag ataatactga accaatattc  13020
caatgtgaaa cgtcctgaat gtttcactgt ttcataataa atggcttttc caggacagcc  13080
agggctatac agagaaaccc tgtctcgaaa aaaaaccaat aaataaataa ataaataaat  13140
aaataaataa aataatatta atagatggct taaaaaaata agaacagata ctaatacagt  13200
gctggttaat atacataaga aacaggaggc aagggccacc ccaaagggtg ctcagggcgt  13260
aaaggcactc gctgagttgg cctggcaagc ctacttctat caagggaatc cactggtaga  13320
aggagaaaac caaccaagtt tcctctggct tctacacatg cactatgaca tgcacacact  13380
ccccagataa gtacattagg aatgatgatg gtgatgatgg tgatgataat gcaaggagct  13440
ggaagcgtag ctgagtgatg gtattcattc gttgtatgct catggtcctg gggatccatt  13500
accagtacca gtcttcttcc tcaaacgcta ggtctggggg aactttgggc caccccgagg  13560
atcagcgctt catttctgct taccttttct caggcctctt gtgtcatctg gatgatgcat  13620
gtgtcagcaa cccctgccat gaggatgcta tctgtgacac aaaccctgtg agtggccggg  13680
ccatctgcac ctgcccacct ggcttcactg gaggggcatg tgaccaggat gtggatgagt  13740
gctcgattgg tgagaagagt accttctgga aaggagcctg aaaacggagg ggtggggcca  13800
tggctggcca cgcccacact ggctgtgtct tctcccccat attccccctt cttgcaggtg  13860
ccaacccctg tgaacatttg ggtcggtgtg tgaatacaca gggctcattc ttgtgccaat  13920
gtggccgtgg ctatactgga cctcgctgtg agactgatgt caatgagtgt ctctccgggc  13980
cctgccgcaa ccaggccacg tgtcttgacc gaattggcca gtttacttgc atctgcatgg  14040
caggtgggtg gtgggtatgg cttgggtggg tcatgaaggc tggggcctgg ggtaaaactt  14100
ggtttattgt tatttacttg aagaaaaaat gctgggcata gagacacatg actgaaatcc  14160
cagcacttgt gaggcagaga taggctcatc tctgtgagtt cgaggccagt ttggtctaca  14220
gggtgagttc taggatggct aggattataa agtgagactc tgtctcaaaa taaataaaat  14280
aaaataaaat aaaataaaac aaaacaaaat aaaaagggga tagagagata gcttagtggt  14340
taagagtcct ccctgctttc tagagggctg agtttggttc tcagtaccca tatggggcag  14400
tgcacaacta tctagctcca ggagatctac aatgctcttt tggcctctga agatacccat  14460
gtgtttggga cacacacaca cacacacaca cacacatgca tgcaaataaa caaaattaaa  14520
caaacaaata aacaaaagac atttcaaaag agctgaagtg gcacagtaag acggtctgga  14580
actcactgtg tagaccaggc tggccttgag ctcacagaga tccacctgcc tctgcttccc  14640
aaatactgga tcgaatggca tgtgcctctc ggcctagtgc actttaacca tgagggttcc  14700
aaattgtcag gcttggcagc aagcatcctt atttgagcca tcttgcttgc ccatgactga  14760
gtttaaagtg aagcttcctg gctggagaaa gagagagaga gttatgtgtg tttaggatga  14820
aaccttgaaa actcgataag gtaggtgcag ggtcagagcg gattttacca gataacatca  14880
aaggggagct tcataaacct tagtccatga ggggccacag ctgggtgagg gtccagcttg  14940
tttgaaacta aatctaagcc tgaaagtgtc gtgcacgcct gttatcccag cacttgagca  15000
gctgaggcag gagcatcatt agtttgaggc cagcctcaag gccatagtaa gaatttatct  15060
caacaaaccc acaaccaaat caaagtcccc aaaccaagtg aagaggcctt ctgagggaac  15120
tttctgggcc ctcataccat tcccttcagg cttcacaggg acctactgtg aggtggacat  15180
cgacgaatgt cagagcagcc catgtgtcaa tggtggtgtc tgcaaggaca gagtcaatgg  15240
cttcagctgc acctgcccat caggtgagga ccctgggaca aggagcctgg tgtgtcaggt  15300
tatgacaatg tggaacttaa aaaaaaaagt aattagttac ttaactcttt tgtgtgtggg  15360
ggttctctcc ttccactatg ttatgtacat tttgggaatt gaactcaggt ggtcaagctt  15420
ggctggcaag catgtttatc ttctgagcca tctctctggg ctagtctgta ttgaaattaa  15480
tttaaaacaa agccaagggg gtttcccact caaataaggc aggctgcctg ctttaactgt  15540
ttgtgtcacc tttcatccac tactcacttc caggattcag tgggtccatg tgtcagctgg  15600
atgtggatga gtgtgcaagc actccctgcc ggaatggtgc caagtgtgtg gaccagcctg  15660
acggctatga gtgtcgctgt gcagagggtg agggcggacc gtgagactgt ggcaagagcc  15720
agaaggtggg ctggtgggcc aatgggtgtc aaggaccaat aacagacttg gggatggcct  15780
cagctaggcc aggtcagggc cagtgacgct gatgatggag gtaggcagag gtcttggcaa  15840
gattcagggt gcagctagca gtgagattta aagtgggcgt ttctgggtca ggaacagagc  15900
ttggagctgg gcagaatgga agggagaagg ggtgaggtct gagagctgag ctggaattgg  15960
gctgagatta cagccatgga gaagtgggca gaccctcacc tcccgttctt gcaggctttg  16020
agggcacttt gtgtgagcga aacgtggatg actgctctcc ggatccctgc caccacgggc  16080
gctgtgtcga tggcattgct agcttctcgt gtgcttgtgc cccaggctat acgggcatac  16140
gctgtgagag ccaggtggat gagtgccgca gccagccctg tcgatatggg ggcaaatgtc  16200
tagacttggt ggacaagtac ctctgccgtt gtcctcccgg aaccacaggt ggggcctggg  16260
gctgggctat aacagtacgt gggggtgtgt gggggtctgt gatgaatttg taactggtgc  16320
ttgacaatag taggtactct tgccatactt cttccctccc tgtaggtgtg aactgtgaag  16380
tcaacattga tgactgtgcc agtaacccct gtacctttgg agtttgccgt gatggcatca  16440
accgttatga ctgtgtctgt cagcctggat tcacaggtgg gtaggtggct gccatgtagt  16500
gggggggggg gggcttgtaa gatagggatt aagacacaag tctcttgggt gtccccactt  16560
tatttttta aaaaaggaaa tattacattt catttatttt gtgtatgtct ggaggtcaga  16620
gggcatctgg ggggagtcag ttctctccgt aaaggtctca gggaccccac tcatgtcatc  16680
aggcttgggg acacgtgtgc tttcccccca gttaagtccc tttcttccct ttatcaagat  16740
tatctccaat actcagaagg ccaaggttgg aggattagtg catgtttgaa gctagtctga  16800
gcatcatagt gagcactagg ccagccaggg ctgcatagca agatcatgtc tcaaaataaa  16860
acaatatata gagagggctg gagagataga tggctcagca gtttcaagca cttgctcttg  16920
cagacgactc gggtttagtt cctagcatta acacgctggc tcacaagtgc atagttttgt  16980
ttttgttttt gtttttttaaa taataaagta aaataagata aaacaaagca aaaaaaaaaa  17040
aaaaaaaaac acatcagaaa tggacaaaac aaaacaaaat caggagggaa aagagcccag  17100
gagaagacac aagaatcgga aactcattca ttcacacact caggagtccc acaaaaacac  17160
```

```
caaactggaa actataatgt ataggcagag ggtctgggga gggcctggca ggctccgtgc  17220
atactgcccc agtcttggtg agattgtctg agctttgata atgttgattt agagggcctt  17280
attttcttga ttttctccat cccctctggc tcccagtctc cttctgcctc ttcttcatcg  17340
gaaaagggat ttgaaggaga cacccccctag gtttcttagt ctctcactct ctgtgtacag  17400
tctaggagtg ggtctttgta tttgttccca tcagctgcag gaggaagcgt ctgtaatgat  17460
ggctgaacaa ggcactggtc tgtgaggtat taggagtcat tttagcctta cctttttttcc  17520
ccttaaggct ggttctaccc ttgccctctg ggctatctag ccgcaggttc ttggtcactg  17580
aagcaatatt gggtatgggt tctgtcttgt ggagtgggcc ttaagtcaca cagatattgg  17640
ttggttactc ctgcaagctc tgtgccacca cagcactagc agatctagag gcaggacacc  17700
actgtagatc aaagggtttg tggttgggtt ggtgtttatg tttctctagc atgcagaaaa  17760
cctttctgta ccaaagaccc tagaatatag aaggctctat gtaggcataa gtttgacttc  17820
tccatgttca gtgagtctca caactgctta taactccaga gtaaacttat aattccagga  17880
atctgacatt ctctgctggc tttcatgggc accaggaatg caccatgatg cactaacata  17940
catccaagca ctcatataaa ataaataaat aaataaataa ataaataatc ttttaaaaag  18000
cagagagaga aagaggagag agatggagag agggagggag ggagggagat aggtgcacac  18060
ctgtgcacac acacacacac acacacacac acacacacac acacaaagtt gggggcgggg  18120
gggggaaacc accttggact atcctgagct tgtttcctca gtggcatggg gctgtcgttc  18180
tgtcagcaga gtgaggtcag gatcagctgt gtgatagaga acaggacgtc cctttccttc  18240
agttggcacc actgtcttcg ttctggaatg aagttgcctg tatgctcccc agggcccctc  18300
tgcaacgtgg agatcaatga gtgtgcatcc agcccatgtg gagagggtgg ctcctgtgtg  18360
gatggggaaa atggcttcca ctgcctctgt ccacctggct ccctgcctcc actttgccta  18420
cctgcgaacc atccctgtgc ccacaagccc tgtagtcatg gagtctgcca tgatgcacca  18480
ggcgggtgag gccctttccc aactcccgac ccctcttctg ctgtctccag ccacctgtca  18540
cacctcactg cctcccccac caggttccgc tgtgtttgtg agcccgggtg gagtggccct  18600
cgctgtagcc agagcctggc tccagatgcc tgtgagtccc agccctgcca ggctggtggc  18660
acctgcacca gtgatggaat aggctttcgc tgcacctgtg cccctggatt ccagggtgtg  18720
tgaccccata ttcctccccc agggcacccg acacccttgt ttcttatgtt tctttcctgc  18780
tttttttgtt tttaaagctt tgcttagtac cttttgttct gtgtgtctct gttacatatg  18840
tctgtgtgtg gagaccagaa ccagaagaag gcatgtgtcg tcttttatca ctctctaccc  18900
attcctctga ggtgtgcagg gtctctccct gaccctgggg tttgtgcttt ctcggatagg  18960
ctggaagcta ctgagtccct gggatgcccc tgttttttctt tcaacttgca gctggggtta  19020
cttgttatag aggtgggagg gtctgagttc tggtcctcat gattgggcct gaggtgctct  19080
taactgctga accatccttc cagccccatc tgcatttcct tccttccttc cttccttcct  19140
tgcttgcttg cttccttcct tccttcttca ttcctttaat ttctctcttt tttgtctttt  19200
ctaaatatca gggtggggac tccagggatg ggggaattgg gagcagtgag tttcaaaact  19260
atctaaacta tctgcttcta acaggccatc agtgtgaggt gctgtccccc tgtactccaa  19320
gcctctgtga gcacggaggc cactgtgagt ctgaccctga ccggctgact gtctgttcct  19380
gtcccccagg ctggcaaggt acactaatat cctcctcttc ttctcgtctc ccttctctct  19440
tctttctctt cctcttcctc ttcccctctt tctcctcttc tgcactttgc tccatgttgg  19500
gcaatgccag ggagcccaga gaggactcag tcctgccctg cctttgaagt tgtttctttc  19560
tgggaaaaga cagctggatc cagacattca cagcccagga gtcagctcag gagaagaggg  19620
aagccatatg gagctgagga cactgggata cctgagattt gatgacattt ttgatcgggt  19680
gacttcagag tgtgtattca acatctaaag agataggcag aatatatttc aggagtggca  19740
tgtgccaaac gcccagggat agcggctggt ctttgctttc cttgactcca ccagcgggtt  19800
cttgagctgc aggcatcctc agacccctttt ttacccctgt aacctcaatt gcttcccctc  19860
tcacctccag gcccacgatg ccagcaggat gtggatgaat gtgccggtgc ctcaccctgc  19920
ggcccccatg gtacctgcac caacctgcca gggaatttca ggtgcatctg ccacagggga  19980
tacactggcc ccttctgtga tcaagacatt gacgactgtg accccagtaa gtgcagggat  20040
ctttggggcg cttccttccc cagggaaccc acccatcaag tcataccatg tcctggcact  20100
gtgttgctgt ttcctgactc tcctgacaac tattactccc ctcattcatg agggtcttac  20160
ttccatccca gcaccactgt agaaatgggc aatgggctgc tgggatgact ctgcagggag  20220
aggcactgcc tctaaacctg atgaacctag gtcagtccta caagttgtct tctgatctct  20280
acatgcctgc tatgcacaca cacacacaca cacacacaca cacacacaca cacacacaca  20340
cagagagaga aagaggggc gggagagaga gaaaaaaata acaataataa cccaaaatag  20400
aataaaaagt taaaaatatg ttttatttaa gccaatatag aaaatatttt catttcacat  20460
ataagccttc aaaaatttaa attttgctaa atgtatttta catttgcagc ttgtctcatt  20520
tggcctggca gtgagatcac gggcctatta acctcatgtg gctagtagta gctacactgg  20580
tcaccacagg ctgtgctgag cgtatgaatc agagcaggca gtggcactac aagtattcct  20640
tggttctttg aggttgttcc cacagcctcc atggattaca gactctatgg gtgtttaagt  20700
cccttattgt caaatggctt aatgtttgca aatagcctct gcatctcctc ccagattatt  20760
taaatcatct ccaaataact ttttatttta aaatgtttac atttacctgt tattgtgtgc  20820
atgtgtgtga gcgtgtatgt accacgtgtg gaggtcatag gacagtatag tccttctacc  20880
ttgtgggatc tggtgttcca actcagggtg ttgggtttgg tggctttact caggctgagt  20940
cctatcatca acccagactt catttttaat tgaactggaa ggagggaggg gggagggagg  21000
gagggaaggt gagagagaag ggggggtgt ggaatgcaaa catgctacat tagattgtgg  21060
aggccagagg acagcttgca ggagttgatt ttcttcttcc accatgaggg ttgcagggat  21120
tgagctcaga caggcagtcc tgggtgggca agcaccttta cctactaaag tcatcttgcc  21180
ggtccctcta gatggcttga cacaccaagt acgatggaca tagcatgtat atgtttgcta  21240
tactctattg tttagaaaat aacaagaaaa tagtgtgcat gttctgccct tgggtaatct  21300
ctgattttcc ctattgtcca tctactggtt gaacccacag attctgaact tcagaatagg  21360
tagggccagt tctatagctc aaagggtttt gtttttgttt ttgtttttgt ttttgttttt  21420
tgtttttcga gacagggttt ctctgtatag tcctggctgt cctggaactc actttgtaga  21480
ccaggctggc ctcaaactca gaaattcgcc tgcctctgcc tcccgagtgc tgggattaaa  21540
ggcgtgcgcc accatgcccg gcactcaaag gggcttttttt taaaaggata tttttaaaat  21600
gtatttattt gtctatgtgt tgcatgacac atttgtctac gtgagccatg acattcacgt  21660
ggtggtcaga ggacatctta tagaggggggg ttgaccacaa aaggggacta actttgatct  21720
ctgaccaaga gtgtctcttg tagtctggga tacacacacg tttaatttct gcacttagaa  21780
ggcagagtgc aggctcatct ctgaactatt caaggccagc ctcatctaca tattgaactc  21840
caggctagtc ttggctacat agtaaaacta tttcaaaaac aagcaagcaa acaaaaagga  21900
```

-continued

```
ctgtcccctc tggcttcttc ctgagtcttc ctgtgtgtaa agcatagctg agtcaggcca  21960
ggctgatgtg ggcataggca ctgaccagat tattttcctg ctcactgcag acccgtgcct  22020
ccatggtggc tcctgccagg atggcgtggg ctccttttcc tgttcttgcc tcgacggctt  22080
tgctggtcct cgctgtgccc gagatgtgga cgaatgtctg agcagcccct gtggccctgg  22140
cacctgtact gatcacgtgg cctccttcac ctgtgcctgt ccacctggtt atggaggctt  22200
ccactgtgag attgacttgc cggactgcag ccccaggtgg gtggagcatg ggctggagac  22260
tcaggggcca gagagggcat cctggactcg gcatctgtta gagggctgga atgatgctgg  22320
cacatggctg aggaatgggc aaggctgctt ggaagtcaca gactccagtt ctttggaggc  22380
ctagactgag gcagcgtccg taggcgaagg agccaggtta gatcttcata gtgctatggc  22440
ttgttgagga tagcaagggt ccgaaattgg gaagtactta gttctagaag gattggggtg  22500
gtctttaagg tcttgaactt cttgtcctgt tctccagttc ctgcttcaat ggagggacct  22560
gtgtggatgg cgtgagctcc ttcagctgtc tgtgtcgccc cggctacaca ggcacacact  22620
gccaatacga ggctgacccc tgcttttccc ggccctgtct gcacgggggc atctgcaacc  22680
ccacccaccc aggatttgaa tgcacctgcc gggagggctt cactgggagt cagtgtcagg  22740
tgggtggtgt ctgaggtcct tggtggaaga gtccagaaat gagggggggac ccgtgggggg  22800
catcctgaag ggataaggcc atctggtttc tagggtctct cccagcactg atcttgaaga  22860
tttcttttgc agaacccagt ggactggtgc agccaggcac cctgtcagaa tgggggtcgc  22920
tgtgtccaga ctggggctta ctgcatttgt ccacctggat ggagtggccg cctgtgcgac  22980
atacaaagcc tgccctgcac ggaggccgca gcccagatgg gtgagggaag catgtggtgc  23040
gtgcgtgtgg ggctgaaggg tggtggtgca tccctcttgc tggcatgagc caaatgagag  23100
cgccatacaa catatgggac taatgaggtg tgtggctcag tatgtgtgtg actggaataa  23160
ctggccagag tgtgactata tctgtcacag tgagacagct gggtgtgtgt gtgactaagc  23220
tgatagagtc atcaaagtgg tgctgtggaa agagaccagg ttagctgaca agtggcctga  23280
cagcttttgg atgtgggtga gacactaggg attgatggca gtggggatgt tagatgaatg  23340
tgtgatgtgg ccggaatagg aaaggtggca tggccacctc tgagtctgat gtcaccctct  23400
gcttttcagg ggtgaggttg gagcagctgt gtcaggaagg tggaaagtgc atagacaagg  23460
gccgctccca ctactgtgtg tgtccagagg gccgtacggg tagtcactgt gaacacgagg  23520
tggatccctg cacggcccag ccttgccagc acgggggcac ttgccgtggt tacatggggg  23580
gctatgtgtg tgaggtaagt gcgtctcagg gagagggaag agaagtcagt catgcttgcc  23640
tgtgtttctg tgtcctggtg tgggtccttc ccctccccg tcggtgggag agcagggatg  23700
tttcatgtgt agtaggtaag cactctgtat cactcagctt catccagagt cagcatggct  23760
gctatagaat ttttttattt tattttattt tttttttttt ttggttagat ttttgagaca  23820
tggtctcgtt atgaagctct ggctgtcctg gaatttgcta tgtagtccaa gctggcttcc  23880
aagtcacagc aatccttctg cctctggctc tatatgagtg ctagataaca gtcatgcgcc  23940
ataatacttg tctgcgtgtc ttttctttcc tccttttctt tatcttttcc tttcccttct  24000
ttccttctct ttctttcttt ctttctttct ttctttcttt ctttctttct ttctttcttt  24060
ctttctttct ttctttctat tttgagacag agtctcacta tgtagctctg gtgggcttaa  24120
actattagag atctacctac ctcagcctcg tgggtgctag gattaaagga atgagcaacc  24180
aggcctggcc tagcagtcct tttatgggta tatgtctgtg tgtgtgtgtg cacaggagtg  24240
taaatgcaga ggtcaggggc agacatcagg tgtcccctct atcactgtac tttgttcgcc  24300
tgcggttctc tcactgaacc tcaagttagg ctgtagatgg tgagccccag tgatcctcct  24360
gcctccccca ccccacacct gggtgacaca catagaagac cacacctagc tttttaagta  24420
ggtactgagg atttgaactc aaatcttcac gtgtgtgcag caagcgctct tacccactga  24480
accatctctg cagctcctta accctcatgc acttgtggat ggacttgggg catgtgagtt  24540
tctgtctcca gttctgtgtc tctctctggg tatgagtgac ttaccattgt gtctggacat  24600
gtggtctggg gtacctgggt atttttcctg cgtgttctca tcagcctatc tccctctgta  24660
ctgagtgtgc tggtggcctt cccagtctca ccctgaccaa tagcaacttg agggaggaga  24720
ggatttactt cagcttacag gttactgtcc atcattgagg gaggctgtga aagaagccca  24780
aggcagggaa ccatcgtcca gaactgaagc agagaccata gaattgtgtt gctttcccgg  24840
agcggtctgg gtcttcccac atcaatcagc actcaagaaa atgcccccac agacatgcta  24900
taggccaatc tgaaggaggc agtttctcaa gcaagattcc ctcttcccag ataggtctag  24960
gtttggttca agttcatgca cacacacaga taacaagtgt gggcacagtg tgtttccttg  25020
tactgggtaa gtctgccccc tacactggct ttgtgttgga tgtctatgtg tgtccttttg  25080
tggtgagatt ctgtgtgctc acaggtatgc cgaggcacgt ctgtgtccct cggggctgag  25140
tgaattcctt tcttgcctca atacagtgtc cagctggcta tgctggtgac agttgtgagg  25200
ataaatataga tgagtgtgct tcccagccct gccagaacgg aggctcctgt atcgatcttg  25260
tggcccgcta tctctgttcc tgtcccccctg gcacactggg tatgttaagg ccagggttgg  25320
gggcaggata agaggatgag tttctagcct ccactgacca tgctcctata ccctaggagt  25380
tctctgtgag atcaatgagg acgactgtga cctaggccca tccttggact caggcgttca  25440
gtgcctacac aatggcacct gtgtggacct ggtgggtggc ttccgctgta actgtccccc  25500
aggatacaca ggtctgcact gtgaggcaga catcaatgag tgtcgcccgg gtgcctgcca  25560
tgcagcgcat actcgggact gcctacaaga tccaggtggg catttccgct gcgtctgcca  25620
tcctggcttc acaggtaaga atggcagaga gcctggccag aaacctgatg tggttctgct  25680
tctgtagttg atcctcctgc atctgtttgt tcagggcctc gctgtcagat tgctctgtcc  25740
ccctgtgagt cccagccatg tcagcatgga ggccagtgcc gtcacagcct aggccgtgga  25800
ggtgggctga ccttcacctg tcactgtgtc ccggtaggtg tgattggtag gggttggaac  25860
ccttggggaa agaaaaggcc tgtggcttta gggaagcata ggtctatacg ggaaaagtag  25920
aaggaaagga ggttctgaaa ttatgaaatt atgaaattat ggtttggagt gtaacttagt  25980
gaaattgtga cttggctttg ttgcctcctg gggaggtatg gcttatcttc aaaatgaggt  26040
cagtagagga aaggttgctg gaattggagg ggtgggggtg gggtgtcagc atttctcaag  26100
tcttgacctc cattcttttc tctcttttcc actctcctgt ttcttctcac taccaatttt  26160
ttctctttct gtctcctcac ttcaccatta gccattctgg ggtctgcgtt gtgagcgggt  26220
ggcacgctct tgccgagagc tgcagtgccc agtgggtatc ccatgccagc agacagcccg  26280
tggaccacgc tgcgcttgtc ctccggggct gtccgggccc tcctgccggg tttctagggc  26340
gtcaccctca ggagctacta acgccagctg cgcctctgcc ccttgtctgc atgggggctc  26400
atgcctacct gtacagagtg tccctttctt ccgctgtgtg tgcgctccgg gctggggcgg  26460
cccgcgttgt gagacccctt ccgcagcccc tgaggtcccc gaggagccac ggtgcccgcg  26520
agcggcttgc caggccaagc gaggggacca gaactgcgat cgtgagtgca acaccccagg  26580
ctgtggctgg gatggcggtg actgctcact gaacgtggac gaccccctgga ggcagtgtga  26640
```

-continued

```
ggcactgcag tgctggcgtc tcttcaacaa cagccggtgt gacccggcct gcagctctcc  26700
agcctgcctc tatgacaact ttgactgcta ctctggtggc cgcgaccgca cctgcaagtg  26760
agccccctga ctctgtcctt ctgtctatct atatgttgca ctgtcagtga gccacatctg  26820
tcccagtttg tctgtcagtc tgtttttggc tcgtctgatg ggctgtccct tccagctgct  26880
accaccaggg cactggtggt ttcatccgcc tgtttccacc catgtgcctc atctctgcct  26940
atttatattt ttacctatat atcttgccca tttgcttctg tctgcctgca gttacacatc  27000
ccatctgtcc acacttagga cttgttcatt tgtctttctt aaaattttaa aaattaaact  27060
gggtctagtt gctcacacat tttaatgcca gcatttcaga ggcatagaca gcaggtctct  27120
gtagggattc aaggccagca tgatctacat agtgagttct aggccagcca aggccacaca  27180
gtgataccct gtctcaaaac aaaaacaaac aaacaaacaa acaaagcaaa acaggagccc  27240
acagcaggtg ctcattcaag agcatacaat agtgatactg gttgagcatc ccaaatccca  27300
aacctgaatc cctgagccat gtggggcatg ggcatgatgc cacagtggaa aattccatcc  27360
tttgccccaa tgataagtta cagtcaaaat tcagacacag gttggtctgt agtggcagag  27420
caccttccta gatggcatgt ggcccttggt tcaatccccg cccagcatgg aaataaaaca  27480
accaccaaag gcaggcacac taaaaatata tagttacttt tgggtatgtg tatttttgtc  27540
tttagacttg ggcctcatcc cagaggtgcc ttatataaat tatgtataga gggctgggga  27600
tgtagctcac ttgatggaat gcttgcctaa catccacaga gccaggcttg ggtccccagc  27660
accacctaaa ctgtgagagg tgctgtgtgc ttgtaatctt ggctctcagc aggtggatca  27720
ggaggataat aagttcaaga tcaccctcag caacatagtt ttgttttctt tgttaaaaat  27780
aaggcttcag ccaggtgtgg tggcgcatgc ctttaattcc agcacttggg aggcagaagc  27840
aagtggatat ctgagttcaa agccagcctg gtctacaaag tgagttccag gacagccaga  27900
gctacacaga gaaaccctgt ctcgaaaaac caaaataaat aaataaaata aataaataaa  27960
taaataataa aaataaaaat agggcctcac aattcctggc tggaattggc tgtgtaaatc  28020
aggctggccc tgaacacaca gagatatcct tgtctctgcc tctggagtac tggaattaaa  28080
ggtatatgcc agcctgtctg actaacatag ggagtttgag gccagcttga gatacatgag  28140
atcttatctt aaaatattta tagaaagata tctcattgca tttatttgca tatataatat  28200
ttaagcatat gtgtaaatat tctaaaacta taatttgaac tctgaaatag ttttagtccc  28260
aattatttca aattaggaac acagaacttg tgcttatgca gccaacgact gcatttgcag  28320
aaagcatatg caagaacatt tcccaccacc accatcccca accccatacc agcactgtcc  28380
actactgcta ttctctgtgt gtgcatttag gtgacccgaa gaatctctga gtttgtgttc  28440
tctgtcccca gccctgttta tgagaagtac tgcgccgacc actttgcaga tggccgttgt  28500
gaccagggct gcaacactga ggaatgcggc tgggatgggc tggactgtgc cagcgaggtc  28560
ccggcccttt tggcccgagg ggttctggtc ctcacagttc ttctgcctcc tgaagagttg  28620
ctgcgctcca gtgccgactt tctgcagcga ctcagcgcta ttctgcgcac ctcactgcgc  28680
ttccgcttgg acgcacgtgg ccaggccatg gtcttcccct atcaccggcc aagccctggc  28740
tctgaatccc gggtccgtcg tgagctgggt cctgaggtga tcgggtgagt gactgtggct  28800
cagggctggg tacagcggtt agggcacccg tggtccagac cgtctgtttc acgcttctta  28860
gttgagagct ctcttggcaa ggcgtcttcc acaggttttt ccgtgtctgt cgggttgaca  28920
tctttgctat gggggggggg ggggttcatc ctctgtacac tacagggagc ctcgctgcag  28980
cgctgagatt ttactcttca aatgcaggtg acagcacctt cttgtgtgca tgatgtgtgt  29040
gtgtaggtcc ccaagtgcca tgacgacgca tgcctgtaga ggttagagga caacagtgtg  29100
aagtcagttc tctcttctca tcaggatgtc aggcttgcat gatgagcatg ttgcctgtga  29160
gccatttcgc tggcttgttt gttgttttct tctcgttgtt tgctttgttt gtgttttata  29220
ggcactaacc tgaaattcaa tctgtagccc aggttggctt tgaactcatg gttctcctac  29280
tcagcccttc caagtactag gattgcaggc atacaatatc gcccccgaca ctcactctct  29340
ttcctcccca ctctcttcat tccccttttcc cctcatctca caaaagttgt agaacttgct  29400
cactggtgac ctggtagggg gaacctgaag tgggagaggc attttttttga gggtggacca  29460
gggcctgaag attgggccct gacaaggaaa ggagagctga actttagaga tgctgtggtt  29520
tgtgggttct gattggatgc aggcagaagt caagtagatg ggtgaggtga cacatggccc  29580
ctttcttggc taaagtggct tagtgatgag gacatagggc taagcagggg ccaccttgga  29640
acttgctatt cttagggggt cttgaggtat ggggaggaac cccaggagat gactgagggc  29700
tgaagatgca tacaagacaa ctgggtattg gaggccattg gagggaaaga agggagaatc  29760
aaggaagcag gagagaagga aatgaagaag gaatctaagg actctcagag acctaagaat  29820
tgggggacag tagaggacgt ggctcagtgg tagagaacct accttgtata ttcaaggccc  29880
caagttcatc tccaatacca caaagaagga taaaggagaa aaagcaagct tttagagaaa  29940
ctgacatggt acactgtccc agcaaagggc gacaccaaca gactctacca gggcgaatga  30000
agacattatt gaattcacag ctttgagaca ctgtgaccaa taagatctgt tgggagagac  30060
agtggagttg gatgccagct gagagctggg tgggtggtag agacatggag agtggagacg  30120
gatgtggctc tctgaggtcg ggtgtctagg atgctgtaga caagtgttga gcctttgggt  30180
ccctctgctc tgttcccaca gctctgtggt gatgctggag attgacaacc ggctctgtct  30240
gcagtcagct gagaatgacc actgcttccc tgatgcccag agtgctgctg actacctggg  30300
agccttgtca gcagtggagc gacttgattt cccataccca cttcgggatg tgcgaggtga  30360
gctgggaaga agagagggta gtacattaga gcgtgtagcc ccagagatgg ttgaatccta  30420
tagtatggtt gaagccctgt gagtaaagcc ccatcttctg gctgaagctg tcccatagct  30480
aagccaaccc catgggtaag agccacttaa aattgaaacc ttacttgtag tcctgctcca  30540
cggctacagc cctgcttata gctgagtatc gcccatggct gaaatctgct cactcgttcc  30600
tgccctgata cttggctgaa ggctcatctg ctgcttccat cctacaggag agccgctgga  30660
ggccccagag cagagcgtgc cactgctgcc actgctggtg gcaggggctg tctttctact  30720
catcatcttc atcctgggtg tcatggttgc caggcgaaag cgagaacaca gcaccctctg  30780
gttccctgag ggttttgcat tacacaagga catagctgct ggccacaagg gccggaggga  30840
gcctgtggga caagatgcac tgggaatgaa gtaagaacct cacatgctct acatccccaa  30900
ctgtgggtcc cttgtaagct ctagaccata ctcacctcgg tcatattcca acctctgacc  30960
ccagcctaac cttaactaca gactccatct gggccttcag tgttaatcct cttgacctat  31020
gaccccatga tccctgagga ttgccccaac ccctatccct tgacgtgatt ttctatttct  31080
atacatttcc tgactcatat ctttccctga cgccatcctg aactaacctc acaaaattca  31140
ttcttatgac tgctaacctc aagacttttg tcatttcaac ctgtccctga ccacgactgt  31200
atccttgatg actcctgaat catctctggc ttcaacccac ctgtaccttt gacctcacct  31260
cagaccccctg tttctaccca atcctgtgtt aattcccttg tgatcctcaa tcccaagcct  31320
tcaacttgac ttattcctca acaccaatag ccatattctg accttaaccc ttccctatga  31380
```

-continued

```
caccataact cctgactcct catcctgatg tttcaagcct ggctatcccg tttgtcacaa  31440
gagagtaact cctcttccat gagctttgat aactccttta tcaaagttat gagaggaaac  31500
ttcctttgcc cctgcagttt gtctcatcta tcctcatgca tccatgttcc attgtgtgtg  31560
ccactcttga ctctgagttc accttatgag tctggccacc tcagatgtga ggtgtggagc  31620
aggtataaag accgttgttt ggatccctag aacctgtata aatgccataa aatccttaag  31680
tgctcagtgg gcccggcagc ctgacttgga agatggagtc ctggtcccta gagcaagctg  31740
actagtgagt ctagtcatat ccgtgagctc ttggtttgat tgagggaccc ttcctcgatg  31800
accaagactg aggagagatt cctctttatc aacctcagac ctgtgcaccc aaaacacaca  31860
cctgcactca cagatggaaa gagaaaacat tttgattgcc acctgacatg cttcctgcaa  31920
cttcatctct atcctcctat ccatcattgg aatctttgtc aacgacccag gacccctcct  31980
cagttcctga ccccttacct acctctatga cctctgcctg aaccaaaccc taaaccctct  32040
tcccaggcca gagttctcta gtgtactttc tcacgtcttt ttcttcttgt tttccccaag  32100
gaacatggcc aagggtgaga gtctgatggg ggaggtggtc acagacttga atgactcaga  32160
atgtccagag gccaagagac tgaaggtatt aacctgcttc tctgactctt tccttcaggg  32220
ttccaagttg ggatccccta acagctggag agcccaggga agtctctctt ctcccgattg  32280
cctcagcccc agacaatttc cacatctgtg tggacctcac ttttccctta atgtgattct  32340
gttgctgtgt tgggaggaac agagatttac catgggttcc ctgggtgggt ggggcttccc  32400
cttcttcata tggttcctcc tcacacaggt tcctgctccc aggtctgcct agggtcaccc  32460
tagagcagca gctcttaacc tgtgggttgt gaacctattt gggctgcgct cttcagtttc  32520
agatggctca gtcggtaaag aaagaaaaga aagccaggcg tcttgtggta cacaggtagt  32580
cccagtgaac aacctttcca cagaggttac ctaagaccat tgaaaaacac aggtttttac  32640
attatgattc ataatagtag caaaattaca gttatgaagt agcagtgaaa ataattttat  32700
ggctgggggg tcatcacaac atgaggaact atattaaagg gtggcagcat taagaagagt  32760
gagaaccaat gccctagagg gaacacccta gtccacagag tgattgtttt ctgttccttg  32820
tctagcatcc ccagcctgaa agtgtcccca gctgctctag ggttccatct atctttagga  32880
accacaccca tttatttggg ctgtgctctt cagtttcaga tggctcagtc gctaaagaaa  32940
aaaaaaaaaa aagaaagcca ggcgcttgtg gtacacaggt agtcccagtg ctggtgaggt  33000
ggcaagagca aactcctggc tggttaacta gcctagcctt cttggcaagt tcttagaaga  33060
accctgtctc ataaaggaag atggatcgtg ccagagagtg gtggcacaca cctttaaccc  33120
cagcactcgg gaggcagagg caggtgtttc tctgagtttg aggccagcct ggtctacaaa  33180
gtgagttcca gtacaaccag ggctacacag agaaaccctg tctcaaaaaa tgacacaata  33240
acaacagtaa caaaaagagg gacagtgcta cagagcaatg acataggagg cggttctttg  33300
gcttccatac acacagacac actcgtgtgc acacacacac aagcttgcac actcatgcaa  33360
cctgagggct gggtaatgta tgaaggaaag gtctttctgc ctcagcttct ccagtagctg  33420
ggactgcagg tttgagtcac aacatccagc ctccatattt cttttaccag ggatctgaag  33480
tatccagggt tggaggacta catttaattt tttaaaattt caaatatttt gctcttttta  33540
tttatttata tttattttta aaaattggag actagagaga tgactcaaca gttaaatgct  33600
ggctgctctt ccagaggacc tgtgtttgat tcccagtacc cacacagtgg cttacaaatg  33660
tctgtaactt cagttcctat agatgtttga cgtcttctgg tctcccacca ggcatgcatg  33720
acaggagtgt gccaccgtga cagctgtagt ttgttaattt aaaaatttgc attcacttat  33780
tatttattta ttttgtgtgt gggccgtgtg agctacatta tgggggaggg aggtcagaga  33840
acaactgtgg gcgttattct ctttccactg tgtgaattcc agagatcaaa ctcaggtcat  33900
tgggcttggt gacaagttat ctcttgtttt gataatttaa ataaaaatat ccttttttctt  33960
ttaaaaaaat attaatttgt ttttttttt gagacaggat ttctctgtgt agccttggct  34020
gcccaggaac tcactctgta gaccaagctg gcctcgaact cagaaatccg cctgcctctg  34080
cctcccaagt gctgggatta aaggcgtgcg ccaccaccac ccggcttaga tctacctatt  34140
tctgtctctt gagtcctggg attaaagatg tcccccactg ccacccagct aaatatttat  34200
ttttgtgtat atgtgtacac attggtgtgt gtgccatggc aatgtgtgga gaagcacatt  34260
taatctgcaa gtacgtttac ctgctgagca ctctccccaa ctctgtttta tttttttgag  34320
acagcaggtt gcttttggtc tcctacacct gatacagctt tatcagcagc actggtggga  34380
atgcccaccc tttttttgtta ctgcctttcc cacagcaaat gagaggtgag cgcctgtatc  34440
tgtgtccctc caggtagagg agccgggcat gggtgcagag gagcctgagg actgtcgcca  34500
gtggacccaa caccacctgg ttgctgctga tatccgtgtg gcaccagcca cagcgctgac  34560
tcctcctcag ggagatgcag atgcagacgg agtggatgtc aacgtccgag ggcctggtga  34620
gtgccctccc aaagaggccc tcattggtcc tacctgctgg atcccatgca ggggttctgg  34680
gagcgtctgg gcctctgggc ctctgggcct ctgggcctct gggcctgctg cgtgtgttgt  34740
attctaagtg attggaacgc catgcaaggt gaagcagaag gtgggctggc tgcaactgag  34800
aaccctgagg ctgtgtggac cctggactct ttcttttatg agattaaaat ttccttcttt  34860
tcttttcttt tcttttcttt tcttttcttt tctttatttt tcttttcttt ttttcttttat  34920
tttttttcttt ttttgttttt cttttttttag atttatttat tattatatct aagtacactg  34980
ttgctctcct cagacacacc agaagagggt gtcagatctc attatgagtg gttgtgagcc  35040
accatgtggt tgctgggatt tgaactcagg accttcagaa gagcagtcag tgcccttacc  35100
agctgagcca tctcaccagc cctctctttt tgtttttcaa gacagggttc tctgtgtagc  35160
cctggctgtc ctggaactca ctctgtaaac caagctggcc tctgaactct gagatccacc  35220
tgcctctgcc tcttgagtgc tggggttgaa ggtgtttgct cccccaaccc cagctctttc  35280
ttcctgtgta gccctggctg tcctggaact tactctgtag accaggctgg ctccaaaccc  35340
atagagctcc acttacctca tcctcccgag tactgggatt aaaggcttgt tccagcacca  35400
ccactgcctg gctcttgctc ttgctctttc tctctttctc tctttctctc tttctctctt  35460
tctctctttc tttctctttc tctttctttc cctttctttc tctctctctc tctctttctc  35520
cttcttcttc ctcctcctct gcctcctctt cctcttccct ctcctcttct tcctcttcct  35580
cttcctcctc ctctttcttg ttatactttt atataagatt tcactatata gctctggcta  35640
tcctggaact cataatgtag atcaagttgt tgtgaagtca cagagatcct cctgcctctg  35700
tcccccaagt gctggaatta aatgtgtatg ccatcatatc cagctgggat ttatttaaaa  35760
atcacactta tttgtgtgta ttcgtgtact cggaagtcag aggacacctt actggagttg  35820
attatctcct atctcggtcc aagagatctc attcacgctg tccagtttct ctgtagcttc  35880
tctatccatc aagctcctgg atgttcaatc cctccttacc cctctagccc ccttagcttc  35940
agccatacag cttgtcagga gagtctcgga ttagttctga cagggtgaac tagaaccacg  36000
tacttattcc tgggccaatg aatgtggcta gggcctataa tatgcagata agccagtccc  36060
catctggtct aagtagggct tgctattagg gaattcgtga ggagaactag ggaaaaggtg  36120
```

-continued

```
gttcccttcc cctttattcc aagtgctcgg cttcctggaa tcgcttttgc ggtccatcat  36180
gtaatcttcg tggggtggct ttgcagttgg gagaatttac ctctgtctgt ggcgctgtgt  36240
gtcacagtgc ccctgacatt tgccccagga agacccctat gcctgtgaca cactactggt  36300
tcctgcagat ggcttcaccc cacttatgct ggcctccttc tgtgggggag ccctggagcc  36360
gatgccagct gaggaggatg aggcggatga cacatcagcc agcattatct cagatctgat  36420
ctgtcaaggg gcccagctcg gggcacggac tgaccgcact ggcgagaccg ccctgcattt  36480
ggctgcccgc tatgctagag cggatgcagc caagcgtctc ctggatgctg gggcggacac  36540
caacgcccag gatcattcgg gccgcacccc cctgcacacc gcagtgacag ctgatgccca  36600
gggtgtcttc caggtgagac aggcctgtct cttcagactg cagagctgct gggaggggat  36660
cagacacacc tagattggag ccccggtctg tcttgcaagg cttttgtcat ttggaaatag  36720
gaataggtag tatctcacct agatttcccg ccggccccccc cccccccccc ccaggacagg  36780
gtttctgtat agtcctggct gtgctagaac tcactccaat aaaccaggct ggcctcgaac  36840
tcagaaagat ccacttgcct ctgcctctgg agtgctagga ttaaaggcat gcaccactaa  36900
cactggatag aattttttttc tttttaatt ttattaatat atgtaagtac actgtagctg  36960
tcttcagaca ctccagaaga gggagtcaga acttgttgca gatggttgta agccaccatg  37020
tggttgctgg gatttgaact ctggaccttc ggaagagcag tcgggtgctc ttacccactg  37080
agccatctca ccagccctgg atagaatttt ttaaaaagta tcattaaaat tacatttatt  37140
tggtgtgtgt gtgtatgtta tgctgattgg tttgtgtttg tttgtgtggc atatgtgtac  37200
ctgggtatgt acattgccca gcttgctgaa gctagaggag gctgttgatt gttctgctct  37260
atcgtgctcc acccaatctt ttgagacaga gcccatcagc gagcctggag ttgagctggt  37320
gtccagaaag ctctcttgat cctcttgtct tcttccccac agccctgggg cacacatgac  37380
caagactggc tttttaggtg gactttgggc tctgacgtca ggtgcttgtc ccctgagcca  37440
tctccctgtc cttccatatc atactgttac ttaaatccat tttgaatgag catatttttt  37500
gatttataat gtgcttagca ggaatagcac ctcattttaa gtcaggagat atctgtagct  37560
cctgggttcc aaagctgtgg catttggggt tcagggtgtg gtatactcct cccttggcat  37620
aatgtcctgc catggctttt gtcgtcgtta gattctcatc aggaaccgct ccactgacct  37680
ggatgcccga atggcagatg gctctactgc actgatcctg gcagcccgcc tggcagtgga  37740
gggcatggtg gaagagctca tcgccagcca tgccgatgtc aatgcagtgg atgagcttgg  37800
taagtgctgc ggaggggatg gggaggggct gtggtgccac tgccctctta atgtgaagtc  37860
acacctacgt tgacagcaag gtgtgcacgc cagggctccc aaacggatgg aacaggaccc  37920
acagagtgtt ctggttcaga aaagatgtag actcccttct cctcccctcc cttccctttt  37980
tcttccactc ccttcctttc ccctccccca tctcctagac cccatccccc actttcacat  38040
tatgatactc ctcttcctcc ccttcctccc gggcttcctt ctagagtcca aatcgttgat  38100
caaacccaaa gtgcttgtct ttgagtctga cttatttcac ttactgtgat gatctccagt  38160
tctattcatt tcttgaagat tgtttaattt ggctccccg acttttgaga cagggtctca  38220
tgcaagctag gctcgcctcc aacttactgt gtagtcaacg accttgaaat ctggaccctc  38280
ctgcctctgt ttcccaagtt aggcattcgt catcacatcc agcccaattt ctttctttgt  38340
tttggttgag tagcattctg ttgtatgcag tgtgggtggg cacctaggct gagcaactcc  38400
attgtatgca gtgtgggtgg gcacttaggc tgactccata gtgtaccggc ttcgaatagc  38460
aatgtggatg ccacagttcg catgggcatg cagacatctc ttattgtatg ctgactcagc  38520
cctcaagtat agacccaggg gcacaggagt gccatacctg aacctagggt agttcttttt  38580
tttttttttt aagaattatt tatttattat atgcaagtac actgtagctg tcttcacaca  38640
ctctagaaga gcgcgtcaga tctcattacg gatggttgtg agccatcatg tggttgctag  38700
gatttgaact caggaccttt ggaagagcag ttactgctct taaccactga gccatctctc  38760
cagccccccta gggtagttct acatttagtt ttttgaggac cctccatagc attctctata  38820
cttactactt agcatactta gttactttat cattaatagg gcatgaagat ccctttctct  38880
agtgtttgta ttctttcttt ctttttccct tttttggctg ttttcatgat tgaagccatt  38940
ctggtagcat ctaagtacag tttttgtctg tttttatttt tttgttttgt tttgttttca  39000
gacagggtta ctctgtgtag ccctggctgg ccatggaact cacactgtag accaggctgg  39060
ccttgaactc agaaatctgc ctgcctctgc ctcctgagtg ctgggatcaa aggccgggat  39120
caccaccacg cccggctgag accctctttt tctgccaggc acagaaaggc cacctttttgc  39180
cttcctgccc agctataggc tattcagctc tttatttaac caatcaggag acgatggaga  39240
acattgtttt acaaaatacc aagttagacc aaagtctgga ctgtaaccag atctctggga  39300
acagaaatca gcatctgaat acacagtgca caaaaccacc ccccaacggg acttcatcgc  39360
caactggggg taaacgctca tgctttgccc acactgacca agcacacgag cttgcttctt  39420
agtgtgctgt ctagatgctt tgttaaggaa acggactctc ctgctacctg ctagacagtg  39480
ggataaactt gcatgtggtg atctgtgggg gcagctgcct ggtagtggcc tgcttggctt  39540
gggtatgtca tgagcaaggg tcacagcaag ggttcttgta ttcacaggcc gcacagctgt  39600
agacactcta agacacttac acacatttgt ttgacgtacc cttggttctc aacttcatca  39660
gcattgacat ctatggttgg gtaattcttg gtctgcgtgt tggatgaagg tctgggctgt  39720
gcactccggc ctgtggggca gcatcccacc aggagcatcc catctctaca atgttactga  39780
gtatagtggg cttcttccct gggtgggcct ttgtttcaac aacaaaagga tttagaaatg  39840
gtctcagaag gaagctcaaa cacagttaga ctagagtttg atagcaaagc aacagatcaa  39900
gcaagctgtc agtctctctg gaatagagag atggagaaga tgcattcatg tcttttgagc  39960
tgtggctgga aagccgcagc ctggtgggag ctgggggaga ggtgagcttc cgaggacaag  40020
tgcgagctca tgtcctggct ttagccagga tctgaaagaa aaggaattga gaagaaagaa  40080
aaggggtgcg gtggccaatg catttgctat gccagggcga agacctgagt ttggatcttc  40140
agaaacctat gtaaatgcta agtgggtgtg atggccacct gtaattccag acacacacac  40200
acacacacac acacacacac acacataccc catgtataca cagaaaaaga aaaaaatatt  40260
cagaaaagct ggcagggtgc ataatggtgg ctccaatgtg ctgcctgcct gatggatgtc  40320
ctgcaagtag ctgctttgag ggagaggctc ctaggaaggg aaaatacaat atgtcattaa  40380
ggggataatt agtccttccc tgtcaatagc atgtctttag gtgactcaga gtttttggcg  40440
ggacaaaggc agactcttgg acagataatt gacagactct attgggatac ctttaaaaat  40500
agtctattta tgtttacttt atgtgtaggg tgtttcgcct gcatgtatgt ctgtgcaccc  40560
cgtgcatgca gtgcccacac aggccagaag aggagagggc atcagatcct ctggaactgg  40620
agttacagac cgttgtgaac tgttatgtgg gtgctgggaa ctgaacctgg gtcttctaga  40680
agatcagcca gtactcttaa ccactgaacc atctcccagc tccccgaatt aactcttaaa  40740
aggagacagt cataagtagc atgttgggtt ccaccaagga ttggaactag aactcagatt  40800
ctatttaaga agcagctttg cattaagtgg gcctcaacaa actcagacac tcccagcttt  40860
```

-continued

```
ttatggcaag ttgatgtctc tcctaagtag tcttagtcct gtaagactac tgtaacaggc  40920
aaatgacctg gggtggggg tggggggagg gcagtcattc atggttgata ttagctaact  40980
tttaaaaggc aacaatagag gggccaaagg tagagagaaa aagacttgat tgtggatgcc  41040
aaaatgccta caggggaaga tgggatgtgc ctcttataag ggaggactcc tgtagtccac  41100
aaggaaagct gggaagtgta gtccttcagc aggaaactcg gtcccaattc tgagaggata  41160
ttaaaaagac gcagggcagg atgtcatagc tttttctttt ctttccccgg aggagagtct  41220
ttatcagagg ggttagttct gggtccagta aagggaaact ctctggccat gttgtatgct  41280
agagtcttga ttagctgtga tggatcaggc cattgtcatt ccgcattcct gaggagagct  41340
gggaaaatat ttattagaag gccacaagca gatgatttgg ttatagagta gagctgagag  41400
attttctggg aaggttgagg gagggggagg agcaggagcc taggcagaag agacaagagt  41460
gagacaaagt gggcagaggc tggtcccagg gtgacagtga ctggtcccat tgccaggact  41520
gctagaaaaa tgagctagca gaagcagcag agggctacaa agcagcagag gacgggaaga  41580
ggggtcaata aagggttaat gtgaagaact gtatctggcc tgtggtggaa gagatcacgg  41640
tcccttttct attcagcacc taaacaattg ttgtttaggt gctgaataga aattgttgtt  41700
gtttctcaga tgtgtcagga acaaatggag ctgttgtggg atgagagcca ctgagagagc  41760
tcgaatggga aattctgcgt gggttcagta agcaaaacat ttaaagacac ggtaaaaatg  41820
taggtattaa gataaagaag ggagaaagcg tgaggcaggg gaagagacag agtgggggga  41880
agccaggagg aacttttgtc tggtccctgt gcctttaggc cccatttcaa accaggcagc  41940
atttgttggc gtggtagcag ccctgatcaa ggagggcagc agtcagagct agtccttttg  42000
agttgtagag taccgcgtcc gtcaaggagt tgacctgctc ctagagggtg tcacgctgat  42060
ctgagctggt gacacagagt tcactgatgc agcgaaggct tcagcccagc tgtgacacag  42120
agaagttcac tgaaggtgtc agtccagctg tttcagtcca gagtggcaag aagaggggtg  42180
gcttggctca ttcatggtcc atcatcccct cttagatgtc gtccaaactg ctcttagggg  42240
cctggggtgt tggtctccct gtgacttctt taaggctggc agaagtggga cgagggggagc  42300
agccgtcaga gtgcctcaga agagggtcca tccaagggga catgatagaa cttaagagtt  42360
ggcaaagatc cagaacataa gtcccagggt gataacacac agctgaatgg agacaaagtt  42420
acagaaggaa aactttgaca accagttgaa tacaactgga caactgactg caccagaagg  42480
atacggtagc tgtaagtagc tctttgtgtg cattagaatc ctgccagcta agaatgactg  42540
tggctcagtg ctggacacta gagctttctc tgaggattgg aaggaatatt tgttggccca  42600
gtctgttttg gctgctactg gcctcttgtg gctgatggcc acttgaaaac tggcttggac  42660
caatgaagag ctgttttctt tagttcatcc aatgtttaca atattgggcc agggatatag  42720
ctcagttggt gaagtaatcc tgctaggtcc attctctact accacataaa atcaggcgtg  42780
ttaatcttag gcaggcccag gatcccaggg ctcaggaccc atctgcagcc aggaggatca  42840
gaagttcgtc ttcaggtgca cagtgagtta caggccagcc taggatactt gagtccttgt  42900
gtttgttttg tttttaacta tttaaaaaaa tatttatttt atgtgtatga gtataccata  42960
gctgtcctca aacacaccag aagagggcat tacagatgtt tgtgagccac catgtggttc  43020
ctgggaattg aactcaggac ctctggcaga ggataacctt ttaaccgctg agccatttct  43080
ccagcccctg agaccttgtc tcaacaacaa caacaacaac aacaacaaca acaacaacaa  43140
cagttaaacg cacatagtgt tcttgcagag gacctgacag gggttcttac cacctaagtt  43200
gggctcccca caaccatctg taactctagt tccagggaat ctgatgccct cttctggacg  43260
ctgcagatac ctgcacccat atgcacctcc cctgtgcaaa cacacatata cacataatta  43320
aaaactataa aaataaatac atcttaaaag gaaaagccca ccctgaacag gcaatctaga  43380
atataaagac tgaaatcata tcgacaactg cctaaagctt gggatgggag gagactgatc  43440
aatgatgagt aattaaagtg atggaaatgt tgtaaaacct gattaattgt aaattatgac  43500
tcaacaaaaa tatagtcttg tatatataca agaaaagata ttaaaaacaa aaattttgag  43560
acatcgtctt agcgttaact gtcaacttga catagcctag agtctctgag aagtgtgtct  43620
cggatcagtg tgattgtctt gattgttaac tgatatagga gggttcagcc cactgtgggc  43680
agcagtgttc tgggccgtgt gatcctgagc tatacaggaa ggttagctaa ggatgaacct  43740
gcaagtgagc tggcggcacc accatcctgc acggtttctg ctgtgctttg gctgggaagt  43800
gagctcctta gttggagcta atgctgtcaa acctgccttc aggttattgc cttacttcac  43860
tcagtgatgg attgtgatct aagagtgcaa gccaaatagg tcccaagtgc tgtgtgtgcc  43920
accacaacgg aggtgctagg gattaaaccc acacctccgt gcatgccagg caagcacgct  43980
actgacttat cgacaagccc agcacatgtt ctaaatattc tatattttaa aaagctttat  44040
tatataaaaa accatgcaag taaatgaaag taccacatat catgctggag acatggctca  44100
gtagttaaga gcactaactg ctcttagaga ggacctgagt tcaggtccca gcatacacag  44160
agtggtttat aacttcctgt agctccagat ccagaaagac atgatgtccc ctctggcctc  44220
cttgggcact acagtcacat gcacataccc ccacacgtac atataaataa taaaagaaaa  44280
aattttaagg gttggagaga tggctcagca gttaagaata ctgtctgctc ttccagaggt  44340
cctgagttca atccctagga accacatggt ggctcacagc catctgtaat gggatctgat  44400
gccctcttct ggcacgcagg tgtacatgca gatagagcac tcatatataa aataaatatt  44460
ttaaaaaatc atatatccaa attaaccaga cccaaagtct atataacgta ataaatttat  44520
atacagttag aattggcctt ctggcagaag ctatgaaact tcacattaaa ttttatattt  44580
ttagtactga acaaatttta gattcttttt tttttttttc ttttttcttt ttgtttttttc  44640
gagacagagt ttctctgtgt agccctggct gtcgtggaac acactttgta gaccaggctg  44700
gcctcgaact cagaaatccg cctgcctctg cctcccgagt gctgggatta aaggcgtgtg  44760
ccaccacgcc cggctatttt aggttcttag gttcttatcc accaccaacc ccaaaagacc  44820
atggcaaatc agaactagaa cacctaagtt tttgtcgtca ttcacaaatg cctcgtgcct  44880
gcacttagtc tttcctcctc ccatacattt agcctttctt gttctcttct ctctgtgttg  44940
tgctgtaccc acatgaacat gtgtggcttt agcttgcatt tccctcatgg gaaatgaacc  45000
tggctaactt ttcacctgat cattggtcgt acgtagatct tccttgagga aataattatt  45060
tggaatttat tttggtggtg ctggagatca aacgcaggct cttctagatg ctactcagcg  45120
ttccagggct cagctgcaca cctaagcacc gagattatca tttctcactg ttattagact  45180
tcatatatat gttagaattg tatatgtgag ccggcagtgg tgacgcacgc ctttaatccc  45240
agcacttggg aggcagaggc aggtggattt ctgagttcaa ggccagcttg gtctacagag  45300
tgagttccag gatagccagg actgcacaga gaaaccctgt ctcgaaaaac caattaaaaa  45360
aaaaagaatt gtgtgtgtgt gtgtgtgtgt gtgtgtgtgt gtgtgtgtgt gtgtgtacac  45420
atacacagat cccattacag atggttgtga gccaccatgt ggttgctggg atttgaactc  45480
aggacctctg gaagagcagt cagtgctctt aactgctgag ccacctctct agtccttgcc  45540
aggccatttt ctacacattt ctgcctgttc tgtaatggag aacctgacat gagcctgaca  45600
```

-continued

```
ctgatgttta tctccttaca gggaaatctg ccttacactg ggctgcagct gtgaacaacg  45660
tggaggctac cttggctctg ctgaaaaatg gagccaacaa ggacatgcag gacagcaagg  45720
tgagccactg gggccctaca gtgctacagc ccctgaatgt gacaaagcag agtcagggag  45780
gaataagcct gttaggggca tccatcttgc ttgcagtcag ctctcaggag tgggattctg  45840
gcctgaaggc tgtgagagca aactgttgaa gtcgctgtgt gacatcgaac gcagttgtcc  45900
ccattgtgac aggggaagca gcagcatgag ctgctgagct tgaacaagcc tacttttctt  45960
ccttccttct ttctttcttt ttgagactaa cttcctacct caggttggcc ttgaactcac  46020
aattctcata tttctactaa ctaaatgctg gtatatgctc tcatgcctgg ctttttcttt  46080
tttcaatgat atattttatt tttaaatagt gtgtgcgtgt aagtatgtgg acatgagttg  46140
cagatatcct tgaagcaaga agagggtgtt gaatccccct agagctgaat ctataggcag  46200
ttgtgaactg cccgtgtgga taccagggat ggcactgaag tcaccaggct gagtgacaag  46260
tgtggttacc cactgtgccg tcttgccgtc ttgccagtct ttacattgtt tccttctctt  46320
ttggagatca tgtcttactg gttaatttag caaaagctga cctcaaactc ttggtgagtc  46380
ttctgcctta gcctctcaag tgctggggtc ataggctcag gttctctctc tgtctgtctc  46440
catctctgtc tttccctccc ttccttcctt ccttccttcc ttccttcctt ccttccttcc  46500
ttccttcctt ctttctttct ttctttcttt ctttctttct ttctttcttt ctttctttct  46560
ttctttcttt ctttcttttct aagacaagga ctcactttgt agaccaggct agcctagaac  46620
tcagagaccc ttttgccttt gtgtcctgga tggtaggact gaaggtgtac aggaccacca  46680
gaaccccaac aactcacttt ttaatctttt gttttttttgg tttttcaaga tagggtttct  46740
ctgtatagtc ctggctgtcc tggacctcac tttgtagacc aggacaaaga aactggtaga  46800
actcagaaat ctgcctgcct ctgcctcccg agtgctggga ttaaaggcgt gctttttaat  46860
cttttataac tctttttaaa acttttataa catcaccatg cagtttattt tgatgactgg  46920
aagttttgat gccccttttaa attttgtgcc taaggtaagt cctggccaga tgtgcctgct  46980
acagagagag cttgtttctt caacagagct ggaatccaaa ctcaggtcca tctatttcca  47040
gggtatcaac tcttagttct caggctgccc tagagattag aaagctaggt gttggccaga  47100
gtgactgacc tccgtgggtt ctgcccctcc cccgcctcag gaagagacgc cgctgttctt  47160
ggccgctcgg gagggcagct atgaggctgc caagctgctg ctggatcatc tcgccaaccg  47220
ggagatcaca gatcacttgg acaggctgcc ccgggacgtg gcccaggagc ggctgcacca  47280
ggacattgtg cggttgctgg accagcccag tggacctcga agtccctctg gtccccatgg  47340
cttagggcca ttgctctgcc caccaggggc cttccttcct ggcctcaaag cggtgcagtc  47400
tgggaccaag aagagcagga ggccacctgg caagaccggg ctggggccac agggaactcg  47460
tggtcggggc aagaagctga cactagcctg tccaggacct ctggcagaca gctctgtcac  47520
actgtcaccg gtggactctc tggactcacc acggcctttc agtgggcccc ctgcttcccc  47580
tggaggcttc cccttggagg gcccctatgc caccacggcc accgcggtgt ccttggcaca  47640
gctaggcgca agtagggcgg gtcctctggg gcgccagcct cctgggggct gtgtgctcag  47700
ctttggtctg ctcaatcctg tagctgttcc cctcgactgg gccaggctgc ctccacctgc  47760
ccctccaggg ccctcattcc tgctgcccct ggctccggga ccccagttgc tcaacccagg  47820
agccccagtt tctccccaag agcggccccc accctacctg gctgctccag gacatggaga  47880
ggaatatcct gcagcaggaa cccgcagtag ccccaccaag gcccgcttcc tgcgggttcc  47940
cagcgagcat ccttatttga ccccgtctcc tgagtcccca gagcactggg ccagcccatc  48000
ccccccatcc ctctcagact ggtctgactc aacacctagc ccagcaactg ctaccaatgc  48060
cacagcctct ggagccctgc ctgctcagcc acaccccata tctgttccct ccctccctca  48120
gtcccagact cagctgggac cccaaccaga agttaccccc aagaggcagg tgatggccta  48180
agttcttgga tttgaggggt gctgaagtga cactcctcta tgacttcttt cttcctcctt  48240
tttaatctta ctctcatccc tttctctctg tcccagcctt cctgcacctc tctgtcttgt  48300
agtgtgacca agttggtcac cagcccagac ccccagtctt cctttattta taatgggtag  48360
gggctgacct tccaccacct tggcccccta agggatctgg gacctccttt tgatccctct  48420
ccctgcctca acttcctccc ccccctcttt ctgcttctca ttgtctcaca ctctgacaag  48480
agtgagttat tattttttttc ttttttacat tttgtataga gacaaattca tttaaacaaa  48540
cttattatta ttattatttt ttacaaaata tatatatgga gttgctccct tccccccgct  48600
gcaaattcct ccagcgcccc cgtggggctg agtctgtggg cccgtttggc caatccggac  48660
tctgtgtact gagtacacag atatgactag ggctccacgt actgagtatg tggccctcgt  48720
atgtaccaag tagccagcct tgggcacacc ctcccctggg gtcaggggac atttgggagc  48780
ctccttcccc tccccattcc ccttcctcac ttcactgcat tccagataag acgtgtagac  48840
tcactgggaa aggggtcttg tctgctcaaa gcctcaactc caggctcacc tcccagagcc  48900
tggctcacct tttagggcct ggggtggggg ggcacgtcag gggagatgta ttttgtatgc  48960
attccacttc taattgtaaa tacagggcag aaggtgggag tggctctccc tcttcctgtt  49020
gttctcttgg ctcagcctgc ctaatagaaa tgtttttagg ctgtttttgt aatatggcac  49080
ctggtcacag tcctttgtag ctgaattccc aggtcctgca ctgtacaacc ctcaccttct  49140
cagttccctt accacctaat aaaggaatag ttaataccca agtgtctggt ttctgtgcaa  49200
ggtccaaagt gggggtttct gggcctcttc ctccacaggg ctaacttgaa ctcccatctt  49260
ggggcagagc catgtgcttt gtcagtccac ctttgactcc tttttggtca ggtatctagc  49320
ttcatttctg ttgctttaag caaataccta acagaaaaga aacttaaggg acagagggac  49380
tttttcctaa ctaaatattc caggttacag tccaacattg tgaagaagag gcaggaactt  49440
aaaatagttc accacatcac accacagtca agagcagaga gaaagaagtg agtggatgca  49500
tgcttgcttc cttgtgtcgg gctgaatcat tacactctta aacagtttag aaacccttgt  49560
ttggggaatg atgccaccca cagtaggcag tgtcttccca cattaatttg acttaattac  49620
gacaatctcc taaagacatt ctttcaggtc aactcgatgt agacaacttc tgttcccagg  49680
tgatttgtaa gttctgtcat tgtgacaaaa ctgatcatca tatcaggtgg tttcaatttt  49740
tgaatcttgg gttggaacca ataaagggac tcaaaacaaa aacaggcaaa caaaccaaaa  49800
ggaaaaaaaa aaaacctaca aaactcaata gtgttatttt gagaacttac tttttttcttt  49860
aaaaatttta ttattattat tatcattgtt gttgtttttt tttgtttgtt tgttttttga  49920
gacagggttt ctctgtgtag ccttagttgt cctggaactc acaaaagaaa acacacaaaa  49980
taacaccaaa cccagtacac aggaagcagg cctggctcac ctgcagaact gcccgaacaa  50040
ggcaagacag cctatgggac agcaaaacag ggcacaaaga atgagagccc aggagagaga  50100
gcaacagaca gaagagacaa acccctaggc gccaccagag aatgattgcc ctggagggga  50160
gaaggtggag tactgggtgc tgggaacacg ccacacacac acactctgtg tgctggtgtt  50220
tgctttgtgc taagccactg agctcaagtg cttgcggttt gcatccagaa actcatccag  50280
ttgagccagt attaccccca gagcaatgtg atggaaatca gcagtggttt gaatccagaa  50340
```

-continued

```
atataaaaac ggcacttttt ttgctcacct atctattcta gacttctgtg cactgatata  50400
ggttccaggg tctcaaatcc cttaaaattc taatcaactg tgatgggcca ggctggaagc  50460
agcgatgaca cgcgtcctgg aaaccctgcc aagctgtcct gtaccgctgc ttctgcgtgt  50520
gttgataatt aatccttcgg agcgggcgca cgaatgtgag aaattggcta ttttccgctt  50580
ctgaatgatg gctctgagcc actacggcag cttttccatt tcaaatctga ctgtcaaaag  50640
tggtgcatta atcagtattt cgttagtttc aacatttcca gaatccgcct ccccaagtgc  50700
acatacaaag tgcagccatc ctcagccgag aaggcaaggg cggggccttg cttcaggtga  50760
cgactctttc tttctctttg caccactcca tcctctgaga ggctatggct gtgactccgg  50820
agctcacttc cctgcaaagt agtggctctt ggctgagtac ttccaacagg gagacagaac  50880
aggaccggag ggtggcagac ggtgcctcta tccaatggcc ccctgggtga cttccccaga  50940
agcactttat tattattatt attattatta ttattattat tattattatt attattggtg  51000
tggttagttg ttttgagaca ggattgctct ttgtagccca ggctggccgt gaactcagaa  51060
gtccacctgc ctctgcatct ggtgtgctga ttctgatgtc accaccagat gtgagcctcc  51120
accatcagac tcacatccac tacagacgac ctgaatgtct cagccaagct gtatactaga  51180
gaaagtggct actgttacaa aactcagtgg agacacagct ctagcagatg taggtctggc  51240
tgaccacata agcactgact agtgctggag acacactggt actgagcgac agctgtgctg  51300
agaaccatat ctggctgagg tgctgcttgg gtcaacctct cagagtgtcc agcaggaggc  51360
agggcttcca gacctactga tggatgagtc tgggggctgg gcaaactgga cagcattatt  51420
ctgtggagaa gccttagact gtcccccaaa gtaaaagcac cccaaccagc ctgttatact  51480
tcctccctcc cactgtcagg gccaccaacg cccaagagtg caaaaggcac ccaggaaaga  51540
gaaagttaaa aaaacaaggg aaggttgatt ttcctacttc ctgctgcccc taactgccag  51600
acgaggcttc tccccctgcc cctcaagcaa ccctcagact ccgcccatgt ccgtgccccg  51660
ccccctcctc tccaacagtg acgcgtgctg tgctggcatg gctgccggtg ggcaggtgat  51720
gcacatccca ggaacatttt gcccgcccca actgcttcat caccaagcct ccagcaaaga  51780
ggctcaggca gcctgaagcc tcgctgcctg gcatagcgca tttagagtaa cagctcagct  51840
aatctcttcc aagggaggca gagctgctca gcacagcagg agtggggcga gctctggaat  51900
attccagtgt ggttctccca caggcatcta gggacagaga ggagtgtggg ggtgggggac  51960
aagctgagcc tcacaggtgt tcctaggctg atgcttaagt                        52000

SEQ ID NO: 81          moltype = DNA  length = 16
FEATURE                Location/Qualifiers
source                 1..16
                       mol_type = other DNA
                       organism = synthetic construct
SEQUENCE: 81
ggaatattgg ttcagt                                                  16

SEQ ID NO: 82          moltype = DNA  length = 16
FEATURE                Location/Qualifiers
source                 1..16
                       mol_type = other DNA
                       organism = synthetic construct
SEQUENCE: 82
tgtcgaagct caaccc                                                  16

SEQ ID NO: 83          moltype = DNA  length = 16
FEATURE                Location/Qualifiers
source                 1..16
                       mol_type = other DNA
                       organism = synthetic construct
SEQUENCE: 83
atctatgtca ctttgg                                                  16

SEQ ID NO: 84          moltype = DNA  length = 16
FEATURE                Location/Qualifiers
source                 1..16
                       mol_type = other DNA
                       organism = synthetic construct
SEQUENCE: 84
gaatattggt tcagta                                                  16

SEQ ID NO: 85          moltype = DNA  length = 16
FEATURE                Location/Qualifiers
source                 1..16
                       mol_type = other DNA
                       organism = synthetic construct
SEQUENCE: 85
tgtatgtcgc acaggc                                                  16

SEQ ID NO: 86          moltype = DNA  length = 16
FEATURE                Location/Qualifiers
source                 1..16
                       mol_type = other DNA
                       organism = synthetic construct
```

-continued

```
SEQUENCE: 86
acaattctat ggtctc                                               16

SEQ ID NO: 87           moltype = DNA  length = 20
FEATURE                 Location/Qualifiers
source                  1..20
                        mol_type = other DNA
                        organism = synthetic construct
SEQUENCE: 87
catggtcttc ccctatcacc                                           20

SEQ ID NO: 88           moltype = DNA  length = 20
FEATURE                 Location/Qualifiers
source                  1..20
                        mol_type = other DNA
                        organism = synthetic construct
SEQUENCE: 88
tgtcaatctc cagcatcacc                                           20

SEQ ID NO: 89           moltype = DNA  length = 22
FEATURE                 Location/Qualifiers
source                  1..22
                        mol_type = other DNA
                        organism = synthetic construct
SEQUENCE: 89
atcacctcag gacccagctc ac                                        22

SEQ ID NO: 90           moltype = RNA  length = 23
FEATURE                 Location/Qualifiers
source                  1..23
                        mol_type = other RNA
                        organism = synthetic construct
modified_base           22..23
                        mod_base = OTHER
                        note = thymine
SEQUENCE: 90
ataaaatcta cagtcatagg att                                       23

SEQ ID NO: 91           moltype = DNA  length = 24
FEATURE                 Location/Qualifiers
source                  1..24
                        mol_type = other DNA
                        organism = synthetic construct
SEQUENCE: 91
caaaggaggg acatgtatca acac                                      24

SEQ ID NO: 92           moltype = DNA  length = 20
FEATURE                 Location/Qualifiers
source                  1..20
                        mol_type = other DNA
                        organism = synthetic construct
SEQUENCE: 92
ctggcaatgt ttcccagtga                                           20

SEQ ID NO: 93           moltype = DNA  length = 24
FEATURE                 Location/Qualifiers
source                  1..24
                        mol_type = other DNA
                        organism = synthetic construct
SEQUENCE: 93
cccaatgggc cacactgtct ctgc                                      24
```